United States Patent
Ermann et al.

(10) Patent No.: US 10,472,341 B2
(45) Date of Patent: Nov. 12, 2019

(54) BICYCLIC TETRAHYDROTHIAZEPINE DERIVATIVES USEFUL FOR THE TREATMENT OF NEOPLASTIC AND/OR INFECTIOUS DISEASES

(71) Applicants: APEIRON BIOLOGICS AG, Vienna (AT); EVOTEC AG, Hamburg (DE)

(72) Inventors: Monika Ermann, Oxfordshire (GB); Guenther Lametschwandtner, Vienna (AT); Patricia Leonie Amouzegh, Oxfordshire (GB); Russell Stuart Craft, Groningen (NL); Thomas Hanke, Hamburg (DE); Timothy Robin James, Oxfordshire (GB); Severine Danielle Jones, Oxfordshire (GB); Hans Loibner, Vienna (AT); Pui Leng Loke, Oxfordshire (GB); Ina Sternberger, Hamburg (DE); Anton Stuetz, Altmuenster (AT); Roland Wehr, Goettingen (DE); Mark Whittaker, Oxfordshire (GB)

(73) Assignees: APEIRON BIOLOGICS AG, Vienna (AT); EVOTEC SE, Hamburg (DE)

( * ) Notice: Subject to any disclaimer, the term of this patent is extended or adjusted under 35 U.S.C. 154(b) by 0 days.

(21) Appl. No.: 15/554,354

(22) PCT Filed: Feb. 29, 2016

(86) PCT No.: PCT/EP2016/054228
§ 371 (c)(1),
(2) Date: May 10, 2018

(87) PCT Pub. No.: WO2016/139181
PCT Pub. Date: Sep. 9, 2016

(65) Prior Publication Data
US 2018/0170888 A1   Jun. 21, 2018

(30) Foreign Application Priority Data

Mar. 2, 2015 (EP) .................................... 15157175

(51) Int. Cl.
| | |
|---|---|
| *C07D 285/36* | (2006.01) |
| *C07D 417/12* | (2006.01) |
| *C07D 417/14* | (2006.01) |
| *A61P 35/00* | (2006.01) |
| *A61K 31/554* | (2006.01) |
| *A61K 45/06* | (2006.01) |
| *C07D 417/06* | (2006.01) |
| *C07D 417/10* | (2006.01) |
| *C07D 513/04* | (2006.01) |
| *C12N 5/0781* | (2010.01) |
| *C12N 5/0783* | (2010.01) |

(52) U.S. Cl.
CPC .......... *C07D 285/36* (2013.01); *A61K 31/554* (2013.01); *A61K 45/06* (2013.01); *A61P 35/00* (2018.01); *C07D 417/06* (2013.01); *C07D 417/10* (2013.01); *C07D 417/12* (2013.01); *C07D 417/14* (2013.01); *C07D 513/04* (2013.01); *C12N 5/0635* (2013.01); *C12N 5/0636* (2013.01); *C12N 5/0646* (2013.01); *C12N 2501/2302* (2013.01); *C12N 2501/999* (2013.01)

(58) Field of Classification Search
CPC .................................................. C07D 285/36
See application file for complete search history.

(56) References Cited

FOREIGN PATENT DOCUMENTS

| EP | 0433683 A2 | 6/1991 |
|---|---|---|
| WO | 98/35941 A1 | 8/1998 |
| WO | 03/031376 A1 | 4/2003 |
| WO | 2014/125444 A1 | 8/2014 |

OTHER PUBLICATIONS

Pinedo et al. (2000).*
MaMahon et al. (2000).*
Ahmadzadeh et al., "Tumor antigen-specific CD8 T cells infiltrating the tumor express high levels of PD-1 and are functionally impaired," Blood 114(8):1537-1544 (2009).
Ayral et al., "Design, synthesis, and biological evaluation of 1,3-benzothiazepine-4-one derivatives targeting factor VIIa/tissue factor," Bioorganic & Medicinal Chemistry Letters 19:1386-1391 (2009).
Breitschuh et al., "Herstellung von steroisomeren 3-Sulfinylbuttersauren aus (R)- and (S)-4-Methyl-2-oxetanon," Synthesis 1-2:83-89 (1992).
Gladue et al., "The CD40 agonist antibody CP-870,893 enhances dendritic cell and B-cell activity and promotes anti-tumor efficacy in SCID-hu mice," Cancer Immunol. Immunother. 60:1009-1017 (2011).
Herpin et al., "Directed Sorting Approach for the Synthesis of Large Combinatorial Libraries of Discrete Compounds," Methods in Enzymology 369:75-99 (2003).

(Continued)

Primary Examiner — Paul V Ward
(74) Attorney, Agent, or Firm — J.A. Lindeman & Co. PLLC; Jeffrey Lindeman; Aaron Raphael

(57) ABSTRACT

The present invention relates to bicyclic tetrahydrothiazepine of formula (I), wherein $R^1$ to $R^3$, $X^1$, $X^2$ and $R^{18}$ have the meaning as indicated in the description and claims. The invention further relates to pharmaceutical compositions comprising such compounds as well as their use as medicaments, especially in methods for the treatment or prevention of a neoplastic and/or infectious disease and in vitro methods.

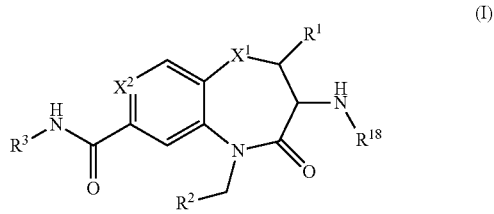

(I)

30 Claims, No Drawings

(56) References Cited

OTHER PUBLICATIONS

Hirsch et al., "Effects of In Vivo Adminstration of Anti-CD3 Monoclonal Antibody on T Cell Function in Mice," J. Immunol. 142(3):737-743 (1989).
Ma et al., "The role of CD40 and CD40L in Dendritic Cells," Semin. Immunol. 21(5):265-272 (2009).
Morton et al., "Novel solid-phase synthesis of 1,5-benzothiazepine-4-one derivatives," Tetrahedron Letters 41:3029-3033 (2000).
Otsuki et al., "Chemical tagging of a drug target using 5-sulfonyl tetrazole," Bioorganic & Medicinal Chemistry Letters 23:1608-1611 (2013).
De Paola et al., "Restored T-cell activation mechanisms in human tumour-infiltrating lymphocytes from melanomas and colorectal carcinomas after exposure to interleukin-2," British Journal of Cancer 88:320-326 (2003).
Parmiani et al., "Cytokines in cancer therapy," Immunology Letters 74:41-44 (2000).
Rosenberg, "The Emergence of Modern Cancer Immunotherapy," Annals of Surgical Oncology 12(5):1-3 (2005).
Schroder et al., "Interferon-γ: an overview of signals, mechanisms and functions," Journal of Leukocyte Biology, 75:163-189 (2004).
Sensi et al., "Unique Tumor Antigens: Evidence for Immune Control of Genome Integrity and Immuogenic Targets for T Cell-Mediated Patient-Specific Immunotherapy," Clin. Cancer Res. 12(17):5023-5032 (2006).
Van Kooten et al., "CD40-CD40 Ligand," Journal of Leukocyte Biology (67):2-17 (2000).
Yuan et al., "CTLA-4 blockade enhances polyfunctional NY-ESO-1 specific T cell responses in metastatic melanoma patients with clinical benefit," PNAS 105(51):20410-20415 (2008).

\* cited by examiner

BICYCLIC TETRAHYDROTHIAZEPINE DERIVATIVES USEFUL FOR THE TREATMENT OF NEOPLASTIC AND/OR INFECTIOUS DISEASES

The present invention relates to bicyclic tetrahydrothiazepine derivatives. The invention further relates to pharmaceutical compositions comprising such compounds as well as their use as medicaments, especially in methods for the treatment or prevention of a neoplastic and/or infectious disease and in vitro methods.

Today, malignant neoplasia (cancer) and infectious diseases are two of the main causes of death allover the world. In an increasing number of cases, it is known that there is often interdependency between neoplastic and infectious diseases, such as, e.g., between cervix neoplasia and herpes simplex virus infections. Although a large variety of compounds for treating and preventing these diseases has been found, it is well-known that such compounds bear significant drawbacks such as provoking severe side effects. Therefore, there is still an unmet need for new compounds for treating and preventing neoplastic and/or infectious diseases.

In order to overcome these drawbacks, therapeutic and prophylactic approaches based on modulating the immune response of the patient gain increasing importance in today's medicine. The immunological activity of the patient is hereby often supported by a medicinal treatment. In practice, in this context, immunologic treatments against neoplastic and infectious diseases are of particular interest. In this regard, it is well-known that in a body several types of immune cells such as, e.g., natural killer (NK) cells, T cells, B cells, dendritic cells, monocytes and macrophages, are often involved in the inactivation and removal of pathogens. With respect to neoplasia for instance, it is known that each matured neoplasm (tumor) bears specific antigens and/or neo-antigens (e.g., Sensi and Anichini, 2006, Clin Cancer Res. 12:5023-5032). This may in general trigger the adaptive immune system (e.g., T cells and/or B cells) as well as the innate immune system (e.g., natural killer (NK) cells). The immune system in a healthy body is mostly effective enough to prevent or cure said body from neoplastic and infectious diseases.

In some cases, the immune system however fails to eliminate such neoplastic or infectious disease and such disease becomes chronic. In these cases, in particular when the patient suffers from malignant neoplasia (cancer), the immune system is often down-regulated. Whereas in a healthy body (i.e., in a non-suppressed immune environment) a suitable expression of major histocompatibility complex I (MHC I) presenting antigens to immune cells, e.g. cytotoxic CD8 T cells is found, the expression of MHC I is down-regulated in tumor cells. This can be countered by NK cells, specifically recognizing and destroying cells with decreased MHC-I surface expression. However, during the maturation of neoplasms (in particular tumor progression), due to a multitude of immunosuppressive mechanisms leading to immune tolerance, maturating neoplasms can increasingly escape the immune system, i.e., the neoplastic antigen is not recognized as non-self, and the immune system is not activated. This mechanism is a general principle of maturating neoplasm and is neither restricted to specific neoplasms nor dependent on specific neoplastic antigens. Notably, it has been found that in most cancer patients, tumor-associated T cells and NK cells exist, but do not produce sufficient amounts of a number of cytokines (such as e.g., IL-2 and IFN-γ) or exert cytotoxic activity towards the tumor since suppression by various mechanisms hinders efficient anti-tumor immune responses (De Paola et al., 2003, British Journal of Cancer 88:320-326; Ahmadzadeh et al., 2009, Blood 114:1537-1544, in particular pages 1541-1542, section "PD-1+ TILs display an impaired effector function"). This is evidently also one of the reasons why tumor vaccination often fails.

Likewise, numerous infections are known to down-regulate the patient's immune system, in particular viral infections such as, e.g., human immunodeficiency virus (HIV) infections or herpes simplex virus (HSV) infections. Also in this context, the production of cytokines by T cells and other anti-viral immune cells is disordered.

Briefly summarized, a number of cytokines is well-known to facilitate stimulating the immune system and evidently plays an important role in activating the immune response. Such cytokine secretion plays an important role for triggering immune responses towards neoplastic and/or infectious pathogens, particularly towards cancer and/or virus infections.

Accordingly, it has been considered to supplement patients suffering from neoplasia or infectious diseases with administrations of one or more cytokine(s) in order to systemically increase the respective cytokine levels and thereby upregulate and trigger the immune system in the patient's body. In this context, in particular the cytokines interleukin 2 (IL-2), interferon gamma (IFN-γ) and—initially—tumor necrosis factor alpha (TNF-α) have been considered.

IL-2 is a factor for efficient immune responses in the human organism, since it mediates on the one hand proliferation and maintenance of CD4 helper and CD8 killer T cells (CD4+ and CD8+ T cells)) and on the other hand supports and activates NK cells (Parmiani et al, 2000, Immunology Letters 74:41-44). Due to its high bioactivity, in the physiologic context of the body, the production of IL-2 is stringently controlled and tightly linked to antigen-activation of T cells via the T cell receptor. Thereby, the body prevents autoimmune effects of excessive systemic production of IL-2. As IL-2 represents a highly active anti-pathogen (e.g., anti-tumor) agent, systemic administration of IL-2 has been used as a therapeutic means for treating neoplasia in a patient (Rosenberg, 2005, Annals of Surgical Oncology 12(5):1-3). IFN-γ has been recognized as another key factor for anti-tumor immunity. Mice deficient in IFN-γ production suffer from increased tumor incidence. IFN-γ uses several mechanisms to foster anti-tumor immunity. It increases the MHC I-expression of tumor cells, which is, as indicated above, often aberrantly low and it induces the expression of several receptors that enhance responsiveness to immune-cell mediated apoptosis (Schroder et al., 2004, Journal of Leukocyte Biology 75:163-189, in particular page 165, left column, last paragraph, and pages 170ff, section "Cellular Effects of IFN-γ").

The systemic administration of cytokines however bears a number of significant drawbacks. First, increased levels of the cytokines often cause severe undesired side effects. Exemplarily, the systemic administration of IL-2 may even cause life-threatening vascular leakage-related side effects, since IL-2 targets all T and NK cells in the patient, but not selectively those that are involved in local anti-pathogen (e.g., anti-tumor) reactions. The same applies to TNF-α administration which is also well-known as being life-threatening above a certain dose-range. Likewise, also IFN-γ administration bears severe drawbacks due to its systemic activity. Secondly, cytokines such as IL-2, IFN-γ and TNF-α are comparably expensive. And thirdly, such cytokines bear unfavourable pharmacokinetic and pharmacologic properties.

Accordingly, strategies for increasing the cytokine levels without the need of systemic administration thereof are desired. Exemplarily, therapeutic interventions for enhancing the IL-2 and IFN-γ production of activated T cells, e.g., by a blockade of CTLA4 signaling, have been considered as anti-cancer therapies. For instance, CTLA4-blockade can induce complete remission in patients suffering from late-stage metastatic melanoma, a widely progressed neoplasia. The clinical benefit of such treatment has been shown to correlate with enhanced T cell responses, particularly with IFN-γ and TNF-α production by CD8 and CD4 T cells (Yuan et al., 2008, PNAS 105(51):20410-20415, in particular pages 20411-20412, section "Evaluation of NY-ESO-1 Specific T Cell Response").

In the view of the above, it is evident that cytokines like IL-2, IFN-γ and TNF-α are well-established markers for immunoreactivity correlating with the clinical outcome in immune therapies. Further, it is also evident that a local or systemic increase of the level of one or more of such cytokines also activates immune cells of the innate and the adaptive immune system such as, exemplarily, T cells and/or NK cells, subjected to such increased cytokine levels.

Likewise, also a variety of other markers correlating with immunologic activity usable in this context are known such as, e.g., the expression level of CD40 ligand (CD40L, also known as CD154) as well as the proliferation rates of immune cells such as T cells, NK cells, B cells and/or monocytes. In more detail, the surface expression of CD40L is a well-known marker for T cell activity. CD40L binds to the CD40 receptor that is expressed prominently on B cells and professional antigen presenting cells like dendritic cells (Ma and Clark, 2009, Semin Immunol. 21(5):265-272, in particular page 2, forth paragraph, and pages 8-10). Ligation of the CD40 receptor results in the intracellular transmission of activating signals in these cells. For B cells, efficient ligation of the CD40 receptor is a central factor for B cell survival, proliferation and class switching, which are essential for the development and maintenance of protective humoral immunity (van Kooten and Banchereau, 2000, Journal of Leukocyte Biology 67:2-17, in particular Abstract). For dendritic cells, ligation of the CD40 receptor results in enhanced activation of dendritic cells that in turn up-regulates co-stimulatory surface molecules (e.g., of the B7 family) resulting in stronger and more sustained T cell activation. Moreover, CD40 ligation on dendritic cells is also important for the secretion of cytokines centrally involved in anti-tumor immunity like interleukin 12 (IL-12) (Gladue et al., 2011, Cancer Immunol Immunother. 60:1009-1017, in particular Abstract, and pages 1010 and 1016, left columns each).

It is evident that compounds leading to an increase in such markers of immunologic activity, in particular of the above-mentioned cytokines (e.g., IL-2, IFN-γ and/or TNF-α), are able to increase immunologic activity and are, thus, usable as compounds for effectively treating neoplastic and/or infectious diseases.

Today, there is still an unmet need for such compounds enabling to increase immunologic activity and thereby enable the treatment and/or prevention of neoplastic and/or infectious diseases.

An interesting class of compounds are 2,3,4,5-tetrahydro-1,5-benzothiazepine derivatives. Such compounds are known in the art.

WO 2003/031376 A1 describes solid phase synthesis of 1,5-benzodiazepine-2-one and 1,5-benzothiazepine-4-ones.

E. Ayral et al., Bioorganic & Medicinal Chemistry Letters 19 (2009) 1386-1391, describe 1,5-benzothiazepine-4-one derivatives targeting factor VIIa/tissue factor.

T. F. Herpin et al., Methods in enzymology 369 (2003) 75-98 and Tetrahedron Letters 41 (2000), 3029-3033, disclose 1,5-benzothiazepin-4-one derivatives as examples of a directed sorting approach for the synthesis of large combinatorial libraries.

WO 2014/125444 A1 discloses heterocyclic amides as kinase inhibitors. WO 98/35941 A1 describes benzolactam derivatives and medicinal compositions containing the same.

EP 0 433 683 A2 describes the use of benzothiazepines as potentiators of anti-cancer drugs.

However the above-mentioned type of compounds is not described for the treatment and/or prevention of neoplastic and/or infectious diseases.

Thus an object of the invention is to provide new bicyclic tetrahydrothiazepine compounds which can be used as outlined above.

The object is achieved by compounds of formula (I)

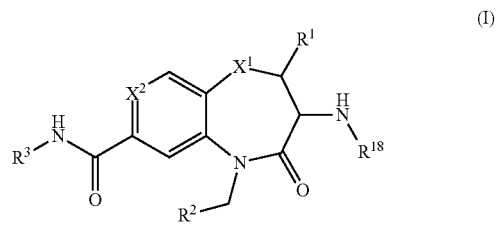

or a pharmaceutically acceptable salt thereof, wherein
$X^1$ is S; S(O); or S(O)$_2$;
$X^2$ is N; or C($R^4$);
$R^1$ is H; or methyl;
$R^2$ is phenyl; 3 to 7 membered heterocyclyl; or 7 to 11 membered heterobicyclyl, wherein $R^2$ is optionally substituted with one or more $R^5$, which are the same or different;
$R^5$ is halogen; CN; C(O)O$R^6$; O$R^6$; C(O)$R^6$; C(O)N($R^6R^{6a}$); S(O)$_2$N($R^6R^{6a}$); S(O)N($R^6R^{6a}$); S(O)$_2R^6$; S(O)$R^6$; N($R^6$)S(O)$_2$N($R^{6a}R^{6b}$); S$R^6$; N($R^6R^{6a}$); OC(O)$R^6$; N($R^6$)C(O)$R^{6a}$; N($R^6$)S(O)$_2R^{6a}$; N($R^6$)S(O)$R^{6a}$; N($R^6$)C(O)O$R^6$a; N($R^6$)C(O)N($R^{6a}R^{6b}$); OC(O)N($R^6R^{6a}$); oxo (=O), where the ring is at least partially saturated; $T^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;
$R^6$, $R^{6a}$, $R^{6b}$ are independently selected from the group consisting of H; $C_{1-6}$ alkyl, $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;
$T^1$ is phenyl; $C_{3-7}$ cycloalkyl; or 3 to 7 membered heterocyclyl, wherein $T^1$ is optionally substituted with one or more $R^7$, which are the same or different;
$R^7$ is halogen; CN; C(O)O$R^8$; O$R^8$; C(O)$R^8$; C(O)N($R^8R^{8a}$); S(O)$_2$N($R^8R^{8a}$); S(O)N($R^8R^{8a}$); S(O)$_2R^8$; S(O)$R^8$; N($R^8$) S(O)$_2$N($R^{8a}R^{8b}$); S$R^8$; N($R^8R^{8a}$); OC(O)$R^8$; N($R^8$)C(O) $R^{8a}$; N($R^8$)S(O)$_2R^{8a}$; N($R^8$)S(O)$R^{8a}$; N($R^8$)C(O)O$R^8$a; N($R^8$)C(O)N($R^{8a}R^{8b}$); OC(O)N($R^8R^{8a}$); oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^8$, $R^{8a}$, $R^{8b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^3$ is $R^{3a}$; $OR^3a$; $NHR^{3a}$; or $NHC(O)R^{3a}$;

$R^{3a}$ is $T^2$; $C_{1-12}$ alkyl; $C_{2-12}$ alkenyl; or $C_{2-12}$ alkynyl, wherein $C_{1-12}$ alkyl; $C_{2-12}$ alkenyl; and $C_{2-12}$ alkynyl are optionally substituted with one or more $R^9$, which are the same or different;

$R^9$ is halogen; CN; $C(O)OR^{10}$; $OR^{10}$; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $S(O)R^{10}$; $N(R^{10})S(O)_2N(R^{10a}R^{10b})$; $SR^{10}$; $N(R^{10}R^{10a})$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; $T^2$; $C_{1-12}$ alkyl; $C_{2-12}$ alkenyl; or $C_{2-12}$ alkynyl, wherein $C_{1-12}$ alkyl; $C_{2-12}$ alkenyl; and $C_{2-12}$ alkynyl are optionally substituted with one or more $R^{11}$, which are the same or different;

$R^{10}$, $R^{10a}$, $R^{10b}$ are independently selected from the group consisting of H; $T^2$; $C_{1-12}$ alkyl; $C_{2-12}$ alkenyl; and $C_{2-12}$ alkynyl, wherein $C_{1-12}$ alkyl; $C_{2-12}$ alkenyl; and $C_{2-12}$ alkynyl are optionally substituted with one or more $R^{11}$, which are the same or different;

$T^2$ is phenyl; $C_{3-7}$ cycloalkyl; 3 to 7 membered heterocyclyl; or 7 to 11 membered heterobicyclyl, wherein $T^2$ is optionally substituted with one or more $R^{12}$, which are the same or different;

$R^{12}$ is halogen; CN; $C(O)OR^{13}$; $OR^{13}$; $C(O)R^{13}$; $C(O)N(R^{13}R^{13a})$; $S(O)_2N(R^{13}R^{13a})$; $S(O)N(R^{13}R^{13a})$; $S(O)_2R^{13}$; $S(O)R^{13}$; $N(R^{13})S(O)_2N(R^{13a}R^{13b})$; $SR^{13}$; $N(R^{13}R^{13a})$; $OC(O)R^{13}$; $N(R^{13})C(O)R^{13a}$; $N(R^{13})S(O)_2R^{13a}$; $N(R^{13})S(O)R^{13a}$; $N(R^{13})C(O)OR^{13}a$; $N(R^{13})C(O)N(R^{13a}R^{13b})$; $OC(O)N(R^{13}R^{13a})$; oxo (=O), where the ring is at least partially saturated; $T^3$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;

$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;

$R^{11}$, $R^{14}$ are independently selected from the group consisting of halogen; CN; $C(O)OR^{15}$; $OR^{15}$; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b})$; $SR^{15}$; $N(R^{15}R^{15a})$; $OC(O)R^{15}$; $N(R^{15})C(O)R^{15a}$; $N(R^{15})S(O)_2R^{15a}$; $N(R^{15})S(O)R^{15a}$; $N(R^{15})C(O)OR^{15}a$; $N(R^{15})C(O)N(R^{15a}R^{15b})$; $OC(O)N(R^{15}R^{15a})$; and $T^3$;

$R^{15}$, $R^{15a}$, $R^{15b}$ are independently selected from the group consisting of H; $T^3$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^3$ is phenyl; $C_{3-7}$ cycloalkyl; or 3 to 7 membered heterocyclyl, wherein $T^3$ is optionally substituted with one or more $R^{16}$, which are the same or different;

$R^{16}$ is halogen; CN; $C(O)OR^{17}$; $OR^{17}$; $C(O)R^{17}$; $C(O)N(R^{17}R^{17a})$; $S(O)_2N(R^{17}R^{17a})$; $S(O)N(R^{17}R^{17a})$; $S(O)_2R^{17}$; $S(O)R^{17}$; $N(R^{17})S(O)_2N(R^{17a}R^{17b})$; $SR^{17}$; $N(R^{17}R^{17a})$; $OC(O)R^{17}$; $N(R^{17})C(O)R^{17a}$; $N(R^{17})S(O)_2R^{17a}$; $N(R^{17})S(O)R^{17a}$; $N(R^{17})C(O)OR^{17}a$; $N(R^{17})C(O)N(R^{17a}R^{17b})$; $OC(O)N(R^{17}R^{17a})$; oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{17}$, $R^{17a}$, $R^{17b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^4$ is H; F; Cl; or $N(CH_3)_2$;

$R^{18}$ is H; $C_{1-6}$ alkyl; $C_{2-6}$ alkenyl; or $C_{2-6}$ alkynyl; wherein $C_{1-6}$ alkyl; $C_{2-6}$ alkenyl; and $C_{2-6}$ alkynyl are optionally substituted with one or more $R^{19}$, which are the same or different;

$R^{19}$ is halogen; CN; $C(O)OR^{20}$; $OR^{20}$; $C(O)R^{20}$; $C(O)N(R^{20}R^{20a})$; $S(O)_2N(R^{20}R^{20a})$; $S(O)N(R^{20}R^{20a})$; $S(O)_2R^{20}$; $S(O)R^{20}$; $N(R^{20})S(O)_2N(R^{20a}R^{20b})$; $SR^{20}$; $N(R^{20}R^{20a})$; $NO_2$; $OC(O)R^{20}$; $N(R^{20})C(O)R^{20a}$; $N(R^{20})SO_2R^{20a}$; $N(R^{20})S(O)R^{20a}$; $N(R^{20})C(O)N(R^{20a}R^{20b})$; $N(R^{20})C(O)OR^{20}a$; or $OC(O)N(R^{20}R^{20a})$;

$R^{20}$, $R^{20a}$, $R^{20b}$ are independently selected from the group consisting of H; and $C_{1-6}$ alkyl, wherein $C_{1-6}$ alkyl is optionally substituted with one or more halogen, which are the same or different.

Surprisingly it was found that compounds of the invention are useful for the treatment and/or prevention of neoplastic and/or infectious diseases. Interestingly, these compounds are suitable for enhancing the cytokine level secreted by stimulated immune cells and thereby increase the local activity of immune cells in proximity to said stimulated immune cells. With regard to formula (I) it was surprisingly found that it is advantageous for activity if both nitrogen, the amine nitrogen —NH($R^{18}$) as well as the amine of the amide function —C(O)NH($R^3$), bear a hydrogen.

In example 6 of WO 03/031376 A1 an intermediate is described of the following formula:

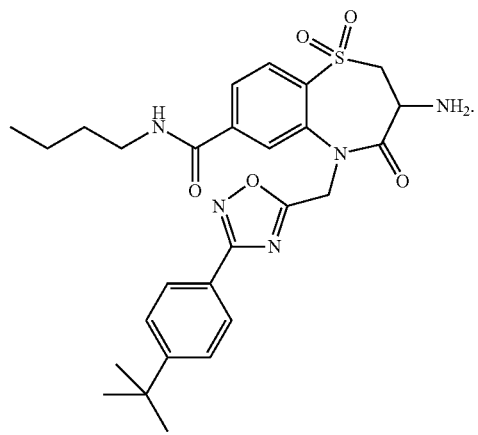 [SMILES: CCCCNC(=O)c1ccc2c(c1)N(Cc1nc(-c3ccc(C(C)(C)C)cc3)no1)C(=O)C(N)CS2(=O)=O]

Accordingly said compound or a pharmaceutical acceptable salt thereof may be excluded from the scope of the present invention.

In example 8 of WO 03/031376 A1 several lists of various starting materials are described and multiple selections of said lists are required in order to end up with compounds of formula (I) of the present invention. Accordingly the following compounds or pharmaceutically acceptable salts thereof may be excluded from the scope of the present invention:

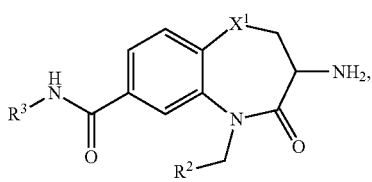

wherein $X^1$ has the meaning as indicated herein;
$R^2$ is phenyl; 3-chlorophenyl; 4-fluorophenyl; 4-methoxyphenyl; 3,5-dimethyl-1,2-oxazol-4-yl; 2-chlorothiophen-5-yl; pyridin-4-yl; 1,3-benzodioxol-5-yl; 5-phenyl-1,2,4-oxadiazol-3-yl; 3-(4-tert butylphenyl)-1,2,4-oxadiazol-5-yl; biphen-4-yl; or 3,4,5-trimethoxyphenyl;
$R^3$ is n-butyl; 2-hydroxy-1-hydroxycarbonyl-ethyl; 2-hydroxycarbonylethyl; phenyl; or benzyl;
or

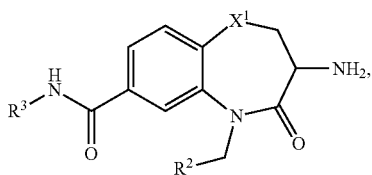

wherein $X^1$ and $R^2$ have the meaning as indicated herein;
$R^3$ is n-butyl; 2-hydroxy-1-hydroxycarbonyl-ethyl; 2-hydroxycarbonylethyl; phenyl; or benzyl.

In a preferred embodiment of the present invention, these compounds or pharmaceutically acceptable salts thereof are excluded from the scope of the present invention.

As these compounds or pharmaceutically salts thereof do not relate to any pharmaceutical use, these are preferably only excluded from the scope of the present invention insofar compounds and their pharmaceutically acceptable salts as such are concerned. However in a less preferred embodiment these compounds and pharmaceutically acceptable salts thereof are also excluded insofar their use as medicament or in methods of treatment or for the production of activated immune cells or pharmaceutical compositions of the present invention are concerned.

With regard to formula (I) in case a variable or substituent can be selected from a group of different variants and such variable or substituent occurs more than once the respective variants can be the same or different.

Within the meaning of the present invention the terms are used as follows:

The term "optionally substituted" means unsubstituted or substituted. Generally—but not limited to—, "one or more substituents" means one, two or three, preferably one or two substituents and more preferably one substituent. Generally these substituents can be the same or different.

"Alkyl" means a straight-chain or branched hydrocarbon chain. Each hydrogen of an alkyl carbon may be replaced by a substituent as further specified herein.

"Alkenyl" means a straight-chain or branched hydrocarbon chain that contains at least one carbon-carbon double bond. Each hydrogen of an alkenyl carbon may be replaced by a substituent as further specified herein.

"Alkynyl" means a straight-chain or branched hydrocarbon chain that contains at least one carbon-carbon triple bond. Each hydrogen of an alkynyl carbon may be replaced by a substituent as further specified herein.

"$C_{1-3}$ alkyl" means an alkyl chain having 1-3 carbon atoms, e.g. if present at the end of a molecule: methyl, ethyl, n-propyl, isopropyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-3}$ alkyl carbon may be replaced by a substituent as further specified herein.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent as further specified herein.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent as further specified herein. The term "$C_{1-12}$ alkyl" is defined accordingly.

"$C_{2-6}$ alkenyl" means an alkenyl chain having 2 to 6 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-6}$ alkenyl carbon may be replaced by a substituent as further specified herein. The term "$C_{2-12}$ alkenyl" is defined accordingly.

"$C_{2-6}$ alkynyl" means an alkynyl chain having 2 to 6 carbon atoms, e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-6}$ alkynyl carbon may be replaced by a substituent as further specified herein. The term "$C_{2-12}$ alkynyl" is defined accordingly.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cycloalkyl refers to cyclopropyl, cyclobutyl, cyclopentyl, cyclohexyl, or cycloheptyl. Each hydrogen of a cycloalkyl carbon may be replaced by a substituent as further specified herein.

"Halogen" means fluoro, chloro, bromo or iodo. It is generally preferred that halogen is fluoro or chloro.

"3 to 7 membered heterocyclyl" or "3 to 7 membered heterocycle" means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3 to 7 membered heterocycles are aziridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole, pyridine, pyrimidine, pyridazine, pyrazine, triazine.

"5 membered aromatic heterocyclyl" or "5 membered aromatic heterocycle" means a heterocycle derived from cyclopentadienyl, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 7 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 11 membered heterobicycle also includes spiro structures of two rings like 2-oxaspiro[3.3]heptane, 6-oxa-2-azaspiro[3,4]octane, 2-oxa-6-azaspiro[3.3]heptan-6-yl or 2,6-diazaspiro[3.3]heptan-6-yl or bridged heterocycles like 8-azabicyclo[3.2.1]octane or 2,5-diazabicyclo[2.2.2]octan-2-yl or 3,8-diazabicyclo[3.2.1]octane.

"9 to 11 membered aromatic heterobicyclyl" or "9 to 11 membered aromatic heterobicycle" means a heterocyclic system of two rings, wherein at least one ring is aromatic and wherein the heterocyclic ring system has 9 to 11 ring atoms, where two ring atoms are shared by both rings and that may contain up to the maximum number of double bonds (fully or partially aromatic) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered aromatic heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, tetrahydroquinoline, isoquinoline, tetrahydroisoquinoline, dihydroisoquinoline, benzazepine, purine or pteridine.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios unless specifically indicated, and their pharmaceutically acceptable salts.

In preferred embodiments of the present invention, the substituents mentioned below independently have the following meaning. Hence, one or more of these substituents can have the preferred or more preferred meanings given below.

Preferably $R^{18}$ is H.
Preferably $X^1$ is $S(O)_2$.
Preferably $R^1$ is H.
Preferably $X^2$ is $C(R^4)$.
Preferably $R^4$ is H; F; or $N(CH_3)_2$. More preferably $R^4$ is H; or F.

Preferably $R^2$ is phenyl, 5 to 6 membered aromatic heterocyclyl, or 9 to 11 membered aromatic heterobicyclyl; more preferably phenyl, pyridyl, thiadiazolyl, or quinolinyl; even more preferably phenyl, or pyridyl; even more preferably phenyl, wherein $R^2$ is optionally substituted with one or two $R^5$, which are the same or different.

Preferably, $R^2$ is substituted with one or two $R^5$, which are the same or different.

Preferably $T^1$ is cyclopropyl; or 3 to 7 membered heterocyclyl (more preferably 3 to 7 membered heterocyclyl), wherein $T^1$ is unsubstituted or substituted with unsubstituted $C_{1-6}$ alkyl.

Preferably $R^5$ is halogen; CN; $OR^6$; $C(O)N(R^6R^{6a})$; $T^1$; or $C_{1-6}$ alkyl, wherein $C_{1-6}$ alkyl is optionally substituted with one or more halogen, which are the same or different. More preferably $R^5$ is F; Cl; Br; CN; $OCH_3$; $OCHF_2$; $OCF_3$; $C(O)NH_2$; 1H-1,2,4-triazol-1-yl; cyclopropyl; 5-methyl-1,2,4-oxadiazol-3-yl; 1,2,3-thiadiazol-4-yl; morpholin-4-yl; tert-butyl; or $CF_3$. Even more preferably $R^5$ is F; Cl; CN; $OCF_3$; $C(O)NH_2$; 1H-1,2,4-triazol-1-yl; cyclopropyl; 5-methyl-1,2,4-oxadiazol-3-yl; 1,2,3-thiadiazol-4-yl; morpholin-4-yl; tert-butyl; or $CF_3$.

Preferably $R^2$ in formula (I) is selected to give formula (IIaa) or (IIab)

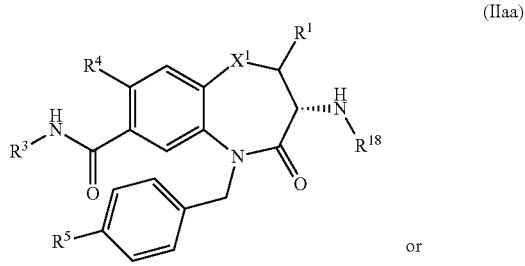

(IIaa)

or

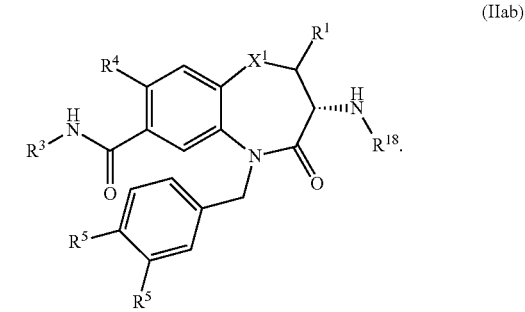

(IIab)

Preferably $R^{3a}$ is $T^2$; $C_{1-12}$ alkyl; unsubstituted $C_{2-12}$ alkenyl; or unsubstituted $C_{2-12}$ alkynyl, wherein $C_{1-12}$ alkyl is optionally substituted with one, two or three $R^9$, which are the same or different. More preferably $R^{3a}$ is $T^2$; $C_{1-12}$ alkyl; or $C_{2-12}$ alkenyl, wherein $C_{1-12}$ alkyl is optionally substituted with one, two or three $R^9$, which are the same or different. Even more preferably $R^{3a}$ is $T^2$; $CH_2T^2$; $CH_2CH_2T^2$; $C(CH_3)T^2$; unsubstituted $C_{1-12}$ alkyl; unsubstituted $C_{2-12}$ alkenyl; $C_{1-12}$ alkyl which is substituted with $OR^{10}$; $N(R^{10})C(O)R^{10a}$; $C_{1-12}$ alkyl; or $CF_3$.

Preferably $T^2$ is phenyl; $C_{3-7}$ cycloalkyl; or 3 to 7 membered heterocyclyl, wherein $T^2$ is optionally substituted with one or more $R^{12}$, which are the same or different.

Preferably $T^2$ is unsubstituted or substituted with one or two $R^{12}$, which are the same or different.

Preferably $R^{12}$ is halogen; $OR^{13}$; unsubstituted $T^3$; $T^3$ which is substituted with unsubstituted $C_{1-6}$ alkyl; or unsubstituted $C_{1-6}$ alkyl.

Compounds of the formula (I) in which some or all of the above-mentioned groups have the preferred or more preferred meanings are also an object of the present invention.

Preferred specific compounds or pharmaceutical acceptable salts thereof of the present invention are selected from the group consisting of (3R)-3-amino-5-[(4-chlorophenyl)methyl]-N-(2,2-difluorocyclopropyl)-8-fluoro-1,1,4-trioxo-2,3,4,5-tetrahydro-1λ⁶,5-benzothiazepine-7-carboxamide;

(3R)-3-amino-N-butyl-5-[(4-tert-butylphenyl)methyl]-4-oxo-2,3,4,5-tetrahydro-1,5-benzothiazepine-7-carboxamide;

(3R)-3-amino-N-butyl-4-oxo-5-{[4-(trifluoromethoxy)phenyl]methyl}-2,3,4,5-tetrahydro-1,5-benzothiazepine-7-carboxamide;

(3R)-3-amino-5-[(4-tert-butylphenyl)methyl]-4-oxo-N-(propan-2-yl)-2,3,4,5-tetrahydro-1,5-benzothiazepine-7-carboxamide;

(3R)-3-amino-N-butyl-8-fluoro-4-oxo-5-{[4-(trifluoromethoxy)phenyl]methyl}-2,3,4,5-tetrahydro-1,5-benzothiazepine-7-carboxamide;

(3R)-3-amino-N-benzyl-4-oxo-5-{[4-(trifluoromethoxy)phenyl]methyl}-2,3,4,5-tetrahydro-1,5-benzothiazepine-7-carboxamide;

(3R)-3-amino-N-[(4-methoxyphenyl)methyl]-4-oxo-5-{[4-(trifluoromethoxy)-phenyl]methyl}-2,3,4,5-tetrahydro-1,5-benzothiazepine-7-carboxamide;

(3R)-3-amino-N-(oxan-4-yl)-4-oxo-5-{[4-(trifluoromethoxy)phenyl]methyl}-2,3,4,5-tetrahydro-1,5-benzothiazepine-7-carboxamide;

(3R)-3-amino-N-butyl-4-oxo-5-{[3-(trifluoromethoxy)phenyl]methyl}-2,3,4,5-tetrahydro-1,5-benzothiazepine-7-carboxamide;

(3R)-3-amino-N-butyl-5-[(4-chlorophenyl)methyl]-4-oxo-2,3,4,5-tetrahydro-1,5-benzothiazepine-7-carboxamide;

(3R)-3-amino-N-{[4-(morpholin-4-yl)phenyl]methyl}-4-oxo-5-{[4-(trifluoromethoxy)-phenyl]methyl}-2,3,4,5-tetrahydro-1,5-benzothiazepine-7-carboxamide;

N-(3-{[(3R)-3-amino-4-oxo-5-{[4-(trifluoromethoxy)phenyl]methyl}-2,3,4,5-tetrahydro-1,5-benzothiazepin-7-yl]formamido}propyl)-2,2-dimethylpropanamide;

(3R)-3-amino-N-butyl-5-{[4-(morpholin-4-yl)phenyl]methyl}-4-oxo-2,3,4,5-tetrahydro-1,5-benzothiazepine-7-carboxamide;

(3R)-3-amino-8-fluoro-N-(oxan-4-yl)-4-oxo-5-{[4-(trifluoromethoxy)phenyl]methyl}-2,3,4,5-tetrahydro-1,5-benzothiazepine-7-carboxamide;

(3R)-3-amino-8-fluoro-4-oxo-N-(propan-2-yl)-5-{[4-(trifluoromethoxy)phenyl]-methyl}-2,3,4,5-tetrahydro-1,5-benzothiazepine-7-carboxamide;

(3R)-3-amino-N-benzyl-8-fluoro-4-oxo-5-{[4-(trifluoromethoxy)phenyl]methyl}-2,3,4,5-tetrahydro-1,5-benzothiazepine-7-carboxamide;

(3R)-3-amino-N-methyl-4-oxo-5-{[4-(trifluoromethoxy)phenyl]methyl}-2,3,4,5-tetrahydro-1,5-benzothiazepine-7-carboxamide;

(3R)-3-amino-N-ethyl-4-oxo-5-{[4-(trifluoromethoxy)phenyl]methyl}-2,3,4,5-tetrahydro-1,5-benzothiazepine-7-carboxamide;

(3R)-3-amino-N-({4-[(5-acetamidopentyl)oxy]phenyl}methyl)-4-oxo-5-{[4-(trifluoromethoxy)phenyl]methyl}-2,3,4,5-tetrahydro-1,5-benzothiazepine-7-carboxamide;

(3R)-3-amino-5-[(4-chlorophenyl)methyl]-N-(2-methoxyethyl)-4-oxo-2,3,4,5-tetrahydro-1,5-benzothiazepine-7-carboxamide;

(3R)-3-amino-N-butyl-5-[(4-cyanophenyl)methyl]-4-oxo-2,3,4,5-tetrahydro-1,5-benzothiazepine-7-carboxamide;

(3R)-3-amino-5-[(4-chlorophenyl)methyl]-4-oxo-N-(4,4,4-trifluorobutyl)-2,3,4,5-tetrahydro-1,5-benzothiazepine-7-carboxamide;

(3R)-3-amino-5-[(4-chlorophenyl)methyl]-N-(oxan-4-ylmethyl)-4-oxo-2,3,4,5-tetrahydro-1,5-benzothiazepine-7-carboxamide;

(3R)-3-amino-N-(5-tert-butyl-1,2-oxazol-3-yl)-5-[(4-chlorophenyl)methyl]-4-oxo-2,3,4,5-tetrahydro-1,5-benzothiazepine-7-carboxamide;

(3R)-3-amino-4-oxo-N-(pyridin-3-yl)-5-{[4-(trifluoromethoxy)phenyl]methyl}-2,3,4,5-tetrahydro-1,5-benzothiazepine-7-carboxamide;

(3R)-3-amino-5-[(4-chlorophenyl)methyl]-N-[(4-fluorophenyl)methyl]-4-oxo-2,3,4,5-tetrahydro-1,5-benzothiazepine-7-carboxamide;

(3R)-3-amino-5-[(4-chlorophenyl)methyl]-N-[(1R)-1-(4-methoxyphenyl)ethyl]-4-oxo-2,3,4,5-tetrahydro-1,5-benzothiazepine-7-carboxamide;

(3R)-3-amino-5-[(4-chlorophenyl)methyl]-N-(oxan-3-ylmethyl)-4-oxo-2,3,4,5-tetrahydro-1,5-benzothiazepine-7-carboxamide;

(3R)-3-amino-4-oxo-N-(4,4,4-trifluorobutyl)-5-{[4-(trifluoromethoxy)phenyl]methyl}-2,3,4,5-tetrahydro-1,5-benzothiazepine-7-carboxamide;

(3R)-3-amino-N-(oxan-4-ylmethyl)-4-oxo-5-{[4-(trifluoromethoxy)phenyl]methyl}-2,3,4,5-tetrahydro-1,5-benzothiazepine-7-carboxamide;

(3R)-3-amino-N-[(4-fluorophenyl)methyl]-4-oxo-5-{[4-(trifluoromethoxy)phenyl]-methyl}-2,3,4,5-tetrahydro-1,5-benzothiazepine-7-carboxamide;

(3R)-3-amino-N-[(4-fluorophenyl)methyl]-4-oxo-5-{[4-(1,2,3-thiadiazol-4-yl)phenyl]-methyl}-2,3,4,5-tetrahydro-1,5-benzothiazepine-7-carboxamide;

(3R)-3-amino-5-[(4-chlorophenyl)methyl]-N-(4,4-difluorocyclohexyl)-4-oxo-2,3,4,5-tetrahydro-1,5-benzothiazepine-7-carboxamide;

(3R)-3-amino-5-[(4-chlorophenyl)methyl]-N-[1-(4-fluorophenyl)ethyl]-4-oxo-2,3,4,5-tetrahydro-1,5-benzothiazepine-7-carboxamide;

(3R)-3-amino-5-[(4-chlorophenyl)methyl]-N-[(1S)-1-(4-methoxyphenyl)ethyl]-4-oxo-2,3,4,5-tetrahydro-1,5-benzothiazepine-7-carboxamide;

(3R)-3-amino-4-oxo-N-(4,4,4-trifluorobutyl)-5-{[6-(trifluoromethyl)pyridin-3-yl]methyl}-2,3,4,5-tetrahydro-1,5-benzothiazepine-7-carboxamide;

(3R)-3-amino-N-[(4-fluorophenyl)methyl]-4-oxo-5-{[6-(trifluoromethyl)pyridin-3-yl]methyl}-2,3,4,5-tetrahydro-1,5-benzothiazepine-7-carboxamide;

(3R)-3-amino-5-[(4-chlorophenyl)methyl]-N-[(1R)-1-(4-fluorophenyl)ethyl]-4-oxo-2,3,4,5-tetrahydro-1,5-benzothiazepine-7-carboxamide;

(3R)-3-amino-5-[(4-chlorophenyl)methyl]-8-fluoro-N-[(4-fluorophenyl)methyl]-4-oxo-2,3,4,5-tetrahydro-1,5-benzothiazepine-7-carboxamide;

(3R)-3-amino-5-[(4-chlorophenyl)methyl]-8-fluoro-4-oxo-N-(4,4,4-trifluorobutyl)-2,3,4,5-tetrahydro-1,5-benzothiazepine-7-carboxamide;

(3R)-3-amino-N-butyl-5-[(4-chlorophenyl)methyl]-8-fluoro-4-oxo-2,3,4,5-tetrahydro-1,5-benzothiazepine-7-carboxamide;

(3R)-3-amino-5-[(4-chlorophenyl)methyl]-8-fluoro-N-(oxan-4-ylmethyl)-4-oxo-2,3,4,5-tetrahydro-1,5-benzothiazepine-7-carboxamide;

(3R)-3-amino-5-[(4-chlorophenyl)methyl]-8-fluoro-N-[(4-methoxyphenyl)methyl]-4-oxo-2,3,4,5-tetrahydro-1,5-benzothiazepine-7-carboxamide;

(3R)-3-amino-5-{[4-(5-methyl-1,2,4-oxadiazol-3-yl)phenyl]methyl}-N-(oxan-4-ylmethyl)-4-oxo-2,3,4,5-tetrahydro-1,5-benzothiazepine-7-carboxamide;

(3R)-3-amino-5-[(4-fluorophenyl)methyl]-N-(oxan-4-ylmethyl)-4-oxo-2,3,4,5-tetrahydro-1,5-benzothiazepine-7-carboxamide;

(3R)-3-amino-N-butyl-4-oxo-5-{[4-(1H-1,2,4-triazol-1-yl)phenyl]methyl}-2,3,4,5-tetrahydro-1,5-benzothiazepine-7-carboxamide;

(3R)-3-amino-N-butyl-5-[(4-carbamoylphenyl)methyl]-4-oxo-2,3,4,5-tetrahydro-1,5-benzothiazepine-7-carboxamide;

(3R)-3-amino-5-[(4-chlorophenyl)methyl]-N-(2-hydroxy-2-methyl propyl)-4-oxo-2,3,4,5-tetrahydro-1,5-benzothiazepine-7-carboxamide;

(3R)-3-amino-5-[(4-chlorophenyl)methyl]-N-[(1S)-1-(4-fluorophenyl)ethyl]-4-oxo-2,3,4,5-tetrahydro-1,5-benzothiazepine-7-carboxamide;

(3R)-3-amino-5-[(4-chlorophenyl)methyl]-8-fluoro-N-(2-hydroxy-2-methylpropyl)-4-oxo-2,3,4,5-tetrahydro-1,5-benzothiazepine-7-carboxamide;

(2R,3R)-3-amino-5-[(4-chlorophenyl)methyl]-2-methyl-4-oxo-N-(4,4,4-trifluorobutyl)-2,3,4,5-tetrahydro-1,5-benzothiazepine-7-carboxamide;

(3R)-3-amino-5-[(4-chlorophenyl)methyl]-8-fluoro-N'-(4-fluorophenyl)-4-oxo-2,3,4,5-tetrahydro-1,5-benzothiazepine-7-carbohydrazide;

(3R)-3-amino-N-butanoyl-5-[(4-chlorophenyl)methyl]-4-oxo-2,3,4,5-tetrahydro-1,5-benzothiazepine-7-carbohydrazide;

(3R)-3-amino-N-butyl-5-[(4-chloro-2-fluorophenyl)methyl]-8-fluoro-4-oxo-2,3,4,5-tetrahydro-1,5-benzothiazepine-7-carboxamide;

(3R)-3-amino-5-[(4-chloro-2-fluorophenyl)methyl]-8-fluoro-N-(oxan-4-ylmethyl)-4-oxo-2,3,4,5-tetrahydro-1,5-benzothiazepine-7-carboxamide;

(3R)-3-amino-5-[(4-chloro-3-fluorophenyl)methyl]-8-fluoro-N-(oxan-4-ylmethyl)-4-oxo-2,3,4,5-tetrahydro-1,5-benzothiazepine-7-carboxamide;

(3R)-3-amino-N-butyl-5-[(4-chloro-3-fluorophenyl)methyl]-8-fluoro-4-oxo-2,3,4,5-tetrahydro-1,5-benzothiazepine-7-carboxamide;

(3R)-3-amino-5-[(4-chlorophenyl)methyl]-8-fluoro-4-oxo-N-propoxy-2,3,4,5-tetrahydro-1,5-benzothiazepine-7-carboxamide;

(3R)-3-amino-5-[(4-chlorophenyl)methyl]-8-fluoro-N-(2-methylpropoxy)-4-oxo-2,3,4,5-tetrahydro-1,5-benzothiazepine-7-carboxamide;

(3R)-3-amino-5-[(4-chlorophenyl)methyl]-8-fluoro-N'-(2-methylpropyl)-4-oxo-2,3,4,5-tetrahydro-1,5-benzothiazepine-7-carbohydrazide;

(3R)-3-amino-5-[(4-chlorophenyl)methyl]-4-oxo-N-(propan-2-yl)-2,3,4,5-tetrahydro-1,5-benzothiazepine-7-carboxamide;

(3R)-3-amino-5-[(4-chlorophenyl)methyl]-N-(2-methylpropoxy)-4-oxo-2,3,4,5-tetrahydro-1,5-benzothiazepine-7-carboxamide;

(3R)-3-amino-5-[(4-chlorophenyl)methyl]-N-(3-methylbutan-2-yl)-4-oxo-2,3,4,5-tetrahydro-1,5-benzothiazepine-7-carboxamide;

(3R)-3-amino-N-(but-3-en-1-yl)-5-[(4-chlorophenyl)methyl]-4-oxo-2,3,4,5-tetrahydro-1,5-benzothiazepine-7-carboxamide;

(3R)-3-amino-5-[(4-chlorophenyl)methyl]-N'-(2-methylpropyl)-4-oxo-2,3,4,5-tetrahydro-1,5-benzothiazepine-7-carbohydrazide;

(3R)-3-amino-N-butyl-5-[(4-chlorophenyl)methyl]-1,4-dioxo-2,3,4,5-tetrahydro-1$\lambda^4$,5-benzothiazepine-7-carboxamide;

(3R)-3-amino-N-butyl-1,1,4-trioxo-5-{[4-(trifluoromethoxy)phenyl]methyl}-2,3,4,5-tetrahydro-1$\lambda^6$,5-benzothiazepine-7-carboxamide;

(3R)-3-amino-5-[(4-chlorophenyl)methyl]-8-fluoro-N-[(4-fluorophenyl)methyl]-1,1,4-trioxo-2,3,4,5-tetrahydro-1$\lambda^6$,5-benzothiazepine-7-carboxamide;

(3R)-3-amino-N-butyl-5-[(4-chlorophenyl)methyl]-8-fluoro-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-1,1,4-trioxo-N-(4,4,4-trifluoro-butyl)-2,3,4,5-tetrahydro-1$\lambda^6$,5-benzothiazepine-7-carboxamide;

(3R)-3-amino-5-[(4-chlorophenyl)methyl]-8-fluoro-N-(oxan-4-ylmethyl)-1,1,4-trioxo-2,3,4,5-tetrahydro-1$\lambda^6$,5-benzothiazepine-7-carboxamide;

(3R)-3-amino-8-fluoro-N-(oxan-4-ylmethyl)-1,1,4-trioxo-5-{[4-(trifluoromethoxy)-phenyl]methyl}-2,3,4,5-tetrahydro-1$\lambda^6$,5-benzothiazepine-7-carboxamide;

(3R)-3-amino-8-fluoro-1,1,4-trioxo-N-(4,4,4-trifluorobutyl)-5-{[4-(trifluoromethoxy)-phenyl]methyl}-2,3,4,5-tetrahydro-1$\lambda^6$,5-benzothiazepine-7-carboxamide;

(3R)-3-amino-8-fluoro-1,1,4-trioxo-N-phenoxy-5-{[4-(trifluoromethoxy)phenyl]methyl}-2,3,4,5-tetrahydro-1$\lambda^6$,5-benzothiazepine-7-carboxamide;

(3R)-3-amino-5-[(4-chlorophenyl)methyl]-8-fluoro-N-(2-methylpropoxy)-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-1,1,4-trioxo-N-phenoxy-2,3,4,5-tetrahydro-1$\lambda^6$,5-benzothiazepine-7-carboxamide;

(3R)-3-amino-5-[(4-chlorophenyl)methyl]-8-fluoro-1,1,4-trioxo-N-(propan-2-yl)-2,3,4,5-tetrahydro-1$\lambda^6$,5-benzothiazepine-7-carboxamide;

(3R)-3-amino-5-[(4-chlorophenyl)methyl]-N-({4-[(5-acetamidopentyl)oxy]phenyl}-methyl)-1,1,4-trioxo-2,3,4,5-tetrahydro-1$\lambda^6$,5-benzothiazepine-7-carboxamide;

(3R)-3-amino-5-[(4-chlorophenyl)methyl]-1,1,4-trioxo-N-(propan-2-yl)-2,3,4,5-tetrahydro-1$\lambda^6$,5-benzothiazepine-7-carboxamide;

(3R)-3-amino-5-[(4-chlorophenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-5-[(4-chlorophenyl)methyl]-N-(2-methyl propoxy)-1,1,4-trioxo-2,3,4,5-tetrahydro-1λ⁶,5-benzothiazepine-7-carboxamide;
(3R)-3-amino-5-[(4-chlorophenyl)methyl]-1,1,4-trioxo-N-propoxy-2,3,4,5-tetrahydro-1λ⁶,5-benzothiazepine-7-carboxamide;
(3R)-3-amino-5-[(4-chlorophenyl)methyl]-N-(3-methyl butan-2-yl)-1,1,4-trioxo-2,3,4,5-tetrahydro-1λ⁶,5-benzothiazepine-7-carboxamide;
(3R)-3-amino-N-(but-3-en-1-yl)-5-[(4-chlorophenyl) methyl]-1,1,4-trioxo-2,3,4,5-tetrahydro-1λ⁶,5-benzothiazepine-7-carboxamide;
(3R)-3-amino-5-[(4-chlorophenyl)methyl]-N-cyclopropyl-8-fluoro-1,1,4-trioxo-2,3,4,5-tetrahydro-1λ⁶,5-benzothiazepine-7-carboxamide;
(3R)-3-amino-5-[(4-chlorophenyl)methyl]-N-cyclobutyl-8-fluoro-1,1,4-trioxo-2,3,4,5-tetrahydro-1λ⁶,5-benzothiazepine-7-carboxamide;
(3R)-3-amino-5-[(4-chloro-2-fluorophenyl)methyl]-8-fluoro-1,1,4-trioxo-N-(propan-2-yl)-2,3,4,5-tetrahydro-1λ⁶,5-benzothiazepine-7-carboxamide;
(3R)-3-amino-5-[(3,4-dichlorophenyl)methyl]-1,1,4-trioxo-N-(propan-2-yl)-2,3,4,5-tetrahydro-1λ⁶,5-benzothiazepine-7-carboxamide;
(3R)-3-amino-5-[(4-chloro-3-fluorophenyl)methyl]-1,1,4-trioxo-N-(propan-2-yl)-2,3,4,5-tetrahydro-1λ⁶,5-benzothiazepine-7-carboxamide;
(3R)-3-amino-5-[(4-chlorophenyl)methyl]-N-(cyclohexyloxy)-1,1,4-trioxo-2,3,4,5-tetrahydro-1λ⁶,5-benzothiazepine-7-carboxamide;
(3R)-3-amino-5-[(4-chlorophenyl)methyl]-N-(cyclohexylmethoxy)-1,1,4-trioxo-2,3,4,5-tetrahydro-1λ⁶,5-benzothiazepine-7-carboxamide;
(3R)-3-amino-5-[(4-chlorophenyl)methyl]-8-fluoro-1,1,4-trioxo-N-(2,2,2-trifluoro-ethyl)-2,3,4,5-tetrahydro-1λ⁶,5-benzothiazepine-7-carboxamide;
(3R)-3-amino-5-[(4-chlorophenyl)methyl]-8-fluoro-1,1,4-trioxo-N-(3,3,3-trifluoro-propyl)-2,3,4,5-tetrahydro-1λ⁶,5-benzothiazepine-7-carboxamide;
(3R)-3-amino-5-[(4-chlorophenyl)methyl]-8-fluoro-1,1,4-trioxo-N-[(2S)-1,1,1-trifluoropropan-2-yl]-2,3,4,5-tetrahydro-1λ⁶,5-benzothiazepine-7-carboxamide;
(3R)-3-amino-N-(butan-2-yl)-5-[(4-chlorophenyl)methyl]-8-fluoro-1,1,4-trioxo-2,3,4,5-tetrahydro-1λ⁶,5-benzothiazepine-7-carboxamide;
(3R)-3-amino-N-tert-butyl-5-[(4-chlorophenyl)methyl]-8-fluoro-1,1,4-trioxo-2,3,4,5-tetrahydro-1λ⁶,5-benzothiazepine-7-carboxamide;
(3R)-3-amino-N-(tert-butoxy)-5-[(4-chlorophenyl)methyl]-1,1,4-trioxo-2,3,4,5-tetrahydro-1λ⁶,5-benzothiazepine-7-carboxamide;
(3R)-3-amino-5-[(4-chlorophenyl)methyl]-8-fluoro-1,1,4-trioxo-N-[(1S,2R)-2-phenylcyclopropyl]-2,3,4,5-tetrahydro-1λ⁶,5-benzothiazepine-7-carboxamide;
(3R)-3-amino-5-[(4-chlorophenyl)methyl]-8-fluoro-N-(1-methylcyclopropyl)-1,1,4-trioxo-2,3,4,5-tetrahydro-1λ⁶,5-benzothiazepine-7-carboxamide;
(3R)-3-amino-5-[(4-chlorophenyl)methyl]-8-fluoro-N-(1-methylcyclobutyl)-1,1,4-trioxo-2,3,4,5-tetrahydro-1λ⁶,5-benzothiazepine-7-carboxamide;
(3R)-3-amino-5-[(4-chlorophenyl)methyl]-N-(2,2-dimethylcyclopropyl)-8-fluoro-1,1,4-trioxo-2,3,4,5-tetrahydro-1λ⁶,5-benzothiazepine-7-carboxamide;
(3R)-3-amino-5-[(4-chlorophenyl)methyl]-N-(3,3-difluorocyclobutyl)-8-fluoro-1,1,4-trioxo-2,3,4,5-tetrahydro-1λ⁶,5-benzothiazepine-7-carboxamide;
(3R)-3-amino-N-benzyl-5-[(4-chlorophenyl)methyl]-8-fluoro-1,1,4-trioxo-2,3,4,5-tetrahydro-1λ⁶,5-benzothiazepine-7-carboxamide;
(3R)-3-amino-5-[(4-chlorophenyl)methyl]-8-fluoro-N-heptyl-1,1,4-trioxo-2,3,4,5-tetrahydro-1λ⁶,5-benzothiazepine-7-carboxamide;
(3R)-3-amino-5-[(4-chlorophenyl)methyl]-N-(3,3-difluorocyclopentyl)-8-fluoro-1,1,4-trioxo-2,3,4,5-tetrahydro-1λ⁶,5-benzothiazepine-7-carboxamide;
(3R)-3-amino-5-[(4-chlorophenyl)methyl]-N-[(1R)-2,2-difluorocyclopropyl]-8-fluoro-1,1,4-trioxo-2,3,4,5-tetrahydro-1λ⁶,5-benzothiazepine-7-carboxamide;
(3R)-3-amino-5-[(4-chlorophenyl)methyl]-N-[(1S)-2,2-difluorocyclopropyl]-8-fluoro-1,1,4-trioxo-2,3,4,5-tetrahydro-1λ⁶,5-benzothiazepine-7-carboxamide;
(2R,3R)-3-amino-5-[(4-chlorophenyl)methyl]-N-(2,2-difluorocyclopropyl)-2-methyl-1,1,4-trioxo-2,3,4,5-tetrahydro-1λ⁶,5-benzothiazepine-7-carboxamide;
(3R)-3-amino-5-[(4-chlorophenyl)methyl]-8-fluoro-N-hexadecyl-1,1,4-trioxo-2,3,4,5-tetrahydro-1λ⁶,5-benzothiazepine-7-carboxamide;
(3R)-3-amino-5-[(4-chlorophenyl)methyl]-N-(cyclopropylmethyl)-8-fluoro-1,1,4-trioxo-2,3,4,5-tetrahydro-1λ⁶,5-benzothiazepine-7-carboxamide;
(2R,3R)-3-amino-5-[(4-chlorophenyl)methyl]-2-methyl-1,1,4-trioxo-N-(4,4,4-trifluorobutyl)-2,3,4,5-tetrahydro-1λ⁶,5-benzothiazepine-7-carboxamide;
(3R)-3-amino-N-butyl-8-fluoro-4-oxo-5-(quinolin-2-ylmethyl)-2,3,4,5-tetrahydro-1,5-benzothiazepine-7-carboxamide;
(3R)-3-amino-5-[(5-cyclopropyl-1,3,4-thiadiazol-2-yl) methyl]-8-fluoro-N-[(4-fluorophenyl)methyl]-4-oxo-2,3,4,5-tetrahydro-1,5-benzothiazepine-7-carboxamide;
(3R)-3-amino-N-butyl-5-[(4-chlorophenyl)methyl]-8-(dimethylamino)-1,1,4-trioxo-2,3,4,5-tetrahydro-1λ⁶,5-benzothiazepine-7-carboxamide;
tert-butyl N-(5-{[(3R)-5-[(4-chlorophenyl)methyl]-8-fluoro-7-{[(4-methoxyphenyl)methyl]carbamoyl}-4-oxo-2,3,4,5-tetrahydro-1,5-benzothiazepin-3-yl] amino}pentyl)carbamate; and
(3R)-3-amino-N-butyl-1-[(4-chlorophenyl)methyl]-2,5,5-trioxo-1H,2H,3H,4H-5λ⁶-pyrido[3,4-b][1,4]thiazepine-8-carboxamide.

Further preferred specific compounds or pharmaceutical acceptable salts thereof of the present invention are selected from the group consisting of
(3R)-3-amino-N-benzyl-5-[(4-chlorophenyl)methyl]-8-(dimethylamino)-1,1,4-trioxo-2,3,4,5-tetrahydro-1λ⁶,5-benzothiazepine-7-carboxamide;
(3R)-3-amino-N-(2,2-difluorocyclopropyl)-8-fluoro-5-{[4-methoxy-3-(trifluoromethyl)phenyl]methyl}-1,1,4-trioxo-2,3,4,5-tetrahydro-1λ⁶,5-benzothiazepine-7-carboxamide;
(2R,3R)-3-amino-5-[(4-chlorophenyl)methyl]-8-fluoro-2-methyl-1,1,4-trioxo-N-(4,4,4-trifluorobutyl)-2,3,4,5-tetrahydro-1λ⁶,5-benzothiazepine-7-carboxamide;
(3R)-3-amino-5-{[4-(5-methyl-1,2,4-oxadiazol-3-yl)phenyl]methyl}-1,1,4-trioxo-N-(4,4,4-trifluorobutyl)-2,3,4,5-tetrahydro-1λ⁶,5-benzothiazepine-7-carboxamide;
(3R)-3-amino-5-[(4-chlorophenyl)methyl]-8-fluoro-N-(2-methoxyethyl)-1,1,4-trioxo-2,3,4,5-tetrahydro-1λ⁶,5-benzothiazepine-7-carboxamide;
(3R)-3-amino-N-(2,2-difluorocyclopropyl)-5-{[4-(5-methyl-1,2,4-oxadiazol-3-yl)phenyl]methyl}-1,1,4-trioxo-2,3,4,5-tetrahydro-1λ⁶,5-benzothiazepine-7-carboxamide;

(1S,3R)-3-amino-5-[(4-chlorophenyl)methyl]-8-fluoro-4-oxo-7-[(4,4,4-trifluorobutyl)carbamoyl]-2,3,4,5-tetrahydro-1H-1,5-benzothiazepin-1-ium-1-olate;

(1R,3R)-3-amino-5-[(4-chlorophenyl)methyl]-8-fluoro-4-oxo-7-[(4,4,4-trifluorobutyl)carbamoyl]-2,3,4,5-tetrahydro-1H-1,5-benzothiazepin-1-ium-1-olate;

(3R)-3-amino-5-[(4-cyanophenyl)methyl]-N-(2,2-difluorocyclopropyl)-8-fluoro-1,1,4-trioxo-2,3,4,5-tetrahydro-1$\lambda^6$,5-benzothiazepine-7-carboxamide;

(3R)-3-amino-5-[(4-cyanophenyl)methyl]-8-fluoro-1,1,4-trioxo-N-(4,4,4-trifluorobutyl)-2,3,4,5-tetrahydro-1$\lambda^6$,5-benzothiazepine-7-carboxamide;

(3R)-3-amino-5-[(4-chlorophenyl)methyl]-N-(4,4-difluorocyclohexyl)-8-fluoro-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-1,1,4-trioxo-N-[2-(trifluoromethyl)cyclopropyl]-2,3,4,5-tetrahydro-1$\lambda^6$,5-benzothiazepine-7-carboxamide;

(3R)-3-amino-5-[(4-chlorophenyl)methyl]-N-(3,3-difluorocyclobutyl)-8-fluoro-4-oxo-2,3,4,5-tetrahydro-1,5-benzothiazepine-7-carboxamide;

(3R)-3-amino-8-fluoro-5-[(4-fluorophenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-N-(2,2-difluorocyclopropyl)-8-fluoro-5-[(4-fluorophenyl)methyl]-1,1,4-trioxo-2,3,4,5-tetrahydro-1$\lambda^6$,5-benzothiazepine-7-carboxamide;

(3R)-3-amino-N-butyl-8-fluoro-5-[(4-fluorophenyl)methyl]-4-oxo-2,3,4,5-tetrahydro-1,5-benzothiazepine-7-carboxamide;

(3R)-3-amino-N-benzyl-8-fluoro-5-[(4-fluorophenyl)methyl]-4-oxo-2,3,4,5-tetrahydro-1,5-benzothiazepine-7-carboxamide;

(3R)-3-amino-N-butyl-8-fluoro-5-[(4-fluorophenyl)methyl]-1,1,4-trioxo-2,3,4,5-tetrahydro-1$\lambda^6$,5-benzothiazepine-7-carboxamide;

(3R)-3-amino-N-benzyl-8-fluoro-5-[(4-fluorophenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-N-[2-(oxan-4-yl)ethyl]-1,1,4-trioxo-2,3,4,5-tetrahydro-1$\lambda^6$,5-benzothiazepine-7-carboxamide;

(3R)-3-amino-5-benzyl-8-fluoro-1,1,4-trioxo-N-(4,4,4-trifluoro butyl)-2,3,4,5-tetrahydro-1$\lambda^6$,5-benzothiazepine-7-carboxamide;

(3R)-3-amino-5-[(4-chlorophenyl)methyl]-8-fluoro-N-[(4-methoxyphenyl)methyl]-1,1,4-trioxo-2,3,4,5-tetrahydro-1$\lambda^6$,5-benzothiazepine-7-carboxamide;

(3R)-3-amino-5-[(5-cyclopropyl-1,3,4-thiadiazol-2-yl)methyl]-8-fluoro-N-[(4-fluorophenyl)methyl]-1,1,4-trioxo-2,3,4,5-tetrahydro-1$\lambda^6$,5-benzothiazepine-7-carboxamide;

(3R)-3-amino-8-fluoro-5-[(4-fluorophenyl)methyl]-N-[(oxan-4-yl)methyl]-1,1,4-trioxo-2,3,4,5-tetrahydro-1$\lambda^6$,5-benzothiazepine-7-carboxamide;

(3R)-3-amino-N-(3,3-difluorocyclobutyl)-8-fluoro-5-[(4-fluorophenyl)methyl]-1,1,4-trioxo-2,3,4,5-tetrahydro-1$\lambda^6$,5-benzothiazepine-7-carboxamide;

(3R)-3-amino-8-fluoro-5-[(4-methoxyphenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-8-fluoro-5-[(4-methoxyphenyl)methyl]-N-[(oxan-4-yl)methyl]-1,1,4-trioxo-2,3,4,5-tetrahydro-1$\lambda^6$,5-benzothiazepine-7-carboxamide;

(3R)-3-amino-N-(2,2-difluorocyclopropyl)-8-fluoro-5-[(4-methoxyphenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-N-(oxan-4-yl)-1,1,4-trioxo-2,3,4,5-tetrahydro-1$\lambda^6$,5-benzothiazepine-7-carboxamide;

(3R)-3-amino-5-[(4-chlorophenyl)methyl]-N-(3,3-difluorocyclobutyl)-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1S)-3,3-difluorocyclopentyl]-8-fluoro-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1R,2S)-2-fluorocyclopropyl]-1,1,4-trioxo-2,3,4,5-tetrahydro-1$\lambda^6$,5-benzothiazepine-7-carboxamide;

(3R)-3-amino-N-(3,3-difluorocyclobutyl)-5-[(2-fluorophenyl)methyl]-1,1,4-trioxo-2,3,4,5-tetrahydro-1$\lambda^6$,5-benzothiazepine-7-carboxamide;

(3R)-3-amino-N-(3,3-difluorocyclobutyl)-5-[(3-methoxyphenyl)methyl]-1,1,4-trioxo-2,3,4,5-tetrahydro-1$\lambda^6$,5-benzothiazepine-7-carboxamide;

(3R)-3-amino-5-[(4-methoxyphenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-N,5-bis[(4-methoxyphenyl)methyl]-1,1,4-trioxo-2,3,4,5-tetrahydro-1$\lambda^6$,5-benzothiazepine-7-carboxamide;

(3R)-3-amino-5-benzyl-N-[(4-methoxyphenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(4-methoxyphenyl)methyl]-1,1,4-trioxo-2,3,4,5-tetrahydro-1$\lambda^6$,5-benzothiazepine-7-carboxamide;

(3R)-3-amino-N-(4,4-difluorocyclohexyl)-5-[(4-methoxyphenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-1,1,4-trioxo-N-(3,3,3-trifluoropropyl)-2,3,4,5-tetrahydro-1$\lambda^6$,5-benzothiazepine-7-carboxamide;

(3R)-3-amino-5-[(4-chlorophenyl)methyl]-1,1,4-trioxo-N-[(3R)-oxolan-3-yl]-2,3,4,5-tetrahydro-1$\lambda^6$,5-benzothiazepine-7-carboxamide;

(3R)-3-amino-5-[(4-chlorophenyl)methyl]-1,1,4-trioxo-N-[(oxolan-3-yl)methyl]-2,3,4,5-tetrahydro-1$\lambda^6$,5-benzothiazepine-7-carboxamide;

(3R)-3-amino-5-[(4-chlorophenyl)methyl]-N-[(1R)-2,2-difluorocyclopropyl]-1,1,4-trioxo-2,3,4,5-tetrahydro-1$\lambda^6$,5-benzothiazepine-7-carboxamide;

(3R)-3-amino-5-[(4-cyclopropylphenyl)methyl]-N-[(1R)-2,2-difluorocyclopropyl]-1,1,4-trioxo-2,3,4,5-tetrahydro-1$\lambda^6$,5-benzothiazepine-7-carboxamide;

(3R)-3-amino-N-[(1R)-2,2-difluorocyclopropyl]-5-{[4-(difluoromethoxy)phenyl]methyl}-1,1,4-trioxo-2,3,4,5-tetrahydro-1$\lambda^6$,5-benzothiazepine-7-carboxamide;

(3R)-3-amino-N-[(1R)-2,2-difluorocyclopropyl]-5-[(4-methoxyphenyl)methyl]-1,1,4-trioxo-2,3,4,5-tetrahydro-1$\lambda^6$,5-benzothiazepine-7-carboxamide;

(3R)-3-amino-5-benzyl-1,1,4-trioxo-N-(4,4,4-trifluoro butyl)-2,3,4,5-tetrahydro-1$\lambda^6$,5-benzothiazepine-7-carboxamide;

(3R)-3-amino-8-chloro-5-[(4-chlorophenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-5-{[4-(difluoromethoxy)phenyl]methyl}-N-[(oxan-4-yl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(4-fluorooxan-4-yl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1R)-1-(oxan-4-yl)ethyl]-1,1,4-trioxo-2,3,4,5-tetrahydro-1λ⁶,5-benzothiazepine-7-carboxamide;

(3R)-3-amino-5-benzyl-N-[(1R)-2,2-difluorocyclopropyl]-1,1,4-trioxo-2,3,4,5-tetrahydro-1λ⁶,5-benzothiazepine-7-carboxamide;

(3R)-3-amino-5-[(4-chlorophenyl)methyl]-N-[(6-methylpyridin-3-yl)methyl]-1,1,4-trioxo-2,3,4,5-tetrahydro-1λ⁶,5-benzothiazepine-7-carboxamide;

(3R)-3-amino-5-[(4-chlorophenyl)methyl]-N-[(1R)-3,3-difluorocyclopentyl]-1,1,4-trioxo-2,3,4,5-tetrahydro-1λ⁶,5-benzothiazepine-7-carboxamide;

(3R)-3-amino-5-[(4-cyanophenyl)methyl]-8-fluoro-N-[(4-fluorophenyl)methyl]-1,1,4-trioxo-2,3,4,5-tetrahydro-1λ⁶,5-benzothiazepine-7-carboxamide;

(3R)-3-amino-5-[(4-chlorophenyl)methyl]-N-[(3,3-difluorocyclobutyl)methyl]-1,1,4-trioxo-2,3,4,5-tetrahydro-1λ⁶,5-benzothiazepine-7-carboxamide;

(3R)-3-amino-5-[(4-chlorophenyl)methyl]-8-fluoro-N-[2-(2-methoxyethoxy)ethyl]-1,1,4-trioxo-2,3,4,5-tetrahydro-1λ⁶,5-benzothiazepine-7-carboxamide;

(3R)-3-amino-N-(but-3-yn-1-yl)-5-[(4-chlorophenyl)methyl]-8-fluoro-1,1,4-trioxo-2,3,4,5-tetrahydro-1λ⁶,5-benzothiazepine-7-carboxamide;

(3R)-3-amino-5-[(4-chlorophenyl)methyl]-8-fluoro-1,1,4-trioxo-N-(pent-4-yn-1-yl)-2,3,4,5-tetrahydro-1λ⁶,5-benzothiazepine-7-carboxamide;

(3R)-3-amino-8-chloro-5-[(4-chlorophenyl)methyl]-N-[(1R)-2,2-difluorocyclopropyl]-1,1,4-trioxo-2,3,4,5-tetrahydro-1λ⁶,5-benzothiazepine-7-carboxamide;

(3R)-3-amino-5-[(4-chlorophenyl)methyl]-N-[2-(morpholin-4-yl)ethyl]-1,1,4-trioxo-2,3,4,5-tetrahydro-1λ⁶,5-benzothiazepine-7-carboxamide;

(3R)-3-amino-5-[(4-chlorophenyl)methyl]-N-[(6-methoxypyridin-3-yl)methyl]-1,1,4-trioxo-2,3,4,5-tetrahydro-1λ⁶,5-benzothiazepine-7-carboxamide;

(3R)-3-amino-5-[(4-chlorophenyl)methyl]-8-fluoro-1,1,4-trioxo-N-{[4-(prop-2-yn-1-yloxy)phenyl]methyl}-2,3,4,5-tetrahydro-1λ⁶,5-benzothiazepine-7-carboxamide;

(3R)-3-amino-N-[(1R)-2,2-difluorocyclopropyl]-1,1,4-trioxo-5-{[4-(trifluoromethyl)phenyl]methyl}-2,3,4,5-tetrahydro-1λ⁶,5-benzothiazepine-7-carboxamide;

(3R)-3-amino-5-[(4-bromophenyl)methyl]-N-(2,2-difluorocyclopropyl)-1,1,4-trioxo-2,3,4,5-tetrahydro-1λ⁶,5-benzothiazepine-7-carboxamide;

(3R)-3-amino-5-[(4-chlorophenyl)methyl]-N-{2-oxaspiro[3.3]heptan-6-yl}-1,1,4-trioxo-2,3,4,5-tetrahydro-1λ⁶,5-benzothiazepine-7-carboxamide; and (3R)-5-[(4-chlorophenyl)methyl]-3-(ethylamino)-8-fluoro-1,1,4-trioxo-N-(4,4,4-trifluorobutyl)-2,3,4,5-tetrahydro-1λ⁶,5-benzothiazepine-7-carboxamide.

Where tautomerism, like e.g. keto-enol tautomerism, of compounds of formula (I) may occur, the individual forms, like e.g. the keto and enol form, are comprised separately and together as mixtures in any ratio. Same applies for stereoisomers, like e.g. enantiomers, cis/trans isomers, conformers unless specifically indicated and the like.

Especially, when enantiomeric or diastereomeric forms are given in a compound according to formula (I) each pure form separately and any mixture of at least two of the pure forms in any ratio is comprised by formula (I) and is a subject of the present invention unless specifically indicated.

By way of example with regard to the amine —NH($R^{18}$) in formula (I), R- and S-form are comprised since no specific orientation is indicated. However, the R-form is preferred.

Accordingly a preferred structure of formula (I) is given by formula (IIa)

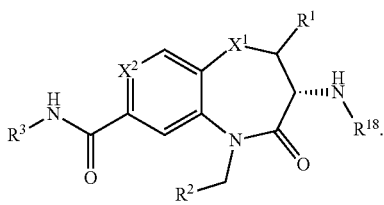

(IIa)

With regard to $R^1$ as being methyl a cis- and trans-diastereomeric form relative to the amine —NH($R^{18}$) are comprised by formula (I) since no specific orientation is indicated. However the cis-diastereomere is preferred.

Isotopic labeled compounds of formula (I) are also within the scope of the present invention. Methods for isotope labeling are known in the art. Preferred isotopes are those of the elements H, C, N, O and S. Solvates of compounds of formula (I) are also within the scope of the present invention.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

In general the compounds of the present invention are preferably used in form of a pharmaceutically acceptable salt, like in form of their hydrochlorides.

As indicated above, the present invention also refers to the use of the compound of the present invention in a pharmaceutical context. Herein, a pharmaceutical context may be understood in the broadest sense as any means for improving a patient's health status and/or wellness. The terms "pharmaceutical" and "medicinal" may be understood interchangeably.

A further aspect of the present invention refers to a pharmaceutical composition comprising at least one compound of the present invention and at least one pharmaceutically acceptable carrier.

In this aspect relating to a pharmaceutical composition, the definitions as laid out in detail above also apply mutatis mutandis.

A pharmaceutically acceptable carrier according the present invention may be any additive that is pharmaceutically acceptable, therefore, any additive that is non-toxic to the patient. Exemplarily, a pharmaceutically acceptable carrier may comprise a solvent such as, e.g., water, dimethyl sulfoxide (DMSO), ethanol, vegetable oil, paraffin oil or combinations thereof. Furthermore, a carrier may contain one or more detergent(s), one or more foaming agent(s) (e.g., sodium lauryl sulfate (SLS)/sodium doceyl sulfate (SDS)), one or more coloring agent(s) (e.g., $TiO_2$, food coloring), one or more vitamin(s), one or more salt(s) (e.g., sodium, potassium, calcium, zinc salts), one or more humectant(s) (e.g., sorbitol, glycerol, mannitol, propylene glycol, polydextrose), one or more enzyme(s), one or more preserving agent(s) (e.g., benzoic acid, methylparabene), one or more texturing agent(s) (e.g., carboxymethyl cellulose (CMC), polyethylene glycol (PEG), sorbitol), one or more emulsifier(s), one or more bulking agent(s), one or more glacing agent(s), one or more separating agent(s), one or more antioxidant(s), one or more herbal and plant extract(s), one or more stabilizing agent(s), one or more polymer(s) (e.g., hydroxypropyl methacrylamide (HPMA), polyethylene imine (PEI), carboxymethyl cellulose (CMC), polyethylene glycol (PEG)), one or more uptake mediator(s) (e.g., polyethylene imine (PEI), dimethyl sulfoxide (DMSO), a cell-penetrating peptide (CPP), a protein transduction domain (PTD), an antimicrobial peptide, etc.) one or more antibody/antibodies, one or more sweetener(s) (e.g., sucrose, acesulfame K, saccharin Na, stevia), one or more counterstain dye(s) (e.g., fluorescein, fluorescein derivatives, Cy dyes, an Alexa Fluor dye(s), S dye(s), rhodamine, quantum dot(s), etc.), one or more homeopathic ingredient(s) one or more gustatory substance(s) and/or one or more fragrance(s).

The pharmaceutical composition of the present invention comprises at least one compound of the present invention. Optionally, the pharmaceutical composition may also comprise more than one compound of the present invention such as the combination of two, three, four, five or even more compounds of the present invention.

Optionally, the pharmaceutical composition may also comprise one or more other pharmaceutically active agent(s), such as, e.g., one or more further stimulating agent(s) activating immune cells which may be other pharmaceutically active ingredients of the pharmaceutical composition other than the compounds of the present invention. Examples for such further stimulating agent(s) activating immune cells are provided below.

As already indicated above, the compound as well as the pharmaceutical composition of the present invention may be used as a medicament.

Therefore, another aspect of the present invention relates to the compound or the pharmaceutical composition of the present invention for use as a medicament.

In this aspect relating to the use as medicament, the definitions as laid out in detail above also apply mutatis mutandis.

In the context of the present invention, the terms "medicament", "therapeutic", "medicine", "drug", "therapeutic agent", "pharmaceutic", "pharmaceutical agent", "prophylactic agent" etc. may be understood in the broadest sense as any kind of compound suitable for being used in a medicinal context, i.e., for treating and/or preventing a pathological condition.

A compound or a pharmaceutical composition comprising such may be administered to the patient by any means known in the art such as, e.g, orally, via injection, nasally, transdermally/percutaneously, etc. Administration may be local administration (e.g., intratumorally, intranodally (i.e., into lymph nodes), intrathecally, intracerebroventricularly (icy), topically or intravitreally) or systemic administration (e.g., intravenously (i.v.), intraarterially (i.a.), intraperitoneally (i.p.), intramusculary (i.m.), subcutaneously (s.c.), orally, nasally). Preferably, administration is oral, intraveneous, subcutaneous, intratumoral or intranodal administration, in particular oral or intraveneous administration.

Administration may be administration once ((acute) single administration) or may be a repeated administration such as, e.g., administration of repeated pulse doses or chronic administration. Repeated administration may exemplarily be administration two times, three times, four times, five times, six times, seven times, eight times, nine times, ten times, more than ten times or even permanently. Between two administrations, there may be a time interval of less than one hour, one hour or more, six hours or more, twelve hours or more, 24 hours or more. Administration may be daily, may be twice daily, three times daily, four times daily, every second day, every three days, weekly, biweekly, monthly, twice a year or yearly. Clinically viable administration schemes may be determined by the person skilled in the art based on balancing efficacy and toxicity.

Preferably, the medicament is suitable for treating or preventing pathologic conditions associated with an insufficient immune response. In other words, the present invention also relates to a medicament suitable for increasing an immune response. As used in the context of the activity of an immune response, the terms "activating", "enhancing", "strengthening", "increasing", "triggering", "stimulating" and the like may be understood interchangeably in the broadest sense as the provision of an increased activity of an immune response.

In the context of the present invention, an increase of the immune response is preferably a local increase of the immune response, i.e., an increase of the immune response in proximity of the antigen recognized by the immune cells responsible for the respective immune response.

More specifically, the immune cells subjected to a compound of the present invention show a significantly increased secretion of several cytokines such as, e.g., IL-2, IFN-γ and/or TNF-α, whereas corresponding un-stimulated immune cells do not. This leads to a local secretion of cytokines in the proximity of the neoplasm and/or infectious pathogen improving the local immune response to said neoplasm and/or infectious pathogen. More preferably, the compounds of the present invention provide a therapeutic or prophylactic intervention that increases the local effector efficiency of anti-tumor or anti-viral T cells, B cells and NK cells. The undesired significant increase of the systemic level of the cytokine may however be widely avoided. When the antigen is exemplarily localized on the surface of neoplastic cells (e.g., maturated neoplastic cells (cancer cells)), the activity of immune cells, in particular T cells, contacted with such antigen may be increased. It has been found that upon administration of the compounds of the present invention, stimulated immune cells, in particular activated T cells contacted with their cognate antigen (e.g., a tumor and/or pathogen antigen), show increased local activation of the immune system. Therefore, the immune response in the proximity to the neoplasm is then increased. When the antigen is exemplarily localized on the surface of virus-infected cells (e.g., HIV infected cells), the activity of immune cells contacted with such antigen may be increased.

Notably, in contrast to vaccination-based strategies (e.g., tumor vaccination), for their activity, the compounds of the present invention do not necessarily require that the immune cells have been contacted with a specific tumor antigen, but stimulation of the cells can also be achieved by other means, e.g. stimulating the TCR/CD3 pathway and/or a costimulatory pathway such as CD28. In the context of the present invention, an increased immune response is preferably characterized by an increase in the secretion of at least one cytokine, more preferably by an increase in the secretion of at least one cytokine selected from the group consisting of IL-2, IFN-γ, TNF-α, IL-1 and IL-6, even more preferably in the secretion of at least one cytokine selected from the group consisting of IL-2, IFN-γ and TNF-α. Particularly preferably, an increased immune response is preferably characterized by an increase in the secretion of at least two cytokines such as, particularly preferred, IL-2 and IFN-γ, IL-2 and TNF-α, or IFN-γ and TNF-α. Also highly preferred is an increase in at least three cytokines such as of IL-2, IFN-γ and TNF-α. Additionally or alternatively, also other markers associated with immunologic activity may be increased in expression such as, e.g., CD40 ligand (CD40L, also known as CD154), granzyme/perforine, CD69, CD25 and/or CD71. Preferably such marker is CD40L.

As laid out above, enhanced IL-2 and IFN-gamma production by tumor infiltrating lymphocytes (TILs), in particular T cells specific for neoplastic and/or infectious antigens, is known to be linked to improved immunity against the neoplastic and/or infectious lesion(s). TNF-alpha has such effects as well. IL-2 may directly activate CD8 cells and natural killer (NK) cells. Therefore, its release may be beneficial at a neoplastic and/or infectious lesion, but also may have a general role for fostering T cell survival. Therefore its release during antigen-presenting cell (APC) stimulation of T cells (e.g., in the lymph nodes) may also enhance an immune response.

Granzyme/perforine is considered as an effector molecule and consequently a marker for direct killing of neoplastic cells, in particular tumor cells, and may be released specifically proximal to or even in a neoplasm. Likewise, also IFN-gamma and TNF-alpha may activate immune cells (such as, e.g., NK cells and myeolid cells) but also directly upregulate apoptosis pathways in neoplastic cells.

IL-6 is a pleiotropic cytokine, which is particularly known to support B cell survival and its release in the lymph node, therefore, may also support B cell survival.

Release of IL-1 and IL-6 may enhance the development of T helper cells (e.g. Th17 cells), which are known to play a considerably role in immunity against neoplastic and infectious diseases. Therefore, the presence of enhanced levels of Il-6 and IL-1 both at a neoplastic and/or infectious lesion and a lymph node may have beneficial effects on the immune response.

CD25, CD69, CD71 and CD40L are well-known surface markers for T cell activation and are known to demonstrate effects of the compounds on the level of individual T cell activation. CD69 is particularly an early marker of T cell activation. CD25 is the IL-2 receptor and high(er) expression typically supports (more) rapid expansion of activated T cells. CD71 is the receptor for transferrin and typically supports T cells to supply with Fe for proliferation. CD40L is a receptor on T helper cells which is known to support both APC and B cell activation and survival and proliferation.

In particular, an increase of IL-2, IFN-γ and/or TNF-α secretion, and/or CD40L expression is also exemplified in the Example section below. All these markers are well-known factors in anti-neoplastic immune response evidencing the anti-neoplastic (in particular, anti-tumor) activity of the compounds of the present invention.

Such increase of the secretion of cytokines by immune cells may be an increase of at least 10%, of at least 20%, of at least 30%, of at least 40%, of at least 50%, of at least 75%, of at least 2fold, of at least 3fold, of at least 4fold, or of at least 5fold compared to the secretion of the corresponding cytokine by immune cells subjected to the same stimulating agent and cultivated under comparable conditions but without being subjected to the compound of the present invention. The person skilled in the art will notice that the rate of an increase will typically also depend on the amount of the compound of the present invention subjected to the respective immune cells in a dose-dependent manner. Accordingly, it will, in many cases also depend on the dose of the compound of the present invention subjected to a patient in a dose-dependent manner. Within a suitable dose range, a higher dose will typically also lead to a higher increase. The person skilled in the art will further know that the dose-dependency also relates to the patient's body weight, the patient's fat and body water content, the patient's individual metabolism rate of deactivating and/or eliminating the compound, the patient's individual immunologic condition etc. Therefore, the person skilled in the art may adjust the dose accordingly.

Additionally or alternatively, also the proliferation rates of immune cells such as T cells, NK cells, B cells and/or monocytes may be increased. Exemplarily, the proliferation of CD4+ and/or CD8+ cells may be increased. Additionally or alternatively, also the maintenance (i.e, the survival rates, activity time or live time) of immune cells such as, e.g., T cells, NK cells, B cells and/or monocytes (e.g., CD4+ and/or CD8+ cells) may be increased.

Notably, the compounds of the present invention may also increase T cell reactivity to tumor antigens presented by MHC I to CD8 T cells or by MHC II to CD4 T cells independently of the tumor type and independently of the tumor antigens. Furthermore, the compounds of the present invention may increase the immunologic activity of the patient's NK cells to aid destruction of tumor cells that have decreased the MHC-I mediated display of tumor antigens. Moreover, strong antigen-specific T cell responses may be further increased by B cells and other immune cells, which may be also targeted by the compounds of the present invention. Thus, the compounds of the present invention may also abolish immunological ignorance towards neoplasia and/or infectious pathogens, so that the patient's specific tumor antigens are recognized as non-self and thus, the patient's own immune system may be re-activated to attack those tumor cells present in the patient, independently of the respective type of neoplastic and/or infectious disease.

In the view of the above, in a further aspect, the present invention relates to the compound or pharmaceutical composition of the present invention for use in a method for the treatment or prevention of a neoplastic and/or infectious disease.

In other words, the present invention relates to a method of treating or preventing a neoplastic and/or infectious disease in a patient, comprising administering to said patient an amount of a compound or pharmaceutical composition of the present invention sufficient for treating or preventing said neoplastic and/or infectious disease in said patient.

In this aspect relating to such medical use and method of treatment or prevention, respectively, the definitions as laid out in detail above (in particular, in the context of the compound, the pharmaceutical composition and the use thereof as a medicament) also apply mutatis mutandis.

As used throughout the present invention, the term "patient" may be understood in the broadest sense as any subject or individual to be prevented or treated by means of a compound or pharmaceutical composition of the present invention, in particular having or being at risk of developing a neoplastic and/or infectious disease, irrespective whether clinical symptoms occur or do not occur. The patient may be any animal, including humans. Preferably, the patient is a mammal (e.g., a human, a mouse, a rat, a cow, a pig, a dog, a cat, a horse, a donkey, a goat, etc.), most preferably a human.

In the context of the present invention, the term "disease" may be understood in the broadest sense as any pathologic condition, irrespective whether clinical symptoms occur or do not occur. Therefore, the disease may be associated with a phenotype or may be latent. Preferably, a disease is a pathologic condition accompanied by one or more clinical symptom(s).

A disease in the context of the present invention may be a chronic and/or an acute disease. Preferably, it is a chronic disease. A chronic disease is persistent or otherwise long-lasting in its effects. In the context of the present invention, a chronic disease also includes a disease with a recurrent course, i.e., a recurrent disease relapsing repeatedly, with periods of remission in between. Accordingly, as used herein, a chronic disease may be understood in the broadest sense as any disease that lasts for at least a week, at least a month, at least three months, at least six month, at least a year or even several years (with or without clinical symptoms). When the patient is a human, a chronic disease is usually understood as lasting for at least one month or preferably at least three months. This understanding may also be applied to the present invention. In this context, it may be understood that, for instance, a neoplasm may typically but not necessarily grow for several months or even years until the first clinical symptoms occur. Nevertheless, the neoplastic disease already exists from the occasion of the first neoplastic cells, typically not associated with any clinical symptoms. Therefore, a recognized neoplastic disease is typically but not necessarily a chronic disease per se. Likewise, an infectious disease like a human immunodeficiency virus (HIV) infection is typically a chronic disease when it starts to provoke clinical symptoms and is first recognized.

As used herein, a neoplastic disease may be understood in the broadest sense as any tissue resulting from miss-controlled cell growth. In many cases a neoplasm leads to at least bulky tissue mass optionally innervated by blood vessels. It may or may not comprise the formation of one or more metastasis/metastases. A neoplastic disease of the present invention may be any neoplasm as classified by the International Statistical Classification of Diseases and Related Health Problems 10th Revision (ICD-10) classes C00-D48.

Exemplarily, a neoplastic disease according to the present invention may be the presence of one or more malignant neoplasm(s) (tumors) (ICD-10 classes C00-C97), may be the presence of one or more in situ neoplasm(s) (ICD-10 classes D00-D09), may be the presence of one or more benign neoplasm(s) (ICD-10 classes D10-D36), or may be the presence of one or more neoplasm(s) of uncertain or unknown behavior (ICD-10 classes D37-D48). Preferably, a neoplastic disease according to the present invention refers to the presence of one or more malignant neoplasm(s), i.e., is malignant neoplasia (ICD-10 classes C00-C97).

In a more preferred embodiment, the neoplastic disease is cancer.

Cancer may be understood in the broadest sense as any malignant neoplastic disease, i.e., the presence of one or more malignant neoplasm(s) in the patient. Cancer may be solid or hematologic malignancy. Preferably, the cancer is such accessible to at least one kind of immunotherapy (including, e.g., therapeutic antibodies targeted against tumor antigens and/or experimental approaches such as, e.g., cancer vaccination).

Subtypes of cancer may be classified in different ways such as by the location in the body the main or only tumor bulk is found or by the tissue of origin the tumor(s) is/are derived from.

Exemplarily, such malignant neoplasm according to the present invention may be located on or in the lip, oral cavity and pharynx (ICD-10 classes C00-C14), on or in the digestive organs (ICD-10 classes C15-C26), on or in the respiratory system and intrathoracic organs (ICD-10 classes C30-C39), on or in the bone and articular cartilage (ICD-10 classes C40-C41), on or in the skin (ICD-10 classes C43-C44), on or in the connective and soft tissue (ICD-10 classes C45-C49), on or in the breast and female genital organs (ICD-10 classes C50-C58), on or in the male genital organs (ICD-10 classes C60-C63), on or in the urinary organs (ICD-10 classes C64-C68), on or in the eye, brain and central nervous system (ICD-10 classes C69-C72), on or in the endocrine glands and related structures (ICD-10 classes C73-C75), may be secondary and ill-defined neoplasms (ICD-10 classes C76-C80), may be stated or presumed to be primary, of lymphoid, haematopoietic and related tissue neoplasms (ICD-10 classes C81-C96), and/or may be neoplasms of independent (primary) multiple sites (ICD-10 class C97).

Exemplarily, cancers in the context of the present invention may be selected from the group consisting of carcinoma (i.e., cancers derived from epithelial cells; e.g., adenocarcinoma, squamous cell carcinoma, adenosquamous carcinoma, anaplastic carcinoma, large cell carcinoma, and small cell carcinoma), sarcoma (i.e, cancers derived from connective tissue; e.g., Askin's tumor, sarcoma botryoides, chondrosarcoma, Ewing's sarcoma, malignant hemangioendothelioma, malignant Schwannoma, osteosarcoma, and soft tissue sarcomas), lymphoma and leukemia (i.e., cancers derived from hematopoietic (blood-forming) cells; e.g., mature B-cell neoplasms, mature T cell and natural killer (NK) cell neoplasms, Hodgkin lymphoma, immunodeficiency-associated lymphoproliferative disorders, lymphocytic leukemia, myelogenous leukemia), germ cell tumor (i.e., cancers derived from pluripotent cells in the sexual organs; e.g., germinoma (including dysgerminoma and seminoma), dysgerminoma, seminoma), blastoma (i.e., cancers derived from immature "precursor" cells or embryonic tissue; e.g., hepatoblastoma, medulloblastoma, nephroblastoma, neuroblastoma, pancreatoblastoma, pleuropulmonary blastoma, retinoblastoma, glioblastoma), and melanoma and preforms thereof (i.e., cancers derived from melanocytes; e.g., Lentigo maligna, superficial spreading melanoma, acral lentiginous melanoma, mucosal melanoma, nodular melanoma, polypoid melanoma, desmoplastic melanoma, amelanotic melanoma, soft-tissue melanoma), and nonmelanoma skin cancer (i.e., non-melanoma cancers derived from skin, e.g. basal cell carcinoma, squamous cell carcinoma, dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, angiosarcoma) and glioma (i.e., cancers derived from brain or spine cells, e.g., ependymoma, astrocytoma, oligodendrogliomas, brainstem glioma, optic nerve glioma, mixed glioma).

Preferably, cancer may be the formation of one or more solid tumor(s) such as, e.g., those selected from the group consisting of melanoma, non-small-cell lung cancer, small cell lung cancer and renal cell carcinoma, in addition breast cancer, prostate cancer, colorectal cancer, hepato-cellular carcinoma, brain cancer, bladder cancer, esophageal cancer, pancreatic cancer, gastric cancer, ovarian cancer, mesothelioma, and head-and-neck cancer.

Alternatively, cancer may be the formation of one or more hematopoietic tumor(s) such as, e.g., those selected from the group consisting of multiple myeloma, Non-Hodgkin lymphoma, AML (Acute Myeloid leukemia, DLBCL (Diffuse Large B-cell Lymphoma), and B-CLL (B-cell chronic lymphocytic lymphoma).

In an alternative preferred embodiment, the disease may be an infectious disease.

As used in the context of the present invention, the term "infectious disease" may be understood in the broadest sense as any pathologic condition cased by the invasion of a patient's body by one or more biological agent(s) foreign to the body able to provoke an immune reaction in the patient's body. An infectious disease may or may not be accompanied by an inflammatory response (inflammation). Preferably, an infectious disease in the context of the present invention is accompanied by an inflammatory response. Exemplarily, such immune reaction in the patient's body may be in more detail caused by a biological agent itself (e.g., by the presence of surface antigens thereof), by antigens originating from a biological agent provided on a major histocompatibility complex I or II (MHC I or MHC II), by the multiplication of a biological agent, by the reaction of host tissues to such biological agent, by compounds produced or caused by such biological agent (e.g., toxins, semiochemicals, cytokines, etc.), or by the formation of an antigen from a haptene originating from such biological agent. Such biological agents may be non-living or living agents. Exemplarily, an infectious disease may be caused by biological agents selected from the group consisting of viruses, viroids, prions, microorganisms such as bacteria, nematodes such as roundworms and pinworms, arthropods (e.g., ticks, mites, fleas, and lice), fungi, ringworms, and tapeworms. Preferably, an infectious disease according to the present invention is caused by viruses or bacteria, in particular is a virus infection.

A viral infection in the context of the present invention may be an infection by any virus. The viral infection may be an acute viral infection or a chronic viral infection. Preferably, it is a chronic viral infection. Nonrestrictive examples of clinically important virus families and species in the context of the present invention include Adenovirus, Herpes simplex, type 1, Herpes simplex, type 2, Varicella-zoster virus, Epstein-barr virus, Human cytomegalovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, Human immunodeficiency virus, Influenza virus, Guanarito virus, Junin virus, Lassa virus, Machupo virus, Sabia virus, Crimean-Congo hemorrhagic fever virus, Ebola virus, Marburg virus, Measles virus, Mumps virus, Parainfluenza virus, Respiratory syncytial virus, Human metapneumovirus, Hendra virus, Nipah virus, Rabies virus, Hepatitis D, Rotavirus, Orbivirus, Coltivirus, and Banna virus.

In the context of the present invention, those virus infections associated with a down-regulation of the immune response are of particular interest, such as, e.g., a Human immunodeficiency virus (HIV) infection, without symptoms or associated with symptoms (Acquired Immune Deficiency Syndrome (AIDS)).

Further, also such virus infections associated with neoplasia such as, e.g., Herpes simplex virus (HSV), type 1 or 2, are also of particular interest. Here, the compounds or pharmaceutical composition of the present invention may concomitantly be pharmaceutically active against the virus infection as well as the neoplasm resulting from said virus infection.

Further, also such virus infections being latent for a longer time and, thus, hiding from the immune system, such as, e.g., HSV 1 or HSV2, are also of particular interest.

Optionally but not necessarily, an infectious disease, in particular a chronic infectious disease (e.g., a chronic virus infection), may be associated with inflammation. In this context, inflammation may be characterized by an increase in the NF-κB activity, C-reactive protein (CRP) level, interferon-gamma (IFN-gamma) level, interleukin 1 (IL-1) level and/or interleukin 8 (IL-8) level.

In the context of a treatment or prevention of a neoplastic and/or infectious disease, the compound(s) of the present invention may be administered as the sole pharmaceutically active agent or may be administered in combination with one or more other pharmaceutically active agent(s). Exemplarily, such other pharmaceutically active agent may be a stimulating agent activating immune cells, may be an antiproliferative agent (e.g., an anti-cancer agent such as a chemotherapeutic, an antimetabolite, a hormone, an antibody (Ab)), an antiviral agent, and/or an antibiotic.

Preferably, such other pharmaceutically active agent is a biological compound such as a therapeutic monoclonal antibody which has been shown to be efficacious in treating neoplasms. Exemplarily, such therapeutic monoclonal antibody is directed against the PD-1 molecule, the PD-L1 molecule or another ligand of the PD-1 molecule, the CTLA-4 molecule, the TIM3 molecule, the LAG3 molecule, the VISTA molecule or the BTLA-4 molecule.

The application of such combination therapy will depend on the pharmacokinetic and pharmacodynamics properties of the chosen compounds and agents used in such combination therapy (adjunction).

Optionally, the further agent may be administered concomitantly, previously or subsequently with one or more compound(s) of the present invention. As used herein, a concomitant administration may be an administration in a single composition (e.g., combined in the pharmaceutical composition of the present invention) or in two separate compositions that may also, optionally, be administered via the same or different routes of administration (e.g., via injection, orally, nasally, percutaneously, etc.). As used herein, when administering the compound of the present invention previously or subsequently, there may be a time interval between the administration of said compound(s) and the further agent(s) of less than one hour, one hour or more, three hours or more, six hours or more, twelve hours or more, 24 hours or more, two days or more or a week or more.

As mentioned in the context of the compound of the present invention above, also the one or more further agent(s) may be administered once (single administration) or may be a repeated administration such as, e.g., two times, three times, four times, five times, six times, seven times, eight times, nine times, ten times, more than ten times or even permanently. Between two administrations, there may be a time interval of less than one hour, one hour or more, six hours or more, twelve hours or more, 24 hours or more. Administration may be daily, may be twice daily, three times daily, four times daily, every second day, every three days, weekly, biweekly, monthly, twice a year or yearly.

In a preferred embodiment, the compound or pharmaceutical composition of the present invention is administered in combination with one or more further stimulating agent(s) activating immune cells.

Immune cells as used in the context of the present invention may be any immune cells known in the art. Immune cells may be cells of the adaptive immune system (e.g., T cells or B cells, cells of the innate immune system (natural killer (NK) cells, macrophages, monocytes), and/or cells subsumable under both groups (e.g., dendritic cells (DCs); antigen-presenting cells (APCs))) and/or cells known for phagocytic activity such as basophilic, neutrophilic or eosinophilic granulocytes.

In a preferred embodiment, the immune cells are peripheral blood mononuclear cells (PBMCs).

In a preferred embodiment, the immune cells are selected from those bearing T cell antigen receptor (TCR) and a CD4 and/or CD8 co-receptor on their cellular surface. Those immune cells bearing a CD4 co-receptor on their cellular surface may be selected from the group consisting of T helper cells (Th cells), macrophages, and dendritic cells (DCs). Those immune cells bearing a CD8 co-receptor on their cellular surface may be selected from the group consisting of cytotoxic T cells, natural killer (NK) cells, cortical thymocytes, and dendritic cells (DCs).

In another preferred embodiment, the immune cells are selected from the group consisting of T cells, NK cells, monocytes and B cells.

In a particularly preferred embodiment, the immune cells are T cells and/or NK cells.

T cells and NK cells are well-known to bear particular efficiency against neoplasia (particularly anti-tumor immunity) and infectious diseases. NK cells are preferably lymphocytes which can be stimulated via the Fc receptor (FcR). In particular in the context of antibody dependent cellular cytotoxicity (ADCC), this may be of some benefit in the context of the present invention (e.g., as single application or when co-administering a therapeutic antibody against neoplastic and/or infectious antigens).

B cells are well-known to play a considerable role in humoral response to infectious pathogens. It is been further known in the art that also B cells may also play a role in developing humoral immunity against neoplastic cells.

Monocytes may be understood as the transient phenotype of myeolid cells present in large numbers in PBMCs. Moreover, myeloid cells include dendritic cells (DCs). Macrophages may bear both positive and suppressive effects on immunity, in particular anti-neoplastic therapies. Macrophages of particular interest include M1-type macrophages. Myeloid cells may also include myeloid-derived suppressor cells (MDSCs) bearing a negative effect in anti-neoplastic immune response. Myeloid cells can be stimulated via the FC receptor (FcR). In particular in the context of antibody dependent cellular cytotoxicity (ADCC), this may be of some benefit in the context of the present invention (e.g., as single application or when co-administering a therapeutic antibody against neoplastic and/or infectious antigens). It may also be enhancing the effect of naturally developed humoral immunity against tumor antigens in the patient.

An activation of immune cells may be understood in the broadest sense as the increase of immunologic activity of such cell and/or the increase of cell proliferation of such cells.

In a more preferred embodiment, the further stimulating agent(s) activating immune cells is/are selected from the group consisting of one or more antigen(s) of the neoplasm and/or infectious pathogen to be treated, one or more TCR or CD3 agonist(s), one or more CD28 agonist(s), one or more agonist(s) to other costimulatory T cell surface receptors such as CD40L, CD69, OX40, GITR, CD137, CD27 and/or HVEM, and a combination of two or more thereof.

A TCR/CD3 agonist may be any agent triggering CD3. It may be a peptide or non-peptide agonist binding to the extracellular side of TCR/CD3 in the context or absence of MHC-dependent antigen presentation, may be an agonist binding to the intracellular side of TCR/CD3, or may be an agent activating the intracellular signal transduction pathway triggered by TCR/CD3 engagement. Preferably, a CD3 agonist may be an anti-CD3 antibody, a peptide antigen presented by MHC I or MHC II, an anti-CD3 antibody fragment or an anti-CD3 antibody mimic. Highly preferably, a CD3 agonist is a tumor antigen presented by MHC I or MHC II.

A CD28 agonist may be any agent triggering CD28. It may be an agonist binding to the extracellular side of CD28, may be an agonist binding to the intracellular side of CD28, or may be an agent activating the intracellular signal transduction pathway triggered by CD28. Preferably, a CD28 agonist may be an anti-CD28 antibody, an anti-CD28 antibody fragment, an anti-CD28 antibody mimetic or a protein containing a natural ligand for CD28 such as B7.1 or B7.2. Highly preferably, a CD28 agonist is an (agonistic) anti-CD28 antibody or an Ig fusion protein containing a natural ligand for CD28 such as B7.1 or B7.2.

An antibody in the context of the present invention may be a monoclonal or a polyclonal antibody of any species or origin. It may bind to any epitope(s) comprised in the polypeptide bearing the respective cognate antigen (e.g, CD3 or CD28, respectively) including its posttranslational modifications. The cognate antigen may exemplarily be a linear epitope, a structural epitope, a primary epitope, and/or a secondary epitope. An antibody may be of natural origin, of gene technologic origin and/or of synthetic origin.

An antibody fragment may be understood in the broadest sense as any fragment of an antibody that still bears binding affinity to its target polypeptide. Exemplarily, the antibody fragment may be a fragment antigen binding (Fab fragment), a truncated antibody comprising one or both complementarity determining region(s) (CDR(s)) or the variable fragment (Fv) of an antibody. The antibody fragments may be of natural origin, of gene technologic origin and/or of synthetic origin.

An antibody mimetic may be understood in the broadest sense as organic compounds that, like antibodies, can specifically bind antigens and that typically have a molecular mass in a range of from approximately 3 kDa to approximately 25 kDa. Antibody mimetics may be, e.g., Affibody molecules (Affibodies), Affilins, Affitins, Anticalins, Avimers, DARPins, Fynomers, Kunitz domain peptides, single-domain antibodies (e.g., VHH antibodies or VNAR antibodies) Monobodies, Diabodies, Triabodies, flexibodies and tandabs. The antibody mimetics may be of natural origin, of gene technologic origin and/or of synthetical origin.

Peptide antigens may be understood in the broadest sense as organic compounds that specifically bind to MHC I or MHC II molecules and that typically consist of 8-30 amino acids and preferably consist of 9-25 amino acids. The peptides may be of natural origin, of gene technologic origin and/or of synthetical origin.

Preferably, the further stimulating agents activating immune cells are a combination of one or more CD3 agonist(s) and one or more CD28 agonist(s). Particularly preferably, the further stimulating agents activating immune cells are a combination of at least one (agonistic) anti-CD3 antibody and at least one (agonistic) anti-CD28 antibody. As it is evident from the Examples shown below, a stimulation of the immune cells by means of contacting these with (agonistic) anti-CD3 antibodies and/or (agonistic) anti-CD28 antibodies mechanistically simulates T cells, irrespective of the individual TCR-recognized specific antigen. A stimulation with (agonistic) anti-CD3 antibodies and (agonistic) anti-CD28 antibodies very well mimics activation of T cells in a patient's body in vivo.

Additionally or alternatively, the immune cells may also be triggered by an antigen of the neoplasm and/or infectious pathogen (e.g., by means of vaccinating the patient with one or more antigen(s)). Then, the antigen is considered as a stimulating agent. An antigen of the neoplasm and/or infectious pathogen may be, exemplarily, a vaccine comprising one or more antigen(s) of the neoplasm and/or infectious pathogen, such as e.g, a polypeptide-based vaccine, a polynucleotide vaccine, an oligosaccharide vaccine, or a vaccine based on fragments of neoplasms of the same type or on fragments of infectious pathogens of the same type. The person skilled in the art knows numerous methods for providing such vaccines. Several anti-tumor and antiviral vaccines are also commercially available.

Additionally or alternatively, the immune cells may also be triggered by antigen-loaded antigen-presenting cells (APCs). Then, the antigen-loaded APCs are considered as a further stimulating agent. In this context, the antigens are also antigens of the neoplasm and/or infectious pathogen as mentioned before.

Additionally or alternatively, the one or more further stimulating agent(s) may be selected from the group consisting of checkpoint blockade therapeutics (in particular T cell surface receptor-binding agents such as, e.g., those binding one or more selected from the group consisting of CTLA4, PD-1, PDL-1, TIM3, LAG3, BTLA, VISTA and/or a ligand thereof (e.g., anti-CTLA4, anti-PD-1 and/or anti-PDL-1 antibodies)), cytokines (e.g., IL-2, IL-15 and/or IL-7), activating agents of APCs (e.g., CD40 agonists), adoptive cellular agents (in particular adoptive T cells (e.g., chimeric immune receptor T cell therapy such as, e.g., CAR T cell therapy), dendritic cell therapy (e.g., sipuleucel-T) and/or natural killer cell therapies), enhancers of T cell functions (e.g., lenalidomide and related agents), enhancers of natural killer cell functions (e.g., anti-KIR antibodies), and therapeutic antibodies directed against tumor antigens.

Optionally, in particular when the patient is suffering from a neoplastic disease, the patient may be further administered with one or more chemotherapeutic(s), cytokine(s) and/or other anti-neoplastic agent(s) in addition to one or more compound(s) of the present invention. Exemplarily, such chemotherapeutics, cytokines and anti cancer agents may be selected from the group consisting of polyclonal or monoclonal antibodies (e.g., rituximab, trastuzumab, cetuximab, bevacizumab, basiliximab, daclizumab), anti-metabolites (e.g., 5-fluorouracil, azathioprine, 6-mercaptopurine, mercaptopurine, pyrimidines, thioguanine, fludarabine, floxuridine, cytosine arabinoside (cytarabine), pemetrexed, raltitrexed, pralatrexate, methotrexate), alkylating agents (e.g., mechlorethamine, cyclophosphamide, chlorambucil, Ifosfamide), platins (e.g., cisplatin, carboplatin, oxaliplatin), plant alkaloids and terpenoids (e.g., vinca alkaloids (vincristine, vinblastine, vinorelbine, vindesine), taxanes (e.g., paclitaxel), cytoxan), topoisomerase inhibitors (e.g., camptothecins: irinotecan, topotecan, etoposide, etoposide phosphate, teniposide), melphalan, antineoplastica (e.g., doxorubicin (adriamycin), doxorubicin lipo, epirubicin, bleomycin)), actinomycin D, aminoglutethimide, amsacrine, anastrozole, antagonists of purine and pyrimidine bases, anthracyclines, aromatase inhibitors, asparaginase, antiestrogens, bexarotene, buserelin, busulfan, camptothecin derivatives, capecitabine, carmustine, cladribine, cytarabine, cytosine arabinoside, alkylating cytostatics, dacarbazine, daunorubicin, docetaxel, epirubicin, estramustine, etoposide, exemestane, fludarabine, fluorouracil, folic acid antagonists, formestane, gemcitabine, glucocorticoids, goserelin, hormones and hormone antagonists, hycamtin, hydroxyurea, idarubicin, irinotecan, letrozole, leuprorelin, lomustine, mercaptopurine, miltefosine, mitomycins, mitosis inhibitors, mitoxantrone, nimustine, procarbazine, tamoxifen, temozolomide, teniposide, testolactone, thiotepa, topoisomerase inhibitors, treosulfan, tretinoin, triptorelin, trofosfamide, cytostatically active antibiotics, everolimus, pimecrolimus, tacrolimus, azithromycin, spiramycin, sirolimus (rapamycin), roxithromycin, ascomycin, bafilomycin, erythromycin, midecamycin, josamycin, concancamycin, clarithromycin, troleandomycin, folimycin, tobramycin, mutamycin, dactinomycin, dactinomycin, rebeccamycin, a statin (e.g., cerivastatin, simvastatin, lovastatin, somatostatin, fluvastatin, nystatin, rosuvastatin, atorvastatin, pravastatin, pitavastatin, pentostatin,), 4-hydroxyoxycyclophosphamide, bendamustine, thymosin α-1, aclarubicin, fludarabine-5'-dihydrogen phosphate, hydroxycarbamide, aldesleukin, pegaspargase, cepharanthine, epothilone A and B, azathioprine, mycophenolate mofetil, c-myc antisense, b-myc antisense, betulinic acid, camptothecin, melanocyte stimulating hormone (α-MSH), activated protein C, IL-1β inhibitor, fumaric acid and esters thereof, dermicidin, calcipotriol, taclacitol, lapachol, β-lapachone, podophyllotoxin, betulin, podophyllic acid 2-ethyl hydrazide, sagramostim, (rhuGM-CSF), peginterferon α-2b, lenograstim (r-HuG-CSF), filgrastim, macrogol, cephalomannine, selectin (cytokine antagonist), CETP inhibitor, cadherins, cytokinin inhibitors, COX inhibitor (COX-2 or COX-3 inhibitor), angiopeptin, ciprofloxacin, flurobastin, bFGF antagonists, probucol, prostaglandins, 1,11-dimethoxyeanthin-6-one, 1-hydroxy-11-methoxycanthin-6-one, scopoletin, colchicine, NO donors, pentaerythrityl tetranitrate, sydnonimines, S-nitroso derivatives, staurosporine, β-estradiol, α-estradiol, estriol, estrone, ethinyl estradiol, fosfestrol, medroxyprogesterone, estradiol cypionates, estradiol benzoates, tranilast, kamebakaurin, verapamil, ciclosporin A, paclitaxel and derivatives thereof such as 6-α-hydroxy paclitaxel, baccatin, taxotere, mofebutazone, acemetacin, diclofenac, lonazolac, dapsone, o-carbamoyl-phenoxy-acetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterol, ademetionine, myrtecaine, polidocanol, nonivamide, levomenthol, benzocaine, aescin, elipticine, Calbiochem D-24851, colcemid, cytochalasin A-E, indanocine, nocodazole, bacitracin, vitronectin receptor antagonists, azelastine, free nucleic acids, nucleic acids incorporated into virus transmitters, DNA and RNA fragments, plasminogen activator inhibitor-1, plasminogen activator inhibitor-2, antisense oligonucleotide, VEGF inhibitors, IGF-1, active agents from the group of antibiotics such as cefadroxil, cefazolin, cefaclor, cefoxitin, gentamicin, penicillins, dicloxacillin, oxacillin, sulfonamides, metronidazole, antithrombotics, argatroban, aspirin, abciximab, synthetic antithrombin, bivalirudin, coumadin, enoxaparin, GpIIb/IIIa platelet membrane receptor, antibodies to factor Xa inhibitor, heparin, hirudin, r-hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, NF-kB or Bcl-xL antisense oligonucleotides, halofuginone, nifedipine, tocopherol, molsidomine, tea polyphenols, epicatechin gallate, epigallocatechin gallate, boswellic acids and derivatives thereof, leflunomide, anakinra, etanercept, sulfasalazine, tetracycline, triamcinolone, procainimide, retinoic acid, quinidine, disopyramide, flecainide, propafenone, sotalol, amiodarone, natural and synthetically obtained steroids such as bryophyllin A, inotodiol, maquiroside A, mansonine, strebloside, hydrocortisone, betamethasone, dexamethasone, fenoprofen, ibuprofen, indomethacin, naproxen, phenylbutazone, acyclovir, ganciclovir, zidovudine, antimycotics, clotrimazole, flucytosine, griseofulvin, ketoconazole, miconazole, terbinafine, chloroquine, mefloquine, quinine, natural terpenoids, hippocaesculin, barringtogenol-C21-angelate 14-dehydroagrostistachin, agroskerin, agrostistachin, 17-hydroyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrine, taxamairin A and B, regenilol, triptolide, cymarin, apocymarin, aristolochic acid, anopterin, hydroxyanopterin, anemonin, protoanemonin, berberine, cheliburin chloride, cicutoxin, sinococuline, combrestatin A and B, cudraisoflavone A, curcumin, dihydronitidine, nitidine chloride, 12-beta-hydroxypregnadiene-3,20-dione bilobol, ginkgol, ginkgolic acid, helenalin, indicine, indicine-N-oxide, lasiocarpine, inotodiol, glycoside 1a, justicidin A and B, larreatin, malloterin, mallotochromanol, isobutyrylmallotochromanol, marchantin A, maytansine, lycoridicin, margetine, pancratistatin, liriodenine, bisparthenolidine, oxoushinsunine, aristolactam-AII, periplocoside A, ghalakinoside, deoxypsorospermin, psychorubin, ricin A, sanguinarine, manwu wheat acid, methylsorbifolin, chromones of spathelia, stizophyllin, akagerine, dihydrousambaraensine, hydroxyusambarine, strychnopentamine, strychnophylline, usambarine, usambarensine, daphnoretin, lariciresinol, methoxylariciresinol, syringaresinol, umbelliferone, afromoson, acetylvismione B, desacetylvismione A, vismione A and B), radiation therapy (e.g, Intensity-Modulated Radiation Therapy (IMRT), 3-Dimensional Conformal Radiotherapy (3DCRT), Stereotactic body radiation therapy (SBRT), Stereotactic radiosurgery (SRS), image-guided radiation therapy (IGRT), Particle Therapy (e.g, proton therapy), Brachytherapy, Radioisotope Therapy (RIT) (e.g., with iodine-131, lutetium-177, strontium-89 and samarium (153Sm) lexidronam and/or yttrium-90)), antiangiogenic therapy (e.g., carboxyamidotriazole, TNP-470, CM101, Suramin, SU5416, Thrombospondin, VEGFR antagonists, angiostatic steroids+heparin, Cartilage-Derived Angiogenesis Inhibitory Factor, matrix metalloproteinase inhibitors, 2-methoxyestradiol, Tecogalan, tetrathiomolybdate, thalidomide, thrombospondin, soluble VEGFR-1 and NRP-1, Angiopoietin 2, angiostatin (e.g., TSP-1 and TSP-2 angiostatin), endostatin, vasostatin, canstatin, calreticulin, platelet factor-4, TIMP and CDAI, Meth-1 and Meth-2, CXCL10prothrombin (kringle domain-2), antithrombin III fragment prolactin, VEGI, SPARC, osteopontin, maspin, proliferin-related protein, restin), kinase inhibitors (e.g., imatinib, imatinib mesylate, gefitinib, erlotinib, pazopanib, apatinib), proteasome inhibitors (e.g., bortezomib), PARP inhibitors (e.g., iniparib, olaparib), and combinations of two or more thereof.

Alternatively or additionally, the patient is suffering from or being at risk of developing a neoplastic and/or infectious disease, may be further administered with one or more cytokines, hormones or analogues thereof (e.g., selective estrogen receptor modulator tamoxifen, IL-2, IFN-α, IFN-β, IFN-γ, IL-4, IL-12, IL-18, platelet factor-4, TNF-α). These cytokines, hormones or analogues thereof may further trigger the patient's immune system. As mentioned before, high doses of many of such agents may provoke severe side effects. However, lower doses may optionally be used to support the treatment or prevention of the present invention.

Optionally, in particular when the patient is suffering from a viral infection, the patient may be further administered with one or more antiviral compound(s) in addition to one or more compound(s) of the present invention. Such antiviral compound may exemplarily be selected from the group consisting of an entry or fusion inhibitor, a nucleoside/nucleotide reverse transcriptase inhibitor, a non-nucleoside reverse transcriptase inhibitor, an integrase inhibitor, and a protease inhibitor.

Optionally, in particular when the patient is suffering from a bacterial infection, the patient may be further administered with one or more antibacterial antibiotic(s) in addition to one or more compound(s) of the present invention. Such antibacterial antibiotic may exemplarily be selected from the group consisting of antibiotics targeting the bacterial cell wall (e.g., penicillins and cephalosporins) or the cell membrane (e.g., polymyxins), interfering with essential bacterial enzymes (e.g., rifamycins, lipiarmycins, quinolones, and sulfonamides), and/or targeting polypeptide synthesis (e.g., macrolides, lincosamides and tetracyclines).

Further, a treatment or prevention according to the present invention may also be combined with other means of treatment such as, e.g., radiation therapy (exemplarily based on x-ray radiation, ultraviolet (UV) radiation (e.g., UV-A, UV-B, and/or UV-C radiation), alpha radiation, beta radiation, gamma radiation, or cosmic radiation), and/or surgery.

As laid out above, it will be understood that the compounds of the present invention may be very well used for the treatment and/or prevention of neoplastic and/or infectious diseases in a patient in vivo. However, a compound of the present invention may not merely be used for in vivo application, but likewise also for any kind of ex vivo and/or in vitro use. Exemplarily, it may also be used for activating immune cells in vivo, ex vivo and in vitro.

Exemplarily, the compounds of the present invention may be used in any method supporting the generation and/or amplification of immune cells ex vivo and/or in vitro, in particular but not necessarily for further use in an adoptive cell therapy (ACT). For ACT preferably antigen-specific T cells may be used. Such methods may also provide activated DCs which may optionally be useful for DC vaccination approaches.

Therefore, a further aspect of the present invention refers to a method for the production of activated immune cells comprising the steps of:
(i) providing immune cells;
(ii) contacting the cells of step (i) with:
   (a) at least one compound or pharmaceutically acceptable salt thereof of the present invention, and optionally
   (b) one or more further stimulating agents activating said immune cells; and
(iii) cultivating the cells of step (ii) under conditions suitable for maintaining the viability of said cells.

In this aspect relating to such method, the definitions as laid out in detail above also apply mutatis mutandis.

Preferably, the method is conducted ex vivo and/or in vitro, i.e., is an ex vivo and/or in vitro method. Therefore, in the context of this aspect relating to such method, the immune cells are preferably activated outside of a living being, in particular outside a patient.

Preferably, the immune cells (e.g., T cells and/or natural killer cells) are mature immune cells. Such cells (in particular the T cells) may be CD4+ and/or CD8+ cells. The immune cells may be obtained from any source suitable for this purpose. Alternatively or additionally, the cells may also be B cells such as, e.g., CD19+ B cells. The person skilled in the art knows various ways of obtaining such immune cells. Exemplarily, mature immune cells may be obtained from a blood sample (e.g., a stored blood preservation or fresh blood). Then, peripheral blood mononuclear cells (PBMCs) may exemplarily be obtained from the buffy coat after centrifugation of a blood sample and optionally further isolated/purified, exemplarily, by means of labeling cell type-specific surface markers with fluorescence-labeled antibodies followed by fluorescence activated cell sorting (flow cytometry) or by labeling cell type-specific surface markers with metal bead-labelled antibodies followed by magnetic extraction of the desired cells. Alternatively, mature immune cells may also be obtained from cell culture. The ways of obtaining a buffy coat and isolating and purifying the cells further is exemplified in the example section below. (Mature) immune cells are also commercially available.

Alternatively, immature immune cells or precursors thereof may be used and matured in an intermediate step by well-known means of supplementation with the respective cytokines and growth factors.

The immune cells are subsequently contacted with at least one compound of the present invention and optionally one or more further stimulating agent(s) activating immune cells. The person skilled in the art will immediately notice that these compound(s) and agent(s) may be added to the cells in any kind of solution or medium suitable for the cells. Exemplarily, such solution or medium may also comprise ingredients defined in the context of a pharmaceutical composition above. A further stimulating agent activating immune killer cells may be understood in the broadest sense as defined above. Optionally, the further agent may be administered concomitantly, previously or subsequently with one or more compound(s) of the present invention. The cells may be contacted with the compound(s) and/or agent(s) for less that 30 min, at least 30 min, at least 1 h, for at least 2 h, for at least 5 h, for at least 12 h, for at least 1 day or longer.

Subsequent to or concomitant with contacting the cells with the compound(s) and optional agent(s) (step (ii)), the cells are cultivated under conditions suitable for maintaining the viability of said cells (step (iii)). Therefore, steps (ii) and (iii) may be conducted as one step (simultaneously) or two separate steps (subsequently) or with a partly temporal overlap. Typically, the cells are cultivated in a suitable cell culture medium (e.g., X-Vivo 15) optimized to allow cell culture in the absence of FCS RPMI 1640) optionally supplemented with fetal calf serum (FCS) at 5% $CO_2$ and a temperature of 30° C.-39° C., preferably (approximately) 37° C. Preferably, the cells are cultivated for at least 1 h, for at least 2 h, for at least 5 h, for at least 12 h, for at least 1 day or for at least 3 days.

As a result from the method of the present invention, activated immune cells (e.g., T cells and/or natural killer cells) may be obtained.

These activated immune cells may be optionally isolated by any means known in the art (optional step (iv)). Optionally, as a further step (v), the activated immune cells may subsequently be administered to a patient in need thereof. Alternatively, the isolated activated immune cells obtained from step (iv) or the cells of step (iii) may also be stored and/or preserved (e.g., dispersed in a DMSO-containing medium and stored at −80° C.). Alternatively, the isolated activated immune cells of step (iv) or the cells of step (iii) may be used for any other in vitro and/or in vivo purposes.

Exemplarily, such activated immune cells may be used for research purposes intended to further investigate activated immune cells (in particular activated T cells and/or natural killer cells).

Exemplarily, the activated immune cells (in particular activated T cells and/or natural killer cells) may be used for the production of cytokines secreted by the cells. Then, a further step (iv) is the cultivating of the cells until the level(s) of the desired cytokine(s) secreted into the medium reach(es) the desired level, followed by step (v) of isolating and, optionally purifying the desired cytokine(s). The isolation and optional purification of cytokines may be performed by any means known in the art such as, e.g., chromatographic means. Optionally, such cytokine(s) may subsequently be stored and/or preserved (e.g., frozen, dried or freeze-dried).

Furthermore, a compound of the present invention may be further used as a research tool for investigating immune cell activation in more detail.

The invention is further explained by the following examples, which are intended to illustrate, but not limit the scope of the present invention.

EXAMPLES

Abbreviations

The chemical entities, compositions, and methods described herein are further illustrated by the following non-limiting examples.

As used herein, the following abbreviations have the following meaning. If an abbreviation is not defined, it has a generally accepted meaning.

TABLE 1

| Abbreviations | |
|---|---|
| 7-AAD | 7-Aminoactinomycin D |
| CFSE | Carboxyfluorescein succinimidyl ester |
| DCE | 1,2-dichloroethane |
| DCM | dichloromethane |
| DIPEA | N,N-diisopropyl-N-ethylamine |
| DMF | N,N-dimethylformamide |
| DMSO | dimethylsulfoxide |
| eq | Equivalent |
| ES | electron-spray |
| Et$_2$O | Diethylether |
| EtOAc | ethyl acetate |
| EtOH | Ethanol |
| G | Gram |
| H | Hour |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate |
| IFN | Interferon |
| IL | Interleukin |
| IPA | Isopropanol |
| LPS | Lipopolysacharide |
| MACS | Magnetic cell sorting |
| mCPBA | meta-chloroperoxybenzoic acid |
| MeCN | Acetonitrile |
| MeOH | Methanol |
| mHz | Mega Hertz |
| min | Minute |
| NK | Natural killer |
| PBMC | Peripheral blood mononuclear cells |
| PC5/PC7 | Phycoerythrin-Cy5/Phycoerythrin-Cy7 |
| PyBOP | (Benzotriazol-1-yloxy)tripyrrolidinophosphonium hexafluorophosphate |
| RT | room temperature |
| rt | retention time |
| sat. | Saturated |
| SFC | supercritical fluid chromatography |
| TCR | T cell receptor |
| TNF-a | Tumor necrosis factor alpha |
| TEA | N,N,N-triethylamine |
| THF | tetrahydrofuran |
| T3P ® | 2,4,6-Tripropyl-1,3,5,2,4,6-trioxatriphosphorinane-2,4,6-trioxide solution |
| UV | Ultraviolet |
| Vol | Volume |
| WT | Wildtype |

General Experimental Details

Commercially available reagents and solvents (HPLC grade) were used without further purification. 1H NMR spectra were recorded on a Bruker DRX 500 MHz spectrometer or a Bruker DPX 250 MHz spectrometer or Bruker Avance spectrometers 300 MHz or Bruker Avance spectrometer 400 MHz in deuterated solvents. Chemical shifts (δ) are in parts per million.

Compounds were purified by flash column chromatography on normal phase silica on Biotage Isolera systems using the appropriate SNAP cartridge and gradient. Alternatively compounds were purified on reverse phase using Biotage Isolera systems with the appropriate C18 SNAP cartridge and reverse-phase eluent or by preparative HPLC (if stated otherwise).

Analytical HPLC-MS (METCR1278 GENERIC 3.5 Minutes), was performed on Shimadzu LCMS-2010EV systems using reverse phase Atlantis dC18 columns (3 µm, 2.1×50 mm), at a column temperature of 40° C., gradient 5-100% B (A=water/0.1% formic acid, B=acetonitrile/0.1% formic acid) over 2.5 minutes then 100% B for 0.2 minutes, injection volume 3 µL, flow=1.0 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively analytical HPLC-MS (MET-LCMS (MUX)-A-008) is METCR1278 Generic 3.5 minutes performed on a Waters 1525 HPLC system using Waters 2488 Dual wavelength detector and Waters LCT MUX system.

Analytical HPLC-MS (METCR1673 GENERIC 2 Minutes), was performed on Shimadzu LCMS-2010EV systems using reverse phase Supelco Ascentis Express (2.7 µm, 2.1×30 mm), at a column temperature of 40° C., gradient 5-100% B (A=water/0.1% formic acid, B=acetonitrile/0.1% formic acid) over 1.5 minutes then 100% B for 0.1 minutes, injection volume 3 µL, flow=1.0 mL/minute. UV spectra were recorded at 215 nm using a SPD-M20A photo diode array detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, (METCR1416 GENERIC 7 MINUTES) analytical HPLC-MS on Shimadzu LCMS-2010EV systems using reverse phase Water Atlantis dC18 columns (3 µm, 2.1×100 mm), at a column temperature of 40° C., gradient 5-100% B (A=water/0.1% formic acid, B=acetonitrile/0.1% formic acid) over 5.0 minutes then 100% B for 0.4 minutes, injection Volume 3 µL, flow=0.6 mL/minute. UV spectra were recorded at 215 nm using a SPD-M20A photo diode array detector. Mass spectra were obtained over the range m/z 150 to 850 at a sampling rate of 2 scans per second using aLCMS2010EV. Data were integrated and reported using Shimadzu LCMS-Solutions and PsiPort software.

Alternatively, (METCR1410 GENERIC 1.7 MINUTES) analytical HPLC-MS on Shimadzu LCMS-2010EV systems using reverse phase Kinetex Core shell C18 columns (5 µm, 2.1×50 mm), at a column temperature of 40° C., gradient 5-100% B (A=water/0.1% formic acid, B=acetonitrile/0.1% formic acid) over 1.2 minutes then 100% B for 0.1 minutes, injection Volume 3 µL, flow=1.2 mL/minute. UV spectra were recorded at 215 nm using a SPD-M20A photo diode array detector. Mass spectra were obtained over the range m/z 130 to 850 at a sampling rate of 2 scans per second using aLCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 µM, 2.1 mm×100 mm) at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynxsoftware.

Alternatively, (MET-CR1600) analytical HPLC-MS were performed on a Agilent G1312A system with Waters PDA and ELS detectors using a Phenomenex Gemini-NX C-18 column, (3.0 µM, 2.0 mm×100 mm) at a column temperature of 50° C., gradient 5-100% B (A=2 mM ammonium bicarbonate, buffered to pH10 with ammonium hydroxide solution; B=acetonitrile) over 5.5 minutes, then 100% B for 0.4 minute, flow=0.5 mL/minute. UV spectra were recorded at 215 nm using a Waters 2996 photo diode array. Mass spectra were obtained over the range m/z 100 to 1000 at a sampling rate of 5 scans per second using a Waters ZQ. Data were integrated and reported using Waters MassLynx and OpenLynxsoftware.

Alternatively, (MET-CR0990) analytical HPLC-MS were performed on a Agilent G1312A system with Waters PDA and ELS detectors using a Phenomenex Gemini-NX C-18 column, (3.0 µM, 2.0 mm×50 mm) at a column temperature of 60° C., gradient 1-100% B (A=2 mM ammonium bicarbonate, buffered to pH10 with ammonium hydroxide solution; B=acetonitrile) over 1.80 minutes, then 100% B for 0.3 minute, flow=1 mL/minute. UV spectra were recorded at 215 nm using a Waters 2996 photo diode array. Mass spectra were obtained over the range m/z 100 to 1000 at a sampling rate of 5 scans per second using a Waters ZQ. Data were integrated and reported using Waters MassLynx and OpenLynxsoftware.

Alternatively, (METUPLCMS-A-004) analytical HPLC-MS were performed on a Waters Acquity UPLC system with Waters PDA and 3100 MS using a Acquity UPLC BEH C18 (1.7 µM, 2.1 mm×50 mm) at a column temperature of ambient temperature, gradient 5-100% B (A=water:acetonitrile (9:1, with 0.1% formic acid); B=acetonitrile:water (9:1, with 0.1% formic acid)) over 1.5 minutes then 100% B for 0.2 minutes, injection Volume 4 µL, flow=0.7 mL/minute. UV spectra were recorded at 215 nm using a Waters Acquity photo diode array. Mass spectra were obtained over the range m/z 150 to 850 at a sampling rate of 5 scans per second. Data were integrated and reported using Waters MassLynx and OpenLynxsoftware.

Alternatively, (MET-UPLCMS-A-006) analytical HPLC-MS were performed on a Waters Acquity UPLC system with Waters PDA and ELS detectors using a Acquity UPLC HSS T3, (1.8 µM, 2.1 mm×100 mm) at a column temperature of 40° C., gradient 5-100% B (A=water:acetonitrile (9:1, with 0.1% formic acid); B=acetonitrile:water (9:1, with 0.1% formic acid)) over 5.3 minutes, then 100% B for 0.5 minute, flow=0.6 mL/minute. UV spectra were recorded at 215 nm using a Waters Acquity photo diode array. Mass spectra were obtained over the range m/z 150 to 800 at a sampling rate of 5 scans per second using a Waters 3100 spectrometer. Data were integrated and reported using Waters MassLynx and OpenLynxsoftware.

Alternatively, (MET-UPLCMS-B-007) analytical HPLC-MS were performed on a Waters Acquity UPLC system with Waters PDA and ELS detectors using a Acquity UPLC BEH C18, (1.7 µM, 2.1 mm×100 mm) at a column temperature of 40° C., gradient 5-100% B (A=2 mM ammonium bicarbonate, buffered to pH10; B=acetonitrile and 2 mM ammonium bicarbonate buffered to pH10 (95:5)) over 5.30 minutes, then 100% B for 0.5 minute, flow=0.6 mL. UV spectra were recorded at 215 nm using a Waters Acquity photo diode array. Mass spectra were obtained over the range m/z 150 to 800 at a sampling rate of 5 scans per second using a Waters 3100 spectrometer. Data were integrated and reported using Waters MassLynx and OpenLynxsoftware.

Alternatively, (METCR1981 hydrophobic 3 minutes) analytical HPLC-MS on Shimadzu LCMS-2010EV systems using reverse phase waters Symmetryshield RP8 columns (3.5 µm, 2.1×50 mm), at a column temperature of 40° C., gradient 5-100% B (A=water/0.1% formic acid, B=acetonitrile/0.1% formic acid) over 2.2 minutes, the 100% B for 0.5 minutes, injection Volume 3 µL, flow=1 mL/minute. UV spectra were recorded at 215 nm using a SPD-M20A photo diode array detector. Mass spectra were obtained over the range m/z 130 to 850 at a sampling rate of 2 scans per second using aLCMS2010EV. Data were integrated and reported using Shimadzu LCMS-Solutions and PsiPort software.

All compounds displayed a purity >95% as determined by these method unless otherwise stated.

Compound names were generated using ChemAxon software: Instant JChem Excel IUPACName function.

Synthesis of Intermediates/Synthetic Building Blocks

Synthesis of Intermediate A-03

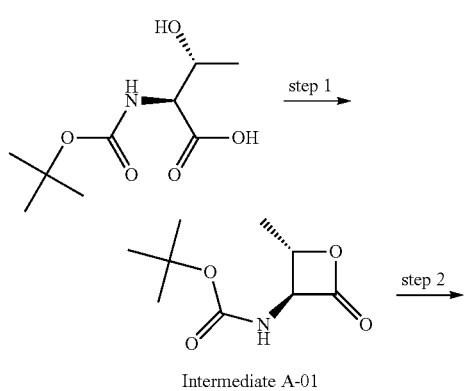

Intermediate A-01

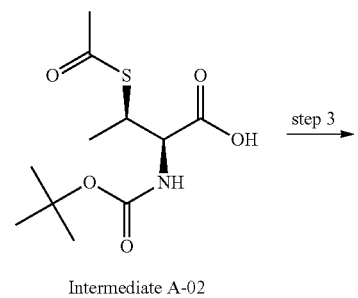

Intermediate A-02

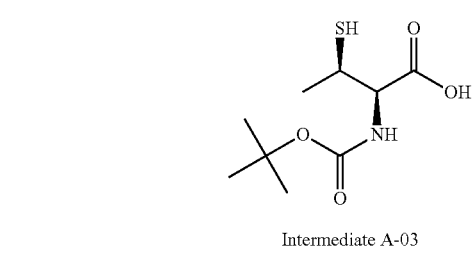

Intermediate A-03

Intermediates A-01, A-02 and A03 were synthesized by adaptation of a method described by R. Breitschuh, D. Seebach Synthesis, 1992, 1-2, 83-89.

Step 1: Synthesis of tert-butyl N-[(2S,3S)-2-methyl-4-oxooxetan-3-yl]carbamate (intermediate A-01)

Et$_3$N (2.67 mL, 19.16 mmol) followed by HBTU (3.63 g, 9.68 mmol) were added to a solution of (2S,3S)-2-{[(tert-butoxy)carbonyl]amino}-3-hydroxybutanoic acid (2 g, 4.79 mmol) in anhydrous DCM (100 mL). The resulting mixture was stirred at RT for 16 h. The solvent was removed under reduced pressure and the residue was purified by flash column chromatography (eluent: heptanes, 0-40% EtOAc) to afford 630 mg of the desired product as a white solid in 65% yield and good purity by NMR (>95%)

NMR: 1H NMR (500 MHz, DMSO-d6) δ 7.79 (d, J=8.0 Hz, 1H), 4.79-4.68 (m, 1H), 4.61 (dd, J=8.0, 4.3 Hz, 1H), 1.47 (d, J=6.2 Hz, 3H), 1.40 (s, 9H).

Step 2: (2R,3R)-3-(acetylsulfanyl)-2-{[(tert-butoxy)carbonyl]-amino}butanoic acid (intermediate A-02)

Intermediate A-01 (95%, 430 mg, 2.03 mmol) was dissolved in anhydrous DMF (14 mL), potassium ethanethioate (348 mg, 3.05 mmol, 1.5 eq) was added and the reaction mixture was stirred at RT under nitrogen (gas outlet scrubbed through aqueous bleach) for 18 h. Further potassium ethanethioate (347.78 mg, 3.05 mmol, and 1.5 eq) was added and stirring was continued for 18 h. The reaction mixture was quenched with 1N aqueous HCl (15 mL) and the mixture was extracted with EtOAc (3×15 mL). The combined organics extracts were washed with water (15 mL) and brine (15 mL) and dried over Na$_2$SO$_4$. Filtration and concentration under reduced pressure afforded 673 mg of the desired product as a white solid in 97% UV purity and quantitative yield, which was used in the next step without further purification.

LCMS: METCR1673 Generic 2 minutes rt=1.12 min, M/Z (ES−)=276 [M−H+], 97% UV

NMR: 1H NMR (500 MHz, DMSO-d6) δ 12.89 (s, 1H), 7.08 (d, J=8.5 Hz, 1H), 4.22 (dd, J=8.1, 5.5 Hz, 1H), 3.93-3.67 (m, 1H), 2.30 (s, 3H), 1.39 (s, 9H), 1.25 (d, J=7.0 Hz, 3H)

Step 3: Synthesis of (2R,3R)-2-{[(tert-butoxy)carbonyl]amino}-3-sulfanylbutanoic acid (intermediate A-03)

1M aqueous LiOH.H$_2$O (12 mL) was added to a solution of intermediate A-02 (673 mg, 2.08 mmol) in MeOH (27 mL). The resulting mixture was stirred at RT for 1.5 h. Saturated aqueous NaHCO$_3$ (13 mL) was added to the reaction mixture and the organic solvent was removed under reduced pressure. The aqueous residue was washed with Et$_2$O (10 mL) and then the pH was adjusted up to pH 1 with aqueous 1M HCl solution. The resulting basic aqueous layer was extracted with EtOAc (2×50 mL). The combined EtOAc extracts were dried over Na$_2$SO$_4$, filtrated and concentrated under reduced pressure to afford 526 mg of the desired product as yellow oil at 80% UV purity in 87% yield, which was used in the next step without further purification.

LCMS: METCR1673 Generic 2 minutes rt=1.09 min, M/Z (ES−)=234 [M−H+], 80% UV

Synthesis of Intermediate I-03

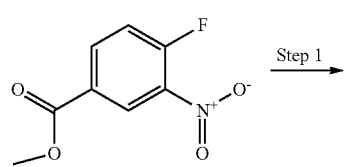

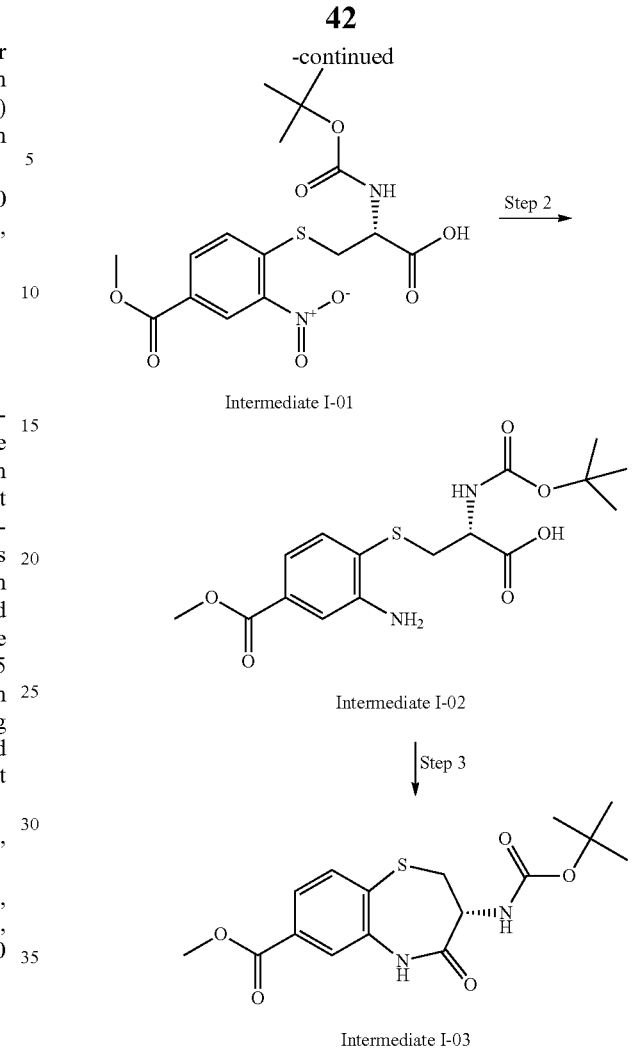

Intermediate I-01

Intermediate I-02

Intermediate I-03

The synthetic route was performed by adaptation of the method described in E. Ayral et al. *Bioorg. Med. Chem. Lett.* 2009, 19, 1386-1391.

Step 1: Synthesis of (2R)-2-{[(tert-butoxy)carbonyl]amino}-3-{[4-(methoxycarbonyl)-2-nitrophenyl]sulfanyl}propanoic acid (intermediate I-01)

Methyl 4-fluoro-3-nitrobenzoate (15 g, 75.33 mmol) was dissolved in 300 mL of EtOH. N-(tert-butoxycarbonyl)-L-cysteine (15.15 g, 68.48 mmol) was added in one portion, followed by a solution of NaHCO$_3$ (12.6 g, 150.6 mmol) in water (75 mL). The bright yellow suspension was stirred at 80° C. for 3 h. The solvent was removed under reduced pressure. The residue was diluted with water (100 mL) and washed with Et$_2$O (3×50 mL). The aqueous phase was acidified with 1M HCl and extracted with EtOAc (2×80 mL). The combined organic phases were washed with brine, dried over Na$_2$SO$_4$, filtered and concentrated under reduced pressure to afford 29.36 g of the desired product as a pale yellow solid in 86.7% yield.

LCMS: METCR1416 Generic 7 minutes rt=3.15 min, M/Z (ES−)=399 [M−H+], 81%

NMR: 1H NMR (500 MHz, CDCl$_3$) δ 8.80 (s, 1H), 8.18 (dd, J=8.5, 1.6 Hz, 2H), 7.62 (d, J=8.3 Hz, 1H), 5.38 (d, J=6.9 Hz, 1H), 4.73-4.67 (m, 1H), 3.96 (s, 3H), 1.43 (s, 9H).

Step 2: Synthesis of (2R)-3-{[2-amino-4-(methoxycarbonyl)phenyl]sulfanyl}-2-{[(tert-butoxy)carbonyl]amino}propanoic acid (intermediate I-02)

1M HCl (6.5 mL, 6.53 mmol, 0.1 eq) was added to intermediate I-01 (89%, 29.4 g, 65.26 mmol, 1 eq) dissolved in 60/1 EtOH/water (610 mL). The reaction mixture was heated at 50° C. then iron (36.44 g, 652.6 mmol, 10 eq) was added to the reaction mixture. The reaction mixture was stirred and heated at 80° C. for 16 h. The reaction mixture was then cooled down and filtered through Celite®. The Celite® was washed with EtOH (4×400 mL). The filtrates were combined and concentrated to 400 mL. The dark solution was filtered once more through Celite and rinsed with EtOH (4×300 mL). The filtrates were combined and concentrated under reduced pressure to afford 24.9 g of the desired product as a dark solid in 80% yield.

LCMS: METCR1673 Generic 2 minutes rt=1.71 min, M/Z (ES+)=393 [M+Na+], 71% UV

Step 3: Synthesis of methyl (3R)-3-{[(tert-butoxy)carbonyl]amino}-4-oxo-2,3,4,5-tetrahydro-1,5-benzothiazepine-7-carboxylate (intermediate I-03)

NaHCO₃ (22.0 g, 262.16 mmol, 5 eq) followed by PyBOP (30.0 g, 57.68 mmol, 1.1 eq) were added to intermediate I-02 (78%, 24.9 g, 52.43 mmol, 1 eq) in anhydrous DMF (500 mL). The reaction mixture was stirred at RT for 2 h. The reaction mixture was concentrated under reduced pressure. The residue was suspended in DCM (500 mL) and the suspension was washed with 1N NaOH (200 mL). The resulting emulsion was filtered through a sinter funnel and the residue was rinsed with DCM (2×150 mL). The filtrates were combined and the layers were separated. The organic layer was washed with sat. NaHCO₃ (2×100 mL), 1% citric acid solution (100 mL) then brine (100 mL), and dried on Na₂SO₄. Filtration and concentration under reduced pressure afforded the crude product as brown oil. Purification by flash column chromatography (silica, eluent: DCM and 0-0.1% MeOH) followed by trituration in Et₂O afforded 9.9 g of the desired compound as an off-white solid in 48% Yield.

LCMS: METCR1673 Generic 2 minutes: rt=1.91 min, M/Z (ES+)=375 [M+Na+], 91% UV

NMR (500 MHz, CDCl3) δ 1.40 (s, 9H), 3.01 (t, J=11.38 Hz, 1H), 3.82 (dd, J=6.27, 10.90 Hz, 1H), 3.93 (s, 3H), 4.42-4.52 (m, 1H), 5.58 (d, J=7.33 Hz, 1H), 7.63-7.72 (m, 2H), 7.76 (d, J=1.56 Hz, 1H), 7.83 (dd, J=1.61, 8.03 Hz, 1H)

Synthesis of Intermediate II-03

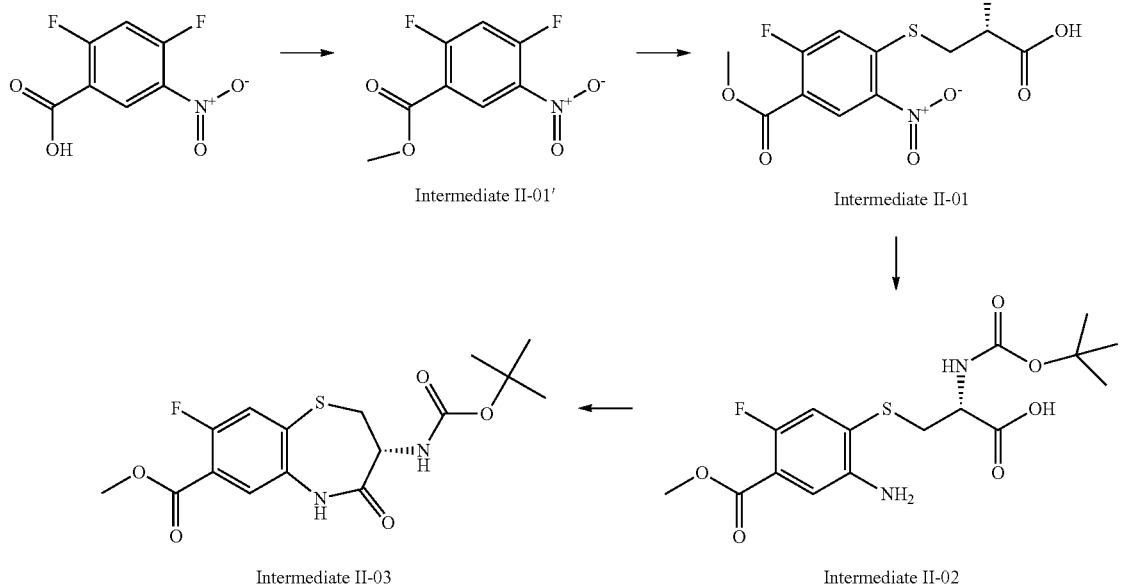

Intermediate II-01'

Intermediate II-01

Intermediate II-03

Intermediate II-02

Step 1: Synthesis of methyl 2,4-difluoro-5-nitrobenzoate (intermediate II-01')

2,4-difluoro-5-nitrobenzoic acid (25.00 g, 123 mmol) was dissolved in MeOH (300 mL). Sulfuric acid (0.7 mL, 12.3 mmol, 0.1 eq) was added dropwise. The reaction was heated to 65° C. for 40 h. The reaction mixture was cooled and concentrated under reduced pressure. The residue was taken up into DCM (100 mL) and washed with water (50 mL), aqueous saturated NaHCO₃ solution (50 mL) and brine (50 mL). The aqueous layer was back-extracted with DCM (2×50 mL). The combined organic phases were dried over Na₂SO₄, filtered and concentrated under reduced pressure to afford 25.21 g of the desired product as a light brown solid. Yield: 93% in 99% purity.

LCMS: METCR1673 Generic 2 minutes rt=1.14 min, M/Z (ES+) no ionisation, 99%;

NMR: 1H NMR (500 MHz, DMSO-d6) δ 8.70-8.58 (m, 1H), 7.90 (t, J=11.0 Hz, 1H), 3.91 (s, 3H).

Step 2: Synthesis of (2R)-2-{[(tert-butoxy)carbonyl]amino}-3-{[5-fluoro-4-(methoxycarbonyl)-2-nitrophenyl]sulfanyl}propanoic acid (intermediate II-01)

To a stirred solution of intermediate II-01' (99%, 24 g, 110 mmol, 1.01 eq) and N-(tert-butoxycarbonyl)-L-cysteine (95%, 5.500 g, 24 mmol, 1 eq) in DCE (700 mL) was added DIPEA (30.55 mL, 219 mmol, 2 eq). The reaction was heated to 80° C. and stirred for 3 h. The reaction mixture was added to water (400 mL) and DCM (200 mL) and acidified to pH 1 with 1N HCl. The organic layer was separated and washed with brine (200 mL), dried over $Na_2SO_4$, filtered and concentrated under reduced pressure to afford the crude product as a yellow foam, which was used in the next step without further purification. Yield 45.90 g, 81% in 81% purity.

LCMS: METCR1673 Generic 2 minutes rt=1.28 min, M/Z (ES+) 441 [M+Na+], 81% UV

NMR: 1H NMR (500 MHz, Chloroform-d) δ 11.33 (s, 1H), 8.88 (d, J=6.6 Hz, 1H), 7.35 (d, J=11.3 Hz, 1H), 5.44 (d, J=6.4 Hz, 1H), 4.77-4.68 (m, 1H), 3.99 (s, 3H), 3.69-3.59 (m, 1H), 3.43 (dt, J=13.2, 6.7 Hz, 1H), 1.46 (s, 9H).

Step 3: Synthesis of (2R)-3-{[2-amino-5-fluoro-4-(methoxycarbonyl)phenyl]sulfanyl}-2-{[(tert-butoxy)carbonyl]amino}propanoic acid (intermediate II-02)

Intermediate II-01 (81%, 45 g, 87 mmol) was dissolved in EtOH (600 mL) and water (100 mL). 1M HCl (8.71 mL, 8.7 mmol, 0.1 eq) was added and the reaction mixture was heated to 50° C. Iron (34.06 g, 610 mmol) was added to the hot and stirred reaction mixture. Heating was continued at 80° C. for 16 h. The reaction mixture was cooled to RT, filtered through Celite®. The filter cake was washed with EtOAc (400 mL×2), filtered once more through Celite® and concentrated under reduced pressure to afford the product as a black solid, which was used in the next step without further purification. Yield 50 g, assumed quantitative (containing traces of iron) in 85% purity (by LCMS).

LCMS: METCR1673 Generic 2 minutes: rt=1.24, M/Z (ES-)=387 [M-H+], 85% UV

Step 4: Synthesis of methyl (3R)-3-{[(tert-butoxy)carbonyl]amino}-8-fluoro-4-oxo-2,3,4,5-tetrahydro-1,5-benzothiazepine-7-carboxylate (intermediate II-03)

Method A:

Intermediate II-02 (85%, 40 g, 87.54 mmol) and DIPEA (54.69 mL, 306 mmol, 3.5 eq) were dissolved in DMF (600 mL). After cooling to 0° C., HATU (49.93 g, 131 mmol, 1.5 eq) was added in portions over 20 minutes, allowing the reaction to warm to RT, which was then stirred for 16 h. The reaction mixture was concentrated under reduced pressure. The residue was dissolved in chloroform: IPA (2:1) (600 mL) and filtered. The filtrate was washed with water (200 mL), followed by brine (200 mL). The aqueous layers were back-extracted with DCM (2×100 mL). The combined organic extracts were concentrated under reduced pressure to yield the crude product as dark brown oil (95 g), which was purified by normal phase flash chromatography (eluent: EtOAc: heptane) to afford the desired product as a yellow solid. Yield 11.2 g, 28% in 85% purity LCMS: METCR1673 Generic 2 minutes: rt=1.24 min, M/Z (ES-)=369 [M-H+], 85% UV;

1H NMR (500 MHz, Chloroform-d) δ 7.71 (d, J=6.2 Hz, 1H), 7.62 (s, 1H), 7.45 (d, J=9.6 Hz, 1H), 5.59 (s, 1H), 4.49 (s, 1H), 3.97 (s, 3H), 3.86-3.77 (m, 1H), 3.03 (t, J=11.2 Hz, 1H), 1.43 (s, 9H).

Method B:

To a suspension of intermediate II-02 (69%, 8 g, 14 mmol) in THF (100 mL) was added DIPEA (6.19 mL, 35.5 mmol) and T3P® 50% solution in EtOAc (16.75 mL, 28 mmol). The reaction was stirred at room temperature for 3 h and then quenched with water (150 mL). The mixture was extracted with EtOAc (150 mL×2). The organic extracts were combined and dried with $MgSO_4$ and the solvent was removed under reduced pressure. The crude product was purified by flash chromatography (eluent: EtOAc: heptane) to afford the desired product as an off-white solid. Yield 4.16 g, 67% in 86% purity.

LCMS: METCR1410 Generic 2 minutes: rt=1.1 min, M/Z (ES-)=369 [M-H+], 86% UV;

1H NMR (250 MHz, DMSO-d6) δ 10.11 (s, 1H), 7.70-7.54 (m, 2H), 7.31 (d, J=8.3 Hz, 1H), 4.21-4.02 (m, 1H), 3.88 (s, 3H), 3.56 (dd, J=11.2, 6.4 Hz, 1H), 3.17 (t, J=11.8 Hz, 1H), 1.34 (s, 9H).

Synthesis of Intermediate III-03

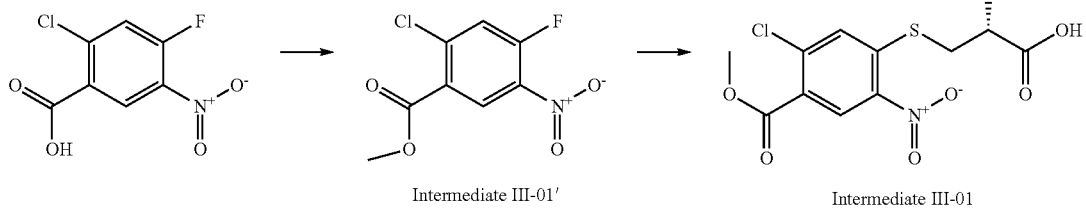

Intermediate III-01'   Intermediate III-01

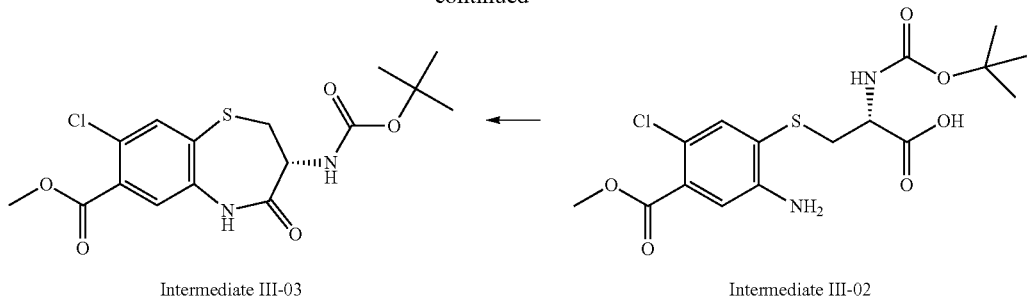

Intermediate III-03                                    Intermediate III-02

Step 1: Synthesis of methyl 2-chloro-4-fluoro-5-nitrobenzoate (intermediate III-01')

To a stirred solution of 2-chloro-4-fluoro-5-nitrobenzoic acid (9.93 g, 45.23 mmol) in MeOH (100 mL) was added sulfuric acid (2.5 ml, 46.9 mmol). The reaction mixture was stirred at 65° C. for 4 h, molecular sieves were added, and the reaction stirred at 65° C. for further 3 h. The reaction mixture was filtered through Celite® to remove sieves, then concentrated under reduced pressure. The residue was taken up into DCM (200 mL), washed with water (150 mL). The aqueous was further extracted with DCM (4×100 mL). The combined organic phases were washed with aqueous saturated NaHCO$_3$ solution (2×150 mL), brine (150 mL), and dried over MgSO$_4$, filtered and concentrated under reduced pressure to afford 7.12 g of the desired product as a pale yellow solid in 67% yield and in 99% purity.

LCMS: METCR1410 Generic 1.7 min rt=1.09 min, M/Z (ES+) no ionisation, 99%;

1H NMR (250 MHz, Chloroform-d) δ 8.67 (d, J=8.0 Hz, 1H), 7.45 (d, J=10.2 Hz, 1H), 3.98 (s, 3H).

Step 2: Synthesis of (2R)-2-{[(tert-butoxy)carbonyl]amino}-3-{[5-chloro-4-(methoxycarbonyl)-2-nitrophenyl]sulfanyl}propanoic acid (intermediate III-01)

To a stirred solution of intermediate III-01' (99.5%, 2 g, 8.52 mmol) and N,N-diethylethanamine (2.46 ml, 17.65 mmol) in DCE (25 mL) was added portion wise N-(tert-butoxycarbonyl)-L-cysteine (1.98 g, 8.95 mmol). The exothermic reaction caused internal temperature to rise to ~30° C. The reaction was stirred for a further 1.5 h. The reaction mixture was diluted with DCM (20 mL), washed with water (3×20 mL), 1M aqueous HCl solution (2×20 mL), brine (20 mL), dried over MgSO$_4$, filtered and concentrated under reduced pressure to afford 3.5 g of the crude product as a yellow foam, which was used in the next step without further purification in 85% yield and in 90% purity.

LCMS: METCR1410 Generic 1.7 min rt=1.17 min, M/Z (ES+) 433/435 [M+H+], 94% UV

1H NMR (250 MHz, Chloroform-d) δ 8.76 (s, 1H), 7.59 (s, 1H), 5.37 (d, J=7.3 Hz, 1H), 4.73 (s, 1H), 3.96 (s, 3H), 3.70-3.55 (m, 1H), 3.49-3.32 (m, 1H), 1.44 (s, 9H).

Step 3: Synthesis of (2R)-3-{[2-amino-5-chloro-4-(methoxycarbonyl)phenyl]sulfanyl}-2-{[(tert-butoxy)carbonyl]amino}propanoic acid (intermediate III-02)

Intermediate III-01 (3.5 g, 8.05 mmol) was dissolved in EtOH (100 mL) and water (25 mL). 1M aqueous HCl solution (0.8 mL, 0.8 mmol) was added and the reaction mixture was heated to 50° C. Iron (900 mg, 16.12 mmol) was added to the hot and stirred reaction mixture. Heating was continued at 80° C. for 0.5 h. The reaction mixture was cooled to 70° C. and treated with further iron (500 mg, 8.95 mmol), then heating was continued at 80° C. for 6.5 h. The reaction mixture was filtered through Celite®. The filter cake was washed with EtOAc (50 mL×2), and concentrated under reduced pressure to afford the product as a dark brown solid, which was used in the next step without further purification. Yield 3.49 g, assumed quantitative (containing traces of iron) in 89% purity (by LCMS).

LCMS: METCR1410 Generic 1.7 min, rt=1.07, M/Z (ES+)=304.95 [M-Boc+H+], 348.8 [M-tBu+H+], 89% UV

Step 4: Synthesis of methyl (3R)-3-{[(tert-butoxy)carbonyl]amino}-8-chloro-4-oxo-2,3,4,5-tetrahydro-1,5-benzothiazepine-7-carboxylate (intermediate III-03)

To a stirred solution of intermediate III-02 (89%, 3.49 g, 7.67 mmol) in THF (30 mL) was added DIPEA (3.4 ml, 19.18 mmol) and T3P® 50% solution in EtOAc (9.1 ml, 15.44 mmol). The reaction was stirred at room temperature for 1 h and then concentrated under reduced pressure. The residue was diluted with water (30 mL) and extracted into DCM (3×30 mL), washed with brine, and dried over MgSO$_4$, filtered and concentrated under reduced pressure. The crude product was purified by flash chromatography (eluent: heptanes, 0-100% EtOAc) to afford 2.44 g of the desired product as a cream solid in 79% yield and in 96% UV purity.

LCMS: METCR1410 Generic 1.7 min: rt=1.12 min, M/Z (ES+)=330.9/332.7 [M-tBu+H+], 97% UV 1H NMR: (500 MHz, Chloroform-d) δ 7.80 (s, 1H), 7.73 (s, 1H), 7.61 (s, 1H), 5.56 (d, J=7.6 Hz, 1H), 4.46 (dt, J=13.4, 7.0 Hz, 1H), 3.94 (s, 3H), 3.80 (dd, J=10.9, 6.2 Hz, 1H), 3.01 (t, J=11.4 Hz, 1H), 1.40 (s, 9H).

Synthesis of Intermediate IV-03

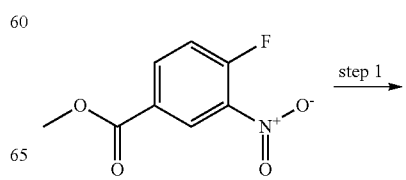

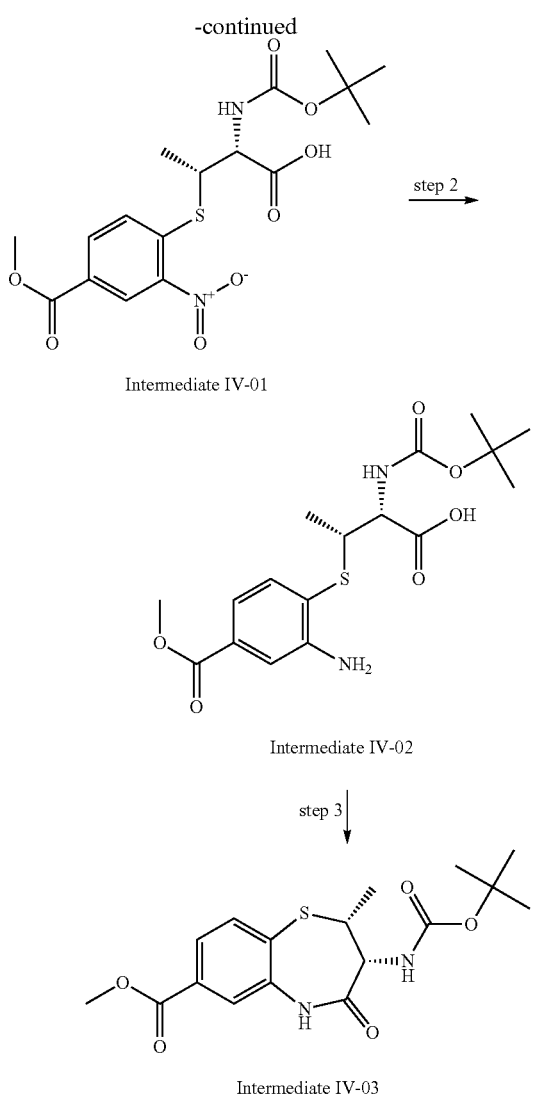

Intermediate IV-01

Intermediate IV-02 step 3

Intermediate IV-03

Step 1: Synthesis of (2R,3R)-2-{[(tert-butoxy)carbonyl]amino}-3-{[4-(methoxycarbonyl)-2-nitrophenyl]sulfanyl}butanoic acid (intermediate IV-01)

Intermediate A-03 (526 mg, 2.01 mmol) was dissolved in MeCN (12 mL) and DIPEA (0.56 mL, 4 mmol) was added. The resulting mixture was stirred at RT for 5 min before adding methyl 4-fluoro-3-nitrobenzoate (361 mg, 1.8 mmol). The resulting mixture was heated to 80° C. for 18 h. The reaction mixture was cooled to RT before addition of 2M aqueous HCl (20 mL). The mixture was extracted with EtOAc (2×15 mL), the combined organic extracts were dried over Na$_2$SO$_4$ and concentrated under reduced pressure to afford 756 mg of the desired product as a yellow solid in 80% UV purity and 72.5% yield, which was used in the next step without further purification.

LCMS: METCR1673 Generic 2 minutes: rt=1.31 min, M/Z (ES+) 437 [M+Na+], 80%

NMR: 1H NMR (500 MHz, DMSO-d6) δ 8.57 (d, J=1.9 Hz, 1H), 8.27-8.10 (m, 1H), 7.90 (d, J=8.6 Hz, 1H), 7.36 (d, J=9.0 Hz, 1H), 4.33-4.20 (m, 1H), 4.06-3.98 (m, 1H), 3.91 (s, 3H), 1.43-1.32 (m, 12H).

Step 2: Synthesis of (2R,3R)-3-{[2-amino-4-(methoxycarbonyl)phenyl]sulfanyl}-2-{[(tert-butoxy)carbonyl]amino}butanoic acid (intermediate IV-02)

Intermediate IV-01 (80%, 1.04 g, 2.09 mmol) was dissolved in a mixture of EtOH (20 mL) and water (2 mL). 1N HCl (0.2 mL) was added and the reaction mixture was heated to 50° C. Iron (586 mg, 10.44 mmol) was added to the hot stirred reaction mixture. The dark reaction mixture was stirred at 80° C. for 2.5 h. After cooling, the mixture was filtered through Celite® and the filter cake was washed with EtOAc (3×100 mL), followed by mEtOH (1×50 mL). The combined filtrates were concentrated under reduced pressure to afford 1.29 g of the desired product as a black solid at 72% UV purity (containing iron residues), which was used without further purification in the next step.

LCMS: METCR1673 Generic 2 minutes: rt=1.65 min, M/Z (ES−) 383 [M−H+], 72% UV;

Step 3: Synthesis of methyl (2R,3R)-3-{[(tert-butoxy)carbonyl]amino}-2-methyl-4-oxo-2,3,4,5-tetrahydro-1,5-benzothiazepine-7-carboxylate (intermediate IV-03)

Intermediate IV-02 (72%, 1035 mg, 1.94 mmol) and DIPEA (0.338 mL, 1.94 mmol) were dissolved in DMF (20 mL). After cooling to 0° C., HATU (811 mg, 2.13 mmol) was added portionwise. The reaction was allowed to warm up to RT and was stirred for 18 h. The mixture was concentrated under reduced pressure. The residue was partitioned between EtOAc (50 mL) and 1N NaOH (50 mL). The organic layer was washed with 1N HCl (50 mL) and brine (50 mL). Both the aqueous layers (acidic and basic) were separately reextracted with IPA/chloroform mixture (1/1). The combined organic extracts were dried over Na$_2$SO$_4$, filtered and the filtrate was concentrated under reduced pressure. The crude residue was purified by column chromatography (silica, eluent: heptanes, 0-50% EtOAc) to afford 341 mg of the desired product as a yellow solid at 97% UV purity in 47% yield.

LCMS: METCR1673 Generic 2 minutes rt=1.32 min, M/Z (ES−) 365 [M−H+], 97% UV

NMR: 1H NMR (500 MHz, DMSO-d6) δ 10.34 (s, 1H), 7.87-7.56 (m, 3H), 6.99 (d, J=8.2 Hz, 1H), 4.33 (dd, J=8.0, 5.3 Hz, 1H), 3.93 (m, 1H), 3.87 (s, 3H), 1.37-1.21 (m, 12H)

Synthesis of Intermediate V-03

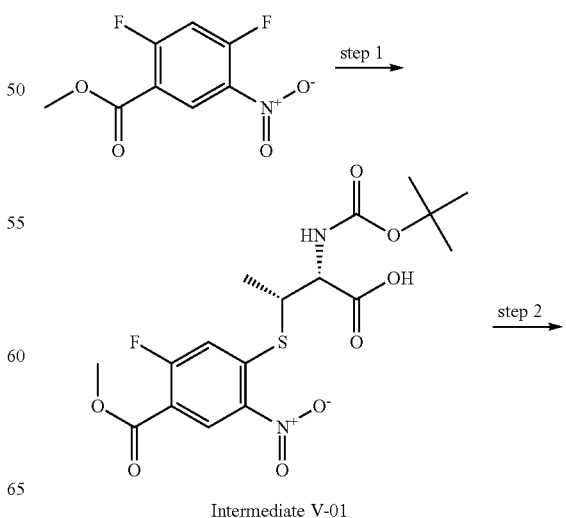

Intermediate V-01

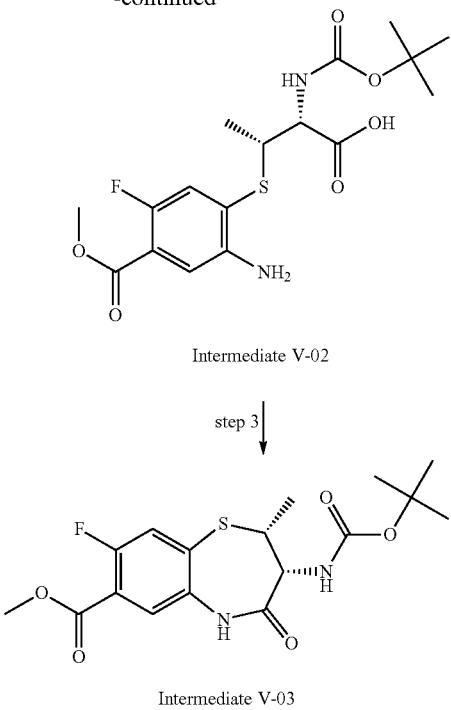

Intermediate V-02 step 3

Intermediate V-03

Step 1: Synthesis of (2R,3R)-2-{[(tert-butoxy)carbonyl]amino}-3-{[5-fluoro-4-(methoxycarbonyl)-2-nitrophenyl]sulfanyl}butanoic acid (intermediate V-01)

Intermediate A-03 (466 mg, 1.78 mmol) was dissolved in 1,2-dichloroethane (30 mL). Then, DIPEA (0.50 mL, 3.57 mmol) was added. The resulting mixture was stirred at RT for 5 min before adding methyl 2,4-difluoro-5-nitrobenzoate (387 mg, 1.78 mmol). The resulting mixture was stirred for 22 h, before it was partitioned between DCM (40 mL) and water (40 mL). The pH was adjusted to pH=1 by addition of 1M aqueous HCl. The organic phase was separated and dried over MgSO$_4$, filtered and the filtrate was concentrated under reduced pressure to afford 767 mg of a yellow oil in 55% UV purity and 55% yield.

LCMS: METCR1410 Generic 1.5 minutes, rt=1.16 min, M/Z (ES+) 455 [M+Na+], 55% UV

NMR: 1H NMR (250 MHz, DMSO-d6) δ 13.21 (br. s, 1H), 8.62 (d, J=7.0 Hz, 1H), 7.76 (d, J=11.6 Hz, 1H), 7.39 (d, J=7.8 Hz, 1H), 4.30 (s, 1H), 4.04 (t, J=6.4 Hz, 1H), 3.93-3.89 (m, 3H), 1.38 (d, J=9.4 Hz, 12H)

Step 2: Synthesis of (2R,3R)-3-{[2-amino-5-fluoro-4-(methoxycarbonyl)phenyl]sulfanyl}-2-{[(tert-butoxy)carbonyl]amino}butanoic acid (intermediate V-02)

Intermediate V-01 (55%, 0.76 g, 0.98 mmol) was dissolved in EtOH (9 mL) and water (2 mL). 1N HCl (0.1 mL) was added and the reaction mixture was heated to 50° C. Iron (381 mg, 6.83 mmol) was added and the reaction heated to 80° C. for 2 h. The reaction mixture was left to cool to RT and filtered through Celite® eluting with EtOAc (3×100 mL). The filtrate was concentrated under reduced pressure to afford 0.69 g of a dark brown oil at 55% UV purity and 97% yield, which was used in the next step without further purification.

LCMS: METCR1410 Generic 1.5 minutes rt=1.10 min, M/Z (ES−) 401 [M−H+], 55% UV

Step 3: Synthesis of methyl (2R,3R)-3-{[(tert-butoxy)carbonyl]amino}-8-fluoro-2-methyl-4-oxo-2,3,4,5-tetrahydro-1,5-benzothiazepine-7-carboxylate (intermediate V-03)

Intermediate V-02 (55%, 690 mg, 0.94 mmol) and DIPEA (0.411 mL, 2.36 mmol) were dissolved in THF (20 mL). T3P® 50% in EtOAc (1.11 mL, 1.89 mmol) was added and the reaction was stirred for 1.5 h at RT. The mixture was quenched with water (15 mL) and extracted with EtOAc (15 mL×2). The extracts were dried over MgSO$_4$ and the solvent was removed under reduced pressure to give a crude oil. The crude was purified by flash chromatography (eluent: heptanes, 10%-100% EtOAc) to give 341 mg of a yellow solid at 90% UV purity in 74% yield.

LCMS: METCR1410 Generic 1.5 minutes, rt=1.26 min, M/Z (ES−) 383 [M−H+], 90% UV;

NMR: 1H NMR (250 MHz, DMSO-d6) δ 10.26 (s, 1H), 7.64-7.54 (m, 2H), 6.99 (d, J=8.1 Hz, 1H), 4.34 (dd, J=8.0, 5.3 Hz, 1H), 4.00-3.90 (m, 1H), 3.86 (s, 3H), 1.41-1.22 (m, 12H).

The corresponding (2S,3R)-diastereoisomers of intermediate IV-03 and V-03 can be synthesized using (2R,3S)-2-{[(tert-butoxy)carbonyl]amino}-3-hydroxybutanoic acid according to above procedures.

Synthesis of Intermediate (1R)-2,2-difluorocyclopropan-1-amine hydrochloride

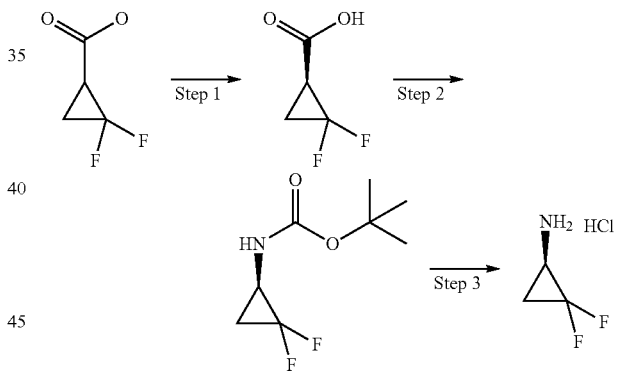

Step 1: Synthesis of (1S)-2,2-difluorocyclopropane-1-carboxylic acid

To a stirred solution of 2,2-difluorocyclopropane-1-carboxylic acid (50%, 36 g, 147.46 mmol) in MeCN (300 ml) was added (1S)-1-(4-methoxyphenyl)ethan-1-amine (43.55 ml, 147.46 mmol). The reaction was stirred at RT for 4 h until the precipitation of a thick off white solid occurred. The desired (S) enantiomer of the acid precipitates out of solution forming a conglomerate with (1S)-1-(4-methoxyphenyl)ethan-1-amine and the undesired (R) enantiomer stays in solution and can be washed out during filtration (Reference: WO 2014/170197 A1). The initial precipitated conglomerate (49 g), was recrystallized from hot MeCN (×8). The crystalline solid was isolated by filtration and rinsed with cold MeCN. The 22.8 g of conglomerate was then separated by SCX-2 cartridges (2×70 g, eluent MeOH) and the fractions were concentrated under reduced pressure to afford 8.56 g of the desired product as of an off white solid in 47.5% yield and 100% purity as determined by NMR.

NMR: 1H NMR (250 MHz, Chloroform-d) δ 9.65 (s, 1H), 2.45 (ddd, J=12.6, 10.7, 7.8 Hz, 1H), 2.09 (dtd, J=12.1, 7.8, 6.5 Hz, 1H), 1.92-1.59 (m, 1H).

Step 2: Synthesis of tert-butyl N-[(1R)-2,2-difluorocyclopropyl]carbamate

To a stirred solution of (1S)-2,2-difluorocyclopropane-1-carboxylic acid (8.56 g, 70.12 mmol) in tBuOH (100 ml) was added TEA (11.83 ml, 84.15 mmol) followed by diphenylphosphoryl azide (18.09 ml, 84.15 mmol) at RT. The reaction was then heated at 90° C. for 18 h. The reaction was monitored by thin-layer chromatography (eluent: heptanes, 10% EtOAc, staining KMnO$_4$, R$_f$ 0.27). The solvent was removed under reduced pressure and the crude residue obtained was purified by column chromatography (100 g SNAP, eluent: heptanes, 0-10% EtOAc) to afford 8.1 g of the desired product as a white solid in 60% yield and in 100% purity as determined by NMR.

NMR: 1H NMR (250 MHz, Chloroform-d) δ 4.82 (s, 1H), 3.14 (s, 1H), 1.85-1.62 (m, 1H), 1.46 (s, 1H), 1.34 (td, J=9.0, 4.1 Hz, 1H).

Step 3: Synthesis of (1R)-2,2-difluorocyclopropan-1-amine hydrochloride

To a stirred solution of tert-butyl N-[(1R)-2,2-difluorocyclopropyl]carbamate (8.1 g, 41.93 mmol) in dioxane (5 mL) was added 4M HCl solution in 1,4-dioxane (41.93 mL). The reaction was stirred for 3 h at RT. Reaction progress was monitored by thin-layer chromatography (eluent: heptanes, 10% EtOAc, staining KMnO$_4$, disappearance of R$_f$ 0.27). The precipitate was isolated by filtration, rinsed with 1,4-dioxane and dried under reduced pressure to yield 3.38 g of the desired product as a white solid. In 62% yield and 100% purity as determined by NMR.

NMR: 1H NMR (250 MHz, DMSO-d6) δ 9.02 (s, 2H), 3.52-3.32 (m, 1H), 2.21-2.00 (m, 1H), 1.99-1.80 (m, 1H).

General Procedures for 2,3,4,5-tetrahydro-1,5-benzothiazepine Derivatives

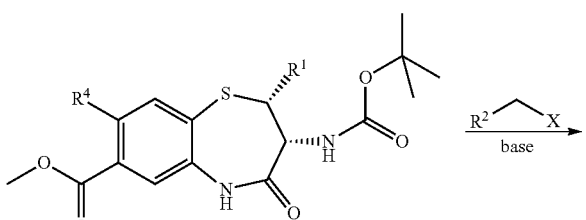

Intermediates (I, II, IV, V)-03

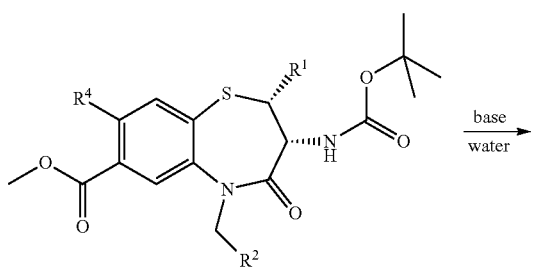

Intermediate VI

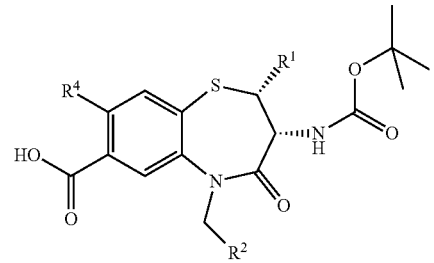

intermediate VII

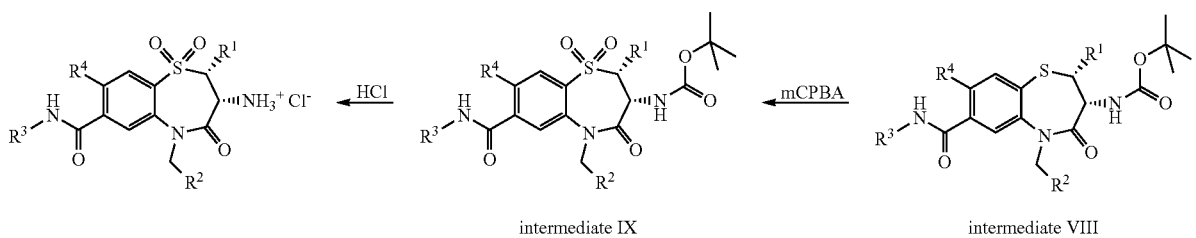

intermediate IX     intermediate VIII

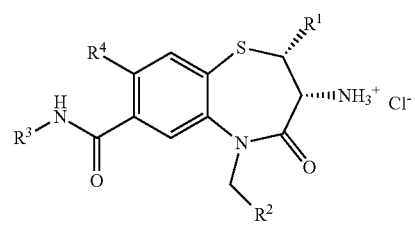

General Procedure 1 (GP1): Synthesis of Intermediate VI

Conditions 1: To a stirred solution of intermediate (I-II, IV-V)-03 in anhydrous DMSO (20 Vol) were added $K_2CO_3$ (3 eq), $R^2$—$CH_2$—X (1.5 eq) (X representing halo or appropriate leaving group) and KI (0.5 eq). The reaction mixture was stirred at RT for 16 h. Water (50 Vol) was added dropwise to the mixture and cooled to 0° C., which formed a precipitate. The precipitate was filtered and washed with water (2×50 Vol) and then purified by flash column chromatography to afford the desired intermediate VI.

Conditions 2: A suspension of NaH (60%, 1.2 eq) in anhydrous THF (20 Vol.) (or DMF) at 0° C. was added drop-wise to a solution of intermediate (I-II, IV-V)-03 in anhydrous THF (10 Vol) (or DMF). The reaction mixture was stirred at 0° C. for 20 min then $R^2$—$CH_2$—X (1.5 eq) (X representing halo or appropriate leaving group) was added slowly. The reaction mixture was allowed to warm to RT and stirred for 18 h. The reaction mixture was quenched with water (10 Vol). DCM was added and the aqueous layer was extracted with further DCM (2×15 Vol). The combined organic layers were washed with brine, dried over $Na_2SO_4$, filtered and concentrated under reduced pressure. The crude product was purified by flash column chromatography to afford the desired intermediate VI.

General Procedure 2 (GP2): Synthesis of Intermediate VII

Intermediate VI was dissolved in a mixture of THF/MeOH/water (10/1/3; 10 Vol). Lithium hydroxide hydrate (2 eq) was added and the reaction mixture was stirred for 16 h or until completion.

The reaction mixture was concentrated under reduced pressure. The residue was dissolved in DCM (10 Vol) and washed with 2N HCl (3 Vol). The aqueous layer was back-extracted with DCM (2×10 Vol) and a mixture of IPA/chloroform (1/1, 10 Vol). The combined organic layers were washed with brine (10 Vol), dried on $Na_2SO_4$ and filtered. The filtrate was concentrated under reduced pressure to afford intermediate VII, which was used in the next step without further purification.

General Procedure 3 (GP3): Synthesis of Intermediate VIII
Amide Coupling Using HATU as Reagent Intermediate VII was dissolved in DMF (3 Vol) and DIPEA (3.5 eq) was added. After cooling to 0° C., HATU (1.5-3 eq) was added to the reaction mixture, which was stirred at 0° C. for 20 min. Amine $R^3NH_2$ (1.2 eq) was added and the reaction was stirred at 0° C. for 5 min and then stirred at RT for 16 h. The mixture was concentrated under reduced pressure and the residue treated to afford the desired intermediate VIII by either of the following methods or adaptations thereof:

Work-Up Method a:

DCM was added to the residue, it was washed with water twice and brine once. The organic phases were recombined dried over $Na_2SO_4$ and concentrated under reduced pressure. The residue was purified by column chromatography Work-Up Method b:

DCM was added to the residue, it was washed with water, 1N HCl, 1N NaOH and brine once. The organic phases were recombined dried over $Na_2SO_4$ and concentrated under reduced pressure. The residue was purified by column chromatography Work-Up Method c:

The reaction mixture was concentrated under reduced pressure and the residue was purified by column chromatography.

Amide Coupling Using T3P® as Reagent

To solution of intermediate VII (700 mg, 1.36 mmol) in DCM (10 Vol) was added TEA (5 eq) and 50% solution of T3P® in EtOAc (2 eq). The reaction mixture was stirred at room temperature for 10 min. Then Amine $R^3NH_2$ (0.9 eq) was added. The reaction mixture was stirred at room temperature for 8 h. The reaction mixture was diluted with water and DCM and saturated $K_2CO_3$ solution was added. The aqueous layer was extracted with DCM. The combined organic extracts were washed with water, dried over sodium sulfate and concentrated under reduced pressure to afford crude intermediate VIII, which was purified by column chromatography (if required).

General Procedure 4 (GP4): Synthesis of Intermediate IX

Intermediate VIII was dissolved in DCM (2 Vol) and the reaction mixture was cooled to 0° C. m-CPBA (3.5 eq) was added portion-wise and the reaction mixture was stirred at 0° C. for 15 to 30 min. and at RT for 16 to 54 h until completion. The reaction mixture was diluted with DCM and washed with aqueous 1M NaOH solution (×2) and brine. The organic layer was dried over sodium sulfate, filtered and the filtrate concentrated under reduced pressure. The residue was purified by reverse phase column chromatography (Biotage neutral pH) to afford the desired intermediate IX.

General Procedure 5 (GP5): Synthesis of Final Compounds (Examples 1-183)

Intermediate VIII or intermediate IX were deprotected to release the primary amine by treating with an excess of an ethereal solution of HCl, e.g. 4N HCl in dioxane. After stirring at RT for 2-12 h the reaction mixture was concentrated under reduced pressure to afford the desired compounds as hydrochloride salts.

Occasionally further purification was required which was performed by reverse phase column chromatography, after which the pure product was retreated with HCl in dioxane or used as the freebase (as indicated).

Alternatively the hydrochloride salts can be converted into the freebase by adaptation of one of the following methods:

Free Base Method 1: SCX-2 Cartridge

The HCl salt of the final compound was dissolved in minimal MeOH and the solution loaded onto the SCX-2 cartridge. The cartridge was flushed with MeOH (3×10 mL). The compound was then eluted with 7M $NH_3$ in MeOH solution (3×10 mL). The fractions were combined and concentrated under reduced pressure to afford the free base of the final compound.
Free Base Method 2: KP-NH Column The HCl salt of the final compound was dissolved in DCM (with MeOH if necessary) and freebased by eluting from a Biotage SNAP KP-NH basic silica cartridge Biotage Isolera (gradient 0-10% MeOH in DCM). The fractions were combined and concentrated under reduced pressure to afford the free base of the final compound.
Free Base Method 3: Aqueous Extraction The HCl salt of the final product was suspended in DCM (5 mL) and saturated aqueous NaHCO₃ (1 mL) solution and water (5 mL) was added. The layers were separated and the organic layer was washed with water (5 mL), passed through a TELOS hydrophobic phase separator and concentrated under reduced pressure to afford the free base of the final compound.

Racemic mixtures of compounds of claim (I) can be synthesized according to above procedures using the appropriate racemic starting materials or intermediates.

The manner in which the compounds of the invention can be made will be further understood by way of the following examples.

Example GP1

Synthesis of methyl (3R)-3-{[(tert-butoxy)carbonyl] amino}-5-[(4-chlorophenyl)methyl]-8-fluoro-4-oxo-2,3,4,5-tetrahydro-1,5-benzothiazepine-7-carboxylate (Intermediate VI-01)

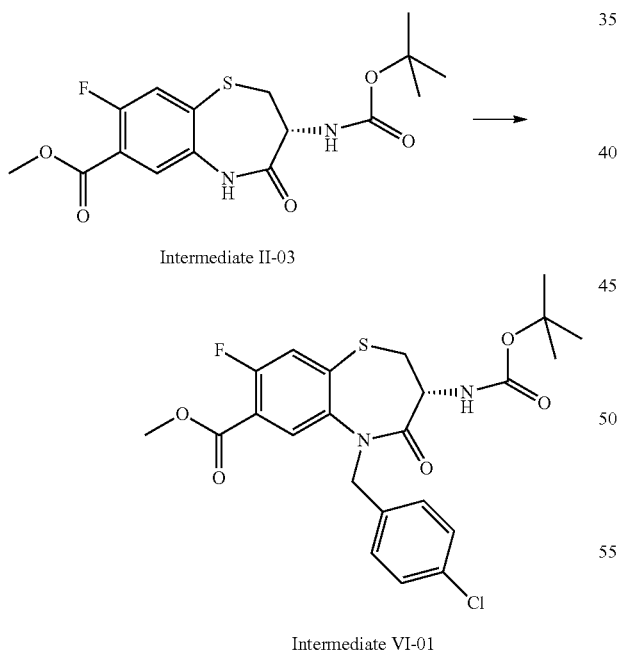

Intermediate II-03

Intermediate VI-01

To a stirred solution of intermediate II-03 (86%, 3.00 g, 6.97 mmol) in anhydrous DMSO (40 mL), K₂CO₃ (2.89 g, 20.9 mmol, 3 eq) were added 1-(bromomethyl)-4-chlorobenzene (98%, 2.19 g, 10.5 mmol, 1.5 eq) and KI (0.58 g, 3.48 mmol, 0.5 eq). The reaction mixture was stirred at room temperature for 16 h. The reaction mixture was cooled and water (50 mL) was added. The resulting precipitate was isolated by filtration and rinsed with water (50 mL). The isolated solid was further purified by column chromatography (silica, eluent: heptanes, 0-50% EtOAc) to afford the desired intermediate VI-01 as an off-white solid. Yield 2.00 g, 57% in 98% purity;

LCMS: METCR1440 Generic 1.5 minutes: rt=1.35 min, M/Z (ES+) 517/519 [M+Na+]; 98% UV 1H NMR (500 MHz, Chloroform-d) d 8.94 (d, J=10.7 Hz, 1H), 7.73 (dd, J=10.5, 6.4 Hz, 1H), 7.61-7.55 (m, 1H), 7.45 (d, J=8.4 Hz, 1H), 7.29 (q, J=8.4 Hz, 4H), 5.31-5.19 (m, 1H), 4.89 (d, J=15.6 Hz, 1H), 4.16 (dt, J=12.1, 7.6 Hz, 1H), 3.49 (dd, J=11.2, 7.0 Hz, 2H), 3.13 (t, J=11.8 Hz, 1H), 2.04-1.91 (m, 1H), 1.62 (dd, J=14.0, 5.5 Hz, 1H), 1.36 (s, 9H).

Example GP2

Synthesis of (3R)-3-{[(tert-butoxy)carbonyl] amino}-5-[(4-chlorophenyl)methyl]-8-fluoro-4-oxo-2,3,4,5-tetrahydro-1,5-benzothiazepine-7-carboxylic acid (intermediate VII-01)

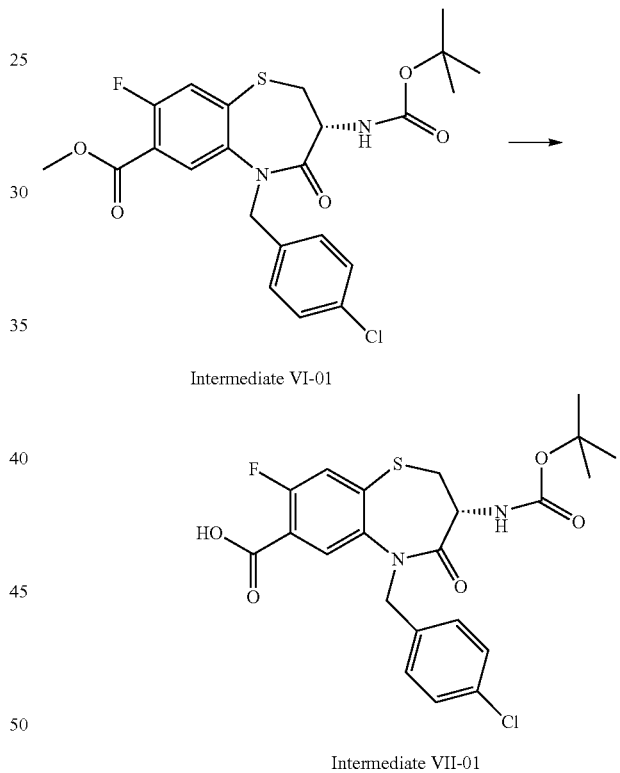

Intermediate VI-01

Intermediate VII-01

Intermediate VI-01 (2 g, 3.96 mmol) was dissolved in a mixture of THF/MeOH/water (7/1/2, 27.7 mL). Lithium hydroxide hydrate (0.19 g, 7.92 mmol, 2 eq) was added and the reaction was stirred for 3 h at RT. The reaction mixture was concentrated under reduced pressure and the residue was dissolved in DCM (30 mL). The solution was washed with 1N HCl (30 mL×2), water (30 mL) and brine (30 mL). The aqueous layers were back-extracted with DCM (50 mL). The combined organic extracts were dried (Na₂SO₄), filtered and the filtrate was concentrated under reduced pressure to afford intermediate VII-01 as a yellow solid (2 g, 100%) in 95% purity.

LCMS: METCR1440 Generic 1.5 minutes: rt 1.23 min, M/Z (ES−) 479/481 [M−H+], 95% UV 1H NMR (500 MHz, Chloroform-d) d 7.87 (d, J=6.7 Hz, 1H), 7.58 (d, J=9.9 Hz, 1H), 7.47 (d, J=8.2 Hz, 1H), 7.30 (q, J=8.5 Hz, 4H), 5.18 (d, J=15.8 Hz, 1H), 4.94 (d, J=15.7 Hz, 1H), 4.17 (dt, J=12.2, 7.8 Hz, 1H), 3.49 (dd, J=11.2, 6.8 Hz, 1H), 3.14 (t, J=11.7 Hz, 1H), 1.36 (s, 9H).

Example GP3

Synthesis of N-[(3R)-5-[(4-chlorophenyl)methyl]-7-[(2,2-difluorocyclopropyl)carbamoyl]-8-fluoro-4-oxo-2,3,4,5-tetrahydro-1,5-benzothiazepin-3-yl]carbamate (intermediate VIII-01)

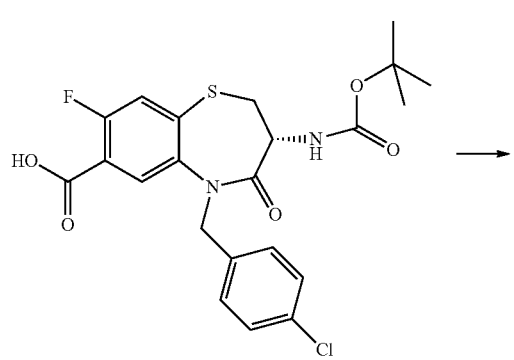

Intermediate VII-01

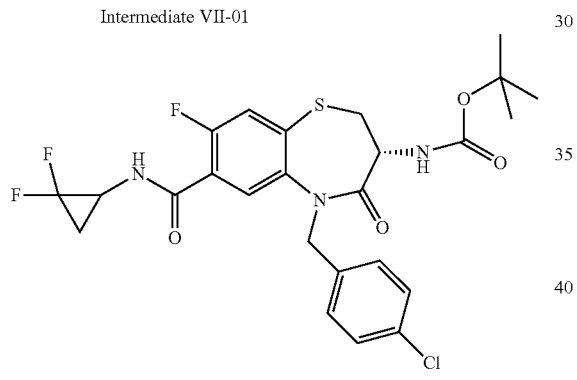

Intermediate VIII-01

Intermediate VII-01 (90%, 2 g, 3.83 mmol) was dissolved in DMF (20 mL) and DIPEA (3 mL, 17.24 mmol, 4.5 eq) was added. The mixture was cooled to 0° C., HATU (4.37 g, 11.49 mmol, 3 eq) was added and the mixture stirred for 30 min. The reaction was warmed to RT, 2,2-difluorocyclopropanamine hydrochloride (1:1) (0.744 g, 5.75 mmol, 1.5 eq) was added and stirring was continued for 4 h. The solvent was removed under reduced pressure. The residue was dissolved in DCM (100 mL), washed with water (50 mL×2) and brine (50 mL). The organic phase was dried over sodium sulfate, filtered and the filtrate concentrated under reduced pressure. The residue was purified by column chromatography (silica, eluent: heptanes, 0-50% EtOAc) to obtain the desired intermediate VIII-01 as an off-white solid (1.03 g, 47%) in 99% purity.

LCMS: METCR1440 Generic 1.5 minutes: rt=1.31 min, M/Z (ES+) 578/580 [M+Na+], 99% UV;

1H NMR (500 MHz, DMSO-d6) δ 8.94 (d, J=10.8 Hz, 1H), 7.73 (dd, J=10.5, 6.4 Hz, 1H), 7.58 (d, J=9.2 Hz, 1H), 7.45 (d, J=8.3 Hz, 1H), 7.29 (q, J=8.4 Hz, 4H), 5.34-5.15 (m, 1H), 4.89 (d, J=15.6 Hz, 1H), 4.16 (dt, J=12.1, 7.8 Hz, 1H), 3.49 (dd, J=11.2, 6.9 Hz, 2H), 3.13 (t, J=11.7 Hz, 1H), 2.05-1.91 (m, 1H), 1.68-1.54 (m, 1H), 1.36 (s, 9H).

Example GP4

Synthesis tert-butyl N-[(3R)-5-[(4-chlorophenyl)methyl]-7-[(2,2-difluorocyclopropyl)-carbamoyl]-8-fluoro-1,1,4-trioxo-2,3,4,5-tetrahydro-1λ⁶,5-benzothiazepin-3-yl]carbamate (intermediate IX-01)

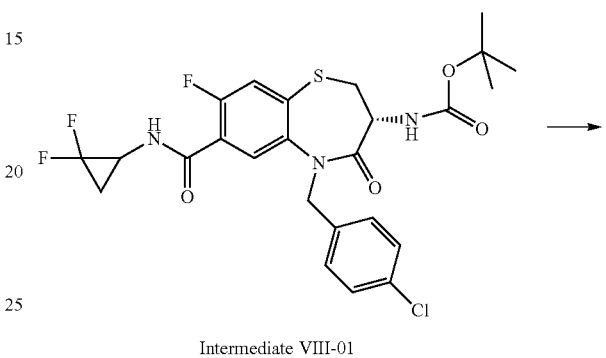

Intermediate VIII-01

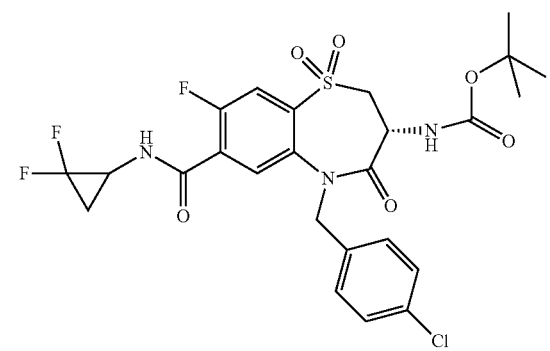

Intermediate IX-01

Intermediate VIII-01 (99%, 1.03 g, 1.83 mmol) was dissolved in DCM (30 mL) and the reaction mixture was cooled down to 0° C. under nitrogen atmosphere. m-CPBA (77%, 1 g, 4.49 mmol, 2.5 eq) was added portion-wise. The reaction mixture was stirred at 0° C. for 15 min and then at RT for 18 h or until completion. After dilution with DCM (50 mL), the mixture was washed with aqueous 1N NaOH solution (50 mL×2) and brine (50 mL). The organic phase was dried over sodium sulfate, filtered and the filtrate was concentrated under reduced pressure. The residue was purified by reverse-phase column chromatography (Biotage C18 120 g SNAP® cartridge, eluent: water, 0-100% MeCN) to afford intermediate IX-01 as a white solid (0.92 g, 86%) in 99% purity.

LCMS: METCR1440 Generic 1.5 minutes: rt=1.25 min, M/Z (ES+) 610/612 [M+Na+], 99% UV, 1H NMR (500 MHz, DMSO-d6) δ 9.13 (d, J=13.6 Hz, 1H), 7.76 (d, J=8.4 Hz, 1H), 7.63 (dd, J=5.4, 3.0 Hz, 1H), 7.53 (d, J=8.0 Hz, 1H), 7.34 (d, J=1.5 Hz, 4H), 5.23-5.12 (m, 1H), 4.87-4.79 (m, 1H), 4.49-4.36 (m, 1H), 4.13-4.04 (m, 1H), 3.82-3.72 (m, 1H), 3.50 (s, 1H), 2.00 (s, 1H), 1.65-1.57 (m, 1H), 1.37 (s, 9H).

Example GP5

Synthesis (3R)-3-amino-5-[(4-chlorophenyl)methyl]-N-(2,2-difluorocyclopropyl)-8-fluoro-1,1,4-trioxo-2,3,4,5-tetrahydro-1λ⁶,5-benzothiazepine-7-carboxamide hydrochloride (Example 1)

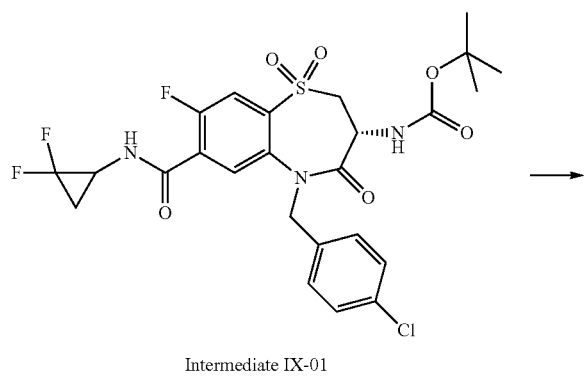

Intermediate IX-01

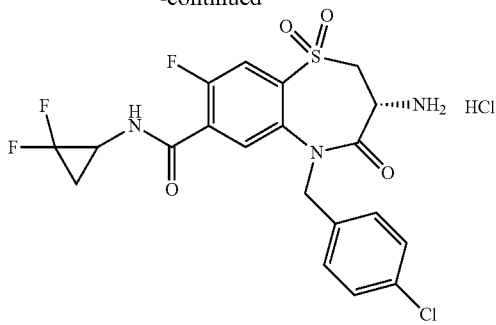

Example 1

Intermediate IX-01 (99%, 0.166 g, 0.279 mmol) was dissolved in 4N HCl in dioxane (3 mL) and the reaction was stirred at RT for 2.5 h or until completion. The mixture was concentrated under reduced pressure dried in the vacuum oven to afford Example 1 as a white solid (0.134 g, 91.4%) in 100% purity.

LCMS: METCR1416 GENERIC 7 MINUTES: rt=3.02 min, M/Z (ES+) 488/490 [M+H+], 100% UV, $^1$H NMR (500 MHz, DMSO-d$_6$) δ 9.14 (d, J=15.1 Hz, 1H), 8.43 (s, 3H), 7.85 (d, J=8.4 Hz, 1H), 7.73 (dd, J=20.2, 5.4 Hz, 1H), 7.42-7.36 (m, 4H), 5.25-5.14 (m, 1H), 4.99-4.86 (m, 1H), 4.47 (q, J=9.9 Hz, 1H), 4.18-4.09 (m, 1H), 4.04-3.93 (m, 1H), 3.57-3.45 (m, 1H), 2.07-1.96 (m, 1H), 1.70-1.57 (m, 1H).

General Procedure 6 (GP6): Variation of Order of Reactions

The above general procedures can be adapted by changing the order of reaction steps

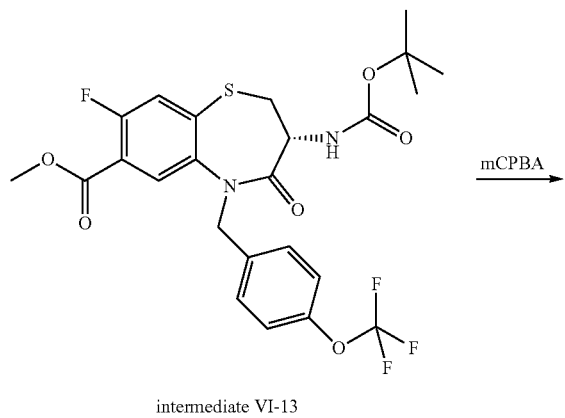

intermediate VI-13

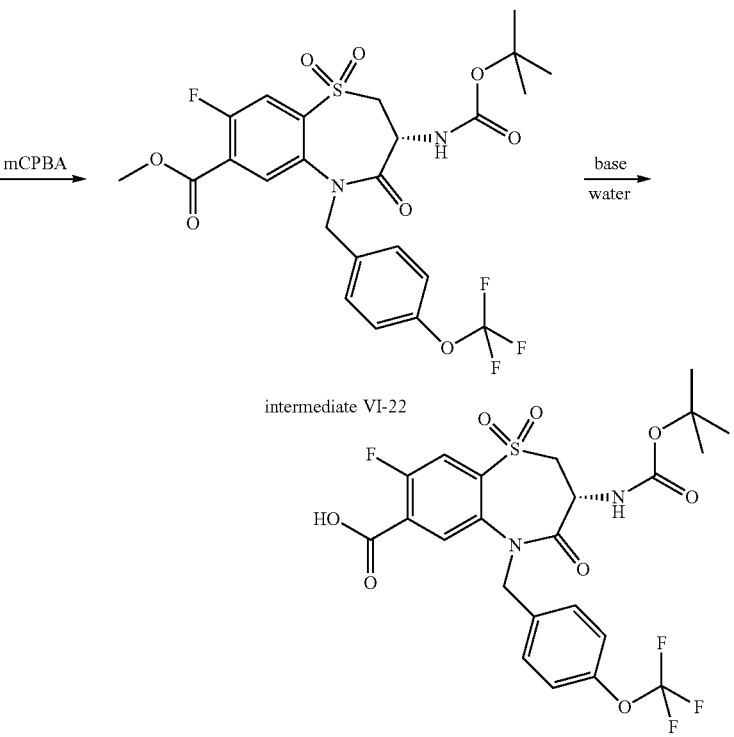

intermediate VI-22 intermediate VII-22

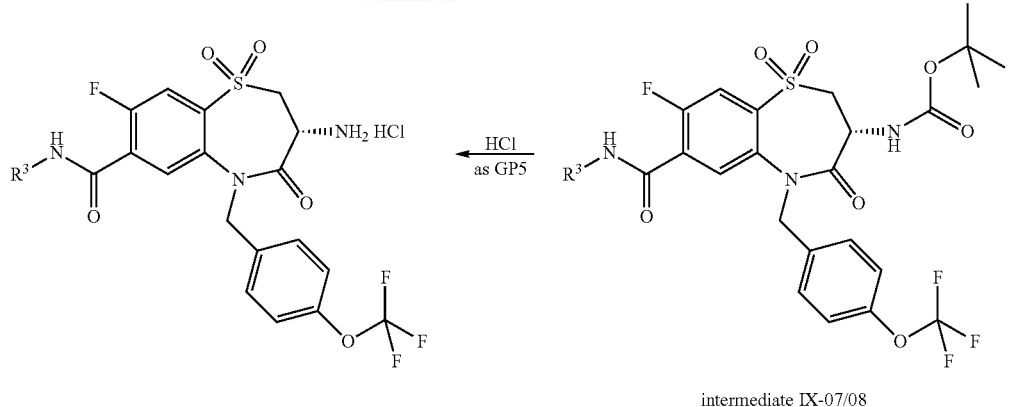

intermediate IX-07/08

Synthesis of methyl (3R)-3-{[(tert-butoxy)carbonyl]amino}-8-fluoro-1,1,4-trioxo-5-{[4-(trifluoromethoxy) phenyl]methyl}-2,3,4,5-tetrahydro-1λ⁶,5-benzothiazepine-7-carboxylate (intermediate VI-22)

m-CPBA (1.1 g, 4.89 mmol, 5 eq) was added to Intermediate VI-13 (92%, 579 mg, 0.98 mmol) in anhydrous DCM (20 mL). Reaction mixture was stirred at RT until completion. The reaction mixture was washed with 1N NaOH (2×15 mL) and the organic layer was dried over sodium sulfate, filtered and the filtrate concentrated under reduced pressure. The residue was purified by column chromatography (silica, heptanes, 5-50% EtOAc) to afford intermediate VI-22, 0.41 g as off-white solid, 71% Yield in 98% UV purity.

LCMS: METCR1673 GENERIC 2 MINUTES: rt=1.50 min, M/Z (ES+) 599 [M+Na+], 98% UV

1H NMR (500 MHz, CDCl3) δ 1.41 (s, 9H), 3.51 (dd, J=11.03, 13.28 Hz, 1H), 3.92 (s, 3H), 4.08 (dd, J=6.90, 13.35 Hz, 1H), 4.53 (dt, J=7.13, 10.86 Hz, 1H), 4.59 (d, J=15.23 Hz, 1H), 5.40 (d, J=15.23 Hz, 1H), 5.68 (d, J=7.15 Hz, 1H), 7.20 (d, J=8.14 Hz, 2H), 7.36 (d, J=8.61 Hz, 2H), 7.67 (d, J=5.61 Hz, 1H), 7.83 (d, J=8.65 Hz, 1H).

Synthesis of (3R)-3-{[(tert-butoxy)carbonyl]amino}-8-fluoro-1,1,4-trioxo-5-{[4-(trifluoromethoxy)phenyl]methyl}-2,3,4,5-tetrahydro-1λ⁶,5-benzothiazepine-7-carboxylic acid (intermediate VII-22)

Lithium hydroxide hydrate (1:1:1) (58.3 mg, 1.39 mmol, 2 eq) was added to intermediate VI-22 (98%, 408.6 mg, 0.70 mmol, 1 eq) in 8/2/1 THF/water/MeOH (11 mL). The reaction mixture was stirred at RT until completion, then concentrated under reduced pressure. The residue was dissolved in DCM (5 mL) and washed with 1N HCl (3 mL). The aqueous layer was extracted with DCM (2×5 mL). The combined organic layers were dried over sodium sulfate, filtered and the filtrate concentrated under reduced pressure to afford intermediate VII-22 as light yellow solid. Yield 212 mg, 38% in 70% UV purity.

LCMS: METCR1673 GENERIC 2 MINUTES: rt=1.50 min, M/Z (ES+) 585 [M+Na+], 70% UV

1H NMR (500 MHz, DMSO-d6) δ 1.36 (s, 9H), 3.72-3.82 (m, 1H), 4.06 (dd, J=7.32, 13.20 Hz, 1H), 4.44 (dt, J=7.64, 11.73 Hz, 1H), 4.77 (d, J=16.13 Hz, 1H), 5.28 (d, J=16.16 Hz, 1H), 7.29 (d, J=8.19 Hz, 2H), 7.43 (d, J=8.44 Hz, 2H), 7.52 (d, J=8.09 Hz, 1H), 7.71-7.79 (m, 2H)

Synthesis of tert-butyl N-[(3R)-8-fluoro-1,1,4-trioxo-7-[(4,4,4-trifluorobutyl)carbamoyl]-5-{[4-(trifluoromethoxy)phenyl]methyl}-2,3,4,5-tetrahydro-1λ⁶,5-benzothiazepin-3-yl]carbamate (intermediate IX-08)

DIPEA (54 µL, 0.31 mmol, 3.5 eq) was added to intermediate VII-22 (70%, 70 mg, 0.09 mmol, 1 eq) in DMF (1.5 mL). The mixture was cooled to 0° C.; then HATU (50 mg, 0.13 mmol, 1.5 eq) was added in one portion. The reaction was stirred at 0° C. for 15 min; then 4,4,4-trifluorobutan-1-amine (13 µL, 0.13 mmol, 1.5 eq) was added. After 15 min at 0° C., the reaction was allowed to warm to RT and stirred until completion. The mixture was concentrated under reduced pressure and the residue was purified by preparative LC (neutral pH method) to give intermediate IX-08 as yellow solid. Yield: 32 mg, 53% in 96% UV purity.

LCMS: METCR1673 GENERIC 2 MINUTES: rt=1.49 min, M/Z (ES+) 694 [M+Na+], 96% UV

1H NMR (500 MHz, Chloroform-d) δ 1.40 (s, 9H), 1.92 (dt, J=7.19, 14.69 Hz, 2H), 2.11-2.26 (m, 2H), 3.55 (qd, J=8.97, 13.63 Hz, 3H), 4.08 (dd, J=6.71, 13.53 Hz, 1H), 4.53 (dt, J=7.00, 10.86 Hz, 1H), 4.84 (d, J=15.25 Hz, 1H), 5.22 (d, J=15.24 Hz, 1H), 5.70 (d, J=7.13 Hz, 1H), 6.77 (dt, J=5.76, 11.56 Hz, 1H), 7.16 (d, J=8.08 Hz, 2H), 7.37 (d, J=8.63 Hz, 2H), 7.82 (d, J=9.87 Hz, 1H), 7.99 (d, J=6.04 Hz, 1H)

General Procedure 7 (GP7): Variation of Order of Reactions

The above general procedures can be adapted by changing the order of reaction steps

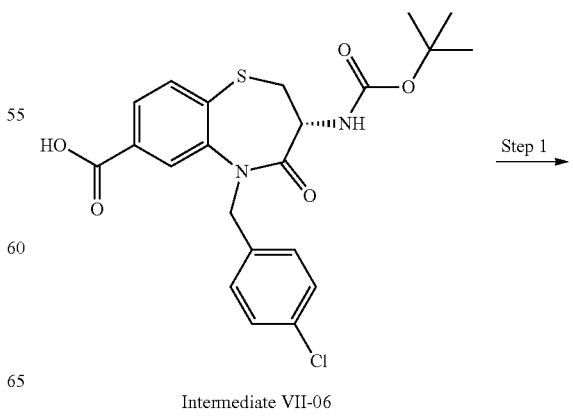

Intermediate VII-06

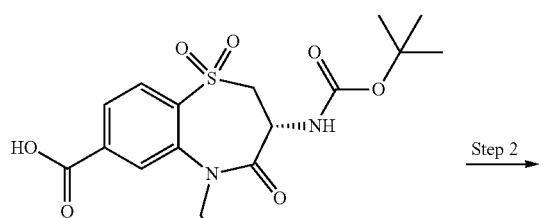

Intermediate VII-35

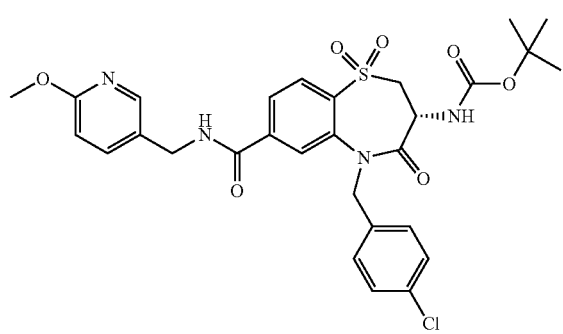

Intermediate IX-104

Step 1: Synthesis of (3R)-3-{[(tert-butoxy)carbonyl]amino}-5-[(4-chlorophenyl)methyl]-1,1,4-trioxo-2,3,4,5-tetrahydro-1$\lambda^6$,5-benzothiazepine-7-carboxylic acid (Intermediate VII-35)

3-Chlorobenzenecarboperoxoic acid (77%, 733 mg, 3.27 mmol) was added to a stirred solution of Intermediate VII-06 (94%, 700 mg, 1.42 mmol) in DCM (30 mL). The reaction was stirred for 18 h at RT and a white precipitate formed. The precipitate was isolated by filtration to give 120 mg (17%) of the title compound as a white solid. The filtrate was concentrated and the residue slurried in MeCN. The solid was collected by filtration to give 131 mg (18%) of the title compound. The resultant filtrate was concentrated to give a crude residue. Purification of the crude residue by reverse phase column chromatography (Biotage, 60 g SNAP Ultra, 5-100% MeCN in water) afforded another portion of the title compound (278 mg 37%). The combined yield was 529 mg, 72% (93% purity)

LCMS: METCR1410 Generic 1.7 min rt=1.11 min, M/Z (ES−) 493/495 [M−H+] 93% UV

1H NMR (500 MHz, DMSO-d6) δ 8.08-7.98 (m, 2H), 7.80 (s, 1H), 7.53 (d, J=8.0 Hz, 1H), 7.41-7.33 (m, 4H), 5.30 (d, J=16.2 Hz, 1H), 4.73 (d, J=16.3 Hz, 1H), 4.39 (dt, J=11.7, 7.6 Hz, 1H), 4.09 (dd, J=13.2, 7.3 Hz, 1H), 3.75 (t, J=12.5 Hz, 1H), 1.36 (s, 9H).

Step 2: Synthesis of tert-butyl N-[(3R)-5-[(4-chlorophenyl)methyl]-7-{[(6-methoxypyridin-3-yl)methyl]carbamoyl}-1,1,4-trioxo-2,3,4,5-tetrahydro-1$\lambda^6$,5-benzothiazepin-3-yl]carbamate (Intermediate IX-104)

Intermediate IX-104 was prepared from Intermediate VII-35 following procedure described in GP3 (Amide coupling using T3P® as reagent). Yield=78%

LCMS: METCR1410 Generic 1.7 min rt=1.17 min, M/Z (ES+) 615/617 [M+H+] 96% UV

1H NMR (500 MHz, DMSO-d6) δ 9.31 (t, J=5.7 Hz, 1H), 8.12 (d, J=2.3 Hz, 1H), 8.01-7.94 (m, 2H), 7.84 (s, 1H), 7.63 (dd, J=8.5, 2.4 Hz, 1H), 7.51 (d, J=8.0 Hz, 1H), 7.37-7.30 (m, 4H), 6.79 (d, J=8.5 Hz, 1H), 5.19 (d, J=16.0 Hz, 1H), 4.85 (d, J=16.0 Hz, 1H), 4.43-4.33 (m, 3H), 4.07 (dd, J=13.1, 7.2 Hz, 1H), 3.83 (s, 3H), 3.76-3.69 (m, 1H), 1.35 (s, 9H).

According to the above described and exemplified general procedure GP1 the following methyl ester intermediates VI were synthesized from the appropriate intermediate (I-V)-03 using the appropriate alkylating agent R²—CH₂—X and base:

Synthesis of methyl (3R)-3-{[(tert-butoxy)carbonyl]amino}-5-[(4-tert-butylphenyl)methyl]-4-oxo-2,3,4,5-tetrahydro-1,5-benzothiazepine-7-carboxylate (Intermediate VI-02)

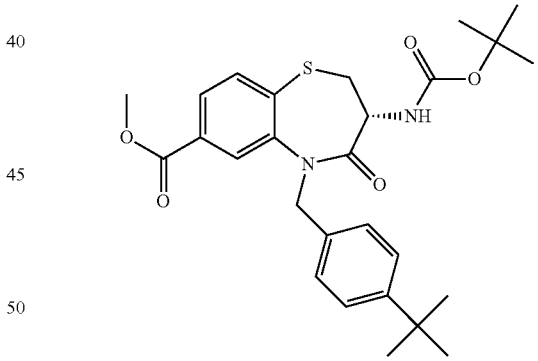

The title compound was synthesized according to general procedure GP1 to afford the title compound as white solid in 64% Yield.

LCMS: METUPLCMS-A-004, rt=1.8 min, M/Z (ES+) 499 [M+H+], 522 [M+Na+] 78% UV

NMR Data: 1H NMR (400 MHz, Chloroform-d) d 7.92 (d, J=1.7 Hz, 1H), 7.81 (dd, J=8.0, 1.6 Hz, 1H), 7.65 (d, J=8.0 Hz, 1H), 7.27 (d, J=8.0 Hz, 2H), 7.21 (d, J=8.4 Hz, 2H), 5.59 (d, J=8.3 Hz, 1H), 5.27 (d, J=15.1 Hz, 1H), 4.91 (d, J=15.1 Hz, 1H), 4.43 (dd, J=11.7, 6.7 Hz, 1H), 3.94 (s, 3H), 3.72 (dd, J=10.8, 6.6 Hz, 1H), 2.94 (t, J=11.3 Hz, 1H), 1.39 (s, 9H), 1.28-1.25 (m, 9H).

Synthesis of methyl (3R)-3-{[(tert-butoxy)carbonyl]amino}-4-oxo-5-{[4-(trifluoromethoxy)phenyl]methyl}-2,3,4,5-tetrahydro-1,5-benzothiazepine-7-carboxylate (Intermediate VI-03)

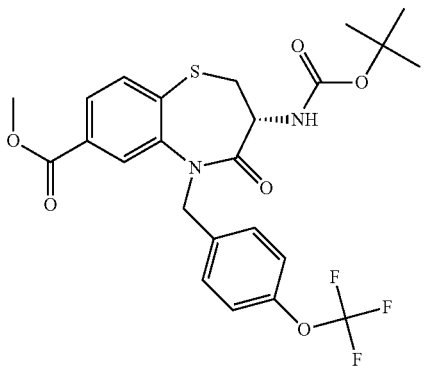 [SMILES: COC(=O)c1ccc2c(c1)N(Cc1ccc(OC(F)(F)F)cc1)C(=O)[C@@H](NC(=O)OC(C)(C)C)CS2]

The title compound was synthesized according to general procedure GP1 to afford the title compound as white solid in 81% Yield.

LCMS: METCR1278 Generic 3.5 minutes, rt=2.34 min, M/Z (ES+) 549 [M+H+], 526 [M+Na+] 90% UV NMR Data: 1HNMR (500 MHz, DMSO-d6) d 7.95 (s, 1H), 7.84-7.74 (m, 2H), 7.49 (d, J=8.2 Hz, 1H), 7.40 (d, J=8.5 Hz, 2H), 7.25 (d, J=8.2 Hz, 2H), 5.18 (d, J=15.9 Hz, 1H), 5.08 (d, J=16.0 Hz, 1H), 4.15 (dt, J=12.3, 7.6 Hz, 1H), 3.85 (s, 3H), 3.50 (dd, J=11.2, 6.8 Hz, 1H), 3.15 (t, J=11.8 Hz, 1H), 1.35 (s, 9H).

Synthesis of methyl (3R)-3-{[(tert-butoxy)carbonyl]amino}-4-oxo-5-{[4-(trifluoromethyl)phenyl]methyl}-2,3,4,5-tetrahydro-1,5-benzothiazepine-7-carboxylate (Intermediate VI-04)

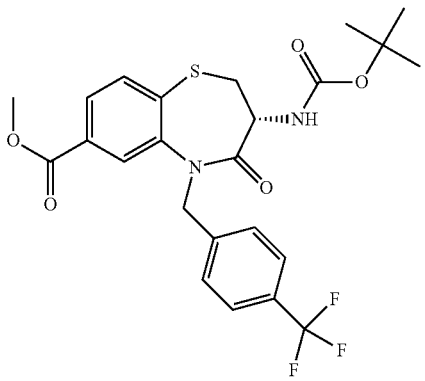 [SMILES: COC(=O)c1ccc2c(c1)N(Cc1ccc(C(F)(F)F)cc1)C(=O)[C@@H](NC(=O)OC(C)(C)C)CS2]

The title compound was synthesized according to general procedure GP1 to afford the title compound as pale yellow solid in 100% yield.

LCMS: METCR1410 Generic 1.7 min, rt=1.35 min, M/Z (ES+) 533.2 [M+Na+], 455.0 [M-tBu+H+] 96% UV NMR Data: 1H NMR (500 MHz, DMSO-d6) d 7.97-7.93 (m, 1H), 7.80 (dd, J=8.0, 1.5 Hz, 1H), 7.76 (d, J=8.0 Hz, 1H), 7.62 (d, J=8.1 Hz, 2H), 7.53-7.48 (m, 3H), 5.26 (d, J=16.3 Hz, 1H), 5.14 (d, J=16.2 Hz, 1H), 4.16 (dt, J=12.2, 7.5 Hz, 1H), 3.84 (s, 3H), 3.50 (dd, J=11.2, 6.8 Hz, 1H), 3.15 (t, J=11.8 Hz, 1H), 1.35 (s, 9H).

Synthesis of methyl (3R)-3-{[(tert-butoxy)carbonyl]amino}-4-oxo-5-{[3-(trifluoromethoxy)phenyl]methyl}-2,3,4,5-tetrahydro-1,5-benzothiazepine-7-carboxylate (Intermediate VI-05)

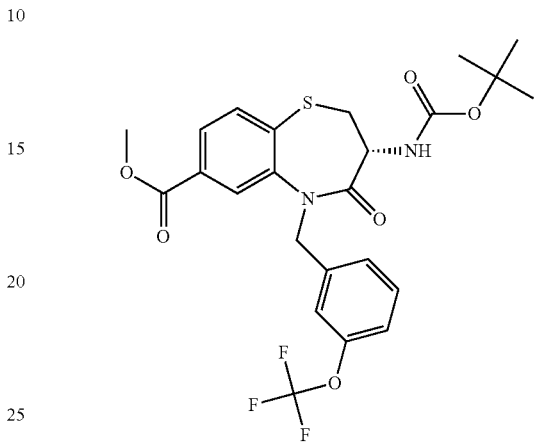

The title compound was synthesized according to general procedure GP1 to afford the title compound as white solid in 76% Yield.

LCMS: METUPLCMS-A-004, rt=1.74 min, M/Z (ES+) 527, 83% UV

Synthesis of methyl (3R)-3-{[(tert-butoxy)carbonyl]amino}-5-[(4-chlorophenyl)methyl]-4-oxo-2,3,4,5-tetrahydro-1,5-benzothiazepine-7-carboxylate (Intermediate VI-06)

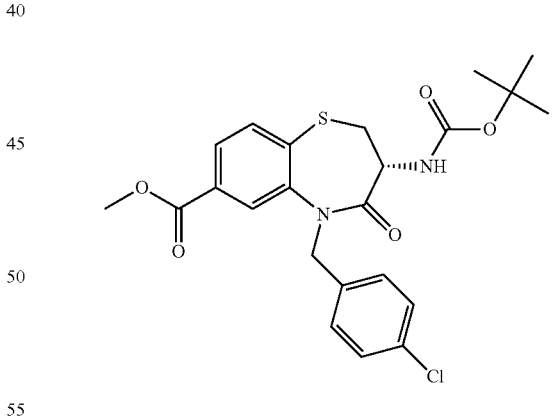

The title compound was synthesized according to general procedure GP1 to afford the title compound as white solid in 69% Yield.

LCMS: METCR1278 Generic 3.5 minutes, rt=2.32 min, M/Z (ES+) 499/501 [M+Na+] 100% UV NMR Data: 1H NMR (500 MHz, Chloroform-d) δ 7.93 (d, J=1.7 Hz, 1H), 7.82 (dd, J=8.0, 1.5 Hz, 1H), 7.64 (d, J=8.0 Hz, 1H), 7.20 (s, 4H), 5.55 (d, J=8.2 Hz, 1H), 5.44 (d, J=15.1 Hz, 1H), 4.75 (d, J=15.1 Hz, 1H), 4.41 (dt, J=14.3, 7.4 Hz, 1H), 3.92 (s, 3H), 3.71 (dd, J=10.8, 6.6 Hz, 1H), 2.93 (t, J=11.3 Hz, 1H), 1.39 (s, 9H).

Synthesis of methyl (3R)-3-{[(tert-butoxy)carbonyl]amino}-5-{[4-(morpholin-4-yl)phenyl]methyl}-4-oxo-2,3,4,5-tetrahydro-1,5-benzothiazepine-7-carboxylate (Intermediate VI-07)

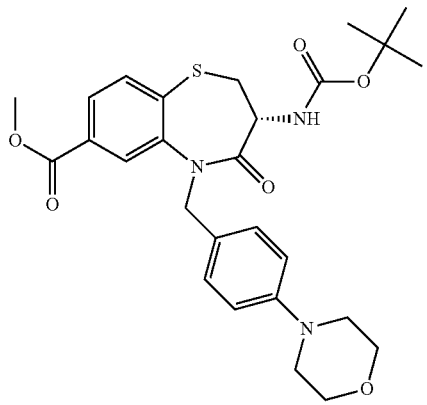 [SMILES: COC(=O)c1ccc2c(c1)N(Cc1ccc(N3CCOCC3)cc1)C(=O)[C@@H](NC(=O)OC(C)(C)C)CS2]

The title compound was synthesized according to general procedure GP1 to afford the title compound as Off-white solid in 46% Yield.

LCMS: METUPLCMS-A-004, rt=1.72 min, M/Z (ES+) 528 [M+H+] 86% UV

Synthesis of methyl (3R)-3-{[(tert-butoxy)carbonyl]amino}-5-[(4-cyanophenyl)methyl]-4-oxo-2,3,4,5-tetrahydro-1,5-benzothiazepine-7-carboxylate (Intermediate VI-08)

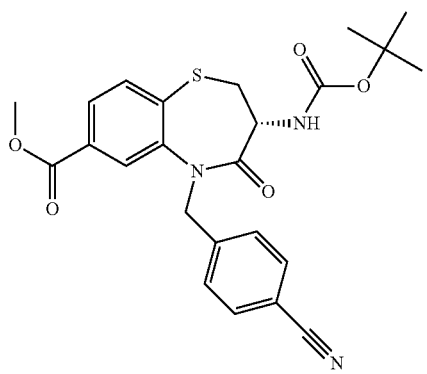 [SMILES: COC(=O)c1ccc2c(c1)N(Cc1ccc(C#N)cc1)C(=O)[C@@H](NC(=O)OC(C)(C)C)CS2]

The title compound was synthesized according to general procedure GP1 to afford the title compound as white solid in 65% Yield.

LCMS: MET-LCMS (MUX)-A-008, rt=1.54 min, M/Z (ES+) 368 [M+H-boc] 93% UV

NMR Data: 1H NMR (400 MHz, Chloroform-d) 1.40 (s, 9H), 2.94 (t, J=11.2 Hz, 1H), 3.72 (dd, J=10.7, 6.5 Hz, 1H), 3.93 (s, 3H), 4.45 (m, 1H), 4.85 (d, J=15.5 Hz, 1H), 5.49 (d, J=15.9 Hz, 2H), 7.41 (d, J=8.5 Hz, 2H), 7.57-7.53 (m, 2H), 7.67 (d, J=8.0 Hz, 1H), 7.84 (dd, J=8.0, 1.7 Hz, 1H), 7.93 (d, J=1.7 Hz, 1H).

Synthesis of methyl (3R)-3-{[(tert-butoxy)carbonyl]amino}-4-oxo-5-{[6-(trifluoromethyl)pyridin-3-yl]methyl}-2,3,4,5-tetrahydro-1,5-benzothiazepine-7-carboxylate (Intermediate VI-09)

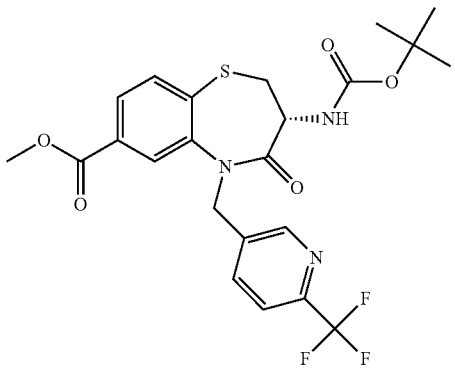 [SMILES: COC(=O)c1ccc2c(c1)N(Cc1ccc(C(F)(F)F)nc1)C(=O)[C@@H](NC(=O)OC(C)(C)C)CS2]

The title compound was synthesized according to general procedure GP1 to afford the title compound as white solid in 22% Yield.

LCMS: METCR1673 Generic 2 minutes, rt=1.44 min, M/Z (ES−) 510 [M−H+] 87% UV

NMR Data: 1H NMR (500 MHz, Chloroform-d) d 8.52 (s, 1H), 7.93 (d, J=1.7 Hz, 1H), 7.83-7.77 (m, 2H), 7.60 (d, J=8.0 Hz, 1H), 7.51 (d, J=8.1 Hz, 1H), 5.57 (d, J=15.4 Hz, 1H), 5.43 (d, J=8.1 Hz, 1H), 4.71 (d, J=15.4 Hz, 1H), 4.40-4.31 (m, 1H), 3.87 (s, 3H), 3.64 (dd, J=11.0, 6.6 Hz, 1H), 2.85 (t, J=11.3 Hz, 1H), 1.33 (s, 9H).

Synthesis of methyl (3R)-3-{[(tert-butoxy)carbonyl]amino}-5-{[4-(5-methyl-1,2,4-oxadiazol-3-yl)phenyl]methyl}-4-oxo-2,3,4,5-tetrahydro-1,5-benzothiazepine-7-carboxylate (Intermediate VI-10)

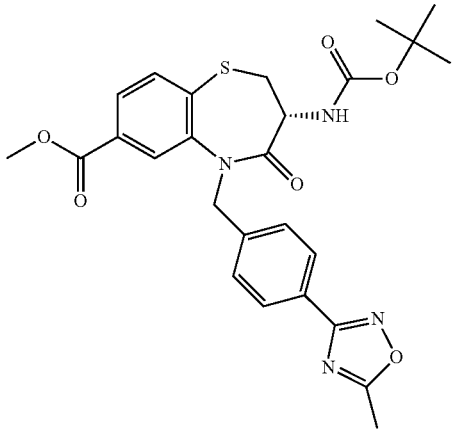 [SMILES: COC(=O)c1ccc2c(c1)N(Cc1ccc(-c3noc(C)n3)cc1)C(=O)[C@@H](NC(=O)OC(C)(C)C)CS2]

The title compound was synthesized according to general procedure GP1 to afford the title compound as white solid in 73% Yield.

LCMS: METCR1673 Generic 2 minutes, rt=1.43 min, M/Z (ES+) 425 [M+H-boc] 99% UV

NMR Data: 1H NMR (500 MHz, DMSO-d6) d 7.95 (s, 1H), 7.86 (d, J=8.2 Hz, 2H), 7.82-7.72 (m, 2H), 7.51 (d, J=8.3 Hz, 1H), 7.46 (d, J=8.1 Hz, 2H), 5.24-5.09 (m, 2H), 4.16 (dt, J=12.5, 7.8 Hz, 1H), 3.83 (s, 3H), 3.50 (dd, J=11.1, 6.8 Hz, 1H), 3.16 (t, J=11.8 Hz, 1H), 2.64 (s, 3H), 1.35 (s, 9H).

Synthesis of methyl (3R)-3-{[(tert-butoxy)carbonyl]amino}-5-[(4-fluorophenyl)methyl]-4-oxo-2,3,4,5-tetrahydro-1,5-benzothiazepine-7-carboxylate (Intermediate VI-11)

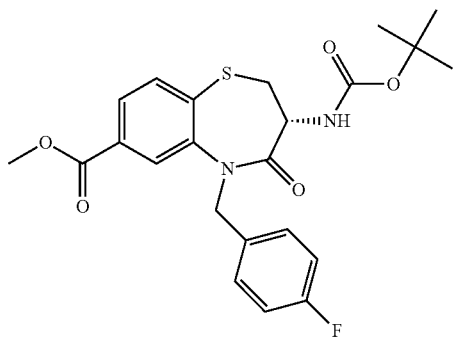 [SMILES: COC(=O)c1ccc2c(c1)N(Cc1ccc(F)cc1)C(=O)[C@@H](NC(=O)OC(C)(C)C)CS2]

The title compound was synthesized according to general procedure GP1 to afford the title compound as white solid in 51% Yield.

LCMS: METCR1673 Generic 2 minutes, rt=1.46 min, M/Z (ES+) 483 [M+Na+], 84% UV

NMR Data: 1H NMR (500 MHz, DMSO-d6) d 7.97 (s, 1H), 7.79 (dd, J=8.0, 1.6 Hz, 1H), 7.74 (d, J=8.0 Hz, 1H), 7.47 (d, J=8.3 Hz, 1H), 7.29 (dd, J t=8.3, 5.6 Hz, 2H), 7.06 (t, J=8.8 Hz, 2H), 5.21 (d, J=15.6 Hz, 1H), 4.98 (d, J=15.6 Hz, 1H), 4.13 (dd, J=7.4, 4.7 Hz, 1H), 3.86 (s, 3H), 3.48 (dd, J=11.2, 6.8 Hz, 1H), 3.14 (t, J=11.8 Hz, 1H), 1.35 (s, 9H).

Synthesis of methyl (3R)-3-{[(tert-butoxy)carbonyl]amino}-4-oxo-5-{[4-(1H-1,2,4-triazol-1-yl)phenyl]methyl}-2,3,4,5-tetrahydro-1,5-benzothiazepine-7-carboxylate (Intermediate VI-12)

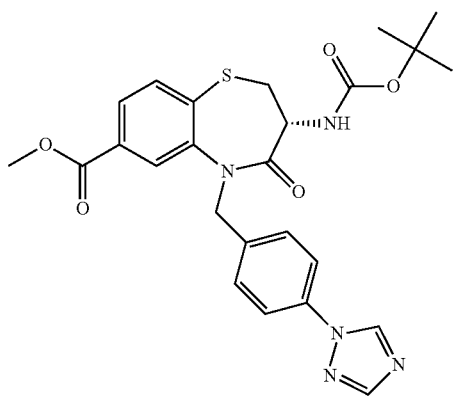 [SMILES: COC(=O)c1ccc2c(c1)N(Cc1ccc(-n3cncn3)cc1)C(=O)[C@@H](NC(=O)OC(C)(C)C)CS2]

The title compound was synthesized according to general procedure GP1 to afford the title compound as yellow solid in 66% Yield.

LCMS: METCR1673 Generic 2 minutes, rt=1.29 min, M/Z (ES+) 510 [M+H+], 79% UV

NMR Data: 1H NMR (500 MHz, DMSO-d6) d 9.21 (s, 1H), 8.17 (s, 1H), 7.96 (d, J=1.5 Hz, 1H), 7.75 (dd, J=8.0, 1.6 Hz, 1H), 7.70 (dd, J=8.2, 4.9 Hz, 3H), 7.50 (d, J=8.3 Hz, 1H), 7.40 (d, J=8.5 Hz, 2H), 5.24 (d, J=15.9 Hz, 1H), 5.04 (d, J=15.9 Hz, 1H), 4.11 (dt, J=12.4, 7.7 Hz, 1H), 3.81 (s, 3H), 3.46 (dd, J=11.2, 6.8 Hz, 1H), 3.12 (t, J=11.8 Hz, 1H), 1.31 (s, 9H).

Synthesis of methyl (3R)-3-{[(tert-butoxy)carbonyl]amino}-8-fluoro-4-oxo-5-{[4-(trifluoromethoxy)phenyl]methyl}-2,3,4,5-tetrahydro-1,5-benzothiazepine-7-carboxylate (Intermediate VI-13)

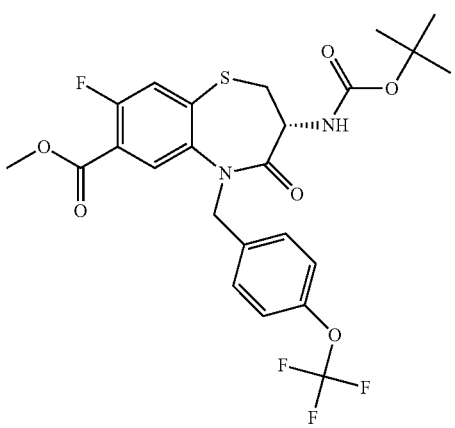 [SMILES: COC(=O)c1cc2c(cc1F)SC[C@H](NC(=O)OC(C)(C)C)C(=O)N2Cc1ccc(OC(F)(F)F)cc1]

The title compound was synthesized according to general procedure GP1 to afford the title compound as white foamy Solid in 43% Yield.

LCMS: METCR1278 Generic 3.5 minutes, rt=2.39 min, M/Z (ES+) 608 [M+Na+MeCN] 88% UV NMR Data: 1H NMR (500 MHz, Chloroform-d) d 7.82 (d, J=6.4 Hz, 1H), 7.39 (d, J=9.6 Hz, 1H), 7.29 (d, J=8.6 Hz, 2H), 7.10 (d, J=8.1 Hz, 2H), 5.54 (d, J=7.7 Hz, 1H), 5.38-5.34 (m, 1H), 4.78 (d, J=15.1 Hz, 1H), 4.42 (dt, J=11.6, 7.5 Hz, 1H), 3.93 (s, 3H), 3.71 (dd, J=10.9, 6.5 Hz, 1H), 2.93 (t, J=11.3 Hz, 1H), 1.40 (s, 9H).

Synthesis of methyl (3R)-3-{[(tert-butoxy)carbonyl]amino}-4-oxo-5-{[4-(1,2,3-thiadiazol-4-yl)phenyl]methyl}-2,3,4,5-tetrahydro-1,5-benzothiazepine-7-carboxylate (Intermediate VI-14)

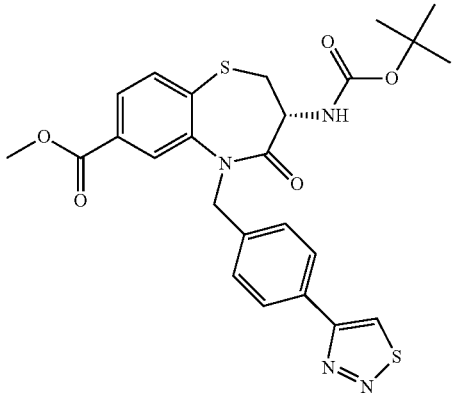 [SMILES: COC(=O)c1ccc2c(c1)N(Cc1ccc(-c3csnn3)cc1)C(=O)[C@@H](NC(=O)OC(C)(C)C)CS2]

The title compound was synthesized according to general procedure GP1 to afford the title compound as white solid in 44% Yield.

LCMS: METCR1673 Generic 2 minutes, rt=1.43 min, M/Z (ES+) 549 [M+Na+], 427 [M+H-boc] 86% UV NMR Data: 1H NMR (500 MHz, Chloroform-d) d 8.59 (s, 1H), 7.99 (d, J=1.6 Hz, 1H), 7.92 (d, J=8.2 Hz, 2H), 7.82 (d, J=7.9 Hz, 1H), 7.65 (d, J=8.0 Hz, 1H), 7.43 (d, J=8.2 Hz, 2H), 5.55 (d, J=15.2 Hz, 2H), 4.86 (d, J=15.2 Hz, 1H), 4.45 (d, J=11.8 Hz, 1H), 3.92 (s, 3H), 3.73 (dd, J=10.8, 6.6 Hz, 1H), 2.96 (t, J=11.3 Hz, 1H), 1.40 (s, 9H).

Synthesis of methyl (3R)-3-{[(tert-butoxy)carbonyl]amino}-5-[(4-carbamoylphenyl)methyl]-4-oxo-2,3,4,5-tetrahydro-1,5-benzothiazepine-7-carboxylate (Intermediate VI-15)

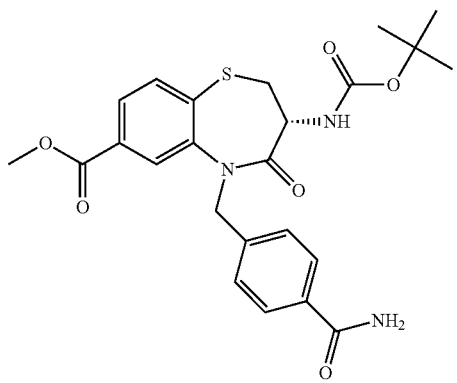 [SMILES: COC(=O)c1ccc2c(c1)N(Cc1ccc(C(N)=O)cc1)C(=O)[C@@H](NC(=O)OC(C)(C)C)CS2]

The title compound was synthesized according to general procedure GP1 to afford the title compound as white solid in 76% Yield.

LCMS: METCR1673 Generic 2 minutes, rt=1.22 min, M/Z (ES+) 508 [M+H+Na+] 90% UV

NMR Data: 1H NMR (500 MHz, Chloroform-d) d 7.94 (d, J=1.7 Hz, 1H), 7.81 (dd, J=8.0, 1.5 Hz, 1H), 7.69 (d, J=8.3 Hz, 2H), 7.64 (d, J=8.0 Hz, 1H), 7.37 (d, J=8.2 Hz, 2H), 6.05 (s, 1H), 5.71-5.41 (m, 3H), 4.85 (d, J=15.3 Hz, 1H), 4.43 (dt, J=12.7, 6.8 Hz, 1H), 3.92 (s, 3H), 3.72 (dd, J=10.9, 6.5 Hz, 1H), 2.94 (t, J=11.3 Hz, 1H), 1.40 (s, 9H).

Synthesis of methyl (2R,3R)-3-{[(tert-butoxy)carbonyl]amino}-5-[(4-chlorophenyl)methyl]-2-methyl-4-oxo-2,3,4,5-tetrahydro-1,5-benzothiazepine-7-carboxylate (Intermediate VI-16)

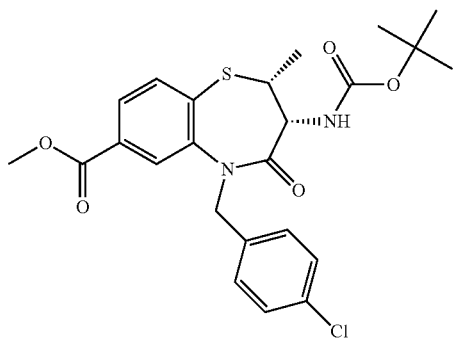 [SMILES: COC(=O)c1ccc2c(c1)N(Cc1ccc(Cl)cc1)C(=O)[C@@H](NC(=O)OC(C)(C)C)[C@@H](C)S2]

The title compound was synthesized according to general procedure GP1 to afford the title compound as Off-white solid in 100% Yield.

LCMS: METCR1673 Generic 2 minutes, rt=1.68 min, M/Z (ES+) 513/515 [M+Na+] 93% UV NMR Data: 1H NMR (500 MHz, DMSO-d6) d 7.99 (s, 1H), 7.79 (dd, J=8.0, 1.7 Hz, 1H), 7.73 (d, J=8.0 Hz, 1H), 7.31 (s, 4H), 7.12 (d, J=8.3 Hz, 1H), 5.31 (d, J=16.0 Hz, 1H), 4.98 (d, J=15.9 Hz, 1H), 4.42-4.30 (m, 1H), 3.86 (m, 4H), 1.43-1.26 (m, 12H).

Synthesis of methyl (3R)-3-{[(tert-butoxy)carbonyl]amino}-5-[(4-chloro-2-fluorophenyl)methyl]-8-fluoro-4-oxo-2,3,4,5-tetrahydro-1,5-benzothiazepine-7-carboxylate (Intermediate VI-17)

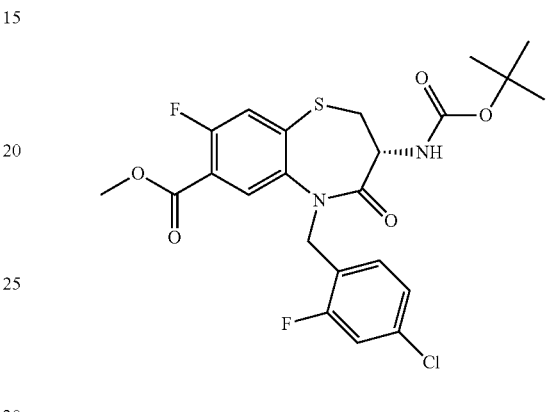

The title compound was synthesized according to general procedure GP1 to afford the title compound as a colourless solid in 55% Yield.

LCMS: METCR1673 Generic 2 minutes, rt=1.63 min, M/Z (ES+) 535/537 [M+Na+] 87% UV NMR Data: 1H NMR (500 MHz, CDCl3) d 7.89 (d, J=6.4 Hz, 1H), 7.43-7.36 (m, 2H), 7.05 (dd, J=8.3, 1.8 Hz, 1H), 6.98 (dd, J=9.6, 2.0 Hz, 1H), 5.52 (d, J=7.9 Hz, 1H), 5.37 (d, J=15.2 Hz, 1H), 4.79 (d, J=15.2 Hz, 1H), 4.40 (dt, J=14.1, 7.1 Hz, 1H), 3.95 (s, 3H), 3.68 (dd, J=10.9, 6.5 Hz, 1H), 2.89 (t, J=11.3 Hz, 1H), 1.40 (s, 9H).

Synthesis of methyl (3R)-3-{[(tert-butoxy)carbonyl]amino}-5-[(4-chloro-3-fluorophenyl)methyl]-8-fluoro-4-oxo-2,3,4,5-tetrahydro-1,5-benzothiazepine-7-carboxylate (Intermediate VI-18)

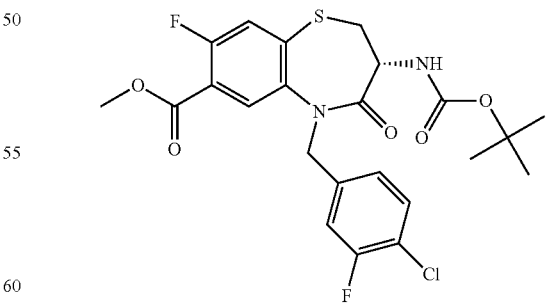

The title compound was synthesized according to general procedure GP1 to afford the title compound as off-white solid in 44% Yield.

LCMS: METCR1673 Generic 2 minutes, rt=1.52 min, M/Z (ES+) 535/537 [M+Na+] 81% UV NMR Data: 1H NMR (500 MHz, CDCl3) d 7.83 (d, J=6.4 Hz, 1H), 7.40 (d, J=9.5 Hz, 1H), 7.28-7.24 (m, 1H), 7.12 (dd, J=9.6, 1.9 Hz, 1H), 7.01-6.93 (m, 1H), 5.52 (d, J=7.9 Hz, 1H), 5.38 (d, J=15.3 Hz, 1H), 4.69 (d, J=15.1 Hz, 1H), 4.49-4.34 (m, 1H), 3.94 (s, 3H), 3.71 (dd, J=11.0, 6.4 Hz, 1H), 2.94 (t, J=11.3 Hz, 1H), 1.40 (s, 9H).

Synthesis of methyl (3R)-3-{[(tert-butoxy)carbonyl]amino}-5-[(3,4-dichlorophenyl)methyl]-4-oxo-2,3,4,5-tetrahydro-1,5-benzothiazepine-7-carboxylate (Intermediate VI-19)

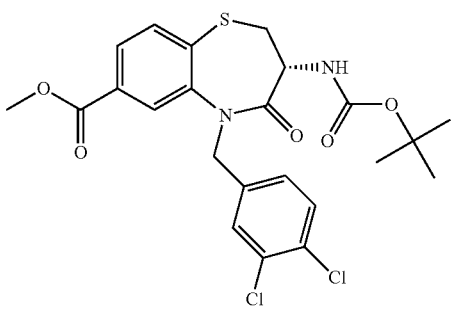 [SMILES: COC(=O)c1ccc2c(c1)N(Cc1ccc(Cl)c(Cl)c1)C(=O)[C@@H](NC(=O)OC(C)(C)C)CS2]

The title compound was synthesized according to general procedure GP1 to afford the title compound as cream solid in 51% Yield.

LCMS: METCR1673 Generic 2 minutes, rt=1.64 min, M/Z (ES+) 533/535/537 [M+Na+] 61% UV NMR Data: 1H NMR (500 MHz, Chloroform-d) d 1.40 (s, 9H), 2.94 (t, J=11.28 Hz, 1H), 3.71 (dd, J=6.63, 10.86 Hz, 1H), 3.93 (s, 3H), 4.40-4.45 (m, 1H), 4.72 (d, J=15.3 Hz, 1H), 5.42 (d, J=15.3 Hz, 1H), 5.52 (d, J=8.09 Hz, 1H), 7.12 (dt, J=2.38, 8.23 Hz, 1H), 7.30 (d, J=8.25 Hz, 1H), 7.42 (d, J=2.15 Hz, 1H), 7.67 (d, J=8.01 Hz, 1H), 7.84 (dd, J=1.66, 7.99 Hz, 1H), 7.93 (d, J=1.69 Hz, 1H).

Synthesis of methyl (3R)-3-{[(tert-butoxy)carbonyl]amino}-8-fluoro-4-oxo-5-(quinolin-2-ylmethyl)-2,3,4,5-tetrahydro-1,5-benzothiazepine-7-carboxylate (Intermediate VI-20)

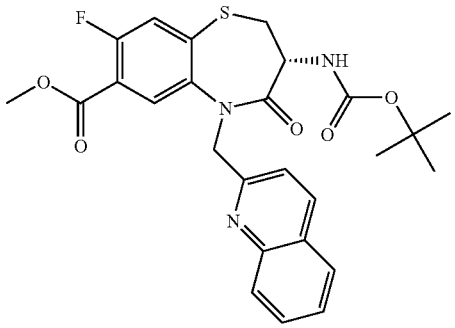 [SMILES: COC(=O)c1cc2c(cc1F)SC[C@H](NC(=O)OC(C)(C)C)C(=O)N2Cc1ccc2ccccc2n1]

The title compound was synthesized according to general procedure GP1 to afford the title compound as beige solid in 53% Yield.

LCMS: METCR1673 Generic 2 minutes, rt=1.41 min, M/Z (ES+) 512 [M+Na+] 99% UV

NMR Data: 1H NMR (500 MHz, Chloroform-d) δ 8.80-7.61 (m, 7H), 7.44 (d, J=9.5 Hz, 1H), 5.81 (s, 1H), 5.55-5.45 (m, 2H), 4.58-4.45 (m, 1H), 3.94 (s, 3H), 3.78 (dd, J=10.8, 6.8 Hz, 1H), 2.98 (t, J=11.4 Hz, 1H), 1.40 (d, J=7.0 Hz, 9H).

Synthesis of methyl (3R)-3-{[(tert-butoxy)carbonyl]amino}-5-[(5-cyclopropyl-1,3,4-thiadiazol-2-yl)methyl]-8-fluoro-4-oxo-2,3,4,5-tetrahydro-1,5-benzothiazepine-7-carboxylate (Intermediate VI-21)

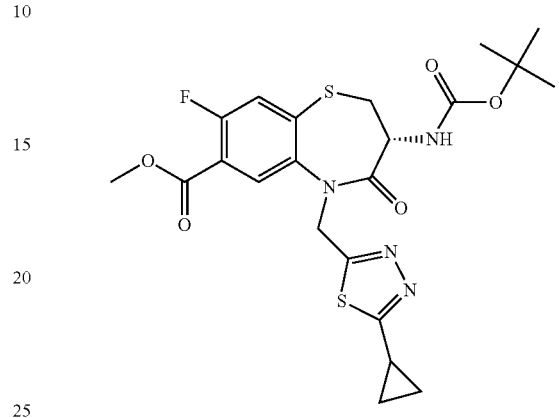

The title compound was synthesized according to general procedure GP1 to afford the title compound as orange solid in 66% Yield.

LCMS: METCR1673 Generic 2 minutes, rt=1.28 min, M/Z (ES+) 509 [M+H+] 90% UV

NMR Data: 1H NMR (500 MHz, DMSO-d6) d 8.18 (d, J=6.5 Hz, 1H), 7.67 (d, J=10.0 Hz, 1H), 7.50 (d, J=8.2 Hz, 1H), 5.43 (d, J=15.6 Hz, 1H), 5.18 (d, J=15.7 Hz, 1H), 4.12 (dt, J=11.8, 7.3 Hz, 1H), 3.90 (s, 3H), 3.48 (dd, J=11.4, 6.9 Hz, 1H), 3.10 (t, J=11.8 Hz, 1H), 2.48-2.43 (m, 1H), 1.35 (s, 9H), 1.19 (dd, J=11.4, 9.3 Hz, 2H), 1.03-0.93 (m, 2H).

Synthesis of methyl (3R)-3-{[(tert-butoxy)carbonyl]amino}-5-[(2-fluorophenyl)methyl]-4-oxo-2,3,4,5-tetrahydro-1,5-benzothiazepine-7-carboxylate (Intermediate VI-22)

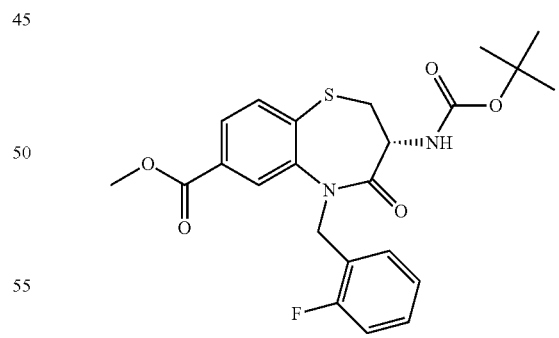

The title compound was synthesized according to general procedure GP1 to afford the title compound as Pale yellow solid in 47% yield.

LCMS: METCR1410 Generic 1.7 min, rt=1.27 min, M/Z (ES+) 483 [M+Na+] 95% UV

NMR Data: 1H NMR (250 MHz, Chloroform-d) d 7.97 (d, J=1.7 Hz, 1H), 7.83 (dd, J=8.0, 1.7 Hz, 1H), 7.64 (d, J=8.0 Hz, 1H), 7.46 (t, J=6.9 Hz, 1H), 7.22-7.14 (m, 1H), 7.11-6.89 (m, 2H), 5.56 (d, J=8.0 Hz, 1H), 5.40 (d, J=15.3

Hz, 1H), 4.96 (d, J=15.3 Hz, 1H), 4.40 (s, 1H), 3.92 (s, 3H), 3.70 (dd, J=10.9, 6.5 Hz, 1H), 2.91 (t, J=11.3 Hz, 1H), 1.39 (s, 9H).

Synthesis of methyl (3R)-3-{[(tert-butoxy)carbonyl]amino}-5-[(3-methoxyphenyl)methyl]-4-oxo-2,3,4,5-tetrahydro-1,5-benzothiazepine-7-carboxylate (Intermediate VI-23)

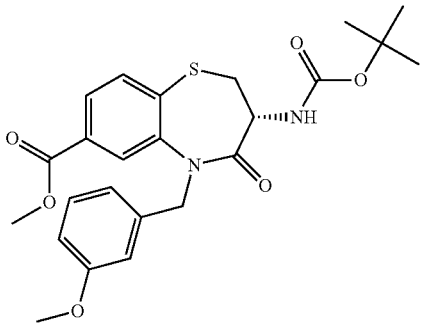 [SMILES: COC(=O)c1ccc2c(c1)N(Cc1cccc(OC)c1)C(=O)[C@@H](NC(=O)OC(C)(C)C)CS2]

The title compound was synthesized according to general procedure GP1 to afford the title compound as white solid in 70% yield.

LCMS: METCR1410 Generic 1.7 min, rt=1.26 min, M/Z (ES+) 495.2 [M+Na+] 96% UV

Synthesis of methyl (3R)-3-{[(tert-butoxy)carbonyl]amino}-5-[(4-methoxyphenyl)methyl]-4-oxo-2,3,4,5-tetrahydro-1,5-benzothiazepine-7-carboxylate (Intermediate VI-24)

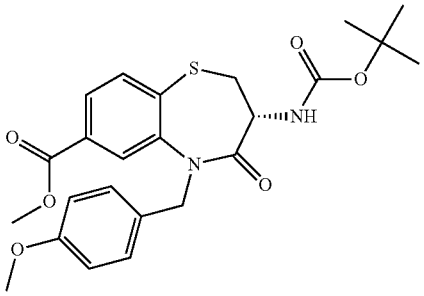 [SMILES: COC(=O)c1ccc2c(c1)N(Cc1ccc(OC)cc1)C(=O)[C@@H](NC(=O)OC(C)(C)C)CS2]

The title compound was synthesized according to general procedure GP1 to afford the title compound as yellow solid in 100% yield.

LCMS: METCR1410 Generic 1.7 min, rt=1.26 min, M/Z (ES+) 417.15 [M-tBu+H+], 495.15 [M+Na+], 88% UV NMR Data: 1H NMR (500 MHz, DMSO-d6) d 7.98 (d, J=1.3 Hz, 1H), 7.81-7.66 (m, 2H), 7.44 (d, J=8.4 Hz, 1H), 7.16 (d, J=8.6 Hz, 2H), 6.78 (d, J=8.6 Hz, 2H), 5.18 (d, J=15.4 Hz, 1H), 4.90 (d, J=15.4 Hz, 1H), 4.22-4.07 (m, 1H), 3.85 (s, 3H), 3.68 (s, 3H), 3.47 (dd, J=11.2, 6.8 Hz, 1H), 3.14 (t, J=11.8 Hz, 1H), 1.35 (s, 9H).

Synthesis of methyl (3R)-3-{[(tert-butoxy)carbonyl]amino}-8-fluoro-5-[(4-fluorophenyl)methyl]-4-oxo-2,3,4,5-tetrahydro-1,5-benzothiazepine-7-carboxylate (Intermediate VI-25)

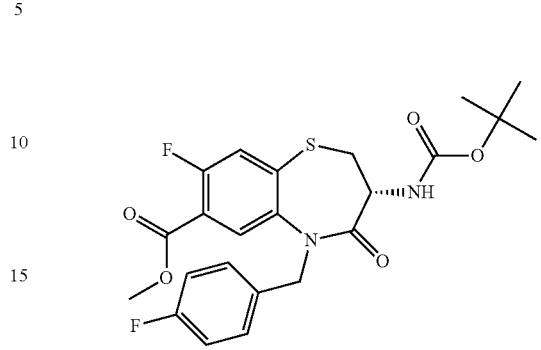

The title compound was synthesized according to general procedure GP1 to afford the title compound as very pale yellow solid in 96% yield.

LCMS: METCR1410 Generic 1.7 min, rt=1.31 min, M/Z (ES+) 423.05 [M-tBu+H+], 96% UV NMR Data: 1H NMR (500 MHz, Chloroform-d) d 7.83 (d, J=6.5 Hz, 1H), 7.37 (d, J=9.7 Hz, 1H), 7.22 (dd, J=8.6, 5.4 Hz, 2H), 6.92 (t, J=8.6 Hz, 2H), 5.55 (d, J=7.9 Hz, 1H), 5.39 (d, J=14.9 Hz, 1H), 4.70 (d, J=14.9 Hz, 1H), 4.40 (dt, J=12.7, 6.3 Hz, 1H), 3.94 (s, 3H), 3.70 (dd, J=10.9, 6.5 Hz, 1H), 2.92 (t, J=11.3 Hz, 1H), 1.40 (s, 9H).

Synthesis of methyl (3R)-3-{[(tert-butoxy)carbonyl]amino}-5-[(4-cyclopropylphenyl)methyl]-4-oxo-2,3,4,5-tetrahydro-1,5-benzothiazepine-7-carboxylate (Intermediate VI-26)

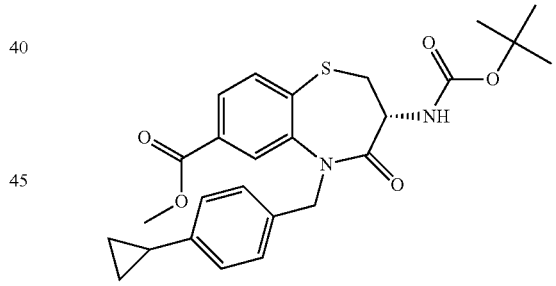

A stirred solution of Intermediate VI-32 (93%, 190 mg, 0.34 mmol), cyclopropylboronic acid (73 mg, 0.85 mmol) and tripotassium phosphate (215.8 mg, 1.02 mmol) in a mixture of toluene (4 mL) and water (0.2 mL) was degassed with $N_2$ for 5 min at RT. Pd(OAc)$_2$ (7.61 mg, 0.03 mmol) and P(Cy)$_3$ (9.5 mg, 0.03 mmol) were added and the reaction mixture was heated to 110° C. for 2 h. The reaction mixture was diluted with EtOAc and washed with water (×2), then brine. Then the organic layer was dried (Na$_2$SO$_4$), filtered and concentrated under reduced pressure to give a brown oil (350 mg), which was purified by reverse phase column chromatography (SNAP Ultra C18, 12 g, 5-100% MeCN in water) to give 121 mg (71%) of the title compound as a yellow solid.

The title compound was synthesized according to general procedure GP1 to afford the title compound as yellow solid in 71% yield.

LCMS: METCR1410 Generic 1.7 min, rt=1.36 min, M/Z (ES+) 505.1 [M+Na+], 427.1 [M-tBu+H+], 100% UV; NMR Data: 1H NMR (500 MHz, Chloroform-d) d 7.92 (d, J=1.7 Hz, 1H), 7.80 (dd, J=8.0, 1.6 Hz, 1H), 7.62 (d, J=8.0 Hz, 1H), 7.14 (d, J=8.1 Hz, 2H), 6.92 (d, J=8.1 Hz, 2H), 5.58 (d, J=8.1 Hz, 1H), 5.36 (d, J=15.0 Hz, 1H), 4.79 (d, J=15.0 Hz, 1H), 4.45-4.35 (m, 1H), 3.91 (s, 3H), 3.71 (dd, J=10.9, 6.7 Hz, 1H), 2.93 (t, J=11.2 Hz, 1H), 1.81 (ddd, J=13.5, 8.4, 5.0 Hz, 1H), 1.39 (s, 9H), 0.94-0.88 (m, 2H), 0.65-0.60 (m, 2H).

Synthesis of methyl (3R)-3-{[(tert-butoxy)carbonyl]amino}-5-[(4-cyanophenyl)methyl]-8-fluoro-4-oxo-2,3,4,5-tetrahydro-1,5-benzothiazepine-7-carboxylate (Intermediate VI-27)

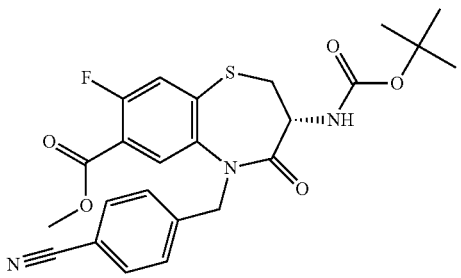 [SMILES: COC(=O)c1cc2c(cc1F)SC[C@H](NC(=O)OC(C)(C)C)C(=O)N2Cc1ccc(C#N)cc1]

The title compound was synthesized according to general procedure GP1 to afford the title compound as cream solid in 100% yield.

LCMS: METCR1673 Generic 2 minutes, rt=1.23 min, M/Z (ES+) 430 [M-tBu+H+] 88% UV

NMR Data: 1H NMR (500 MHz, DMSO-d6) d 7.91 (d, J=6.5 Hz, 1H), 7.75 (d, J=8.3 Hz, 2H), 7.66 (d, J=9.8 Hz, 1H), 7.51 (d, J=8.2 Hz, 1H), 7.47 (d, J=8.2 Hz, 2H), 5.25 (d, J=16.2 Hz, 1H), 5.06 (d, J=16.2 Hz, 1H), 4.18 (dt, J=12.4, 7.7 Hz, 1H), 3.86 (s, 3H), 3.51 (dd, J=11.2, 6.8 Hz, 1H), 3.16 (t, J=11.8 Hz, 1H), 1.36 (s, 9H).

Synthesis of methyl (3R)-3-{[(tert-butoxy)carbonyl]amino}-8-fluoro-5-[(4-methoxyphenyl)methyl]-4-oxo-2,3,4,5-tetrahydro-1,5-benzothiazepine-7-carboxylate (Intermediate VI-28)

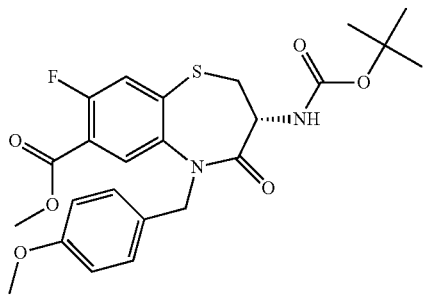 [SMILES: COC(=O)c1cc2c(cc1F)SC[C@H](NC(=O)OC(C)(C)C)C(=O)N2Cc1ccc(OC)cc1]

The title compound was synthesized according to general procedure GP1 to afford the title compound as yellow solid in 74% yield.

LCMS: METCR1410 Generic 1.7 min, rt=1.31 min, M/Z (ES+) 513.2 [M+Na+], 435.1 [M-tBu+H+] 91% UV; NMR Data: 1H NMR (500 MHz, Chloroform-d) d 7.83 (d, J=6.5 Hz, 1H), 7.35 (d, J=9.7 Hz, 1H), 7.19-7.11 (m, 2H), 6.83-6.69 (m, 2H), 5.58 (d, J=7.8 Hz, 1H), 5.36 (d, J=14.8 Hz, 1H), 4.67 (d, J=14.8 Hz, 1H), 4.39 (dt, J=11.6, 7.3 Hz, 1H), 3.93 (s, 3H), 3.75 (s, 3H), 3.69 (dd, J=10.9, 6.5 Hz, 1H), 2.92 (t, J=11.2 Hz, 1H), 1.40 (s, 9H).

Synthesis of methyl (2R,3R)-3-{[(tert-butoxy)carbonyl]amino}-5-[(4-chlorophenyl)methyl]-8-fluoro-2-methyl-4-oxo-2,3,4,5-tetrahydro-1,5-benzothiazepine-7-carboxylate (Intermediate VI-29)

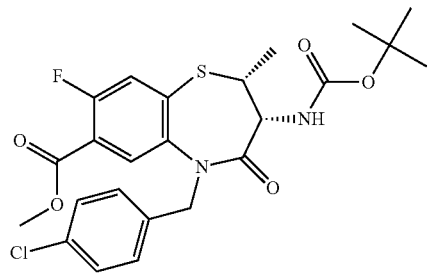 [SMILES: COC(=O)c1cc2c(cc1F)S[C@H](C)[C@H](NC(=O)OC(C)(C)C)C(=O)N2Cc1ccc(Cl)cc1]

The title compound was synthesized according to general procedure GP1 to afford the title compound as yellow oil in 92% yield.

LCMS: METCR1673 Generic 2 minutes, rt=1.43 min, M/Z (ES+) 452.75/454.90 [M-tBu+H+] 82% UV NMR Data: 1H NMR (250 MHz, DMSO-d6) d 7.94 (d, J=6.6 Hz, 1H), 7.61 (d, J=10.1 Hz, 1H), 7.30 (d, J=2.2 Hz, 4H), 7.12 (d, J=8.3 Hz, 1H), 5.31 (d, J=15.9 Hz, 1H), 4.89 (d, J=15.7 Hz, 1H), 4.45-4.34 (m, 1H), 3.86 (m, 4H), 1.40-1.27 (m, 12H).

Synthesis of methyl (3R)-3-{[(tert-butoxy)carbonyl]amino}-5-{[4-(difluoromethoxy)phenyl]methyl}-4-oxo-2,3,4,5-tetrahydro-1,5-benzothiazepine-7-carboxylate (Intermediate VI-30)

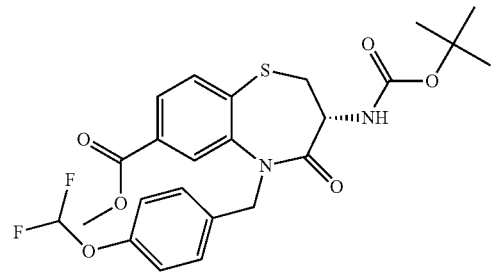 [SMILES: COC(=O)c1ccc2c(c1)N(Cc1ccc(OC(F)F)cc1)C(=O)[C@@H](NC(=O)OC(C)(C)C)CS2]

The title compound was synthesized according to general procedure GP1 to afford the title compound as white solid in 83% yield.

LCMS: METCR1410 Generic 1.7 min, rt=1.28 min, M/Z (ES+) 531 [M+Na+] 97% UV

NMR Data: 1H NMR (250 MHz, Chloroform-d) d 7.86 (d, J=1.7 Hz, 1H), 7.75 (dd, J=8.0, 1.7 Hz, 1H), 7.58 (d, J=8.0 Hz, 1H), 7.22 (s, 2H), 6.91 (d, J=8.6 Hz, 2H), 6.39 (td, J=73.9, 7.4 Hz, 1H), 5.48 (d, J=8.1 Hz, 1H), 5.35 (d, J=15.1 Hz, 1H), 4.81-4.63 (m, 1H), 4.41 (d, J=46.4 Hz, 1H), 3.86 (d, J=5.5 Hz, 3H), 3.64 (dd, J=10.9, 6.6 Hz, 1H), 2.86 (t, J=11.3 Hz, 1H), 1.32 (s, 9H).

Synthesis of methyl (3R)-3-{[(tert-butoxy)carbonyl]amino}-8-chloro-5-[(4-chlorophenyl)methyl]-4-oxo-2,3,4,5-tetrahydro-1,5-benzothiazepine-7-carboxylate (Intermediate VI-31)

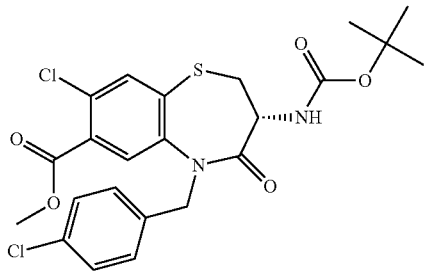 [SMILES: COC(=O)c1cc2c(cc1Cl)SC[C@H](NC(=O)OC(C)(C)C)C(=O)N2Cc1ccc(Cl)cc1]

The title compound was synthesized according to general procedure GP1 to afford the title compound as cream solid in 98% yield.

LCMS: METCR1410 Generic 1.7 min, rt=1.37 min, M/Z (ES+) 533.05/535.05 [M+Na+] 100% UV NMR Data: 1H NMR (250 MHz, Chloroform-d) d 7.70 (d, J=12.3 Hz, 2H), 7.21 (d, J=2.0 Hz, 4H), 5.52 (d, J=7.6 Hz, 1H), 5.35 (d, J=15.1 Hz, 1H), 4.73 (d, J=15.1 Hz, 1H), 4.50-4.32 (m, 1H), 3.93 (s, 3H), 3.70 (dd, J=10.9, 6.5 Hz, 1H), 2.93 (t, J=11.3 Hz, 1H), 1.40 (s, 9H).

Synthesis of methyl (3R)-5-[(4-bromophenyl)methyl]-3-{[(tert-butoxy)carbonyl]amino}-4-oxo-2,3,4,5-tetrahydro-1,5-benzothiazepine-7-carboxylate (Intermediate VI-32)

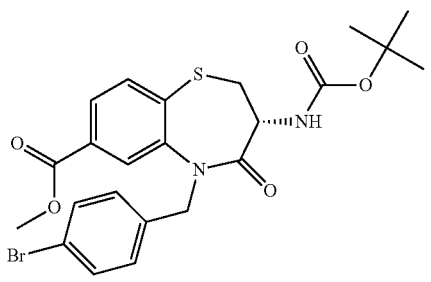 [SMILES: COC(=O)c1ccc2c(c1)N(Cc1ccc(Br)cc1)C(=O)[C@@H](NC(=O)OC(C)(C)C)CS2]

The title compound was synthesized according to general procedure GP1 to afford the title compound as pale yellow solid in 66% yield.

LCMS: METCR1410 Generic 1.7 min, rt=1.34 min, M/Z (ES+) 543.05/544.85 [M+Na+], 96% UV NMR Data: 1H NMR (250 MHz, Chloroform-d) d 7.93 (d, J=1.7 Hz, 1H), 7.82 (dd, J=8.0, 1.7 Hz, 1H), 7.64 (d, J=8.0 Hz, 1H), 7.40-7.29 (m, 2H), 7.15 (d, J=8.4 Hz, 2H), 5.54 (d, J=7.6 Hz, 1H), 5.42 (d, J=15.1 Hz, 1H), 4.73 (d, J=15.1 Hz, 1H), 4.49-4.31 (m, 1H), 3.92 (s, 3H), 3.70 (dd, J=10.9, 6.6 Hz, 1H), 2.92 (t, J=11.3 Hz, 1H), 1.39 (s, 9H).

Synthesis of methyl (3R)-3-{[(tert-butoxy)carbonyl]amino}-8-fluoro-5-{[4-methoxy-3-(trifluoromethyl)phenyl]methyl}-4-oxo-2,3,4,5-tetrahydro-1,5-benzothiazepine-7-carboxylate (Intermediate VI-33)

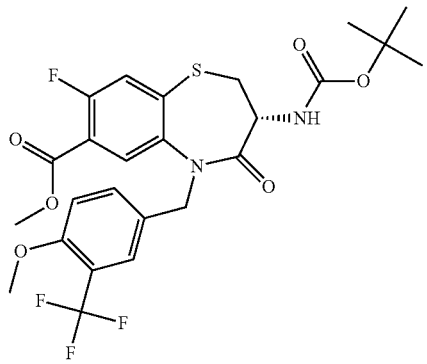 [SMILES: COC(=O)c1cc2c(cc1F)SC[C@H](NC(=O)OC(C)(C)C)C(=O)N2Cc1ccc(OC)c(C(F)(F)F)c1]

The title compound was synthesized according to general procedure GP1 to afford the title compound as beige solid in 87% yield.

LCMS: METCR1410 Generic 1.7 min, rt=1.36 min, M/Z (ES+) 580 [M+Na+] 87% UV

NMR Data: 1H NMR (500 MHz, DMSO-d6) δ 7.95 (d, J=6.6 Hz, 1H), 7.63 (d, J=10.0 Hz, 1H), 7.54 (s, 1H), 7.46 (t, J=6.9 Hz, 2H), 7.13 (d, J=8.6 Hz, 1H), 5.24 (d, J=15.4 Hz, 1H), 4.91 (d, J=15.4 Hz, 1H), 4.15 (dt, J=12.2, 7.4 Hz, 1H), 3.87 (s, 3H), 3.83 (s, 3H), 3.49 (dd, J=11.3, 6.8 Hz, 1H), 3.15 (t, J=11.7 Hz, 1H), 1.35 (s, 9H).

According to the above described and exemplified general procedure GP2 the following acid intermediates VII were synthesized from the appropriate intermediate VI:

Synthesis of (3R)-3-{[(tert-butoxy)carbonyl]amino}-5-[(4-tert-butylphenyl)methyl]-4-oxo-2,3,4,5-tetrahydro-1,5-benzothiazepine-7-carboxylic acid (Intermediate VII-02)

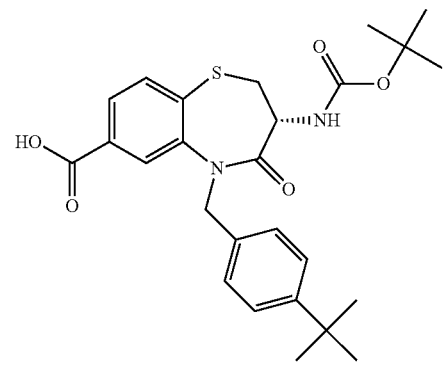 [SMILES: CC(C)(C)OC(=O)N[C@H]1CSc2ccc(C(=O)O)cc2N(Cc2ccc(C(C)(C)C)cc2)C1=O]

The title compound was synthesized according to general procedure GP2 to afford the title compound as yellow solid in 91% Yield and 91% purity as assessed by NMR.

NMR Data: 1H NMR (400 MHz, DMSO-d6) δ 7.94 (s, 1H), 7.79-7.76 (m, 1H), 7.64 (d, J=7.9 Hz, 1H), 7.47 (d, J=8.5 Hz, 1H), 7.32 (d, J=8.3 Hz, 2H), 7.27 (d, J=8.4 Hz, 2H), 5.12-5.06 (m, 2H), 4.28-4.19 (m, 1H), 3.56-3.49 (m, 1H), 3.16 (t, J=11.8 Hz, 1H), 1.41 (s, 9H), 1.29 (s, 9H). [OH not visible]

Synthesis of (3R)-3-{[(tert-butoxy)carbonyl]amino}-4-oxo-5-{[4-(trifluoromethoxy)phenyl]methyl}-2,3,4,5-tetrahydro-1,5-benzothiazepine-7-carboxylic acid (Intermediate VII-03)

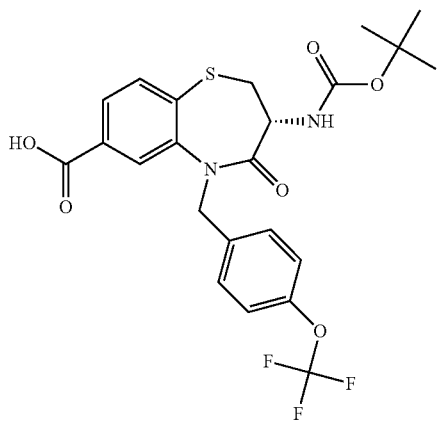 [SMILES: CC(C)(C)OC(=O)N[C@H]1CSc2ccc(C(=O)O)cc2N(Cc2ccc(OC(F)(F)F)cc2)C1=O]

The title compound was synthesized according to general procedure GP2 to afford the title compound as white foam in 98% Yield.

LCMS: METCR1278 Generic 3.5 minutes, rt=2.1 min, M/Z (ES−) 511.10[M−H+], 100% UV NMR Data: 1H NMR (500 MHz, DMSO-d6) d 7.92 (d, J=1.6 Hz, 1H), 7.79 (dd, J=8.0, 1.7 Hz, 1H), 7.74 (d, J=8.0 Hz, 1H), 7.53 (d, J=8.3 Hz, 1H), 7.41 (d, J=8.6 Hz, 2H), 7.26 (d, J=8.2 Hz, 2H), 5.16 (d, J=16.1 Hz, 1H), 5.09 (d, J=16.1 Hz, 1H), 4.15 (dt, J=12.3, 7.6 Hz, 1H), 3.53-3.45 (m, 1H), 3.21-3.04 (m, 1H), 1.42-1.28 (m, 9H). [OH not visible]

Synthesis of (3R)-3-{[(tert-butoxy)carbonyl]amino}-4-oxo-5-{[4-(trifluoromethyl)phenyl]methyl}-2,3,4,5-tetrahydro-1,5-benzothiazepine-7-carboxylic acid (Intermediate VII-04)

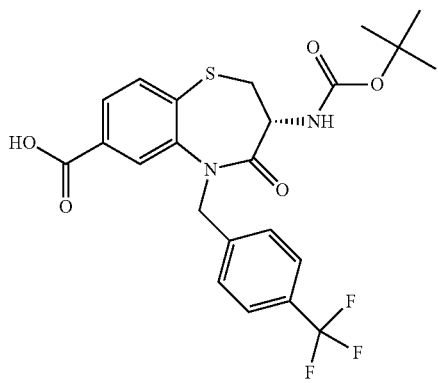 [SMILES: CC(C)(C)OC(=O)N[C@H]1CSc2ccc(C(=O)O)cc2N(Cc2ccc(C(F)(F)F)cc2)C1=O]

The title compound was synthesized according to general procedure GP2 to afford the title compound as white solid in 92% yield.

LCMS: METCR1410 Generic 1.7 min, rt=1.2 min, M/Z (ES+) 441.0 [M−tBu+H+], 519.1 [M+Na+] 96% UV NMR Data: 1H NMR (500 MHz, DMSO-d6) d 7.92 (d, J=1.3 Hz, 1H), 7.78 (dd, J=8.0, 1.6 Hz, 1H), 7.74 (d, J=8.0 Hz, 1H), 7.63 (d, J=8.2 Hz, 2H), 7.55-7.47 (m, 3H), 5.23 (d, J=16.2 Hz, 1H), 5.16 (d, J=16.3 Hz, 1H), 4.17 (dt, J=12.3, 7.6 Hz, 1H), 3.50 (dd, J=11.2, 6.9 Hz, 1H), 3.15 (t, J=11.8 Hz, 1H), 1.35 (s, 9H) [OH not visible]

Synthesis of (3R)-3-{[(tert-butoxy)carbonyl]amino}-4-oxo-5-{[3-(trifluoromethoxy)phenyl]methyl}-2,3,4,5-tetrahydro-1,5-benzothiazepine-7-carboxylic acid (Intermediate VII-05)

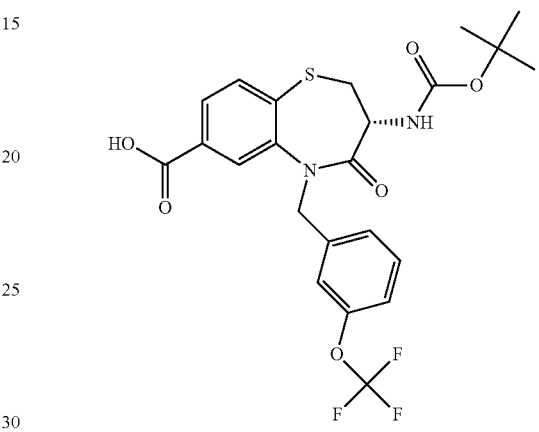

The title compound was synthesized according to general procedure GP2 to afford the title compound as yellow solid in 97% Yield.

LCMS: METUPLCMS-A-004, rt=1.49 min, M/Z (ES−) 511 [M−H+] 95% UV

Synthesis of (3R)-3-{[(tert-butoxy)carbonyl]amino}-5-[(4-chlorophenyl)methyl]-4-oxo-2,3,4,5-tetrahydro-1,5-benzothiazepine-7-carboxylic acid (Intermediate VII-06)

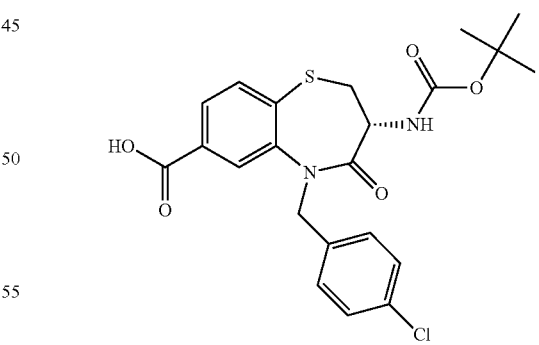

The title compound was synthesized according to general procedure GP2 to afford the title compound as white solid in 91% Yield.

LCMS: METCR1278 Generic 3.5 minutes, rt=1.35 min, M/Z (ES−) 461/463 [M−H+] 97% UV NMR Data: 1H NMR (500 MHz, DMSO-d6) δ 7.93-7.90 (m, 1H), 7.76 (dd, J=8.0, 1.6 Hz, 1H), 7.70 (d, J=8.0 Hz, 1H), 7.47 (d, J=8.1 Hz, 1H), 7.31-7.28 (m, 4H), 5.15 (d, J=15.9 Hz, 1H), 5.01 (d, J=15.9 Hz, 1H), 4.14 (dt, J=12.3, 7.4 Hz, 1H), 3.50-3.47 (m, 1H), 3.14 (d, J=11.8 Hz, 1H), 1.35 (s, 9H). [OH not visible]

Synthesis of (3R)-3-{[(tert-butoxy)carbonyl]amino}-5-{[4-(morpholin-4-yl)phenyl]methyl}-4-oxo-2,3,4,5-tetrahydro-1,5-benzothiazepine-7-carboxylic acid (Intermediate VII-07)

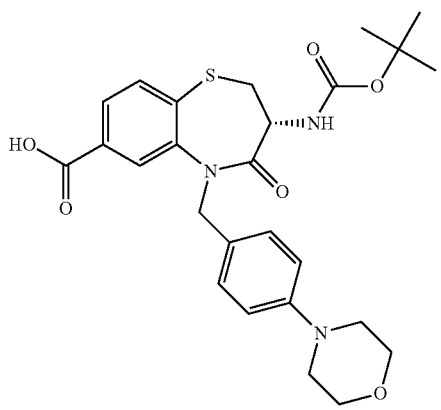 [SMILES: CC(C)(C)OC(=O)N[C@H]1CSc2ccc(C(=O)O)cc2N(Cc2ccc(N3CCOCC3)cc2)C1=O]

The title compound was synthesized according to general procedure GP2 to afford the title compound as brown solid in 41% Yield (73% purity by NMR).

NMR Data: 1H NMR (400 MHz, chloroform-d) δ 7.95 (d, J=1.6 Hz, 1H), 7.79 (d, J=8.0 Hz, 1H), 7.64 (d, J=8.0 Hz, 1H), 7.16 (d, J=8.7 Hz, 2H), 6.76 (d, J=8.8 Hz, 2H), 5.66 (d, J=8.2 Hz, 1H), 5.39 (d, J=14.8 Hz, 1H), 4.72 (d, J=14.7 Hz, 1H), 3.85-3.77 (m, 4H), 3.72 (dd, J=10.9, 6.5 Hz, 2H), 3.12-3.06 (m, 4H), 2.95 (t, J=11.2 Hz, 1H), 1.40 (s, 9H). [OH not visible]

Synthesis of (3R)-3-{[(tert-butoxy)carbonyl]amino}-5-[(4-cyanophenyl)methyl]-4-oxo-2,3,4,5-tetrahydro-1,5-benzothiazepine-7-carboxylic acid (Intermediate VII-08)

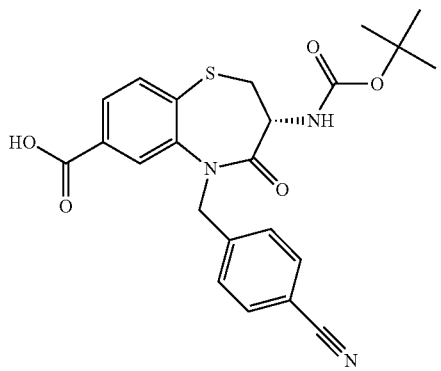 [SMILES: CC(C)(C)OC(=O)N[C@H]1CSc2ccc(C(=O)O)cc2N(Cc2ccc(C#N)cc2)C1=O]

The title compound was synthesized according to general procedure GP2 to afford the title compound as colourless solid in 69% Yield.

LCMS: METUPLCMS-A-004, rt=1.28 min, M/Z (ES–) 452 [M–H+] 73% UV

NMR Data: 1H NMR (400 MHz, chloroform-d) δ 1.41 (s, 9H), 2.97 (t, J=11.3 Hz, 1H), 3.82-3.70 (m, 1H), 4.61-4.46 (m, 1H), 4.86 (d, J=15.7 Hz, 1H), 5.48 (d, J=15.6 Hz, 1H), 5.66 (d, J=8.4 Hz, 1H), 7.42 (d, J=8.2 Hz, 2H), 7.54 (d, J=8.2 Hz, 2H), 7.81-7.63 (m, 2H), 7.92 (s, 1H). [OH not visible]

Synthesis of (3R)-3-{[(tert-butoxy)carbonyl]amino}-4-oxo-5-{[6-(trifluoromethyl)pyridin-3-yl]methyl}-2,3,4,5-tetrahydro-1,5-benzothiazepine-7-carboxylic acid (Intermediate VII-09)

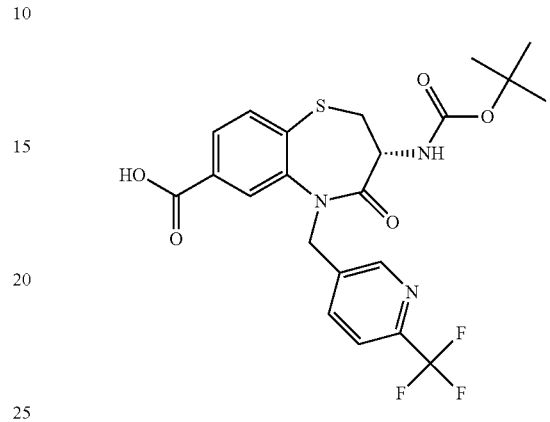

The title compound was synthesized according to general procedure GP2 to afford the title compound as white solid in 27% Yield.

LCMS: METCR1673 Generic 2 minutes, rt=1.3 min, M/Z (ES–) 496 [M–H+] 98% UV

NMR Data: 1H NMR (500 MHz, DMSO-d6) d 8.67 (s, 1H), 7.98 (d, J=1.3 Hz, 1H), 7.94 (d, J=8.5 Hz, 1H), 7.83-7.79 (m, 2H), 7.74 (d, J=8.0 Hz, 1H), 7.50 (d, J=8.2 Hz, 1H), 5.75 (s, 1H), 5.35 (d, J=16.2 Hz, 1H), 5.12 (d, J=16.1 Hz, 1H), 4.14 (dt, J=12.2, 7.5 Hz, 1H), 3.49 (dd, J=11.3, 6.8 Hz, 1H), 3.13 (t, J=11.8 Hz, 1H), 1.34 (s, 9H).

Synthesis of (3R)-3-{[(tert-butoxy)carbonyl]amino}-5-{[4-(5-methyl-1,2,4-oxadiazol-3-yl)phenyl]methyl}-4-oxo-2,3,4,5-tetrahydro-1,5-benzothiazepine-7-carboxylic acid (Intermediate VII-10)

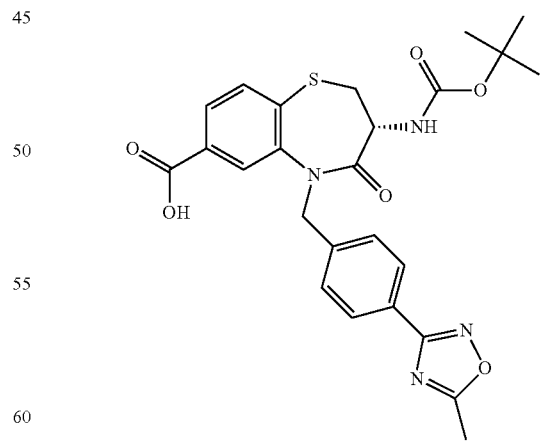

The title compound was synthesized according to general procedure GP2 to afford the title compound as off-white solid in 91% Yield.

LCMS: METCR1673 Generic 2 minutes, rt=1.29 min, M/Z (ES–) 509 [M–H+] 100% UV

NMR Data: 1H NMR (500 MHz, DMSO-d6) d 7.92-7.86 (m, 3H), 7.79-7.71 (m, 2H), 7.49 (dd, J=17.4, 8.2 Hz, 3H), 5.17 (s, 2H), 4.18 (dt, J=12.3, 7.7 Hz, 1H), 3.51 (dd, J=11.2, 6.8 Hz, 2H), 3.16 (t, J=11.8 Hz, 1H), 2.64 (s, 3H), 1.36 (s, 9H).

Synthesis of (3R)-3-{[(tert-butoxy)carbonyl]amino}-5-[(4-fluorophenyl)methyl]-4-oxo-2,3,4,5-tetrahydro-1,5-benzothiazepine-7-carboxylic acid (Intermediate VII-11)

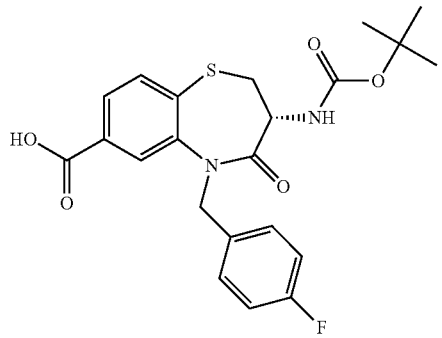 [SMILES: CC(C)(C)OC(=O)N[C@H]1CSc2ccc(C(=O)O)cc2N(Cc2ccc(F)cc2)C1=O]

The title compound was synthesized according to general procedure GP2 to afford the title compound as White Solid in 96% Yield.
LCMS: METCR1673 Generic 2 minutes, rt=1.31 min, M/Z (ES−) 445 [M−H+] 100% UV
NMR Data: 1H NMR (500 MHz, DMSO-d6) d 7.92 (s, 1H), 7.77 (dd, J=8.0, 1.6 Hz, 1H), 7.71 (d, J=8.0 Hz, 1H), 7.47 (d, J=8.3 Hz, 1H), 7.30 (dd, J=8.4, 5.7 Hz, 2H), 7.07 (t, J=8.8 Hz, 2H), 5.17 (d, J=15.8 Hz, 1H), 5.00 (d, J=15.7 Hz, 1H), 4.14 (dt, J=12.2, 7.7 Hz, 1H), 3.48 (dd, J=11.3, 6.8 Hz, 1H), 3.13 (t, J=11.7 Hz, 1H), 1.35 (s, 9H). [OH not visible]

Synthesis of (3R)-3-{[(tert-butoxy)carbonyl]amino}-4-oxo-5-{[4-(1H-1,2,4-triazol-1-yl)phenyl]methyl}-2,3,4,5-tetrahydro-1,5-benzothiazepine-7-carboxylic acid (Intermediate VII-12)

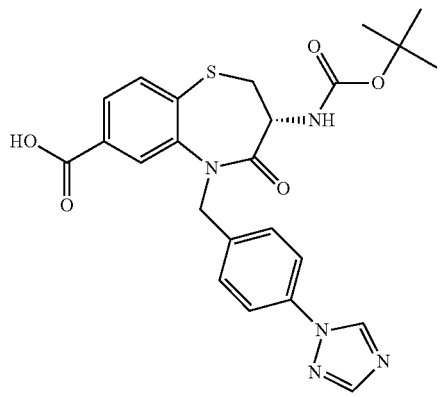 [SMILES: CC(C)(C)OC(=O)N[C@H]1CSc2ccc(C(=O)O)cc2N(Cc2ccc(-n3cncn3)cc2)C1=O]

The title compound was synthesized according to general procedure GP2 to afford the title compound as White Solid in 95% Yield.
LCMS: METCR1673 Generic 2 minutes, rt=1.18 min, M/Z (ES+) 496 [M+H+] 90% UV NMR Data: 1H NMR (500 MHz, DMSO-d6) d 9.24 (s, 1H), 8.20 (s, 1H), 7.94 (s, 1H), 7.80-7.66 (m, 4H), 7.47 (dd, J=16.0, 8.4 Hz, 3H), 5.23 (d, J=15.9 Hz, 1H), 5.10 (d, J=15.9 Hz, 1H), 4.27-4.03 (m, 1H), 3.49 (dd, J=11.3, 6.8 Hz, 1H), 3.15 (t, J=11.7 Hz, 1H), 1.35 (s, 9H). [OH not visible]

Synthesis of (3R)-3-{[(tert-butoxy)carbonyl]amino}-8-fluoro-4-oxo-5-{[4-(trifluoromethoxy)phenyl]methyl}-2,3,4,5-tetrahydro-1,5-benzothiazepine-7-carboxylic acid (Intermediate VII-13)

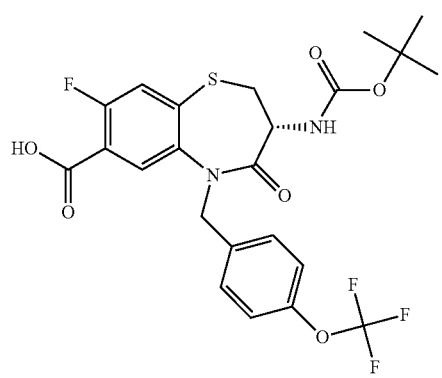 [SMILES: CC(C)(C)OC(=O)N[C@H]1CSc2cc(F)c(C(=O)O)cc2N(Cc2ccc(OC(F)(F)F)cc2)C1=O]

The title compound was synthesized according to general procedure GP2 to afford the title compound as Pale Yellow solid in 83% Yield.
LCMS: METCR1278 Standard 3.5 minutes, rt=2.16 min, M/Z (ES−) 529 [M−H+] 100% UV
NMR Data: 1H NMR (500 MHz, chloroform-d) δ 7.87 (d, J=6.7 Hz, 1H), 7.60 (d, J=9.9 Hz, 1H), 7.52 (d, J=8.2 Hz, 1H), 7.38 (d, J=8.7 Hz, 2H), 7.25 (d, J=8.1 Hz, 2H), 5.17 (d, J=15.9 Hz, 1H), 5.00 (d, J=15.9 Hz, 1H), 4.16 (dt, J=12.3, 7.6 Hz, 1H), 3.13 (t, J=11.8 Hz, 2H), 1.35 (s, 9H). [OH not visible]

Synthesis of (3R)-3-{[(tert-butoxy)carbonyl]amino}-4-oxo-5-{[4-(1,2,3-thiadiazol-4-yl)phenyl]methyl}-2,3,4,5-tetrahydro-1,5-benzothiazepine-7-carboxylic acid (Intermediate VII-14)

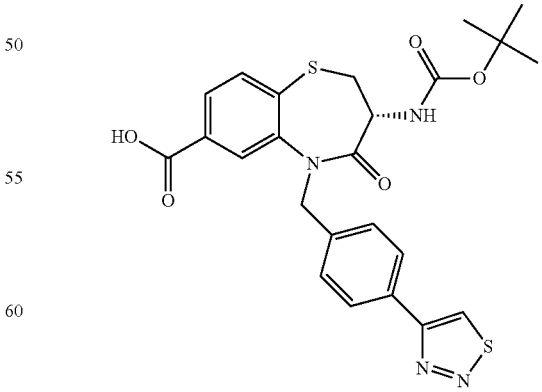

The title compound was synthesized according to general procedure GP2 to afford the title compound as yellow solid in 71% Yield.

LCMS: METCR1673 Generic 2 minutes, rt=1.3 min M/Z (ES−) 511 [M−H−] 77% UV

NMR Data: 1H NMR (500 MHz, DMSO-d6) d 13.28 (s, 1H), 9.57 (s, 1H), 8.02 (d, J=8.2 Hz, 2H), 7.95 (s, 1H), 7.80-7.65 (m, 3H), 7.45 (d, J=8.2 Hz, 2H), 5.22 (d, J=16.1 Hz, 1H), 5.14 (d, J=16.1 Hz, 1H), 4.24-4.13 (m, 1H), 3.51 (dd, J=10.4, 5.9 Hz, 2H), 1.35 (d, J=6.6 Hz, 9H). [OH not visible]

Synthesis of (3R)-3-{[(tert-butoxy)carbonyl]amino}-5-[(4-carbamoylphenyl)methyl]-4-oxo-2,3,4,5-tetrahydro-1,5-benzothiazepine-7-carboxylic acid (Intermediate VII-15)

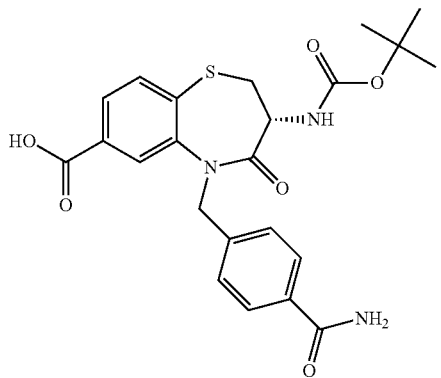 [SMILES: CC(C)(C)OC(=O)N[C@H]1CSc2ccc(C(=O)O)cc2N(Cc2ccc(C(N)=O)cc2)C1=O]

The title compound was synthesized according to general procedure GP2 to afford the title compound as white solid in 25% Yield.

LCMS: METCR1673 Generic 2 minutes, rt=1.1 min, M/Z (ES−) 470 [M−H+] 100% UV

NMR Data: 1H NMR (500 MHz, Chloroform-d) δ 7.86 (d, J=1.6 Hz, 1H), 7.77 (d, J=7.9 Hz, 1H), 7.63 (d, J=8.3 Hz, 2H), 7.58 (d, J=8.0 Hz, 1H), 7.31 (d, J=8.3 Hz, 2H), 5.34 (d, J=15.3 Hz, 1H), 4.85 (d, J=15.3 Hz, 1H), 4.40-4.33 (m, 1H), 3.71-3.59 (m, 2H), 2.94-2.85 (m, 1H), 1.33 (s, 9H). [OH and NH2 not visible]

Synthesis of (2R,3R)-3-{[(tert-butoxy)carbonyl]amino}-5-[(4-chlorophenyl)methyl]-2-methyl-4-oxo-2,3,4,5-tetrahydro-1,5-benzothiazepine-7-carboxylic acid (Intermediate VII-16)

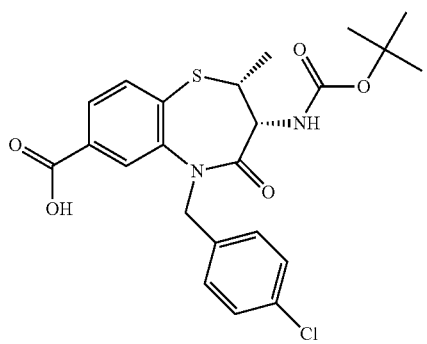 [SMILES: C[C@H]1Sc2ccc(C(=O)O)cc2N(Cc2ccc(Cl)cc2)C(=O)[C@H]1NC(=O)OC(C)(C)C]

The title compound was synthesized according to general procedure GP2 to afford the title compound as white fluffy solid in 82% Yield.

LCMS: METCR1673 Generic 2 minutes, rt=1.49 min, M/Z (ES+) 499/501 [M+Na+] 93% UV NMR Data: 7.94 (d, J=1.4 Hz, 1H), 7.77 (dd, J=8.0, 1.6 Hz, 1H), 7.70 (d, J=7.9 Hz, 1H), 7.31 (s, 4H), 7.10 (d, J=8.2 Hz, 1H), 5.27 (d, J=15.8 Hz, 1H), 5.00 (d, J=16.0 Hz, 1H), 4.46-4.34 (m, 1H), 3.93-3.80 (m, 1H), 1.39-1.22 (m, 12H). [OH not visible]

Synthesis of (3R)-3-{[(tert-butoxy)carbonyl]amino}-5-[(4-chloro-2-fluorophenyl)methyl]-8-fluoro-4-oxo-2,3,4,5-tetrahydro-1,5-benzothiazepine-7-carboxylic acid (Intermediate VII-17)

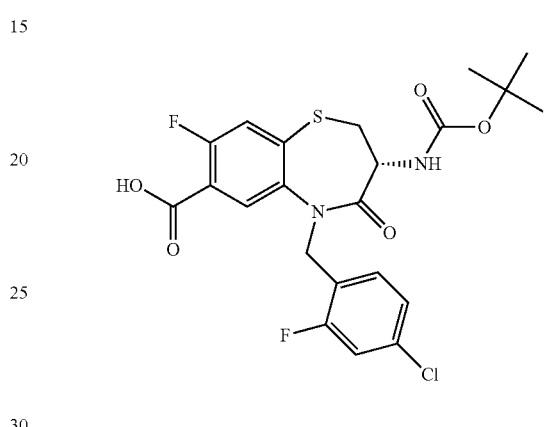

The title compound was synthesized according to general procedure GP2 to afford the title compound as beige foam in 87% Yield.

LCMS: METCR1673 Generic 2 minutes, rt=1.36 min, M/Z (ES−) 497 [M−H+] 100% UV

NMR Data: 1H NMR (500 MHz, Chloroform-d) d 7.89 (d, J=6.5 Hz, 1H), 7.41 (dd, J=8.8, 4.8 Hz, 2H), 7.08-7.03 (m, 1H), 6.97 (dd, J=9.6, 2.0 Hz, 1H), 5.61 (d, J=8.5 Hz, 1H), 5.37 (d, J=15.1 Hz, 1H), 4.79 (d, J=15.1 Hz, 1H), 4.55-4.44 (m, 1H), 3.72 (dd, J=11.0, 6.5 Hz, 1H), 2.91 (t, J=11.3 Hz, 1H), 1.41 (s, 9H). [OH not visible]

Synthesis of (3R)-3-{[(tert-butoxy)carbonyl]amino}-5-[(4-chloro-3-fluorophenyl)methyl]-8-fluoro-4-oxo-2,3,4,5-tetrahydro-1,5-benzothiazepine-7-carboxylic acid (Intermediate VII-18)

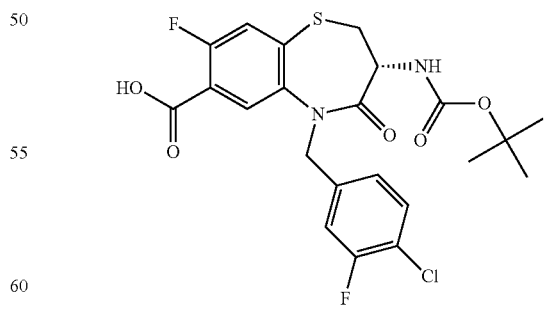

The title compound was synthesized according to general procedure GP2 to afford the title compound as yellow gum in 94% Yield.

LCMS: METCR1673 Generic 2 minutes, rt=1.36 min, M/Z (ES+) 521/523 [M+Na+] 98% UV NMR Data: 1H NMR (500 MHz, Chloroform-d) d 7.82 (d, J=6.6 Hz, 1H), 7.43 (d, J=9.6 Hz, 1H), 7.26 (t, J=7.9 Hz, 1H), 7.15 (dd, J=9.8, 1.8 Hz, 1H), 7.04-6.93 (m, 1H), 5.72 (d, J=8.2 Hz, 1H), 5.36 (d, J=15.4 Hz, 1H), 4.69 (d, J=15.4 Hz, 1H), 4.65-4.54 (m, 1H), 3.76 (dd, J=10.9, 6.6 Hz, 1H), 2.97 (t, J=11.3 Hz, 1H), 1.42 (s, 9H). [OH not visible]

Synthesis of (3R)-3-{[(tert-butoxy)carbonyl]amino}-5-[(3,4-dichlorophenyl)methyl]-4-oxo-2,3,4,5-tetrahydro-1,5-benzothiazepine-7-carboxylic acid (Intermediate VII-19)

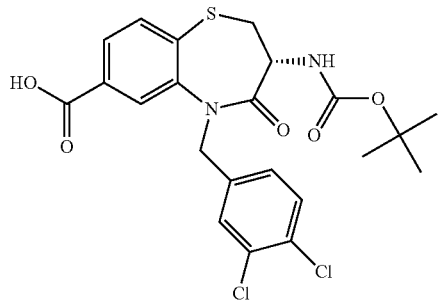 [SMILES: CC(C)(C)OC(=O)N[C@H]1CSc2ccc(C(=O)O)cc2N(Cc2ccc(Cl)c(Cl)c2)C1=O]

The title compound was synthesized according to general procedure GP2 to afford the title compound as cream solid in 94% Yield.

LCMS: METCR1673 Generic 2 minutes, rt=1.4 min, M/Z (ES+) 519/521/523 [M+Na+] 97% UV NMR Data: 1H NMR (500 MHz, DMSO-d6) d 1.35 (s, 9H), 3.08 (t, J=11.8 Hz, 1H), 3.45 (dd, J=6.9, 11.31 Hz, 1H), 4.14 (dt, J=7.5, 12.2 Hz, 1H), 5.04 (s, 2H), 7.27 (dd, J=1.6, 8.3 Hz, 1H), 7.44 (d, J=8.2 Hz, 1H), 7.52 (d, J=8.3 Hz, 1H), 7.56 (d, J=7.9 Hz, 1H), 7.57-7.61 (m, 1H), 7.72 (d, J=7.8 Hz, 1H), 7.82 (s, 1H). [OH not visible]

Synthesis of (3R)-3-{[(tert-butoxy)carbonyl]amino}-8-fluoro-4-oxo-5-(quinolin-2-ylmethyl)-2,3,4,5-tetrahydro-1,5-benzothiazepine-7-carboxylic acid (Intermediate VII-20)

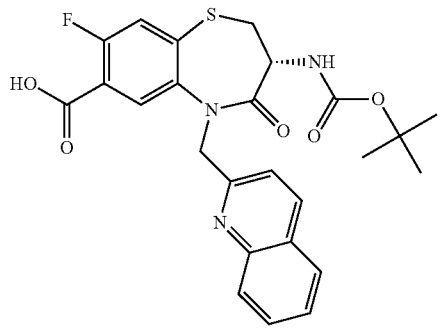 [SMILES: CC(C)(C)OC(=O)N[C@H]1CSc2cc(F)c(C(=O)O)cc2N(Cc2ccc3ccccc3n2)C1=O]

The title compound was synthesized according to general procedure GP2 to afford the title compound as orange foamy solid in 75% Yield.

LCMS: METCR1673 Generic 2 minutes, rt=1.26 min, M/Z (ES+) 498[M+H+] 97% UV

NMR Data: 1H NMR (500 MHz, DMSO-d6) d 1.34 (s, 9H), 3.18 (t, J=11.7 Hz, 1H), 3.53 (dd, J=6.8, 11.2 Hz, 1H), 4.27 (dt, J=7.9, 12.3 Hz, 1H), 5.21 (d, J=16.3 Hz, 1H), 5.35 (d, J=16.3 Hz, 1H), 7.45 (d, J=8.3 Hz, 1H), 7.55-7.67 (m, 3H), 7.75 (t, J=7.7 Hz, 1H), 7.95 (dd, J=8.3, 19.2 Hz, 2H), 8.03 (d, J=6.7 Hz, 1H), 8.35 (d, J=8.5 Hz, 1H). [OH not visible]

Synthesis of (3R)-3-{[(tert-butoxy)carbonyl]amino}-5-[(5-cyclopropyl-1,3,4-thiadiazol-2-yl)methyl]-8-fluoro-4-oxo-2,3,4,5-tetrahydro-1,5-benzothiazepine-7-carboxylic acid (Intermediate VII-21)

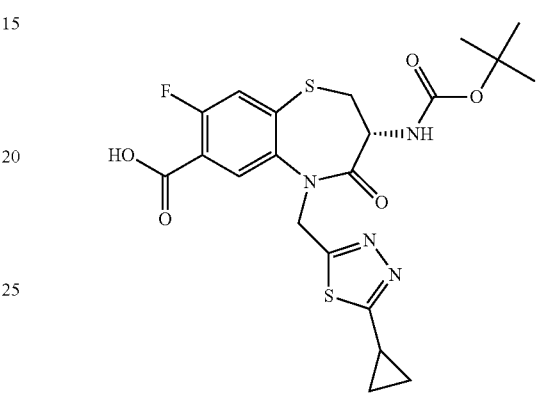

The title compound was synthesized according to general procedure GP2 to afford the title compound as brown solid in 93% Yield.

LCMS: METCR1981 Hydrophobic 3 min, rt=1.68 min, M/Z (ES+) 494.95[M+H+] 90% UV

NMR Data: 1H NMR (500 MHz, DMSO-d6) d 8.13 (d, J=6.6 Hz, 1H), 7.63 (d, J=9.8 Hz, 1H), 7.49 (d, J=8.3 Hz, 1H), 5.40 (d, J=15.6 Hz, 1H), 5.20 (d, J=15.7 Hz, 1H), 4.34 (s, 1H), 4.12 (dt, J=12.0, 7.8 Hz, 1H), 3.48 (dd, J=11.3, 6.9 Hz, 1H), 3.14-3.04 (m, 1H), 2.50-2.42 (m, 1H), 1.35 (s, 9H), 1.22-1.12 (m, 2H), 0.94 (s, 2H).

Synthesis of (3R)-3-{[(tert-butoxy)carbonyl]amino}-5-[(2-fluorophenyl)methyl]-4-oxo-2,3,4,5-tetrahydro-1,5-benzothiazepine-7-carboxylic acid (Intermediate VII-22)

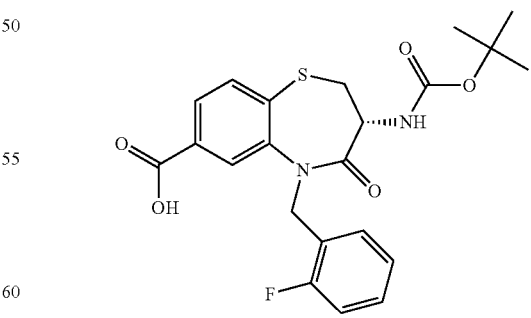

The title compound was synthesized according to general procedure GP2 to afford the title compound as off white solid in 85% yield.

LCMS: METCR1410 Generic 1.7 min, rt=1.14 min, M/Z (ES+) 469.1 [M+Na+] 97% UV

NMR Data: 1H NMR (250 MHz, Chloroform-d) d 7.98 (d, J=1.5 Hz, 1H), 7.80 (d, J=7.8 Hz, 1H), 7.66 (d, J=8.0 Hz, 1H), 7.48 (t, J=6.8 Hz, 1H), 7.25-7.12 (m, 1H), 7.05 (t, J=6.9 Hz, 1H), 7.00-6.83 (m, 1H), 5.66 (d, J=8.2 Hz, 1H), 5.39 (d, J=15.3 Hz, 1H), 4.97 (d, J=15.4 Hz, 1H), 4.48 (s, 1H), 3.74-3.69 (m, 1H), 2.94 (t, J=11.3 Hz, 1H), 1.40 (s, 9H), [OH not visible]

Synthesis of (3R)-3-{[(tert-butoxy)carbonyl] amino}-5-[(3-methoxyphenyl)methyl]-4-oxo-2,3,4,5-tetrahydro-1,5-benzothiazepine-7-carboxylic acid (Intermediate VII-23)

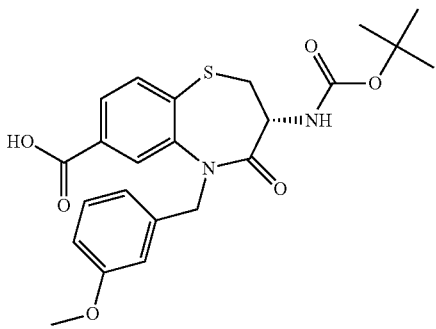 [SMILES: COc1cccc(CN2C(=O)[C@@H](NC(=O)OC(C)(C)C)CSc3ccc(C(=O)O)cc32)c1]

The title compound was synthesized according to general procedure GP2 to afford the title compound as off white solid in 89% yield.

LCMS: METCR1410 Generic 1.7 min, rt=1.13 min, M/Z (ES+) 481 [M+Na+] 95% UV

NMR Data: 1H NMR (250 MHz, Chloroform-d) d 7.93 (d, J=1.5 Hz, 1H), 7.77 (d, J=8.0 Hz, 1H), 7.66 (d, J=8.0 Hz, 1H), 7.14 (t, J=7.9 Hz, 1H), 6.84 (d, J=7.4 Hz, 2H), 6.78-6.65 (m, 1H), 5.70 (d, J=8.2 Hz, 1H), 5.43 (d, J=15.2 Hz, 1H), 4.82 (d, J=15.2 Hz, 1H), 4.51 (s, 1H), 3.74 (m, 4H), 2.99 (t, J=11.2 Hz, 1H), 1.41 (s, 9H), [OH not visible]

Synthesis of (3R)-3-{[(tert-butoxy)carbonyl] amino}-5-[(4-methoxyphenyl)methyl]-4-oxo-2,3,4,5-tetrahydro-1,5-benzothiazepine-7-carboxylic acid (Intermediate VII-24)

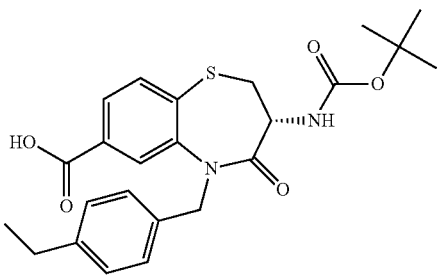 [SMILES: CCc1ccc(CN2C(=O)[C@@H](NC(=O)OC(C)(C)C)CSc3ccc(C(=O)O)cc32)cc1]

The title compound was synthesized according to general procedure GP2 to afford the title compound as yellow foam in 93% yield.

LCMS: METCR1410 Generic 1.7 min, rt=1.12 min, M/Z (ES+) 481.15 [M+Na+] 83% UV

NMR Data: 1H NMR (250 MHz, Chloroform-d) d 7.95 (d, J=1.5 Hz, 1H), 7.76 (d, J=8.0 Hz, 1H), 7.64 (d, J=8.0 Hz, 1H), 7.17 (d, J=8.7 Hz, 2H), 6.79-6.70 (m, 2H), 5.76 (d, J=8.2 Hz, 1H), 5.44 (d, J=14.8 Hz, 1H), 4.71 (d, J=14.9 Hz, 1H), 4.48 (dt, J=11.6, 7.5 Hz, 1H), 3.73 (m, 4H), 2.96 (t, J=11.3 Hz, 1H), 1.41 (s, 9H), [OH not visible]

Synthesis of (3R)-3-{[(tert-butoxy)carbonyl] amino}-8-fluoro-5-[(4-fluorophenyl)methyl]-4-oxo-2,3,4,5-tetrahydro-1,5-benzothiazepine-7-carboxylic acid (Intermediate VII-25)

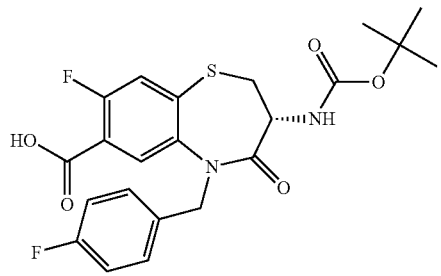 [SMILES: CC(C)(C)OC(=O)N[C@H]1CSc2cc(F)c(C(=O)O)cc2N(Cc2ccc(F)cc2)C1=O]

The title compound was synthesized according to general procedure GP2 to afford the title compound as yellow solid (foam) in 96% yield.

LCMS: METCR1410 Generic 1.7 min, rt=1.14 min, M/Z (ES+) 409.35 [M-tBu+] 96% UV

NMR Data: 1H NMR (250 MHz, Chloroform-d) d 7.81 (d, J=6.5 Hz, 1H), 7.40 (d, J=9.8 Hz, 1H), 7.21 (dd, J=8.6, 5.4 Hz, 2H), 6.91 (t, J=8.7 Hz, 2H), 5.74 (d, J=8.3 Hz, 1H), 5.43 (d, J=14.9 Hz, 1H), 4.73-4.59 (m, 1H), 4.53 (dt, J=11.5, 5.9 Hz, 1H), 3.82-3.77 (m, 1H), 2.95 (t, J=11.3 Hz, 1H), 1.42 (s, 9H), [OH not visible]

Synthesis of (3R)-3-{[(tert-butoxy)carbonyl] amino}-5-[(4-cyclopropylphenyl)methyl]-4-oxo-2,3,4,5-tetrahydro-1,5-benzothiazepine-7-carboxylic acid (Intermediate VII-26)

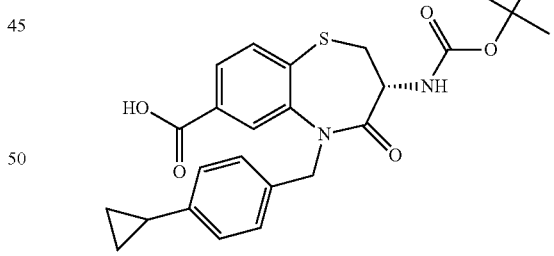

The title compound was synthesized according to general procedure GP2 to afford the title compound as off-white solid in 99% yield.

LCMS: METCR1410 Generic 1.7 min, rt=1.21 min, M/Z (ES+) 491.10 [M+Na+] 100% UV

NMR Data: 1H NMR (500 MHz, Chloroform-d) d 7.94 (d, J=1.4 Hz, 1H), 7.77 (d, J=7.9 Hz, 1H), 7.64 (d, J=8.0 Hz, 1H), 7.14 (d, J=8.1 Hz, 2H), 6.92 (d, J=8.2 Hz, 2H), 5.69 (d, J=8.1 Hz, 1H), 5.40 (d, J=15.0 Hz, 1H), 4.76 (d, J=15.0 Hz, 1H), 4.47 (dt, J=11.4, 7.4 Hz, 1H), 4.01-3.90 (m, 1H), 2.95 (t, J=11.2 Hz, 2H), 1.83-1.77 (m, 1H), 1.40 (s, 9H), 0.93-0.86 (m, 2H), 0.65-0.59 (m, 2H).

Synthesis of (3R)-3-{[(tert-butoxy)carbonyl]amino}-5-[(4-cyanophenyl)methyl]-8-fluoro-4-oxo-2,3,4,5-tetrahydro-1,5-benzothiazepine-7-carboxylic acid (Intermediate VII-27)

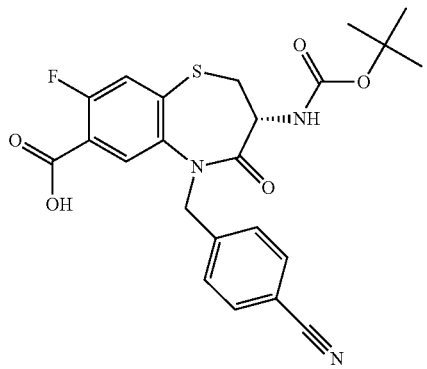 [SMILES: CC(C)(C)OC(=O)N[C@H]1CSc2cc(F)c(C(=O)O)cc2N(Cc2ccc(C#N)cc2)C1=O]

The title compound was synthesized according to general procedure GP2 to afford the title compound as light yellow solid in 100% yield.

LCMS: METCR1410 Generic 1.7 min, rt=1.1 min, M/Z (ES−) 469.70 [M−H+] 88% UV

NMR Data: 1H NMR (500 MHz, DMSO-d6) d 13.65 (s, 1H), 7.84 (d, J=6.5 Hz, 1H), 7.75 (d, J=8.2 Hz, 2H), 7.60 (d, J=9.8 Hz, 1H), 7.51-7.46 (m, 3H), 5.22 (d, J=16.4 Hz, 1H), 5.09 (d, J=16.3 Hz, 1H), 4.19 (dt, J=12.1, 7.4 Hz, 1H), 3.51 (dd, J=11.2, 6.7 Hz, 1H), 3.15 (t, J=11.7 Hz, 1H), 1.36 (s, 9H).

Synthesis of (3R)-3-{[(tert-butoxy)carbonyl]amino}-8-fluoro-5-[(4-methoxyphenyl)methyl]-4-oxo-2,3,4,5-tetrahydro-1,5-benzothiazepine-7-carboxylic acid (Intermediate VII-28)

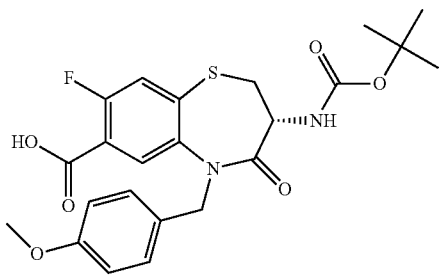 [SMILES: COc1ccc(CN2C(=O)[C@@H](NC(=O)OC(C)(C)C)CSc3cc(F)c(C(=O)O)cc32)cc1]

The title compound was synthesized according to general procedure GP2 to afford the title compound as off-white solid in 96% yield.

LCMS: METCR1410 Generic 1.7 min, rt=1.12 min, M/Z (ES+) 499.5 [M+Na+] 96% UV

NMR Data: 1H NMR (500 MHz, DMSO-d6) d 7.89 (d, J=6.7 Hz, 1H), 7.56 (d, J=9.9 Hz, 1H), 7.44 (d, J =8.4 Hz, 1H), 7.15 (d, J=8.6 Hz, 2H), 6.79 (d, J=8.6 Hz, 2H), 5.17 (d, J=15.4 Hz, 1H), 4.84 (d, J=15.4 Hz, 1H), 4.15 (dt, J=12.2, 7.5 Hz, 1H), 3.69 (s, 3H), 3.48 (dd, J=11.2, 6.8 Hz, 1H), 3.14 (t, J=11.7 Hz, 1H), 1.36 (s, 9H), [OH not visible]

Synthesis of (2R,3R)-3-{[(tert-butoxy)carbonyl]amino}-5-[(4-chlorophenyl)methyl]-8-fluoro-2-methyl-4-oxo-2,3,4,5-tetrahydro-1,5-benzothiazepine-7-carboxylic acid (Intermediate VII-29)

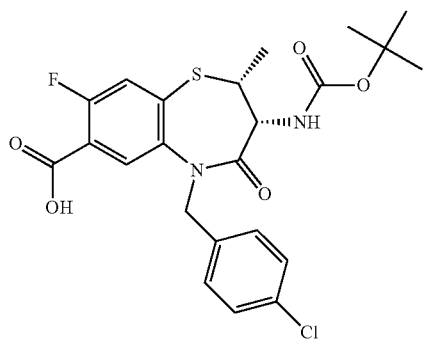 [SMILES: C[C@H]1Sc2cc(F)c(C(=O)O)cc2N(Cc2ccc(Cl)cc2)C(=O)[C@H]1NC(=O)OC(C)(C)C]

The title compound was synthesized according to general procedure GP2 to afford the title compound as colourless foam in 99% yield.

LCMS: METCR1410 Generic 1.7 min, rt=1.29 min, M/Z (ES+) 517/519 [M+Na+] 97% UV

NMR Data: 1H NMR (250 MHz, DMSO-d6) d 7.87 (d, J=6.7 Hz, 1H), 7.54 (d, J=9.9 Hz, 1H), 7.40-7.24 (m, 4H), 7.09 (d, J=7.7 Hz, 1H), 5.27 (d, J=15.5 Hz, 1H), 4.90 (d, J=15.7 Hz, 1H), 4.44-4.32 (m, 1H), 3.92-3.80 (m, 1H), 1.43-1.20 (m, 12H), [OH not visible]

Synthesis of (3R)-3-{[(tert-butoxy)carbonyl]amino}-5-{[4-(difluoromethoxy)phenyl]methyl}-4-oxo-2,3,4,5-tetrahydro-1,5-benzothiazepine-7-carboxylic acid (Intermediate VII-30)

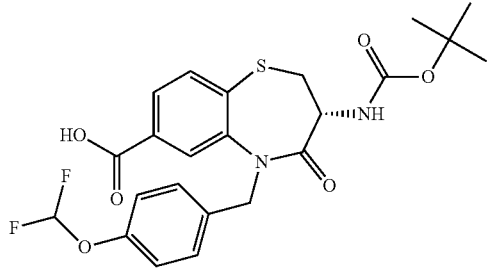 [SMILES: CC(C)(C)OC(=O)N[C@H]1CSc2ccc(C(=O)O)cc2N(Cc2ccc(OC(F)F)cc2)C1=O]

The title compound was synthesized according to general procedure GP2 to afford the title compound as white solid in 94% yield.

LCMS: METCR1410 Generic 1.7 min, rt=1.1 min, M/Z (ES+) 517.45 [M+Na+] 87% UV

NMR Data: 1H NMR (500 MHz, Chloroform-d) d 7.86 (d, J=1.3 Hz, 1H), 7.71 (d, J=8.0 Hz, 1H), 7.60 (d, J=8.0 Hz, 1H), 7.21 (d, J=8.6 Hz, 2H), 6.91 (d, J=8.5 Hz, 2H), 6.37 (t, J=74.0 Hz, 1H), 5.61 (d, J=8.3 Hz, 1H), 5.36 (d, J=15.1 Hz, 1H), 4.71 (d, J=15.2 Hz, 1H), 4.43 (dt, J=11.5, 7.6 Hz, 1H), 3.70-3.64 (m, 1H), 2.89 (t, J=11.3 Hz, 1H), 1.34 (s, 9H), [OH not visible]

Synthesis of (3R)-3-{[(tert-butoxy)carbonyl]amino}-8-chloro-5-[(4-chlorophenyl)methyl]-4-oxo-2,3,4,5-tetrahydro-1,5-benzothiazepine-7-carboxylic acid (Intermediate VII-31)

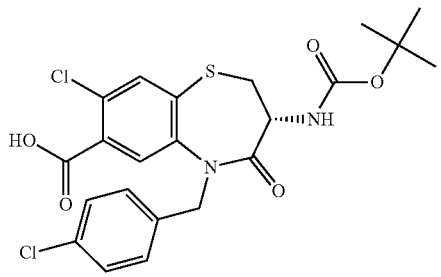 [SMILES: CC(C)(C)OC(=O)N[C@H]1CSc2cc(Cl)c(C(=O)O)cc2N(Cc2ccc(Cl)cc2)C1=O]

The title compound was synthesized according to general procedure GP2 to afford the title compound as cream solid in 99% yield.

LCMS: METCR1410 Generic 1.7 min, rt=1.21 min, M/Z (ES+) 440.85/442.90 [M-tBu+], 519/521.05 [M+Na+] 94.3% UV NMR Data: 1H NMR (500 MHz, DMSO-d6) d 7.58 (s, 2H), 7.45 (d, J=8.3 Hz, 1H), 7.33-7.24 (m, 4H), 5.14 (d, J=15.9 Hz, 1H), 4.93 (d, J=15.9 Hz, 1H), 4.14 (dt, J=12.1, 7.6 Hz, 1H), 3.49-3.44 (m, 1H), 3.08 (t, J=11.8 Hz, 1H), 1.35 (s, 9H), [OH not visible]

Synthesis of (3R)-5-[(4-bromophenyl)methyl]-3-{[(tert-butoxy)carbonyl]amino}-4-oxo-2,3,4,5-tetrahydro-1,5-benzothiazepine-7-carboxylic acid (Intermediate VII-32)

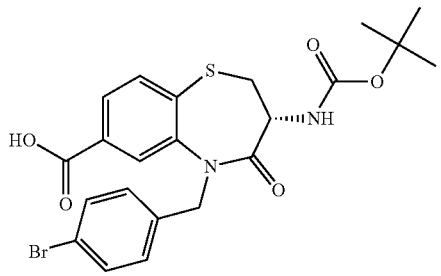 [SMILES: CC(C)(C)OC(=O)N[C@H]1CSc2ccc(C(=O)O)cc2N(Cc2ccc(Br)cc2)C1=O]

The title compound was synthesized according to general procedure GP2 to afford the title compound as white solid in 96% yield.

LCMS: METCR1410 Generic 1.7 min, rt=1.23 min, M/Z (ES+) 451.0/453.05 [M-tBu+H+], 529.1/531.1 [M+Na+] 99% UV NMR Data: 1H NMR (500 MHz, DMSO-d6) d 7.91 (d, J=1.4 Hz, 1H), 7.77 (dd, J=8.0, 1.6 Hz, 1H), 7.71 (d, J=8.0 Hz, 1H), 7.47 (d, J=8.3 Hz, 1H), 7.44 (d, J=8.4 Hz, 2H), 7.23 (d, J=8.3 Hz, 2H), 5.14 (d, J=16.0 Hz, 1H), 5.00 (d, J=15.9 Hz, 1H), 4.14 (dt, J=12.3, 7.6 Hz, 1H), 3.48 (dd, J=11.2, 6.8 Hz, 1H), 3.13 (t, J=11.8 Hz, 1H), 1.35 (s, 9H), [OH not visible]

Synthesis of (3R)-3-{[(tert-butoxy)carbonyl]amino}-8-fluoro-5-{[4-methoxy-3-(trifluoromethyl)phenyl]methyl}-4-oxo-2,3,4,5-tetrahydro-1,5-benzothiazepine-7-carboxylic acid (Intermediate VII-33)

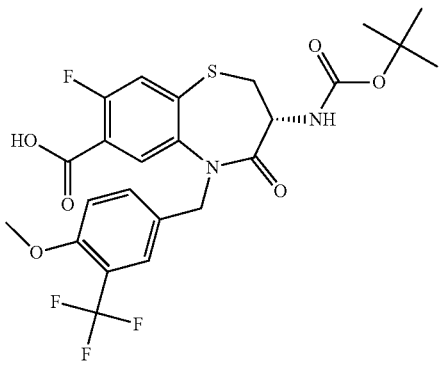 [SMILES: COc1ccc(CN2C(=O)[C@@H](NC(=O)OC(C)(C)C)CSc3cc(F)c(C(=O)O)cc32)cc1C(F)(F)F]

The title compound was synthesized according to general procedure GP2 to afford the title compound as beige solid in 100% yield.

LCMS: METCR1410 Generic 1.7 min, rt=1.21 min, M/Z (ES+) 566.90 [M+Na+] 94% UV

NMR Data: 1H NMR (500 MHz, DMSO-d6) d 7.81 (d, J=6.3 Hz, 1H), 7.54 (s, 1H), 7.51-7.40 (m, 3H), 7.13 (d, J=8.6 Hz, 1H), 5.22 (d, J=15.6 Hz, 1H), 4.89 (d, J=15.6 Hz, 1H), 4.15 (dt, J=12.1, 7.6 Hz, 1H), 3.91-3.85 (m, 1H), 3.83 (s, 3H), 3.47 (dd, J=11.3, 6.8 Hz, 1H), 3.11 (t, J=11.7 Hz, 1H), 1.35 (s, 9H), [OH not visible]

According to the above described and exemplified general procedure GP3 the following amide intermediates VIII were synthesized from acid intermediate VII and the appropriate amine R³—NH₂:

Synthesis of tert-butyl N-[(3R)-5-[(4-chlorophenyl)methyl]-4-oxo-7-[(propan-2-yl)carbamoyl]-2,3,4,5-tetrahydro-1,5-benzothiazepin-3-yl]carbamate (Intermediate VIII-02)

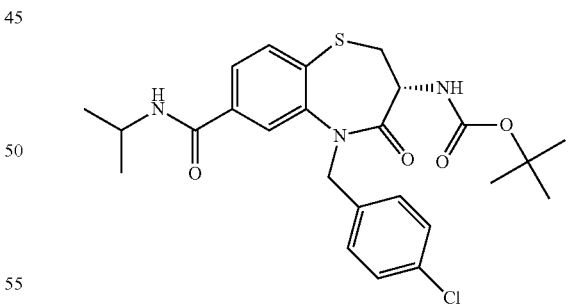

The title compound was synthesized according to general procedure GP3 to afford the title compound as off-white solid in 53% Yield.

LCMS: METCR1673 Generic 2 minutes, rt=1.43 min, M/Z (ES+) 526/528 [M+Na+] 100% UV NMR Data: 1H NMR (500 MHz, Chloroform-d) d 1.25 (dd, J=5.2, 6.5 Hz, 6H), 1.39 (s, 9H), 2.90 (t, J=11.3 Hz, 1H), 3.67 (dd, J=6.6, 11.0 Hz, 1H), 4.23 (dp, J=6.6, 13.2 Hz, 1H), 4.39 (dt, J=7.5, 11.4 Hz, 1H), 4.81 (d, J=15.0 Hz, 1H), 5.31 (d, J=15.0 Hz, 1H), 5.58 (d, J=8.0 Hz, 1H), 5.91 (d, J=7.5

Hz, 1H), 7.17-7.24 (m, 4H), 7.46 (dd, J=1.8, 8.0 Hz, 1H), 7.60 (d, J=8.0 Hz, 1H), 7.66 (d, J=1.5 Hz, 1H)

Synthesis of tert-butyl N-[(3R)-7-({[4-(morpholin-4-yl)phenyl]methyl}carbamoyl)-4-oxo-5-{[4-(trifluoromethoxy)phenyl]methyl}-2,3,4,5-tetrahydro-1,5-benzothiazepin-3-yl]carbamate (Intermediate VIII-03)

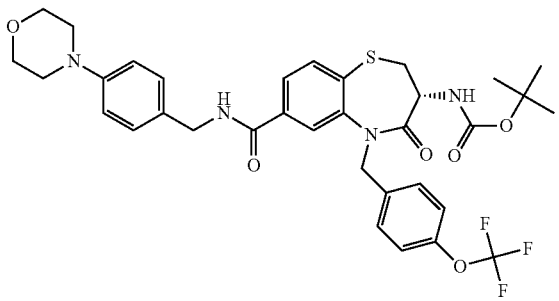 [SMILES: CC(C)(C)OC(=O)N[C@H]1CSc2ccc(C(=O)NCc3ccc(N4CCOCC4)cc3)cc2N(Cc2ccc(OC(F)(F)F)cc2)C1=O]

The title compound was synthesized according to general procedure GP3 to afford the title compound and was used in the next step without further analysis Synthesis of tert-butyl N-[(3R)-7-[(but-3-en-1-yl)carbamoyl]-5-[(4-chlorophenyl)methyl]-4-oxo-2,3,4,5-tetrahydro-1,5-benzothiazepin-3-yl]carbamate (Intermediate VIII-04)

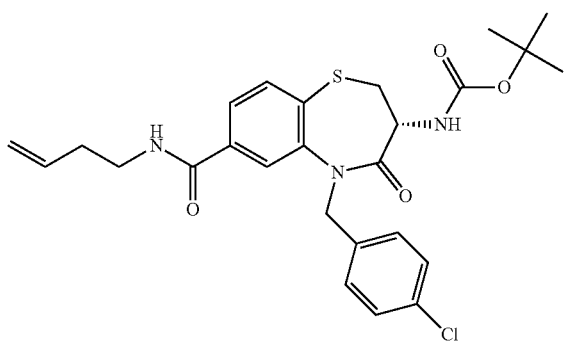 [SMILES: C=CCCNC(=O)c1ccc2c(c1)N(Cc1ccc(Cl)cc1)C(=O)[C@@H](NC(=O)OC(C)(C)C)CS2]

The title compound was synthesized according to general procedure GP3 to afford the title compound as Off-white solid in 84% Yield.

LCMS: METCR1673 Generic 2 minutes, rt=1.44 min, M/Z (ES−) 514/516 [M−H+] 100% UV NMR Data: 1H NMR (500 MHz, DMSO-d6) d 8.63 (t, J=5.6 Hz, 1H), 7.91 (s, 1H), 7.67 (s, 2H), 7.45 (d, J=8.3 Hz, 1H), 7.28 (s, 4H), 5.82 (ddt, J=17.0, 10.2, 6.7 Hz, 1H), 5.29 (d, J=15.7 Hz, 1H), 5.11-4.99 (m, 2H), 4.91 (d, J=15.7 Hz, 1H), 4.13 (dt, J=12.2, 7.6 Hz, 1H), 3.46 (dd, J=11.3, 6.8 Hz, 1H), 3.11 (t, J=11.8 Hz, 1H), 2.52 (d, J=1.9 Hz, 2H), 2.28 (q, J=7.0 Hz, 2H), 1.34 (s, 9H).

Synthesis of tert-butyl N-[(3R)-7-[({4-[(5-acetamidopentyl)oxy]phenyl}methyl)carbamoyl]-4-oxo-5-{[4-(trifluoromethoxy)phenyl]methyl}-2,3,4,5-tetrahydro-1,5-benzothiazepin-3-yl]carbamate (Intermediate VIII-05)

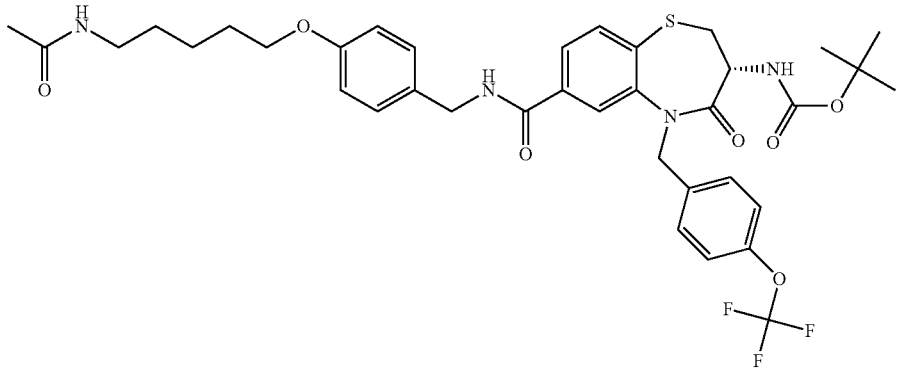 [SMILES: CC(=O)NCCCCCOc1ccc(CNC(=O)c2ccc3c(c2)N(Cc2ccc(OC(F)(F)F)cc2)C(=O)[C@@H](NC(=O)OC(C)(C)C)CS3)cc1]

The title compound was synthesized according to general procedure GP3 to afford the title compound as off-white solid in 14% Yield (95% purity by NMR)

NMR Data: 1H NMR (400 MHz, DMSO-d6) δ 1.35-1.21 (m, 9H), 1.48-1.35 (m, 4H), 1.72-1.62 (m, 2H), 1.76 (s, 3H), 3.01 (q, J=6.4 Hz, 2H), 3.10 (t, J=11.8 Hz, 1H), 3.46 (dd, J=11.3, 6.9 Hz, 1H), 3.91 (t, J=6.5 Hz, 2H), 4.10 (d, J=6.9 Hz, 1H), 4.39 (qd, J=14.7, 5.6 Hz, 2H), 4.97 (d, J=15.7 Hz, 1H), 5.28 (d, J=15.8 Hz, 1H), 6.87 (d, J=8.7 Hz, 2H), 7.22 (dd, J=8.8, 2.6 Hz, 4H), 7.38 (d, J=8.7 Hz, 2H), 7.46 (d, J=8.4 Hz, 1H), 7.68 (d, J=8.0 Hz, 1H), 7.73 (dd, J=8.0, 1.6 Hz, 1H), 7.79 (s, 1H), 7.96 (d, J=1.5 Hz, 1H), 9.13 (t, J=5.9 Hz, 1H).

Synthesis of tert-butyl N-[(3R)-5-[(4-chlorophenyl)methyl]-7-(cyclopropylcarbamoyl)-8-fluoro-4-oxo-2,3,4,5-tetrahydro-1,5-benzothiazepin-3-yl]carbamate (Intermediate VIII-06)

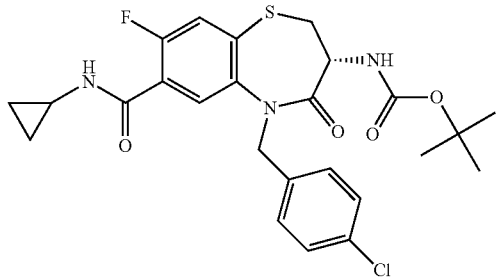 [SMILES: CC(C)(C)OC(=O)N[C@H]1CSc2cc(F)c(C(=O)NC3CC3)cc2N(Cc2ccc(Cl)cc2)C1=O]

The title compound was synthesized according to general procedure GP3 to afford the title compound as beige solid in 88% Yield.

LCMS: METCR1673 Generic 2 minutes, rt=1.41 min, M/Z (ES+) 542/544 [M+Na+] 95% UV NMR Data: 1H NMR (500 MHz, DMSO-d6) d 8.54 (d, J=4.1 Hz, 1H), 7.68 (d, J=6.4 Hz, 1H), 7.53 (d, J=9.3 Hz, 1H), 7.43 (d, J=8.4 Hz, 1H), 7.34-7.23 (m, 4H), 5.26 (d, J=15.6 Hz, 1H), 4.87 (d, J=15.5 Hz, 1H), 4.14 (dt, J=12.2, 7.9 Hz, 2H), 3.15-3.06 (m, 1H), 2.76 (s, 1H), 1.35 (s, 9H), 0.75-0.65 (m, 2H), 0.54 (d, J=2.0 Hz, 2H)

Synthesis of tert-butyl N-[(3R)-5-[(4-chlorophenyl)methyl]-4-oxo-7-(propoxycarbamoyl)-2,3,4,5-tetrahydro-1,5-benzothiazepin-3-yl]carbamate (Intermediate VIII-07)

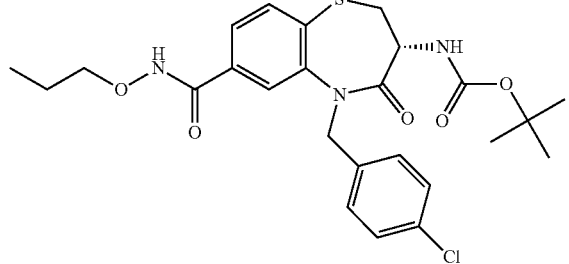

The title compound was synthesized according to general procedure GP3 to afford the title compound as yellow solid in 52% Yield.

LCMS: METCR1673 Generic 2 minutes, rt=1.41 min, M/Z (ES-) 518/520 [M-H+] 100% UV NMR Data: 1H NMR (500 MHz, Chloroform-d) d 8.66 (s, 1H), 7.73-7.41 (m, 3H), 7.20 (s, 4H), 5.58 (d, J=8.2 Hz, 1H), 5.34 (t, J=14.6 Hz, 1H), 4.79 (dd, J=15.0, 8.6 Hz, 1H), 4.45-4.34 (m, 1H), 4.03 (dt, J=65.1, 6.7 Hz, 2H), 3.68 (dd, J=11.0, 6.6 Hz, 1H), 2.98-2.85 (m, 1H), 1.73 (h, J=7.1, 6.5 Hz, 2H), 1.40 (s, 9H), 0.99 (dt, J=11.7, 7.5 Hz, 3H)

Synthesis of tert-butyl N-[(3R)-5-[(4-chlorophenyl)methyl]-8-fluoro-4-oxo-7-[(propan-2-yl)carbamoyl]-2,3,4,5-tetrahydro-1,5-benzothiazepin-3-yl]carbamate (Intermediate VIII-08)

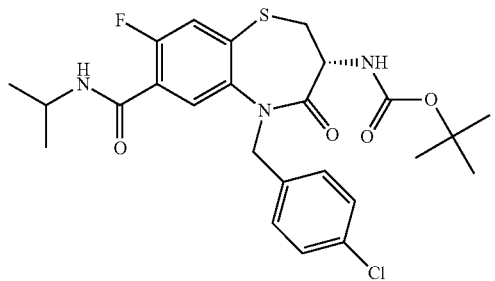 [SMILES: CC(C)NC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as yellow solid in 51% Yield.

LCMS: METCR1673 Generic 2 minutes, rt=1.47 min, M/Z (ES+) 544/546 [M+Na+] 99% UV NMR Data: 1H NMR (500 MHz, Chloroform-d) d 8.05 (d, J=7.1 Hz, 1H), 7.34 (d, J=10.8 Hz, 1H), 7.23-7.16 (m, 4H), 6.54-6.42 (m, 1H), 5.56 (d, J=7.7 Hz, 1H), 5.51 (d, J=15.1 Hz, 1H), 4.64 (d, J=15.1 Hz, 1H), 4.43-4.34 (m, 1H), 4.29 (dt, J=11.8, 6.5 Hz, 1H), 3.70 (dd, J=10.9, 6.5 Hz, 1H), 2.92 (t, J=11.3 Hz, 1H), 1.39 (s, 9H), 1.27 (d, J=6.6 Hz, 6H)

Synthesis of tert-butyl N-[(3R)-5-[(4-chloro-3-fluorophenyl)methyl]-4-oxo-7-[(propan-2-yl)carbamoyl]-2,3,4,5-tetrahydro-1,5-benzothiazepin-3-yl] carbamate (Intermediate VIII-09)

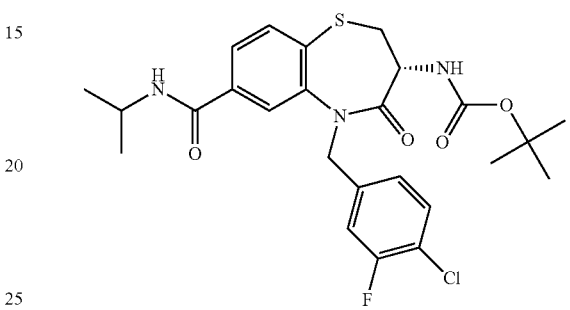

The title compound was synthesized according to general procedure GP3 to afford the title compound as colourless oil in 74% Yield.

LCMS: METCR1673 Generic 2 minutes, rt=1.45 min, M/Z (ES+) 544/546 [M+Na+] 98% UV NMR Data: 1H NMR (500 MHz, Chloroform-d) d 1.25 (dd, J=4.2, 6.5 Hz, 6H), 1.39 (s, 9H), 2.91 (t, J=11.3 Hz, 1H), 3.68 (dd, J=6.6, 11.0 Hz, 1H), 4.24 (dp, J=6.6, 13.2 Hz, 1H), 4.40 (dt, J=7.5, 11.5 Hz, 1H), 4.77 (d, J=15.2 Hz, 1H), 5.36 (d, J=15.2 Hz, 1H), 5.56 (d, J=8.1 Hz, 1H), 5.94 (d, J=7.5 Hz, 1H), 6.96-7.02 (m, 1H), 7.14 (dd, J=1.9, 9.8 Hz, 1H), 7.24 (t, J=7.9 Hz, 1H), 7.46 (dd, J=1.8, 8.0 Hz, 1H), 7.62 (d, J=8.0 Hz, 1H), 7.68-7.74 (m, 1H).

Synthesis of tert-butyl N-[(3R)-7-{[(4-methoxyphenyl)methyl]carbamoyl}-4-oxo-5-{[4-(trifluoromethoxy)phenyl]methyl}-2,3,4,5-tetrahydro-1,5-benzothiazepin-3-yl]carbamate (Intermediate VIII-10)

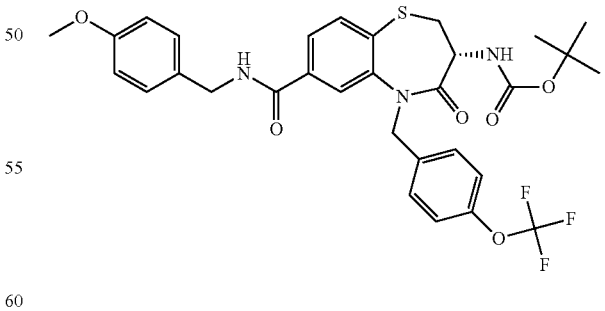

The title compound was synthesized according to general procedure GP3 to afford the title compound as white solid in 62% Yield.

LCMS: MET-UPLCMS-A-006, rt=4.08 min, M/Z (ES+) 632 [M+H+] 94% UV

NMR Data: 1H NMR (400 MHz, Chloroform-d) d 1.39 (s, 9H), 2.91 (t, J=11.3 Hz, 1H), 3.74-3.59 (m, 1H), 3.81 (s, 3H), 4.47-4.34 (m, 1H), 4.61-4.49 (m, 2H), 4.84 (d, J=15.2 Hz, 1H), 5.37 (d, J=15.2 Hz, 1H), 6.93-6.87 (m, 2H), 7.06 (d, J=8.0 Hz, 2H), 7.33-7.23 (m, 6H), 7.47 (dd, J=8.0, 1.8 Hz, 1H), 7.62 (d, J=8.0 Hz, 1H), 7.76 (d, J=1.7 Hz, 1H).

Synthesis of tert-butyl N-[(3R)-7-(butylcarbamoyl)-5-[(4-carbamoylphenyl)methyl]-4-oxo-2,3,4,5-tetrahydro-1,5-benzothiazepin-3-yl]carbamate (Intermediate VIII-11)

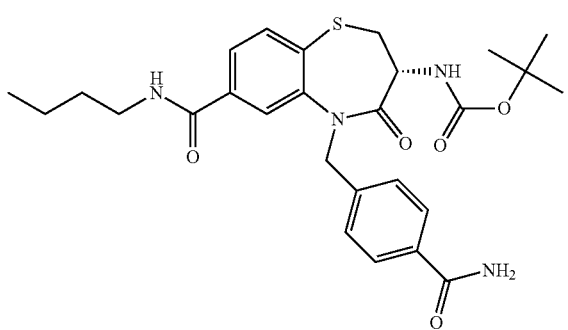 [SMILES: CCCCNC(=O)c1ccc2c(c1)N(Cc1ccc(C(N)=O)cc1)C(=O)[C@@H](NC(=O)OC(C)(C)C)CS2]

The title compound was synthesized according to general procedure GP3 to afford the title compound as White Solid in 35% Yield.

LCMS: METCR1673 Generic 2 minutes, rt=1.22 min, M/Z (ES+) 549 [M+Na+], 427 [M+H-boc] 100% UV NMR Data: 1H NMR (500 MHz, DMSO-d6) d 8.56 (t, J=5.6 Hz, 1H), 7.88 (d, J=12.0 Hz, 2H), 7.72 (d, J=8.2 Hz, 2H), 7.66 (s, 2H), 7.45 (d, J=8.4 Hz, 1H), 7.33 (d, J=8.2 Hz, 2H), 7.27 (s, 1H), 5.29 (d, J=15.8 Hz, 1H), 5.01 (d, J=16.0 Hz, 1H), 4.15 (dt, J=11.9, 7.8 Hz, 1H), 3.46 (dd, J=11.3, 6.8 Hz, 1H), 3.24 (dt, J=13.0, 6.6 Hz, 2H), 3.12 (t, J=11.8 Hz, 1H), 1.49 (p, J=7.1 Hz, 2H), 1.34 (s, 9H), 1.31-1.25 (m, 2H), 0.89 (t, J=7.4 Hz, 3H).

Synthesis of tert-butyl N-[(3R)-5-[(4-chlorophenyl)methyl]-7-[(3-methylbutan-2-yl)carbamoyl]-4-oxo-2,3,4,5-tetrahydro-1,5-benzothiazepin-3-yl]carbamate (Intermediate VIII-12)

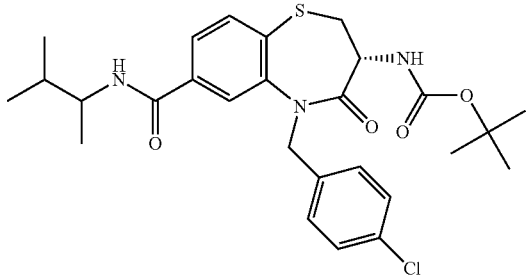 [SMILES: CC(C)C(C)NC(=O)c1ccc2c(c1)N(Cc1ccc(Cl)cc1)C(=O)[C@@H](NC(=O)OC(C)(C)C)CS2]

The title compound was synthesized according to general procedure GP3 to afford the title compound as yellow solid in 69% Yield.

LCMS: METCR1673 Generic 2 minutes, rt=1.53 min, M/Z (ES+) 554/556 [M+Na+] 100% UV NMR Data: 1H NMR (500 MHz, Chloroform-d) d 7.66-7.58 (m, 2H), 7.49-7.43 (m, 1H), 7.22 (s, 4H), 5.74 (t, J=9.7 Hz, 1H), 5.56 (d, J=8.0 Hz, 1H), 5.21 (dd, J=27.0, 15.1 Hz, 1H), 4.98-4.86 (m, 1H), 4.41 (s, 1H), 4.10-3.97 (m, 1H), 3.70 (dd, J=10.9, 6.6 Hz, 1H), 2.91 (t, J=11.3 Hz, 1H), 1.86-1.73 (m, 1H), 1.40 (s, 9H), 1.17 (dd, J=6.7, 1.5 Hz, 3H), 0.99-0.90 (m, 6H)

Synthesis of tert-butyl N-[(3R)-5-[(4-chlorophenyl)methyl]-7-[N'-(2-methylpropyl)hydrazinecarbonyl]-4-oxo-2,3,4,5-tetrahydro-1,5-benzothiazepin-3-yl]carbamate (Intermediate VIII-13)

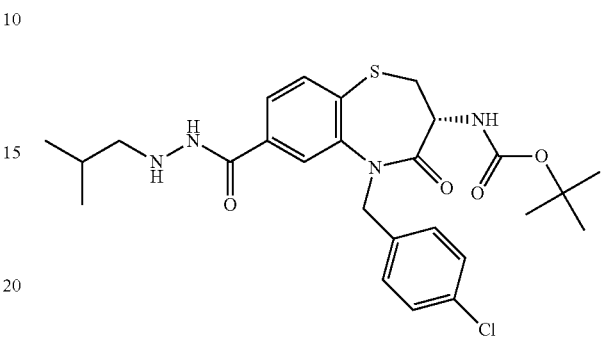

The title compound was synthesized according to general procedure GP3 to afford the title compound as white solid in 26% Yield.

LCMS: METCR1673 Generic 2 minutes, rt=1.44 min, M/Z (ES−) 531/533 [M−H+] 95% UV

NMR Data: 1H NMR (500 MHz, Chloroform-d) d 7.69 (d, J=1.7 Hz, 1H), 7.64 (d, J=8.0 Hz, 1H), 7.48-7.41 (m, 1H), 7.21 (s, 4H), 5.55 (d, J=8.1 Hz, 1H), 5.35 (d, J=15.2 Hz, 1H), 4.81 (d, J=15.2 Hz, 1H), 4.41 (dt, J=11.7, 7.4 Hz, 1H), 3.70 (dd, J=10.9, 6.6 Hz, 1H), 2.98-2.86 (m, 1H), 2.76 (dd, J=6.8, 1.2 Hz, 2H), 1.81 (tt, J=13.4, 6.7 Hz, 1H), 1.40 (s, 9H), 0.99 (d, J=6.7 Hz, 6H). [NH—NH not visible]

Synthesis of tert-butyl N-[(3R)-5-[(4-chlorophenyl)methyl]-7-(cyclobutylcarbamoyl)-8-fluoro-4-oxo-2,3,4,5-tetrahydro-1,5-benzothiazepin-3-yl]carbamate (Intermediate VIII-14)

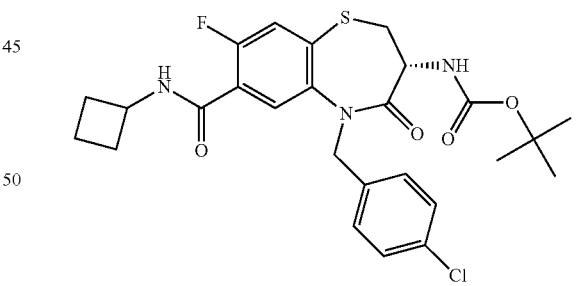

The title compound was synthesized according to general procedure GP3 to afford the title compound as white solid in 81% Yield.

LCMS: METCR1673 Generic 2 minutes, rt=1.5 min, M/Z (ES+) 556/558 [M+Na+] 97% UV

NMR Data: 1H NMR (500 MHz, Chloroform-d) d 8.04 (d, J=7.1 Hz, 1H), 7.35 (d, J=10.9 Hz, 1H), 7.23-7.14 (m, 4H), 6.79 (dd, J=13.3, 7.4 Hz, 1H), 5.56 (d, J=7.3 Hz, 1H), 5.51 (d, J=15.1 Hz, 1H), 4.63 (d, J=15.1 Hz, 1H), 4.61-4.50 (m, 1H), 4.43-4.33 (m, 1H), 3.70 (dd, J=10.9, 6.4 Hz, 1H), 2.93 (t, J=11.2 Hz, 1H), 2.50-2.40 (m, 2H), 2.04-1.93 (m, 2H), 1.88-1.75 (m, 2H), 1.39 (s, 9H)

Synthesis of tert-butyl N-[(3R)-5-[(4-chlorophenyl)methyl]-8-fluoro-7-[(1-methylcyclopropyl)-carbamoyl]-4-oxo-2,3,4,5-tetrahydro-1,5-benzothiazepin-3-yl]carbamate (Intermediate VIII-15)

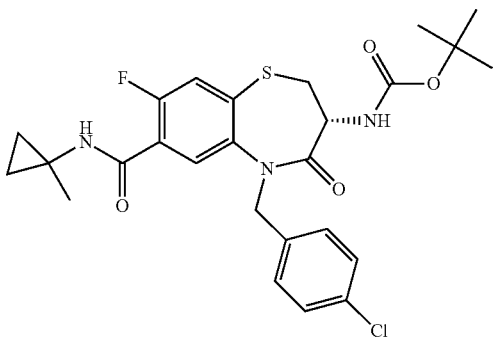 [SMILES: CC1(NC(=O)c2cc3c(cc2F)SC[C@H](NC(=O)OC(C)(C)C)C(=O)N3Cc2ccc(Cl)cc2)CC1]

The title compound was synthesized according to general procedure GP3 to afford the title compound as brown oil in 54% Yield.

LCMS: METCR1673 Generic 2 minutes, rt=1.47 min, M/Z (ES−) 532/534 [M−H+] 98% UV

NMR Data: 1H NMR (500 MHz, DMSO-d6) d 8.67 (s, 1H), 8.15 (s, 1H), 7.65 (d, J=6.4 Hz, 1H), 7.51 (d, J=9.3 Hz, 1H), 7.42 (d, J=8.3 Hz, 1H), 7.28 (q, J=8.5 Hz, 3H), 5.24 (d, J=15.6 Hz, 1H), 4.86 (d, J=15.6 Hz, 1H), 4.12 (dt, J=12.1, 7.7 Hz, 1H), 3.47-3.45 (m, 1H), 3.12-3.07 (m, 1H), 1.39-1.26 (m, 12H), 0.76-0.69 (m, 2H), 0.63-0.58 (m, 2H).

Synthesis of tert-butyl N-[(3R)-5-[(4-chlorophenyl)methyl]-7-[(2-hydroxy-2-methylpropyl)-carbamoyl]-4-oxo-2,3,4,5-tetrahydro-1,5-benzothiazepin-3-yl]carbamate (Intermediate VIII-16)

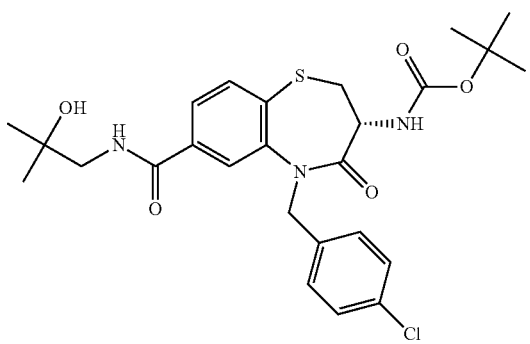 [SMILES: CC(C)(O)CNC(=O)c1ccc2c(c1)N(Cc1ccc(Cl)cc1)C(=O)[C@@H](NC(=O)OC(C)(C)C)CS2]

The title compound was synthesized according to general procedure GP3 to afford the title compound as yellow solid in 95% Yield.

LCMS: METCR1673 Generic 2 minutes, rt=1.32 min, M/Z (ES+) 556/558 [M+Na] 100% UV NMR Data: 1H NMR (500 MHz, Chloroform-d) d d 7.72 (d, J=1.8 Hz, 1H), 7.64 (d, J=8.0 Hz, 1H), 7.52 (dd, J=8.0, 1.7 Hz, 1H), 7.21 (s, 4H), 6.47 (t, J=5.6 Hz, 1H), 5.56 (d, J=8.2 Hz, 1H), 5.31 (d, J=15.1 Hz, 1H), 4.85 (d, J=15.1 Hz, 1H), 4.45-4.37 (m, 1H), 3.70 (dd, J=11.0, 6.6 Hz, 1H), 3.51-3.40 (m, 2H), 2.91 (t, J=11.3 Hz, 1H), 1.89 (s, 1H), 1.40 (s, 9H), 1.29 (s, 6H).

Synthesis of tert-butyl N-[(3R)-5-[(4-chlorophenyl)methyl]-7-[(2-methylpropoxy)carbamoyl]-4-oxo-2,3,4,5-tetrahydro-1,5-benzothiazepin-3-yl]carbamate (Intermediate VIII-17)

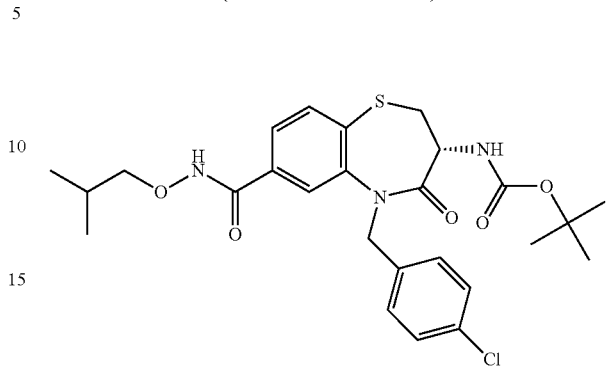

The title compound was synthesized according to general procedure GP3 to afford the title compound as white solid in 25% Yield.

LCMS: METCR1673 Generic 2 minutes, rt=1.46 min, M/Z (ES−) 532/534 [M−H+] 100% UV NMR Data: 1H NMR (500 MHz, Chloroform-d) d 8.53 (s, 1H), 7.73-7.37 (m, 3H), 7.20 (s, 4H), 5.56 (d, J=8.2 Hz, 1H), 5.33 (t, J=15.8 Hz, 1H), 4.80 (dd, J=15.0, 7.4 Hz, 1H), 4.46-4.34 (m, 1H), 3.85 (dd, J=61.1, 6.8 Hz, 2H), 3.69 (dd, J=11.0, 6.6 Hz, 1H), 2.97-2.84 (m, 1H), 2.12-2.02 (m, 1H), 1.40 (s, 9H), 0.98 (dd, J=15.8, 6.7 Hz, 6H)

Synthesis of tert-butyl N-[(3R)-7-[(tert-butoxy)carbamoyl]-5-[(4-chlorophenyl)methyl]-4-oxo-2,3,4,5-tetrahydro-1,5-benzothiazepin-3-yl]carbamate (Intermediate VIII-18)

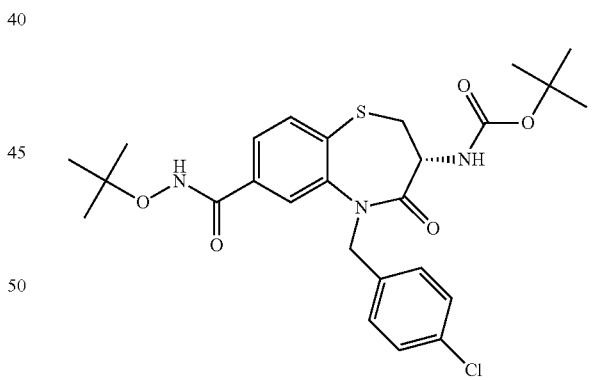

The title compound was synthesized according to general procedure GP3 to afford the title compound as brown solid in 35% Yield.

LCMS: METCR1673 Generic 2 minutes, rt=1.43 min, M/Z (ES−) 532/534 [M−H+] 94% UV

NMR Data: 1H NMR (500 MHz, DMSO-d6) d 11.08 (s, 1H), 8.13 (s, 1H), 7.79 (s, 1H), 7.68 (d, J=8.0 Hz, 1H), 7.61 (d, J=7.9 Hz, 1H), 7.45 (d, J=8.3 Hz, 1H), 7.30 (s, 3H), 5.19 (d, J=15.6 Hz, 1H), 4.99 (d, J=15.6 Hz, 1H), 4.14 (dt, J=12.3, 7.7 Hz, 1H), 3.47 (dd, J=11.3, 6.9 Hz, 1H), 3.12 (t, J=11.8 Hz, 1H), 1.35 (s, 9H), 1.22 (s, 9H).

Synthesis of tert-butyl N-[(3R)-7-(butylcarbamoyl)-5-[(4-chlorophenyl)methyl]-8-fluoro-4-oxo-2,3,4,5-tetrahydro-1,5-benzothiazepin-3-yl]carbamate (Intermediate VII 1-19)

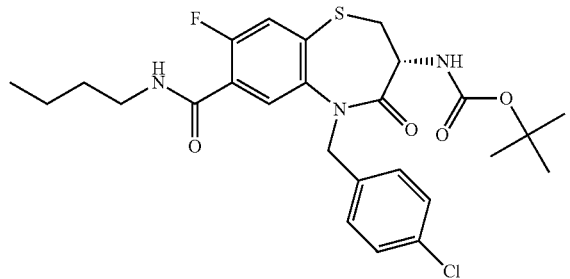 [SMILES: CCCCNC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as pale yellow solid in 74% Yield.

LCMS: METuPLCAB101 uPLC 7 minutes, rt=4.3 min, M/Z (ES+) 558/560 [M+Na+] 100% UV NMR Data: 1H NMR (500 MHz, Chloroform-d) d 8.06 (d, J=7.1 Hz, 1H), 7.35 (d, J=10.9 Hz, 1H), 7.23-7.17 (m, 4H), 6.71-6.62 (m, 1H), 5.61-5.47 (m, 2H), 4.64 (d, J=15.1 Hz, 1H), 4.39 (dt, J=13.3, 6.9 Hz, 1H), 3.70 (dd, J=10.8, 6.5 Hz, 1H), 3.54-3.41 (m, 2H), 2.93 (t, J=11.2 Hz, 1H), 1.61 (dt, J=15.0, 7.3 Hz, 2H), 1.39 (s, 11H), 0.97 (t, J=7.4 Hz, 3H).

Synthesis of tert-butyl N-[(3R)-7-[(butan-2-yl)carbamoyl]-5-[(4-chlorophenyl)methyl]-8-fluoro-4-oxo-2,3,4,5-tetrahydro-1,5-benzothiazepin-3-yl]carbamate (Intermediate VIII-20)

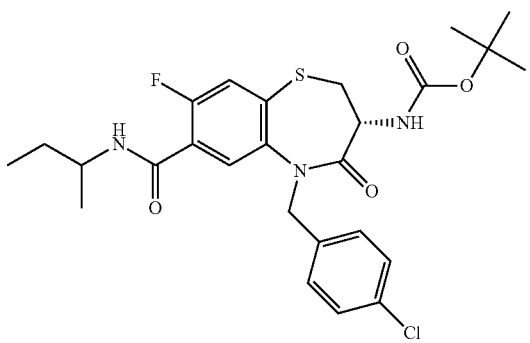 [SMILES: CCC(C)NC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as White Solid in 43% Yield.

LCMS: METCR1673 Generic 2 minutes, rt=1.55 min, M/Z (ES+) 558/560 [M+Na+] 100% UV NMR Data: 1H NMR (500 MHz, DMSO-d6) d 8.25 (d, J=8.2 Hz, 1H), 7.62 (d, J=6.4 Hz, 1H), 7.54 (d, J=9.1 Hz, 1H), 7.43 (d, J=8.4 Hz, 1H), 7.32-7.26 (m, 4H), 5.20 (d, J=15.7 Hz, 1H), 4.93 (s, 1H), 4.15 (dt, J=12.1, 7.5 Hz, 1H), 3.86 (dt, J=14.3, 6.9 Hz, 1H), 3.47 (dd, J=11.4, 6.9 Hz, 1H), 3.11 (t, J=11.8 Hz, 1H), 1.50-1.43 (m, 2H), 1.35 (s, 9H), 1.11 (d, J=6.6 Hz, 3H), 0.85 (t, J=7.4 Hz, 3H).

Synthesis of tert-butyl N-[(3R)-7-(tert-butylcarbamoyl)-5-[(4-chlorophenyl)methyl]-8-fluoro-4-oxo-2,3,4,5-tetrahydro-1,5-benzothiazepin-3-yl]carbamate (Intermediate VIII-21)

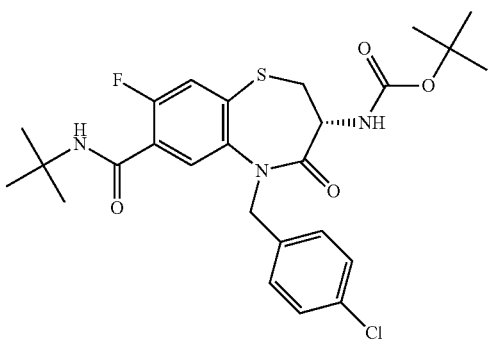 [SMILES: CC(C)(C)NC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as Off-White Solid in 45% Yield.

LCMS: METCR1673 Generic 2 minutes, rt=1.58 min, M/Z (ES+) 558/560 [M+Na+] 100% UV NMR Data: 1H NMR (500 MHz, DMSO-d6) d 8.01 (s, 1H), 7.62 (d, J=6.4 Hz, 1H), 7.51 (d, J=9.1 Hz, 1H), 7.41 (d, J=8.3 Hz, 1H), 7.31-7.27 (m, 4H), 5.22 (d, J=15.7 Hz, 1H), 4.90 (d, J=15.7 Hz, 1H), 4.15 (dt, J=12.2, 8.1 Hz, 1H), 3.46 (dd, J=11.4, 6.9 Hz, 1H), 3.10 (t, J=11.8 Hz, 1H), 1.35-1.34 (m, 18H).

Synthesis of tert-butyl N-[(3R)-5-[(3,4-dichlorophenyl)methyl]-4-oxo-7-[(propan-2-yl)carbamoyl]-2,3,4,5-tetrahydro-1,5-benzothiazepin-3-yl]carbamate (Intermediate VIII-22)

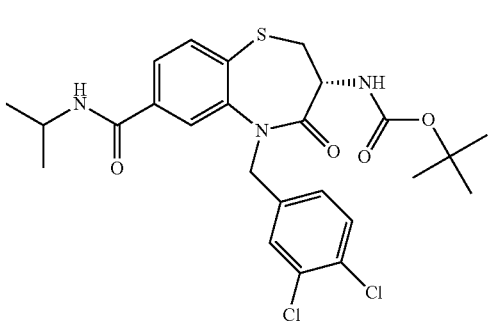 [SMILES: CC(C)NC(=O)c1ccc2c(c1)N(Cc1ccc(Cl)c(Cl)c1)C(=O)[C@@H](NC(=O)OC(C)(C)C)CS2]

The title compound was synthesized according to general procedure GP3 to afford the title compound as colourless oil in 74% Yield.

LCMS: METCR1673 Generic 2 minutes, rt=1.5 min, M/Z (ES+) 560/562 [M+Na+] 100% UV NMR Data: 1H NMR (500 MHz, Chloroform-d) d 1.26 (dd, J=5.1, 6.5 Hz, 6H), 1.39 (s, 9H), 2.91 (t, J=11.3 Hz, 1H), 3.68 (dd, J=6.6, 11.0 Hz, 1H), 4.24 (dp, J=6.6, 13.1 Hz, 1H), 4.40 (dt, J=7.5, 11.5 Hz, 1H), 4.75 (d, J=15.2 Hz, 1H), 5.36 (d, J=15.2 Hz, 1H), 5.56 (d, J=8.1 Hz, 1H), 5.94 (d, J=7.5 Hz, 1H), 7.11 (dd, J=1.9, 8.3 Hz, 1H), 7.29 (d, J=8.3 Hz, 1H), 7.42 (d, J=2.0 Hz, 1H), 7.47 (dd, J=1.8, 8.0 Hz, 1H), 7.62 (d, J=8.0 Hz, 1H), 7.68-7.73 (m, 1H).

Synthesis of tert-butyl N-[(3R)-5-[(4-chlorophenyl) methyl]-8-fluoro-4-oxo-7-(propoxycarbamoyl)-2,3, 4,5-tetrahydro-1,5-benzothiazepin-3-yl]carbamate (Intermediate VIII-23)

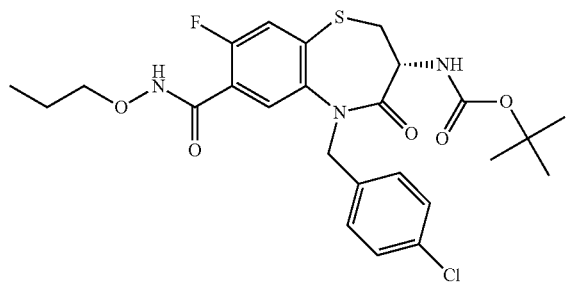 [SMILES: CCCONC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as yellow solid in 72% Yield.

LCMS: METCR1673 Generic 2 minutes, rt=1.44 min, M/Z (ES+) 560/562 [M+Na+] 99% UV NMR Data: 1H NMR (500 MHz, Chloroform-d) d 9.09 (d, J=11.6 Hz, 1H), 8.05 (d, J=6.5 Hz, 1H), 7.37 (d, J=10.5 Hz, 1H), 7.20 (s, 4H), 5.57 (d, J=7.7 Hz, 1H), 5.52 (d, J=15.1 Hz, 1H), 4.65 (d, J=15.1 Hz, 1H), 4.44-4.35 (m, 1H), 4.01 (t, J=6.7 Hz, 2H), 3.71 (dd, J=10.9, 6.4 Hz, 1H), 2.94 (t, J=11.2 Hz, 1H), 1.76 (h, J=7.2 Hz, 2H), 1.40 (s, 9H), 1.02 (t, J=7.4 Hz, 3H)

Synthesis of tert-butyl N-[(3R)-5-[(4-fluorophenyl) methyl]-7-[(oxan-4-ylmethyl)carbamoyl]-4-oxo-2,3, 4,5-tetrahydro-1,5-benzothiazepin-3-yl]carbamate (Intermediate VIII-24)

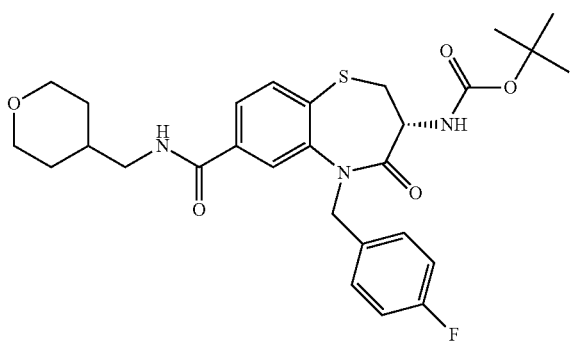 [SMILES: CC(C)(C)OC(=O)N[C@H]1CSc2ccc(C(=O)NCC3CCOCC3)cc2N(Cc2ccc(F)cc2)C1=O]

The title compound was synthesized according to general procedure GP3 to afford the title compound as light brown solid in 51% Yield.

LCMS: METCR1673 Generic 2 minutes, rt=1.32 min, M/Z (ES+) 566 [M+Na+] 94% UV

NMR Data: 1H NMR (500 MHz, DMSO-d6) δ 8.67 (t, J=5.8 Hz, 1H), 7.92 (d, J=1.4 Hz, 1H), 7.74-7.62 (m, 2H), 7.49 (d, J=8.4 Hz, 1H), 7.29 (dd, J=8.6, 5.6 Hz, 2H), 7.06 (t, J=8.9 Hz, 2H), 5.29 (d, J=15.5 Hz, 1H), 4.92 (d, J=15.5 Hz, 1H), 4.25-4.06 (m, 1H), 3.91-3.80 (m, 2H), 3.46 (dd, J=11.3, 6.9 Hz, 1H), 3.31-3.23 (m, 2H), 3.22-3.05 (m, 3H), 1.78 (tt, J=7.6, 4.0 Hz, 1H), 1.58 (d, J=11.6 Hz, 2H), 1.35 (s, 9H), 1.19 (qd, J=12.2, 4.5 Hz, 3H).

Synthesis of tert-butyl N-[(3R)-7-(N'-butanoylhydrazinecarbonyl)-5-[(4-chlorophenyl)methyl]-4-oxo-2,3,4,5-tetrahydro-1,5-benzothiazepin-3-yl]carbamate (Intermediate VIII-25)

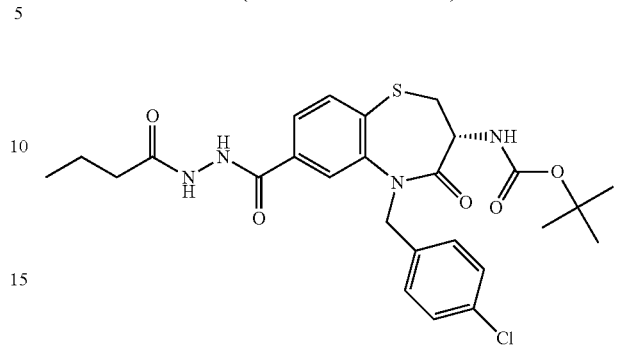

The title compound was synthesized according to general procedure GP3 to afford the title compound as yellow solid in 27% Yield.

LCMS: METCR1673 Generic 2 minutes, rt=1.3 min, M/Z (ES-) 545 [M-H+] 74% UV

NMR Data: 1H NMR (500 MHz, Chloroform-d) d 8.93 (s, 1H), 8.37 (s, 1H), 7.78 (d, J=1.7 Hz, 1H), 7.65 (dd, J=8.0, 2.9 Hz, 1H), 7.57-7.49 (m, 1H), 7.20 (d, J=2.7 Hz, 4H), 5.56 (d, J=8.1 Hz, 1H), 5.41 (dd, J=15.1, 12.2 Hz, 1H), 4.79-4.73 (m, 1H), 4.42 (s, 1H), 3.70 (dd, J=10.9, 6.6 Hz, 1H), 2.92 (q, J=10.7, 10.2 Hz, 1H), 2.30 (q, J=7.7 Hz, 2H), 1.79-1.71 (m, 2H), 1.39 (s, 9H), 1.01 (t, J=7.4 Hz, 3H)

Synthesis of tert-butyl N-[(3R)-5-[(4-chlorophenyl) methyl]-8-fluoro-7-[(1-methylcyclobutyl)-carbamoyl]-4-oxo-2,3,4,5-tetrahydro-1,5-benzothiazepin-3-yl]carbamate (Intermediate VIII-26)

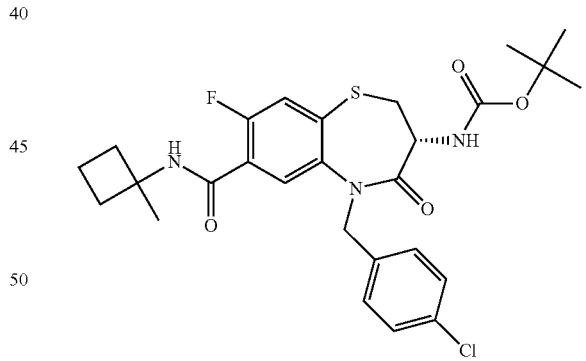

The title compound was synthesized according to general procedure GP3 to afford the title compound as Brown Solid in 49% Yield.

LCMS: METCR1673 Generic 2 minutes, rt=1.55 min, M/Z (ES-) 546/548 [M-H+] 100% UV NMR Data: 1H NMR (500 MHz, DMSO-d6) d 8.47 (s, 1H), 7.67 (d, J=6.4 Hz, 1H), 7.52 (d, J=9.2 Hz, 1H), 7.42 (d, J=8.4 Hz, 1H), 7.32-7.27 (m, 4H), 5.24 (d, J=15.7 Hz, 1H), 4.89 (d, J=15.6 Hz, 1H), 4.14 (dt, J=12.1, 7.7 Hz, 1H), 3.46 (dd, J=11.3, 6.9 Hz, 1H), 3.11 (t, J=11.7 Hz, 1H), 2.33-2.29 (m, 2H), 2.00-1.91 (m, 2H), 1.85-1.76 (m, 2H), 1.46 (s, 3H), 1.35 (s, 9H).

Synthesis of tert-butyl N-[(3R)-5-[(4-chlorophenyl)methyl]-7-[(2,2-dimethylcyclopropyl)-carbamoyl]-8-fluoro-4-oxo-2,3,4,5-tetrahydro-1,5-benzothiazepin-3-yl]carbamate (Intermediate VIII-27)

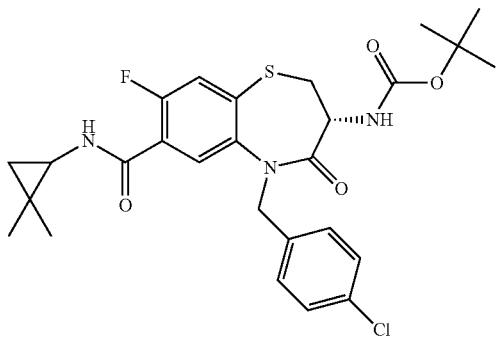 [SMILES: CC(C)(C)OC(=O)N[C@H]1CSc2cc(F)c(C(=O)NC3CC3(C)C)cc2N(Cc2ccc(Cl)cc2)C1=O]

The title compound was synthesized according to general procedure GP3 to afford the title compound as Brown Solid in 55% Yield.

LCMS: METCR1673 Generic 2 minutes, rt=1.58 min, M/Z (ES−) 546/548 [M−H+] 100% UV NMR Data: 1H NMR (500 MHz, DMSO-d6) d 8.44 (d, J=3.9 Hz, 1H), 7.63 (d, J=6.4 Hz, 1H), 7.54 (d, J=9.1 Hz, 1H), 7.44 (d, J=8.4 Hz, 1H), 7.32-7.26 (m, 4H), 5.19 (d, J=15.7 Hz, 1H), 4.93 (d, J=15.7 Hz, 1H), 4.16 (dt, J=12.2, 7.6 Hz, 1H), 3.48 (dd, J=11.3, 6.9 Hz, 1H), 3.12 (t, J=11.7 Hz, 1H), 2.55 (dt, J=8.2, 4.1 Hz, 1H), 1.35 (s, 9H), 1.07 (s, 3H), 0.98 (s, 3H), 0.67 (dd, J=7.9, 5.2 Hz, 1H), 0.47 (t, J=4.7 Hz, 1H).

Synthesis of tert-butyl N-[(3R)-5-[(4-chlorophenyl)methyl]-8-fluoro-7-[N'-(2-methylpropyl)hydrazinecarbonyl]-4-oxo-2,3,4,5-tetrahydro-1,5-benzothiazepin-3-yl]carbamate (Intermediate VIII-28)

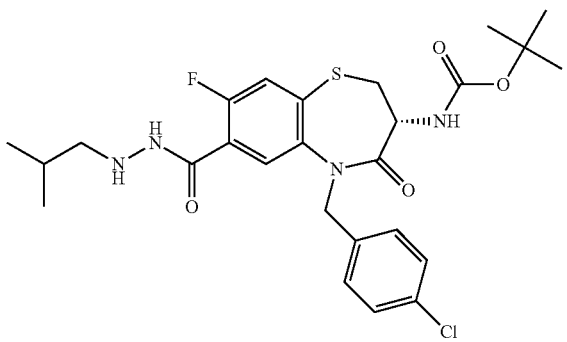 [SMILES: CC(C)CNNC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as Off-White Solid in 28% Yield.

LCMS: METCR1673 Generic 2 minutes, rt=1.49 min, M/Z (ES+) 573/575 [M+Na+] 94% UV NMR Data: 1H NMR (500 MHz, DMSO-d6) d 9.92 (s, 1H), 7.63 (d, J=6.3 Hz, 1H), 7.55 (d, J=9.2 Hz, 1H), 7.46-7.42 (m, 1H), 7.32-7.27 (m, 4H), 5.22-5.10 (m, 2H), 4.92 (d, J=15.7 Hz, 1H), 4.15 (dt, J=12.1, 7.7 Hz, 1H), 3.48 (dd, J=11.4, 6.9 Hz, 1H), 3.11 (t, J=11.7 Hz, 1H), 2.60 (d, J=6.4 Hz, 2H), 1.71 (m, 6.7 Hz, 1H), 1.35 (s, 9H), 0.90 (d, J=6.7 Hz, 6H).

Synthesis of tert-butyl N-[(3R)-7-(butylcarbamoyl)-4-oxo-5-{[4-(1H-1,2,4-triazol-1-yl)phenyl]-methyl}-2,3,4,5-tetrahydro-1,5-benzothiazepin-3-yl]carbamate (Intermediate VIII-29)

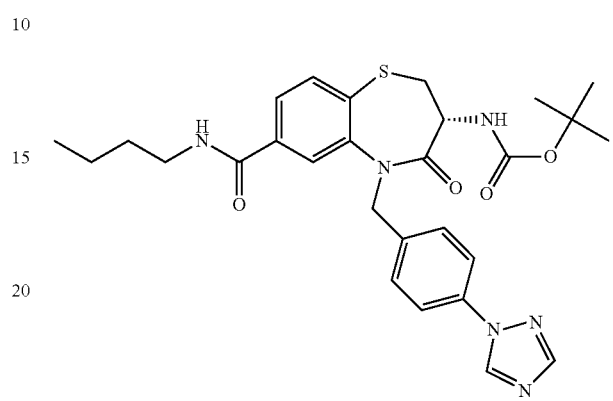

The title compound was synthesized according to general procedure GP3 to afford the title compound as White solid in 37% Yield.

LCMS: METCR1673 Generic 2 minutes, rt=1.3 min, M/Z (ES−) 549 [M−H+] 99% UV

NMR Data: 1H NMR (500 MHz, DMSO-d6) d 9.22 (s, 1H), 8.58 (t, J=5.6 Hz, 1H), 8.19 (s, 1H), 7.94 (s, 1H), 7.72 (d, J=8.5 Hz, 2H), 7.66 (d, J=8.0 Hz, 2H), 7.45 (t, J=7.6 Hz, 3H), 5.36 (d, J=15.8 Hz, 1H), 5.00 (d, J=15.7 Hz, 1H), 4.15 (dt, J=12.2, 7.7 Hz, 1H), 3.47 (dd, J=11.4, 6.8 Hz, 1H), 3.28-3.22 (m, 2H), 3.13 (t, J=11.8 Hz, 1H), 1.50 (m, 2H), 1.35 (s, 9H), 1.32-1.28 (m, 2H), 0.89 (t, J=7.4 Hz, 3H).

Synthesis of tert-butyl N-[(2R,3R)-5-[(4-chlorophenyl)methyl]-7-[(2,2-difluorocyclopropyl)-carbamoyl]-2-methyl-4-oxo-2,3,4,5-tetrahydro-1,5-benzothiazepin-3-yl]carbamate (Intermediate VIII-30)

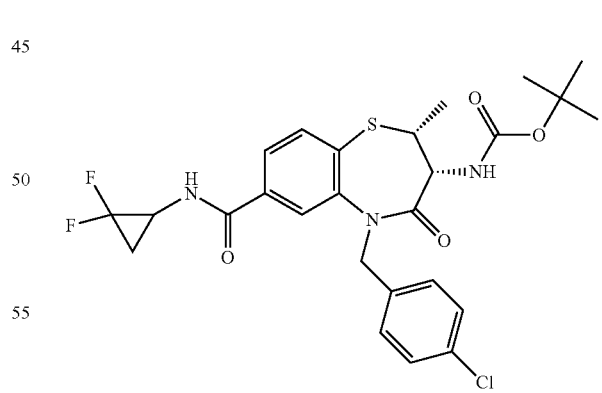

The title compound was synthesized according to general procedure GP3 to afford the title compound as off white solid in 33% Yield.

LCMS: METCR1673 Generic 2 minutes, rt=1.35 min, M/Z (ES+) 574/576 [M+Na+] 100% UV NMR Data: 1H NMR (500 MHz, DMSO-d6) d 8.96 (s, 1H), 7.96 (d, J=8.2 Hz, 1H), 7.74-7.66 (m, 2H), 7.30 (s, 4H), 7.08 (d, J=8.0 Hz, 1H), 5.47-5.34 (m, 1H), 4.90 (dd, J=15.7, 3.5 Hz, 1H), 4.41-4.33 (m, 1H), 3.87-3.78 (m, 1H), 3.46 (s, 1H), 2.06-1.93 (m, 1H), 1.67 (s, 1H), 1.39-1.25 (m, 12H).

Synthesis of tert-butyl N-[(3R)-5-[(4-chlorophenyl)methyl]-8-fluoro-7-[(2-hydroxy-2-methyl-propyl)carbamoyl]-4-oxo-2,3,4,5-tetrahydro-1,5-benzothiazepin-3-yl]carbamate (Intermediate VIII-31)

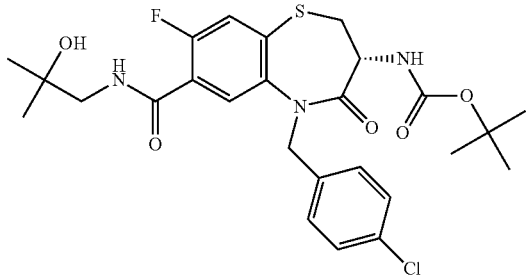 [SMILES: CC(C)(O)CNC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as yellow solid in 47% Yield.

LCMS: METCR1673 Generic 2 minutes, rt=1.36 min, M/Z (ES+) 574/576 [M+Na+] 100% UV NMR Data: 1H NMR (500 MHz, Chloroform-d) d 8.05 (d, J=7.0 Hz, 1H), 7.37 (d, J=10.8 Hz, 1H), 7.20 (s, 4H), 5.56 (s, 1H), 5.50 (d, J=15.1 Hz, 1H), 4.66 (d, J=15.1 Hz, 1H), 4.39 (s, 1H), 3.71 (dd, J=10.8, 6.5 Hz, 1H), 3.58-3.43 (m, 2H), 2.93 (t, J=11.2 Hz, 1H), 1.40 (s, 9H), 1.31 (s, 6H) [2×NH not visible]

Synthesis of tert-butyl N-[(3R)-5-[(4-chlorophenyl)methyl]-8-fluoro-7-[(2-methylpropoxy)-carbamoyl]-4-oxo-2,3,4,5-tetrahydro-1,5-benzothiazepin-3-yl]carbamate (Intermediate VIII-32)

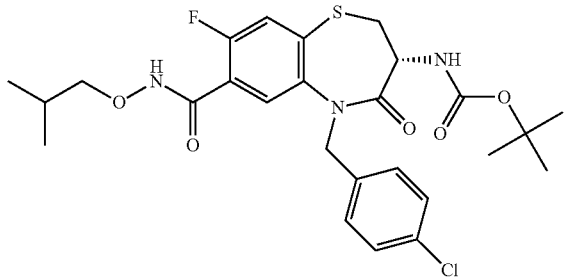 [SMILES: CC(C)CONC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as yellow glassy oil in 98% Yield.

LCMS: METCR1673 Generic 2 minutes, rt=1.51 min, M/Z (ES+) 574/576 [M+Na+] 97% UV NMR Data: 1H NMR (500 MHz, Chloroform-d) d 9.12 (d, J=11.8 Hz, 1H), 8.04 (d, J=6.5 Hz, 1H), 7.36 (d, J=10.5 Hz, 1H), 7.19 (s, 4H), 5.57 (d, J=7.8 Hz, 1H), 5.52 (d, J=15.1 Hz, 1H), 4.63 (d, J=15.1 Hz, 1H), 4.39 (dt, J=11.6, 7.1 Hz, 1H), 3.83 (d, J=6.7 Hz, 2H), 3.70 (dd, J=10.9, 6.4 Hz, 1H), 2.94 (t, J=11.2 Hz, 1H), 2.04 (s, 1H), 1.39 (s, 9H), 1.01 (d, J=6.7 Hz, 6H)

Synthesis of tert-butyl N-[(3R)-7-{[3-(2,2-dimethyl-propanamido)propyl]carbamoyl}-4-oxo-5-{[4-(trifluoromethoxy)phenyl]methyl}-2,3,4,5-tetrahydro-1,5-benzothiazepin-3-yl]carbamate (Intermediate VIII-33)

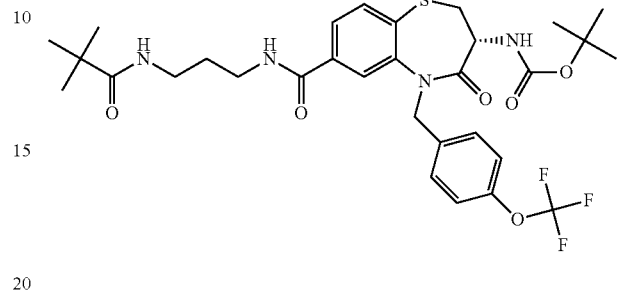

The title compound was synthesized according to general procedure GP3 to afford the title compound as white solid in 23% Yield.

LCMS: MET-UPLCMS-A-006, rt=4.31 min, M/Z (ES+) 653 [M+H+] 99% UV

NMR Data: 1H NMR (400 MHz, DMSO-d6) d 1.07 (s, 9H), 1.30 (s, 9H), 1.63 (p, J=6.9 Hz, 2H), 3.13-3.03 (m, 3H), 3.28-3.18 (m, 2H), 3.45 (dd, J=11.3, 6.9 Hz, 1H), 4.18-4.05 (m, 1H), 4.97 (d, J=15.8 Hz, 1H), 5.30 (d, J=15.8 Hz, 1H), 7.22 (d, J=8.0 Hz, 2H), 7.39 (d, J=8.7 Hz, 2H), 7.49 (dd, J=14.6, 7.1 Hz, 2H), 7.72-7.64 (m, 2H), 7.93 (s, 1H), 8.64 (t, J=5.7 Hz, 1H).

Synthesis of tert-butyl N-[(3R)-7-(benzylcarbamoyl)-8-fluoro-4-oxo-5-{[4-(trifluoromethoxy)-phenyl]methyl}-2,3,4,5-tetrahydro-1,5-benzothiazepin-3-yl]carbamate (Intermediate VIII-34)

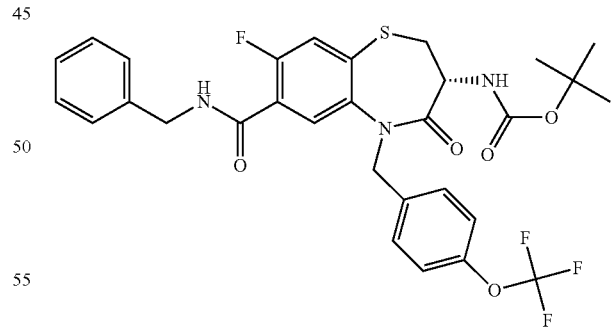

The title compound was synthesized according to general procedure GP3 to afford the title compound as brown solid in 53% Yield (92% purity by NMR)

NMR Data: 1H NMR (400 MHz, Chloroform-d) δ 8.12 (d, J=7.0 Hz, 1H), 7.40-7.28 (m, 8H), 7.08 (d, J=7.9 Hz, 2H), 7.05-6.97 (m, 1H), 5.55 (t, J=11.5 Hz, 2H), 4.67 (td, J=14.8, 6.3 Hz, 3H), 4.46-4.35 (m, 1H), 3.71 (dd, J=10.8, 6.4 Hz, 1H), 2.94 (t, J=11.3 Hz, 1H), 1.40 (s, 9H).

Synthesis of tert-butyl N-[(3R)-7-(butylcarbamoyl)-5-[(4-chloro-2-fluorophenyl)methyl]-8-fluoro-4-oxo-2,3,4,5-tetrahydro-1,5-benzothiazepin-3-yl]carbamate (Intermediate VIII-35)

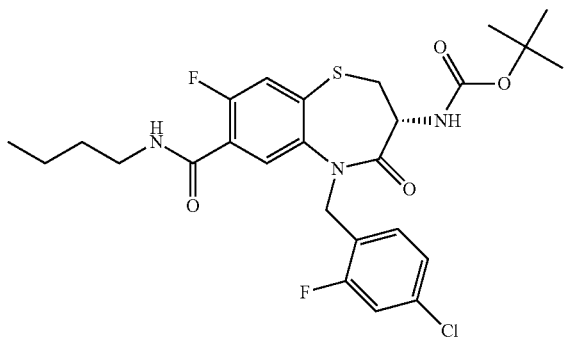 [SMILES: CCCCNC(=O)c1cc2c(cc1F)SC[C@H](NC(=O)OC(C)(C)C)C(=O)N2Cc1ccc(Cl)cc1F]

The title compound was synthesized according to general procedure GP3 to afford the title compound as pale brown solid in 75% Yield.

LCMS: METCR1416 generic 7 minutes, rt=4.89 min, M/Z (ES+) 576/578 [M+Na+] 100% UV NMR Data: 1H NMR (500 MHz, Chloroform-d) d 8.09 (d, J=7.0 Hz, 1H), 7.44-7.32 (m, 2H), 7.04 (dd, J=8.2, 1.6 Hz, 1H), 6.97 (dd, J=9.6, 2.0 Hz, 1H), 6.73-6.59 (m, 1H), 5.54 (d, J=7.8 Hz, 1H), 5.40 (d, J=15.3 Hz, 1H), 4.79 (d, J=15.2 Hz, 1H), 4.43-4.34 (m, 1H), 3.68 (dd, J=11.6, 7.2 Hz, 1H), 3.48 (dq, J=13.2, 6.5 Hz, 2H), 2.88 (t, J=11.3 Hz, 1H), 1.62 (p, J=7.2 Hz, 2H), 1.46-1.40 (m, 2H), 1.39 (s, 9H), 0.97 (t, J=7.4 Hz, 3H).

Synthesis of tert-butyl N-[(3R)-7-(butylcarbamoyl)-5-[(4-chloro-3-fluorophenyl)methyl]-8-fluoro-4-oxo-2,3,4,5-tetrahydro-1,5-benzothiazepin-3-yl]carbamate (Intermediate VIII-36)

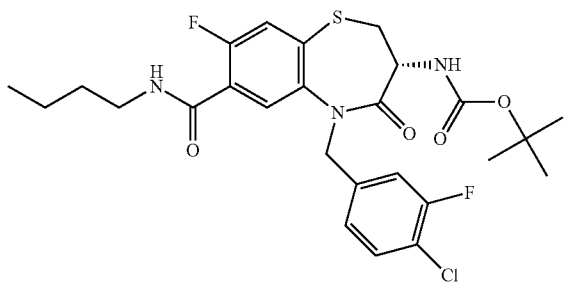 [SMILES: CCCCNC(=O)c1cc2c(cc1F)SC[C@H](NC(=O)OC(C)(C)C)C(=O)N2Cc1ccc(Cl)c(F)c1]

The title compound was synthesized according to general procedure GP3 to afford the title compound as off-white solid in 68% Yield.

LCMS: METCR1673 Generic 2 minutes, rt=1.56 min, M/Z (ES+) 576/578 [M+Na] 90% UV

NMR Data: 1H NMR (500 MHz, Chloroform-d) d 8.06 (d, J=7.0 Hz, 1H), 7.37 (d, J=10.8 Hz, 1H), 7.25-7.22 (m, 1H), 7.13 (d, J=9.8 Hz, 1H), 7.02-6.96 (m, 1H), 6.72-6.63 (m, 1H), 5.54 (d, J=8.4 Hz, 1H), 5.50 (d, J=15.3 Hz, 1H), 4.64 (d, J=15.7 Hz, 1H), 4.46-4.34 (m, 1H), 3.78-3.63 (m, 1H), 3.54-3.38 (m, 2H), 2.94 (t, J=11.4 Hz, 1H), 1.66-1.58 (m, 2H), 1.48-1.41 (m, 2H), 1.40 (s, 9H), 0.97 (t, J=7.3 Hz, 3H).

Synthesis of tert-butyl N-[(3R)-5-[(4-chlorophenyl)methyl]-7-[(oxan-4-ylmethyl)carbamoyl]-4-oxo-2,3,4,5-tetrahydro-1,5-benzothiazepin-3-yl]carbamate (Intermediate VIII-37)

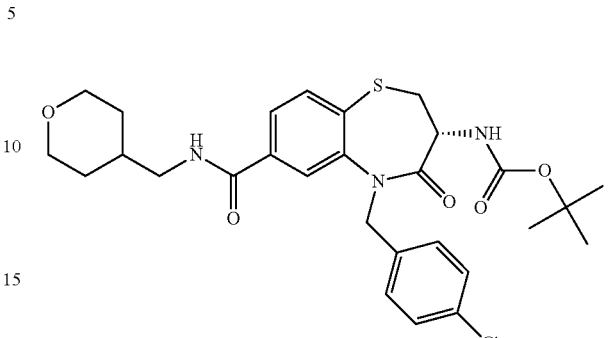

The title compound was synthesized according to general procedure GP3 to afford the title compound as white solid in 100% Yield.

LCMS: METCR1673 Generic 2 minutes, rt=1.37 min, M/Z (ES+) 560/562 [M+H+] 98% UV

NMR Data: 1H NMR (500 MHz, Chloroform-d) d 7.67 (d, J=1.8 Hz, 1H), 7.63 (d, J=8.0 Hz, 1H), 7.46 (dd, J=8.0, 1.8 Hz, 1H), 7.21 (s, 4H), 6.07 (t, J=5.9 Hz, 1H), 5.55 (d, J=8.1 Hz, 1H), 5.28 (d, J=15.2 Hz, 1H), 4.86 (d, J=15.1 Hz, 1H), 4.45-4.36 (m, 1H), 4.00 (dd, J=11.3, 3.2 Hz, 2H), 3.69 (dd, J=11.0, 6.6 Hz, 1H), 3.46-3.27 (m, 4H), 2.91 (t, J=11.3 Hz, 1H), 1.87 (ddt, J=11.6, 8.4, 4.2 Hz, 1H), 1.65 (d, J=12.4 Hz, 2H), 1.40 (s, 11H)

Synthesis of tert-butyl N-[(3R)-5-[(4-chlorophenyl)methyl]-7-[(oxan-3-ylmethyl)carbamoyl]-4-oxo-2,3,4,5-tetrahydro-1,5-benzothiazepin-3-yl]carbamate (Intermediate VIII-38)

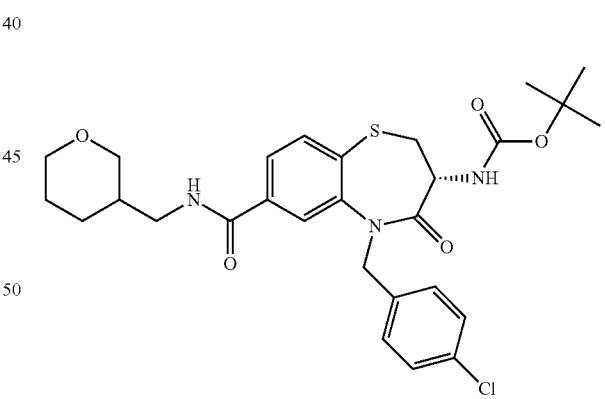

The title compound was synthesized according to general procedure GP3 to afford the title compound as Off-white solid in 74% Yield.

LCMS: METCR1673 Generic 2 minutes, rt=1.4 min, M/Z (ES+) 560/562 [M+H+] 100% UV

NMR Data: 1H NMR (500 MHz, DMSO-d6) d 8.61 (s, 1H), 7.89 (s, 1H), 7.66 (s, 2H), 7.43 (d, J=8.3 Hz, 1H), 7.27 (s, 4H), 5.27 (d, J=15.7 Hz, 1H), 4.91 (d, J=15.6 Hz, 1H), 4.12 (dt, J=12.3, 8.0 Hz, 1H), 3.76-3.69 (m, 3H), 3.26-2.92 (m, 4H), 1.76 (d, J=14.2 Hz, 2H), 1.58 (d, J=13.5 Hz, 2H), 1.33 (s, 9H), 1.26 (s, 2H).

Synthesis of tert-butyl N-[(3R)-5-[(4-chlorophenyl)methyl]-7-[(cyclohexyloxy)carbamoyl]-4-oxo-2,3,4,5-tetrahydro-1,5-benzothiazepin-3-yl]carbamate (Intermediate VIII-39)

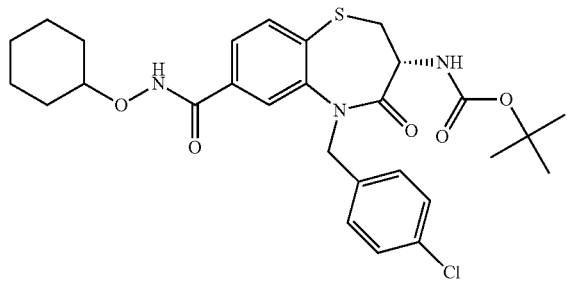 [SMILES: CC(C)(C)OC(=O)N[C@H]1CSc2ccc(C(=O)NOC3CCCCC3)cc2N(Cc2ccc(Cl)cc2)C1=O]

The title compound was synthesized according to general procedure GP3 to afford the title compound as off-white solid in 84% Yield.

LCMS: METCR1673 Generic 2 minutes, rt=1.52 min, M/Z (ES+) 582/584 [M+Na+] 100% UV NMR Data: 1H NMR (500 MHz, Chloroform-d) d 1.16-1.49 (m, 14H), 1.51-1.63 (m, 1H), 1.77 (s, 2H), 1.92-2.06 (m, 2H), 2.89 (t, J=11.27 Hz, 1H), 3.52-3.76 (m, 1H), 3.84-4.15 (m, 1H), 4.28-4.47 (m, 1H), 4.63-4.88 (m, 1H), 5.31-5.45 (m, 1H), 5.51-5.80 (m, 1H), 7.13-7.23 (m, 4H), 7.42-7.95 (m, 3H), 9.73 (s, 1H)

Synthesis of tert-butyl N-[(3R)-5-[(4-chlorophenyl)methyl]-8-fluoro-4-oxo-7-[(2,2,2-trifluoroethyl)carbamoyl]-2,3,4,5-tetrahydro-1,5-benzothiazepin-3-yl]carbamate (Intermediate VIII-40)

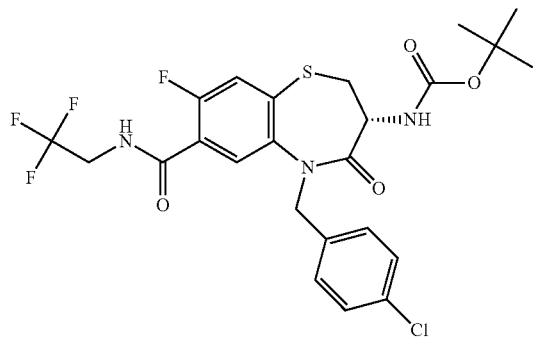 [SMILES: CC(C)(C)OC(=O)N[C@H]1CSc2cc(F)c(C(=O)NCC(F)(F)F)cc2N(Cc2ccc(Cl)cc2)C1=O]

The title compound was synthesized according to general procedure GP3 to afford the title compound as off white solid in 71% Yield.

LCMS: METCR1673 Generic 2 minutes, rt=1.48 min, M/Z (ES+) 584/586 [M+Na+] 97% UV NMR Data: 1H NMR (500 MHz, Chloroform-d) d 8.06 (d, J=7.0 Hz, 1H), 7.40 (d, J=11.0 Hz, 1H), 7.20 (s, 4H), 6.92 (dt, J=13.3, 6.4 Hz, 1H), 5.63-5.44 (m, 2H), 4.65 (d, J=15.1 Hz, 1H), 4.39 (dt, J=14.4, 7.2 Hz, 1H), 4.16 (ddt, J=24.6, 16.9, 8.1 Hz, 2H), 3.71 (dd, J=10.9, 6.4 Hz, 1H), 2.95 (t, J=11.2 Hz, 1H), 1.40 (s, 9H).

Synthesis of tert-butyl N-[(3R)-8-fluoro-7-[(oxan-4-yl)carbamoyl]-4-oxo-5-{[4-(trifluoromethoxy)-phenyl]methyl}-2,3,4,5-tetrahydro-1,5-benzothiazepin-3-yl]carbamate (Intermediate VIII-41)

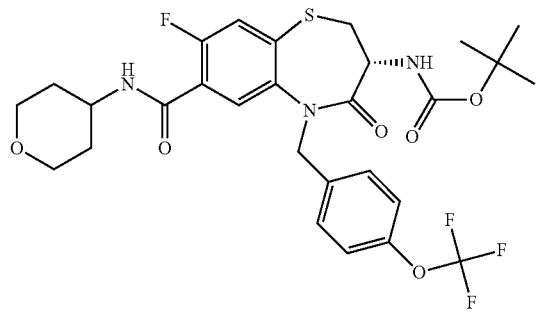 [SMILES: CC(C)(C)OC(=O)N[C@H]1CSc2cc(F)c(C(=O)NC3CCOCC3)cc2N(Cc2ccc(OC(F)(F)F)cc2)C1=O]

The title compound was synthesized according to general procedure GP3 to afford the title compound as Off-White Solid in 67% Yield.

LCMS: METUPLCMS-A-004, rt=1.46 min, M/Z (ES+) 614 [M+H+] 92% UV

NMR Data: 1H NMR (400 MHz, Chloroform-d) δ 8.05 (d, J=7.1 Hz, 1H), 7.38 (d, J=10.9 Hz, 1H), 7.31 (d, J=8.7 Hz, 2H), 7.08 (d, J=8.0 Hz, 2H), 6.63-6.50 (m, 1H), 5.56 (d, J=8.1 Hz, 1H), 5.51 (d, J=15.1 Hz, 1H), 4.71 (d, J=15.2 Hz, 1H), 4.37 (d, J=7.5 Hz, 1H), 4.22 (s, 1H), 4.00 (d, J=11.7 Hz, 2H), 3.70 (dd, J=10.8, 6.4 Hz, 1H), 3.54 (ddd, J=11.7, 9.3, 2.5 Hz, 2H), 2.94 (t, J=11.2 Hz, 1H), 2.07-1.96 (m, 2H), 1.66-1.57 (m, 2H), 1.40 (s, 9H).

Synthesis of tert-butyl N-[(3R)-7-(butylcarbamoyl)-4-oxo-5-{[4-(trifluoromethoxy)phenyl]methyl}-2,3,4,5-tetrahydro-1,5-benzothiazepin-3-yl]carbamate (Intermediate VIII-42)

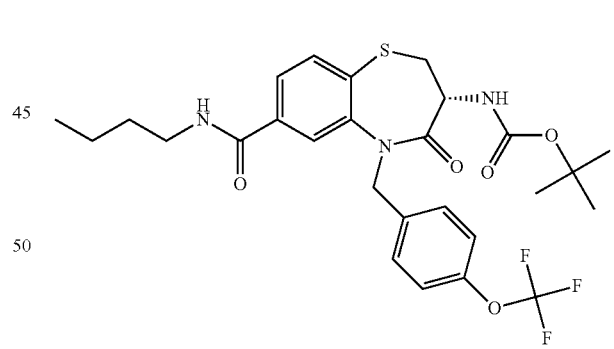

The title compound was synthesized according to general procedure GP3 to afford the title compound as white solid in 85% Yield.

LCMS: METCR1278 Standard 3.5 minute, rt=2.33 min, M/Z (ES+) 590 [M+Na+] 96% UV

NMR Data: 1H NMR (500 MHz, CDCl3) d 1.14 (t, J=7.4 Hz, 3H), 1.50-1.67 (m, 11H), 1.70-1.82 (m, 2H), 3.11 (t, J=11.3 Hz, 1H), 3.57 (p, J=6.4 Hz, 2H), 3.83 (dd, J=6.6, 11.0 Hz, 1H), 4.60 (dt, J=7.7, 11.3 Hz, 1H), 4.95 (d, J=15.1 Hz, 1H), 5.60 (d, J=15.1 Hz, 1H), 6.01 (d, J=8.3 Hz, 1H), 7.06-7.16 (m, 1H), 7.25 (d, J=8.3 Hz, 2H), 7.49 (d, J=8.5 Hz, 2H), 7.72-7.82 (m, 2H), 7.93 (s, 1H)

Synthesis of tert-butyl N-[(3R)-5-[(4-chlorophenyl)methyl]-7-[(3,3-difluorocyclobutyl)carbamoyl]-8-fluoro-4-oxo-2,3,4,5-tetrahydro-1,5-benzothiazepin-3-yl]carbamate (Intermediate VIII-43)

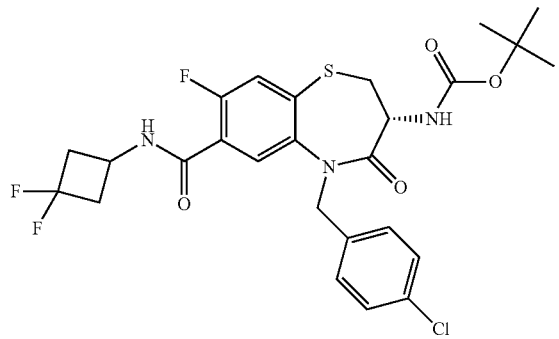 [SMILES: CC(C)(C)OC(=O)N[C@H]1CSc2cc(F)c(C(=O)NC3CC(F)(F)C3)cc2N(Cc2ccc(Cl)cc2)C1=O]

The title compound was synthesized according to general procedure GP3 to afford the title compound as Pale-yellow solid in 40% Yield.

LCMS: METCR1673 Generic 2 minutes, rt=1.52 min, M/Z (ES+) 592/594 [M+Na+] 88% UV NMR Data: 1H NMR (500 MHz, DMSO-d6) d 8.95 (d, J=6.5 Hz, 1H), 7.75 (d, J=6.4 Hz, 1H), 7.57 (d, J=9.3 Hz, 1H), 7.44 (d, J=8.4 Hz, 1H), 7.30 (d, J=8.5 Hz, 2H), 7.27 (d, J=8.6 Hz, 2H), 5.27 (d, J=15.5 Hz, 1H), 4.87 (d, J=15.6 Hz, 1H), 4.29-4.19 (m, 1H), 4.19-4.10 (m, 1H), 3.48 (dd, J=11.3, 6.9 Hz, 1H), 3.12 (t, J=11.8 Hz, 1H), 3.03-2.91 (m, 2H), 2.79-2.65 (m, 2H), 1.35 (s, 9H).

Synthesis of tert-butyl N-[(3R)-5-[(4-chlorophenyl)methyl]-7-{[(4-fluorophenyl)methyl]-carbamoyl}-4-oxo-2,3,4,5-tetrahydro-1,5-benzothiazepin-3-yl]carbamate (Intermediate VIII-44)

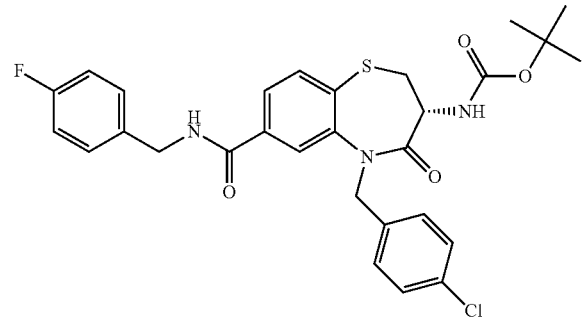

The title compound was synthesized according to general procedure GP3 to afford the title compound as White solid in 73% Yield.

LCMS: METCR 1278 Generic 3 minutes, rt=2.26 min, M/Z (ES+) 570/572 [M+H+] 99% UV NMR Data: 1H NMR (500 MHz, Chloroform-d) d 7.73 (d, J=1.6 Hz, 1H), 7.62 (d, J=8.0 Hz, 1H), 7.48 (dd, J=8.0, 1.7 Hz, 1H), 7.31 (dd, J=8.5, 5.4 Hz, 3H), 7.19 (d, J=3.3 Hz, 5H), 6.32 (s, 1H), 5.55 (d, J=8.0 Hz, 1H), 5.33 (d, J=15.1 Hz, 1H), 4.81 (d, J=15.1 Hz, 1H), 4.59 (dd, J=8.4, 5.8 Hz, 2H), 3.68 (s, 1H), 2.91 (s, 1H), 1.39 (s, 9H). [NH not visible]

Synthesis of tert-butyl N-[(3R)-7-(benzylcarbamoyl)-5-[(4-chlorophenyl)methyl]-8-fluoro-4-oxo-2,3,4,5-tetrahydro-1,5-benzothiazepin-3-yl]carbamate (Intermediate VIII-45)

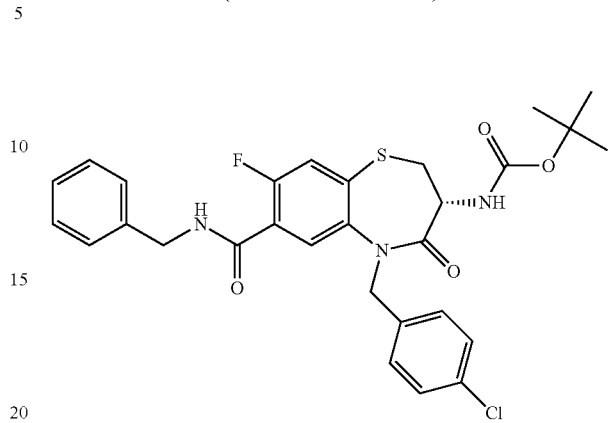

The title compound was synthesized according to general procedure GP3 to afford the title compound as Off white solid in 100% Yield.

LCMS: METCR1673 Generic 2 minutes, rt=1.56 min, M/Z (ES+) 592/594 [M+Na+] 99% UV NMR Data: 1H NMR (500 MHz, DMSO-d6) d 9.04 (t, J=5.8 Hz, 1H), 7.75 (d, J=6.5 Hz, 1H), 7.58 (d, J=9.4 Hz, 1H), 7.45 (d, J=8.3 Hz, 1H), 7.40-7.23 (m, 9H), 5.22 (d, J=15.7 Hz, 1H), 4.92 (d, J=15.6 Hz, 1H), 4.55-4.39 (m, 2H), 4.17 (dt, J=12.1, 7.4 Hz, 1H), 3.49 (dd, J=11.3, 6.9 Hz, 1H), 3.12 (t, J=11.7 Hz, 1H), 1.41-1.25 (m, 9H).

Synthesis of tert-butyl N-[(3R)-5-[(4-chlorophenyl)methyl]-8-fluoro-4-oxo-7-(phenoxycarbamoyl)-2,3,4,5-tetrahydro-1,5-benzothiazepin-3-yl]carbamate (Intermediate VIII-46)

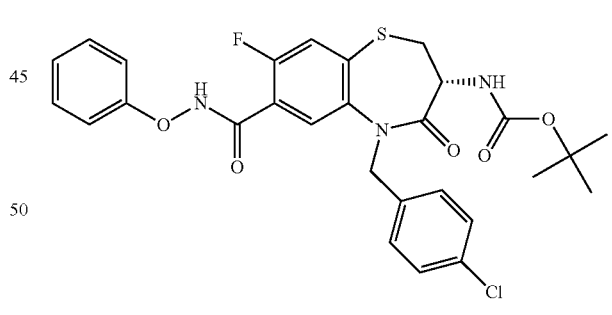

The title compound was synthesized according to general procedure GP3 to afford the title compound as off-white solid in 67% Yield.

LCMS: METCR1673 Generic 2 minutes, rt=1.5 min, M/Z (ES+) 594/596 [M+Na+] 100% UV NMR Data: 1H NMR (500 MHz, Chloroform-d) d 1.39 (s, 9H), 2.96 (t, J=11.3 Hz, 1H), 3.70 (dd, J=6.4, 10.8 Hz, 1H), 4.41 (dt, J=7.2, 11.7 Hz, 1H), 4.65 (d, J=15.1 Hz, 1H), 5.48 (d, J=15.1 Hz, 1H), 5.60 (d, J=7.8 Hz, 1H), 7.12-7.07 (m, 3H), 7.19 (s, 4H), 7.33 (t, J=8.0 Hz, 2H), 7.41 (d, J=10.3 Hz, 1H), 8.03 (d, J=4.9 Hz, 1H), 9.72 (d, J=9.6 Hz, 1H).

Synthesis of tert-butyl N-[(3R)-5-[(4-chlorophenyl)methyl]-7-[(cyclohexylmethoxy)carbamoyl]-4-oxo-2,3,4,5-tetrahydro-1,5-benzothiazepin-3-yl]carbamate (Intermediate VIII-47)

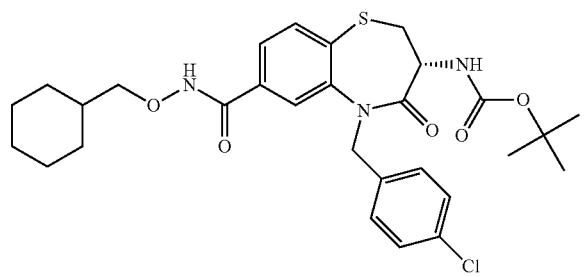 [SMILES: CC(C)(C)OC(=O)N[C@H]1CSc2ccc(C(=O)NOCC3CCCCC3)cc2N(Cc2ccc(Cl)cc2)C1=O]

The title compound was synthesized according to general procedure GP3 to afford the title compound as off-white solid in 73% Yield.

LCMS: METCR1673 Generic 2 minutes, rt=1.61 min, M/Z (ES+) 596/598 [M+Na+] 99% UV NMR Data: 1H NMR (500 MHz, Chloroform-d) d 0.87-1.08 (m, 2H), 1.08-1.33 (m, 3H), 1.40 (s, 9H), 1.58-1.91 (m, 6H), 2.89 (t, J=11.1 Hz, 1H), 3.53-3.71 (m, 1H), 3.71-4.00 (m, 2H), 4.27-4.48 (m, 1H), 4.55-4.87 (m, 1H), 5.30-5.50 (m, 1H), 5.50-5.83 (m, 1H), 7.06-7.24 (m, 4H), 7.38-7.81 (m, 3H), 9.71 (s, 1H)

Synthesis of tert-butyl N-[(3R)-5-[(4-chlorophenyl)methyl]-8-fluoro-4-oxo-7-[(3,3,3-trifluoropropyl)carbamoyl]-2,3,4,5-tetrahydro-1,5-benzothiazepin-3-yl]carbamate (Intermediate VIII-48)

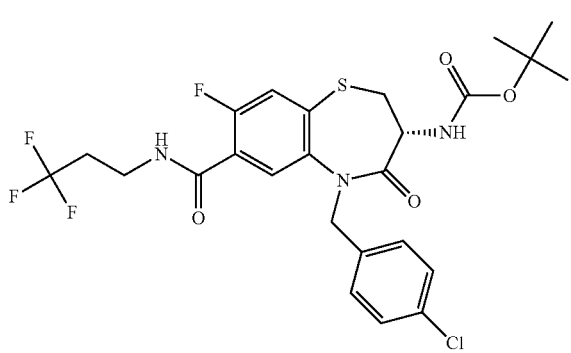 [SMILES: CC(C)(C)OC(=O)N[C@H]1CSc2cc(F)c(C(=O)NCCC(F)(F)F)cc2N(Cc2ccc(Cl)cc2)C1=O]

The title compound was synthesized according to general procedure GP3 to afford the title compound as colourless oil in 64% Yield.

LCMS: METCR1673 Generic 2 minutes, rt=1.55 min, M/Z (ES+) 598/600 [M+Na+] 100% UV NMR Data: 1H NMR (500 MHz, Chloroform-d) d 8.04 (d, J=7.0 Hz, 1H), 7.37 (d, J=10.9 Hz, 1H), 7.20 (s, 4H), 6.96 (s, 1H), 5.68-5.44 (m, 2H), 4.65 (d, J=15.1 Hz, 1H), 4.41 (s, 1H), 3.84-3.64 (m, 3H), 2.94 (t, J=11.3 Hz, 1H), 2.49 (ddt, J=17.0, 10.8, 5.4 Hz, 2H), 1.40 (s, 9H).

Synthesis of tert-butyl N-[(3R)-5-[(4-chlorophenyl)methyl]-8-fluoro-4-oxo-7-{[(2S)-1,1,1-trifluoropropan-2-yl]carbamoyl}-2,3,4,5-tetrahydro-1,5-benzothiazepin-3-yl]carbamate (Intermediate VIII-49)

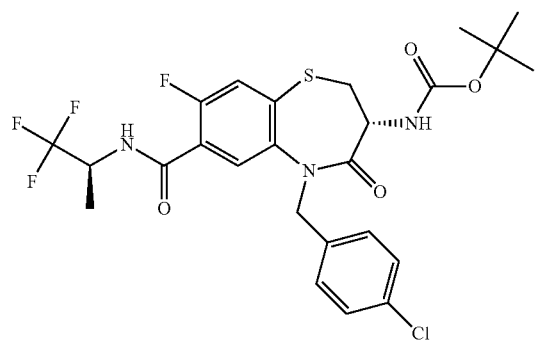 [SMILES: C[C@H](NC(=O)c1cc2c(cc1F)SC[C@H](NC(=O)OC(C)(C)C)C(=O)N2Cc1ccc(Cl)cc1)C(F)(F)F]

The title compound was synthesized according to general procedure GP3 to afford the title compound as pale yellow oil in 70% Yield.

LCMS: METCR1673 Generic 2 minutes, rt=1.54 min, M/Z (ES+) 598/600 [M+Na+] 99% UV NMR Data: 1H NMR (500 MHz, Chloroform-d) d 8.04 (d, J=7.0 Hz, 1H), 7.39 (d, J=11.0 Hz, 1H), 7.20 (s, 4H), 6.70 (dd, J=13.4, 9.4 Hz, 1H), 5.64-5.39 (m, 2H), 5.12-4.77 (m, 1H), 4.65 (d, J=15.1 Hz, 1H), 4.38 (dt, J=11.6, 7.2 Hz, 1H), 3.69 (dd, J=10.9, 6.4 Hz, 1H), 2.95 (t, J=5.6 Hz, 1H), 1.45 (d, J=7.0 Hz, 3H), 1.39 (s, 9H)

Synthesis of tert-butyl N-[(3R)-5-[(4-chlorophenyl)methyl]-8-fluoro-7-[(oxan-4-ylmethyl)-carbamoyl]-4-oxo-2,3,4,5-tetrahydro-1,5-benzothiazepin-3-yl]carbamate (Intermediate VIII-50)

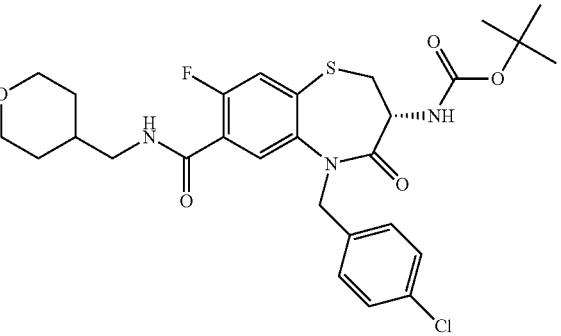

The title compound was synthesized according to general procedure GP3 to afford the title compound as Pale Orange Solid in 76% Yield.

LCMS: METuPLCAB101 uPLC 7 minute, rt=3.8 min, M/Z (ES+) 578/580 [M+H+] 98% UV

NMR Data: 1H NMR (500 MHz, Chloroform-d) d 8.04 (d, J=7.1 Hz, 1H), 7.36 (d, J=10.9 Hz, 1H), 7.23-7.17 (m, 4H), 6.76 (dt, J=12.7, 5.9 Hz, 1H), 5.61-5.47 (m, 2H), 4.65 (d, J=15.1 Hz, 1H), 4.39 (dt, J=13.9, 7.1 Hz, 1H), 4.00 (dd, J=11.4, 3.9 Hz, 2H), 3.70 (dd, J=10.9, 6.5 Hz, 1H), 3.42-3.37 (m, 4H), 2.93 (t, J=11.3 Hz, 1H), 1.89 (ttt, J=10.7, 7.1, 3.7 Hz, 1H), 1.71-1.63 (m, 2H), 1.44-1.33 (m, 11H).

Synthesis of tert-butyl N-[(3R)-5-[(4-chlorophenyl)methyl]-8-fluoro-7-(heptylcarbamoyl)-4-oxo-2,3,4,5-tetrahydro-1,5-benzothiazepin-3-yl]carbamate (Intermediate VIII-51)

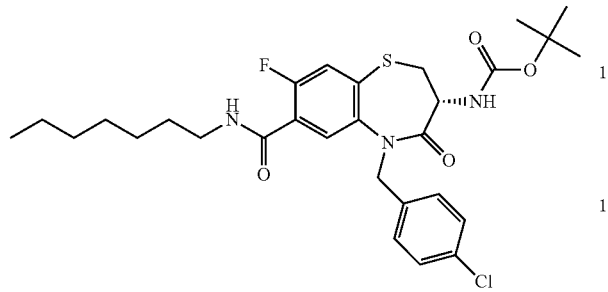

The title compound was synthesized according to general procedure GP3 to afford the title compound as off white solid in 60% Yield.

LCMS: METCR1673 Generic 2 minutes, rt=1.78 min, M/Z (ES+) 600/602 [M+Na+] 100% UV NMR Data: 1H NMR (500 MHz, DMSO-d6) d 8.44 (s, 1H), 7.66 (d, J=6.3 Hz, 1H), 7.54 (d, J=9.2 Hz, 1H), 7.44 (d, J=8.3 Hz, 1H), 7.33-7.25 (m, 4H), 5.20 (d, J=15.6 Hz, 1H), 4.91 (d, J=15.7 Hz, 1H), 4.19-4.11 (m, 1H), 3.47 (dd, J=11.1, 6.9 Hz, 1H), 3.21 (dt, J=13.6, 7.0 Hz, 2H), 3.11 (t, J=11.7 Hz, 1H), 1.50 (d, J=11.2 Hz, 2H), 1.31 (m, 17H), 0.86 (t, J=6.8 Hz, 3H).

Synthesis of tert-butyl N-[(3R)-5-[(4-chlorophenyl)methyl]-7-[(4,4-difluorocyclohexyl)carbamoyl]-4-oxo-2,3,4,5-tetrahydro-1,5-benzothiazepin-3-yl]carbamate (Intermediate VIII-52)

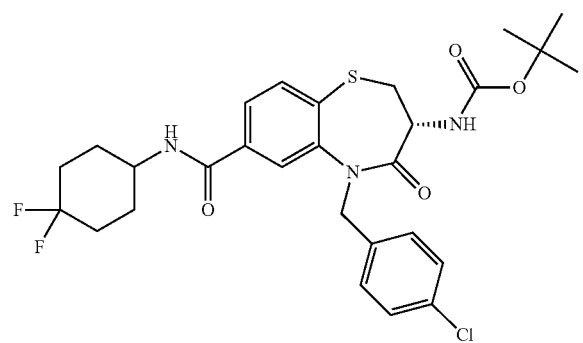 [SMILES: CC(C)(C)OC(=O)N[C@H]1CSc2ccc(C(=O)NC3CCC(F)(F)CC3)cc2N(Cc2ccc(Cl)cc2)C1=O]

The title compound was synthesized according to general procedure GP3 to afford the title compound as White solid in 56% Yield.

LCMS: METCR1673 Generic 2 minutes, rt=1.6 min, M/Z (ES+) 602/604 [M+Na+] 99% UV

NMR Data: 1H NMR (500 MHz, DMSO-d6) d 8.44 (d, J=7.6 Hz, 1H), 7.93 (s, 1H), 7.74-7.65 (m, 2H), 7.45 (d, J=8.3 Hz, 1H), 7.33-7.25 (m, 4H), 5.29 (d, J=15.6 Hz, 1H), 4.92 (d, J=15.6 Hz, 1H), 4.12 (dt, J=12.2, 7.6 Hz, 1H), 3.98 (s, 1H), 3.46 (dd, J=11.3, 6.8 Hz, 1H), 3.11 (t, J=11.8 Hz, 1H), 2.03 (d, J=30.8 Hz, 2H), 1.98-1.85 (m, 4H), 1.64 (q, J=12.3, 11.2 Hz, 2H), 1.35 (s, 9H).

Synthesis of tert-butyl N-[(3R)-5-[(4-chlorophenyl)methyl]-7-[(3,3-difluorocyclopentyl)carbamoyl]-8-fluoro-4-oxo-2,3,4,5-tetrahydro-1,5-benzothiazepin-3-yl]carbamate (Intermediate VIII-53)

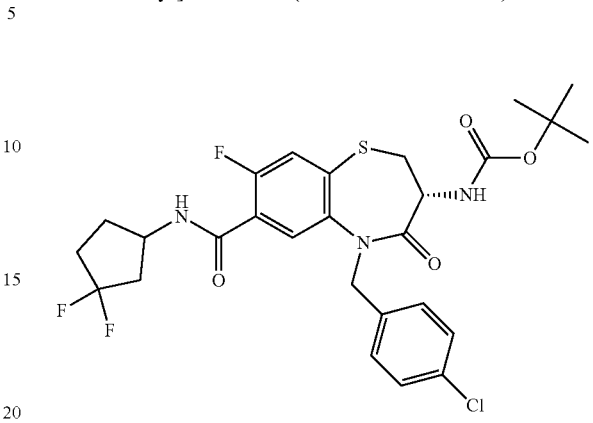

The title compound was synthesized according to general procedure GP3 to afford the title compound as off-white solid in 33% Yield.

LCMS: METCR1673 Generic 2 minutes, rt=1.53 min, M/Z (ES+) 606/608 [M+Na+] 100% UV NMR Data: 1H NMR (500 MHz, DMSO-d6) d 8.72 (d, J=4.0 Hz, 1H), 7.71 (d, J=6.4 Hz, 1H), 7.57 (d, J=9.2 Hz, 1H), 7.45 (d, J=8.3 Hz, 1H), 7.29 (q, J=8.5 Hz, 4H), 5.26 (d, J=14.0 Hz, 1H), 4.89 (d, J=15.6 Hz, 1H), 4.39 (q, J=7.5 Hz, 1H), 4.15 (dt, J=12.1, 8.0 Hz, 1H), 3.48 (dd, J=11.4, 6.9 Hz, 1H), 3.12 (t, J=11.8 Hz, 1H), 2.34-2.03 (m, 5H), 1.86-1.73 (m, 1H), 1.36 (s, 9H).

Synthesis of tert-butyl N-[(3R)-5-[(4-chlorophenyl)methyl]-7-{[1-(4-fluorophenyl)ethyl]-carbamoyl}-4-oxo-2,3,4,5-tetrahydro-1,5-benzothiazepin-3-yl]carbamate (Intermediate VIII-54)

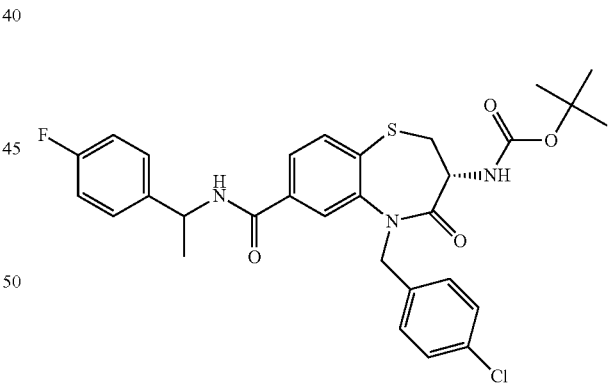

The title compound was synthesized according to general procedure GP3 to afford the title compound as White solid in 74% Yield.

LCMS: METCR1673 Generic 2 minutes, rt=1.64 min, M/Z (ES+) 584 [M+H+] 99% UV

NMR Data: 1H NMR (500 MHz, DMSO-d6) d 8.95 (d, J=7.6 Hz, 1H), 7.96 (s, OH), 7.75 (t, J=7.3 Hz, 1H), 7.69 (d, J=8.0 Hz, 1H), 7.48-7.37 (m, 3H), 7.29 (s, 4H), 7.16 (td, J=8.9, 2.3 Hz, 2H), 5.28 (dd, J=15.7, 5.4 Hz, 1H), 5.20-5.11 (m, 1H), 4.94 (d, J=15.7 Hz, 1H), 4.14 (dt, J=12.2, 7.7 Hz, 1H), 3.46 (dd, J=11.3, 6.9 Hz, 1H), 3.12 (t, J=11.8 Hz, 1H), 1.48 (dd, J=7.0, 2.2 Hz, 3H), 1.35 (s, 9H).

Synthesis of tert-butyl N-[(3R)-5-[(4-chlorophenyl)methyl]-7-{[(1S)-1-(4-fluorophenyl)ethyl]-carbamoyl}-4-oxo-2,3,4,5-tetrahydro-1,5-benzothiazepin-3-yl]carbamate (Intermediate VIII-55)

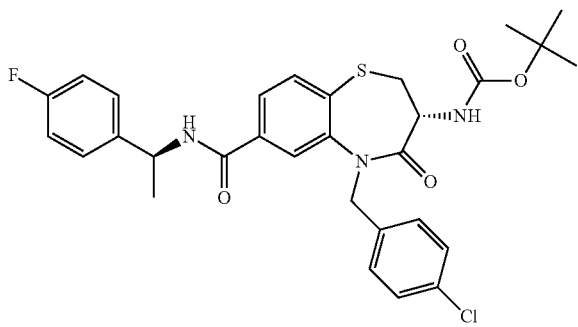 [SMILES: C[C@H](NC(=O)c1ccc2c(c1)N(Cc1ccc(Cl)cc1)C(=O)[C@@H](NC(=O)OC(C)(C)C)CS2)c1ccc(F)cc1]

The title compound was synthesized according to general procedure GP3 to afford the title compound as white solid in 86% Yield.

LCMS: METCR1673 Generic 2 minutes, rt=1.54 min, M/Z (ES+) 606/608 [M+Na+] 99% UV NMR Data: 1H NMR (500 MHz, DMSO-d6) d 8.95 (d, J=7.9 Hz, 1H), 7.95 (d, J=1.4 Hz, 1H), 7.77-7.71 (m, 1H), 7.69 (d, J=8.0 Hz, 1H), 7.48-7.38 (m, 3H), 7.29 (s, 4H), 7.15 (t, J=8.9 Hz, 2H), 5.28 (d, J=15.6 Hz, 1H), 5.23-5.10 (m, 1H), 4.94 (d, J=15.6 Hz, 1H), 4.20-4.06 (m, 1H), 3.46 (dd, J=11.5, 6.8 Hz, 1H), 3.10 (d, J=11.7 Hz, 1H), 1.48 (d, J=7.1 Hz, 3H), 1.35 (s, 9H).

Synthesis of tert-butyl N-[(2R,3R)-5-[(4-chlorophenyl)methyl]-2-methyl-4-oxo-7-[(4,4,4-trifluorobutyl)carbamoyl]-2,3,4,5-tetrahydro-1,5-benzothiazepin-3-yl]carbamate (Intermediate VIII-56)

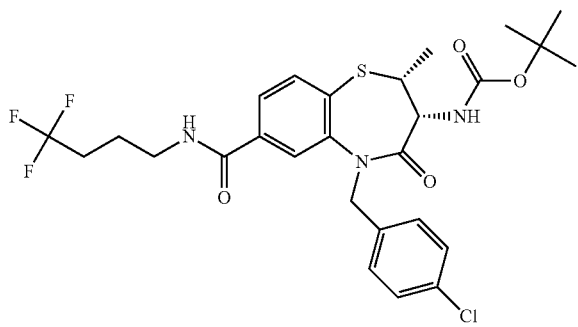 [SMILES: C[C@H]1Sc2ccc(C(=O)NCCCC(F)(F)F)cc2N(Cc2ccc(Cl)cc2)C(=O)[C@H]1NC(=O)OC(C)(C)C]

The title compound was synthesized according to general procedure GP3 to afford the title compound as off white solid in 80% Yield.

LCMS: METCR1673 Generic 2 minutes, rt=1.61 min, M/Z (ES+) 608/610 [M+Na+] 98% UV NMR Data: 1H NMR (500 MHz, DMSO-d6) d 8.68 (t, J=5.5 Hz, 1H), 7.94 (s, 1H), 7.73-7.64 (m, 2H), 7.30 (s, 4H), 7.06 (d, J=8.3 Hz, 1H), 5.40 (d, J=15.7 Hz, 1H), 4.91 (d, J=15.7 Hz, 1H), 4.43-4.34 (m, 1H), 3.88-3.78 (m, 1H), 3.39-3.33 (m, 2H), 2.38-2.26 (m, 2H), 1.76 (p, J=7.1 Hz, 2H), 1.38-1.27 (m, 12H).

Synthesis of tert-butyl N-[(3R)-7-(butylcarbamoyl)-8-fluoro-4-oxo-5-{[4-(trifluoromethoxy)-phenyl]methyl}-2,3,4,5-tetrahydro-1,5-benzothiazepin-3-yl]carbamate (Intermediate VIII-57)

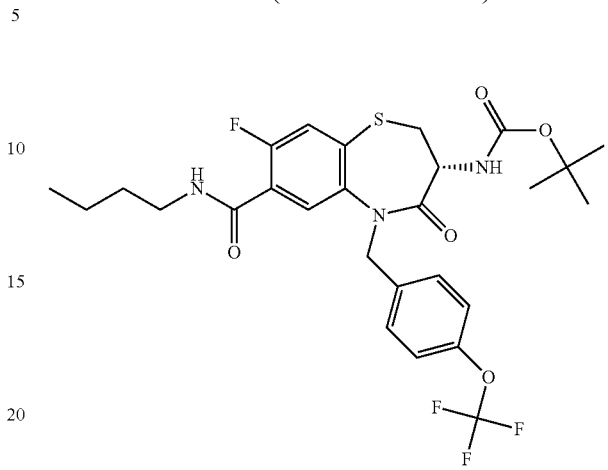

The title compound was synthesized according to general procedure GP3 to afford the title compound as White solid in 64% Yield.

LCMS: METCR1416 Generic 2 minutes, rt=4.91 min, M/Z (ES+) 608 [M+Na+] 100% UV

NMR Data: 1H NMR (500 MHz, DMSO-d6) d 8.45 (s, 1H), 7.67 (d, J=6.4 Hz, 1H), 7.56 (d, J=9.3 Hz, 1H), 7.45 (d, J=8.3 Hz, 1H), 7.40 (d, J=8.6 Hz, 2H), 7.25 (d, J=8.2 Hz, 2H), 5.20 (d, J=15.8 Hz, 1H), 4.98 (d, J=15.9 Hz, 1H), 4.17 (dt, J=12.0, 7.4 Hz, 1H), 3.49 (dd, J=11.3, 6.9 Hz, 1H), 3.29-3.16 (m, 2H), 3.12 (t, J=11.7 Hz, 1H), 1.48 (p, J=7.0 Hz, 2H), 1.40-1.21 (m, 11H), 0.89 (t, J=7.4 Hz, 3H).

Synthesis of tert-butyl N-[(3R)-5-[(4-chlorophenyl)methyl]-8-fluoro-7-{[(4-fluorophenyl)methyl]carbamoyl}-4-oxo-2,3,4,5-tetrahydro-1,5-benzothiazepin-3-yl]carbamate (Intermediate VIII-58)

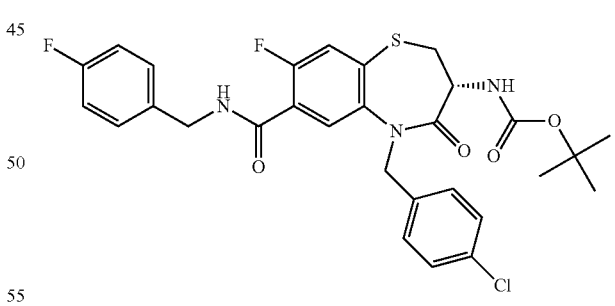

The title compound was synthesized according to general procedure GP3 to afford the title compound as Pale yellow solid in 83% Yield.

LCMS: METuPLCAB101 uPLC 7 minute, rt=4.29 min, M/Z (ES+) 588 [M+H+]100% UV

NMR Data: 1H NMR (500 MHz, Chloroform-d) d 8.08 (d, J=7.1 Hz, 1H), 7.38-7.30 (m, 3H), 7.20 (d, J=1.3 Hz, 4H), 7.08-6.95 (m, 3H), 5.60-5.50 (m, 2H), 4.70-4.57 (m, 3H), 4.39 (dt, J=11.6, 7.3 Hz, 1H), 3.70 (dd, J=10.9, 6.5 Hz, 1H), 2.94 (t, J=11.3 Hz, 1H), 1.40 (s, 9H).

Synthesis of tert-butyl N-[(3R)-5-[(4-chlorophenyl)methyl]-8-fluoro-7-[N'-(4-fluorophenyl)-hydrazinecarbonyl]-4-oxo-2,3,4,5-tetrahydro-1,5-benzothiazepin-3-yl]carbamate (Intermediate VIII-59)

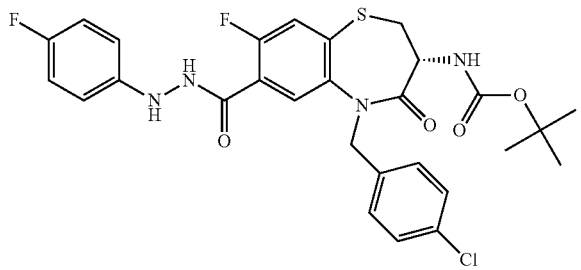 [SMILES: CC(C)(C)OC(=O)N[C@H]1CSc2cc(F)c(C(=O)NNc3ccc(F)cc3)cc2N(Cc2ccc(Cl)cc2)C1=O]

The title compound was synthesized according to general procedure GP3 to afford the title compound as yellow oil in 21% Yield.

LCMS: METCR1673 Generic 2 minutes, rt=1.48 min, M/Z (ES+) 611/613 [M+Na+] 97% UV NMR Data: 1H NMR (500 MHz, Chloroform-d) d 1.40 (s, 9H), 2.96 (t, J=11.3 Hz, 1H), 3.72 (dd, J=6.4, 10.9 Hz, 1H), 4.41 (dt, J=7.2, 13.9 Hz, 1H), 4.64 (d, J=15.1 Hz, 1H), 5.48 (d, J=15.1 Hz, 1H), 5.58 (d, J=7.9 Hz, 1H), 6.86-6.91 (m, 2H), 6.94-7.00 (m, 2H), 7.19 (s, 4H), 7.44 (d, J=10.6 Hz, 1H), 8.02 (d, J=6.7 Hz, 1H), 8.41 (d, J=12.0 Hz, 1H) [NH not visible].

Synthesis of tert-butyl N-[(3R)-4-oxo-7-[(pyridin-3-yl)carbamoyl]-5-{[4-(trifluoromethoxy)-phenyl]methyl}-2,3,4,5-tetrahydro-1,5-benzothiazepin-3-yl]carbamate (Intermediate VIII-60)

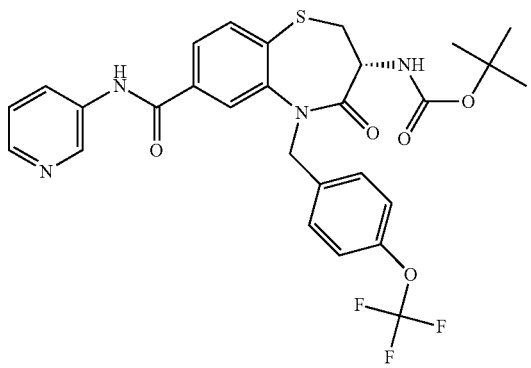 [SMILES: CC(C)(C)OC(=O)N[C@H]1CSc2ccc(C(=O)Nc3cccnc3)cc2N(Cc2ccc(OC(F)(F)F)cc2)C1=O]

The title compound was synthesized according to general procedure GP3 to afford the title compound as white solid in 55% Yield.

LCMS: METCR1673 Generic 2 minutes, rt=1.31 min, M/Z (ES+) 589 [M+H+] 100% UV

NMR Data: 1H NMR (500 MHz, DMSO-d6) d 10.61 (s, 1H), 8.91 (d, J=2.3 Hz, 1H), 8.35 (dd, J=4.7, 1.2 Hz, 1H), 8.18 (d, J=8.4 Hz, 1H), 8.10 (d, J=1.5 Hz, 1H), 7.85 (dd, J=8.0, 1.6 Hz, 1H), 7.78 (d, J=8.0 Hz, 1H), 7.48 (d, J=8.4 Hz, 1H), 7.43 (dd, J=8.4, 4.0 Hz, 3H), 7.24 (d, J=8.2 Hz, 2H), 5.36 (d, J=15.8 Hz, 1H), 5.02 (d, J=15.8 Hz, 1H), 4.20 (dt, J=12.2, 7.7 Hz, 1H), 3.51 (dd, J=11.3, 6.8 Hz, 1H), 3.19-3.12 (m, 1H), 1.35 (s, 9H).

Synthesis of tert-butyl N-[(3R)-5-[(4-chlorophenyl)methyl]-8-fluoro-4-oxo-7-[(4,4,4-trifluorobutyl)carbamoyl]-2,3,4,5-tetrahydro-1,5-benzothiazepin-3-yl]carbamate (Intermediate VIII-61)

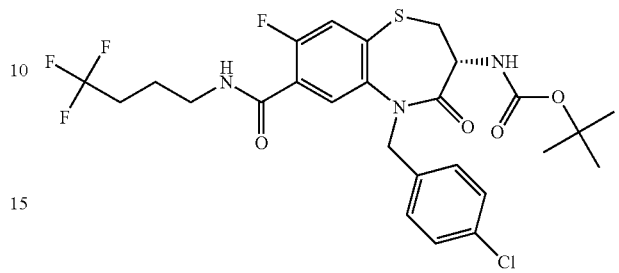

The title compound was synthesized according to general procedure GP3 to afford the title compound as White Solid in 78% Yield.

LCMS: METuPLCAB101 uPLC 7 minute, rt=4.2 min, M/Z (ES+) 590/592 [M+H+] 97% UV

NMR Data: 1H NMR (500 MHz, Chloroform-d) d 8.04 (d, J=7.1 Hz, 1H), 7.37 (d, J=10.9 Hz, 1H), 7.20 (s, 4H), 6.76 (dt, J=12.3, 5.9 Hz, 1H), 5.61-5.49 (m, 2H), 4.64 (d, J=15.1 Hz, 1H), 4.39 (dt, J=13.7, 7.1 Hz, 1H), 3.70 (dd, J=10.9, 6.5 Hz, 1H), 3.55 (dh, J=13.4, 6.8 Hz, 2H), 2.94 (t, J=11.3 Hz, 1H), 2.25-2.13 (m, 2H), 1.92 (dt, J=14.8, 6.9 Hz, 2H), 1.39 (s, 9H).

Synthesis of tert-butyl N-[(3R)-5-[(4-chlorophenyl)methyl]-8-fluoro-4-oxo-7-{[(1S,2R)-2-phenylcyclopropyl]carbamoyl}-2,3,4,5-tetrahydro-1,5-benzothiazepin-3-yl]carbamate (Intermediate VIII-62)

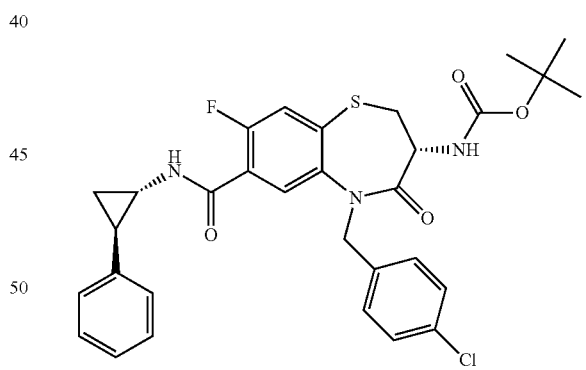

The title compound was synthesized according to general procedure GP3 to afford the title compound as Off-White Solid In 48% Yield.

LCMS: METCR1673 Generic 2 minutes, rt=1.62 min, M/Z (ES−) 594 [M−H+] 100% UV

NMR Data: 1H NMR (500 MHz, DMSO-d6) d 8.79 (d, J=4.1 Hz, 1H), 7.73 (dd, J=6.4, 2.9 Hz, 1H), 7.55 (d, J=9.2 Hz, 1H), 7.44 (d, J=8.2 Hz, 1H), 7.29 (q, J=8.3 Hz, 7H), 5.27 (d, J=15.6 Hz, 1H), 4.87 (d, J=15.6 Hz, 1H), 4.15 (dt, J=12.0, 8.1 Hz, 1H), 3.50-3.46 (m, 2H), 3.13 (t, J=11.9 Hz, 1H), 2.11-2.07 (m, 1H), 1.35 (s, 9H), 1.19-1.11 (m, 2H). [2×NH not visible]

Synthesis of tert-butyl N-[(3R)-5-[(4-chloro-2-fluorophenyl)methyl]-8-fluoro-7-[(oxan-4-ylmethyl)carbamoyl]-4-oxo-2,3,4,5-tetrahydro-1,5-benzothiazepin-3-yl]carbamate (Intermediate VIII-63)

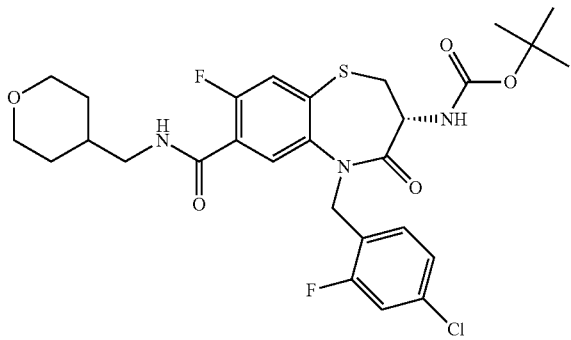 [SMILES: CC(C)(C)OC(=O)N[C@H]1CSc2cc(F)c(C(=O)NCC3CCOCC3)cc2N(Cc2ccc(Cl)cc2F)C1=O]

The title compound was synthesized according to general procedure GP3 to afford the title compound as pale yellow coloured solid in 77% Yield.

LCMS: METCR1416 generic 7 min, rt=4.49 min, M/Z (ES+) 618/620 [M+Na+] 100% UV

NMR Data: 1H NMR (500 MHz, Chloroform-d) d 8.08 (d, J=7.1 Hz, 1H), 7.43-7.34 (m, 2H), 7.04 (dd, J=8.2, 1.6 Hz, 1H), 6.97 (dd, J=9.6, 2.0 Hz, 1H), 6.81-6.70 (m, 1H), 5.54 (d, J=7.8 Hz, 1H), 5.40 (d, J=15.2 Hz, 1H), 4.79 (d, J=15.2 Hz, 1H), 4.42-4.33 (m, 1H), 4.00 (dd, J=11.3, 3.9 Hz, 2H), 3.71-3.64 (m, 1H), 3.47-3.30 (m, 4H), 2.89 (t, J=11.3 Hz, 1H), 1.95-1.84 (m, 1H), 1.71-1.64 (m, 2H), 1.42-1.36 (m, 11H).

Synthesis of tert-butyl N-[(3R)-5-[(4-chloro-3-fluorophenyl)methyl]-8-fluoro-7-[(oxan-4-ylmethyl)carbamoyl]-4-oxo-2,3,4,5-tetrahydro-1,5-benzothiazepin-3-yl]carbamate (Intermediate VIII-64)

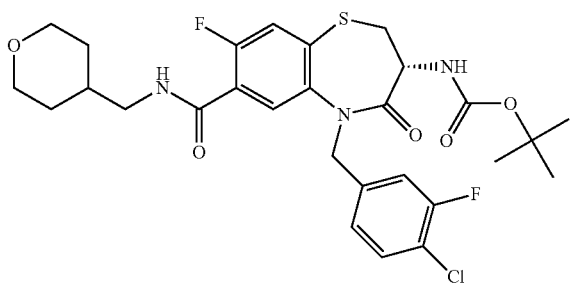 [SMILES: CC(C)(C)OC(=O)N[C@H]1CSc2cc(F)c(C(=O)NCC3CCOCC3)cc2N(Cc2ccc(Cl)c(F)c2)C1=O]

The title compound was synthesized according to general procedure GP3 to afford the title compound as off-white solid in 44% Yield.

LCMS: METCR1673 Generic 2 minutes, rt=1.42 min, M/Z (ES+) 618/620 [M+Na+] 100% UV NMR Data: 1H NMR (500 MHz, Chloroform-d) d 8.05 (d, J=7.0 Hz, 1H), 7.39 (d, J=11.0 Hz, 1H), 7.25-7.23 (m, 1H), 7.12 (d, J=9.8 Hz, 1H), 6.99 (d, J=6.7 Hz, 1H), 5.54 (d, J=8.0 Hz, 1H), 5.49 (d, J=15.3 Hz, 1H), 4.65 (d, J=15.3 Hz, 1H), 4.00 (dd, J=11.6, 3.9 Hz, 2H), 3.71 (dd, J=10.9, 6.5 Hz, 1H), 3.48-3.29 (m, 4H), 2.94 (t, J=11.3 Hz, 1H), 1.96-1.83 (m, 1H), 1.67 (d, J=11.0 Hz, 2H), 1.44-1.33 (m, 11H). [2×NH not visible]

Synthesis of tert-butyl N-[(3R)-5-[(4-chlorophenyl)methyl]-7-{[(1R)-1-(4-methoxyphenyl)ethyl]-carbamoyl}-4-oxo-2,3,4,5-tetrahydro-1,5-benzothiazepin-3-yl]carbamate (Intermediate VIII-65)

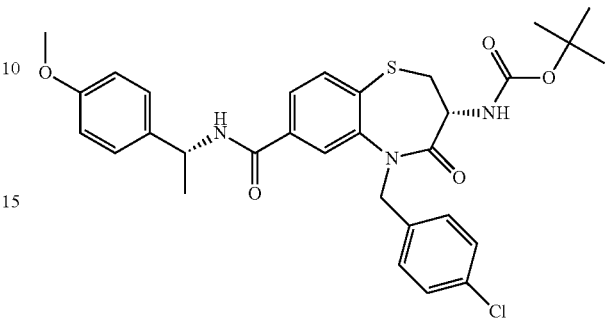

The title compound was synthesized according to general procedure GP3 to afford the title compound as Off-white solid in 73% Yield.

LCMS: METCR1673 Generic 2 minutes, rt=1.52 min, M/Z (ES+) 596/598 [M+H+] 100% UV NMR Data: 1H NMR (500 MHz, DMSO-d6) d 8.87 (d, J=8.0 Hz, 1H), 7.94 (d, J=1.3 Hz, 1H), 7.74 (dd, J=8.0, 1.5 Hz, 1H), 7.68 (d, J=8.0 Hz, 1H), 7.29 (d, J=7.3 Hz, 6H), 6.89 (d, J=8.7 Hz, 2H), 5.26 (d, J=15.6 Hz, 1H), 5.17-5.04 (m, 1H), 4.94 (d, J=15.6 Hz, 1H), 4.13 (dt, J=12.3, 7.6 Hz, 1H), 3.73 (s, 3H), 3.11 (s, 1H), 1.46 (d, J=7.0 Hz, 3H), 1.34 (s, 9H), 1.26 (s, 1H). [NH not visible]

Synthesis of tert-butyl N-[(3R)-5-[(4-chlorophenyl)methyl]-7-{[(1S)-1-(4-methoxyphenyl)ethyl]-carbamoyl}-4-oxo-2,3,4,5-tetrahydro-1,5-benzothiazepin-3-yl]carbamate (Intermediate VIII-66)

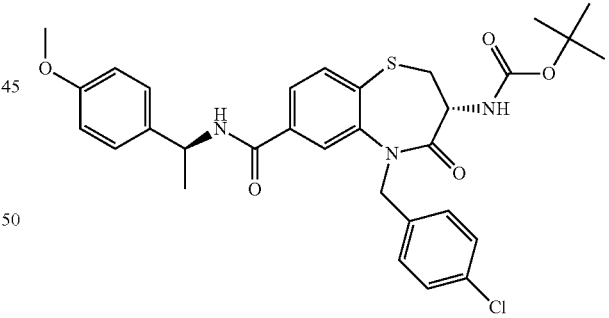

The title compound was synthesized according to general procedure GP3 to afford the title compound as White solid in 64% Yield.

LCMS: METCR1673 Generic 2 minutes, rt=1.61 min, M/Z (ES+) 596/598 [M+H+] 100% UV NMR Data: 1H NMR (500 MHz, DMSO-d6) d 8.88 (d, J=8.0 Hz, 2H), 7.94 (s, 1H), 7.78-7.71 (m, 1H), 7.68 (d, J=8.0 Hz, 2H), 7.45 (d, J=8.4 Hz, 2H), 7.30 (d, J=8.4 Hz, 4H), 6.89 (d, J=8.7 Hz, 1H), 5.28 (d, J=15.6 Hz, 1H), 5.12 (q, J=7.3 Hz, 1H), 4.94 (d, J=15.6 Hz, 1H), 4.12 (s, 1H), 3.73 (s, 3H), 3.46 (dd, J=11.3, 6.8 Hz, 1H), 3.11 (t, J=11.8 Hz, 1H), 1.47 (d, J=7.0 Hz, 3H), 1.35 (s, 9H).

Synthesis of tert-butyl N-[(3R)-5-[(4-chlorophenyl)methyl]-8-fluoro-7-{[(4-methoxyphenyl)-methyl]carbamoyl}-4-oxo-2,3,4,5-tetrahydro-1,5-benzothiazepin-3-yl]carbamate (Intermediate VIII-67)

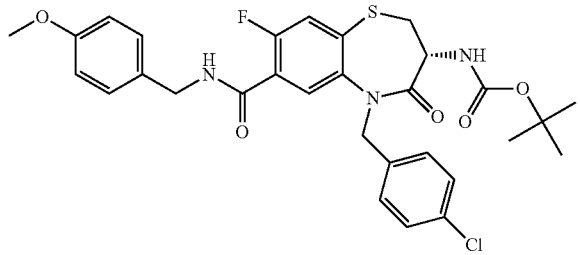 [SMILES: COc1ccc(CNC(=O)c2cc3c(cc2F)SC[C@H](NC(=O)OC(C)(C)C)C(=O)N3Cc2ccc(Cl)cc2)cc1]

The title compound was synthesized according to general procedure GP3 to afford the title compound as white foam in 86% Yield.

LCMS: METCR1416 Generic 7 minutes, rt=4.22 min, M/Z (ES+) 600/602 [M+Na+] 97% UV NMR Data: 1H NMR (500 MHz, chloroform-d) d 8.09 (d, J=7.0 Hz, 1H), 7.34 (d, J=10.8 Hz, 1H), 7.28 (d, J=8.6 Hz, 2H, partially obscured by CHCl3), 7.22-7.18 (m, 4H), 6.92-6.88 (m, 2H), 5.59-5.50 (m, 2H), 4.68-4.55 (m, 3H), 4.39 (dt, J=14.4, 7.2 Hz, 1H), 3.81 (s, 3H), 3.70 (dd, J=10.9, 6.4 Hz, 1H), 2.93 (t, J=11.3 Hz, 1H), 1.40 (s, 9H).

Synthesis of tert-butyl N-[(3R)-5-{[4-(5-methyl-1,2,4-oxadiazol-3-yl)phenyl]methyl}-7-[(oxan-4-ylmethyl)carbamoyl]-4-oxo-2,3,4,5-tetrahydro-1,5-benzothiazepin-3-yl]carbamate (Intermediate VIII-68)

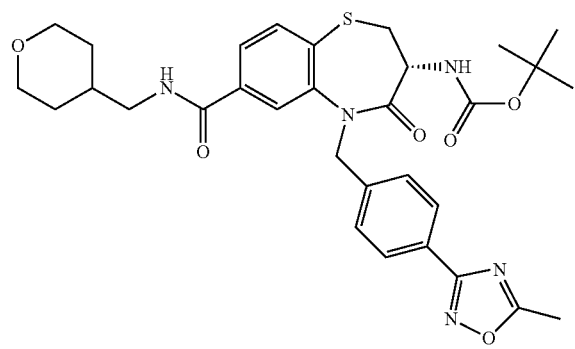 [SMILES: Cc1nc(-c2ccc(CN3C(=O)[C@@H](NC(=O)OC(C)(C)C)CSc4ccc(C(=O)NCC5CCOCC5)cc43)cc2)no1]

The title compound was synthesized according to general procedure GP3 to afford the title compound as Off-white solid in 61% Yield.

LCMS: METCR1673 Generic 2 minutes, rt=1.3 min, M/Z (ES−) 606 [M−H+] 100% UV

NMR Data: 1H NMR (500 MHz, DMSO-d6) d 8.66 (t, J=5.8 Hz, 1H), 7.94-7.82 (m, 3H), 7.68 (s, 2H), 7.52 (d, J=8.3 Hz, 1H), 7.46 (d, J=8.3 Hz, 2H), 5.27 (d, J=16.0 Hz, 1H), 5.08 (d, J=15.9 Hz, 1H), 4.23-4.09 (m, 1H), 3.82 (dd, J=11.0, 3.1 Hz, 2H), 3.47 (dd, J=11.3, 6.8 Hz, 1H), 3.28-3.20 (m, 2H), 3.19-3.05 (m, 3H), 2.64 (s, 3H), 1.76 (ddd, J=11.2, 7.4, 4.0 Hz, 1H), 1.56 (d, J=11.5 Hz, 2H), 1.34 (s, 9H), 1.16 (qd, J=12.4, 4.6 Hz, 2H).

Synthesis of tert-butyl N-[(3R)-7-[(oxan-4-ylmethyl)carbamoyl]-4-oxo-5-{[4-(trifluoromethoxy)phenyl]methyl}-2,3,4,5-tetrahydro-1,5-benzothiazepin-3-yl]carbamate (Intermediate VIII-69)

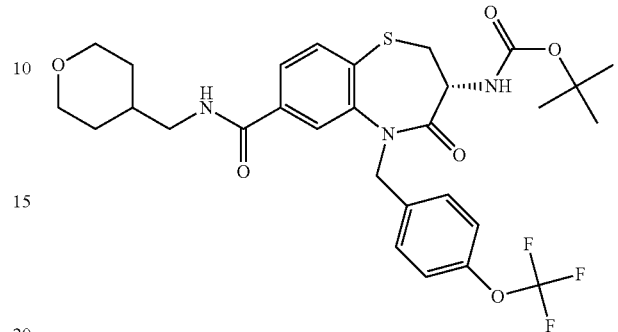

The title compound was synthesized according to general procedure GP3 to afford the title compound as cream solid in 72% Yield.

LCMS: METCR1278 Standard 3.5 minutes, rt=2.15 min, M/Z (ES+) 632 [M+Na+] 97% UV

NMR Data: 1H NMR (500 MHz, chloroform-d) d 1.30-1.46 (m, 11H), 1.64-1.72 (m, 2H), 1.80-1.94 (m, 1H), 2.92 (t, J=11.3 Hz, 1H), 3.26-3.46 (m, 4H), 3.69 (dd, J=6.6, 10.9 Hz, 1H), 4.00 (dd, J=3.6, 11.3 Hz, 2H), 4.42 (dt, J=7.2, 13.8 Hz, 1H), 4.88 (d, J=15.2 Hz, 1H), 5.34 (d, J=15.2 Hz, 1H), 5.55 (d, J=8.0 Hz, 1H), 6.12 (t, J=5.9 Hz, 1H), 7.08 (d, J=8.3 Hz, 2H), 7.31 (d, J=8.5 Hz, 2H), 7.46 (d, J=7.9 Hz, 1H), 7.64 (d, J=7.9 Hz, 1H), 7.71 (s, 1H)

Synthesis of tert-butyl N-[(3R)-7-{[(4-fluorophenyl)methyl]carbamoyl}-4-oxo-5-{[4-(1,2,3-thiadiazol-4-yl)phenyl]methyl}-2,3,4,5-tetrahydro-1,5-benzothiazepin-3-yl]carbamate (Intermediate VIII-70)

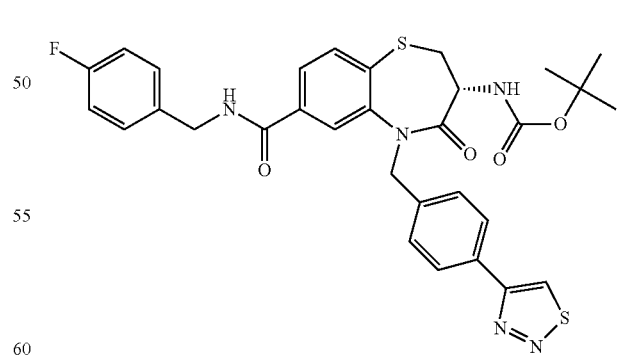

The title compound was synthesized according to general procedure GP3 to afford the title compound as Brown solid in 46% Yield.

LCMS: METCR1673 Generic 2 minutes, rt=1.43 min, M/Z (ES+) 642 [M+Na+] 100% UV

NMR Data: 1H NMR (500 MHz, DMSO-d6) d 9.55 (s, 1H), 9.22 (t, J=5.9 Hz, 1H), 8.01 (d, J=8.5 Hz, 3H), 7.77-7.67 (m, 2H), 7.46 (t, J=7.1 Hz, 3H), 7.35 (dd, J=8.4, 5.7 Hz, 2H), 7.14 (t, J=8.8 Hz, 2H), 5.37 (d, J=15.8 Hz, 1H), 5.04 (d, J=15.8 Hz, 1H), 4.46 (q, J=9.2 Hz, 2H), 4.18 (dt, J=12.3, 7.8 Hz, 1H), 3.15 (t, J=11.7 Hz, 2H), 1.36 (s, 9H).

Synthesis of tert-butyl N-[(3R)-7-{[(4-fluorophenyl)methyl]carbamoyl}-4-oxo-5-{[4-(trifluoromethoxy)phenyl]methyl}-2,3,4,5-tetrahydro-1,5-benzothiazepin-3-yl]carbamate (Intermediate VIII-71)

Synthesis of tert-butyl N-[(3R)-4-oxo-7-[(4,4,4-trifluorobutyl)carbamoyl]-5-{[4-(trifluoromethoxy)phenyl]methyl}-2,3,4,5-tetrahydro-1,5-benzothiazepin-3-yl]carbamate (Intermediate VIII-72)

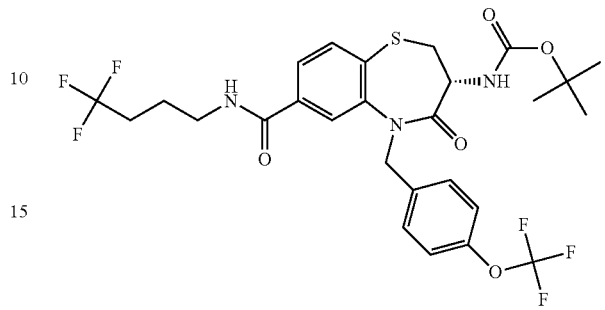

The title compound was synthesized according to general procedure GP3 to afford the title compound as cream solid in 78% Yield.

LCMS: METCR1278 Standard 3.5 minute, rt=2.31 min, M/Z (ES+) 644 [M+Na+] 96% UV

NMR Data: 1H NMR (500 MHz, chloroform-d) d 1.40 (s, 9H), 1.90 (p, J=7.3 Hz, 2H), 2.12-2.26 (m, 2H), 2.92 (t, J=11.3 Hz, 1H), 3.53 (q, J=6.7 Hz, 2H), 3.70 (dd, J=6.6, 10.9 Hz, 1H), 4.35-4.48 (m, 1H), 4.86 (d, J=15.2 Hz, 1H), 5.36 (d, J=15.2 Hz, 1H), 5.55 (d, J=8.1 Hz, 1H), 6.12 (t, J=5.8 Hz, 1H), 7.09 (d, J=8.2 Hz, 2H), 7.31 (d, J=8.6 Hz, 2H), 7.46 (dd, J=1.7, 7.9 Hz, 1H), 7.65 (d, J=8.0 Hz, 1H), 7.72 (d, J=1.4 Hz, 1H)

Synthesis of tert-butyl N-[(3R)-5-[(4-chlorophenyl)methyl]-7-[({4-[(5-acetamidopentyl)-oxy]phenyl}methyl)-carbamoyl]-4-oxo-2,3,4,5-tetrahydro-1,5-benzothiazepin-3-yl]carbamate (Intermediate VIII-73)

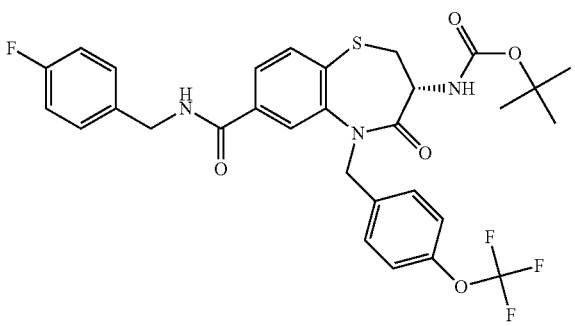 [SMILES: CC(C)(C)OC(=O)N[C@H]1CSc2ccc(C(=O)NCc3ccc(F)cc3)cc2N(Cc2ccc(OC(F)(F)F)cc2)C1=O]

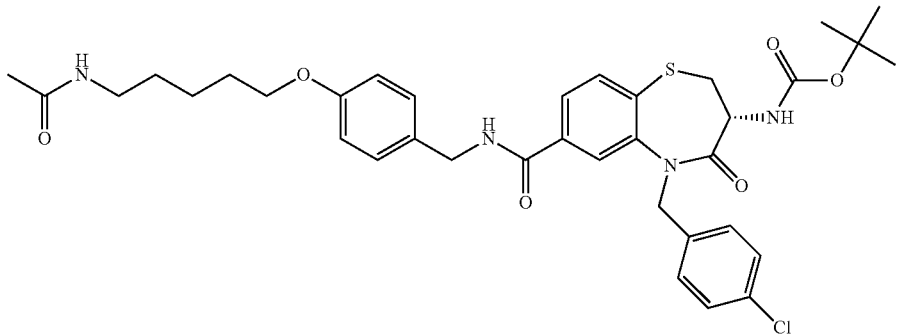 [SMILES: CC(=O)NCCCCCOc1ccc(CNC(=O)c2ccc3c(c2)N(Cc2ccc(Cl)cc2)C(=O)[C@@H](NC(=O)OC(C)(C)C)CS3)cc1]

The title compound was synthesized according to general procedure GP3 to afford the title compound as white solid in 81% Yield.

LCMS: METCR1278 Standard 3.5 minute, rt=2.34 min, M/Z (ES+) 642 [M+Na+] 100% UV

NMR Data: 1H NMR (500 MHz, chloroform-d) d 1.39 (s, 9H), 2.91 (t, J=11.3 Hz, 1H), 3.67 (dd, J=6.6, 11.0 Hz, 1H), 4.40 (dt, J=7.3, 11.5 Hz, 1H), 4.49-4.64 (m, 2H), 4.81 (d, J=15.2 Hz, 1H), 5.36 (d, J=15.2 Hz, 1H), 5.57 (d, J=8.0 Hz, 1H), 6.47 (t, J=5.00 Hz, 1H), 7.00-7.09 (m, 4H), 7.27-7.33 (m, 4H), 7.49 (dd, J=1.7, 8.0 Hz, 1H), 7.62 (d, J=8.0 Hz, 1H), 7.72-7.77 (m, 1H).

The title compound was synthesized according to general procedure GP3 to afford the title compound as beige solid in 75% Yield.

LCMS: METCR1673 Generic 2 minutes, rt=1.39 min, M/Z (ES+) 695/696 [M+H+] 97% UV

NMR Data: 1H NMR (500 MHz, DMSO-d6) d 9.12 (t, J=5.8 Hz, 1H), 7.97 (s, 1H), 7.79 (s, 1H), 7.76-7.70 (m, 1H), 7.68 (d, J=8.0 Hz, 1H), 7.45 (d, J=8.3 Hz, 1H), 7.29 (s, 4H), 7.23 (d, J=8.5 Hz, 2H), 6.89 (d, J=8.6 Hz, 2H), 5.30 (d, J=15.6 Hz, 1H), 4.92 (d, J=15.7 Hz, 1H), 4.41 (qd, J=15.0, 6.1 Hz, 2H), 4.12 (d, J=7.6 Hz, 1H), 3.93 (t, J=6.5 Hz, 2H), 3.47 (dd, J=11.3, 6.8 Hz, 1H), 3.12 (t, J=11.8 Hz, 1H), 3.03 (q, J=6.5 Hz, 2H), 1.78 (s, 3H), 1.70 (p, J=6.6 Hz, 2H), 1.47-1.30 (m, 13H).

Synthesis of tert-butyl N-[(3R)-5-[(4-chlorophenyl)methyl]-8-fluoro-7-(hexadecylcarbamoyl)-4-oxo-2,3,4,5-tetrahydro-1,5-benzothiazepin-3-yl]carbamate (Intermediate VIII-74)

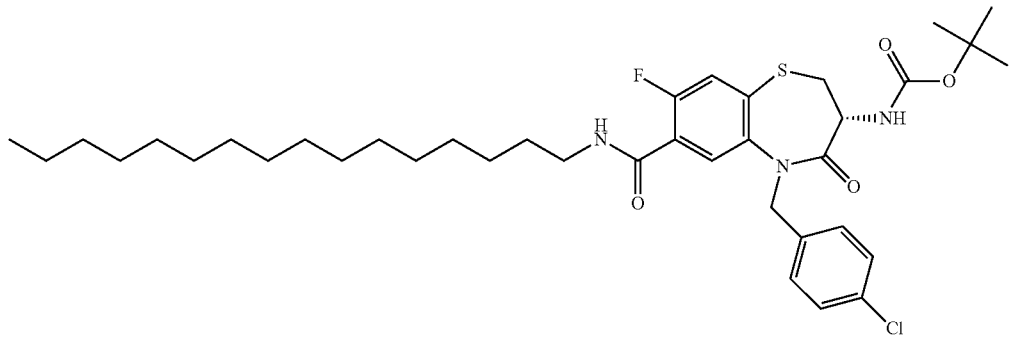 [SMILES: CCCCCCCCCCCCCCCCNC(=O)c1cc2c(cc1F)SC[C@H](NC(=O)OC(C)(C)C)C(=O)N2Cc1ccc(Cl)cc1]

The title compound was synthesized according to general procedure GP3 to afford the title compound as clear oil in 47% Yield.

LCMS: METCR1981 Hydrophobic 3 min, rt=2.69 min, M/Z (ES+) 726/728 [M+Na+] 92% UV NMR Data: 1H NMR (500 MHz, DMSO-d6) d 8.44 (s, 1H), 7.67 (d, J=6.4 Hz, 1H), 7.55 (d, J=9.3 Hz, 1H), 7.45 (d, J=8.4 Hz, 1H), 7.35-7.24 (m, 4H), 5.21 (d, J=15.7 Hz, 1H), 4.92 (d, J=15.7 Hz, 1H), 4.16 (dt, J=12.1, 7.7 Hz, 1H), 3.48 (dd, J=11.3, 6.8 Hz, 1H), 3.25-3.20 (m, 2H), 3.12 (t, J=11.8 Hz, 1H), 1.54-1.45 (m, 2H), 1.30 (m, 40H), 0.86 (t, J=6.9 Hz, 3H).

Synthesis of tert-butyl N-[(3R)-5-[(4-chloro-2-fluorophenyl)methyl]-8-fluoro-4-oxo-7-[(propan-2-yl)carbamoyl]-2,3,4,5-tetrahydro-1,5-benzothiazepin-3-yl]carbamate (Intermediate VIII-75)

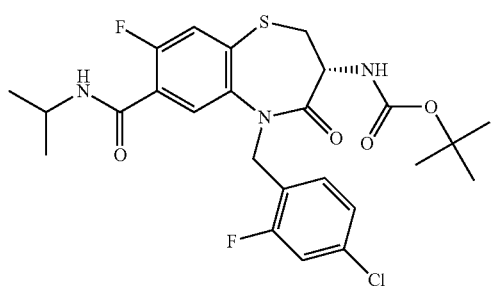 [SMILES: CC(C)NC(=O)c1cc2c(cc1F)SC[C@H](NC(=O)OC(C)(C)C)C(=O)N2Cc1ccc(Cl)cc1F]

The title compound was synthesized according to general procedure GP3 to afford the title compound as off white solid in 60% Yield.

LCMS: METCR1673 Generic 2 minutes, rt=1.52 min, M/Z (ES+) 562/564 [M+Na+] 100% UV NMR Data: 1H NMR (500 MHz, DMSO-d6) δ 8.10 (d, J=7.0 Hz, 1H), 7.49-7.34 (m, 2H), 7.05-7.01 (m, 2H), 6.51 (dd, J=12.0, 7.8 Hz, 1H), 5.56 (d, J=7.8 Hz, 1H), 5.42 (d, J=15.2 Hz, 1H), 4.81 (d, J=15.2 Hz, 1H), 4.39-4.33 (m, 2H), 3.70 (dd, J=10.9, 6.5 Hz, 1H), 2.90 (t, J=11.3 Hz, 1H), 1.41 (s, 9H), 1.30 (d, J=6.6 Hz, 6H).

Synthesis of tert-butyl N-[(3R)-5-[(4-chlorophenyl)methyl]-4-oxo-7-[(4,4,4-trifluorobutyl)-carbamoyl]-2,3,4,5-tetrahydro-1,5-benzothiazepin-3-yl]carbamate (Intermediate VIII-76)

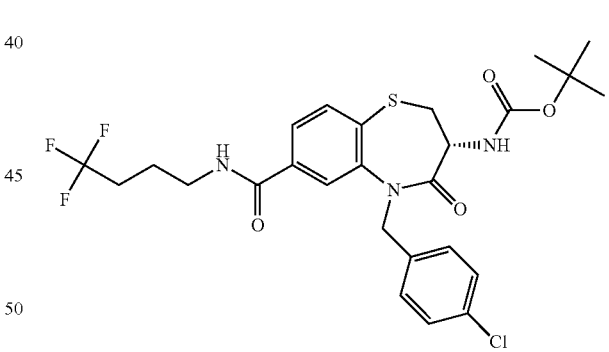

The title compound was synthesized according to general procedure GP3 to afford the title compound as white solid in 32% Yield.

LCMS: METCR1673 Generic 2 minutes, rt=1.52 min, M/Z (ES+) 594/596 [M+Na+] 100% UV NMR Data: 1H NMR (500 MHz, Chloroform-d) d 7.70 (d, J=1.6 Hz, 1H), 7.64 (d, J=8.0 Hz, 1H), 7.45 (dd, J=8.0, 1.6 Hz, 1H), 7.21 (s, 4H), 6.11 (s, 1H), 5.56 (d, J=7.8 Hz, 1H), 5.36 (d, J=15.1 Hz, 1H), 4.80 (d, J=15.1 Hz, 1H), 4.41 (dt, J=11.4, 7.6 Hz, 1H), 3.69 (dd, J=10.9, 6.6 Hz, 1H), 3.53 (q, J=6.7 Hz, 2H), 2.92 (t, J=11.3 Hz, 1H), 2.27-2.09 (m, 2H), 1.96-1.84 (m, 2H), 1.40 (s, 9H).

Synthesis of tert-butyl N-[(3R)-7-[(5-tert-butyl-1,2-oxazol-3-yl)carbamoyl]-5-[(4-chlorophenyl)methyl]-4-oxo-2,3,4,5-tetrahydro-1,5-benzothiazepin-3-yl]carbamate (Intermediate VIII-77)

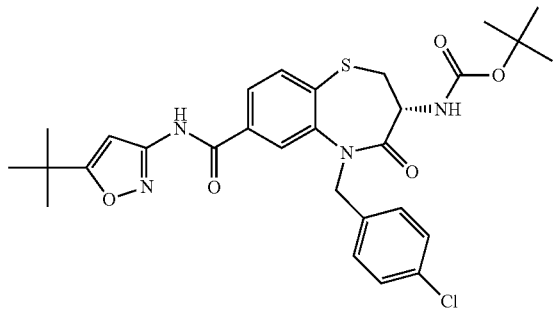 [SMILES: CC(C)(C)OC(=O)N[C@H]1CSc2ccc(C(=O)Nc3cc(C(C)(C)C)on3)cc2N(Cc2ccc(Cl)cc2)C1=O]

The title compound was synthesized according to general procedure GP3 to afford the title compound as white solid in 26% Yield.

LCMS: METCR1673 Generic 2 minutes, rt=1.62 min, M/Z (ES−) 583/585 [M−H+] 100% UV NMR Data: 1H NMR (500 MHz, Chloroform-d) d 9.19 (s, 1H), 7.92 (s, 1H), 7.78-7.64 (m, 2H), 7.23 (s, 4H), 6.84 (s, 1H), 5.61 (d, J=8.1 Hz, 1H), 5.49 (d, J=15.2 Hz, 1H), 4.79 (d, J=15.2 Hz, 1H), 4.52-4.41 (m, 1H), 3.76 (dd, J=10.9, 6.5 Hz, 1H), 2.98 (t, J=11.3 Hz, 1H), 1.42 (s, 9H), 1.40 (s, 9H).

Synthesis of tert-butyl N-[(3R)-7-{[(4-fluorophenyl)methyl]carbamoyl}-4-oxo-5-{[6-(trifluoromethyl)pyridin-3-yl]methyl}-2,3,4,5-tetrahydro-1,5-benzothiazepin-3-yl]carbamate (Intermediate VIII-78)

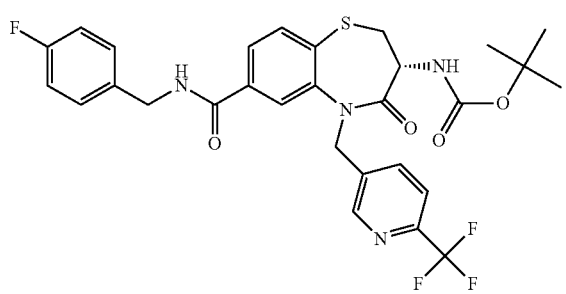 [SMILES: CC(C)(C)OC(=O)N[C@H]1CSc2ccc(C(=O)NCc3ccc(F)cc3)cc2N(Cc2ccc(C(F)(F)F)nc2)C1=O]

The title compound was synthesized according to general procedure GP3 to afford the title compound as white solid in 63% Yield.

LCMS: METCR1673 Generic 2 minutes, rt=1.43 min, M/Z (ES+) 627 [M+Na+] 100% UV

NMR Data: 1H NMR (500 MHz, Chloroform-d) d 8.61 (s, 1H), 7.94-7.87 (m, 2H), 7.67 (d, J=8.0 Hz, 1H), 7.59 (d, J=8.1 Hz, 1H), 7.50 (dd, J=8.0, 1.8 Hz, 1H), 7.35 (dd, J=8.6, 5.3 Hz, 2H), 7.11-7.05 (m, 2H), 6.39 (t, J=5.5 Hz, 1H), 5.66 (d, J=15.3 Hz, 1H), 5.52 (d, J=8.2 Hz, 1H), 4.78 (d, J=15.4 Hz, 1H), 4.69-4.58 (m, 2H), 4.44 (dt, J=11.5, 7.5 Hz, 1H), 3.71 (dd, J=11.0, 6.7 Hz, 1H), 2.92 (t, J=11.3 Hz, 1H), 1.42 (s, 9H).

Synthesis of tert-butyl N-[(3R)-7-(butylcarbamoyl)-5-[(4-cyanophenyl)methyl]-4-oxo-2,3,4,5-tetrahydro-1,5-benzothiazepin-3-yl]carbamate (Intermediate VIII-79)

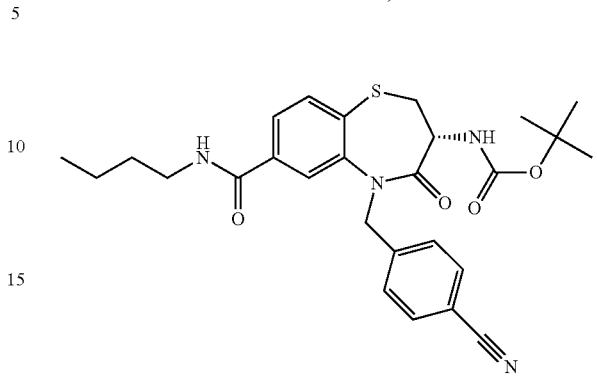

The title compound was synthesized according to general procedure GP3 to afford the title compound as yellow Solid in 53% Yield.

LCMS: METUPLCMS-A-004, rt=1.47 min, M/Z (ES+) 509 [M+H+] 57% UV

Synthesis of tert-butyl N-[(3R)-7-(butylcarbamoyl)-5-[(4-chlorophenyl)methyl]-4-oxo-2,3,4,5-tetrahydro-1,5-benzothiazepin-3-yl]carbamate (Intermediate VIII-80)

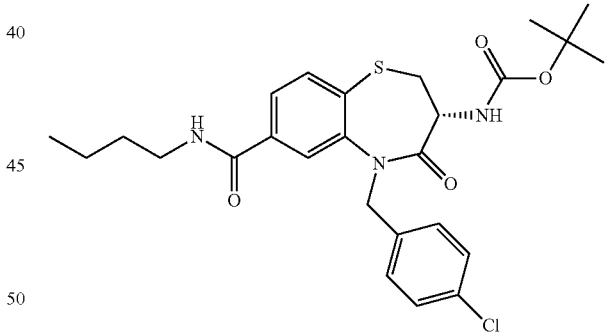

The title compound was synthesized according to general procedure GP3 to afford the title compound as white solid in 89% Yield.

LCMS: METUPLCMS-A-004, rt=1.67 min, M/Z (ES+) 518/520 [M+H+] 99% UV

NMR Data: 1H NMR (400 MHz, chloroform-d) δ 7.69 (d, J=1.8 Hz, 1H), 7.62 (d, J=8.0 Hz, 1H), 7.46 (dd, J=8.0, 1.8 Hz, 1H), 7.22 (d, J=9.3 Hz, 4H), 6.00 (s, 1H), 5.57 (d, J=8.1 Hz, 1H), 5.32 (t, J=9.9 Hz, 1H), 4.82 (d, J=15.1 Hz, 1H), 4.41 (dt, J=11.7, 7.3 Hz, 1H), 3.69 (dd, J=11.0, 6.6 Hz, 1H), 3.52-3.34 (m, 2H), 2.91 (t, J=11.3 Hz, 1H), 1.66-1.49 (m, 3H), 1.46-1.41 (m, 1H), 1.40 (s, 9H), 0.97 (t, J=7.3 Hz, 3H).

Synthesis of tert-butyl N-[(3R)-5-[(4-chlorophenyl)methyl]-7-[(2-methoxyethyl)carbamoyl]-4-oxo-2,3,4,5-tetrahydro-1,5-benzothiazepin-3-yl]carbamate (Intermediate VIII-81)

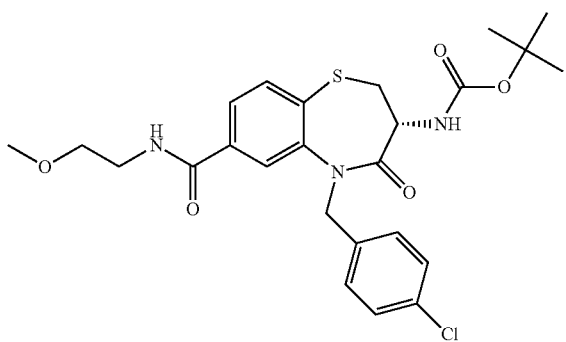 [SMILES: COCCNC(=O)c1ccc2c(c1)N(Cc1ccc(Cl)cc1)C(=O)[C@@H](NC(=O)OC(C)(C)C)CS2]

The title compound was synthesized according to general procedure GP3 to afford the title compound which was used in the next step without further analysis or purification.

Synthesis of tert-butyl N-[(3R)-7-(methylcarbamoyl)-4-oxo-5-{[4-(trifluoromethoxy)phenyl]methyl}-2,3,4,5-tetrahydro-1,5-benzothiazepin-3-yl]carbamate (Intermediate VIII-82)

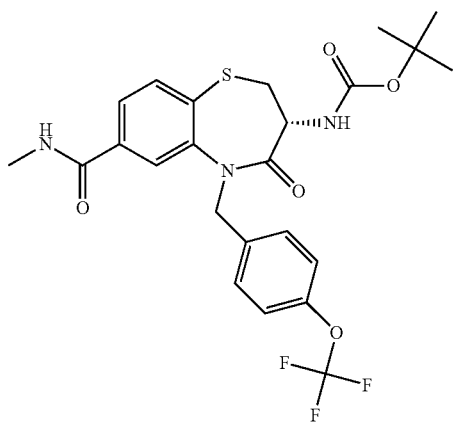 [SMILES: CNC(=O)c1ccc2c(c1)N(Cc1ccc(OC(F)(F)F)cc1)C(=O)[C@@H](NC(=O)OC(C)(C)C)CS2]

The title compound was synthesized according to general procedure GP3 to afford the title compound which was used in the next step without further analysis or purification.

Synthesis of tert-butyl N-[(3R)-5-[(4-tert-butylphenyl)methyl]-4-oxo-7-[(propan-2-yl)carbamoyl]-2,3,4,5-tetrahydro-1,5-benzothiazepin-3-yl]carbamate (Intermediate VIII-83)

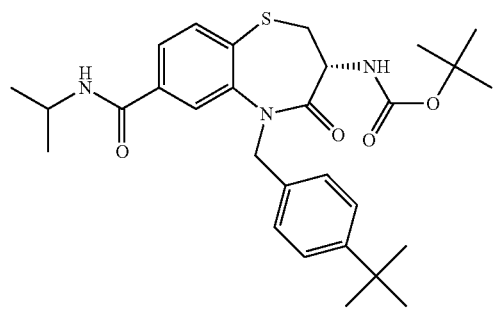 [SMILES: CC(C)NC(=O)c1ccc2c(c1)N(Cc1ccc(C(C)(C)C)cc1)C(=O)[C@@H](NC(=O)OC(C)(C)C)CS2]

The title compound was synthesized according to general procedure GP3 to afford the title compound as Off white solid in 62% Yield.

LCMS: METUPLCMS-A-004, rt=1.76 min, M/Z (ES+) 526 [M+H+] 92% UV

NMR Data: 1H NMR (400 MHz, Chloroform-d) δ 7.62 (dd, J=6.1, 5.0 Hz, 2H), 7.50 (dd, J=7.9, 1.7 Hz, 1H), 7.29 (d, J=8.5 Hz, 2H), 7.23 (d, J=8.4 Hz, 2H), 5.74 (d, J=7.7 Hz, 1H), 5.59 (d, J=8.0 Hz, 1H), 5.06 (s, 2H), 4.42 (dt, J=11.2, 7.4 Hz, 1H), 4.31-4.17 (m, 1H), 3.70 (dd, J=11.0, 6.6 Hz, 1H), 2.92 (t, J=11.3 Hz, 1H), 1.40 (s, 9H), 1.27 (s, 9H), 1.24 (d, J=3.1 Hz, 3H), 1.23 (d, J=3.1 Hz, 3H).

Synthesis of tert-butyl N-[(3R)-5-[(4-chlorophenyl)methyl]-7-[(cyclopropylmethyl)carbamoyl]-8-fluoro-4-oxo-2,3,4,5-tetrahydro-1,5-benzothiazepin-3-yl]carbamate (Intermediate VIII-84)

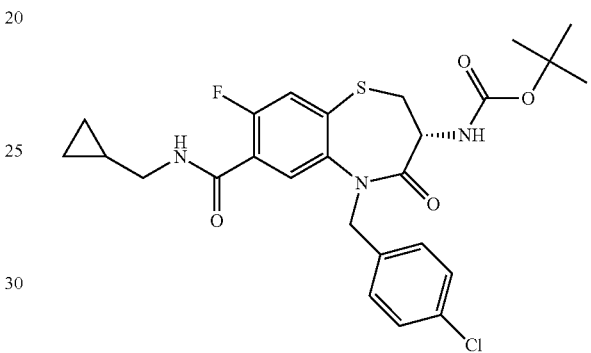

The title compound was synthesized according to general procedure GP3 to afford the title compound as Off white solid in 62% Yield.

LCMS METCR1673 Generic 2 minutes, rt=1.52 min, M/Z (ES−) 534/536 [M−H+] 99% UV

NMR Data: 1H NMR (500 MHz, DMSO-d6) δ 8.54 (s, 1H), 7.69 (d, J=6.5 Hz, 1H), 7.55 (d, J=9.4 Hz, 1H), 7.44 (d, J=8.3 Hz, 1H), 7.35-7.25 (m, 4H), 5.21 (d, J=15.7 Hz, 1H), 4.91 (d, J=15.7 Hz, 1H), 4.16 (dt, J=12.1, 7.2 Hz, 1H), 3.48 (dd, J=11.3, 6.9 Hz, 1H), 3.17-3.12 (m, 3H), 1.35 (s, 9H), 1.05-0.95 (m, 1H), 0.51-0.37 (m, 2H), 0.22 (q, J=4.9, 4.4 Hz, 2H).

Synthesis of tert-butyl N-[(3R)-7-(ethylcarbamoyl)-4-oxo-5-{[4-(trifluoromethoxy)phenyl]methyl}-2,3,4,5-tetrahydro-1,5-benzothiazepin-3-yl]carbamate (Intermediate VIII-85)

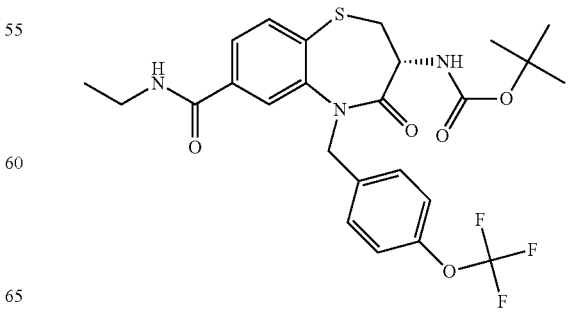

The title compound was synthesized according to general procedure GP3 to afford the title compound which was used in the next step without further analysis or purification.

Synthesis of tert-butyl N-[(3R)-7-(butylcarbamoyl)-5-[(4-tert-butylphenyl)methyl]-4-oxo-2,3,4,5-tetrahydro-1,5-benzothiazepin-3-yl]carbamate (Intermediate VIII-86)

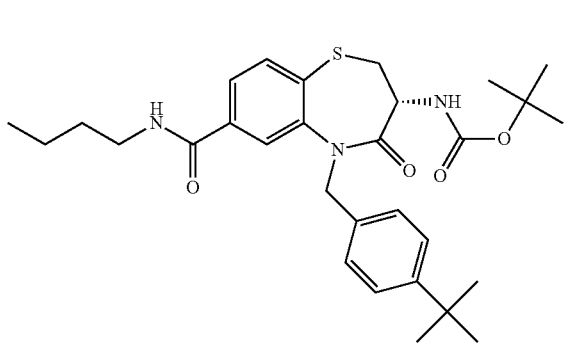 [SMILES: CCCCNC(=O)c1ccc2c(c1)N(Cc1ccc(C(C)(C)C)cc1)C(=O)[C@@H](NC(=O)OC(C)(C)C)CS2]

The title compound was synthesized according to general procedure GP3 to afford the title compound as white solid in 65% Yield.

LCMS: METUPLCMS-A-004, rt=1.85 min, M/Z (ES+) 540 [M+H+] 99% UV

Synthesis of tert-butyl N-[(3R)-7-(butylcarbamoyl)-4-oxo-5-{[3-(trifluoromethoxy)phenyl]methyl}-2,3,4,5-tetrahydro-1,5-benzothiazepin-3-yl]carbamate (Intermediate VIII-87)

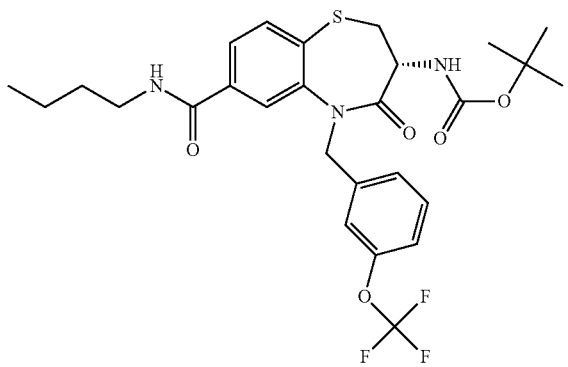 [SMILES: CCCCNC(=O)c1ccc2c(c1)N(Cc1cccc(OC(F)(F)F)c1)C(=O)[C@@H](NC(=O)OC(C)(C)C)CS2]

The title compound was synthesized according to general procedure GP3 to afford the title compound as yellow solid in 81% Yield.

LCMS: METUPLCMS-A-004, rt=1.7 min, M/Z (ES+) 568 [M+H+] 97% UV

NMR Data: 1H NMR (300 MHz, Chloroform-d) δ 0.98 (t, J=7.3 Hz, 3H), 1.41 (s, 9H), 1.69-1.54 (m, 3H), 2.93 (t, J=11.3 Hz, 1H), 3.45 (dd, J=12.9, 7.0 Hz, 2H), 3.71 (dd, J=11.0, 6.6 Hz, 1H), 4.44 (dt, J=11.3, 7.2 Hz, 1H), 4.86 (d, J=15.2 Hz, 1H), 5.43 (d, J=15.2 Hz, 1H), 5.59 (d, J=8.1 Hz, 1H), 6.09 (s, 1H), 7.08 (d, J=7.9 Hz, 1H), 7.28-7.16 (m, 3H), 7.49 (dd, J=8.0, 1.8 Hz, 1H), 7.64 (d, J=8.0 Hz, 1H), 7.73 (d, J=1.6 Hz, 1H). [NH not visible]

Synthesis of tert-butyl N-[(3R)-7-(butylcarbamoyl)-5-{[4-(morpholin-4-yl)phenyl]methyl}-4-oxo-2,3,4,5-tetrahydro-1,5-benzothiazepin-3-yl]carbamate (Intermediate VIII-88)

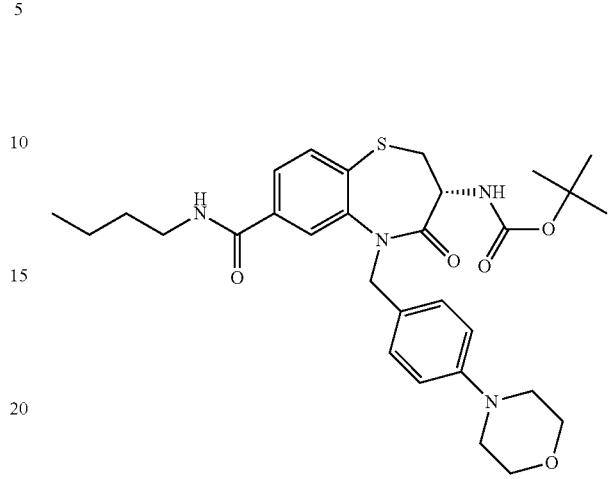

The title compound was synthesized according to general procedure GP3 to afford the title compound as Off-White Solid in 34% Yield.

LCMS: METUPLCMS-A-004, rt=1.47 min, M/Z (ES+) 569 [M+H+] 95% UV

Synthesis of tert-butyl N-[(3R)-8-fluoro-4-oxo-7-[(propan-2-yl)carbamoyl]-5-{[4-(trifluoromethoxy)phenyl]methyl}-2,3,4,5-tetrahydro-1,5-benzothiazepin-3-yl]carbamate (Intermediate VIII-89)

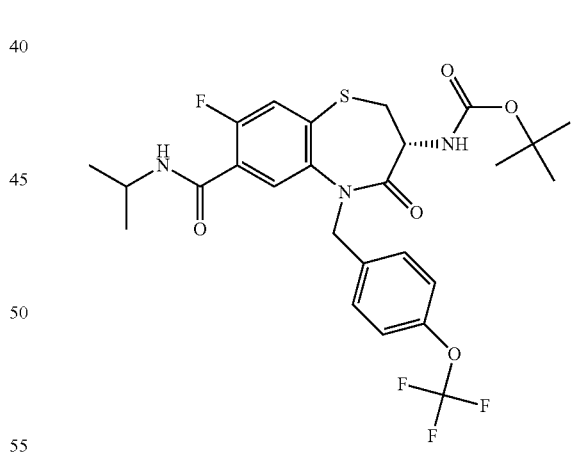

The title compound was synthesized according to general procedure GP3 to afford the title compound as Off-White Solid in 55% Yield.

LCMS: METUPLCMS-A-004, rt=1.55 min, M/Z (ES+) 572 [M+H+] 92% UV

NMR Data: 1H NMR (400 MHz, Chloroform-d) δ 8.06 (d, J=7.1 Hz, 1H), 7.37-7.29 (m, 3H), 7.07 (d, J=8.0 Hz, 2H), 6.56-6.43 (m, 1H), 5.61-5.47 (m, 2H), 4.69 (d, J=15.1 Hz, 1H), 4.44-4.24 (m, 2H), 3.70 (dd, J=11.0, 6.5 Hz, 1H), 2.96-2.90 (m, 1H), 1.39 (s, 9H), 1.28 (d, J=6.6 Hz, 6H).

Synthesis of tert-butyl N-[(3R)-5-[(4-chlorophenyl)methyl]-7-{[(1R)-1-(4-fluorophenyl)-ethyl]carbamoyl}-4-oxo-2,3,4,5-tetrahydro-1,5-benzothiazepin-3-yl]carbamate (Intermediate VIII-90)

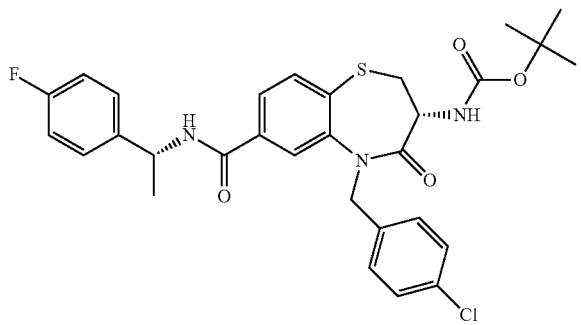

The title compound was synthesized according to general procedure GP3 to afford the title compound as White Solid in 96% Yield.

LCMS: METCR1416, generic 7 minutes, rt=3.32 min, M/Z (ES+) 484/486 [M+H-boc] 97% UV NMR Data: 1H NMR (500 MHz, DMSO-d6) d 8.98 (d, J=7.9 Hz, 1H), 8.00 (s, 1H), 7.81 (d, J=8.0 Hz, 1H), 7.72 (d, J=8.0 Hz, 1H), 7.41 (dd, J=8.7, 5.6 Hz, 2H), 7.31 (q, J=8.6 Hz, 4H), 7.15 (t, J=8.9 Hz, 2H), 5.37 (d, J=15.4 Hz, 1H), 5.15 (t, J=7.3 Hz, 1H), 4.97 (d, J=15.4 Hz, 1H), 3.99-3.89 (m, 1H), 3.62-3.56 (m, 1H), 3.18 (t, J=11.7 Hz, 1H), 1.48 (d, J=7.0 Hz, 3H), 1.40 (s, 9H). [NH not visible]

Synthesis of tert-butyl N-[(3R)-7-[(oxan-4-yl)carbamoyl]-4-oxo-5-{[4-(trifluoromethoxy)-phenyl]methyl}-2,3,4,5-tetrahydro-1,5-benzothiazepin-3-yl]carbamate (Intermediate VIII-91)

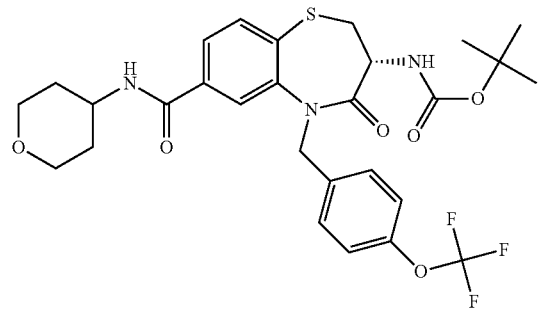 [SMILES: CC(C)(C)OC(=O)N[C@H]1CSc2ccc(C(=O)NC3CCOCC3)cc2N(Cc2ccc(OC(F)(F)F)cc2)C1=O]

The title compound was synthesized according to general procedure GP3 to afford the title compound as White Solid in 46% Yield.

LCMS: METUPLCMS-A-004, rt=1.53 min, M/Z (ES+) 596 [M+H+] 80% UV

NMR Data: 1H NMR (400 MHz, Chloroform-d) δ 7.70 (d, J=1.6 Hz, 1H), 7.64 (d, J=8.0 Hz, 1H), 7.47 (dd, J=8.0, 1.8 Hz, 1H), 7.32 (d, J=8.7 Hz, 2H), 7.09 (d, J=7.9 Hz, 2H), 5.87 (d, J=7.9 Hz, 1H), 5.54 (d, J=8.3 Hz, 1H), 5.42-5.27 (m, 2H), 4.88 (d, J=15.2 Hz, 1H), 4.39 (d, J=8.1 Hz, 1H), 4.18 (dd, J=7.8, 3.7 Hz, 1H), 4.01 (d, J=12.0 Hz, 3H), 3.69 (dd, J=11.0, 6.7 Hz, 1H), 3.57-3.49 (m, 2H), 2.92 (t, J=11.3 Hz, 1H), 1.99 (d, J=12.6 Hz, 2H), 1.40 (s, 9H). [NH not visible]

Synthesis of tert-butyl N-[(3R)-7-(benzylcarbamoyl)-4-oxo-5-{[4-(trifluoromethoxy)phenyl]methyl}-2,3,4,5-tetrahydro-1,5-benzothiazepin-3-yl]carbamate (Intermediate VIII-92)

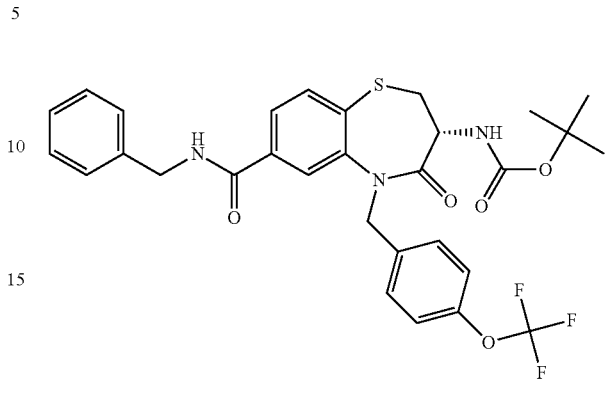

The title compound was synthesized according to general procedure GP3 to afford the title compound as White Solid in 78% Yield.

LCMS: MET-UPLCMS-A-006, rt=4.14 min, M/Z (ES+) 602 [M+H+] 92% UV

NMR Data: 1H NMR (400 MHz, Chloroform-d) δ 1.39 (s, 9H), 2.91 (t, J=11.3 Hz, 1H), 3.69 (dd, J=11.0, 6.6 Hz, 1H), 4.47-4.38 (m, 1H), 4.69-4.57 (m, 2H), 4.84 (d, J=15.2 Hz, 1H), 5.38 (d, J=15.2 Hz, 1H), 5.55 (d, J=8.1 Hz, 1H), 6.30 (s, 1H), 7.06 (d, J=8.0 Hz, 2H), 7.41-7.28 (m, 7H), 7.49 (dd, J=8.0, 1.8 Hz, 1H), 7.63 (d, J=8.0 Hz, 1H), 7.78 (d, J=1.7 Hz, 1H).

Synthesis of tert-butyl N-[(3R)-4-oxo-7-[(4,4,4-trifluorobutyl)carbamoyl]-5-{[6-(trifluoromethyl)pyridin-3-yl]methyl}-2,3,4,5-tetrahydro-1,5-benzothiazepin-3-yl]carbamate (Intermediate VIII-93)

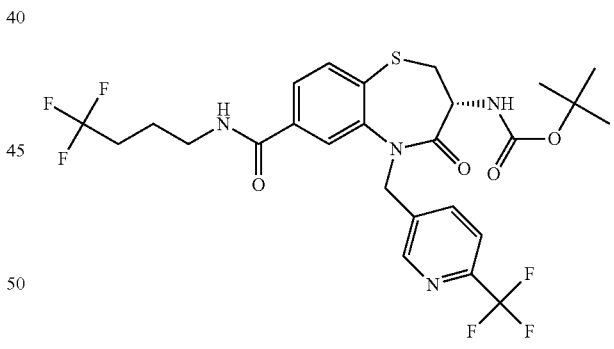

The title compound was synthesized according to general procedure GP3 to afford the title compound as white solid in 35% Yield.

LCMS: METCR1673 Generic 2 minutes, rt=1.43 min, M/Z (ES+) 629 [M+Na] 100% UV

NMR Data: 1H NMR (500 MHz, Chloroform-d) δ 8.59 (s, 1H), 7.90-7.83 (m, 2H), 7.66 (d, J=8.0 Hz, 1H), 7.58 (d, J=8.1 Hz, 1H), 7.47 (dd, J=8.0, 1.8 Hz, 1H), 6.23 (t, J=5.5 Hz, 1H), 5.64 (d, J=15.4 Hz, 1H), 5.52 (d, J=8.2 Hz, 1H), 4.76 (d, J=15.4 Hz, 1H), 4.42 (dt, J=11.6, 7.5 Hz, 1H), 3.69 (dd, J=11.0, 6.6 Hz, 1H), 3.55 (q, J=6.7 Hz, 2H), 2.90 (t, J=11.3 Hz, 1H), 2.27-2.15 (m, 2H), 1.92 (p, J=7.2 Hz, 2H), 1.40 (s, 9H).

Synthesis of tert-butyl N-[(3R)-7-(butylcarbamoyl)-8-fluoro-4-oxo-5-(quinolin-2-ylmethyl)-2,3,4,5-tetrahydro-1,5-benzothiazepin-3-yl]carbamate (Intermediate VIII-94)

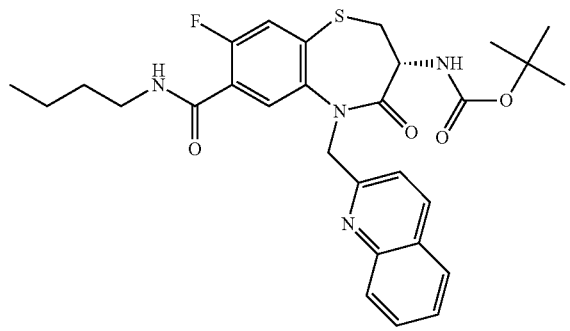 [SMILES: CCCCNC(=O)c1cc2c(cc1F)SC[C@H](NC(=O)OC(C)(C)C)C(=O)N2Cc1ccc2ccccc2n1]

The title compound was synthesized according to general procedure GP3 to afford the title compound as yellow oil in 66% Yield.

LCMS: METCR1673 Generic 2 minutes, rt=1.43 min, M/Z (ES+) 553 [M+H+] 100% UV

NMR Data: 1H NMR (250 MHz, Chloroform-d) δ 0.95 (t, J=7.2 Hz, 3H), 1.26-1.49 (m, 11H), 1.60 (dt, J=7.2, 14.5 Hz, 2H), 2.97 (t, J=11.2 Hz, 1H), 3.45 (q, J=6.8 Hz, 2H), 3.76 (dd, J=6.5, 10.7 Hz, 1H), 4.40-4.59 (m, 1H), 5.26-5.49 (m, 2H), 5.49-5.63 (m, 1H), 6.75 (s, 1H), 7.37 (d, J=10.6 Hz, 1H), 7.54 (t, J=7.6 Hz, 1H), 7.64-7.78 (m, 2H), 7.80 (d, J=7.8 Hz, 1H), 8.10 (d, J=8.2 Hz, 1H), 8.19 (d, J=8.5 Hz, 1H), 8.32 (d, J=7.0 Hz, 1H).

Synthesis of tert-butyl N-[(3R)-5-[(5-cyclopropyl-1,3,4-thiadiazol-2-yl)methyl]-8-fluoro-7-{[(4-fluorophenyl)methyl]carbamoyl}-4-oxo-2,3,4,5-tetrahydro-1,5-benzothiazepin-3-yl]carbamate (Intermediate VIII-95)

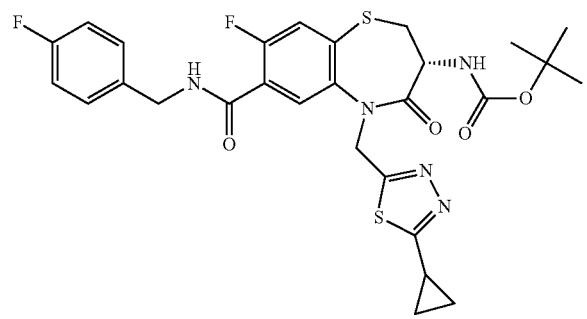 [SMILES: CC(C)(C)OC(=O)N[C@H]1CSc2cc(F)c(C(=O)NCc3ccc(F)cc3)cc2N(Cc2nnc(C3CC3)s2)C1=O]

The title compound was synthesized according to general procedure GP3 to afford the title compound as Off white solid in 46% Yield.

LCMS: METCR1673 Generic 2 minutes, rt=1.36 min, M/Z (ES+) 602 [M+Na+] 100% UV

NMR Data: 1H NMR (500 MHz, Chloroform-d) δ 8.16 (d, J=6.9 Hz, 1H), 7.39 (d, J=10.6 Hz, 1H), 6.81-6.68 (m, 1H), 5.58-5.45 (m, 2H), 5.13 (d, J=15.2 Hz, 1H), 4.45-4.33 (m, 1H), 3.69 (dd, J=10.9, 6.6 Hz, 1H), 3.63-3.51 (m, 2H), 2.86 (t, J=11.2 Hz, 1H), 2.39-2.30 (m, 1H), 2.27-2.14 (m, 2H), 1.97-1.86 (m, 2H), 1.39 (s, 9H), 1.25-1.17 (m, 2H), 1.13-1.06 (m, 2H).

Synthesis of tert-butyl N-[(3R)-7-[(2,2-difluorocyclopropyl)carbamoyl]-8-fluoro-5-{[4-methoxy-3-(trifluoromethyl)phenyl]methyl}-4-oxo-2,3,4,5-tetrahydro-1,5-benzothiazepin-3-yl]carbamate (Intermediate VIII-96)

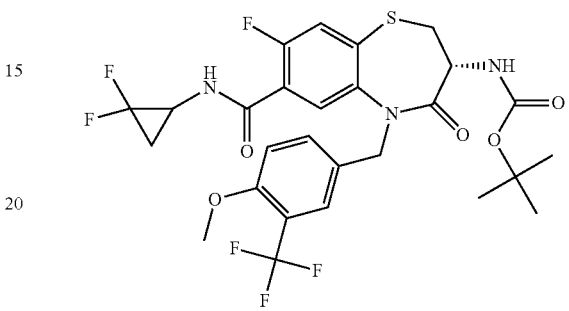

The title compound was synthesized according to general procedure GP3 to afford the title compound as off white solid in 59% yield.

LCMS: METCR1410 Generic 1.7 min, rt=1.28 min, M/Z (ES+) 641.90 [M+Na+] 97% UV

NMR Data: 1H NMR (500 MHz, DMSO-d6) d 8.94 (d, J=8.1 Hz, 1H), 7.76 (dd, J=12.5, 6.4 Hz, 1H), 7.59 (dd, J=9.3, 2.5 Hz, 1H), 7.55 (s, 1H), 7.45 (t, J=7.8 Hz, 2H), 7.13 (d, J=8.6 Hz, 1H), 5.30 (dd, J=15.5, 9.4 Hz, 1H), 4.88 (d, J=15.5 Hz, 1H), 4.15 (dt, J=12.1, 7.8 Hz, 1H), 3.83 (s, 3H), 3.49 (dd, J=11.3, 7.0 Hz, 2H), 3.13 (t, J=11.8 Hz, 1H), 2.05-1.94 (m, 1H), 1.63 (dd, J=9.3, 5.2 Hz, 1H), 1.35 (s, 9H).

Synthesis of tert-butyl N-[(2R,3R)-5-[(4-chlorophenyl)methyl]-8-fluoro-2-methyl-4-oxo-7-[(4,4,4-trifluorobutyl)carbamoyl]-2,3,4,5-tetrahydro-1,5-benzothiazepin-3-yl]carbamate (Intermediate VIII-97)

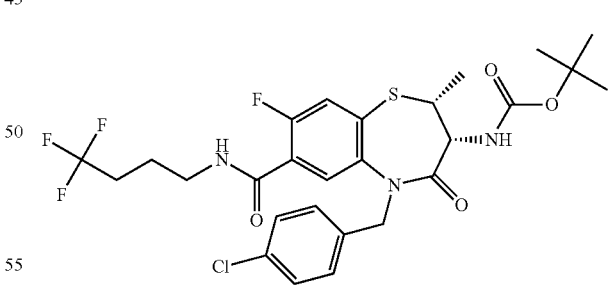

The title compound was synthesized according to general procedure GP3 to afford the title compound as colourless oil in 78% yield.

LCMS: METCR1410 Generic 1.7 min, rt=1.42 min, M/Z (ES+) 625.95/627.90 [M+Na+] 83% UV NMR Data: 1H NMR (500 MHz, DMSO-d6) d 8.02 (d, J=7.0 Hz, 1H), 7.35 (d, J=10.9 Hz, 1H), 7.23-7.16 (m, 4H), 6.77 (dt, J=12.3, 5.8 Hz, 1H), 5.60 (d, J=6.3 Hz, 1H), 5.56 (d, J=15.2 Hz, 1H), 4.62 (d, J=15.2 Hz, 1H), 4.49 (t, J=6.8 Hz, 1H), 3.98 (p, J=6.6 Hz, 1H), 3.55 (dp, J=13.8, 6.9 Hz, 2H), 2.25-2.13 (m, 2H), 1.91 (dt, J=14.8, 7.0 Hz, 2H), 1.39 (s, 9H), 1.32 (d, J=6.8 Hz, 3H).

Synthesis of tert-butyl N-[(3R)-5-{[4-(5-methyl-1,2,4-oxadiazol-3-yl)phenyl]methyl}-4-oxo-7-[(4,4,4-trifluorobutyl)carbamoyl]-2,3,4,5-tetrahydro-1,5-benzothiazepin-3-yl]carbamate (Intermediate VIII-98)

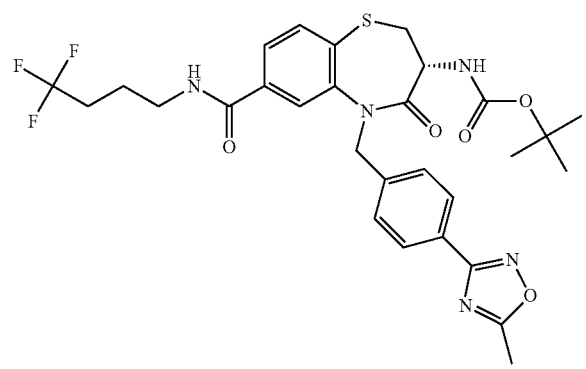 [SMILES: Cc1nc(-c2ccc(CN3C(=O)[C@@H](NC(=O)OC(C)(C)C)CSc4ccc(C(=O)NCCCC(F)(F)F)cc43)cc2)no1]

The title compound was synthesized according to general procedure GP3 to afford the title compound as colourless oil in 92% yield.
LCMS: METCR1410 Generic 1.7 min, rt=1.27 min, M/Z (ES+) 642 [M+Na+] 99% UV
NMR Data: 1H NMR (500 MHz, Chloroform-d) d 7.85 (d, J=8.0 Hz, 2H), 7.66 (s, 1H), 7.54 (d, J=8.0 Hz, 1H), 7.42 (d, J=8.0 Hz, 1H), 7.31 (d, J=8.0 Hz, 2H), 6.49 (s, 1H), 5.56 (s, 1H), 5.38 (d, J=15.2 Hz, 1H), 4.79 (d, J=15.2 Hz, 1H), 4.35 (dt, J=14.0, 7.6 Hz, 1H), 3.61 (dd, J=10.3, 7.0 Hz, 1H), 3.41 (d, J=5.9 Hz, 2H), 2.55 (s, 3H), 2.18-2.02 (m, 2H), 1.80 (p, J=7.2 Hz, 2H), 1.33 (s, 9H). [NH not visible]

Synthesis of tert-butyl N-[(3R)-5-[(4-chlorophenyl)methyl]-8-fluoro-7-[(2-methoxyethyl)carbamoyl]-4-oxo-2,3,4,5-tetrahydro-1,5-benzothiazepin-3-yl]carbamate (Intermediate VIII-99)

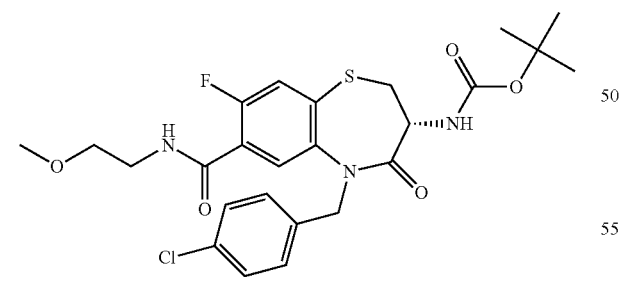

The title compound was synthesized according to general procedure GP3 to afford the title compound as white solid in 47% yield.
LCMS: METCR1410 Generic 1.7 min, rt=1.25 min, M/Z (ES+) 559.90/561.90 [M+Na+], 482.35/483.95 [M-tBu+H+] 100% UV
NMR Data: 1H NMR (500 MHz, DMSO-d6) δ 8.51 (s, 1H), 7.70 (d, J=6.5 Hz, 1H), 7.56 (d, J=9.4 Hz, 1H), 7.45 (d, J=8.3 Hz, 1H), 7.37-7.24 (m, 4H), 5.21 (d, J=15.6 Hz, 1H), 4.91 (d, J=15.7 Hz, 1H), 4.16 (dt, J=12.2, 7.6 Hz, 1H), 3.52-3.37 (m, 5H), 3.27 (s, 3H), 3.12 (t, J=11.7 Hz, 1H), 1.36 (s, 9H).

Synthesis of tert-butyl N-[(3R)-7-[(2,2-difluorocyclopropyl)carbamoyl]-5-{[4-(5-methyl-1,2,4-oxadiazol-3-yl)phenyl]methyl}-4-oxo-2,3,4,5-tetrahydro-1,5-benzothiazepin-3-yl]carbamate (Intermediate VIII-100)

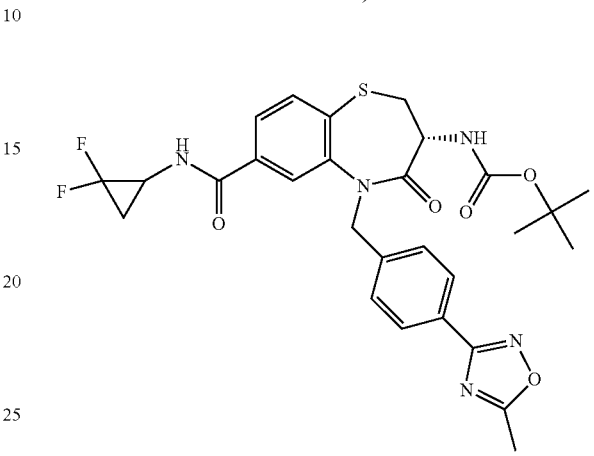

The title compound was synthesized according to general procedure GP3 to afford the title compound as brown solid in 34% yield.
LCMS: METCR1410 Generic 1.7 min, rt=1.21 min, M/Z (ES+) 608 [M+Na+] 100% UV
NMR Data: 1H NMR (500 MHz, Chloroform-d) d 7.92 (dd, J=8.3, 1.6 Hz, 2H), 7.72 (dd, J=6.8, 1.5 Hz, 1H), 7.62 (dd, J=8.0, 2.3 Hz, 1H), 7.51-7.42 (m, 1H), 7.38 (d, J=7.6 Hz, 2H), 6.47-6.34 (m, 1H), 5.66-5.57 (m, 1H), 5.45 (dd, J=15.2, 2.4 Hz, 1H), 4.88 (dd, J=15.2, 6.1 Hz, 1H), 4.42 (dt, J=11.5, 7.5 Hz, 1H), 3.68 (ddd, J=10.3, 6.5, 2.9 Hz, 1H), 3.48 (d, J=5.0 Hz, 1H), 2.94 (t, J=11.3 Hz, 1H), 2.62 (s, 3H), 1.89 (ddd, J=12.9, 6.5, 3.3 Hz, 1H), 1.39 (s, 9H).

Synthesis of tert-butyl N-[(3R)-5-[(4-cyanophenyl)methyl]-7-[(2,2-difluorocyclopropyl)carbamoyl]-8-fluoro-4-oxo-2,3,4,5-tetrahydro-1,5-benzothiazepin-3-yl]carbamate (Intermediate VIII-101)

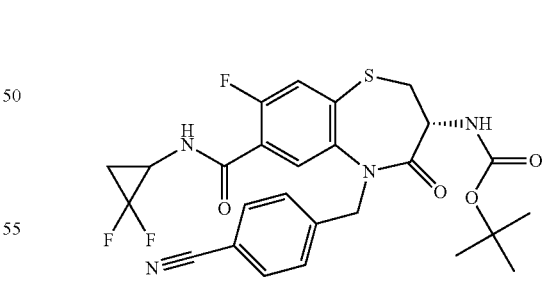

The title compound was synthesized according to general procedure GP3 to afford the title compound as white solid in 57% yield.
LCMS: METCR1410 Generic 1.7 min, rt=1.18 min, M/Z (ES+) 490.95 [M-tBu+H+] 96% UV
NMR Data: 1H NMR (500 MHz, DMSO-d6) d 8.94 (d, J=11.2 Hz, 1H), 7.77-7.68 (m, 3H), 7.61 (d, J=9.2 Hz, 1H), 7.48 (d, J=7.9 Hz, 3H), 5.29 (dd, J=16.1, 7.3 Hz, 1H), 5.03 (d, J=16.2 Hz, 1H), 4.18 (dt, J=12.1, 7.5 Hz, 1H), 3.51 (dd, J=11.2, 6.8 Hz, 2H), 3.14 (t, J=11.7 Hz, 1H), 2.06-1.90 (m, 1H), 1.70-1.55 (m, 1H), 1.35 (s, 9H).

Synthesis of tert-butyl N-[(3R)-5-[(4-cyanophenyl)methyl]-8-fluoro-4-oxo-7-[(4,4,4-trifluorobutyl)carbamoyl]-2,3,4,5-tetrahydro-1,5-benzothiazepin-3-yl]carbamate (Intermediate VIII-102)

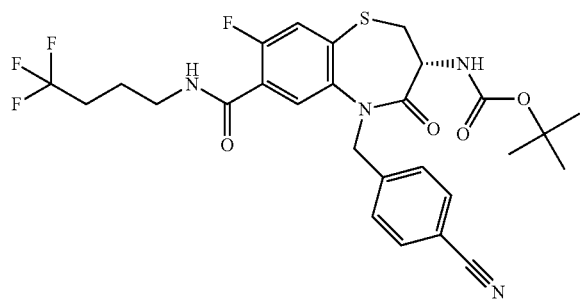 [SMILES: CC(C)(C)OC(=O)N[C@H]1CSc2cc(F)c(C(=O)NCCCC(F)(F)F)cc2N(Cc2ccc(C#N)cc2)C1=O]

The title compound was synthesized according to general procedure GP3 to afford the title compound as off white solid in 76% yield.

LCMS: METCR1410 Generic 1.7 min, rt=1.23 min, M/Z (ES+) 524.95 [M-tBu+H+] 99% UV NMR Data: 1H NMR (500 MHz, DMSO-d6) d 8.59 (t, J=5.5 Hz, 1H), 7.74 (d, J=8.3 Hz, 2H), 7.71 (d, J=6.4 Hz, 1H), 7.59 (d, J=9.3 Hz, 1H), 7.48 (d, J=8.2 Hz, 3H), 5.28 (d, J=16.3 Hz, 1H), 5.04 (d, J=16.3 Hz, 1H), 4.18 (dt, J=12.3, 7.8 Hz, 1H), 3.50 (dd, J=11.3, 6.9 Hz, 1H), 3.38-3.33 (m, 2H), 3.14 (t, J=11.7 Hz, 1H), 2.36-2.24 (m, 2H), 1.73 (dt, J=14.8, 7.0 Hz, 2H), 1.36 (s, 9H).

Synthesis of tert-butyl N-[(3R)-5-[(4-chlorophenyl)methyl]-7-[(4,4-difluorocyclohexyl)carbamoyl]-8-fluoro-4-oxo-2,3,4,5-tetrahydro-1,5-benzothiazepin-3-yl]carbamate (Intermediate VIII-103)

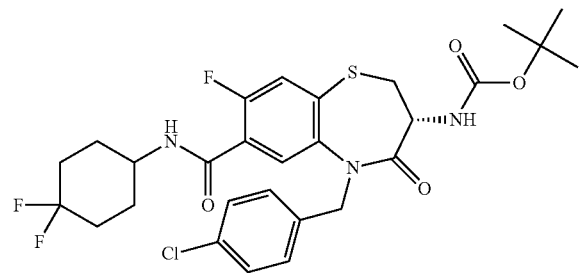 [SMILES: CC(C)(C)OC(=O)N[C@H]1CSc2cc(F)c(C(=O)NC3CCC(F)(F)CC3)cc2N(Cc2ccc(Cl)cc2)C1=O]

The title compound was synthesized according to general procedure GP3 to afford the title compound as off white solid in 70% yield.

LCMS: METCR1410 Generic 1.7 min, rt=1.34 min, M/Z (ES+) 620.10/622.10 [M+Na+] 100% UV NMR Data: 1H NMR (500 MHz, DMSO-d6) d 8.48 (d, J=7.5 Hz, 1H), 7.68 (d, J=6.4 Hz, 1H), 7.56 (d, J=9.2 Hz, 1H), 7.44 (d, J=8.3 Hz, 1H), 7.34-7.25 (m, 4H), 5.24 (d, J=15.7 Hz, 1H), 4.90 (d, J=15.6 Hz, 1H), 4.16 (dt, J=12.2, 8.1 Hz, 1H), 3.96 (s, 1H), 3.48 (dd, J=11.4, 6.9 Hz, 1H), 3.12 (t, J=11.8 Hz, 1H), 2.10-1.83 (m, 6H), 1.61 (s, 2H), 1.36 (s, 9H).

Synthesis of tert-butyl N-[(3R)-5-[(4-chlorophenyl)methyl]-8-fluoro-4-oxo-7-{[2-(trifluoromethyl)cyclopropyl]carbamoyl}-2,3,4,5-tetrahydro-1,5-benzothiazepin-3-yl]carbamate (Intermediate VIII-104)

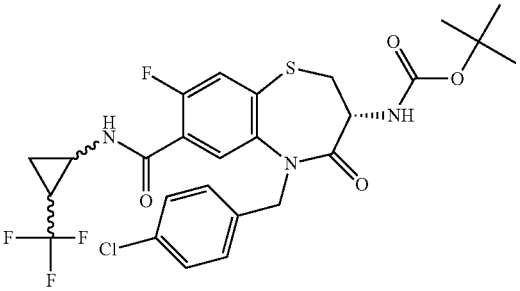 [SMILES: CC(C)(C)OC(=O)N[C@H]1CSc2cc(F)c(C(=O)NC3CC3C(F)(F)F)cc2N(Cc2ccc(Cl)cc2)C1=O]

The title compound was synthesized according to general procedure GP3 to afford the title compound as off white solid in 61% yield.

LCMS: METCR1410 Generic 1.7 min, rt=1.34 min, M/Z (ES+) 610/612 [M+Na+] 86% UV

NMR Data: 1H NMR (500 MHz, DMSO-d6) d 8.82 (t, J=4.1 Hz, 1H), 7.77 (dd, J=6.4, 2.5 Hz, 1H), 7.57 (d, J=9.4 Hz, 1H), 7.45 (d, J=8.3 Hz, 1H), 7.32-7.26 (m, 4H), 5.33-5.27 (m, 1H), 4.85 (d, J=15.6 Hz, 1H), 4.15 (dt, J=12.1, 7.8 Hz, 1H), 3.53-3.45 (m, 1H), 3.24-3.17 (m, 1H), 3.12 (t, J=11.7 Hz, 1H), 2.15-2.01 (m, 1H), 1.36 (s, 9H), 1.31-1.28 (m, 1H), 0.89-0.86 (m, 1H).

Synthesis of tert-butyl N-[(3R)-8-fluoro-5-[(4-fluorophenyl)methyl]-4-oxo-7-[(4,4,4-trifluorobutyl)carbamoyl]-2,3,4,5-tetrahydro-1,5-benzothiazepin-3-yl]carbamate (Intermediate VIII-105)

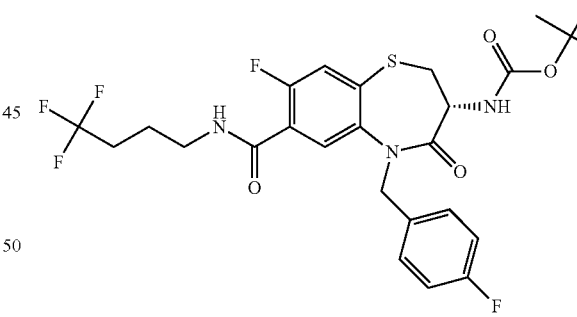

The title compound was synthesized according to general procedure GP3 to afford the title compound as off white solid in 87% yield.

LCMS: METCR1410 Generic 1.7 min, rt=1.29 min, M/Z (ES+) 518.45 [M-tBu+H+] 100% UV NMR Data: 1H NMR (500 MHz, Chloroform-d) d 8.04 (d, J=7.1 Hz, 1H), 7.36 (d, J=10.9 Hz, 1H), 7.23 (dd, J=8.6, 5.4 Hz, 2H), 6.91 (t, J=8.7 Hz, 2H), 6.82-6.70 (m, 1H), 5.58 (d, J=8.0 Hz, 1H), 5.50 (d, J=14.9 Hz, 1H), 4.65 (d, J=15.0 Hz, 1H), 4.38 (ddd, J=19.4, 12.9, 6.8 Hz, 1H), 3.70 (dd, J=10.8, 6.5 Hz, 1H), 3.56 (dp, J=14.0, 6.8 Hz, 2H), 2.93 (t, J=11.2 Hz, 1H), 2.27-2.14 (m, 2H), 1.92 (dt, J=14.6, 7.0 Hz, 2H), 1.40 (s, 9H).

Synthesis of tert-butyl N-[(3R)-7-[(2,2-difluorocyclopropyl)carbamoyl]-8-fluoro-5-[(4-fluorophenyl)methyl]-4-oxo-2,3,4,5-tetrahydro-1,5-benzothiazepin-3-yl]carbamate (Intermediate VIII-106)

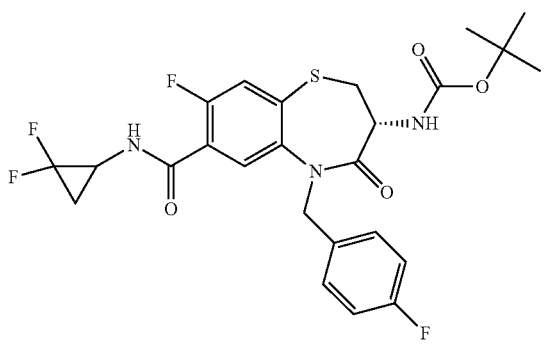 [SMILES: CC(C)(C)OC(=O)N[C@H]1CSc2cc(F)c(C(=O)NC3CC3(F)F)cc2N(Cc2ccc(F)cc2)C1=O]

The title compound was synthesized according to general procedure GP3 to afford the title compound as off white solid in 69% yield.
LCMS: METCR1410 Generic 1.7 min, rt=1.23 min, M/Z (ES+) 484.40 [M-tBu+H+] 98% UV
NMR Data: 1H NMR (500 MHz, Chloroform-d) d 8.05 (dd, J=7.0, 4.5 Hz, 1H), 7.37 (d, J=10.9 Hz, 1H), 7.23 (dd, J=8.0, 5.5 Hz, 2H), 6.91 (td, J=8.7, 2.3 Hz, 3H), 5.57 (d, J=6.4 Hz, 1H), 5.50 (dd, J=15.0, 7.3 Hz, 1H), 4.66 (dd, J=15.0, 5.9 Hz, 1H), 4.45-4.31 (m, 1H), 3.79-3.64 (m, 1H), 3.56 (s, 1H), 2.94 (t, J=11.2 Hz, 1H), 1.92 (ddd, J=13.6, 9.7, 7.0 Hz, 1H), 1.48 (dt, J=14.5, 4.8 Hz, 1H), 1.43-1.33 (m, 9H).

Synthesis of tert-butyl N-[(3R)-7-(butylcarbamoyl)-8-fluoro-5-[(4-fluorophenyl)methyl]-4-oxo-2,3,4,5-tetrahydro-1,5-benzothiazepin-3-yl]carbamate (Intermediate VIII-107)

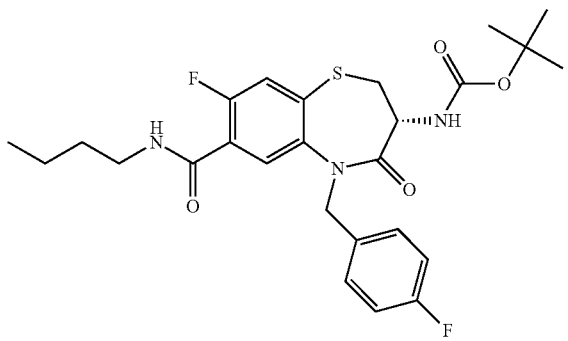 [SMILES: CCCCNC(=O)c1cc2c(cc1F)SC[C@H](NC(=O)OC(C)(C)C)C(=O)N2Cc1ccc(F)cc1]

The title compound was synthesized according to general procedure GP3 to afford the title compound as off white solid in 81% yield.
LCMS: METCR1410 Generic 1.7 min, rt=1.29 min, M/Z (ES+) 464.45 [M-tBu+H+] 100% UV
NMR Data: 1H NMR (500 MHz, Chloroform-d) δ 8.06 (d, J=7.1 Hz, 1H), 7.34 (d, J=10.9 Hz, 1H), 7.25-7.20 (m, 2H), 6.90 (t, J=8.7 Hz, 2H), 6.74-6.60 (m, 1H), 5.58 (d, J=7.8 Hz, 1H), 5.51 (d, J=14.9 Hz, 1H), 4.64 (d, J=15.0 Hz, 1H), 4.38 (dt, J=11.6, 7.1 Hz, 1H), 3.69 (dd, J=10.9, 6.5 Hz, 1H), 3.48 (m, 2H), 2.92 (t, J=11.2 Hz, 1H), 1.65-1.57 (m, 2H), 1.43 (dd, J=15.1, 7.5 Hz, 2H), 1.39 (s, 9H), 0.97 (t, J=7.4 Hz, 3H).

Synthesis of tert-butyl N-[(3R)-7-(benzylcarbamoyl)-8-fluoro-5-[(4-fluorophenyl)methyl]-4-oxo-2,3,4,5-tetrahydro-1,5-benzothiazepin-3-yl]carbamate (Intermediate VIII-108)

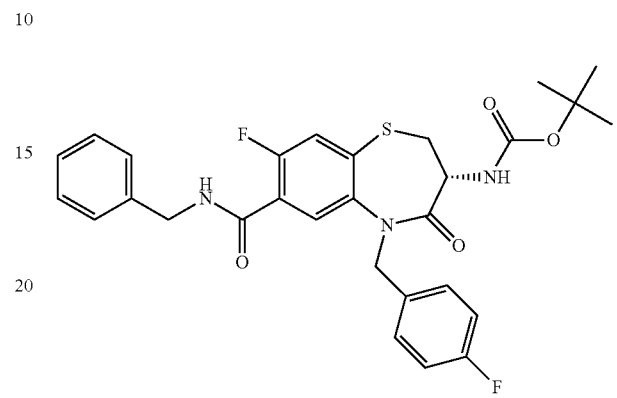

The title compound was synthesized according to general procedure GP3 to afford the title compound as off white solid in 80% yield.
LCMS: METCR1410 Generic 1.7 min, rt=1.35 min, M/Z (ES+) 498.15 [M-tBu+H+] 100% UV
NMR Data: 1H NMR (500 MHz, Chloroform-d) δ 8.10 (d, J=7.1 Hz, 1H), 7.38 (d, J=7.4 Hz, 1H), 7.37-7.33 (m, 4H), 7.33-7.29 (m, 1H), 7.25-7.21 (m, 2H), 7.00 (dt, 1H), 6.94-6.85 (m, 2H), 5.59 (d, J=7.8 Hz, 1H), 5.52 (d, J=15.0 Hz, 1H), 4.74-4.66 (m, 2H), 4.66-4.61 (m, 1H), 4.39 (dt, J=11.6, 7.2 Hz, 1H), 3.70 (dd, J=10.9, 6.5 Hz, 1H), 2.93 (t, J=11.3 Hz, 1H), 1.40 (s, 9H).

Synthesis of tert-butyl N-[(3R)-5-[(4-chlorophenyl)methyl]-8-fluoro-7-{[2-(oxan-4-yl)ethyl]carbamoyl}-4-oxo-2,3,4,5-tetrahydro-1,5-benzothiazepin-3-yl]carbamate (Intermediate VIII-109)

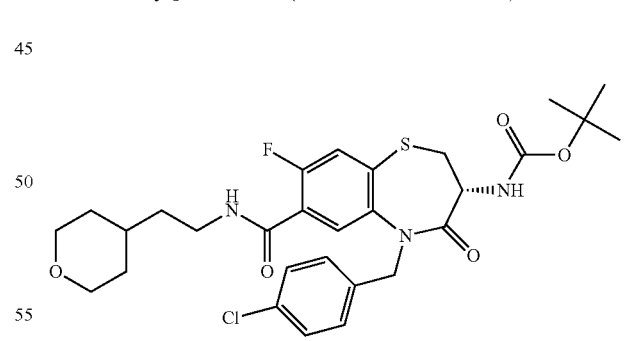

The title compound was synthesized according to general procedure GP3 to afford the title compound as off white fluffy solid in 85% yield.
LCMS: METCR1410 Generic 1.7 min, rt=1.27 min, M/Z (ES+) 614.15/616.20 [M+Na+] 99% UV
NMR Data: 1H NMR (500 MHz, DMSO-d6) d 8.47 (s, 1H), 7.68 (d, J=6.4 Hz, 1H), 7.56 (d, J=9.3 Hz, 1H), 7.45 (d, J=8.3 Hz, 1H), 7.34-7.26 (m, 5H), 5.22 (d, J=15.7 Hz, 1H), 4.92 (d, J=15.7 Hz, 1H), 4.16 (dt, J=12.1, 7.7 Hz, 1H), 3.83 (dd, J=10.3, 4.2 Hz, 3H), 3.48 (dd, J=11.3, 6.9 Hz, 1H), 3.12

(t, J=11.8 Hz, 1H), 1.63-1.51 (m, 4H), 1.45 (q, J=7.1 Hz, 2H), 1.36 (s, 9H), 1.16 (m, 3H).

Synthesis of tert-butyl N-[(3R)-5-benzyl-8-fluoro-4-oxo-7-[(4,4,4-trifluorobutyl)carbamoyl]-2,3,4,5-tetrahydro-1,5-benzothiazepin-3-yl]carbamate (Intermediate VIII-110)

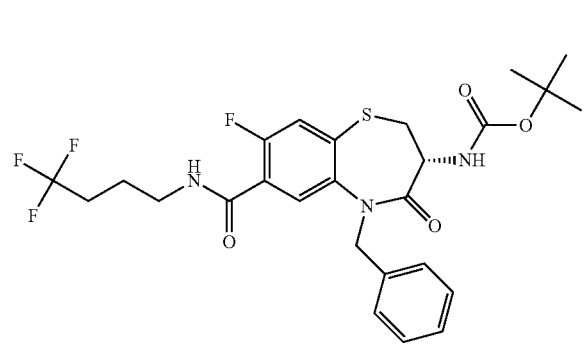 [SMILES: CC(C)(C)OC(=O)N[C@H]1CSc2cc(F)c(C(=O)NCCCC(F)(F)F)cc2N(Cc2ccccc2)C1=O]

The title compound was synthesized according to general procedure GP3 to afford the title compound as white solid in 76% yield.

LCMS: METCR1410 Generic 1.7 min, rt=1.26 min, M/Z (ES+) 500.10 [M-tBu+H+], 578.15[M+Na+] 99% UV; NMR Data: 1H NMR (500 MHz, DMSO-d6) d 8.58 (d, J=5.2 Hz, 1H), 7.71 (d, J=6.4 Hz, 1H), 7.56 (d, J=9.4 Hz, 1H), 7.43 (d, J=8.4 Hz, 1H), 7.30-7.19 (m, 5H), 5.21 (d, J=15.7 Hz, 1H), 4.94 (d, J=15.7 Hz, 1H), 4.18 (dt, J=12.2, 7.5 Hz, 1H), 3.49 (dd, J=11.3, 6.9 Hz, 1H), 3.30 (s, 2H), 3.14 (t, J=11.7 Hz, 1H), 2.33-2.25 (m, 2H), 1.76-1.69 (m, 2H), 1.36 (s, 9H).

Synthesis of tert-butyl N-[(3R)-5-[(4-chlorophenyl)methyl]-8-fluoro-7-{[(4-methoxyphenyl)methyl]carbamoyl}-4-oxo-2,3,4,5-tetrahydro-1,5-benzothiazepin-3-yl]carbamate (Intermediate VIII-111)

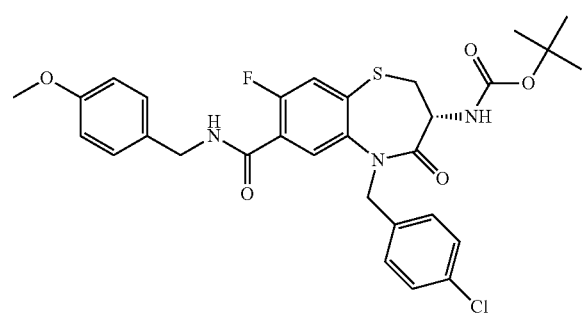 [SMILES: COc1ccc(CNC(=O)c2cc3c(cc2F)SC[C@H](NC(=O)OC(C)(C)C)C(=O)N3Cc2ccc(Cl)cc2)cc1]

The title compound was synthesized according to general procedure GP3 to afford the title compound as white solid in 84% yield.

LCMS: METCR1410 Generic 1.7 min, rt=1.39 min, M/Z (ES+) 544.10/546.15 [M-tBu+H+] 96% UV NMR Data: 1H NMR (250 MHz, Chloroform-d) d 8.15 (d, J=7.1 Hz, 1H), 7.40 (d, J=10.9 Hz, 1H), 7.36-7.32 (m, 6H), 7.05-6.88 (m, 3H), 5.68-5.53 (m, 2H), 4.76-4.63 (m, 3H), 4.53-4.37 (m, 1H), 3.87 (s, 3H), 3.76 (dd, J=10.9, 6.7 Hz, 1H), 2.99 (t, J=11.3 Hz, 1H), 1.46 (s, 9H).

Synthesis of tert-butyl N-[(3R)-5-[(5-cyclopropyl-1,3,4-thiadiazol-2-yl)methyl]-8-fluoro-7-{[(4-fluorophenyl)methyl]carbamoyl}-4-oxo-2,3,4,5-tetrahydro-1,5-benzothiazepin-3-yl]carbamate (Intermediate VIII-112)

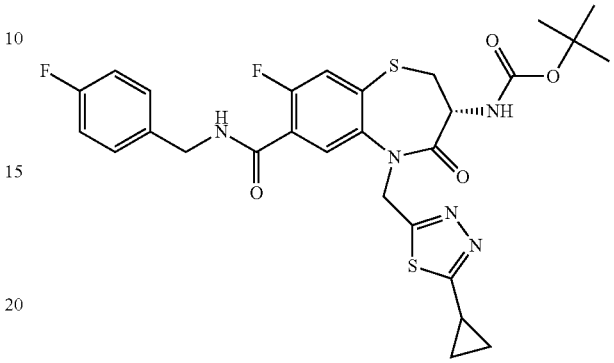

The title compound was synthesized according to general procedure GP3 to afford the title compound as tan solid in 86% yield.

LCMS: METCR1410 Generic 1.7 min, rt=1.19 min, M/Z (ES+) 546.1[M-tBu+H+], 602.5 [M+H+] 99% UV NMR Data: 1H NMR (500 MHz, Chloroform-d) d 8.19 (d, J=6.9 Hz, 1H), 7.37 (d, J=10.6 Hz, 1H), 7.35-7.29 (m, 2H), 7.07-7.01 (m, 2H), 7.02-6.94 (m, 1H), 5.59-5.44 (m, 2H), 5.12 (d, J=15.3 Hz, 1H), 4.67-4.58 (m, 2H), 4.39 (dt, J=11.3, 7.3 Hz, 1H), 3.68 (dd, J=11.0, 6.7 Hz, 1H), 2.86 (t, J=11.3 Hz, 1H), 2.37-2.30 (m, 1H), 1.39 (s, 9H), 1.22-1.17 (m, 2H), 1.11-1.06 (m, 2H).

Synthesis of tert-butyl N-[(3R)-8-fluoro-5-[(4-fluorophenyl)methyl]-7-{[(oxan-4-yl)methyl]carbamoyl}-4-oxo-2,3,4,5-tetrahydro-1,5-benzothiazepin-3-yl]carbamate (Intermediate VIII-113)

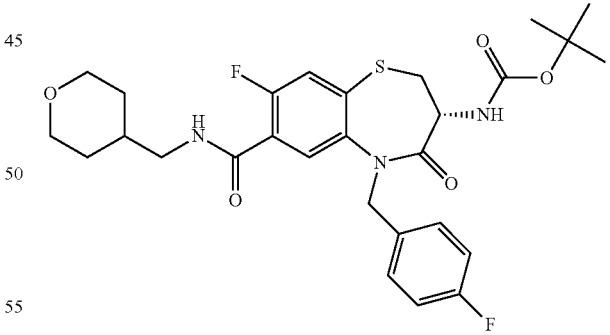

The title compound was synthesized according to general procedure GP3 to afford the title compound as white solid in 76% yield.

LCMS: METCR1410 Generic 1.7 min, rt=1.18 min, M/Z (ES+) 584 [M+Na+] 100% UV

NMR Data: 1H NMR (500 MHz, Chloroform-d) d 8.04 (d, J=7.1 Hz, 1H), 7.35 (d, J=10.9 Hz, 1H), 7.26-7.20 (m, 2H), 6.94-6.87 (m, 2H), 6.81-6.70 (m, 1H), 5.58 (d, J=7.8 Hz, 1H), 5.49 (d, J=15.0 Hz, 1H), 4.65 (d, J=15.0 Hz, 1H), 4.43-4.34 (m, 1H), 4.00 (dd, J=11.3, 3.9 Hz, 2H), 3.69 (dd, J=10.9, 6.5 Hz, 1H), 3.47-3.30 (m, 4H), 2.93 (t, J=11.2 Hz, 1H), 1.89 (ttt, J=10.8, 7.1, 3.8 Hz, 1H), 1.71-1.63 (m, 2H), 1.43-1.33 (m, 11H).

Synthesis of tert-butyl N-[(3R)-7-[(3,3-difluorocyclobutyl)carbamoyl]-8-fluoro-5-[(4-fluorophenyl)methyl]-4-oxo-2,3,4,5-tetrahydro-1,5-benzothiazepin-3-yl]carbamate (Intermediate VIII-114)

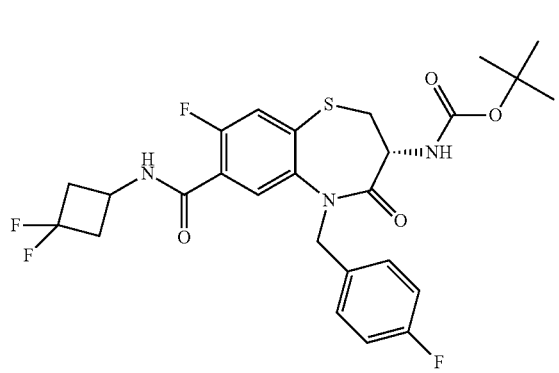 [SMILES: CC(C)(C)OC(=O)N[C@H]1CSc2cc(F)c(C(=O)NC3CC(F)(F)C3)cc2N(Cc2ccc(F)cc2)C1=O]

The title compound was synthesized according to general procedure GP3 to afford the title compound as white solid in 86% yield.

LCMS: METCR1410 Generic 1.7 min, rt=1.24 min, M/Z (ES+) 576 [M+Na+] 100% UV

NMR Data: 1H NMR (500 MHz, Chloroform-d) d 8.02 (d, J=7.1 Hz, 1H), 7.36 (d, J=10.9 Hz, 1H), 7.25-7.18 (m, 2H), 6.94-6.83 (m, 3H), 5.59 (d, J=7.9 Hz, 1H), 5.50 (d, J=15.0 Hz, 1H), 4.64 (d, J=15.0 Hz, 1H), 4.50-4.41 (m, 1H), 4.41-4.32 (m, 1H), 3.69 (dd, J=10.9, 6.4 Hz, 1H), 3.18-3.03 (m, 2H), 2.93 (t, J=11.3 Hz, 1H), 2.66-2.53 (m, 2H), 1.39 (s, 9H).

Synthesis of tert-butyl N-[(3R)-8-fluoro-5-[(4-methoxyphenyl)methyl]-4-oxo-7-[(4,4,4-trifluorobutyl)carbamoyl]-2,3,4,5-tetrahydro-1,5-benzothiazepin-3-yl]carbamate (Intermediate VIII-115)

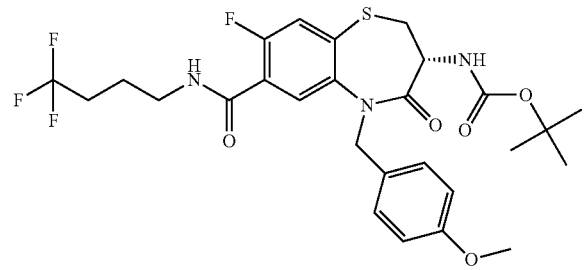 [SMILES: COc1ccc(CN2C(=O)[C@@H](NC(=O)OC(C)(C)C)CSc3cc(F)c(C(=O)NCCCC(F)(F)F)cc32)cc1]

The title compound was synthesized according to general procedure GP3 to afford the title compound as white Solid in 77% yield.

LCMS: METCR1410 Generic 1.7 min, rt=1.26 min, M/Z (ES+) 608.1 [M+Na+], 530.1 [M-tBu+H+] 99% UV; NMR Data: 1H NMR (500 MHz, DMSO-d6) d 8.58 (t, J=5.5 Hz, 1H), 7.74 (d, J=6.5 Hz, 1H), 7.54 (d, J=9.3 Hz, 1H), 7.41 (d, J=8.4 Hz, 1H), 7.16 (d, J=8.6 Hz, 2H), 6.78 (d, J=8.6 Hz, 2H), 5.23 (d, J=15.3 Hz, 1H), 4.79 (d, J=15.3 Hz, 1H), 4.15 (dt, J=12.1, 8.1 Hz, 1H), 3.69 (s, 3H), 3.47 (dd, J=11.3, 6.9 Hz, 1H), 3.12 (t, J=11.7 Hz, 1H), 2.39-2.24 (m, 2H), 1.74 (p, J=7.0 Hz, 2H), 1.36 (s, 9H), 1.32-1.23 (m, 2H).

Synthesis of tert-butyl N-[(3R)-8-fluoro-5-[(4-methoxyphenyl)methyl]-7-{[(oxan-4-yl)methyl]carbamoyl}-4-oxo-2,3,4,5-tetrahydro-1,5-benzothiazepin-3-yl]carbamate (Intermediate VIII-116)

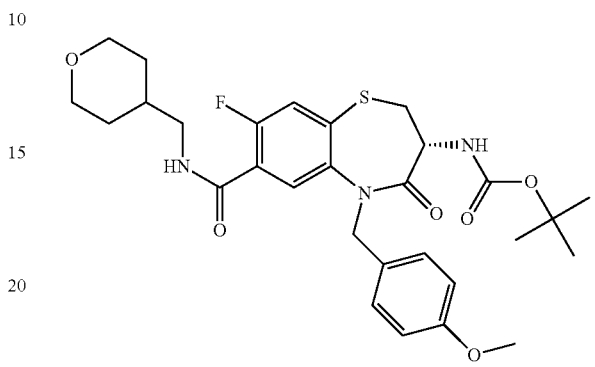

The title compound was synthesized according to general procedure GP3 to afford the title compound as white solid in 80% yield.

LCMS: METCR1410 Generic 1.7 min, rt=1.16 min, M/Z (ES+) 596.2 [M+Na+], 518.1 [M-tBu+H+] 96% UV; NMR Data: 1H NMR (500 MHz, DMSO-d6) d 8.50 (t, J=5.7 Hz, 1H), 7.66 (d, J=6.4 Hz, 1H), 7.52 (d, J=9.2 Hz, 1H), 7.40 (d, J=8.4 Hz, 1H), 7.16 (d, J=8.5 Hz, 2H), 6.78 (d, J=8.6 Hz, 2H), 5.15 (d, J=15.3 Hz, 1H), 4.83 (d, J=15.3 Hz, 1H), 4.14 (dt, J=12.1, 7.6 Hz, 1H), 3.88-3.80 (m, 2H), 3.69 (s, 3H), 3.46 (dd, J=11.3, 6.9 Hz, 1H), 3.26 (t, J=10.8 Hz, 2H), 3.16-3.07 (m, 3H), 1.80-1.68 (m, 1H), 1.57 (d, J=12.8 Hz, 2H), 1.35 (s, 9H), 1.23-1.12 (m, 2H).

Synthesis of tert-butyl N-[(3R)-7-[(2,2-difluorocyclopropyl)carbamoyl]-8-fluoro-5-[(4-methoxyphenyl)methyl]-4-oxo-2,3,4,5-tetrahydro-1,5-benzothiazepin-3-yl]carbamate (Intermediate VIII-117)

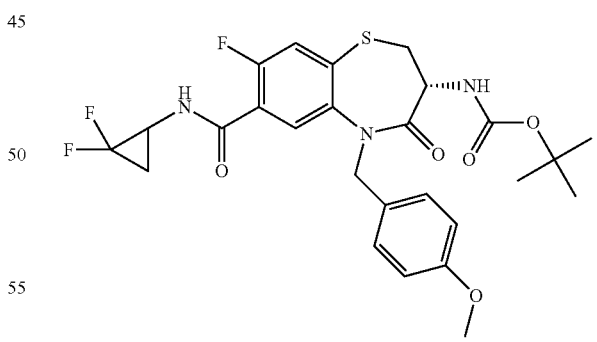

The title compound was synthesized according to general procedure GP3 to afford the title compound as yellow solid in 71% yield.

LCMS: METCR1410 Generic 1.7 min, rt=1.2 min, M/Z (ES+) 574.1 [M+Na+], 496.05 [M-tBu+H+] 93% UV; NMR Data: 1H NMR (500 MHz, DMSO-d6) d 8.93 (d, J=8.8 Hz, 1H), 7.74 (dd, J=9.7, 6.5 Hz, 1H), 7.56 (dd, J=9.3, 2.0 Hz, 1H), 7.41 (d, J=8.4 Hz, 1H), 7.16 (d, J=7.5 Hz, 2H), 6.78 (d, J=7.6 Hz, 2H), 5.23 (dd, J=15.2, 8.7 Hz, 1H), 4.79 (d, J=15.3

Hz, 1H), 4.14 (dt, J=12.1, 7.7 Hz, 1H), 3.69 (s, 3H), 3.47 (dd, J=11.1, 6.9 Hz, 2H), 2.01-1.93 (m, 1H), 1.68-1.55 (m, 1H), 1.36 (s, 9H), 1.18 (t, J=7.1 Hz, 1H).

Synthesis of tert-butyl N-[(3R)-5-[(4-chlorophenyl)methyl]-8-fluoro-7-[(oxan-4-yl)carbamoyl]-4-oxo-2,3,4,5-tetrahydro-1,5-benzothiazepin-3-yl]carbamate (Intermediate VIII-118)

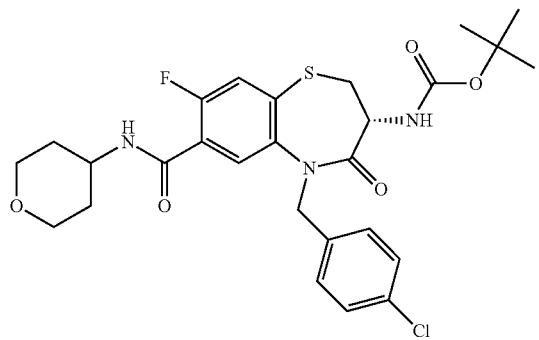 [SMILES: CC(C)(C)OC(=O)N[C@H]1CSc2cc(F)c(C(=O)NC3CCOCC3)cc2N(Cc2ccc(Cl)cc2)C1=O]

The title compound was synthesized according to general procedure GP3 to afford the title compound as white crystalline solid in 60% yield.

LCMS: METCR1410 Generic 1.7 min, rt=1.26 min, M/Z (ES+) 586.15/588.20 [M+Na+] 100% UV NMR Data: 1H NMR (250 MHz, Chloroform-d) d 8.03 (d, J=7.0 Hz, 1H), 7.36 (d, J=10.9 Hz, 1H), 7.20 (s, 4H), 6.58 (s, 1H), 5.49 (d, J=15.0 Hz, 2H), 4.66 (d, J=15.1 Hz, 1H), 4.29 (m, 2H), 4.00 (d, J=11.8 Hz, 2H), 3.70 (dd, J=10.9, 6.5 Hz, 1H), 3.54 (t, J=11.6 Hz, 2H), 2.93 (t, J=11.2 Hz, 1H), 2.02 (d, J=12.0 Hz, 3H), 1.39 (s, 10H).

Synthesis of tert-butyl N-[(3R)-5-[(4-chlorophenyl)methyl]-7-[(3,3-difluorocyclobutyl)carbamoyl]-4-oxo-2,3,4,5-tetrahydro-1,5-benzothiazepin-3-yl]carbamate (Intermediate VIII-119)

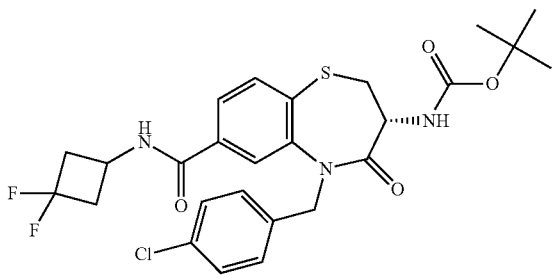 [SMILES: CC(C)(C)OC(=O)N[C@H]1CSc2ccc(C(=O)NC3CC(F)(F)C3)cc2N(Cc2ccc(Cl)cc2)C1=O]

The title compound was synthesized according to general procedure GP3 to afford the title compound as off white solid in 87% yield.

LCMS: METCR1410 Generic 1.7 min, rt=1.28 min, M/Z (ES+) 496.10/498.20 [M-tBu+H+], 574.15/576.20 [M+Na+] 97% UV; NMR Data: 1H NMR (500 MHz, Chloroform-d) d 7.69 (s, 1H), 7.66 (d, J=8.0 Hz, 1H), 7.50 (dd, J=8.0, 1.7 Hz, 1H), 7.23 (s, 4H), 6.39 (d, J=6.4 Hz, 1H), 5.62 (d, J=8.1 Hz, 1H), 5.45-4.76 (m, 2H), 4.42 (dt, J=14.8, 7.3 Hz, 2H), 3.70 (dd, J=11.0, 6.6 Hz, 1H), 3.21-3.03 (m, 2H), 2.94 (t, J=11.3 Hz, 1H), 2.60 (m, 2H), 1.42 (s, 9H).

Synthesis of tert-butyl N-[(3R)-5-[(4-chlorophenyl)methyl]-7-{[(1S)-3,3-difluorocyclopentyl]carbamoyl}-8-fluoro-4-oxo-2,3,4,5-tetrahydro-1,5-benzothiazepin-3-yl]carbamate (Intermediate VIII-120)

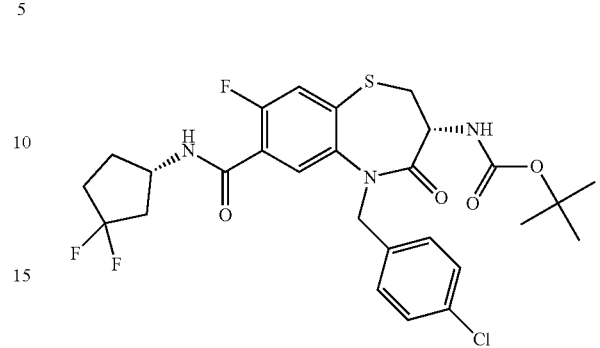

The title compound was synthesized according to general procedure GP3 to afford the title compound as white crystalline solid in 67% yield.

LCMS: METCR1410 Generic 1.7 min, rt=1.32 min, M/Z (ES+) 606.15/608.15 [M+Na+] 99% UV NMR Data: 1H NMR (500 MHz, Chloroform-d) d 8.02 (d, J=7.1 Hz, 1H), 7.36 (d, J=10.9 Hz, 1H), 7.20 (s, 4H), 6.80 (dd, J=13.1, 7.3 Hz, 1H), 5.56 (d, J=7.8 Hz, 1H), 5.50 (d, J=15.1 Hz, 1H), 4.69-4.60 (m, 2H), 4.38 (dt, J=11.6, 7.2 Hz, 1H), 3.69 (dd, J=10.9, 6.5 Hz, 1H), 2.94 (t, J=11.3 Hz, 1H), 2.61 (m, 1H), 2.41-2.24 (m, 2H), 2.23-2.05 (m, 2H), 1.88-1.78 (m, 1H), 1.39 (s, 9H).

Synthesis of tert-butyl N-[(3R)-5-[(4-chlorophenyl)methyl]-7-{[(1R,2S)-2-fluorocyclopropyl]carbamoyl}-4-oxo-2,3,4,5-tetrahydro-1,5-benzothiazepin-3-yl]carbamate (Intermediate VIII-121)

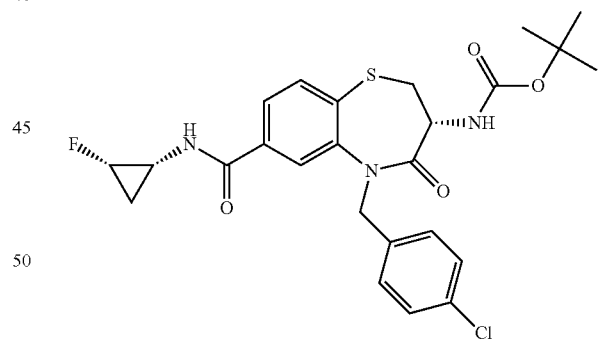

The title compound was synthesized according to general procedure GP3 to afford the title compound as white solid in 63% yield.

LCMS: METCR1410 Generic 1.7 min, rt=1.2 min, M/Z (ES+) 542.1/544.1 [M+Na+] 100% UV NMR Data: 1H NMR (500 MHz, Chloroform-d) δ 7.74 (d, J=1.6 Hz, 1H), 7.65 (d, J=8.0 Hz, 1H), 7.50 (dd, J=8.0, 1.7 Hz, 1H), 7.23 (s, 4H), 6.26 (d, J=3.5 Hz, 1H), 5.58 (d, J=7.9 Hz, 1H), 5.36 (d, J=15.1 Hz, 1H), 4.90-4.80 (m, 1H), 4.77-4.68 (m, 1H), 4.42 (dt, J=11.7, 7.3 Hz, 1H), 3.74-3.69 (m, 1H), 3.16-3.02 (m, 1H), 1.42 (s, 9H), 1.36-1.20 (m, 2H), 1.14-0.98 (m, 1H).

Synthesis of tert-butyl N-[(3R)-7-[(3,3-difluorocyclobutyl)carbamoyl]-5-[(2-fluorophenyl)methyl]-4-oxo-2,3,4,5-tetrahydro-1,5-benzothiazepin-3-yl]carbamate (Intermediate VIII-122)

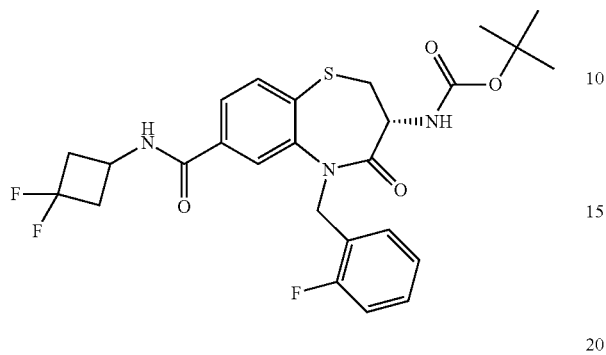

The title compound was synthesized according to general procedure GP3 to afford the title compound as in 79% yield.

LCMS: METCR1410 Generic 1.7 min, rt=1.22 min, M/Z (ES+) 558 [M+Na+] 97% UV

NMR Data: 1H NMR (500 MHz, Chloroform-d) d 7.66 (d, J=9.2 Hz, 2H), 7.55 (dd, J=8.0, 1.6 Hz, 1H), 7.50 (t, J=7.6 Hz, 1H), 7.24 (q, J=5.9 Hz, 1H), 7.09 (t, J=7.3 Hz, 1H), 7.02-6.90 (m, 1H), 6.30 (d, J=6.6 Hz, 1H), 5.59 (d, J=8.1 Hz, 1H), 5.33 (d, J=15.2 Hz, 1H), 5.05 (d, J=15.2 Hz, 1H), 4.43 (dd, J=19.5, 7.6 Hz, 2H), 3.71 (dd, J=10.9, 6.6 Hz, 1H), 3.28-3.00 (m, 2H), 2.94 (m, 1H), 2.77-2.50 (m, 2H), 1.42 (s, 9H).

Synthesis of tert-butyl N-[(3R)-7-[(3,3-difluorocyclobutyl)carbamoyl]-5-[(3-methoxyphenyl)methyl]-4-oxo-2,3,4,5-tetrahydro-1,5-benzothiazepin-3-yl]carbamate (Intermediate VIII-123)

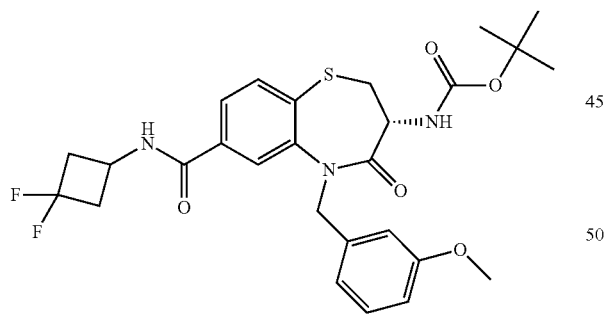

The title compound was synthesized according to general procedure GP3 to afford the title compound as White solid in 73% yield.

LCMS: METCR1410 Generic 1.7 min, rt=1.21 min, M/Z (ES+) 570.15 [M+Na+] 96% UV

NMR Data: 1H NMR (500 MHz, Chloroform-d) d 7.65 (d, J=7.9 Hz, 1H), 7.55 (d, J=1.7 Hz, 1H), 7.50 (dd, J=8.0, 1.7 Hz, 1H), 7.17 (t, J=7.9 Hz, 1H), 6.89-6.82 (m, 2H), 6.78 (dd, J=8.2, 2.3 Hz, 1H), 6.17 (d, J=6.5 Hz, 1H), 5.59 (d, J=7.9 Hz, 1H), 5.16-4.98 (m, 2H), 4.50-4.31 (m, 2H), 3.75 (s, 3H), 3.74-3.65 (m, 1H), 3.08 (m, 2H), 2.67-2.42 (m, 2H), 1.40 (s, 9H), 1.31-1.27 (m, 1H).

Synthesis of tert-butyl N-[(3R)-5-[(4-methoxyphenyl)methyl]-4-oxo-7-[(4,4,4-trifluorobutyl)carbamoyl]-2,3,4,5-tetrahydro-1,5-benzothiazepin-3-yl]carbamate (Intermediate VIII-124)

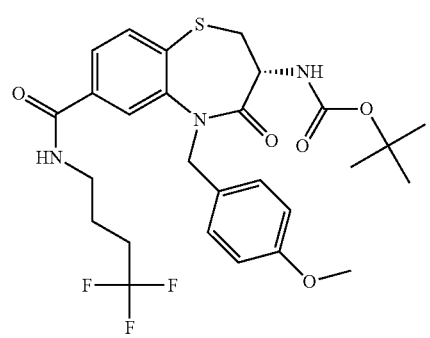 [SMILES: COc1ccc(CN2C(=O)[C@@H](NC(=O)OC(C)(C)C)CSc3ccc(C(=O)NCCCC(F)(F)F)cc32)cc1]

The title compound was synthesized according to general procedure GP3 to afford the title compound as yellow solid in 71% yield.

LCMS: METCR1410 Generic 1.7 min, rt=1.28 min, M/Z (ES+) 512.1 [M-tBu+H+], 590.1 [M+Na]+93% UV; NMR Data: 1H NMR (250 MHz, Chloroform-d) d 7.67-7.56 (m, 2H), 7.48 (dd, J=8.1, 1.5 Hz, 1H), 7.17 (d, J=8.6 Hz, 2H), 6.75 (d, J=8.5 Hz, 2H), 6.24 (t, J=5.6 Hz, 1H), 5.63 (d, J=8.2 Hz, 1H), 5.22 (d, J=14.8 Hz, 1H), 4.84 (d, J=14.8 Hz, 1H), 4.47-4.28 (m, 1H), 3.74 (s, 3H), 3.67 (dd, J=11.0, 6.6 Hz, 1H), 3.49 (q, J=6.8 Hz, 2H), 2.90 (t, J=11.2 Hz, 1H), 2.30-2.09 (m, 2H), 1.88 (dt, J=14.5, 7.2 Hz, 2H), 1.39 (s, 9H).

Synthesis of tert-butyl N-[(3R)-5-[(4-methoxyphenyl)methyl]-7-{[(4-methoxyphenyl)methyl]carbamoyl}-4-oxo-2,3,4,5-tetrahydro-1,5-benzothiazepin-3-yl]carbamate (Intermediate VIII-125)

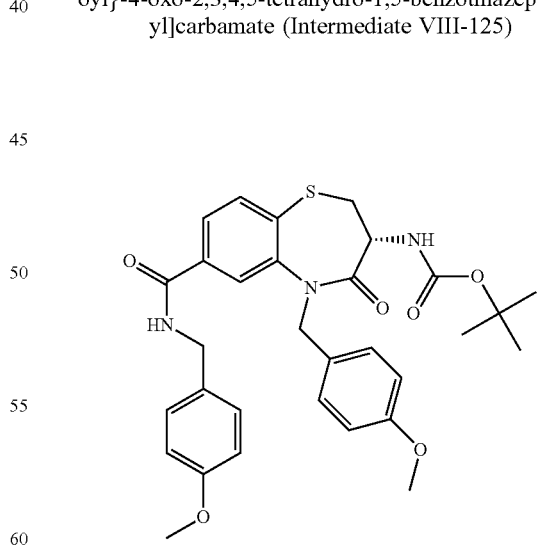

The title compound was synthesized according to general procedure GP3 to afford the title compound as off white solid in 91% yield.

LCMS: METCR1410 Generic 1.7 min, rt=1.23 min, M/Z (ES+) 600.25 [M+Na]+98% UV

Synthesis of tert-butyl N-[(3R)-5-benzyl-7-{[(4-methoxyphenyl)methyl]carbamoyl}-4-oxo-2,3,4,5-tetrahydro-1,5-benzothiazepin-3-yl]carbamate (Intermediate VIII-126)

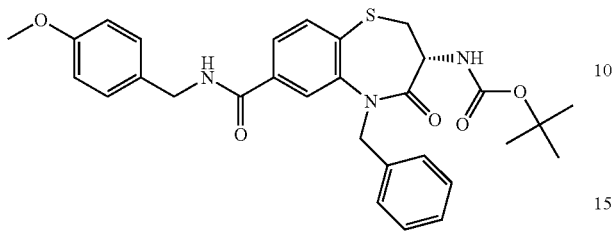

The title compound was synthesized according to general procedure GP3 to afford the title compound as white solid in 97% yield.

LCMS: METCR1410 Generic 1.7 min, rt=1.24 min, M/Z (ES+) 492.1 [M-tBu+H+] 98% UV;

NMR Data: 1H NMR (250 MHz, Chloroform-d) d 7.65-7.56 (m, 2H), 7.49 (dd, J=8.0, 1.7 Hz, 1H), 7.31-7.14 (m, 7H), 6.90 (d, J=8.6 Hz, 2H), 6.20-6.08 (m, 1H), 5.58 (d, J=8.0 Hz, 1H), 5.26-5.12 (m, 1H), 5.05-4.89 (m, 1H), 4.52 (d, J=5.8 Hz, 2H), 4.49-4.32 (m, 1H), 3.82 (s, 3H), 3.69 (dd, J=10.9, 6.6 Hz, 1H), 2.91 (t, J=11.2 Hz, 1H), 1.39 (s, 9H).

Synthesis of tert-butyl N-[(3R)-5-[(4-chlorophenyl)methyl]-7-{[(4-methoxyphenyl)methyl]carbamoyl}-4-oxo-2,3,4,5-tetrahydro-1,5-benzothiazepin-3-yl]carbamate (Intermediate VIII-127)

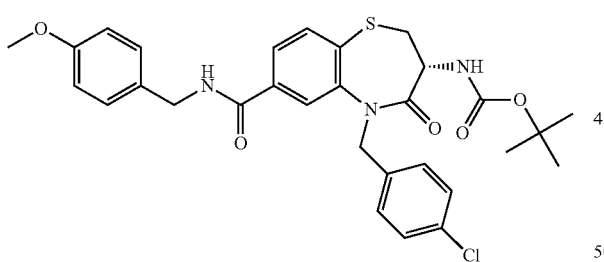

The title compound was synthesized according to general procedure GP3 to afford the title compound as pale yellow solid in 77% yield.

LCMS: METCR1410 Generic 1.7 min, rt=1.3 min, M/Z (ES+) 526.20 [M-tBu+H+], 604.30 [M+Na+] 89% UV;
NMR Data: 1H NMR (500 MHz, DMSO-d6) d 9.11 (t, J=5.7 Hz, 1H), 7.97 (d, J=1.4 Hz, 1H), 7.73 (dd, J=8.0, 1.6 Hz, 1H), 7.67 (d, J=8.0 Hz, 1H), 7.44 (d, J=8.3 Hz, 1H), 7.28 (s, 4H), 7.24 (d, J=8.6 Hz, 2H), 6.89 (d, J=8.6 Hz, 2H), 5.29 (d, J=15.6 Hz, 1H), 4.91 (d, J=15.6 Hz, 1H), 4.41 (ddt, J=20.6, 14.8, 6.6 Hz, 2H), 4.13 (dt, J=12.1, 8.0 Hz, 1H), 3.73 (s, 3H), 3.46 (dd, J=11.3, 6.9 Hz, 1H), 3.11 (t, J=11.8 Hz, 1H), 1.34 (s, 9H).

Synthesis of tert-butyl N-[(3R)-7-[(4,4-difluorocyclohexyl)carbamoyl]-5-[(4-methoxyphenyl)methyl]-4-oxo-2,3,4,5-tetrahydro-1,5-benzothiazepin-3-yl] carbamate (Intermediate VIII-128)

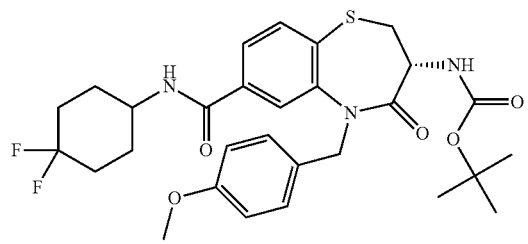 [SMILES: COc1ccc(CN2C(=O)[C@@H](NC(=O)OC(C)(C)C)CSc3ccc(C(=O)NC4CCC(F)(F)CC4)cc32)cc1]

The title compound was synthesized according to general procedure GP3 to afford the title compound as yellow solid in 79% yield.

LCMS: METCR1410 Generic 1.7 min, rt=1.24 min, M/Z (ES+) 520.15 [M-tBu+H+], 598.20 [M+Na+]97% UV;
NMR Data: 1H NMR (500 MHz, DMSO-d6) d 8.43 (d, J=7.7 Hz, 1H), 7.96 (d, J=1.4 Hz, 1H), 7.73-7.63 (m, 2H), 7.41 (d, J=8.5 Hz, 1H), 7.16 (d, J=8.6 Hz, 2H), 6.77 (d, J=8.7 Hz, 2H), 5.30 (d, J=15.2 Hz, 1H), 4.81 (d, J=15.2 Hz, 1H), 4.12 (dt, J=12.2, 8.2 Hz, 1H), 4.04-3.93 (m, 1H), 3.68 (s, 3H), 3.44 (dd, J=11.3, 6.8 Hz, 1H), 3.11 (t, J=11.8 Hz, 1H), 2.08 (d, J=14.2 Hz, 3H), 1.90 (d, J=12.7 Hz, 3H), 1.66 (t, J=11.3 Hz, 2H), 1.35 (s, 9H).

Synthesis of tert-butyl N-[(3R)-5-[(4-chlorophenyl)methyl]-4-oxo-7-[(3,3,3-trifluoropropyl)carbamoyl]-2,3,4,5-tetrahydro-1,5-benzothiazepin-3-yl]carbamate (Intermediate VIII-129)

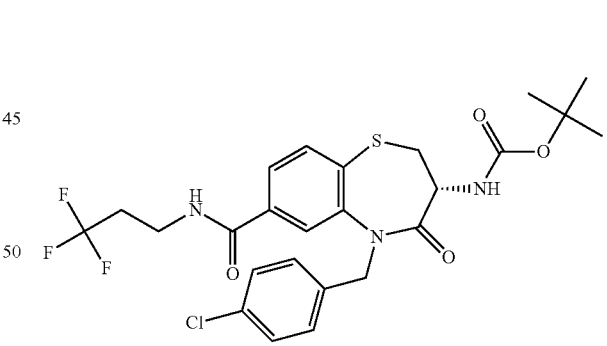

The title compound was synthesized according to general procedure GP3 to afford the title compound as yellow solid in 91% yield.

LCMS: METCR1410 Generic 1.7 min, rt=1.27 min, M/Z (ES+) 580.10/582.15 [M+Na+] 96% UV NMR Data: 1H NMR (500 MHz, DMSO-d6) d 8.85 (t, J=5.6 Hz, 1H), 7.92 (s, 1H), 7.73-7.66 (m, 2H), 7.46 (d, J=8.3 Hz, 1H), 7.32-7.26 (m, 4H), 5.30 (d, J=15.7 Hz, 1H), 4.91 (d, J=15.7 Hz, 1H), 4.13 (dt, J=12.2, 7.5 Hz, 1H), 3.48 (ddd, J=15.3, 11.5, 6.3 Hz, 3H), 3.12 (t, J=11.8 Hz, 1H), 2.57 (dd, J=11.4, 6.8 Hz, 2H), 1.35 (s, 9H).

Synthesis of tert-butyl N-[(3R)-5-[(4-chlorophenyl)methyl]-4-oxo-7-{[(3R)-oxolan-3-yl]carbamoyl}-2,3,4,5-tetrahydro-1,5-benzothiazepin-3-yl]carbamate (Intermediate VIII-130)

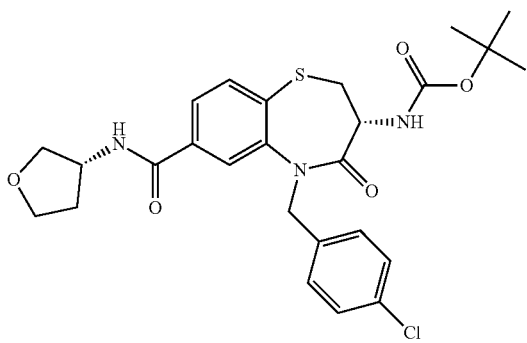 [SMILES: CC(C)(C)OC(=O)N[C@H]1CSc2ccc(C(=O)N[C@@H]3CCOC3)cc2N(Cc2ccc(Cl)cc2)C1=O]

The title compound was synthesized according to general procedure GP3 to afford the title compound as off white solid in 99% yield.

LCMS: METCR1410 Generic 1.7 min, rt=1.17 min, M/Z (ES+) 476.05/478.10 [M-tBu+H+], 554.10/556.15 [M+Na+] 94% UV; NMR Data: 1H NMR (250 MHz, Chloroform-d) d 7.68 (d, J=1.7 Hz, 1H), 7.63 (d, J=8.0 Hz, 1H), 7.48 (dd, J=8.0, 1.9 Hz, 1H), 7.21 (s, 4H), 6.24 (d, J=7.5 Hz, 1H), 5.56 (d, J=7.9 Hz, 1H), 5.34 (d, J=15.1 Hz, 1H), 4.81 (d, J=15.0 Hz, 1H), 4.76-4.61 (m, 1H), 4.48-4.30 (m, 1H), 4.06-3.94 (m, 1H), 3.94-3.74 (m, 3H), 3.68 (dd, J=11.0, 6.6 Hz, 1H), 2.91 (t, J=11.3 Hz, 1H), 2.46-2.27 (m, 1H), 1.98-1.80 (m, 1H), 1.39 (s, 9H).

Synthesis of tert-butyl N-[(3R)-5-[(4-chlorophenyl)methyl]-4-oxo-7-{[(oxolan-3-yl)methyl]carbamoyl}-2,3,4,5-tetrahydro-1,5-benzothiazepin-3-yl]carbamate (Intermediate VIII-131)

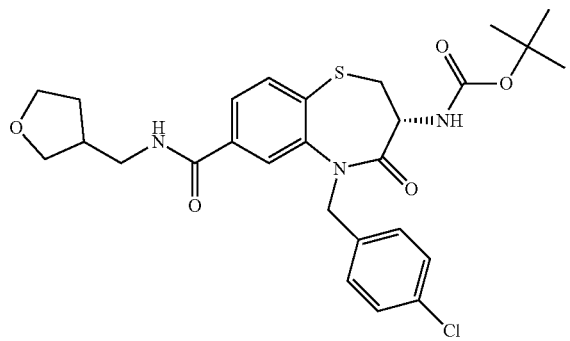 [SMILES: CC(C)(C)OC(=O)N[C@H]1CSc2ccc(C(=O)NCC3CCOC3)cc2N(Cc2ccc(Cl)cc2)C1=O]

The title compound was synthesized according to general procedure GP3 to afford the title compound as in 64% yield.

LCMS: METCR1410 Generic 1.7 min, rt=1.18 min, M/Z (ES+) 568.15/570.15 [M+Na+] 100% UV NMR Data: 1H NMR (250 MHz, Chloroform-d) d 7.68-7.49 (m, 2H), 7.39 (d, J=8.0 Hz, 1H), 7.14 (s, 4H), 6.21 (s, 1H), 5.49 (d, J=8.1 Hz, 1H), 5.26 (d, J=15.0 Hz, 1H), 4.76 (d, J=15.1 Hz, 1H), 4.32 (s, 1H), 3.95-3.50 (m, 5H), 3.41 (q, J=6.2 Hz, 2H), 2.85 (t, J=11.3 Hz, 1H), 2.53 (s, 1H), 2.05 (m, 1H), 1.61 (td, J=12.6, 7.5 Hz, 1H), 1.33 (s, 9H).

Synthesis of tert-butyl N-[(3R)-5-[(4-chlorophenyl)methyl]-7-{[(1R)-2,2-difluorocyclopropyl]carbamoyl}-4-oxo-2,3,4,5-tetrahydro-1,5-benzothiazepin-3-yl]carbamate (Intermediate VIII-132)

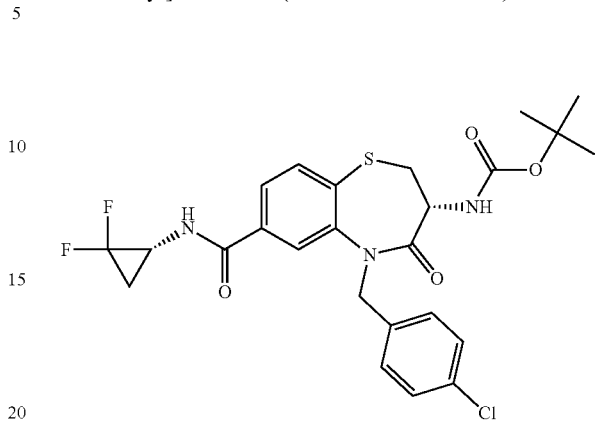

The title compound was synthesized according to general procedure GP3 to afford the title compound as yellow solid in 72% yield.

LCMS: METCR1410 Generic 1.7 min, rt=1.24 min, M/Z (ES+), 482.10/484.05 [M-tBu+H+], 560.05/562.10 [M+Na+] 86% UV; NMR Data: 1H NMR (500 MHz, Chloroform-d) d 7.71 (d, J=1.7 Hz, 1H), 7.65 (d, J=7.9 Hz, 1H), 7.48 (dd, J=8.0, 1.9 Hz, 1H), 7.21 (s, 4H), 6.26 (s, 1H), 5.56 (d, J=8.1 Hz, 1H), 5.36 (d, J=15.1 Hz, 1H), 4.82 (d, J=15.1 Hz, 1H), 4.41 (dt, J=11.2, 7.6 Hz, 1H), 3.70 (dd, J=10.9, 6.6 Hz, 1H), 3.58-3.49 (m, 1H), 2.93 (t, J=11.3 Hz, 1H), 1.98-1.87 (m, 1H), 1.50-1.43 (m, 1H), 1.40 (s, 9H).

Synthesis of tert-butyl N-[(3R)-5-[(4-cyclopropylphenyl)methyl]-7-{[(1R)-2,2-difluorocyclopropyl]carbamoyl}-4-oxo-2,3,4,5-tetrahydro-1,5-benzothiazepin-3-yl]carbamate (Intermediate VIII-133)

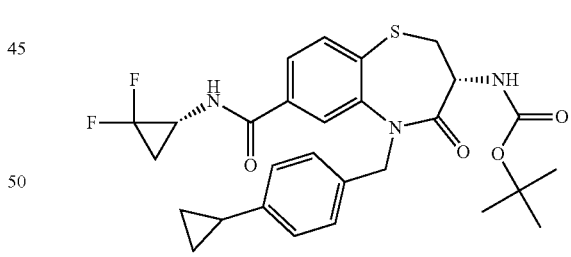

The title compound was synthesized according to general procedure GP3 to afford the title compound as off-white solid in 42% yield.

LCMS: METCR1410 Generic 1.7 min, rt=1.26 min, M/Z (ES+) 566.2 [M+Na+], 488.1 [M-tBu+H+] 80% UV; NMR Data: 1H NMR (500 MHz, Chloroform-d) d 7.64 (d, J=7.9 Hz, 1H), 7.55-7.49 (m, 2H), 7.14 (d, J=8.1 Hz, 2H), 6.95 (d, J=8.1 Hz, 2H), 6.16-6.09 (m, 1H), 5.58 (d, J=8.1 Hz, 1H), 5.09 (d, J=15.0 Hz, 1H), 5.00 (d, J=14.9 Hz, 1H), 4.43-4.36 (m, 1H), 3.69 (dd, J=10.9, 6.5 Hz, 1H), 3.56-3.44 (m, 1H), 1.96-1.77 (m, 2H), 1.39 (s, 9H), 0.96-0.82 (m, 4H), 0.67-0.60 (m, 2H).

Synthesis of tert-butyl N-[(3R)-7-{[(1R)-2,2-difluorocyclopropyl]carbamoyl}-5-{[4-(difluoromethoxy)phenyl]methyl}-4-oxo-2,3,4,5-tetrahydro-1,5-benzothiazepin-3-yl]carbamate (Intermediate VIII-134)

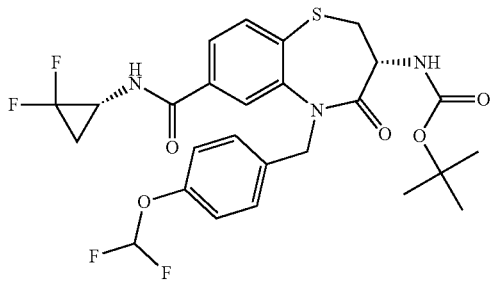 [SMILES: CC(C)(C)OC(=O)N[C@H]1CSc2ccc(C(=O)N[C@@H]3CC3(F)F)cc2N(Cc2ccc(OC(F)F)cc2)C1=O]

The title compound was synthesized according to general procedure GP3 to afford the title compound as yellow solid in 60% yield.

LCMS: METCR1410 Generic 1.7 min, rt=1.21 min, M/Z (ES+) 592.5 [M+Na+], 514.4 [M-tBu+H+] 79% UV; NMR Data: 1H NMR (500 MHz, Chloroform-d) d 7.69 (d, J=1.6 Hz, 1H), 7.65 (d, J=8.0 Hz, 1H), 7.48 (dd, J=8.0, 1.9 Hz, 1H), 7.27 (d, J=8.7 Hz, 2H), 6.99 (d, J=8.6 Hz, 2H), 6.45 (t, J=73.9 Hz, 1H), 6.23 (s, 1H), 5.55 (d, J=7.8 Hz, 1H), 5.32 (d, J=15.2 Hz, 1H), 4.87 (d, J=15.1 Hz, 1H), 4.45-4.34 (m, 1H), 3.70 (dd, J=10.9, 6.6 Hz, 1H), 3.60-3.46 (m, 1H), 2.93 (t, J=11.3 Hz, 1H), 1.98-1.85 (m, 1H), 1.49-1.43 (m, 1H), 1.40 (s, 9H).

Synthesis of tert-butyl N-[(3R)-7-{[(1R)-2,2-difluorocyclopropyl]carbamoyl}-5-[(4-methoxyphenyl)methyl]-4-oxo-2,3,4,5-tetrahydro-1,5-benzothiazepin-3-yl]carbamate (Intermediate VIII-135)

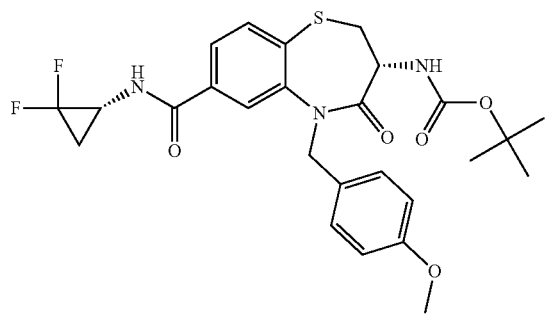 [SMILES: COc1ccc(CN2C(=O)[C@@H](NC(=O)OC(C)(C)C)CSc3ccc(C(=O)N[C@@H]4CC4(F)F)cc32)cc1]

The title compound was synthesized according to general procedure GP3 to afford the title compound as Yellow solid in 70% yield.

LCMS: METCR1410 Generic 1.7 min, rt=1.17 min, M/Z (ES+) 478.1 [M-tBu+H+], 556.1 [M+Na+] 91% UV; NMR Data: 1H NMR (250 MHz, Chloroform-d) δ 7.69-7.53 (m, 2H), 7.50 (dd, J=8.0, 1.8 Hz, 1H), 7.17 (d, J=8.6 Hz, 2H), 6.77 (d, J=8.7 Hz, 2H), 6.22 (s, 1H), 5.59 (d, J=8.1 Hz, 1H), 5.16 (d, J=14.7 Hz, 1H), 4.90 (d, J=14.6 Hz, 1H), 4.47-4.28 (m, 1H), 3.75 (s, 3H), 3.68 (dd, J=11.0, 6.6 Hz, 1H), 3.52 (s, 1H), 2.92 (t, J=11.3 Hz, 1H), 2.02-1.79 (m, 1H), 1.54-1.42 (m, 1H), 1.39 (s, 9H).

Synthesis of tert-butyl N-[(3R)-5-benzyl-4-oxo-7-[(4,4,4-trifluorobutyl)carbamoyl]-2,3,4,5-tetrahydro-1,5-benzothiazepin-3-yl]carbamate (Intermediate VIII-136)

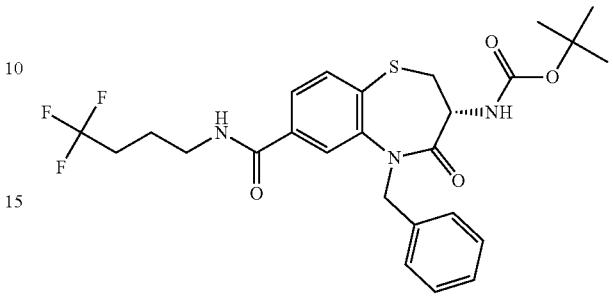

The title compound was synthesized according to general procedure GP3 to afford the title compound as off white solid in 42% yield.

LCMS: METCR1981 Hydrophobic 3 min, rt=1.51 min, M/Z (ES+) 482.1 [M-tBu+H+], 560.15 [M+Na+]100% UV; NMR Data: 1H NMR (500 MHz, Chloroform-d) d 7.64 (d, J=7.9 Hz, 1H), 7.58 (d, J=1.8 Hz, 1H), 7.48 (dd, J=8.0, 1.8 Hz, 1H), 7.30-7.21 (m, 5H), 6.09-5.94 (m, 1H), 5.59 (d, J=8.0 Hz, 1H), 5.18 (d, J=15.1 Hz, 1H), 5.03 (d, J=15.0 Hz, 1H), 4.42 (dt, J=11.5, 7.4 Hz, 1H), 3.70 (dd, J=11.0, 6.6 Hz, 1H), 3.50 (m, 2H), 2.93 (t, J=11.3 Hz, 1H), 2.22-2.09 (m, 2H), 1.87 (dt, J=14.6, 7.1 Hz, 2H), 1.40 (s, 9H).

Synthesis of tert-butyl N-[(3R)-8-chloro-5-[(4-chlorophenyl)methyl]-4-oxo-7-[(4,4,4-trifluorobutyl)carbamoyl]-2,3,4,5-tetrahydro-1,5-benzothiazepin-3-yl]carbamate (Intermediate VIII-137)

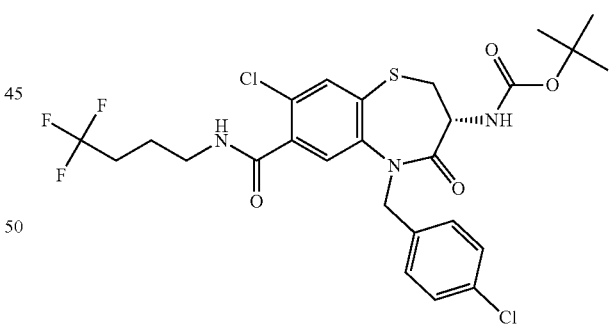

The title compound was synthesized according to general procedure GP3 to afford the title compound as off white solid in 65% yield.

LCMS: METCR1410 Generic 1.7 min, rt=1.61 min, M/Z (ES+) 628.10/629.85 [M+Na]+97% UV;

NMR Data: 1H NMR (500 MHz, Chloroform-d) δ 7.64 (d, J=5.8 Hz, 2H), 7.24-7.16 (m, 4H), 6.47-6.33 (m, 1H), 5.54 (d, J=8.3 Hz, 1H), 5.40 (d, J=15.1 Hz, 1H), 4.71 (d, J=15.2 Hz, 1H), 4.45-4.35 (m, 1H), 3.69 (dd, J=10.9, 6.5 Hz, 1H), 3.63-3.46 (m, 2H), 2.93 (t, J=11.3 Hz, 1H), 2.29-2.16 (m, 2H), 1.98-1.87 (m, 2H), 1.40 (s, 9H).

Synthesis of tert-butyl N-[(3R)-5-{[4-(difluoromethoxy)phenyl]methyl}-7-{[(oxan-4-yl)methyl]carbamoyl}-4-oxo-2,3,4,5-tetrahydro-1,5-benzothiazepin-3-yl]carbamate (Intermediate VIII-138)

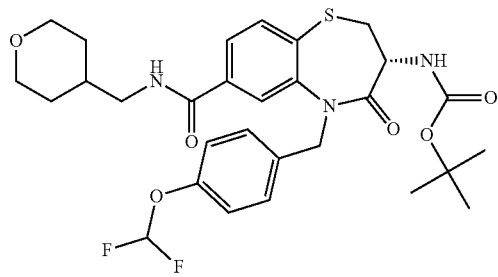 [SMILES: CC(C)(C)OC(=O)N[C@H]1CSc2ccc(C(=O)NCC3CCOCC3)cc2N(Cc2ccc(OC(F)F)cc2)C1=O]

The title compound was synthesized according to general procedure GP3 to afford the title compound as white solid in 89% yield.

LCMS: METCR1410 Generic 1.7 min, rt=1.16 min, M/Z (ES+) 614.2 [M+Na+] 99% UV;

NMR Data: 1H NMR (500 MHz, Chloroform-d) d 7.69 (d, J=1.7 Hz, 1H), 7.63 (d, J=7.9 Hz, 1H), 7.46 (dd, J=7.9, 1.7 Hz, 1H), 7.28 (d, J=8.6 Hz, 2H), 6.99 (d, J=8.5 Hz, 2H), 6.46 (t, J=73.9 Hz, 1H), 6.08 (t, J=6.0 Hz, 1H), 5.55 (d, J=8.4 Hz, 1H), 5.30 (d, J=15.1 Hz, 1H), 4.88 (d, J=15.1 Hz, 1H), 4.45-4.35 (m, 1H), 4.00 (dd, J=10.9, 3.7 Hz, 2H), 3.69 (dd, J=10.9, 6.6 Hz, 1H), 3.45-3.30 (m, 4H), 2.91 (t, J=11.3 Hz, 1H), 1.91-1.82 (m, 1H), 1.70-1.62 (m, 2H), 1.40 (s, 9H). Further 2H under grease peak.

Synthesis of tert-butyl N-[(3R)-5-[(4-chlorophenyl)methyl]-7-{[(4-fluorooxan-4-yl)methyl]carbamoyl}-4-oxo-2,3,4,5-tetrahydro-1,5-benzothiazepin-3-yl]carbamate (Intermediate VIII-139)

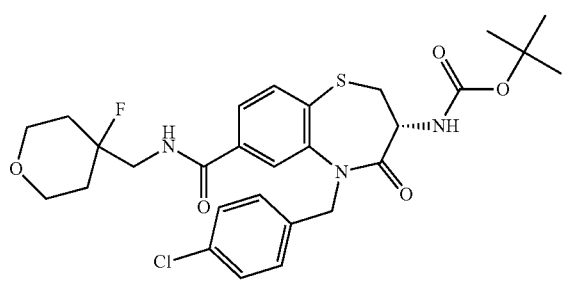 [SMILES: CC(C)(C)OC(=O)N[C@H]1CSc2ccc(C(=O)NCC3(F)CCOCC3)cc2N(Cc2ccc(Cl)cc2)C1=O]

The title compound was synthesized according to general procedure GP3 to afford the title compound as yellow solid in 90% yield.

LCMS: METCR1410 Generic 1.7 min, rt=1.2 min, M/Z (ES+) 522.05/524.05 [M-tBu+H+], 600.15/602.20 [M+Na+] 99% UV; NMR Data: 1H NMR (500 MHz, DMSO-d6) d 8.82 (t, J=6.1 Hz, 1H), 7.96 (s, 1H), 7.76-7.70 (m, 1H), 7.68 (d, J=8.0 Hz, 1H), 7.45 (d, J=8.4 Hz, 1H), 7.29 (s, 4H), 5.28 (d, J=15.6 Hz, 1H), 4.95 (d, J=15.7 Hz, 1H), 4.14 (dt, J=12.2, 7.6 Hz, 1H), 3.73 (d, J=11.5 Hz, 3H), 3.57 (s, 3H), 3.50-3.44 (m, 2H), 3.12 (t, J=11.8 Hz, 1H), 1.73-1.66 (m, 3H), 1.35 (s, 9H).

Synthesis of tert-butyl N-[(3R)-5-[(4-chlorophenyl)methyl]-7-{[(1R)-1-(oxan-4-yl)ethyl]carbamoyl}-4-oxo-2,3,4,5-tetrahydro-1,5-benzothiazepin-3-yl]carbamate (Intermediate VIII-140)

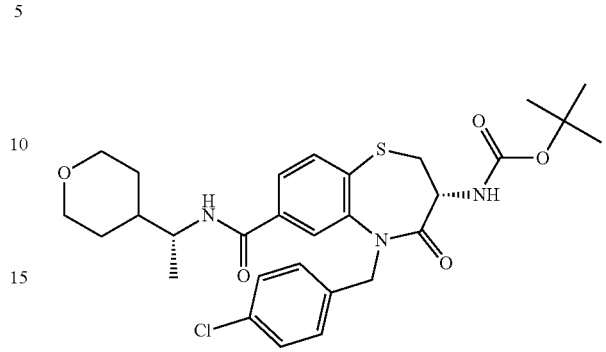

The title compound was synthesized according to general procedure GP3 to afford the title compound as yellow solid in 93% yield.

LCMS: METCR1410 Generic 1.7 min, rt=1.22 min, M/Z (ES+) 596.10/598.20 [M+Na+] 100% UV NMR Data: 1H NMR (500 MHz, DMSO-d6) d 8.30 (d, J=8.6 Hz, 1H), 7.88 (s, 1H), 7.73-7.65 (m, 2H), 7.44 (d, J=8.4 Hz, 1H), 7.34-7.27 (m, 4H), 5.25 (d, J=15.6 Hz, 1H), 4.97 (d, J=15.7 Hz, 1H), 4.18-4.09 (m, 1H), 3.92-3.79 (m, 3H), 3.46 (dd, J=11.3, 6.8 Hz, 1H), 3.28-3.20 (m, 2H), 3.11 (t, J=11.7 Hz, 1H), 1.67-1.54 (m, 3H), 1.35 (s, 9H), 1.21 (td, J=12.2, 3.9 Hz, 2H), 1.13 (d, J=6.7 Hz, 3H).

Synthesis of tert-butyl N-[(3R)-5-benzyl-7-{[(1R)-2,2-difluorocyclopropyl]carbamoyl}-4-oxo-2,3,4,5-tetrahydro-1,5-benzothiazepin-3-yl]carbamate (Intermediate VIII-141)

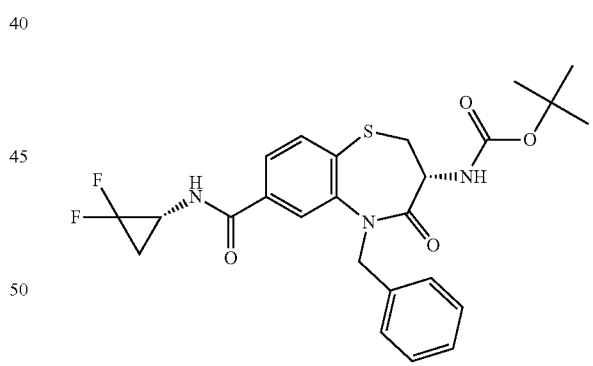

The title compound was synthesized according to general procedure GP3 to afford the title compound as white solid in 25% yield.

LCMS: METCR1410 Generic 1.7 min, rt=1.21 min, M/Z (ES+) 448 [M-tBu+H+], 526 [M+Na+] 98% UV NMR Data: 1H NMR (250 MHz, Chloroform-d) d 7.64 (d, J=7.9 Hz, 1H), 7.57 (d, J=1.8 Hz, 1H), 7.50 (dd, J=8.0, 1.8 Hz, 1H), 7.26 (s, 5H), 6.21 (s, 1H), 5.59 (d, J=8.0 Hz, 1H), 5.19 (d, J=15.0 Hz, 1H), 5.01 (d, J=15.0 Hz, 1H), 4.50-4.31 (m, 1H), 3.70 (dd, J=11.0, 6.6 Hz, 1H), 3.59-3.43 (m, 1H), 2.93 (t, J=11.2 Hz, 1H), 2.02-1.78 (m, 1H), 1.51-1.42 (m, 1H), 1.40 (s, 9H).

Synthesis of tert-butyl N-[(3R)-5-[(4-chlorophenyl)methyl]-7-{[(3,3-difluorocyclobutyl)methyl]carbamoyl}-4-oxo-2,3,4,5-tetrahydro-1,5-benzothiazepin-3-yl]carbamate (Intermediate VIII-142)

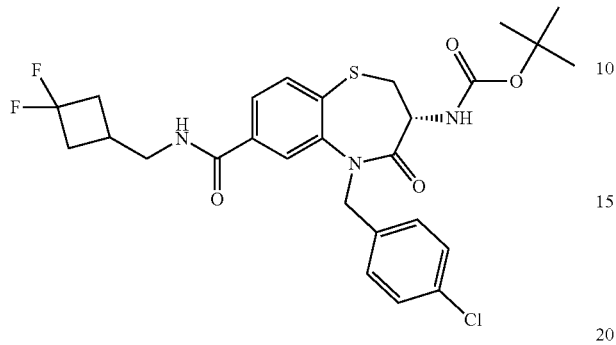

The title compound was synthesized according to general procedure GP3 to afford the title compound as white solid in 52% yield.

LCMS: METCR1410 Generic 1.7 min, rt=1.28 min, M/Z (ES+) 510.10/512.10 [M-tBu+H+] 93% UV NMR Data: 1H NMR (500 MHz, DMSO-d6) d 8.75 (t, J=5.6 Hz, 1H), 7.91 (s, 1H), 7.68 (s, 2H), 7.45 (d, J=8.3 Hz, 1H), 7.28 (s, 4H), 5.29 (d, J=15.5 Hz, 1H), 4.91 (d, J=15.7 Hz, 1H), 4.13 (dt, J=12.1, 7.6 Hz, 1H), 3.46 (dd, J=11.3, 6.7 Hz, 1H), 3.39 (t, J=5.7 Hz, 2H), 3.11 (t, J=11.8 Hz, 1H), 2.70-2.58 (m, 2H), 2.41-2.34 (m, 3H), 1.34 (s, 9H).

Synthesis of tert-butyl N-[(3R)-8-chloro-5-[(4-chlorophenyl)methyl]-7-{[(1R)-2,2-difluorocyclopropyl]carbamoyl}-4-oxo-2,3,4,5-tetrahydro-1,5-benzothiazepin-3-yl]carbamate (Intermediate VIII-143)

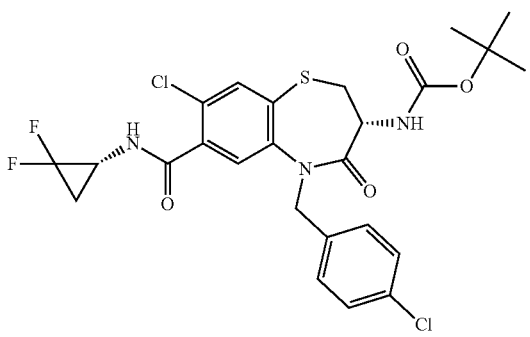 [SMILES: CC(C)(C)OC(=O)N[C@H]1CSc2cc(Cl)c(C(=O)N[C@@H]3CC3(F)F)cc2N(Cc2ccc(Cl)cc2)C1=O]

The title compound was synthesized according to general procedure GP3 to afford the title compound as colourless glass in 53% yield.

LCMS: METCR1410 Generic 1.7 min, rt=1.28 min, M/Z (ES+) 515.95/518.05 [M-tBu+H+], 594/596.05 [M+Na+] 96% UV; NMR Data: 1H NMR (250 MHz, Chloroform-d) d 7.59 (s, 2H), 7.17 (s, 4H), 6.93 (s, 1H), 5.61 (d, J=8.0 Hz, 1H), 5.34 (d, J=15.1 Hz, 1H), 4.67 (d, J=15.1 Hz, 1H), 4.34 (dt, J=11.4, 7.3 Hz, 1H), 3.61 (dd, J=10.9, 6.5 Hz, 1H), 3.47 (dt, J=10.1, 6.0 Hz, 1H), 2.90 (t, J=11.3 Hz, 1H), 1.94-1.77 (m, 1H), 1.56-1.41 (m, 1H), 1.36 (s, 9H).

Synthesis of tert-butyl N-[(3R)-7-{[(1R)-2,2-difluorocyclopropyl]carbamoyl}-4-oxo-5-{[4-(trifluoromethyl)phenyl]methyl}-2,3,4,5-tetrahydro-1,5-benzothiazepin-3-yl]carbamate (Intermediate VIII-144)

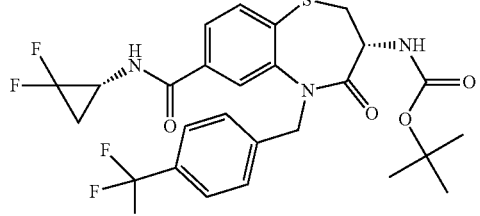

The title compound was synthesized according to general procedure GP3 to afford the title compound as white solid in 53% yield.

LCMS: METCR1410 Generic 1.7 min, rt=1.3 min, M/Z (ES+) 594.2 [M+Na+] 86% UV;

NMR Data: 1H NMR (500 MHz, DMSO-d6) d 8.97 (s, 1H), 7.92 (s, 1H), 7.74-7.67 (m, 2H), 7.61 (d, J=8.2 Hz, 2H), 7.55-7.48 (m, 2H), 7.46 (d, J=8.3 Hz, 1H), 5.32 (d, J=16.1 Hz, 1H), 5.05 (d, J=16.0 Hz, 1H), 4.20-4.11 (m, 1H), 3.47 (dd, J=11.4, 6.9 Hz, 1H), 3.13 (t, J=11.8 Hz, 1H), 2.04-1.92 (m, 1H), 1.70-1.52 (m, 2H), 1.34 (s, 9H).

Synthesis of tert-butyl N-[(3R)-5-[(4-bromophenyl)methyl]-7-[(2,2-difluorocyclopropyl)carbamoyl]-4-oxo-2,3,4,5-tetrahydro-1,5-benzothiazepin-3-yl]carbamate (Intermediate VIII-145)

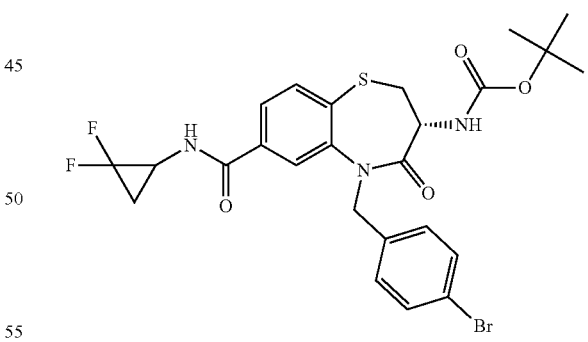

The title compound was synthesized according to general procedure GP3 to afford the title compound as white solid in 71% yield.

LCMS: METCR1410 Generic 1.7 min, rt=1.26 min, M/Z (ES+) 604.0/605.8 [M+Na+] 88% UV NMR Data: 1H NMR (500 MHz, DMSO-d6) d 9.00-8.94 (m, 1H), 7.95 (d, J=12.7 Hz, 1H), 7.71 (s, 2H), 7.48-7.39 (m, 3H), 7.27-7.19 (m, 2H), 5.36-5.22 (m, 1H), 4.95-4.82 (m, 1H), 4.18-4.08 (m, 1H), 3.50-3.43 (m, 2H), 3.12 (t, J=11.7 Hz, 1H), 2.04-1.93 (m, 1H), 1.75-1.56 (m, 1H), 1.35 (s, 9H).

Synthesis of tert-butyl N-[(3R)-5-[(4-cyanophenyl)methyl]-8-fluoro-7-{[(4-fluorophenyl)methyl]carbamoyl}-4-oxo-2,3,4,5-tetrahydro-1,5-benzothiazepin-3-yl]carbamate (Intermediate VIII-146)

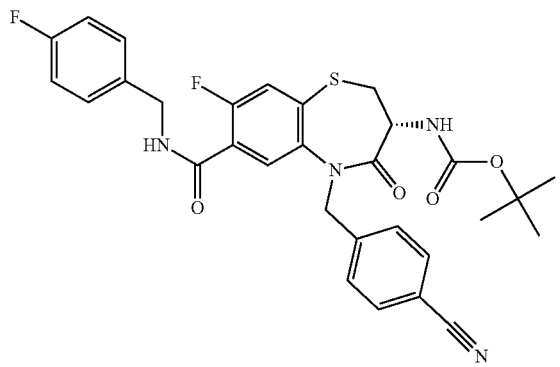 [SMILES: CC(C)(C)OC(=O)N[C@H]1CSc2cc(F)c(C(=O)NCc3ccc(F)cc3)cc2N(Cc2ccc(C#N)cc2)C1=O]

The title compound was synthesized according to general procedure GP3 to afford the title compound as white solid in 78% yield.

LCMS: METCR1410 Generic 1.7 min, rt=1.29 min, M/Z (ES+) 523.2 [M-tBu+H+] 92% UV

NMR Data: 1H NMR (250 MHz, Chloroform-d) d 8.08 (d, J=7.0 Hz, 1H), 7.54 (d, J=8.4 Hz, 2H), 7.45-7.28 (m, 5H), 7.11-6.94 (m, 3H), 5.60-5.48 (m, 2H), 4.77 (d, J=15.6 Hz, 1H), 4.68-4.57 (m, 2H), 4.40 (s, 1H), 3.71 (dd, J=10.9, 6.5 Hz, 1H), 2.94 (t, J=11.3 Hz, 1H), 1.40 (s, 9H).

According to the above described and exemplified general procedure GP4 the following sulfone intermediates IX were synthesized from amide intermediate VIII:

Synthesis of tert-butyl N-[(3R)-7-(butylcarbamoyl)-1,1,4-trioxo-5-{[4-(trifluoromethoxy)-phenyl]methyl}-2,3,4,5-tetrahydro-1λ⁶,5-benzothiazepin-3-yl]carbamate (Intermediate IX-02)

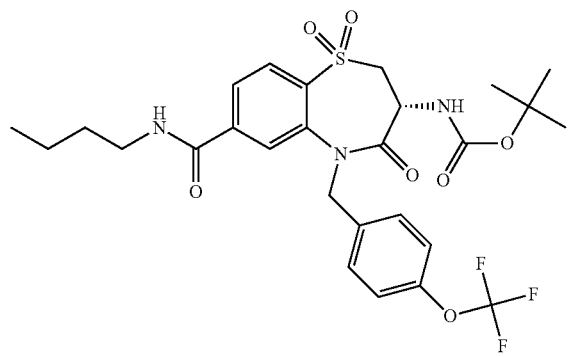 [SMILES: CCCCNC(=O)c1ccc2c(c1)N(Cc1ccc(OC(F)(F)F)cc1)C(=O)[C@@H](NC(=O)OC(C)(C)C)CS2(=O)=O]

The title compound was synthesized according to general procedure GP4 to afford the title compound as white solid in 69% Yield.

LCMS: METCR1673 Generic 2 minutes, rt=1.47 min, M/Z (ES+) 622 [M+Na+] 100% UV

NMR Data: 1H NMR (250 MHz, DMSO-d6) δ 8.76 (d, J=5.3 Hz, 1H), 8.03-7.92 (m, 2H), 7.78 (s, 1H), 7.52 (d, J=7.9 Hz, 1H), 7.46 (d, J=8.4 Hz, 2H), 7.28 (d, J=8.2 Hz, 2H), 5.26 (d, J=16.1 Hz, 1H), 4.85 (d, J=16.2 Hz, 1H), 4.39 (dt, J=11.6, 7.7 Hz, 1H), 4.09 (dd, J=13.2, 7.2 Hz, 1H), 3.74 (t, J=12.5 Hz, 1H), 3.30-3.20 (m, 2H), 1.49 (p, J=7.2 Hz, 2H), 1.39-1.21 (m, 11H), 0.89 (t, J=7.3 Hz, 3H).

Synthesis of tert-butyl N-[(3R)-5-[(4-chlorophenyl)methyl]-8-fluoro-7-{[(4-fluorophenyl)-methyl]carbamoyl}-1,1,4-trioxo-2,3,4,5-tetrahydro-1λ⁶,5-benzothiazepin-3-yl]carbamate (Intermediate IX-03)

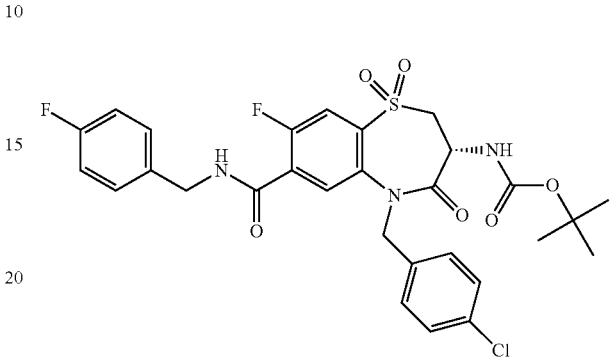

The title compound was synthesized according to general procedure GP4 to afford the title compound as white solid in 21% Yield.

LCMS: METCR1673 Generic 2 minutes, rt=1.46 min, M/Z (ES+) 642 [M+Na+] 90% UV

NMR Data: 1H NMR (250 MHz, Chloroform-d) δ 8.03 (d, J=6.1 Hz, 1H), 7.80 (d, J=9.9 Hz, 1H), 7.35-7.26 (m, 6H), 7.06 (t, J=8.6 Hz, 2H), 5.70 (d, J=7.1 Hz, 1H), 5.17 (d, J=15.2 Hz, 1H), 4.84 (d, J=15.2 Hz, 1H), 4.63 (t, J=6.1 Hz, 2H), 4.54 (s, 1H), 4.16-4.00 (m, 1H), 3.58-3.45 (m, 1H), 1.40 (s, 9H). [NH not visible]

Synthesis of tert-butyl N-[(3R)-7-(butylcarbamoyl)-5-[(4-chlorophenyl)methyl]-8-fluoro-1,1,4-trioxo-2,3,4,5-tetrahydro-1λ⁶,5-benzothiazepin-3-yl]carbamate (Intermediate IX-04)

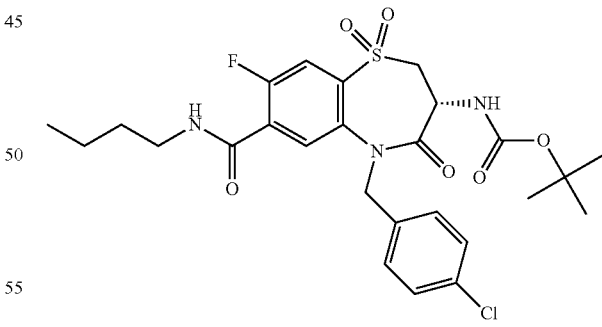

The title compound was synthesized according to general procedure GP4 to afford the title compound as white solid in 89% Yield.

LCMS: METCR1673 Generic 2 minutes, rt=1.45 min, M/Z (ES+) 590 [M+Na+] 97% UV

NMR Data: 1H NMR (500 MHz, DMSO-d6) δ 8.61 (t, J=5.5 Hz, 1H), 7.73 (d, J=8.4 Hz, 1H), 7.53 (dd, J=14.6, 6.8 Hz, 2H), 7.38-7.32 (m, 4H), 5.22 (d, J=16.0 Hz, 1H), 4.77 (d, J=16.0 Hz, 1H), 4.41 (dt, J=11.6, 7.7 Hz, 1H), 4.12-4.04

(m, 1H), 3.83-3.70 (m, 1H), 3.26-3.17 (m, 2H), 1.51-1.42 (m, 2H), 1.36 (s, 9H), 1.29-1.25 (m, 2H), 0.88 (t, J=7.4 Hz, 3H).

Synthesis of tert-butyl N-[(3R)-5-[(4-chlorophenyl) methyl]-8-fluoro-1,1,4-trioxo-7-[(4,4,4-trifluorobutyl)carbamoyl]-2,3,4,5-tetrahydro-1λ⁶,5-benzothiazepin-3-yl]carbamate (Intermediate IX-05)

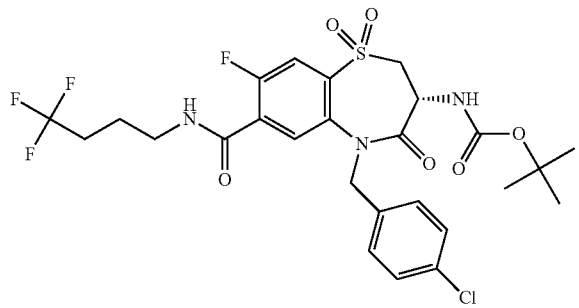 [SMILES: CC(C)(C)OC(=O)N[C@H]1CS(=O)(=O)c2cc(F)c(C(=O)NCCCC(F)(F)F)cc2N(Cc2ccc(Cl)cc2)C1=O]

The title compound was synthesized according to general procedure GP4 to afford the title compound as white solid in 78% yield.
LCMS: METCR1673 Generic 2 minutes, rt=1.48 min, M/Z (ES+) 644 [M+Na+] 100% UV
NMR Data: 1H NMR (500 MHz, DMSO-d6) δ 8.75 (d, J=5.3 Hz, 1H), 7.75 (d, J=8.5 Hz, 1H), 7.64 (d, J=5.5 Hz, 1H), 7.52 (d, J=8.0 Hz, 1H), 7.38-7.29 (m, 4H), 5.19 (d, J=16.0 Hz, 1H), 4.83 (d, J=15.9 Hz, 1H), 4.41 (dt, J=11.7, 7.7 Hz, 1H), 4.09 (dd, J=13.1, 7.4 Hz, 1H), 3.82-3.71 (m, 1H), 3.45-3.35 (m, 2H), 2.29 (dd, J=16.2, 11.4 Hz, 2H), 1.79-1.64 (m, 2H), 1.37 (s, 9H).

Synthesis of tert-butyl N-[(3R)-5-[(4-chlorophenyl) methyl]-8-fluoro-7-[(oxan-4-ylmethyl)-carbamoyl]-1,1,4-trioxo-2,3,4,5-tetrahydro-1λ⁶,5-benzothiazepin-3-yl]carbamate (Intermediate IX-06)

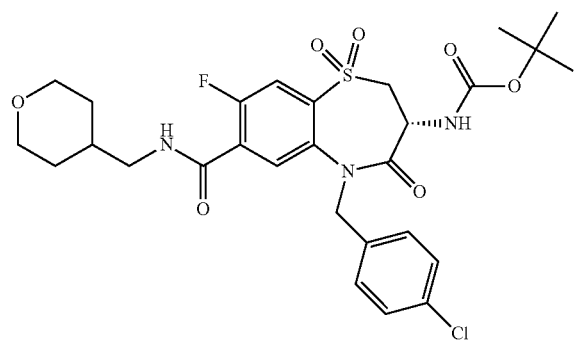 [SMILES: CC(C)(C)OC(=O)N[C@H]1CS(=O)(=O)c2cc(F)c(C(=O)NCC3CCOCC3)cc2N(Cc2ccc(Cl)cc2)C1=O]

The title compound was synthesized according to general procedure GP4 to afford the title compound as white solid in 28% Yield.
LCMS: METCR1673 Generic 2 minutes, rt=1.38 min, M/Z (ES+) 510 [M+H-boc] 98% UV
NMR Data: 1H NMR (500 MHz, Chloroform-d) δ 8.01 (d, J=6.1 Hz, 1H), 7.83 (d, J=9.9 Hz, 1H), 7.30 (d, J=2.5 Hz, 4H), 6.77 (dt, J=11.5, 5.6 Hz, 1H), 5.73 (d, J=7.1 Hz, 1H), 5.19 (d, J=15.2 Hz, 1H), 4.85 (d, J=15.2 Hz, 1H), 4.54 (dt, J=10.9, 7.0 Hz, 1H), 4.10 (dd, J=13.9, 6.3 Hz, 1H), 4.02 (dd, J=11.1, 3.7 Hz, 2H), 3.54 (dd, J=13.2, 11.1 Hz, 1H), 3.50-3.32 (m, 4H), 1.91 (ddt, J=11.4, 8.0, 4.0 Hz, 1H), 1.72-1.63 (m, 2H), 1.61 (s, 2H), 1.48-1.35 (m, 9H).

Synthesis of tert-butyl N-[(3R)-8-fluoro-7-[(oxan-4-ylmethyl)carbamoyl]-1,1,4-trioxo-5-{[4-(trifluoromethoxy)phenyl]methyl}-2,3,4,5-tetrahydro-1λ⁶, 5-benzothiazepin-3-yl]carbamate (Intermediate IX-07)

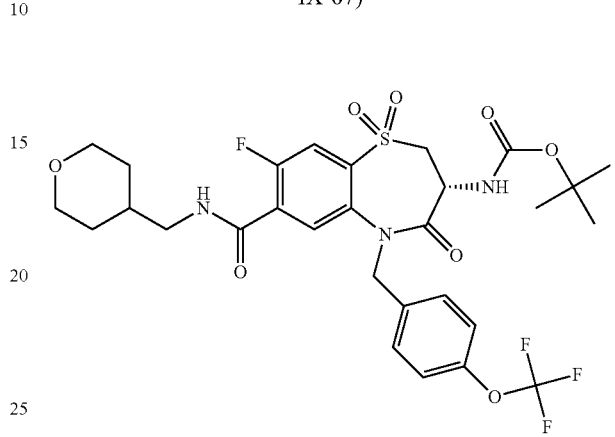

The title compound was synthesized according to general procedure GP6 to afford the title compound as yellow solid in 62% yield.
LCMS: METCR1673 Generic 2 minutes, rt=1.38 min, M/Z (ES+) 682 [M+Na+] 97% UV
NMR Data: 1H NMR (500 MHz, Chloroform-d) δ 1.40 (s, 11H), 1.64 (dt, J=7.0, 14.1 Hz, 2H), 1.88 (ttt, J=3.9, 7.2, 10.9 Hz, 1H), 3.38 (tdq, J=6.8, 13.3, 20.0 Hz, 4H), 3.52 (dd, J=11.2, 13.2 Hz, 1H), 4.00 (dd, J=3.7, 11.2 Hz, 2H), 4.03-4.12 (m, 1H), 4.52 (dt, J=7.0, 10.8 Hz, 1H), 4.84 (d, J=15.3 Hz, 1H), 5.21 (d, J=15.3 Hz, 1H), 5.70 (d, J=7.1 Hz, 1H), 6.76 (dt, J=5.8, 11.8 Hz, 1H), 7.16 (d, J=8.1 Hz, 2H), 7.37 (d, J=8.6 Hz, 2H), 7.82 (d, J=9.9 Hz, 1H), 8.00 (d, J=6.0 Hz, 1H).

Synthesis of tert-butyl N-[(3R)-8-fluoro-1,1,4-trioxo-7-[(4,4,4-trifluorobutyl)carbamoyl]-5-{[4-(trifluoromethoxy)phenyl]methyl}-2,3,4,5-tetrahydro-1λ⁶,5-benzothiazepin-3-yl]carbamate (Intermediate IX-08)

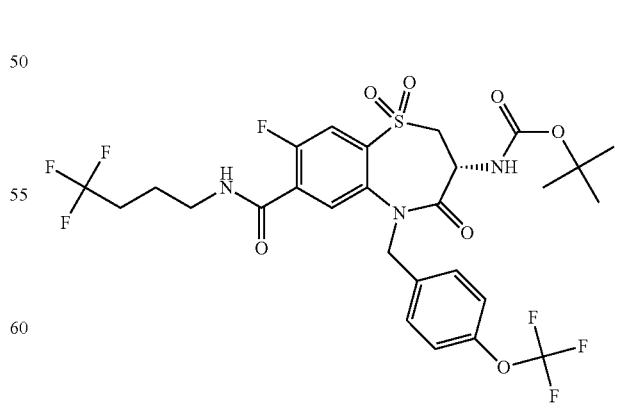

The title compound was synthesized according to general procedure GP6 to afford the title compound as yellow solid in 53% Yield.

LCMS: METCR1673 Generic 2 minutes, rt=1.49 min, M/Z (ES+) 694 [M+Na+] 96% UV

NMR Data: 1H NMR (500 MHz, Chloroform-d) δ 1.40 (s, 9H), 1.92 (dt, J=7.2, 14.7 Hz, 2H), 2.11-2.26 (m, 2H), 3.55 (qd, J=9.0, 13.6 Hz, 3H), 4.08 (dd, J=6.7, 13.5 Hz, 1H), 4.53 (dt, J=7.0, 10.9 Hz, 1H), 4.84 (d, J=15.3 Hz, 1H), 5.22 (d, J=15.2 Hz, 1H), 5.70 (d, J=7.1 Hz, 1H), 6.77 (dt, J=5.8, 11.6 Hz, 1H), 7.16 (d, J=8.1 Hz, 2H), 7.37 (d, J=8.6 Hz, 2H), 7.82 (d, J=9.9 Hz, 1H), 7.99 (d, J=6.0 Hz, 1H)

Synthesis of tert-butyl N-[(3R)-8-fluoro-1,1,4-trioxo-7-(phenoxycarbamoyl)-5-{[4-(trifluoromethoxy)phenyl]methyl}-2,3,4,5-tetrahydro-1λ⁶,5-benzothiazepin-3-yl]carbamate (Intermediate IX-09)

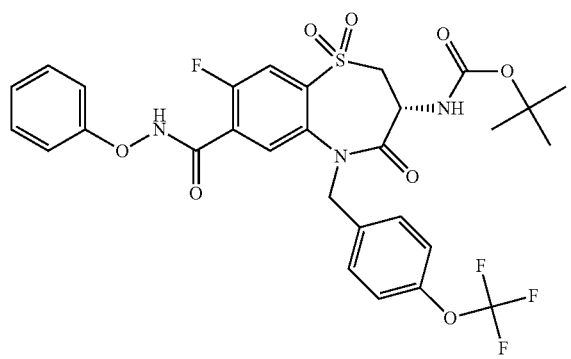 [SMILES: CC(C)(C)OC(=O)N[C@H]1CS(=O)(=O)c2cc(F)c(C(=O)NOc3ccccc3)cc2N(Cc2ccc(OC(F)(F)F)cc2)C1=O]

The title compound was synthesized according to general procedure GP4 to afford the title compound as yellow solid in 40% Yield.

LCMS: METCR1673 Generic 2 minutes, rt=1.47 min, M/Z (ES+) 676 [M+Na+] 97% UV

NMR Data: 1H NMR (500 MHz, Chloroform-d) δ 1.41 (s, 9H), 3.47-3.61 (m, 1H), 4.10 (dd, J=6.9, 13.3 Hz, 1H), 4.55 (h, J=8.7, 9.7 Hz, 1H), 4.84 (d, J=14.9 Hz, 1H), 5.23 (d, J=15.2 Hz, 1H), 5.72 (d, J=7.0 Hz, 1H), 7.04-7.18 (m, 5H), 7.29-7.44 (m, 4H), 7.88 (d, J=9.36 Hz, 1H), 8.03 (s, 1H), 9.62 (d, J=9.7 Hz, 1H)

Synthesis of tert-butyl N-[(3R)-5-[(4-chlorophenyl)methyl]-8-fluoro-7-[(2-methylpropoxy)-carbamoyl]-1,1,4-trioxo-2,3,4,5-tetrahydro-1λ⁶,5-benzothiazepin-3-yl]carbamate (Intermediate IX-10)

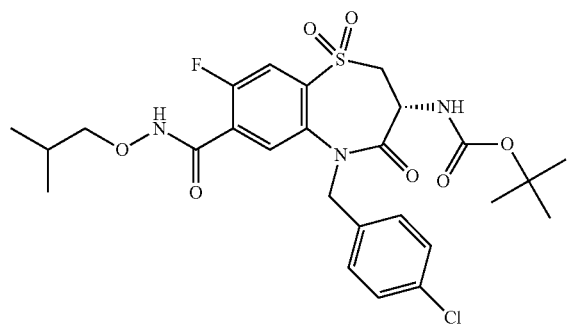 [SMILES: CC(C)CONC(=O)c1cc2c(cc1F)S(=O)(=O)C[C@H](NC(=O)OC(C)(C)C)C(=O)N2Cc1ccc(Cl)cc1]

The title compound was synthesized according to general procedure GP4 to afford the title compound as white solid in 82% Yield.

LCMS: METCR1673 Generic 2 minutes, rt=1.43 min, M/Z (ES+) 606/608 [M+Na+] 100% UV NMR Data: 1H NMR (500 MHz, Chloroform-d) δ 9.11 (d, J=11.2 Hz, 1H), 8.01 (d, J=6.1 Hz, 1H), 7.82 (d, J=9.6 Hz, 1H), 7.30-7.27 (m, 4H), 5.70 (s, 1H), 5.16 (d, J=15.3 Hz, 1H), 4.85 (d, J=15.2 Hz, 1H), 4.52 (s, 1H), 4.08 (d, J=6.7 Hz, 1H), 3.83 (d, J=6.8 Hz, 2H), 3.58-3.48 (m, 1H), 2.12-1.99 (m, 1H), 1.41 (s, 9H), 1.01 (d, J=6.7 Hz, 6H).

Synthesis of tert-butyl N-[(3R)-5-[(4-chlorophenyl)methyl]-8-fluoro-1,1,4-trioxo-7-(phenoxycarbamoyl)-2,3,4,5-tetrahydro-1λ⁶,5-benzothiazepin-3-yl]carbamate (Intermediate IX-11)

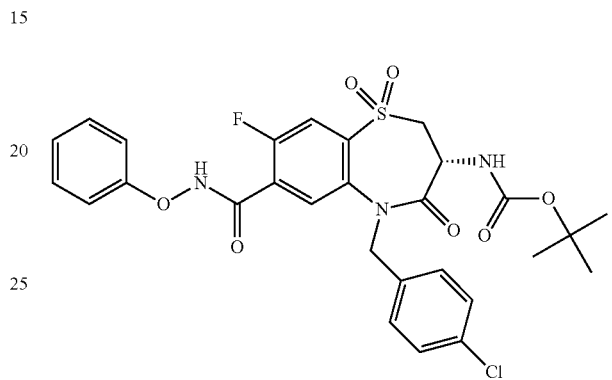

The title compound was synthesized according to general procedure GP4 to afford the title compound as off-white solid in 47% Yield.

LCMS: METCR1673 Generic 2 minutes, rt=1.44 min, M/Z (ES+) 626/628 [M+Na+] 100% UV NMR Data: 1H NMR (500 MHz, Chloroform-d) δ 9.54 (s, 1H), 8.05 (s, 1H), 7.95-7.88 (m, 1H), 7.44-7.35 (m, 2H), 7.34-7.30 (part. obsc. m, 4H), 7.13 (t, J=7.8 Hz, 3H), 5.74 (d, J=7.0 Hz, 1H), 5.22 (d, J=15.2 Hz, 1H), 4.85 (d, J=15.5 Hz, 1H), 4.65-4.52 (m, 1H), 4.13 (dd, J=13.4, 6.8 Hz, 1H), 3.64-3.49 (m, 1H), 1.44 (s, 9H).

Synthesis of tert-butyl N-[(3R)-5-[(4-chlorophenyl)methyl]-8-fluoro-1,1,4-trioxo-7-[(propan-2-yl)carbamoyl]-2,3,4,5-tetrahydro-1λ⁶,5-benzothiazepin-3-yl]carbamate (Intermediate IX-12)

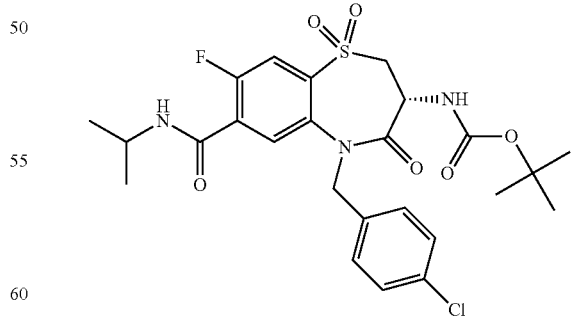

The title compound was synthesized according to general procedure GP4 to afford the title compound as white solid in 82% Yield.

LCMS: METCR1673 Generic 2 minutes, rt=1.40 min, M/Z (ES+) 576/578 [M+Na+] 99% UV NMR Data: 1H NMR (500 MHz, Chloroform-d) δ 8.00 (d, J=6.1 Hz, 1H), 7.79 (d, J=9.8 Hz, 1H), 7.30-7.27 (m, 4H), 6.53-6.40 (m, 1H), 5.70 (d, J=6.8 Hz, 1H), 5.17 (d, J=15.2 Hz, 1H), 4.83 (d, J=15.2 Hz, 1H), 4.56-4.46 (m, 1H), 4.33-4.21 (m, 1H), 4.08 (dd, J=13.3, 6.9 Hz, 1H), 3.51 (dd, J=13.3, 11.0 Hz, 1H), 1.40 (s, 9H), 1.28 (dd, J=6.5, 3.7 Hz, 6H)

Synthesis of tert-butyl N-[(2R,3R)-5-[(4-chlorophenyl)methyl]-2-methyl-1,1,4-trioxo-7-[(4,4,4-trifluorobutyl)carbamoyl]-2,3,4,5-tetrahydro-1λ⁶,5-benzothiazepin-3-yl]carbamate (Intermediate IX-13)

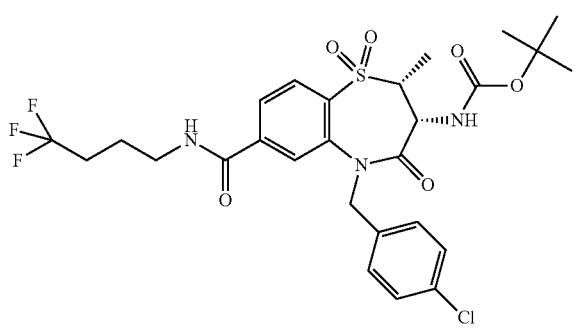 [SMILES: C[C@@H]1[C@H](NC(=O)OC(C)(C)C)C(=O)N(Cc2ccc(Cl)cc2)c2cc(C(=O)NCCCC(F)(F)F)ccc2S1(=O)=O]

The title compound was synthesized according to general procedure GP4 to afford the title compound as white solid in 85% Yield.

LCMS: METCR1673 Generic 2 minutes, rt=1.52 min, M/Z (ES+) 640/642 [M+Na+] 100% UV NMR Data: 1H NMR (500 MHz, DMSO-d6) δ 7.90 (d, J=6.0 Hz, 1H), 7.78 (d, J=9.9 Hz, 1H), 7.23-7.16 (m, 4H), 6.73 (dt, J=11.6, 5.7 Hz, 1H), 5.61 (d, J=6.9 Hz, 1H), 5.07 (d, J=15.3 Hz, 1H), 4.74 (d, J=15.3 Hz, 1H), 4.53 (t, J=6.8 Hz, 1H), 3.96 (p, J=6.9 Hz, 1H), 3.48 (qq, J=13.5, 6.7 Hz, 2H), 2.18-2.05 (m, 2H), 1.85 (dt, J=14.7, 7.2 Hz, 2H), 1.41 (d, J=7.0 Hz, 3H), 1.33 (s, 9H).

Synthesis of tert-butyl N-[(3R)-5-[(4-chlorophenyl)methyl]-7-[({4-[(5-acetamidopentyl)oxy]phenyl}methyl)-carbamoyl]-1,1,4-trioxo-2,3,4,5-tetrahydro-1λ⁶,5-benzothiazepin-3-yl]carbamate (Intermediate IX-14)

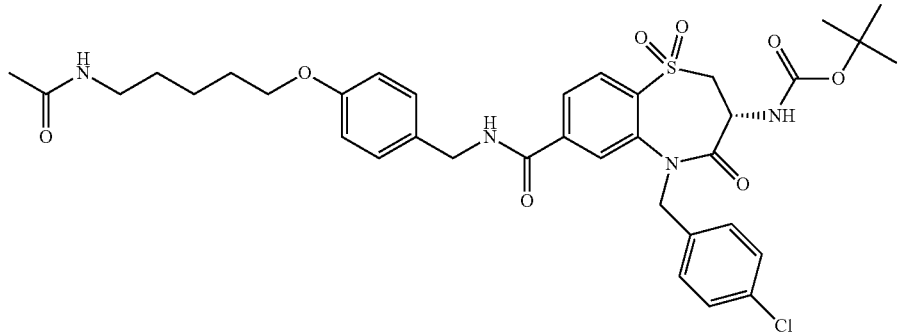 [SMILES: CC(=O)NCCCCCOc1ccc(CNC(=O)c2ccc3c(c2)N(Cc2ccc(Cl)cc2)C(=O)[C@@H](NC(=O)OC(C)(C)C)CS3(=O)=O)cc1]

The title compound was synthesized according to general procedure GP4 to afford the title compound as white solid in 62% Yield.

LCMS: METCR1416 Generic 7 minutes, rt=4.23 min, M/Z (ES+) 727/729 [M+H+], 627/629 [M+H-Boc]100% UV NMR Data: 1H NMR (500 MHz, DMSO-d6) δ 9.29 (t, J=5.8 Hz, 1H), 7.99 (s, 2H), 7.85 (s, 1H), 7.79 (s, 1H), 7.52 (d, J=8.0 Hz, 1H), 7.34 (s, 4H), 7.20 (d, J=8.6 Hz, 2H), 6.88 (d, J=8.6 Hz, 2H), 6.21 (d, J=15.9 Hz, 1H), 4.85 (d, J=16.0 Hz, 1H), 4.37 (s, 3H), 4.08 (dd, J=13.1, 7.3 Hz, 1H), 3.93 (t, J=6.5 Hz, 2H), 3.78-3.68 (m, 1H), 3.03 (q, J=6.5 Hz, 2H), 1.78 (s, 3H), 1.70 (p, J=6.8 Hz, 2H), 1.48-1.37 (m, 4H), 1.36 (s, 9H).

Synthesis of tert-butyl N-[(3R)-5-[(4-chlorophenyl)methyl]-7-[(cyclopropylmethyl)carbamoyl]-8-fluoro-1,1,4-trioxo-2,3,4,5-tetrahydro-1λ⁶,5-benzothiazepin-3-yl]carbamate (Intermediate IX-15)

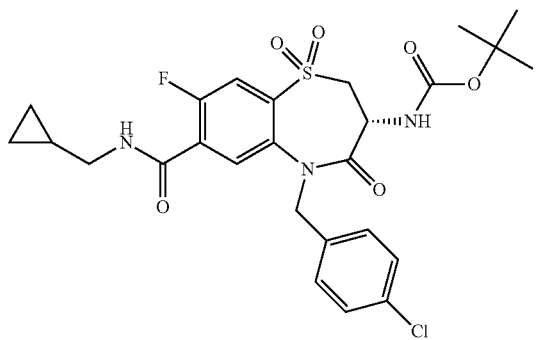 [SMILES: CC(C)(C)OC(=O)N[C@H]1CS(=O)(=O)c2cc(F)c(C(=O)NCC3CC3)cc2N(Cc2ccc(Cl)cc2)C1=O]

The title compound was synthesized according to general procedure GP4 to afford the title compound as white solid in 88% Yield.

LCMS: METCR1673 Generic 2 minutes, rt=1.45 min, M/Z (ES+) 588/590 [M+Na+] 98% UV NMR Data: 1H NMR (500 MHz, DMSO-d6) δ 8.51 (t, J=5.5 Hz, 1H), 7.54 (d, J=8.5 Hz, 1H), 7.37 (d, J=5.4 Hz, 1H), 7.32 (d, J=8.0 Hz, 1H), 7.14 (s, 4H), 5.01 (d, J=16.0 Hz, 1H), 4.58 (d, J=16.0 Hz, 1H), 4.21 (dt, J=11.5, 7.7 Hz, 1H), 3.89 (dd, J=13.3, 7.3 Hz, 1H), 3.60-3.51 (m, 1H), 2.93 (qt, J=13.4, 6.0 Hz, 2H), 1.17 (s, 9H), 0.78 (s, 1H), 0.23 (q, J=5.6 Hz, 2H), −0.00 (q, J=4.9 Hz, 2H).

Synthesis of tert-butyl N-[(3R)-5-[(4-chlorophenyl)methyl]-1,1,4-trioxo-7-[(propan-2-yl)carbamoyl]-2,3,4,5-tetrahydro-1λ⁶,5-benzothiazepin-3-yl]carbamate (Intermediate IX-16)

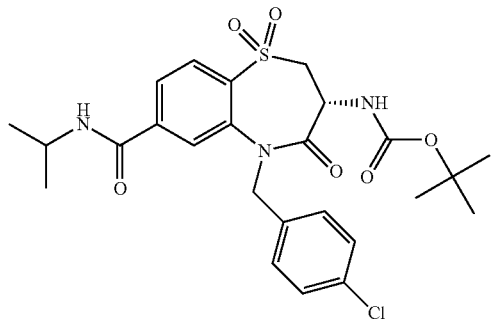 [SMILES: CC(C)NC(=O)c1ccc2c(c1)N(Cc1ccc(Cl)cc1)C(=O)[C@@H](NC(=O)OC(C)(C)C)CS2(=O)=O]

The title compound was synthesized according to general procedure GP4 to afford the title compound as off-white solid in 83% Yield.

LCMS: METCR1673 Generic 2 minutes, rt=1.36 min, M/Z (ES+) 558/560 [M+Na+] 100% UV NMR Data: 1H NMR (500 MHz, Chloroform-d) δ 1.24 (d, J=6.6 Hz, 6H), 1.40 (s, 9H), 3.50 (dd, J=11.1, 13.2 Hz, 1H), 4.05 (dd, J=7.0, 13.3 Hz, 1H), 4.22 (dh, J=6.6, 13.2 Hz, 1H), 4.51 (dt, J=7.2, 10.9 Hz, 1H), 4.60 (d, J=15.2 Hz, 1H), 5.39 (d, J=15.2 Hz, 1H), 5.72 (dd, J=7.5, 18.3 Hz, 2H), 7.26-7.34 (m, 4H), 7.50 (d, J=1.3 Hz, 1H), 7.75 (dd, J=1.3, 8.1 Hz, 1H), 8.06 (d, J=8.1 Hz, 1H)

Synthesis of tert-butyl N-[(3R)-5-[(4-chlorophenyl)methyl]-1,1,4-trioxo-7-[(4,4,4-trifluorobutyl)-carbamoyl]-2,3,4,5-tetrahydro-1λ⁶,5-benzothiazepin-3-yl]carbamate (Intermediate IX-17)

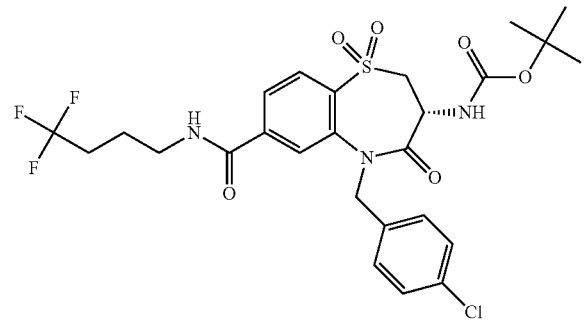 [SMILES: CC(C)(C)OC(=O)N[C@H]1CS(=O)(=O)c2ccc(C(=O)NCCCC(F)(F)F)cc2N(Cc2ccc(Cl)cc2)C1=O]

The title compound was synthesized according to general procedure GP4 to afford the title compound as off-white solid in 93% Yield.

LCMS: METCR1673 Generic 2 minutes, rt=1.43 min, M/Z (ES+) 626/628 [M+Na+] 100% UV NMR Data: 1H NMR (500 MHz, DMSO-d6) δ 8.86 (t, J=5.6 Hz, 1H), 8.01-7.92 (m, 2H), 7.81 (s, 1H), 7.51 (d, J=8.1 Hz, 1H), 7.37-7.30 (m, 4H), 5.20 (d, J=16.0 Hz, 1H), 4.85 (d, J=16.0 Hz, 1H), 4.43-4.33 (m, 1H), 4.07 (dd, J=13.2, 7.3 Hz, 1H), 3.77-3.70 (m, 1H), 3.43-3.34 (m, 2H), 2.36-2.23 (m, 2H), 1.81-1.63 (m, 2H), 1.36 (s, 9H).

Synthesis of tert-butyl N-[(3R)-5-[(4-chlorophenyl)methyl]-7-[(2-methylpropoxy)carbamoyl]-1,1,4-trioxo-2,3,4,5-tetrahydro-1λ⁶,5-benzothiazepin-3-yl]carbamate (Intermediate IX-18)

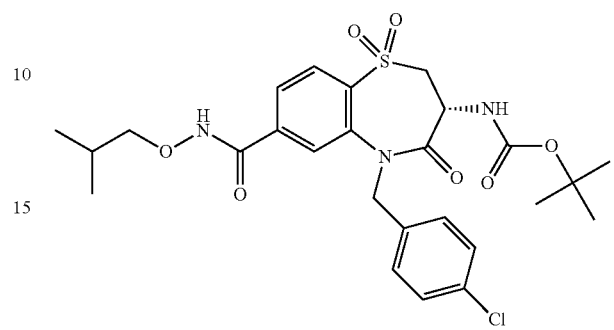

The title compound was synthesized according to general procedure GP4 to afford the title compound as white solid in 72% Yield.

LCMS: METCR1673 Generic 2 minutes, rt=1.41 min, M/Z (ES+) 588/590 [M+Na+] 96% UV NMR Data: 1H NMR (500 MHz, Chloroform-d) δ 8.47-7.41 (m, 4H), 7.33-7.27 (m, 4H), 5.70 (d, J=7.0 Hz, 1H), 5.39 (dd, J=36.7, 15.3 Hz, 1H), 4.66 (d, J=15.4 Hz, 2H), 4.06 (d, J=6.9 Hz, 1H), 3.91 (dd, J=6.9, 1.5 Hz, 1H), 3.76 (s, 1H), 3.57-3.43 (m, 1H), 2.12-1.93 (m, 1H), 1.41 (s, 9H), 0.97 (dd, J=16.1, 6.6 Hz, 6H)

Synthesis of tert-butyl N-[(3R)-5-[(4-chlorophenyl)methyl]-1,1,4-trioxo-7-(propoxycarbamoyl)-2,3,4,5-tetrahydro-1λ⁶,5-benzothiazepin-3-yl]carbamate (Intermediate IX-19)

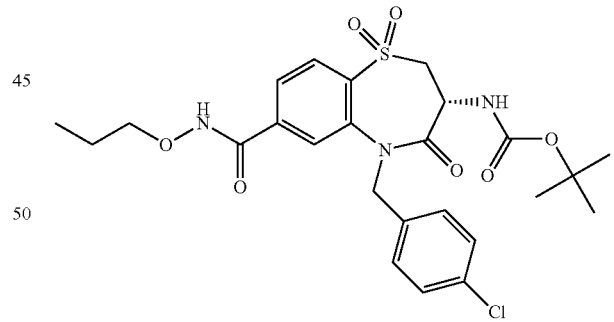

The title compound was synthesized according to general procedure GP4 to afford the title compound as white solid in 49% Yield.

LCMS: METCR1673 Generic 2 minutes, rt=1.35 min, M/Z (ES+) 574/576 [M+Na+] 100% UV NMR Data: 1H NMR (500 MHz, Chloroform-d) δ 8.06 (dd, J=36.0, 8.1 Hz, 4H), 7.35-7.27 (m, 4H), 5.70 (d, J=7.9 Hz, 1H), 5.39 (d, J=15.3 Hz, 1H), 4.65 (d, J=15.3 Hz, 2H), 4.08 (dt, J=14.1, 6.8 Hz, 2H), 3.95 (s, 1H), 3.57-3.42 (m, 1H), 1.72 (p, J=7.1 Hz, 2H), 1.41 (s, 9H), 0.99 (dt, J=14.9, 7.6 Hz, 3H)

Synthesis of tert-butyl N-[(3R)-5-[(4-chlorophenyl)methyl]-7-[(3-methylbutan-2-yl)carbamoyl]-1,1,4-trioxo-2,3,4,5-tetrahydro-1λ⁶,5-benzothiazepin-3-yl]carbamate (Intermediate IX-20)

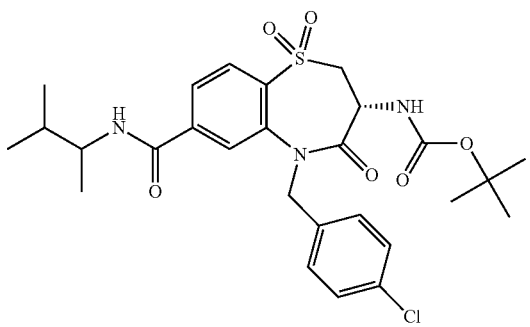 [SMILES: CC(C)C(C)NC(=O)c1ccc2c(c1)N(Cc1ccc(Cl)cc1)C(=O)[C@@H](NC(=O)OC(C)(C)C)CS2(=O)=O]

The title compound was synthesized according to general procedure GP4 to afford the title compound as white solid in 79% Yield.

LCMS: METCR1673 Generic 2 minutes, rt=1.46 min, M/Z (ES+) 586/588 [M+Na+] 99% UV NMR Data: 1H NMR (500 MHz, Chloroform-d) δ 8.09 (dd, J=8.1, 1.9 Hz, 1H), 7.78 (t, J=7.8 Hz, 1H), 7.51-7.41 (m, 1H), 7.34-7.27 (m, 4H), 5.70 (d, J=7.2 Hz, 1H), 5.64 (dd, J=27.2, 8.9 Hz, 1H), 5.46 (dd, J=15.3, 3.1 Hz, 1H), 4.60-4.47 (m, 2H), 4.12-3.96 (m, 2H), 3.51 (dd, J=13.2, 11.0 Hz, 1H), 1.78 (dq, J=13.1, 6.6 Hz, 1H), 1.41 (s, 9H), 1.16 (d, J=6.7 Hz, 3H), 0.92 (ddd, J=6.2, 4.2, 1.5 Hz, 6H)

Synthesis of tert-butyl N-[(3R)-5-[(4-chlorophenyl)methyl]-8-fluoro-7-(hexadecylcarbamoyl)-1,1,4-trioxo-2,3,4,5-tetrahydro-1λ⁶,5-benzothiazepin-3-yl]carbamate (Intermediate IX-21)

The title compound was synthesized according to general procedure GP4 to afford the title compound as white solid in 42% Yield.

LCMS: METCR1981, hydrophobic 3 minutes, rt=2.6 min, M/Z (ES+) 758/760 [M+Na+] 97% UV NMR Data: 1H NMR (500 MHz, DMSO-d6) δ 8.62 (t, J=5.5 Hz, 1H), 7.73 (d, J=8.4 Hz, 1H), 7.57-7.49 (m, 2H), 7.34 (s, 4H), 5.22 (d, J=16.1 Hz, 1H), 4.78 (d, J=16.1 Hz, 1H), 4.42 (dt, J=11.8, 7.8 Hz, 1H), 4.09 (dd, J=13.3, 7.3 Hz, 1H), 3.81-3.70 (m, 1H), 3.25-3.19 (m, 2H), 1.52-1.42 (m, 2H), 1.32-1.17 (m, 35H), 0.88-0.83 (m, 3H).

Synthesis of tert-butyl N-[(3R)-5-[(4-chlorophenyl)methyl]-7-(cyclopropylcarbamoyl)-8-fluoro-1,1,4-trioxo-2,3,4,5-tetrahydro-1λ⁶,5-benzothiazepin-3-yl]carbamate (Intermediate IX-22)

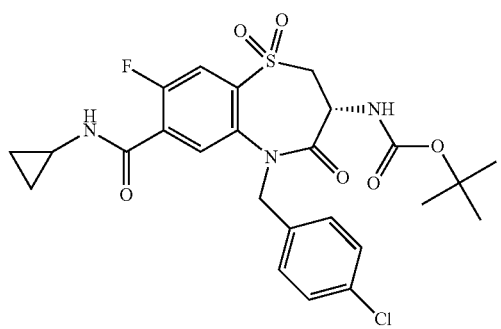

The title compound was synthesized according to general procedure GP4 to afford the title compound as white solid in 80% Yield.

LCMS: METCR1673 Generic 2 minutes, rt=1.35 min, M/Z (ES+) 574/576 [M+Na+] 100% UV NMR Data: 1H NMR (500 MHz, DMSO-d6) δ 8.72 (d, J=4.2 Hz, 1H), 7.72 (d, J=8.4 Hz, 1H), 7.60 (d, J=5.4 Hz, 1H), 7.51 (d, J=8.0 Hz, 1H), 7.39-7.30 (m, 4H), 5.17 (d, J=15.9 Hz, 1H), 4.84 (d, J=15.9 Hz, 1H), 4.39 (dt, J=11.6,

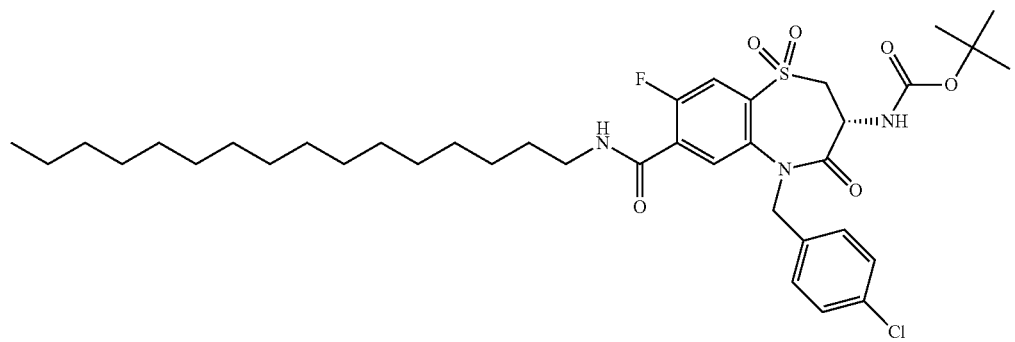 [SMILES: CCCCCCCCCCCCCCCCNC(=O)c1cc2c(cc1F)S(=O)(=O)C[C@H](NC(=O)OC(C)(C)C)C(=O)N2Cc1ccc(Cl)cc1]

7.6 Hz, 1H), 4.09 (dd, J=13.2, 7.4 Hz, 1H), 3.80-3.69 (m, 1H), 2.83 (dq, J=7.3, 3.7 Hz, 1H), 1.37 (s, 9H), 0.72 (d, J=5.5 Hz, 2H), 0.53 (dd, J=3.7, 1.9 Hz, 2H).

Synthesis of tert-butyl N-[(3R)-5-[(4-chlorophenyl)methyl]-7-(cyclobutylcarbamoyl)-8-fluoro-1,1,4-trioxo-2,3,4,5-tetrahydro-1λ⁶,5-benzothiazepin-3-yl]carbamate (Intermediate IX-23)

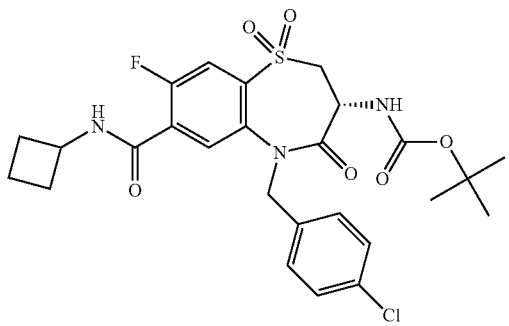 [SMILES: CC(C)(C)OC(=O)N[C@H]1CS(=O)(=O)c2cc(F)c(C(=O)NC3CCC3)cc2N(Cc2ccc(Cl)cc2)C1=O]

The title compound was synthesized according to general procedure GP4 to afford the title compound as white solid in 61% Yield.

LCMS: METCR1673 Generic 2 minutes, rt=1.44 min, M/Z (ES+) 588/590 [M+Na+] 97% UV NMR Data: 1H NMR (500 MHz, Chloroform-d) δ 8.00 (d, J=6.1 Hz, 1H), 7.80 (d, J=9.9 Hz, 1H), 7.30-7.26 (m, 4H), 6.84-6.72 (m, 1H), 5.70 (d, J=7.1 Hz, 1H), 5.16 (d, J=15.2 Hz, 1H), 4.83 (d, J=15.2 Hz, 1H), 4.60-4.46 (m, 2H), 4.08 (dd, J=13.3, 6.9 Hz, 1H), 3.51 (dd, J=13.2, 11.0 Hz, 1H), 2.50-2.40 (m, 2H), 2.05-1.93 (m, 2H), 1.88-1.74 (m, 2H), 1.40 (s, 9H)

Synthesis of tert-butyl N-[(3R)-5-[(4-chloro-2-fluorophenyl)methyl]-8-fluoro-1,1,4-trioxo-7-[(propan-2-yl)carbamoyl]-2,3,4,5-tetrahydro-1λ⁶,5-benzothiazepin-3-yl]carbamate (Intermediate IX-24)

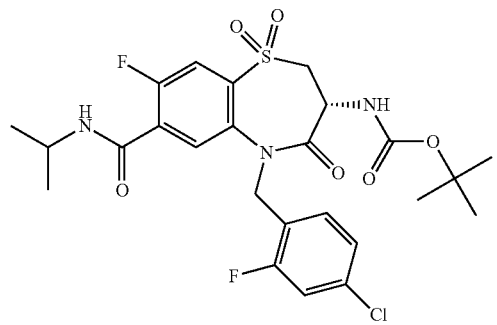 [SMILES: CC(C)NC(=O)c1cc2c(cc1F)S(=O)(=O)C[C@H](NC(=O)OC(C)(C)C)C(=O)N2Cc1ccc(Cl)cc1F]

The title compound was synthesized according to general procedure GP4 to afford the title compound as yellow solid in 85% Yield.

LCMS: METCR1673 Generic 2 minutes, rt=1.41 min, M/Z (ES+) 594/596 [M+Na+] 99% UV NMR Data: 1H NMR (500 MHz, Chloroform-d) δ 8.14 (d, J=6.0 Hz, 1H), 7.80 (d, J=9.8 Hz, 1H), 7.41 (t, J=8.1 Hz, 1H), 7.10 (dd, J=8.3, 1.7 Hz, 1H), 7.04 (dd, J=9.7, 2.0 Hz, 1H), 6.56-6.44 (m, 1H), 5.66 (d, J=7.2 Hz, 1H), 5.08 (d, J=15.2 Hz, 1H), 5.01 (d, J=15.1 Hz, 1H), 4.49 (dt, J=10.9, 7.0 Hz, 1H), 4.34-4.25 (m, 1H), 4.04 (dd, J=13.4, 6.9 Hz, 1H), 3.46 (dd, J=13.3, 11.1 Hz, 1H), 1.40 (s, 9H), 1.30 (dd, J=6.6, 2.0 Hz, 6H)

Synthesis of tert-butyl N-[(3R)-5-[(3,4-dichlorophenyl)methyl]-1,1,4-trioxo-7-[(propan-2-yl)carbamoyl]-2,3,4,5-tetrahydro-1λ⁶,5-benzothiazepin-3-yl]carbamate (Intermediate IX-25)

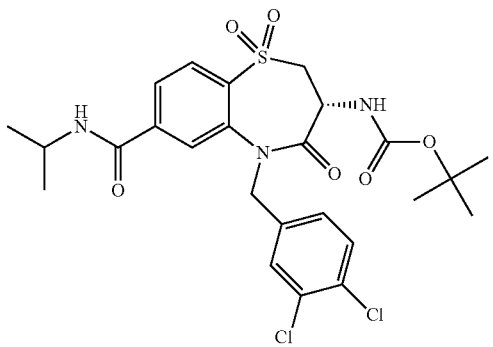 [SMILES: CC(C)NC(=O)c1ccc2c(c1)N(Cc1ccc(Cl)c(Cl)c1)C(=O)[C@@H](NC(=O)OC(C)(C)C)CS2(=O)=O]

The title compound was synthesized according to general procedure GP4 to afford the title compound as cream solid in 90% Yield.

LCMS: METCR1673 Generic 2 minutes, rt=1.42 min, M/Z (ES+) 592/594 [M+Na+] 100% UV NMR Data: 1H NMR (500 MHz, Chloroform-d) δ 8.09 (d, J=8.1 Hz, 1H), 7.75 (dd, J=8.1, 1.4 Hz, 1H), 7.60 (d, J=1.4 Hz, 1H), 7.46 (d, J=2.1 Hz, 1H), 7.41 (d, J=8.2 Hz, 1H), 7.18 (dd, J=8.2, 2.0 Hz, 1H), 5.76 (d, J=7.5 Hz, 1H), 5.66 (d, J=7.3 Hz, 1H), 5.31 (d, J=15.4 Hz, 1H), 4.64 (d, J=15.4 Hz, 1H), 4.53 (dt, J=10.9, 7.2 Hz, 1H), 4.25 (dq, J=13.1, 6.5 Hz, 1H), 4.06 (dd, J=13.4, 7.0 Hz, 1H), 3.50 (dd, J=13.3, 11.1 Hz, 1H), 1.41 (s, 9H), 1.26 (d, J=6.6 Hz, 6H)

Synthesis of tert-butyl N-[(3R)-5-[(4-chloro-3-fluorophenyl)methyl]-1,1,4-trioxo-7-[(propan-2-yl)carbamoyl]-2,3,4,5-tetrahydro-1λ⁶,5-benzothiazepin-3-yl]carbamate (Intermediate IX-26)

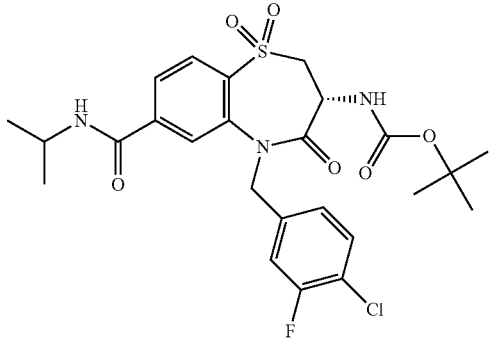 [SMILES: CC(C)NC(=O)c1ccc2c(c1)N(Cc1ccc(Cl)c(F)c1)C(=O)[C@@H](NC(=O)OC(C)(C)C)CS2(=O)=O]

The title compound was synthesized according to general procedure GP4 to afford the title compound as cream solid in 100% Yield.

LCMS: METCR1673 Generic 2 minutes, rt=1.38 min, M/Z (ES+) 576/578 [M+Na+] 100% UV NMR Data: 1H NMR (500 MHz, Chloroform-d) δ 8.09 (d, J=8.1 Hz, 1H), 7.73 (dd, J=8.1, 1.4 Hz, 1H), 7.62 (d, J=1.5 Hz, 1H), 7.36 (t, J=7.8 Hz, 1H), 7.18 (dd, J=9.6, 2.0 Hz, 1H), 7.10-7.03 (m, 1H), 5.77 (d, J=7.4 Hz, 1H), 5.66 (d, J=7.4 Hz, 1H), 5.33 (d, J=15.4 Hz, 1H), 4.65 (d, J=15.4 Hz, 1H), 4.53 (dt, J=10.9, 7.2 Hz, 1H), 4.25 (dq, J=13.2, 6.6 Hz, 1H), 4.06 (dd, J=13.3, 6.9 Hz, 1H), 3.50 (dd, J=13.3, 11.1 Hz, 1H), 1.41 (s, 9H), 1.26 (dd, J=6.6, 0.9 Hz, 6H)

Synthesis of tert-butyl N-[(3R)-5-[(4-chlorophenyl)methyl]-7-[(cyclohexyloxy)carbamoyl]-1,1,4-trioxo-2,3,4,5-tetrahydro-1λ⁶,5-benzothiazepin-3-yl]carbamate (Intermediate IX-27)

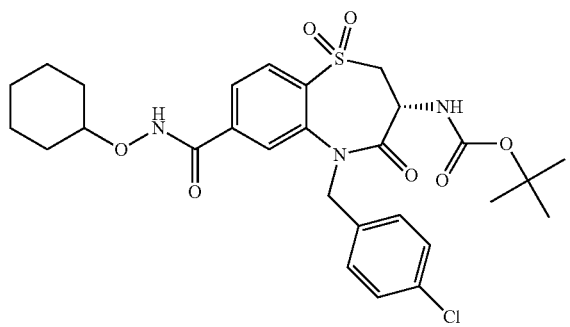 [SMILES: CC(C)(C)OC(=O)N[C@H]1CS(=O)(=O)c2ccc(C(=O)NOC3CCCCC3)cc2N(Cc2ccc(Cl)cc2)C1=O]

The title compound was synthesized according to general procedure GP4 to afford the title compound as colourless oil in 43% Yield.

LCMS: METCR1673 Generic 2 minutes, rt=1.45 min, M/Z (ES+) 614/616 [M+Na+] 91% UV NMR Data: 1H NMR (500 MHz, Chloroform-d) δ 1.18-1.50 (m, 15H), 1.78 (s, 2H), 1.99 (s, 2H), 3.43-3.58 (m, 1H), 3.83-4.15 (m, 2H), 4.42-4.65 (m, 2H), 5.33-5.49 (m, 1H), 5.73 (d, J=7.1 Hz, 1H), 7.26-7.33 (m, 4H), 7.37-7.62 (m, 1H), 7.63-7.93 (m, 1H), 7.93-8.08 (m, 1H), 8.83 (s, 1H).

Synthesis of tert-butyl N-[(3R)-5-[(4-chlorophenyl)methyl]-7-[(cyclohexylmethoxy)carbamoyl]-1,1,4-trioxo-2,3,4,5-tetrahydro-1λ⁶,5-benzothiazepin-3-yl]carbamate (Intermediate IX-28)

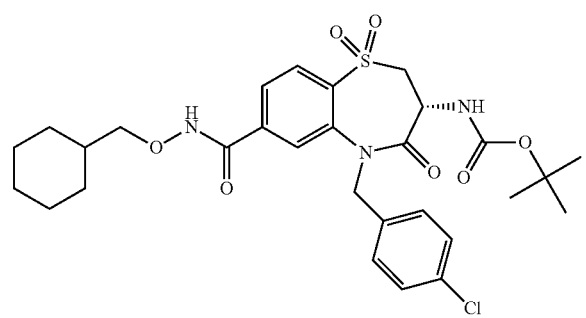 [SMILES: CC(C)(C)OC(=O)N[C@H]1CS(=O)(=O)c2ccc(C(=O)NOCC3CCCCC3)cc2N(Cc2ccc(Cl)cc2)C1=O]

The title compound was synthesized according to general procedure GP4 to afford the title compound as colourless oil in 82% Yield.

LCMS: METCR1673 Generic 2 minutes, rt=1.53 min, M/Z (ES+) 628/630 [M+Na+] 99% UV NMR Data: 1H NMR (500 MHz, Chloroform-d) δ 0.90-1.08 (m, 2H), 1.12-1.34 (m, 3H), 1.40 (s, 9H), 1.64-1.85 (m, 6H), 3.43-3.58 (m, 1H), 3.78 (s, 1H), 3.88-3.98 (m, 1H), 3.98-4.13 (m, 1H), 4.44-4.73 (m, 2H), 5.28-5.44 (m, 1H), 5.66-5.76 (m, 1H), 7.26-7.33 (m, 4H), 7.43-7.94 (m, 2H), 7.98-8.09 (m, 1H), 8.79 (s, 1H)

Synthesis of tert-butyl N-[(3R)-5-[(4-chlorophenyl)methyl]-8-fluoro-1,1,4-trioxo-7-[(2,2,2-trifluoroethyl)carbamoyl]-2,3,4,5-tetrahydro-1λ⁶,5-benzothiazepin-3-yl]carbamate (Intermediate IX-29)

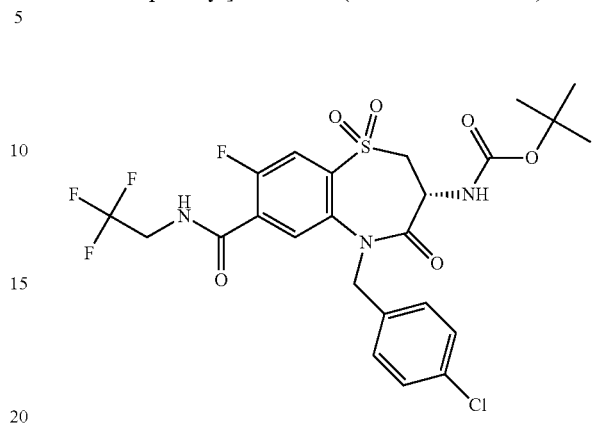

The title compound was synthesized according to general procedure GP4 to afford the title compound as off-white solid in 73% Yield.

LCMS: METCR1673 Generic 2 minutes, rt=1.41 min, M/Z (ES+) 616/618 [M+Na+] 100% UV NMR Data: 1H NMR (500 MHz, DMSO-d6) δ 8.00 (d, J=6.0 Hz, 1H), 7.86 (d, J=9.9 Hz, 1H), 7.27 (d, J=13.2 Hz, 6H), 6.98-6.83 (m, 1H), 5.70 (d, J=7.1 Hz, 1H), 5.19 (d, J=15.2 Hz, 1H), 4.83 (d, J=15.2 Hz, 1H), 4.52 (dt, J=11.0, 7.0 Hz, 1H), 4.25-4.00 (m, 1H), 3.53 (dd, J=13.3, 11.1 Hz, 1H), 1.40 (s, 9H).

Synthesis of tert-butyl N-[(3R)-5-[(4-chlorophenyl)methyl]-8-fluoro-1,1,4-trioxo-7-[(3,3,3-trifluoropropyl)carbamoyl]-2,3,4,5-tetrahydro-1λ⁶,5-benzothiazepin-3-yl]carbamate (Intermediate IX-30)

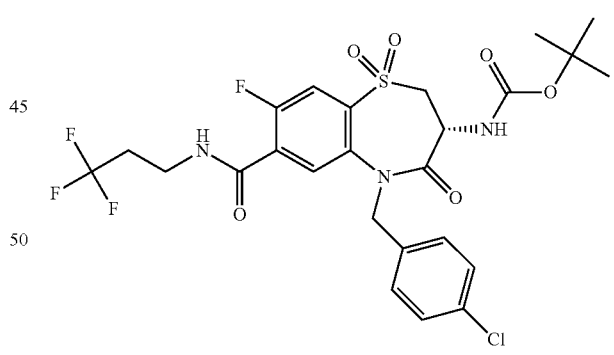

The title compound was synthesized according to general procedure GP4 to afford the title compound as off-white solid in 76% Yield.

LCMS: METCR1673 Generic 2 minutes, rt=1.44 min, M/Z (ES+) 630/632 [M+Na+] 100% UV NMR Data: 1H NMR (500 MHz, DMSO-d6) δ 7.98 (d, J=6.1 Hz, 1H), 7.82 (d, J=9.9 Hz, 1H), 7.31-7.24 (m, 5H), 7.01-6.82 (m, 1H), 5.70 (d, J=7.2 Hz, 1H), 5.19 (d, J=15.2 Hz, 1H), 4.82 (d, J=15.2 Hz, 1H), 4.66-4.41 (m, 1H), 4.09 (dd, J=13.5, 6.9 Hz, 1H), 3.75 (p, J=5.9 Hz, 1H), 3.52 (dd, J=13.4, 11.1 Hz, 1H), 2.54-2.38 (m, 2H), 1.40 (s, 9H).

187

Synthesis of tert-butyl N-[(3R)-5-[(4-chlorophenyl)methyl]-8-fluoro-1,1,4-trioxo-7-{[(2S)-1,1,1-trifluoropropan-2-yl]carbamoyl}-2,3,4,5-tetrahydro-1λ⁶,5-benzothiazepin-3-yl]carbamate (Intermediate IX-31)

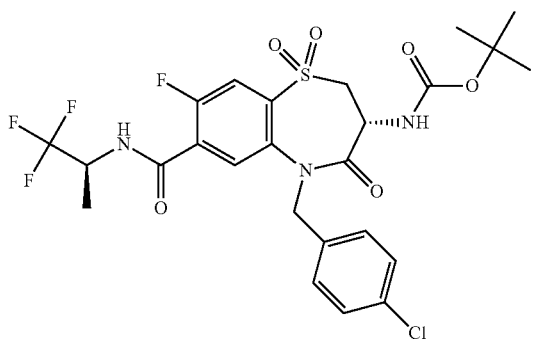 [SMILES: C[C@H](NC(=O)c1cc2c(cc1F)S(=O)(=O)C[C@H](NC(=O)OC(C)(C)C)C(=O)N2Cc1ccc(Cl)cc1)C(F)(F)F]

The title compound was synthesized according to general procedure GP4 to afford the title compound as off-white solid in 85% Yield.

LCMS: METCR1673 Generic 2 minutes, rt=1.46 min, M/Z (ES+) 630/632 [M+Na+] 100% UV Synthesis of tert-butyl N-[(3R)-7-[(butan-2-yl)carbamoyl]-5-[(4-chlorophenyl)methyl]-8-fluoro-1,1,4-trioxo-2,3,4,5-tetrahydro-1λ⁶,5-benzothiazepin-3-yl]carbamate (Intermediate IX-32)

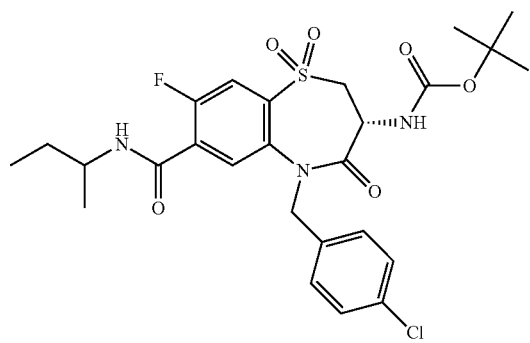 [SMILES: CCC(C)NC(=O)c1cc2c(cc1F)S(=O)(=O)C[C@H](NC(=O)OC(C)(C)C)C(=O)N2Cc1ccc(Cl)cc1]

The title compound was synthesized according to general procedure GP4 to afford the title compound as white solid in 79% Yield.

LCMS: METCR1673 Generic 2 minutes, rt=1.47 min, M/Z (ES+) 590/592 [M+Na+] 100% UV NMR Data: 1H NMR (500 MHz, DMSO-d6) δ 8.41 (d, J=8.2 Hz, 1H), 7.72 (d, J=8.3 Hz, 1H), 7.54-7.48 (m, 2H), 7.33 (s, 4H), 5.23 (d, J=15.9 Hz, 1H), 4.77 (d, J=15.9 Hz, 1H), 4.40 (dt, J=11.7, 7.7 Hz, 1H), 4.09 (dd, J=13.3, 7.3 Hz, 1H), 3.84 (dt, J=14.0, 7.3 Hz, 1H), 3.79-3.73 (m, 1H), 1.45 (ddd, J=20.9, 14.3, 7.0 Hz, 2H), 1.37 (s, 9H), 1.10 (d, J=6.6 Hz, 3H), 0.82 (t, J=7.4 Hz, 3H).

188

Synthesis of tert-butyl N-[(3R)-7-(tert-butylcarbamoyl)-5-[(4-chlorophenyl)methyl]-8-fluoro-1,1,4-trioxo-2,3,4,5-tetrahydro-1λ⁶,5-benzothiazepin-3-yl]carbamate (Intermediate IX-33)

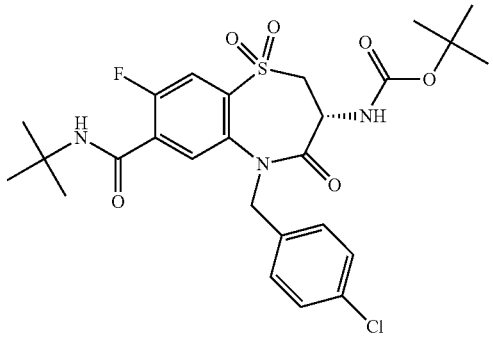 [SMILES: CC(C)(C)NC(=O)c1cc2c(cc1F)S(=O)(=O)C[C@H](NC(=O)OC(C)(C)C)C(=O)N2Cc1ccc(Cl)cc1]

The title compound was synthesized according to general procedure GP4 to afford the title compound as white solid in 55% Yield.

LCMS: METCR1673 Generic 2 minutes, rt=1.49 min, M/Z (ES+) 590/592 [M+Na+] 98% UV NMR Data: 1H NMR (500 MHz, DMSO-d6) δ 8.19 (s, 1H), 7.70 (d, J=8.2 Hz, 1H), 7.50 (dd, J=11.7, 6.8 Hz, 2H), 7.36-7.31 (m, 4H), 5.21 (d, J=15.9 Hz, 1H), 4.79 (d, J=15.9 Hz, 1H), 4.38 (dt, J=11.7, 7.7 Hz, 1H), 4.09 (dd, J=13.3, 7.3 Hz, 1H), 3.80-3.68 (m, 1H), 1.36 (s, 9H), 1.33 (s, 9H).

Synthesis of tert-butyl N-[(3R)-7-[(tert-butoxy)carbamoyl]-5-[(4-chlorophenyl)methyl]-1,1,4-trioxo-2,3,4,5-tetrahydro-1λ⁶,5-benzothiazepin-3-yl]carbamate (Intermediate IX-34)

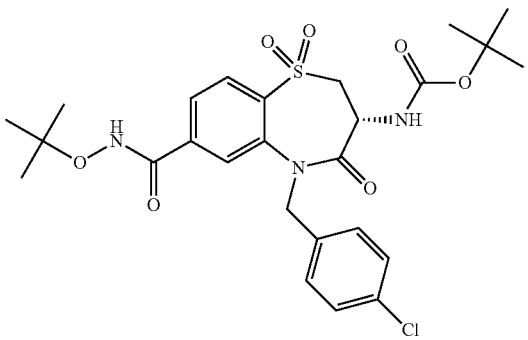 [SMILES: CC(C)(C)ONC(=O)c1ccc2c(c1)N(Cc1ccc(Cl)cc1)C(=O)[C@@H](NC(=O)OC(C)(C)C)CS2(=O)=O]

The title compound was synthesized according to general procedure GP4 to afford the title compound as white solid in 50% Yield.

LCMS: METCR1673 Generic 2 minutes, rt=1.38 min, M/Z (ES+) 588/590 [M+Na+] 99% UV NMR Data: 1H NMR (500 MHz, DMSO-d6) δ 11.23 (s, 1H), 7.98 (d, J=8.2 Hz, 1H), 7.87 (d, J=8.2 Hz, 1H), 7.65 (s, 1H), 7.52 (d, J=8.1 Hz, 1H), 7.39-7.31 (m, 4H), 5.30 (d, J=16.3 Hz, 1H), 4.73 (d, J=16.2 Hz, 1H), 4.39 (dt, J=11.6, 7.6 Hz, 1H), 4.11-4.08 (m, 1H), 3.80-3.71 (m, 1H), 1.37 (s, 9H), 1.19 (s, 9H).

Synthesis of tert-butyl N-[(3R)-7-[(but-3-en-1-yl)carbamoyl]-5-[(4-chlorophenyl)methyl]-1,1,4-trioxo-2,3,4,5-tetrahydro-1λ⁶,5-benzothiazepin-3-yl]carbamate (Intermediate IX-35)

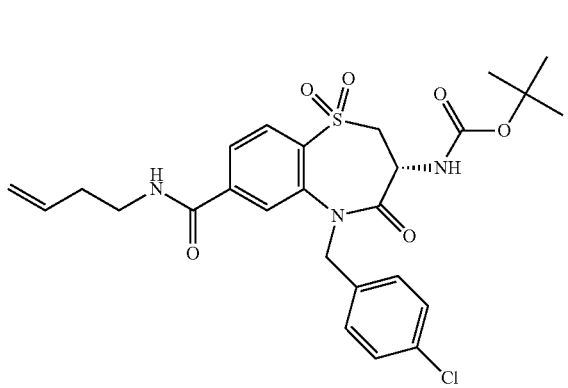 [SMILES: C=CCCNC(=O)c1ccc2c(c1)N(Cc1ccc(Cl)cc1)C(=O)[C@@H](NC(=O)OC(C)(C)C)CS2(=O)=O]

The title compound was synthesized according to general procedure GP4 to afford the title compound as white solid in 13% Yield.

LCMS: METCR1673 Generic 2 minutes, rt=1.38 min, M/Z (ES+) 570/572 [M+Na+] 91% UV

Synthesis of tert-butyl N-[(3R)-5-[(4-chlorophenyl)methyl]-8-fluoro-1,1,4-trioxo-7-{[(1S,2R)-2-phenylcyclopropyl]carbamoyl}-2,3,4,5-tetrahydro-1λ⁶,5-benzothiazepin-3-yl]carbamate (Intermediate IX-36)

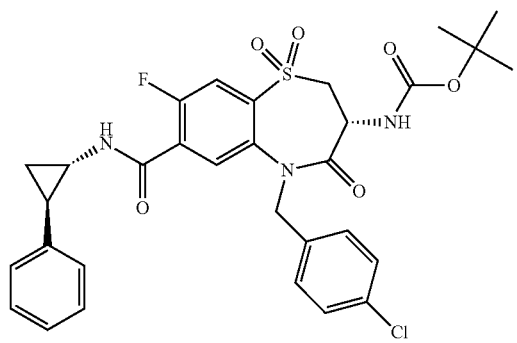 [SMILES: CC(C)(C)OC(=O)N[C@H]1CS(=O)(=O)c2cc(F)c(C(=O)N[C@H]3C[C@@H]3c3ccccc3)cc2N(Cc2ccc(Cl)cc2)C1=O]

The title compound was synthesized according to general procedure GP4 to afford the title compound as white solid in 77% Yield.

LCMS: METCR1673 Generic 2 minutes, rt=1.52 min, M/Z (ES+) 650/652 [M+Na+] 100% UV NMR Data: 1H NMR (500 MHz, DMSO-d6) δ 8.97 (s, 1H), 7.74 (d, J=8.3 Hz, 1H), 7.65 (d, J=5.3 Hz, 1H), 7.51 (d, J=8.0 Hz, 1H), 7.40-7.31 (m, 4H), 7.28 (t, J=7.4 Hz, 2H), 7.17 (dd, J=16.6, 7.6 Hz, 3H), 5.16 (d, J=15.9 Hz, 1H), 4.85 (d, J=15.5 Hz, 1H), 4.43-4.35 (m, 1H), 4.09 (dd, J=12.8, 8.2 Hz, 1H), 3.75 (t, J=12.5 Hz, 1H), 3.06-2.99 (m, 1H), 1.36 (s, 9H), 1.31-1.21 (m, 3H).

Synthesis of tert-butyl N-[(3R)-5-[(4-chlorophenyl)methyl]-8-fluoro-7-[(1-methylcyclopropyl)carbamoyl]-1,1,4-trioxo-2,3,4,5-tetrahydro-1λ⁶,5-benzothiazepin-3-yl]carbamate (Intermediate IX-37)

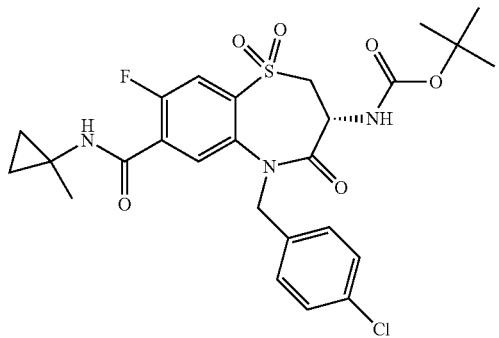 [SMILES: CC1(NC(=O)c2cc3c(cc2F)S(=O)(=O)C[C@H](NC(=O)OC(C)(C)C)C(=O)N3Cc2ccc(Cl)cc2)CC1]

The title compound was synthesized according to general procedure GP4 to afford the title compound as white solid in 63% Yield.

LCMS: METCR1673 Generic 2 minutes, rt=1.41 min, M/Z (ES+) 588/590 [M+Na+] 100% UV NMR Data: 1H NMR (500 MHz, DMSO-d6) δ 8.84 (s, 1H), 7.70 (d, J=8.4 Hz, 1H), 7.55 (d, J=5.5 Hz, 1H), 7.50 (d, J=8.1 Hz, 1H), 7.36-7.29 (m, 4H), 5.17 (d, J=15.8 Hz, 1H), 4.81 (d, J=15.9 Hz, 1H), 4.37 (dt, J=11.7, 7.7 Hz, 1H), 4.07 (dd, J=13.3, 7.3 Hz, 1H), 3.77-3.69 (m, 1H), 1.41-1.27 (m, 12H), 0.74-0.67 (m, 2H), 0.64-0.59 (m, 2H).

Synthesis of tert-butyl N-[(3R)-5-[(4-chlorophenyl)methyl]-8-fluoro-7-[(1-methylcyclobutyl)carbamoyl]-1,1,4-trioxo-2,3,4,5-tetrahydro-1λ⁶,5-benzothiazepin-3-yl]carbamate (Intermediate IX-38)

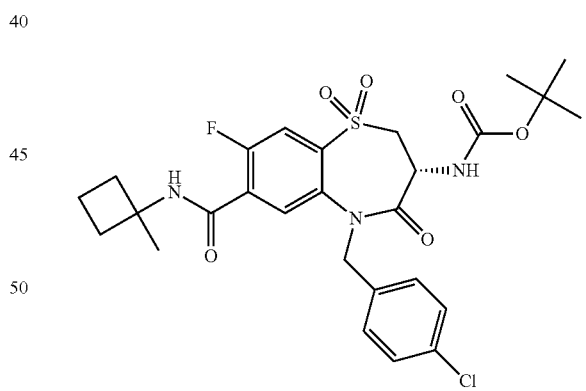

The title compound was synthesized according to general procedure GP4 to afford the title compound as white solid in 66% Yield.

LCMS: METCR1673 Generic 2 minutes, rt=1.51 min, M/Z (ES+) 602/604 [M+Na+] 100% UV NMR Data: 1H NMR (500 MHz, DMSO-d6) δ 8.65 (s, 1H), 7.71 (d, J=8.3 Hz, 1H), 7.55 (d, J=5.5 Hz, 1H), 7.51 (d, J=8.1 Hz, 1H), 7.34 (s, 4H), 5.19 (d, J=15.9 Hz, 1H), 4.81 (d, J=15.9 Hz, 1H), 4.38 (dt, J=11.7, 7.7 Hz, 1H), 4.08 (dd, J=13.3, 7.3 Hz, 1H), 3.80-3.68 (m, 1H), 2.35-2.24 (m, 2H), 1.96 (dt, J=12.2, 6.2 Hz, 2H), 1.80 (ddd, J=15.4, 9.6, 6.5 Hz, 2H), 1.44 (s, 3H), 1.36 (s, 9H).

Synthesis of tert-butyl N-[(3R)-5-[(4-chlorophenyl)methyl]-7-[(2,2-dimethylcyclopropyl)-carbamoyl]-8-fluoro-1,1,4-trioxo-2,3,4,5-tetrahydro-1λ⁶,5-benzothiazepin-3-yl]carbamate (Intermediate IX-39)

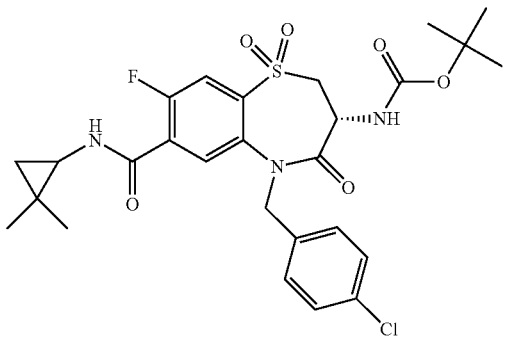 [SMILES: CC(C)(C)OC(=O)N[C@H]1CS(=O)(=O)c2cc(F)c(C(=O)NC3CC3(C)C)cc2N(Cc2ccc(Cl)cc2)C1=O]

The title compound was synthesized according to general procedure GP4 to afford the title compound as white solid in 56% Yield.

LCMS: METCR1673 Generic 2 minutes, rt=1.49 min, M/Z (ES+) 602/604 [M+Na+] 100% UV NMR Data: 1H NMR (500 MHz, DMSO-d6) δ 8.60 (d, J=4.1 Hz, 1H), 7.73 (d, J=8.3 Hz, 1H), 7.51 (dd, J=10.5, 6.7 Hz, 2H), 7.33 (s, 4H), 5.24 (d, J=15.9 Hz, 1H), 4.77 (d, J=15.9 Hz, 1H), 4.40 (dt, J=11.7, 7.8 Hz, 1H), 4.12-4.09 (m, 1H), 3.81-3.73 (m, 1H), 2.55 (dt, J=8.3, 4.3 Hz, 1H), 1.37 (s, 9H), 1.06 (s, 3H), 0.93 (s, 3H), 0.68 (dd, J=7.9, 5.3 Hz, 1H), 0.43 (t, J=4.7 Hz, 1H).

Synthesis of tert-butyl N-[(3R)-5-[(4-chlorophenyl)methyl]-7-[(3,3-difluorocyclobutyl)carbamoyl]-8-fluoro-1,1,4-trioxo-2,3,4,5-tetrahydro-1λ⁶,5-benzothiazepin-3-yl]carbamate (Intermediate IX-40)

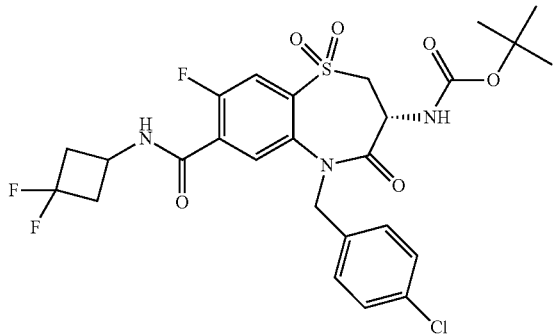

The title compound was synthesized according to general procedure GP4 to afford the title compound as off-white solid in 67% Yield.

LCMS: METCR1673 Generic 2 minutes, rt=1.45 min, M/Z (ES+) 624/626 [M+Na+] 98% UV NMR Data: 1H NMR (500 MHz, DMSO-d6) δ 9.14 (d, J=6.5 Hz, 1H), 7.76 (d, J=8.5 Hz, 1H), 7.66 (d, J=5.5 Hz, 1H), 7.52 (d, J=8.1 Hz, 1H), 7.33 (s, 4H), 5.17 (d, J=15.9 Hz, 1H), 4.85 (d, J=15.9 Hz, 1H), 4.40 (dt, J=11.8, 7.7 Hz, 1H), 4.28-4.19 (m, 1H), 4.10 (dd, J=13.3, 7.3 Hz, 1H), 3.80-3.71 (m, 1H), 3.06-2.91 (m, 2H), 2.76-2.61 (m, 2H), 1.37 (s, 9H).

Synthesis of tert-butyl N-[(3R)-7-(benzylcarbamoyl)-5-[(4-chlorophenyl)methyl]-8-fluoro-1,1,4-trioxo-2,3,4,5-tetrahydro-1λ⁶,5-benzothiazepin-3-yl]carbamate (Intermediate IX-41)

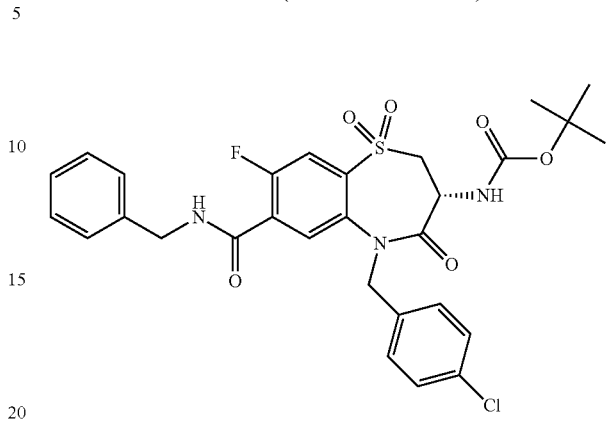

The title compound was synthesized according to general procedure GP4 to afford the title compound as white solid in 70% Yield.

LCMS: METCR1673 Generic 2 minutes, rt=1.49 min, M/Z (ES+) 624/626 [M+Na+] 99% UV NMR Data: 1H NMR (500 MHz, DMSO-d6) δ 9.20 (t, J=5.9 Hz, 1H), 7.75 (d, J=8.5 Hz, 1H), 7.62 (d, J=5.5 Hz, 1H), 7.51 (d, J=8.0 Hz, 1H), 7.40-7.20 (m, 9H), 5.21 (d, J=16.0 Hz, 1H), 4.79 (d, J=16.0 Hz, 1H), 4.52-4.38 (m, 3H), 4.09 (dd, J=12.9, 7.0 Hz, 1H), 3.80-3.71 (m, 1H), 1.36 (s, 9H).

Synthesis of tert-butyl N-[(3R)-5-[(4-chlorophenyl)methyl]-8-fluoro-7-(heptylcarbamoyl)-1,1,4-trioxo-2,3,4,5-tetrahydro-1λ⁶,5-benzothiazepin-3-yl]carbamate (Intermediate IX-42)

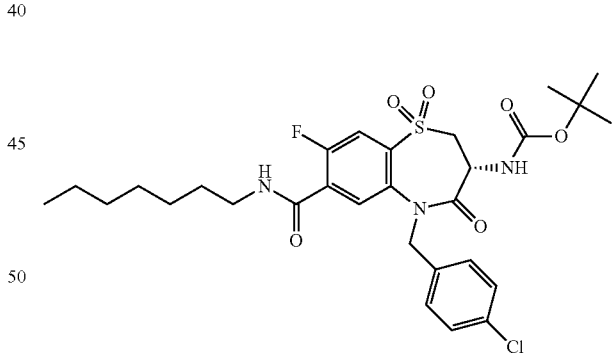

The title compound was synthesized according to general procedure GP4 to afford the title compound as off-white solid in 84% Yield.

LCMS: METCR1673 Generic 2 minutes, rt=1.72 min, M/Z (ES+) 632/634 [M+Na+] 95% UV NMR Data: 1H NMR (500 MHz, DMSO-d6) δ 8.62 (t, J=5.4 Hz, 1H), 7.74 (d, J=8.4 Hz, 1H), 7.59-7.50 (m, 2H), 7.40-7.32 (m, 4H), 5.21 (d, J=16.1 Hz, 1H), 4.79 (d, J=16.0 Hz, 1H), 4.42 (dt, J=11.6, 7.5 Hz, 1H), 4.15-4.04 (m, 1H), 3.84-3.72 (m, 1H), 3.21 (dq, J=12.8, 6.3, 5.8 Hz, 2H), 1.52-1.43 (m, 2H), 1.40-1.19 (m, 17H), 0.87 (t, J=7.0 Hz, 3H).

Synthesis of tert-butyl N-[(3R)-5-[(4-chlorophenyl)methyl]-7-[(3,3-difluorocyclopentyl)carbamoyl]-8-fluoro-1,1,4-trioxo-2,3,4,5-tetrahydro-1λ⁶,5-benzothiazepin-3-yl]carbamate (Intermediate IX-43)

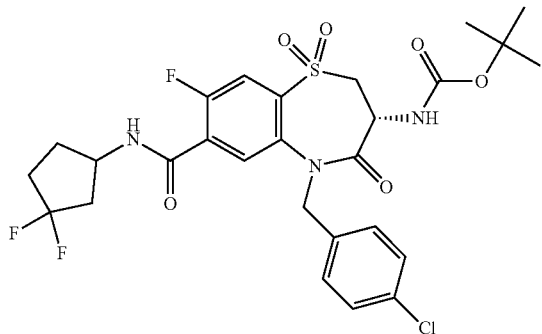 [SMILES: CC(C)(C)OC(=O)N[C@H]1CS(=O)(=O)c2cc(F)c(C(=O)NC3CCC(F)(F)C3)cc2N(Cc2ccc(Cl)cc2)C1=O]

The title compound was synthesized according to general procedure GP4 to afford the title compound as white solid in 75% Yield.

LCMS: METCR1673 Generic 2 minutes, rt=1.31 min, M/Z (ES+) 638/640 [M+Na+] 96% UV NMR Data: 1H NMR (500 MHz, DMSO-d6) δ 8.89 (d, J=6.9 Hz, 1H), 7.75 (d, J=8.4 Hz, 1H), 7.61 (d, J=5.3 Hz, 1H), 7.52 (d, J=8.0 Hz, 1H), 7.34 (s, 4H), 5.19 (d, J=15.9 Hz, 1H), 4.83 (d, J=16.0 Hz, 1H), 4.39 (dq, J=15.3, 7.8 Hz, 2H), 4.10 (dd, J=13.2, 7.3 Hz, 1H), 3.82-3.71 (m, 1H), 2.31-2.18 (m, 1H), 2.18-2.03 (m, 4H), 1.77 (dd, J=20.2, 7.2 Hz, 1H), 1.37 (s, 9H).

Synthesis of tert-butyl N-[(2R,3R)-5-[(4-chlorophenyl)methyl]-7-[(2,2-difluorocyclopropyl)-carbamoyl]-2-methyl-1,1,4-trioxo-2,3,4,5-tetrahydro-1λ⁶,5-benzothiazepin-3-yl]carbamate (Intermediate IX-44)

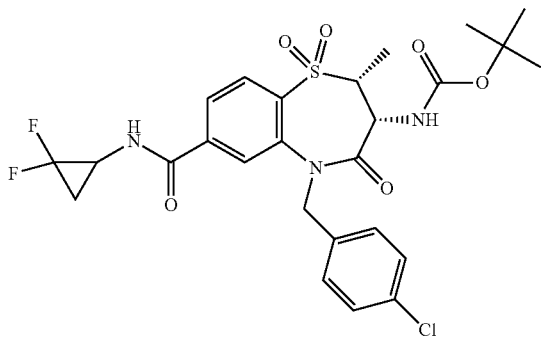 [SMILES: C[C@@H]1[C@H](NC(=O)OC(C)(C)C)C(=O)N(Cc2ccc(Cl)cc2)c2cc(C(=O)NC3CC3(F)F)ccc2S1(=O)=O]

The title compound was synthesized according to general procedure GP4 to afford the title compound as off-white solid in 81% Yield.

LCMS: METCR1673 Generic 2 minutes, rt=1.27 min, M/Z (ES+) 606/608 [M+Na+] 99% UV NMR Data: 1H NMR (500 MHz, DMSO-d6) δ 9.16 (s, 1H), 8.08 (d, J=8.1 Hz, 1H), 8.03-7.96 (m, 1H), 7.83 (d, J=11.1 Hz, 1H), 7.42-7.31 (m, 4H), 7.25 (s, 1H), 5.23-5.12 (m, 1H), 4.88 (t, J=16.4 Hz, 1H), 4.63 (s, 1H), 4.09-3.94 (m, 1H), 3.48 (s, 1H), 2.01 (s, 1H), 1.67 (d, J=6.2 Hz, 1H), 1.46-1.29 (m, 12H)

Synthesis of tert-butyl N-[(3R)-7-(butylcarbamoyl)-5-[(4-chlorophenyl)methyl]-1,4-dioxo-2,3,4,5-tetrahydro-1λ⁴,5-benzothiazepin-3-yl]carbamate (Intermediate IX-45)

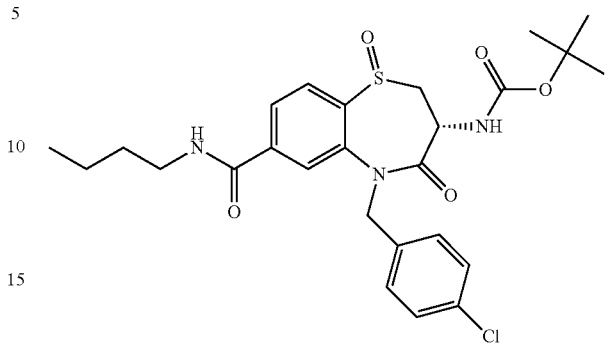

Intermediate VIII-80 (37 mg, 0.07 mmol) was dissolved in MeOH (1 mL) and the reaction mixture was cooled down to 0° C. m-CPBA (77%, 43 mg, 0.22 mmol) in water (1 mL) was added portion-wise. The reaction mixture was stirred at 0° C. for 1 h and then at RT for 12 h. After dilution with EtOAc (8 mL), the mixture was washed with water (5 mL×2) and brine (5 mL). The organic phase was dried over sodium sulfate, filtered and the filtrate was concentrated under reduced pressure. The residue was purified by reverse-phase column chromatography (Biotage C18 SNAP cartridge, eluent: water, 0-100% MeCN) to afford the desired sulfoxide intermediate IX-45 as a white solid (19 mg, 48%) in 94% purity (the corresponding sulfone (Intermediate IX-04) was also isolated as a white solid (10 mg, 24%, analytical data listed above)).

LCMS: METCR1416 Generic 7 minutes, rt=1.41 min, M/Z (ES+) 556/558 [M+Na+] 100% UV NMR Data: 1H NMR (500 MHz, DMSO-d6) δ 8.69 (t, J=5.6 Hz, 1H), 8.03 (dd, J=8.1, 1.2 Hz, 1H), 8.01-7.97 (m, 1H), 7.71 (d, J=8.1 Hz, 1H), 7.45 (d, J=7.9 Hz, 1H), 7.34 (d, J=8.4 Hz, 2H), 7.22 (d, J=8.4 Hz, 2H), 5.32 (d, J=15.2 Hz, 1H), 4.82 (d, J=15.2 Hz, 1H), 4.14 (dt, J=10.7, 8.2 Hz, 1H), 3.98 (t, J=11.1 Hz, 1H), 3.30-3.22 (m, 3H), 1.54 (p, J=7.1 Hz, 2H), 1.35 (s, 11H), 0.92 (t, J=7.4 Hz, 3H).

Syntheses of tert-butyl N-[(3R)-5-[(4-chlorophenyl)methyl]-7-{[(1S)-2,2-difluorocyclopropyl]carbamoyl}-8-fluoro-1,1,4-trioxo-2,3,4,5-tetrahydro-1λ⁶,5-benzothiazepin-3-yl]carbamate (intermediate IX-46) and tert-butyl N-[(3R)-5-[(4-chlorophenyl)methyl]-7-{[(1R)-2,2-difluorocyclopropyl]carbamoyl}-8-fluoro-1,1,4-trioxo-2,3,4,5-tetrahydro-1λ⁶,5-benzothiazepin-3-yl]carbamate (intermediate IX-47)

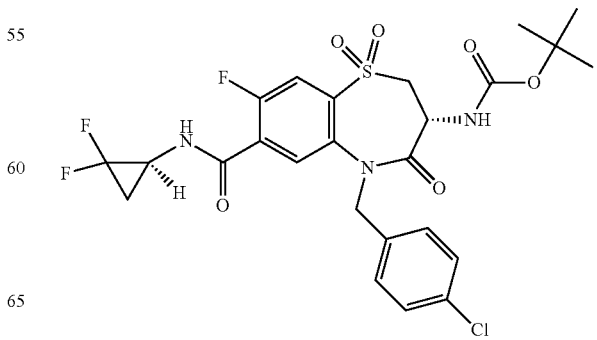

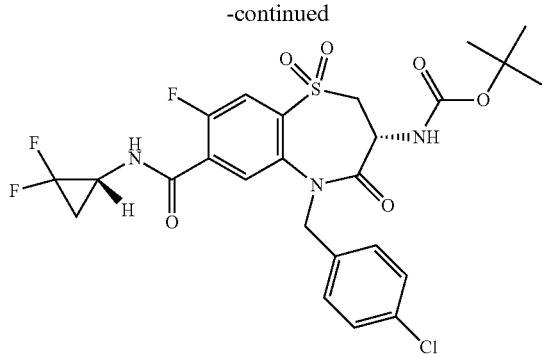

Intermediate IX-01 was resolved into its enantiomers using preparative chiral SFC:

Intermediate IX-01 (125 mg) was dissolved to 25 mg/mL in EtOH and was then purified by SFC. Each injection was 0.75 mL (19 mg). The column used was a YMC AMY-C (20 mm×250 mm, 5 um). The eluent was MeOH/CO$_2$ 15%. The flow rate was 50 mL/min at a wavelength of 225 nm.

The wet fractions were then evaporated to anhydrousness using a rotary evaporator and vacuum oven at 40° C. and 5 mbar to afford constant weight.

The final analysis was performed by SFC using a YMC AMY-C (4.6 mm×250 mm, 5 um). The eluent was MeOH/CO$_2$ 10%. The flow rate was 4 mL/min.

Isomer_1 (intermediate IX 46): Quantity: 48.3 mg
rt=5.21 min, Chemical purity: 99.8%, Enantiomeric excess: 100%

Isomer_2 (intermediate IX 47): Quantity: 47.3 mg
rt=5.24 min, Chemical purity: 99.1%, Enantiomeric excess: 99.4%

Synthesis of tert-butyl N-[(3R)-7-[(2,2-difluorocyclopropyl)carbamoyl]-8-fluoro-5-{[4-methoxy-3-(trifluoromethyl)phenyl]methyl}-1,1,4-trioxo-2,3,4,5-tetrahydro-1λ⁶,5-benzothiazepin-3-yl]carbamate (Intermediate IX-48)

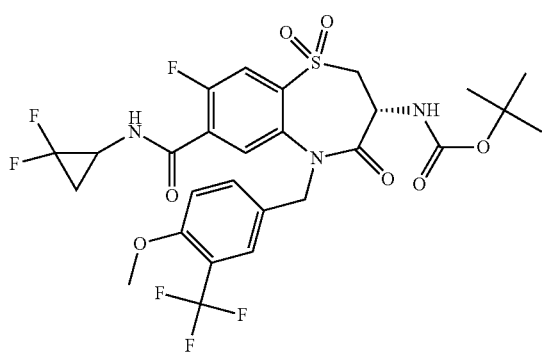 [SMILES: COc1ccc(CN2C(=O)[C@@H](NC(=O)OC(C)(C)C)CS(=O)(=O)c3cc(F)c(C(=O)NC4CC4(F)F)cc32)cc1C(F)(F)F]

The title compound was synthesized according to general procedure GP4 to afford the title compound as white solid in 40% yield.

LCMS: METCR1416 Generic 7 min, rt=4.42 min, M/Z (ES+) 673.90 [M+Na+] 100% UV

NMR Data: 1H NMR (500 MHz, DMSO-d6) 9.14 (d, J=11.3 Hz, 1H), 7.76 (d, J=8.4 Hz, 1H), 7.70 (dd, J=7.3, 5.6 Hz, 1H), 7.60 (s, 1H), 7.51 (t, J=7.4 Hz, 2H), 7.15 (d, J=8.6 Hz, 1H), 5.15 (d, J=15.5 Hz, 1H), 4.91 (dd, J=15.5, 12.7 Hz, 1H), 4.39 (dtd, J=11.7, 7.7, 4.1 Hz, 1H), 4.08 (ddd, J=13.3, 7.4, 3.3 Hz, 1H), 3.85 (d, J=1.1 Hz, 3H), 3.81-3.73 (m, 1H), 3.51 (s, 1H), 2.04-1.96 (m, 1H), 1.60 (d, J=5.3 Hz, 1H), 1.37 (s, 9H).

Synthesis of tert-butyl N-[(2R,3R)-5-[(4-chlorophenyl)methyl]-8-fluoro-2-methyl-1,1,4-trioxo-7-[(4,4,4-trifluorobutyl)carbamoyl]-2,3,4,5-tetrahydro-1λ⁶,5-benzothiazepin-3-yl]carbamate (Intermediate IX-49)

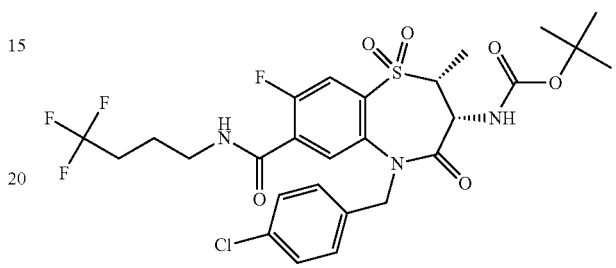

The title compound was synthesized according to general procedure GP4 to afford the title compound as colourless solid in 97% yield.

LCMS: METCR1410 Generic 1.7 min, rt=1.34 min, M/Z (ES+) 657.95/659.90 [M+Na+] 100% UV NMR Data: 1H NMR (500 MHz, Chloroform-d) d 7.90 (d, J=6.0 Hz, 1H), 7.78 (d, J=9.9 Hz, 1H), 7.23-7.16 (m, 4H), 6.73 (dt, J=11.6, 5.7 Hz, 1H), 5.61 (d, J=6.9 Hz, 1H), 5.07 (d, J=15.3 Hz, 1H), 4.74 (d, J=15.3 Hz, 1H), 4.53 (t, J=6.8 Hz, 1H), 3.96 (p, J=6.9 Hz, 1H), 3.48 (m, 2H), 2.18-2.05 (m, 2H), 1.85 (dt, J=14.7, 7.2 Hz, 2H), 1.41 (d, J=7.0 Hz, 3H), 1.33 (s, 9H).

Synthesis of tert-butyl N-[(3R)-5-{[4-(5-methyl-1,2,4-oxadiazol-3-yl)phenyl]methyl}-1,1,4-trioxo-7-[(4,4,4-trifluorobutyl)carbamoyl]-2,3,4,5-tetrahydro-1λ⁶,5-benzothiazepin-3-yl]carbamate (Intermediate IX-50)

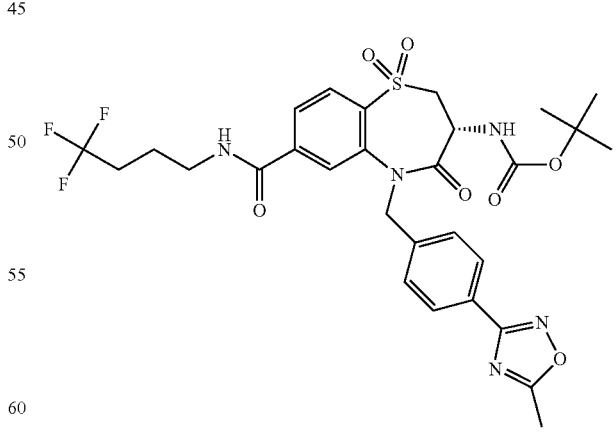

The title compound was synthesized according to general procedure GP4 to afford the title compound as colourless solid in 89% yield.

LCMS: METCR1410 Generic 1.7 min, rt=1.22 min, M/Z (ES+) 674 [M+Na+] 100% UV

NMR Data: 1H NMR (500 MHz, Chloroform-d) d 8.06 (d, J=8.1 Hz, 1H), 8.03 (d, J=8.3 Hz, 2H), 7.78-7.71 (m, 1H), 7.56-7.51 (m, 1H), 7.44 (d, J=8.2 Hz, 2H), 6.10 (t, J=5.7 Hz, 1H), 5.73 (d, J=7.3 Hz, 1H), 5.50 (d, J=15.4 Hz, 1H), 4.66 (d, J=15.4 Hz, 1H), 4.56 (dt, J=10.9, 7.1 Hz, 1H), 4.07 (dd, J=13.3, 7.0 Hz, 1H), 3.52 (dd, J=13.1, 11.2 Hz, 1H), 3.45 (q, J=6.8 Hz, 2H), 2.64 (s, 3H), 2.20-2.05 (m, 2H), 1.82 (p, J=7.4 Hz, 2H), 1.40 (s, 9H).

Synthesis of tert-butyl N-[(3R)-5-[(4-chlorophenyl)methyl]-8-fluoro-7-[(2-methoxyethyl)carbamoyl]-1,1,4-trioxo-2,3,4,5-tetrahydro-1λ⁶,5-benzothiazepin-3-yl]carbamate (Intermediate IX-51)

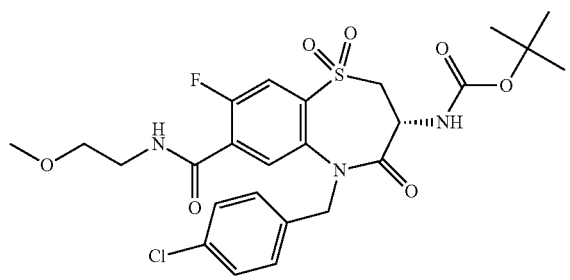 [SMILES: COCCNC(=O)c1cc2c(cc1F)S(=O)(=O)C[C@H](NC(=O)OC(C)(C)C)C(=O)N2Cc1ccc(Cl)cc1]

The title compound was synthesized according to general procedure GP4 to afford the title compound as white solid in 100% yield.

LCMS: METCR1416 generic 7 min, rt=4.23 min, M/Z (ES+) 591.95 [M+Na+], 513.95/515.95 [M-tBu+H]100% UV; NMR Data: 1H NMR (500 MHz, DMSO-d6) d 8.71 (s, 1H), 7.74 (d, J=8.5 Hz, 1H), 7.58 (d, J=5.5 Hz, 1H), 7.52 (d, J=8.0 Hz, 1H), 7.34 (s, 4H), 5.21 (d, J=16.1 Hz, 1H), 4.79 (d, J=16.0 Hz, 1H), 4.41 (dt, J=11.7, 7.7 Hz, 1H), 4.09 (dd, J=13.3, 7.4 Hz, 1H), 3.84-3.67 (m, 1H), 3.50-3.37 (m, 4H), 3.25 (s, 3H), 1.37 (s, 9H).

Synthesis of tert-butyl N-[(3R)-7-[(2,2-difluorocyclopropyl)carbamoyl]-5-{[4-(5-methyl-1,2,4-oxadiazol-3-yl)phenyl]methyl}-1,1,4-trioxo-2,3,4,5-tetrahydro-1λ⁶,5-benzothiazepin-3-yl]carbamate (Intermediate IX-52)

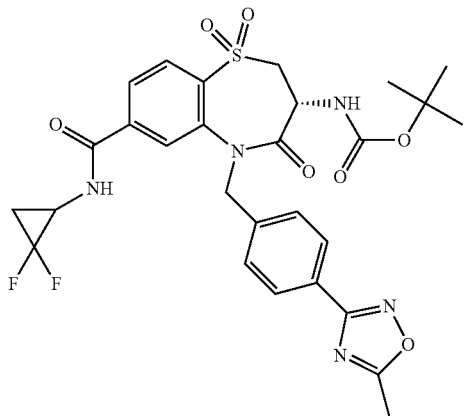 [SMILES: Cc1nc(-c2ccc(CN3C(=O)[C@@H](NC(=O)OC(C)(C)C)CS(=O)(=O)c4ccc(C(=O)NC5CC5(F)F)cc43)cc2)no1]

The title compound was synthesized according to general procedure GP4 to afford the title compound as colourless oil in 69% yield.

LCMS: METCR1410 Generic 1.7 min, rt=1.18 min, M/Z (ES+) 640 [M+Na+] 78% UV

NMR Data: 1H NMR (500 MHz, Chloroform-d) d 8.10-8.00 (m, 2H), 8.00-7.95 (m, 1H), 7.78-7.72 (m, 1H), 7.61-7.53 (m, 2H), 7.47-7.39 (m, 2H), 6.33 (s, 1H), 5.78 (m, 1H), 5.50 (m, 1H), 4.66 (m, 1H), 4.56 (dt, J=11.0, 7.2 Hz, 1H), 4.05 (dd, J=13.3, 6.9 Hz, 1H), 3.58-3.51 (m, 1H), 3.44 (m, 1H), 2.65 (s, 3H), 1.87 (m, 1H), 1.40 (s, 9H).

Synthesis and chiral separation to form (1S,3R)-3-{[(tert-butoxy)carbonyl]amino}-5-[(4-chlorophenyl)methyl]-8-fluoro-4-oxo-7-[(4,4,4-trifluorobutyl)carbamoyl]-2,3,4,5-tetrahydro-1H-1,5-benzothiazepin-1-ium-1-olate (Intermediate IX-53) and (1R,3R)-3-{[(tert-butoxy)carbonyl]amino}-5-[(4-chlorophenyl)methyl]-8-fluoro-4-oxo-7-[(4,4,4-trifluorobutyl)carbamoyl]-2,3,4,5-tetrahydro-1H-1,5-benzothiazepin-1-ium-1-olate (Intermediate IX-54)

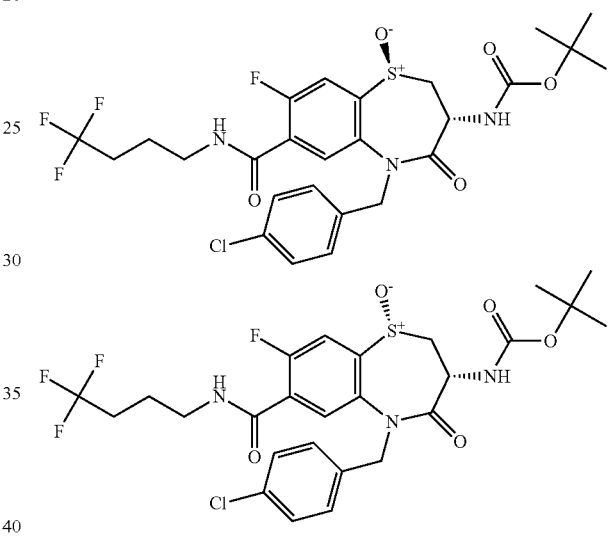

To a solution of Intermediate VIII-61 (100 mg, 0.17 mmol) in DCM (4 mL) was added 3-chlorobenzenecarboperoxoic acid (77%, 36 mg) under nitrogen at 0° C. The reaction mixture was stirred at 0° C. for 1 h. The reaction mixture was diluted with DCM, washed with 1 N aqueous NaOH solution, followed by brine. The organic phase was dried (Na₂SO₄), filtered and concentrated under reduced pressure. The residue was purified by reverse phase prep HPLC to afford mixture of diastereoisomers (61 mg, 55% yield), part thereof (33 mg) was separated by chiral SFC, using a Lux C4 column (20 mm×250 mm, 5 um). The eluent was 25% MeOH/CO₂. The flow rate was 50 mL/min with UV detection at a wavelength of 225 nm. This afforded Intermediate IX-53 (8 mg) and Intermediate IX-54 (4 mg). The stereochemistry of the sulfoxide was arbitrarily assigned.

Intermediate IX-53 (Later Eluting Enantiomer):
LCMS: METCR1416 generic 7 min, rt=4.46 min, M/Z (ES+) 627.90/630 [M+Na+] 99% UV
NMR Data: 1H NMR (500 MHz, Methanol-d4) d 8.65 (s, 1H), 7.87 (d, J=5.5 Hz, 1H), 7.53 (d, J=8.8 Hz, 1H), 7.32-7.22 (m, 4H), 5.41 (d, J=14.9 Hz, 1H), 4.74 (d, J=14.9 Hz, 1H), 4.37 (dd, J=10.6, 8.4 Hz, 1H), 4.01 (t, J=11.2 Hz, 1H), 3.51 (q, J=6.6 Hz, 2H), 3.38-3.35 (m, 1H), 2.36-2.22 (m, 2H), 1.90 (dt, J=14.7, 7.0 Hz, 2H), 1.42 (s, 9H). NH not visible by NMR Intermediate IX-54 (Earlier Eluting Enantiomer):

LCMS: METCR1416 generic 7 min, rt=4.36 min, M/Z (ES+) 627.90/630 [M+Na+] 96% UV

NMR Data: 1H NMR (500 MHz, Methanol-d4) δ 8.59 (s, 1H), 7.62 (d, J=8.6 Hz, 1H), 7.58 (d, J=5.8 Hz, 1H), 7.39 (d, J=8.3 Hz, 2H), 7.31 (q, J=7.2, 6.8 Hz, 3H), 5.36 (d, J=15.8 Hz, 1H), 4.64 (d, J=15.9 Hz, 1H), 4.61-4.55 (m, 1H), 3.93-3.83 (m, 1H), 3.44 (q, J=6.6 Hz, 2H), 3.37-3.34 (m, 1H), 2.30-2.17 (m, 2H), 1.91-1.79 (m, 2H), 1.44 (s, 9H). NH not visible by NMR Synthesis of tert-butyl N-[(3R)-5-[(4-cyanophenyl)methyl]-7-[(2,2-difluorocyclopropyl)carbamoyl]-8-fluoro-1,1,4-trioxo-2,3,4,5-tetrahydro-1λ⁶,5-benzothiazepin-3-yl]carbamate (Intermediate IX-55)

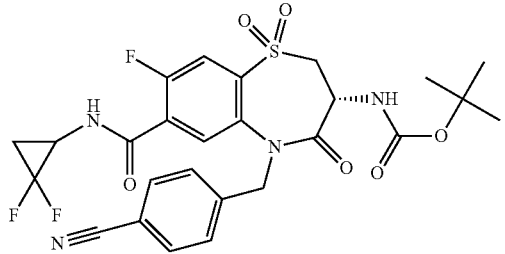 [SMILES: CC(C)(C)OC(=O)N[C@H]1CS(=O)(=O)c2cc(F)c(C(=O)NC3CC3(F)F)cc2N(Cc2ccc(C#N)cc2)C1=O]

The title compound was synthesized according to general procedure GP4 to afford the title compound as off white solid in 81% yield.

LCMS: METCR1410 Generic 1.7 min, rt=1.14 min, M/Z (ES+) 522.95 [M-tBu+H] 99% UV;

NMR Data: 1H NMR (250 MHz, DMSO-d6) d 9.19-9.07 (m, 1H), 7.78 (d, J=8.5 Hz, 3H), 7.64-7.58 (m, 1H), 7.59-7.47 (m, 3H), 5.28 (d, J=16.3 Hz, 1H), 5.04-4.82 (m, 1H), 4.56-4.30 (m, 1H), 4.22-3.96 (m, 1H), 3.90-3.68 (m, 1H), 3.57-3.40 (m, 1H), 2.10-1.90 (m, 1H), 1.73-1.52 (m, 1H), 1.42-1.26 (m, 9H).

Synthesis of tert-butyl N-[(3R)-5-[(4-cyanophenyl)methyl]-8-fluoro-1,1,4-trioxo-7-[(4,4,4-trifluorobutyl)carbamoyl]-2,3,4,5-tetrahydro-1λ⁶,5-benzothiazepin-3-yl]carbamate (Intermediate IX-56)

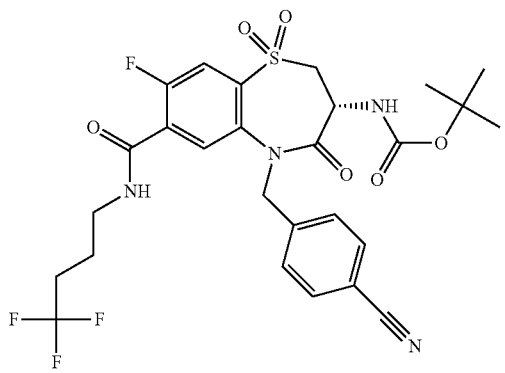 [SMILES: CC(C)(C)OC(=O)N[C@H]1CS(=O)(=O)c2cc(F)c(C(=O)NCCCC(F)(F)F)cc2N(Cc2ccc(C#N)cc2)C1=O]

The title compound was synthesized according to general procedure GP4 to afford the title compound as white solid in 100% yield.

LCMS: METCR1410 Generic 1.7 min, rt=1.27 min, M/Z (ES+) 557 [M+Na+] 100% UV

NMR Data: 1H NMR (500 MHz, DMSO-d6) δ 8.76 (t, J=5.6 Hz, 1H), 7.80-7.74 (m, 3H), 7.61 (d, J=5.5 Hz, 1H), 7.57-7.49 (m, 3H), 5.28 (d, J=16.6 Hz, 1H), 4.91 (d, J=16.5 Hz, 1H), 4.44 (dt, J=11.7, 7.7 Hz, 1H), 4.11 (dd, J=13.2, 7.3 Hz, 1H), 3.83-3.71 (m, 1H), 3.30-3.26 (m, 2H), 2.34-2.19 (m, 2H), 1.71 (dt, J=14.4, 6.8 Hz, 2H), 1.41-1.31 (m, 9H).

Synthesis of tert-butyl N-[(3R)-5-[(4-chlorophenyl)methyl]-7-[(4,4-difluorocyclohexyl)carbamoyl]-8-fluoro-1,1,4-trioxo-2,3,4,5-tetrahydro-1λ⁶,5-benzothiazepin-3-yl]carbamate (Intermediate IX-57)

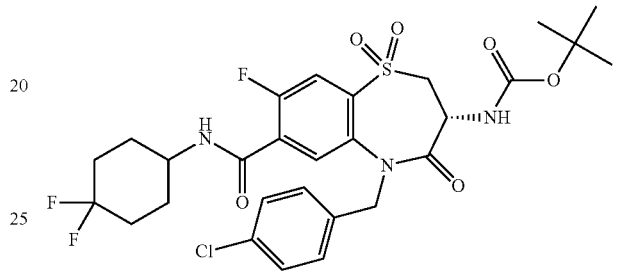

The title compound was synthesized according to general procedure GP4 to afford the title compound as white solid in 77% yield.

LCMS: METCR1410 Generic 1.7 min, rt=1.26 min, M/Z (ES+) 574/576 [M-tBu+H], 652.10/654.20 [M+Na+] 100% UV; NMR Data: 1H NMR (500 MHz, DMSO-d6) d 8.65 (d, J=7.6 Hz, 1H), 7.74 (d, J=8.3 Hz, 1H), 7.57 (d, J=5.5 Hz, 1H), 7.53 (d, J=8.0 Hz, 1H), 7.34 (s, 4H), 5.21 (d, J=15.8 Hz, 1H), 4.81 (d, J=15.9 Hz, 1H), 4.40 (dt, J=11.7, 7.6 Hz, 1H), 4.10 (dd, J=13.3, 7.3 Hz, 1H), 4.00-3.92 (m, 1H), 3.82-3.71 (m, 1H), 2.06-1.80 (m, 6H), 1.60 (d, J=9.1 Hz, 2H), 1.37 (s, 9H).

Synthesis of tert-butyl N-[(3R)-5-[(4-chlorophenyl)methyl]-8-fluoro-1,1,4-trioxo-7-{[2-(trifluoromethyl)cyclopropyl]carbamoyl}-2,3,4,5-tetrahydro-1λ⁶,5-benzothiazepin-3-yl]carbamate (Intermediate IX-58)

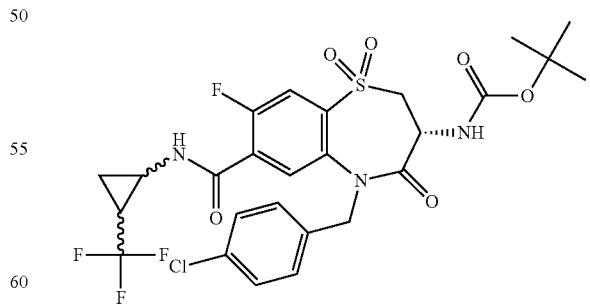

The title compound was synthesized according to general procedure GP4 to afford the title compound as white solid in 50% yield.

LCMS: MET-uPLC-AB-101, rt=3.93 min, M/Z (ES+) 620.1/622.1 [M+H+] 100% UV

NMR Data: 1H NMR (500 MHz, DMSO-d6) d 9.02 (d, J=4.0 Hz, 1H), 7.76 (d, J=8.5 Hz, 1H), 7.69 (d, J=5.3 Hz, 1H), 7.52 (d, J=8.0 Hz, 1H), 7.40-7.30 (m, 4H), 5.14 (d, J=15.9 Hz, 1H), 4.87 (dd, J=16.0, 3.8 Hz, 1H), 4.44-4.35 (m, 1H), 4.15-4.05 (m, 1H), 3.80-3.72 (m, 1H), 3.24-3.18 (m, 1H), 2.13-2.03 (m, 1H), 1.37 (s, 9H), 1.32-1.19 (m, 2H).

Synthesis of tert-butyl N-[(3R)-8-fluoro-5-[(4-fluorophenyl)methyl]-1,1,4-trioxo-7-[(4,4,4-trifluorobutyl)carbamoyl]-2,3,4,5-tetrahydro-1λ⁶,5-benzothiazepin-3-yl]carbamate (Intermediate IX-59)

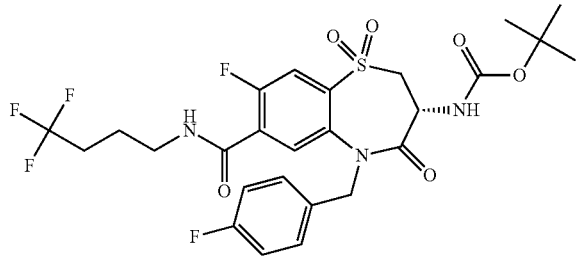 [SMILES: CC(C)(C)OC(=O)N[C@H]1CS(=O)(=O)c2cc(F)c(C(=O)NCCCC(F)(F)F)cc2N(Cc2ccc(F)cc2)C1=O]

The title compound was synthesized according to general procedure GP4 to afford the title compound as off white solid in 86% yield.
LCMS: METCR1410 Generic 1.7 min, rt=1.22 min, M/Z (ES+) 550.05 [M-tBu+H] 99% UV;
NMR Data: 1H NMR (250 MHz, Chloroform-d) d 7.97 (d, J=6.1 Hz, 1H), 7.81 (d, J=10.0 Hz, 1H), 7.37-7.23 (m, 2H), 7.08-6.91 (m, 2H), 6.77 (dt, J=11.7, 5.8 Hz, 1H), 5.72 (d, J=7.1 Hz, 1H), 5.20 (d, J=15.0 Hz, 1H), 4.81 (d, J=15.0 Hz, 1H), 4.51 (dt, J=10.9, 7.0 Hz, 1H), 4.18-3.97 (m, 1H), 3.64-3.43 (m, 3H), 2.32-2.05 (m, 2H), 1.91 (p, J=7.1 Hz, 2H), 1.40 (s, 9H).

Synthesis of tert-butyl N-[(3R)-7-[(2,2-difluorocyclopropyl)carbamoyl]-8-fluoro-5-[(4-fluorophenyl)methyl]-1,1,4-trioxo-2,3,4,5-tetrahydro-1λ⁶,5-benzothiazepin-3-yl]carbamate (Intermediate IX-60)

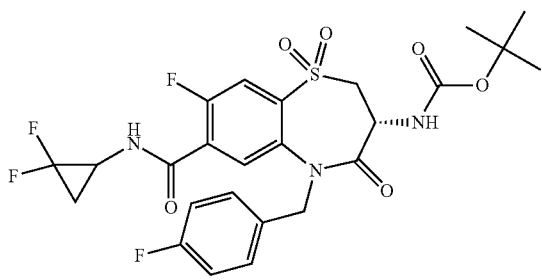 [SMILES: CC(C)(C)OC(=O)N[C@H]1CS(=O)(=O)c2cc(F)c(C(=O)NC3CC3(F)F)cc2N(Cc2ccc(F)cc2)C1=O]

The title compound was synthesized according to general procedure GP4 to afford the title compound as off white solid in 89% yield.
LCMS: METCR1410 Generic 1.7 min, rt=1.16 min, M/Z (ES+) 516.05 [M-tBu+H] 100% UV
NMR Data: 1H NMR (250 MHz, Chloroform-d) d 7.97 (dd, J=6.0, 3.4 Hz, 1H), 7.81 (d, J=9.9 Hz, 1H), 7.38-7.26 (m, 2H), 7.00 (t, J=8.6 Hz, 2H), 6.92 (d, J=13.0 Hz, 1H), 5.73 (d, J=7.0 Hz, 1H), 5.21 (d, J=15.0 Hz, 1H), 4.79 (dd, J=15.1, 1.6 Hz, 1H), 4.60-4.41 (m, 1H), 4.07 (m, 1H), 3.52 (dd, J=13.2, 11.1 Hz, 2H), 1.93 (m, 1H), 1.49 (dt, J=9.7, 4.6 Hz, 1H), 1.40 (s, 9H).

Synthesis of tert-butyl N-[(3R)-7-(butylcarbamoyl)-8-fluoro-5-[(4-fluorophenyl)methyl]-1,1,4-trioxo-2,3,4,5-tetrahydro-1λ⁶,5-benzothiazepin-3-yl]carbamate (Intermediate IX-61)

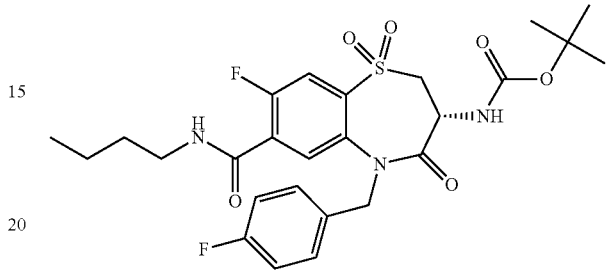

The title compound was synthesized according to general procedure GP4 to afford the title compound as off white solid in 90% yield.
LCMS: METCR1410 Generic 1.7 min, rt=1.27 min, M/Z (ES+) 496.05 [M-tBu+H] 100% UV
NMR Data: 1H NMR (500 MHz, Chloroform-d) d 8.00 (d, J=6.1 Hz, 1H), 7.79 (d, J=9.9 Hz, 1H), 7.34-7.28 (m, 2H), 7.03-6.96 (m, 2H), 6.67 (dt, J=11.1, 5.3 Hz, 1H), 5.73 (d, J=7.1 Hz, 1H), 5.18 (d, J=15.1 Hz, 1H), 4.81 (d, J=15.1 Hz, 1H), 4.50 (dt, J=10.9, 7.0 Hz, 1H), 4.08 (dd, J=13.3, 6.9 Hz, 1H), 3.55-3.41 (m, 3H), 1.64-1.57 (m, 2H), 1.45-1.37 (m, 11H), 0.96 (t, J=7.4 Hz, 3H).

Synthesis of tert-butyl N-[(3R)-7-(benzylcarbamoyl)-8-fluoro-5-[(4-fluorophenyl)methyl]-1,1,4-trioxo-2,3,4,5-tetrahydro-1λ⁶,5-benzothiazepin-3-yl]carbamate (Intermediate IX-62)

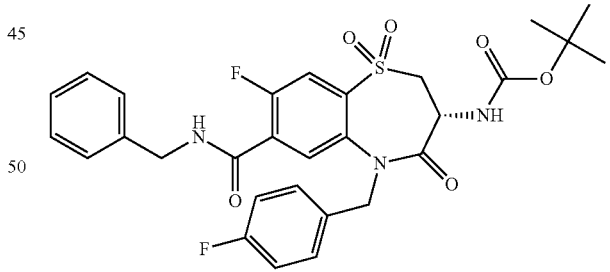

The title compound was synthesized according to general procedure GP4 to afford the title compound as off white solid in 77% yield.
LCMS: METCR1410 Generic 1.7 min, rt=1.28 min, M/Z (ES+) 530.05 [M-tBu+H] 99% UV
NMR Data: 1H NMR (500 MHz, Chloroform-d) d 8.02 (d, J=6.1 Hz, 1H), 7.79 (d, J=9.8 Hz, 1H), 7.42-7.34 (m, 2H), 7.35-7.27 (m, 5H), 7.04-6.95 (m, 3H), 5.73 (d, J=7.1 Hz, 1H), 5.18 (d, J=15.1 Hz, 1H), 4.83 (d, J=15.1 Hz, 1H), 4.74-4.60 (m, 2H), 4.51 (dt, J=10.9, 7.0 Hz, 1H), 4.07 (dd, J=13.4, 6.9 Hz, 1H), 3.51 (dd, J=13.3, 11.1 Hz, 1H), 1.40 (s, 9H).

Synthesis of tert-butyl N-[(3R)-5-[(4-chlorophenyl)methyl]-8-fluoro-7-{[2-(oxan-4-yl)ethyl]carbamoyl}-1,1,4-trioxo-2,3,4,5-tetrahydro-1λ⁶,5-benzothiazepin-3-yl]carbamate (Intermediate IX-63)

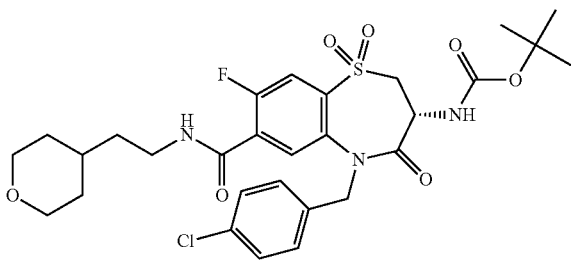 [SMILES: CC(C)(C)OC(=O)N[C@H]1CS(=O)(=O)c2cc(F)c(C(=O)NCCC3CCOCC3)cc2N(Cc2ccc(Cl)cc2)C1=O]

The title compound was synthesized according to general procedure GP4 to afford the title compound as white solid in 59% yield.

LCMS: METCR1410 Generic 1.7 min, rt=1.21 min, M/Z (ES+) 524.10/526.10 [M-Boc+H] 99% UV NMR Data: 1H NMR (500 MHz, DMSO-d6) d 8.64 (t, J=5.5 Hz, 1H), 7.74 (d, J=8.4 Hz, 1H), 7.56 (d, J=5.5 Hz, 1H), 7.53 (d, J=8.1 Hz, 1H), 7.34 (s, 4H), 5.21 (d, J=16.1 Hz, 1H), 4.80 (d, J=16.0 Hz, 1H), 4.42 (dt, J=11.7, 7.7 Hz, 1H), 4.13-4.08 (m, 1H), 3.86-3.73 (m, 3H), 3.29-3.20 (m, 4H), 1.58 (d, J=13.9 Hz, 2H), 1.53-1.47 (m, 1H), 1.43 (q, J=6.8 Hz, 2H), 1.37 (s, 9H), 1.20-1.10 (m, 2H).

Synthesis of tert-butyl N-[(3R)-5-benzyl-8-fluoro-1,1,4-trioxo-7-[(4,4,4-trifluorobutyl)carbamoyl]-2,3,4,5-tetrahydro-1λ⁶,5-benzothiazepin-3-yl]carbamate (Intermediate IX-64)

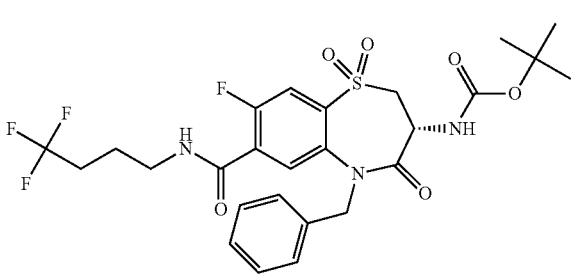 [SMILES: CC(C)(C)OC(=O)N[C@H]1CS(=O)(=O)c2cc(F)c(C(=O)NCCCC(F)(F)F)cc2N(Cc2ccccc2)C1=O]

The title compound was synthesized according to general procedure GP4 to afford the title compound as pale yellow gum in 91% yield.

LCMS: METCR1410 Generic 1.7 min, rt=1.21 min, M/Z (ES+) 532.05 [M-tBu+H], 610.15 [M+Na+] 98% UV; NMR Data: 1H NMR (500 MHz, DMSO-d6) d 8.73 (t, J=5.6 Hz, 1H), 7.76 (d, J=8.5 Hz, 1H), 7.56-7.50 (m, 2H), 7.35-7.24 (m, 5H), 5.29 (d, J=16.1 Hz, 1H), 4.70 (d, J=16.0 Hz, 1H), 4.44 (dt, J=11.7, 7.8 Hz, 1H), 4.11 (dd, J=8.7, 4.6 Hz, 1H), 3.83-3.74 (m, 1H), 3.32-3.27 (m, 2H), 2.34-2.18 (m, 2H), 1.70 (dt, J=14.8, 7.0 Hz, 2H), 1.37 (s, 9H).

Synthesis of tert-butyl N-[(3R)-5-[(4-chlorophenyl)methyl]-8-fluoro-7-{[(4-methoxyphenyl)methyl]carbamoyl}-1,1,4-trioxo-2,3,4,5-tetrahydro-1λ⁶,5-benzothiazepin-3-yl]carbamate (Intermediate IX-65)

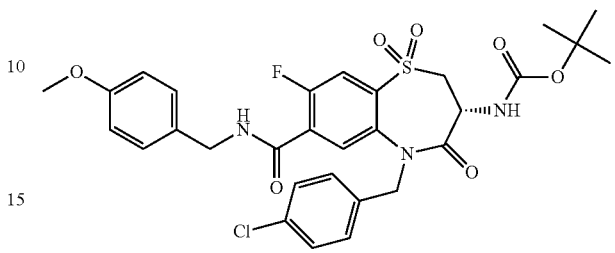

The title compound was synthesized according to general procedure GP4 to afford the title compound as white solid in 46% yield.

LCMS: METCR1410 Generic 1.7 min, rt=1.26 min, M/Z (ES+) 654.15/656.20 [M+Na+] 100% UV NMR Data: 1H NMR (500 MHz, Chloroform-d) d 8.03 (d, J=6.0 Hz, 1H), 7.78 (d, J=9.8 Hz, 1H), 7.31-7.23 (m, 6H), 6.94-6.87 (m, 3H), 5.71 (d, J=7.1 Hz, 1H), 5.16 (d, J=15.2 Hz, 1H), 4.84 (d, J=15.2 Hz, 1H), 4.64-4.54 (m, 2H), 4.51 (dt, J=10.9, 7.0 Hz, 1H), 4.07 (dd, J=13.4, 6.9 Hz, 1H), 3.81 (s, 3H), 3.51 (dd, J=13.3, 11.1 Hz, 1H), 1.40 (s, 9H).

Synthesis of tert-butyl N-[(3R)-5-[(5-cyclopropyl-1,3,4-thiadiazol-2-yl)methyl]-8-fluoro-7-{[(4-fluorophenyl)methyl]carbamoyl}-1,1,4-trioxo-2,3,4,5-tetrahydro-1λ⁶,5-benzothiazepin-3-yl]carbamate (Intermediate IX-66)

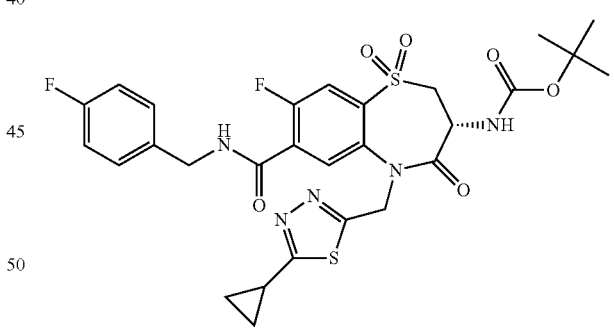

The title compound was synthesized according to general procedure GP4 to afford the title compound as tan solid in 64% yield.

LCMS: METCR1410 Generic 1.7 min, rt=1.21 min, M/Z (ES+) 634.25 [M+H+] 97.9% UV

NMR Data: 1H NMR (250 MHz, Chloroform-d) d 8.40 (d, J=5.9 Hz, 1H), 7.79 (d, J=9.5 Hz, 1H), 7.42-7.29 (m, 2H), 7.15-6.92 (m, 3H), 5.65 (d, J=7.0 Hz, 1H), 5.45 (d, J=15.4 Hz, 1H), 5.02 (d, J=15.4 Hz, 1H), 4.64 (d, J=5.5 Hz, 2H), 4.49 (dt, J=10.9, 7.1 Hz, 1H), 4.09 (dd, J=14.2, 7.1 Hz, 1H), 3.55-3.40 (m, 1H), 2.38 (td, J=8.2, 4.1 Hz, 1H), 1.39 (s, 9H), 1.25-1.18 (m, 2H), 1.18-1.11 (m, 2H).

Synthesis of tert-butyl N-[(3R)-8-fluoro-5-[(4-fluorophenyl)methyl]-7-{[(oxan-4-yl)methyl]carbamoyl}-1,1,4-trioxo-2,3,4,5-tetrahydro-1λ⁶,5-benzothiazepin-3-yl]carbamate (Intermediate IX-67)

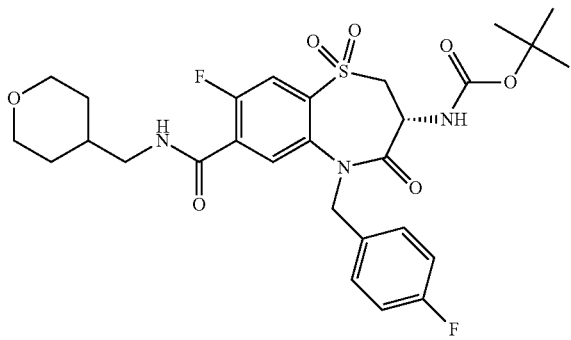 [SMILES: CC(C)(C)OC(=O)N[C@H]1CS(=O)(=O)c2cc(F)c(C(=O)NCC3CCOCC3)cc2N(Cc2ccc(F)cc2)C1=O]

The title compound was synthesized according to general procedure GP4 to afford the title compound as off-white solid in 100% yield.

LCMS: METCR1410 Generic 1.7 min, rt=1.12 min, M/Z (ES+) 616 [M+Na+] 100% UV;

NMR Data: 1H NMR (250 MHz, Chloroform-d) d 7.97 (d, J=6.1 Hz, 1H), 7.80 (d, J=9.9 Hz, 1H), 7.36-7.27 (m, 2H), 7.04-6.95 (m, 2H), 6.82-6.66 (m, 1H), 5.72 (d, J=7.1 Hz, 1H), 5.19 (d, J=15.0 Hz, 1H), 4.81 (d, J=15.0 Hz, 1H), 4.58-4.42 (m, 1H), 4.17-3.93 (m, 3H), 3.58-3.45 (m, 1H), 3.45-3.26 (m, 4H), 1.98-1.78 (m, 1H), 1.72-1.61 (m, 2H), 1.47-1.33 (m, 11H).

Synthesis of tert-butyl N-[(3R)-7-[(3,3-difluorocyclobutyl)carbamoyl]-8-fluoro-5-[(4-fluorophenyl)methyl]-1,1,4-trioxo-2,3,4,5-tetrahydro-1λ⁶,5-benzothiazepin-3-yl]carbamate (Intermediate IX-68)

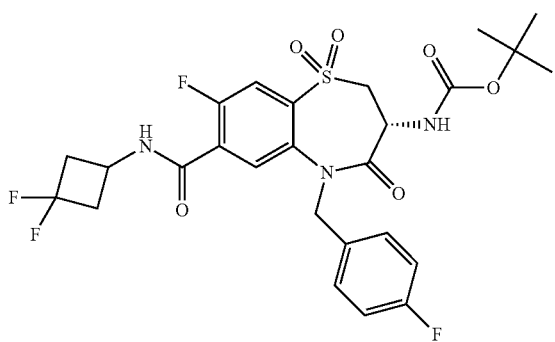 [SMILES: CC(C)(C)OC(=O)N[C@H]1CS(=O)(=O)c2cc(F)c(C(=O)NC3CC(F)(F)C3)cc2N(Cc2ccc(F)cc2)C1=O]

The title compound was synthesized according to general procedure GP4 to afford the title compound as off-white solid in 83% yield.

LCMS: METCR1410 Generic 1.7 min, rt=1.2 min, M/Z (ES+) 608 [M+Na+] 100% UV;

NMR Data: 1H NMR (250 MHz, Chloroform-d) d 7.96 (d, J=6.1 Hz, 1H), 7.82 (d, J=10.0 Hz, 1H), 7.35-7.27 (m, 2H), 7.05-6.95 (m, 2H), 6.94-6.81 (m, 1H), 5.71 (d, J=7.1 Hz, 1H), 5.19 (d, J=15.1 Hz, 1H), 4.82 (d, J=15.1 Hz, 1H), 4.59-4.36 (m, 2H), 4.17-4.01 (m, 1H), 3.52 (dd, J=13.2, 11.1 Hz, 1H), 3.24-2.99 (m, 2H), 2.75-2.47 (m, 2H), 1.40 (s, 9H).

Synthesis of tert-butyl N-[(3R)-8-fluoro-5-[(4-methoxyphenyl)methyl]-1,1,4-trioxo-7-[(4,4,4-trifluorobutyl)carbamoyl]-2,3,4,5-tetrahydro-1λ⁶,5-benzothiazepin-3-yl]carbamate (Intermediate IX-69)

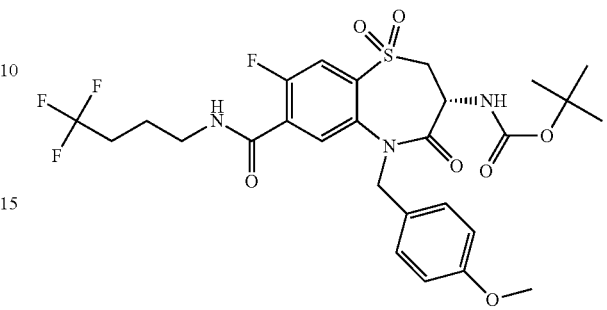

The title compound was synthesized according to general procedure GP4 to afford the title compound as white solid in 100% yield.

LCMS: METCR1410 Generic 1.7 min, rt=1.22 min, M/Z (ES+) 640.2 [M+Na+] 99% UV;

NMR Data: 1H NMR (500 MHz, DMSO-d6) d 8.73 (t, J=5.6 Hz, 1H), 7.73 (d, J=8.5 Hz, 1H), 7.61 (d, J=5.5 Hz, 1H), 7.49 (d, J=8.2 Hz, 1H), 7.22 (d, J=8.6 Hz, 2H), 6.81 (d, J=8.6 Hz, 2H), 5.15 (d, J=15.5 Hz, 1H), 4.73 (d, J=15.5 Hz, 1H), 4.38 (dt, J=11.6, 7.8 Hz, 1H), 4.10-4.00 (m, 1H), 3.79-3.73 (m, 1H), 3.71 (s, 3H), 2.34-2.19 (m, 2H), 1.71 (dt, J=14.6, 7.0 Hz, 2H), 1.37 (s, 9H). [2H under water peak]

Synthesis of tert-butyl N-[(3R)-8-fluoro-5-[(4-methoxyphenyl)methyl]-7-{[(oxan-4-yl)methyl]carbamoyl}-1,1,4-trioxo-2,3,4,5-tetrahydro-1λ⁶,5-benzothiazepin-3-yl]carbamate (Intermediate IX-70)

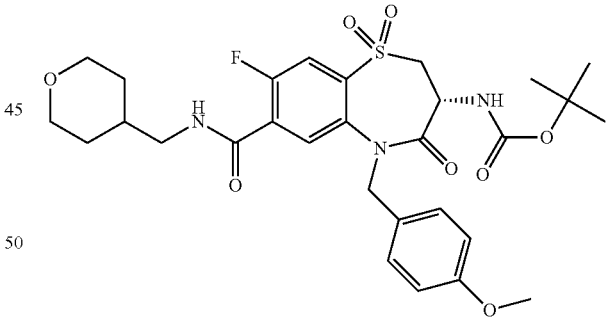

The title compound was synthesized according to general procedure GP4 to afford the title compound as White solid in 89% yield.

LCMS: METCR1410 Generic 1.7 min, rt=1.11 min, M/Z (ES+) 628.2 [M+Na+] 98% UV

NMR Data: 1H NMR (500 MHz, DMSO-d6) d 8.66 (t, J=5.7 Hz, 1H), 7.72 (d, J=8.4 Hz, 1H), 7.50 (dd, J=10.5, 6.9 Hz, 2H), 7.23 (d, J=8.6 Hz, 2H), 6.82 (d, J=8.6 Hz, 2H), 5.21 (d, J=15.6 Hz, 1H), 4.64 (d, J=15.5 Hz, 1H), 4.39 (dt, J=11.6, 7.8 Hz, 1H), 4.08 (dd, J=13.2, 7.3 Hz, 1H), 3.87-3.80 (m, 2H), 3.80-3.73 (m, 1H), 3.72 (s, 3H), 3.25 (t, J=11.2 Hz, 2H), 3.17-3.07 (m, J=6.4 Hz, 2H), 1.77-1.66 (m, 1H), 1.52 (d, J=13.2 Hz, 2H), 1.37 (s, 9H), 1.22-1.11 (m, 2H).

Synthesis of tert-butyl N-[(3R)-7-[(2,2-difluorocyclopropyl)carbamoyl]-8-fluoro-5-[(4-methoxyphenyl)methyl]-1,1,4-trioxo-2,3,4,5-tetrahydro-1λ⁶,5-benzothiazepin-3-yl]carbamate (Intermediate IX-71)

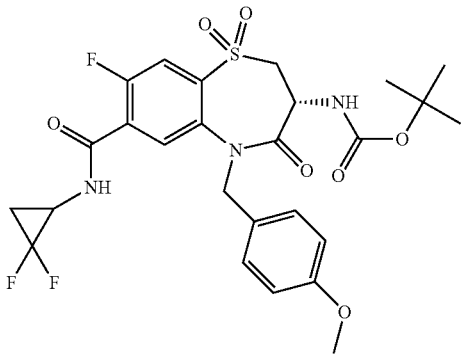 [SMILES: COc1ccc(CN2C(=O)[C@@H](NC(=O)OC(C)(C)C)CS(=O)(=O)c3cc(F)c(C(=O)NC4CC4(F)F)cc32)cc1]

The title compound was synthesized according to general procedure GP4 to afford the title compound as white solid in 75% yield.

LCMS: METCR1410 Generic 1.7 min, rt=1.16 min, M/Z (ES+) 606.2 [M+Na+] 96% UV

NMR Data: 1H NMR (500 MHz, DMSO-d6) d 9.11 (d, J=9.6 Hz, 1H), 7.74 (d, J=8.4 Hz, 1H), 7.60 (d, J=5.4 Hz, 1H), 7.49 (d, J=7.9 Hz, 1H), 7.25-7.16 (m, 2H), 6.82 (dd, J=8.8, 2.4 Hz, 2H), 5.16 (dd, J=15.5, 2.3 Hz, 1H), 4.72 (dd, J=15.5, 9.8 Hz, 1H), 4.38 (dtd, J=11.5, 7.8, 3.7 Hz, 1H), 4.08 (dq, J=9.6, 3.6 Hz, 1H), 3.79-3.73 (m, 1H), 3.72 (s, 3H), 2.05-1.93 (m, 1H), 1.65-1.54 (m, 1H), 1.37 (s, 9H), 1.30-1.22 (m, 1H).

Synthesis of tert-butyl N-[(3R)-5-[(4-chlorophenyl)methyl]-8-fluoro-7-[(oxan-4-yl)carbamoyl]-1,1,4-trioxo-2,3,4,5-tetrahydro-1λ⁶,5-benzothiazepin-3-yl]carbamate (Intermediate IX-72)

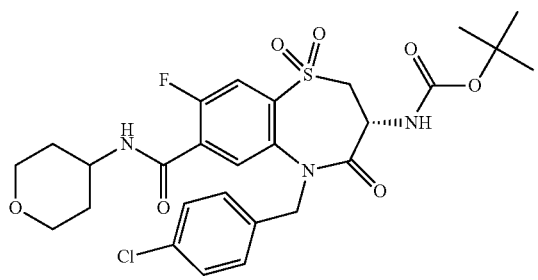 [SMILES: CC(C)(C)OC(=O)N[C@H]1CS(=O)(=O)c2cc(F)c(C(=O)NC3CCOCC3)cc2N(Cc2ccc(Cl)cc2)C1=O]

The title compound was synthesized according to general procedure GP4 to afford the title compound as white crystalline solid in 72% yield.

LCMS: METCR1410 Generic 1.7 min, rt=1.15 min, M/Z (ES+) 618.20/620.25 [M+Na+] 100% UV NMR Data: 1H NMR (250 MHz, Chloroform-d) d 7.91 (d, J=6.1 Hz, 1H), 7.74 (d, J=9.9 Hz, 1H), 7.21 (s, 3H), 6.47 (d, J=11.9 Hz, 1H), 5.63 (d, J=7.1 Hz, 1H), 5.13 (d, J=15.2 Hz, 1H), 4.73 (d, J=15.2 Hz, 1H), 4.42 (s, 1H), 4.02-3.87 (m, 3H), 3.46 (t, J=10.4 Hz, 3H), 1.92 (s, 2H), 1.57 (d, J=7.9 Hz, 2H), 1.33 (s, 9H).

Synthesis of tert-butyl N-[(3R)-5-[(4-chlorophenyl)methyl]-7-[(3,3-difluorocyclobutyl)carbamoyl]-1,1,4-trioxo-2,3,4,5-tetrahydro-1λ⁶,5-benzothiazepin-3-yl]carbamate (Intermediate IX-73)

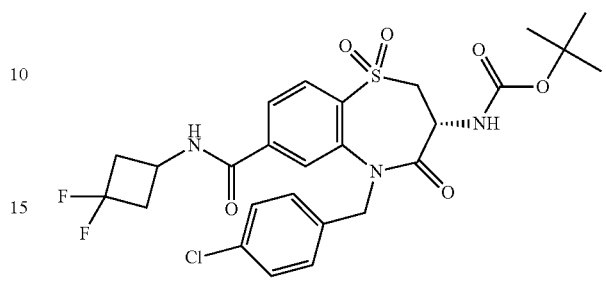

The title compound was synthesized according to general procedure GP4 to afford the title compound as white solid in 94% yield.

LCMS: METCR1410 Generic 1.7 min, rt=1.22 min, M/Z (ES+) 606.20/608.30 [M+Na+] 97% UV NMR Data: 1H NMR (500 MHz, Chloroform-d) d 8.09 (d, J=8.1 Hz, 1H), 7.76 (d, J=8.1 Hz, 1H), 7.53 (d, J=1.3 Hz, 1H), 7.33-7.27 (m, 4H), 6.18 (d, J=6.3 Hz, 1H), 5.69 (d, J=7.3 Hz, 1H), 5.41-4.59 (m, 2H), 4.52 (dt, J=10.8, 7.1 Hz, 1H), 4.42 (d, J=2.0 Hz, 1H), 4.06 (dd, J=13.3, 6.9 Hz, 1H), 3.52 (dd, J=13.2, 11.1 Hz, 1H), 3.16-3.04 (m, 2H), 2.55 (qd, J=13.0, 6.5 Hz, 2H), 1.40 (s, 9H).

Synthesis of tert-butyl N-[(3R)-5-[(4-chlorophenyl)methyl]-7-{[(1S)-3,3-difluorocyclopentyl]carbamoyl}-8-fluoro-1,1,4-trioxo-2,3,4,5-tetrahydro-1λ⁶,5-benzothiazepin-3-yl]carbamate (Intermediate IX-74)

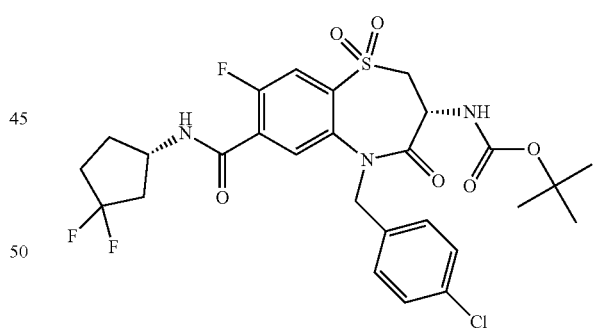

The title compound was synthesized according to general procedure GP4 to afford the title compound as off white solid in 96% yield.

LCMS: METCR1410 Generic 1.7 min, rt=1.25 min, M/Z (ES+) 560.15/562.15 [M-tBu+H] 99% UV NMR Data: 1H NMR (250 MHz, Chloroform-d) δ 7.97 (d, J=6.1 Hz, 1H), 7.81 (d, J=9.9 Hz, 1H), 7.36-7.24 (m, 4H), 6.80 (dd, J=12.1, 7.1 Hz, 1H), 5.70 (d, J=6.8 Hz, 1H), 5.19 (d, J=15.1 Hz, 1H), 4.81 (d, J=15.2 Hz, 1H), 4.70-4.57 (m, 1H), 4.51 (dt, J=10.6, 6.9 Hz, 1H), 4.08 (dt, J=11.2, 4.3 Hz, 1H), 3.62-3.43 (m, 1H), 2.73-2.46 (m, 1H), 2.46-2.24 (m, 2H), 2.24-2.05 (m, 2H), 1.94-1.75 (m, 1H), 1.40 (s, 9H).

Synthesis of tert-butyl N-[(3R)-5-[(4-chlorophenyl)methyl]-7-{[(1R,2S)-2-fluorocyclopropyl]carbamoyl}-1,1,4-trioxo-2,3,4,5-tetrahydro-1λ⁶,5-benzothiazepin-3-yl]carbamate (Intermediate IX-75)

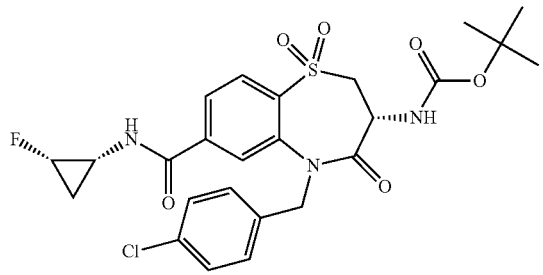 [SMILES: CC(C)(C)OC(=O)N[C@H]1CS(=O)(=O)c2ccc(C(=O)N[C@@H]3C[C@@H]3F)cc2N(Cc2ccc(Cl)cc2)C1=O]

The title compound was synthesized according to general procedure GP4 to afford the title compound as white solid in 41% yield.

LCMS: METCR1410 Generic 1.7 min, rt=1.15 min, M/Z (ES+) 574/576 [M+Na+] 100% UV

NMR Data: 1H NMR (250 MHz, Chloroform-d) δ 8.09 (d, J=8.1 Hz, 1H), 7.77 (dd, J=8.1, 1.6 Hz, 1H), 7.57 (d, J=1.5 Hz, 1H), 7.29 (d, J=2.4 Hz, 4H), 6.13 (s, 1H), 5.70 (d, J=7.0 Hz, 1H), 5.38 (d, J=15.2 Hz, 1H), 4.97-4.87 (m, 1H), 4.70-4.40 (m, 3H), 4.13-4.01 (m, 1H), 3.51 (dd, J=13.3, 11.0 Hz, 1H), 3.03 (dd, J=8.5, 4.9 Hz, 1H), 1.40 (s, 9H), 1.10-0.92 (m, 1H).

Synthesis of tert-butyl N-[(3R)-7-[(3,3-difluorocyclobutyl)carbamoyl]-5-[(2-fluorophenyl)methyl]-1,1,4-trioxo-2,3,4,5-tetrahydro-1λ⁶,5-benzothiazepin-3-yl]carbamate (Intermediate IX-76)

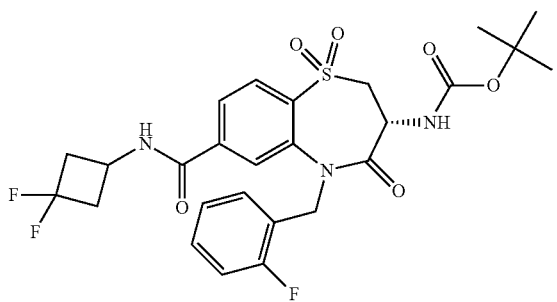 [SMILES: CC(C)(C)OC(=O)N[C@H]1CS(=O)(=O)c2ccc(C(=O)NC3CC(F)(F)C3)cc2N(Cc2ccccc2F)C1=O]

The title compound was synthesized according to general procedure GP4 to afford the title compound as white solid in 33% yield.

LCMS: METCR1410 Generic 1.7 min, rt=1.17 min, M/Z (ES+) 590 [M+Na+] 99% UV

NMR Data: 1H NMR (250 MHz, Chloroform-d) d 8.02 (d, J=8.1 Hz, 1H), 7.74 (d, J=8.1 Hz, 1H), 7.55 (s, 1H), 7.43 (t, J=6.8 Hz, 1H), 7.31-7.21 (m, 1H), 7.12-6.89 (m, 2H), 6.14 (d, J=6.5 Hz, 1H), 5.62 (d, J=6.8 Hz, 1H), 5.29 (d, J=15.3 Hz, 1H), 4.80 (d, J=15.1 Hz, 1H), 4.58-4.27 (m, 2H), 4.02 (m, 1H), 3.43 (dd, J=13.2, 10.9 Hz, 1H), 3.20-2.90 (m, 2H), 2.64-2.31 (m, 2H), 1.33 (s, 9H).

Synthesis of tert-butyl N-[(3R)-7-[(3,3-difluorocyclobutyl)carbamoyl]-5-[(3-methoxyphenyl)methyl]-1,1,4-trioxo-2,3,4,5-tetrahydro-1λ⁶,5-benzothiazepin-3-yl]carbamate (Intermediate IX-77)

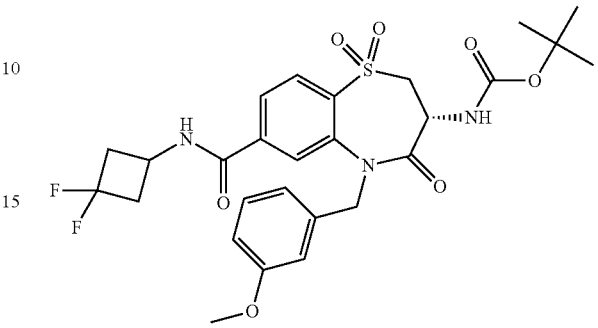

The title compound was synthesized according to general procedure GP4 to afford the title compound as white solid in 40% yield.

LCMS: METCR1410 Generic 1.7 min, rt=1.17 min, M/Z (ES+) 602 [M+Na+] 98% UV

NMR Data: 1H NMR (250 MHz, Chloroform-d) d 8.03 (d, J=8.1 Hz, 1H), 7.75 (d, J=9.6 Hz, 1H), 7.28-7.20 (m, 1H and 0.5H), 6.96-6.69 (m, 3H), 5.77 (dd, J=59.6, 6.7 Hz, 1H and 0.5H), 5.57-5.34 (m, 1H), 4.57-4.23 (m, 3H), 4.14-3.97 (m, 2H), 3.72 (s, 3H), 3.58-3.38 (m, 1H), 3.01 (s, 2H), 2.60-2.26 (m, 2H), 1.34 (s, 9H).

Synthesis of tert-butyl N-[(3R)-5-[(4-methoxyphenyl)methyl]-1,1,4-trioxo-7-[(4,4,4-trifluorobutyl)carbamoyl]-2,3,4,5-tetrahydro-1λ⁶,5-benzothiazepin-3-yl]carbamate (Intermediate IX-78)

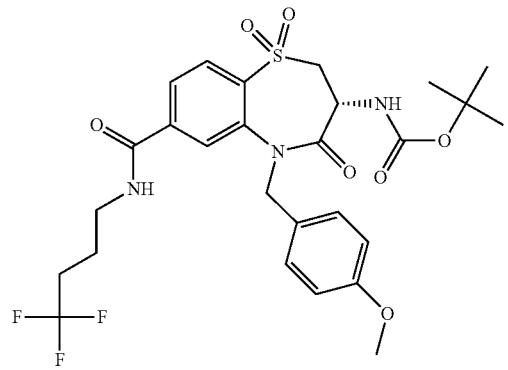 [SMILES: COc1ccc(CN2C(=O)[C@@H](NC(=O)OC(C)(C)C)CS(=O)(=O)c3ccc(C(=O)NCCCC(F)(F)F)cc32)cc1]

The title compound was synthesized according to general procedure GP4 to afford the title compound as white solid in 45% yield.

LCMS: METCR1410 Generic 1.7 min, rt=1.19 min, M/Z (ES+) 622.15 [M+Na+] 100% UV

NMR Data: 1H NMR (500 MHz, Chloroform-d) d 8.05 (d, J=8.1 Hz, 1H), 7.77 (dd, J=8.1, 1.2 Hz, 1H), 7.40 (s, 1H), 7.25 (d, J=8.7 Hz, 2H), 6.86 (d, J=8.7 Hz, 2H), 6.02 (t, J=5.5 Hz, 1H), 5.75 (d, J=7.2 Hz, 1H), 5.44 (d, J=14.9 Hz, 1H), 4.54-4.45 (m, 2H), 4.05 (dd, J=13.3, 6.9 Hz, 1H), 3.78 (s, 3H), 3.56-3.44 (m, 3H), 2.22-2.10 (m, 2H), 1.86 (dt, J=14.8, 7.2 Hz, 2H), 1.40 (s, 9H).

Synthesis of tert-butyl N-[(3R)-5-[(4-methoxyphenyl)methyl]-7-{[(4-methoxyphenyl)methyl]carbamoyl}-1,1,4-trioxo-2,3,4,5-tetrahydro-1λ⁶,5-benzothiazepin-3-yl]carbamate (Intermediate IX-79)

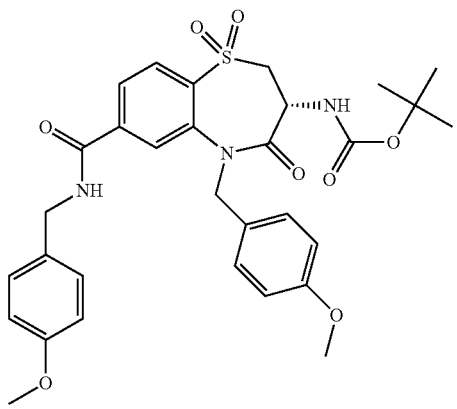 [SMILES: COc1ccc(CNC(=O)c2ccc3c(c2)N(Cc2ccc(OC)cc2)C(=O)[C@@H](NC(=O)OC(C)(C)C)CS3(=O)=O)cc1]

The title compound was synthesized according to general procedure GP4 to afford the title compound as white solid in 71% yield.

LCMS: METCR1410 Generic 1.7 min, rt=1.19 min, M/Z (ES+) 632.2 [M+Na+], 554.1 [M-tBu+H] 100% UV; NMR Data: 1H NMR (500 MHz, Chloroform-d) d 8.04 (d, J=8.1 Hz, 1H), 7.78 (dd, J=8.1, 1.2 Hz, 1H), 7.52-7.46 (m, 1H), 7.25-7.20 (m, 4H), 6.94-6.87 (m, 2H), 6.82-6.76 (m, 2H), 6.14 (t, J=5.1 Hz, 1H), 5.74 (d, J=7.2 Hz, 1H), 5.39 (d, J=14.9 Hz, 1H), 4.58-4.42 (m, 4H), 4.04 (dd, J=13.3, 6.9 Hz, 1H), 3.82 (s, 3H), 3.74 (s, 3H), 3.49 (dd, J=13.2, 11.1 Hz, 1H), 1.39 (s, 9H).

Synthesis of tert-butyl N-[(3R)-5-benzyl-7-{[(4-methoxyphenyl)methyl]carbamoyl}-1,1,4-trioxo-2,3,4,5-tetrahydro-1λ⁶,5-benzothiazepin-3-yl]carbamate (Intermediate IX-80)

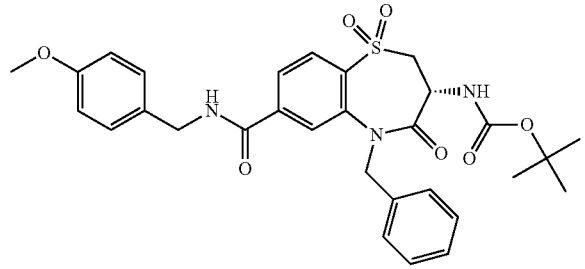 [SMILES: COc1ccc(CNC(=O)c2ccc3c(c2)N(Cc2ccccc2)C(=O)[C@@H](NC(=O)OC(C)(C)C)CS3(=O)=O)cc1]

The title compound was synthesized according to general procedure GP4 to afford the title compound as white solid in 75% yield.

LCMS: METCR1410 Generic 1.7 min, rt=1.19 min, M/Z (ES+) 602.2 [M+Na+] 96% UV

NMR Data: 1H NMR (250 MHz, Chloroform-d) d 8.07 (d, J=8.1 Hz, 1H), 7.81 (dd, J=8.1, 1.5 Hz, 1H), 7.36-7.17 (m, 8H), 6.95-6.87 (m, 2H), 5.99-5.89 (m, 1H), 5.73 (d, J=6.9 Hz, 1H), 5.57 (d, J=15.0 Hz, 1H), 4.58-4.38 (m, 4H), 4.09-4.00 (m, 1H), 3.83 (s, 3H), 3.50 (dd, J=13.3, 11.0 Hz, 1H), 1.40 (s, 9H).

Synthesis of tert-butyl N-[(3R)-5-[(4-chlorophenyl)methyl]-7-{[(4-methoxyphenyl)methyl]carbamoyl}-1,1,4-trioxo-2,3,4,5-tetrahydro-1λ⁶,5-benzothiazepin-3-yl]carbamate (Intermediate IX-81)

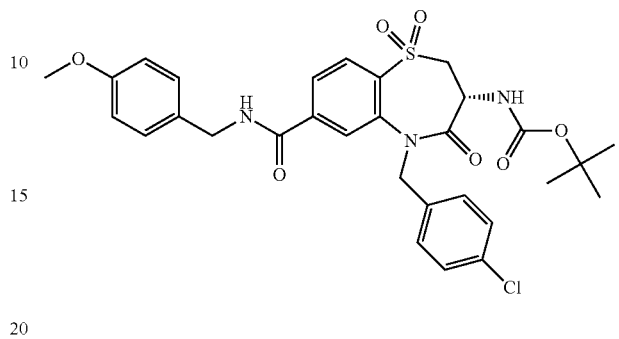

The title compound was synthesized according to general procedure GP4 to afford the title compound as white solid in 97% yield.

LCMS: METCR1416 generic 7 min, rt=1.23 min, M/Z (ES+) 558.05/560.10 [M-tBu+H] 98% UV NMR Data: 1H NMR (250 MHz, DMSO-d6) d 9.28 (t, J=6.0 Hz, 1H), 7.99 (s, 2H), 7.84 (s, 1H), 7.51 (d, J=7.9 Hz, 1H), 7.34 (s, 4H), 7.21 (d, J=8.6 Hz, 2H), 6.89 (d, J=8.6 Hz, 2H), 5.21 (d, J=16.2 Hz, 1H), 4.84 (d, J=15.8 Hz, 1H), 4.40 (d, J=5.8 Hz, 3H), 4.18-3.96 (m, 2H), 3.73 (s, 3H), 1.36 (s, 9H).

Synthesis of tert-butyl N-[(3R)-7-[(4,4-difluorocyclohexyl)carbamoyl]-5-[(4-methoxyphenyl)methyl]-1,1,4-trioxo-2,3,4,5-tetrahydro-1λ⁶,5-benzothiazepin-3-yl]carbamate (Intermediate IX-82)

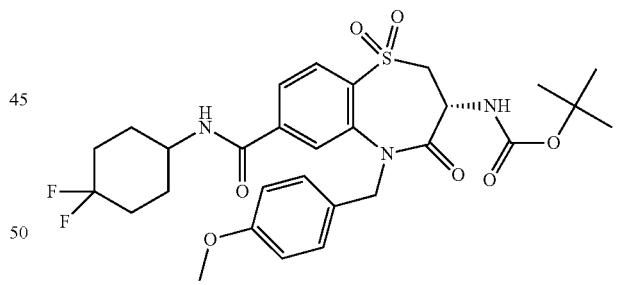

The title compound was synthesized according to general procedure GP4 to afford the title compound as white solid in 42% yield.

LCMS: METCR1410 Generic 1.7 min, rt=1.2 min, M/Z (ES+) 552.15 [M-tBu+H] 630.20 [M+Na+] 96% UV; NMR Data: 1H NMR (500 MHz, DMSO-d6) d 8.59 (d, J=7.6 Hz, 1H), 7.95 (q, J=9.5, 8.8 Hz, 2H), 7.81 (s, 1H), 7.50 (d, J=8.2 Hz, 1H), 7.24 (d, J=8.6 Hz, 2H), 6.82 (d, J=8.7 Hz, 2H), 5.18 (d, J=15.4 Hz, 1H), 4.76 (d, J=15.6 Hz, 1H), 4.35 (dt, J=11.8, 7.7 Hz, 1H), 4.10-4.01 (m, 1H), 3.98 (s, 1H), 3.77-3.74 (m, 1H), 3.72 (s, 3H), 2.05 (s, 3H), 1.96-1.84 (m, 3H), 1.63 (d, J=11.2 Hz, 2H), 1.37 (s, 9H).

Synthesis of tert-butyl N-[(3R)-5-[(4-chlorophenyl)methyl]-1,1,4-trioxo-7-[(3,3,3-trifluoropropyl)carbamoyl]-2,3,4,5-tetrahydro-1λ⁶,5-benzothiazepin-3-yl]carbamate (Intermediate IX-83)

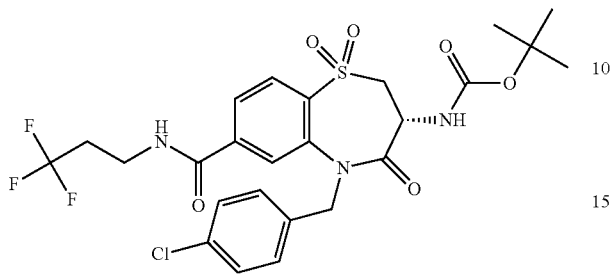

The title compound was synthesized according to general procedure GP4 to afford the title compound as white solid in 47% yield.

LCMS: METCR1410 Generic 1.7 min, rt=1.22 min, M/Z (ES+) 534/536 [M-tBu+H], 612.10/614.10 [M+Na+] 100% UV; NMR Data: 1H NMR (500 MHz, DMSO-d6) d 9.03 (t, J=5.6 Hz, 1H), 8.02 (d, J=8.2 Hz, 1H), 7.97-7.92 (m, 1H), 7.81 (s, 1H), 7.53 (d, J=8.1 Hz, 1H), 7.40-7.31 (m, 4H), 5.21 (d, J=16.0 Hz, 1H), 4.85 (d, J=16.1 Hz, 1H), 4.38 (dt, J=11.8, 7.7 Hz, 1H), 4.14-4.04 (m, 1H), 3.80-3.69 (m, 1H), 3.54-3.48 (m, 2H), 2.59-2.53 (m, 2H), 1.37 (s, 9H).

Synthesis of tert-butyl N-[(3R)-5-[(4-chlorophenyl)methyl]-1,1,4-trioxo-7-{[(3R)-oxolan-3-yl]carbamoyl}-2,3,4,5-tetrahydro-1λ⁶,5-benzothiazepin-3-yl]carbamate (Intermediate IX-84)

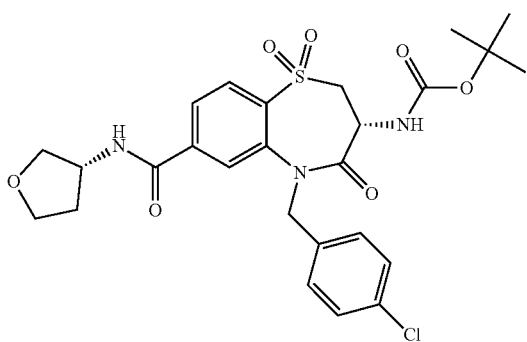 [SMILES: CC(C)(C)OC(=O)N[C@H]1CS(=O)(=O)c2ccc(C(=O)N[C@@H]3CCOC3)cc2N(Cc2ccc(Cl)cc2)C1=O]

The title compound was synthesized according to general procedure GP4 to afford the title compound as White solid in 95% yield.

LCMS: METCR1410 Generic 1.7 min, rt=1.12 min, M/Z (ES+) 508.05/510.10 [M-tBu+H], 586.15/588.15 [M+Na+] 95.2% UV; NMR Data: 1H NMR (500 MHz, Chloroform-d) d 7.75 (d, J=8.0 Hz, 1H), 7.46 (dd, J=8.1, 1.4 Hz, 1H), 6.99 (dd, J=18.7, 9.1 Hz, 5H), 6.00 (s, 1H), 5.42 (d, J=7.2 Hz, 1H), 5.06 (d, J=15.2 Hz, 1H), 4.40-4.35 (m, 1H), 4.33 (d, J=15.3 Hz, 1H), 4.22 (dt, J=10.8, 7.2 Hz, 1H), 3.72 (m, 2H), 3.53 (m, 2H), 3.45 (d, J=9.7 Hz, 1H), 3.21 (dd, J=13.2, 11.1 Hz, 1H), 2.06 (m, 1H), 1.57 (m, 1H), 1.09 (s, 9H).

Synthesis of tert-butyl N-[(3R)-5-[(4-chlorophenyl)methyl]-1,1,4-trioxo-7-{[(oxolan-3-yl)methyl]carbamoyl}-2,3,4,5-tetrahydro-1λ⁶,5-benzothiazepin-3-yl]carbamate (Intermediate IX-85)

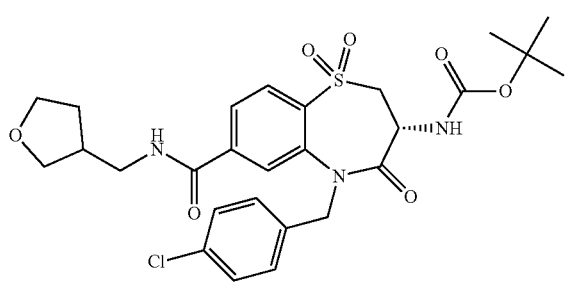 [SMILES: CC(C)(C)OC(=O)N[C@H]1CS(=O)(=O)c2ccc(C(=O)NCC3CCOC3)cc2N(Cc2ccc(Cl)cc2)C1=O]

The title compound was synthesized according to general procedure GP4 to afford the title compound as white solid in 79% yield.

LCMS: METCR1410 Generic 1.7 min, rt=1.12 min, M/Z (ES+) 522.05/524.15 [M-tBu+H], 600.15/602.20 [M+Na+] 84% UV; NMR Data: 1H NMR (250 MHz, DMSO-d6) d 8.89 (t, J=6.2 Hz, 1H), 8.04-7.90 (m, 2H), 7.75 (d, J=14.1 Hz, 1H), 7.52 (d, J=7.9 Hz, 1H), 7.34 (s, 4H), 5.22 (d, J=16.2 Hz, 1H), 4.83 (d, J=15.9 Hz, 1H), 4.49-4.28 (m, 1H), 4.19-3.97 (m, 2H), 3.89 (d, J=8.1 Hz, 1H), 3.81-3.54 (m, 5H), 3.52-3.37 (m, 1H), 1.97-1.82 (m, 1H), 1.71-1.47 (m, 1H), 1.36 (s, 9H).

Synthesis of tert-butyl N-[(3R)-5-[(4-chlorophenyl)methyl]-7-{[(1R)-2,2-difluorocyclopropyl]carbamoyl}-1,1,4-trioxo-2,3,4,5-tetrahydro-1λ⁶,5-benzothiazepin-3-yl]carbamate (Intermediate IX-86)

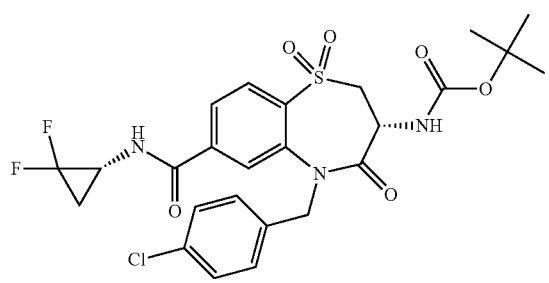 [SMILES: CC(C)(C)OC(=O)N[C@H]1CS(=O)(=O)c2ccc(C(=O)N[C@@H]3CC3(F)F)cc2N(Cc2ccc(Cl)cc2)C1=O]

The title compound was synthesized according to general procedure GP4 to afford the title compound as white solid in 75% yield.

LCMS: METCR1410 Generic 1.7 min, rt=1.18 min, M/Z (ES+) 514/516 [M-tBu+H], 592.10/594.15 [M+Na+] 97% UV; NMR Data: 1H NMR (500 MHz, Chloroform-d) d 8.10 (d, J=8.1 Hz, 1H), 7.76 (dd, J=8.1, 1.4 Hz, 1H), 7.56 (d, J=1.5 Hz, 1H), 7.33-7.29 (m, 2H), 7.29-7.26 (m, 2H), 6.20 (s, 1H), 5.69 (d, J=7.3 Hz, 1H), 5.37 (d, J=15.3 Hz, 1H), 4.65 (d, J=15.2 Hz, 1H), 4.52 (dt, J=10.8, 7.1 Hz, 1H), 4.07 (dd, J=13.3, 6.9 Hz, 1H), 3.56-3.47 (m, 2H), 1.94 (m, 1H), 1.50-1.42 (m, 1H), 1.40 (s, 9H).

Synthesis of tert-butyl N-[(3R)-5-[(4-cyclopropylphenyl)methyl]-7-{[(1R)-2,2-difluorocyclopropyl]carbamoyl}-1,1,4-trioxo-2,3,4,5-tetrahydro-1λ⁶,5-benzothiazepin-3-yl]carbamate (Intermediate IX-87)

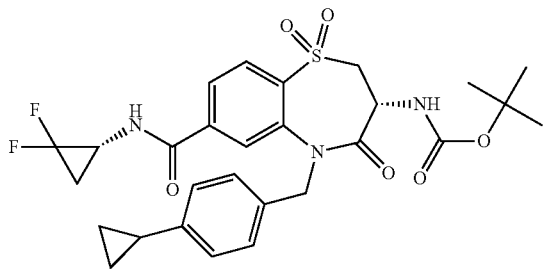 [SMILES: CC(C)(C)OC(=O)N[C@H]1CS(=O)(=O)c2ccc(C(=O)N[C@@H]3CC3(F)F)cc2N(Cc2ccc(C3CC3)cc2)C1=O]

The title compound was synthesized according to general procedure GP4 to afford the title compound as white solid in 76% yield.
LCMS: METCR1410 Generic 1.7 min, rt=1.21 min, M/Z (ES+) 598.2 [M+Na+] 97% UV
NMR Data: 1H NMR (500 MHz, DMSO-d6) d 9.14 (s, 1H), 8.04-7.98 (m, 1H), 7.97-7.92 (m, 1H), 7.80 (s, 1H), 7.50 (d, J=8.2 Hz, 1H), 7.19 (d, J=8.0 Hz, 2H), 6.98 (d, J=8.1 Hz, 2H), 5.21 (d, J=16.0 Hz, 1H), 4.72 (d, J=15.8 Hz, 1H), 4.38 (dt, J=11.7, 7.8 Hz, 1H), 4.07 (dd, J=12.1, 6.2 Hz, 1H), 3.79-3.70 (m, 1H), 3.50-3.42 (m, 1H), 2.05-1.94 (m, 1H), 1.93-1.83 (m, 1H), 1.70-1.61 (m, 1H), 1.37 (s, 9H), 0.95-0.90 (m, 2H), 0.65-0.60 (m, 2H).

Synthesis of tert-butyl N-[(3R)-7-{[(1R)-2,2-difluorocyclopropyl]carbamoyl}-5-{[4-(difluoromethoxy)phenyl]methyl}-1,1,4-trioxo-2,3,4,5-tetrahydro-1λ⁶, 5-benzothiazepin-3-yl]carbamate (Intermediate IX-88)

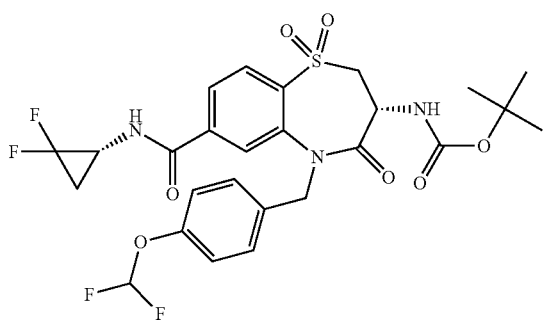 [SMILES: CC(C)(C)OC(=O)N[C@H]1CS(=O)(=O)c2ccc(C(=O)N[C@@H]3CC3(F)F)cc2N(Cc2ccc(OC(F)F)cc2)C1=O]

The title compound was synthesized according to general procedure GP4 to afford the title compound as white solid in 85% yield.
LCMS: METCR1410 Generic 1.7 min, rt=1.16 min, M/Z (ES+) 624.1 [M+Na+] 98% UV
NMR Data: 1H NMR (500 MHz, Chloroform-d) d 8.11 (d, J=8.1 Hz, 1H), 7.77 (dd, J=8.1, 1.4 Hz, 1H), 7.53 (d, J=1.5 Hz, 1H), 7.34 (d, J=8.6 Hz, 2H), 7.09 (d, J=8.5 Hz, 2H), 6.51 (t, J=73.7 Hz, 1H), 6.17-6.11 (m, 1H), 5.69 (d, J=7.2 Hz, 1H), 5.41 (d, J=15.2 Hz, 1H), 4.64 (d, J=15.2 Hz, 1H), 4.52 (dt, J=11.0, 7.0 Hz, 1H), 4.07 (dd, J=13.4, 7.0 Hz, 1H), 3.55-3.46 (m, 2H), 1.98-1.88 (m, 1H), 1.48-1.42 (m, 1H), 1.40 (s, 9H).

Synthesis of tert-butyl N-[(3R)-7-{[(1R)-2,2-difluorocyclopropyl]carbamoyl}-5-[(4-methoxyphenyl)methyl]-1,1,4-trioxo-2,3,4,5-tetrahydro-1λ⁶,5-benzothiazepin-3-yl]carbamate (Intermediate IX-89)

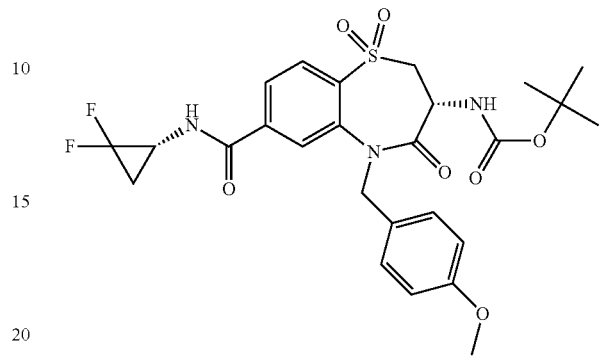

The title compound was synthesized according to general procedure GP4 to afford the title compound as off white solid in 91% yield.
LCMS: METCR1410 Generic 1.7 min, rt=1.14 min, M/Z (ES+) 510.1 [M-tBu+H], 588.15 [M+Na+] 98% UV; NMR Data: 1H NMR (250 MHz, Chloroform-d) d 7.99 (d, J=8.1 Hz, 1H), 7.77 (d, J=8.1 Hz, 1H), 7.44 (d, J=1.4 Hz, 1H), 7.23 (d, J=8.6 Hz, 2H), 6.84 (d, J=8.4 Hz, 2H), 6.49 (s, 1H), 5.77 (d, J=7.2 Hz, 1H), 5.40 (d, J=14.8 Hz, 1H), 4.56-4.39 (m, 2H), 3.99 (dd, J=13.4, 6.9 Hz, 1H), 3.77 (s, 3H), 3.58-3.35 (m, 2H), 1.97-1.71 (m, 1H), 1.46 (dd, J=9.9, 4.7 Hz, 1H), 1.38 (s, 9H).

Synthesis of tert-butyl N-[(3R)-5-benzyl-1,1,4-trioxo-7-[(4,4,4-trifluorobutyl)carbamoyl]-2,3,4,5-tetrahydro-1λ⁶, 5-benzothiazepin-3-yl]carbamate (Intermediate IX-90)

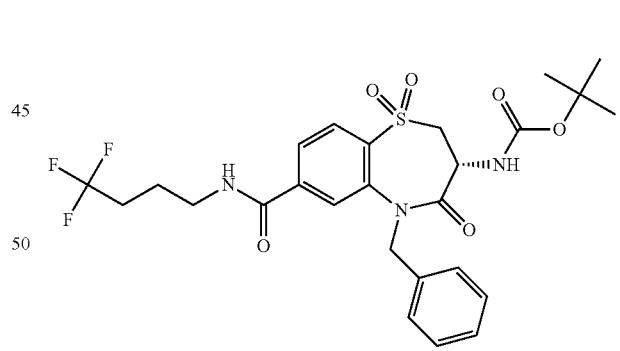

The title compound was synthesized according to general procedure GP4 to afford the title compound as white solid in 89% yield.
LCMS: METCR1410 Generic 1.7 min, rt=1.19 min, M/Z (ES+) 514.1 [M-tBu+H, 592.15 [M+Na+] 96% UV; NMR Data: 1H NMR (500 MHz, Chloroform-d) d 8.06 (d, J=8.1 Hz, 1H), 7.82-7.69 (m, 1H), 7.38 (d, J=1.2 Hz, 1H), 7.37-7.30 (m, 5H), 6.02 (t, J=5.4 Hz, 1H), 5.75 (d, J=7.3 Hz, 1H), 5.57 (d, J=15.1 Hz, 1H), 4.53 (dt, J=10.9, 7.1 Hz, 1H), 4.47 (d, J=15.1 Hz, 1H), 4.06 (dd, J=13.3, 6.9 Hz, 1H), 3.51 (dd, J=13.2, 11.1 Hz, 1H), 3.49-3.42 (m, 2H), 2.19-2.08 (m, 2H), 1.84 (dt, J=14.6, 7.1 Hz, 2H), 1.40 (s, 9H).

Synthesis of tert-butyl N-[(3R)-8-chloro-5-[(4-chlorophenyl)methyl]-1,1,4-trioxo-7-[(4,4,4-trifluorobutyl)carbamoyl]-2,3,4,5-tetrahydro-1λ⁶,5-benzothiazepin-3-yl]carbamate (Intermediate IX-91)

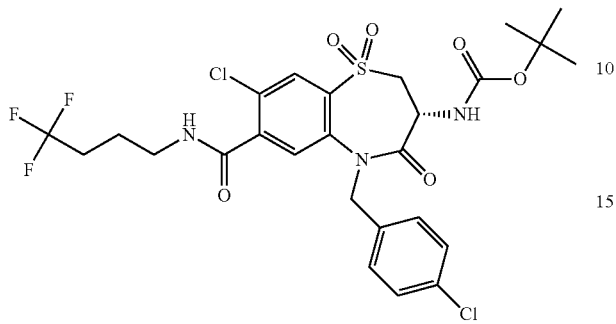

The title compound was synthesized according to general procedure GP4 to afford the title compound as white solid in 88% yield.
LCMS: METCR1410 Generic 1.7 min, rt=1.26 min, M/Z (ES+) 581.9/584.05 [M-tBu+H], 660.10/612.10 [M+Na+] 100% UV; NMR Data: 1H NMR (250 MHz, Chloroform-d) d 7.98 (s, 1H), 7.41 (s, 1H), 7.32-7.18 (m, 4H), 6.37 (t, J=5.7 Hz, 1H), 5.68 (d, J=7.2 Hz, 1H), 5.25 (d, J=15.3 Hz, 1H), 4.63 (d, J=15.3 Hz, 1H), 4.50 (dt, J=10.9, 7.1 Hz, 1H), 4.03 (dd, J=13.7, 7.1 Hz, 1H), 3.56-3.43 (m, 3H), 2.30-2.07 (m, 2H), 1.97-1.79 (m, 2H), 1.38 (s, 9H).

Synthesis of tert-butyl N-[(3R)-5-{[4-(difluoromethoxy)phenyl]methyl}-7-{[(oxan-4-yl)methyl]carbamoyl}-1,1,4-trioxo-2,3,4,5-tetrahydro-1λ⁶,5-benzothiazepin-3-yl]carbamate (Intermediate IX-92)

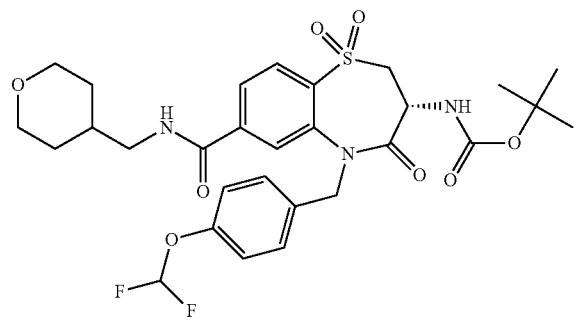 [SMILES: CC(C)(C)OC(=O)N[C@H]1CS(=O)(=O)c2ccc(C(=O)NCC3CCOCC3)cc2N(Cc2ccc(OC(F)F)cc2)C1=O]

The title compound was synthesized according to general procedure GP4 to afford the title compound as white solid in 79% yield.
LCMS: METCR1410 Generic 1.7 min, rt=1.12 min, M/Z (ES+) 524.2 [M-Boc+H+], 646.2 [M+Na+] 99% UV; NMR Data: 1H NMR (500 MHz, DMSO-d6) d 8.79 (t, J=5.6 Hz, 1H), 8.00-7.95 (m, 1H), 7.95-7.90 (m, 1H), 7.77 (s, 1H), 7.51 (d, J=8.1 Hz, 1H), 7.37 (d, J=8.6 Hz, 2H), 7.20 (t, J=74.2 Hz, 1H), 7.07 (d, J=8.5 Hz, 2H), 5.23 (d, J=16.0 Hz, 1H), 4.80 (d, J=15.9 Hz, 1H), 4.37 (dt, J=11.7, 7.7 Hz, 1H), 4.11-4.04 (m, 1H), 3.86-3.80 (m, 2H), 3.78-3.70 (m, 1H), 3.24 (t, J=10.8 Hz, 2H), 3.18-3.11 (m, 2H), 1.82-1.69 (m, 1H), 1.54 (d, J=12.3 Hz, 2H), 1.36 (s, 9H), 1.22-1.10 (m, 2H).

Synthesis of tert-butyl N-[(3R)-5-[(4-chlorophenyl)methyl]-7-{[(4-fluorooxan-4-yl)methyl]carbamoyl}-1,1,4-trioxo-2,3,4,5-tetrahydro-1λ⁶,5-benzothiazepin-3-yl]carbamate (Intermediate IX-93)

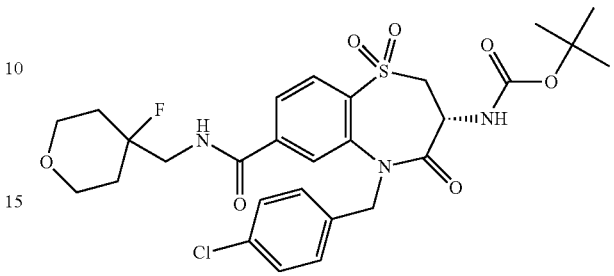

The title compound was synthesized according to general procedure GP4 to afford the title compound as white solid in 63% yield.
LCMS: METCR1410 Generic 1.7 min, rt=1.15 min, M/Z (ES+) 510.10/512.05 [M-Boc+H+]; 632.15/634.20 [M+Na+] 95% UV; NMR Data: 1H NMR (500 MHz, DMSO-d6) d 8.97 (t, J=6.1 Hz, 1H), 8.02-7.94 (m, 2H), 7.80 (s, 1H), 7.52 (d, J=8.1 Hz, 1H), 7.38-7.30 (m, 4H), 5.24 (d, J=16.0 Hz, 1H), 4.83 (d, J=16.0 Hz, 1H), 4.38 (dt, J=11.8, 7.7 Hz, 1H), 4.13-4.05 (m, 1H), 3.79-3.70 (m, 3H), 3.58-3.49 (m, 4H), 1.78-1.70 (m, 1H), 1.66 (d, J=12.2 Hz, 3H), 1.36 (s, 9H).

Synthesis of tert-butyl N-[(3R)-5-[(4-chlorophenyl)methyl]-7-{[(1R)-1-(oxan-4-yl)ethyl]carbamoyl}-1,1,4-trioxo-2,3,4,5-tetrahydro-1λ⁶,5-benzothiazepin-3-yl]carbamate (Intermediate IX-94)

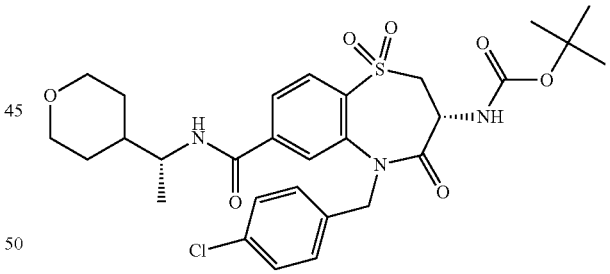

The title compound was synthesized according to general procedure GP4 to afford the title compound as white solid in 71% yield.
LCMS: METCR1410 Generic 1.7 min, rt=1.17 min, M/Z (ES+) 506.10/508.10 [M-Boc+H+], 628.15/630.20 [M+Na+] 100% UV
NMR Data: 1H NMR (500 MHz, DMSO-d6) d 8.45 (d, J=8.7 Hz, 1H), 7.98 (d, J=8.1 Hz, 1H), 7.93 (d, J=8.2 Hz, 1H), 7.72 (s, 1H), 7.53 (d, J=8.0 Hz, 1H), 7.35 (s, 4H), 5.27 (d, J=16.0 Hz, 1H), 4.81 (d, J=16.0 Hz, 1H), 4.38 (dt, J=11.7, 7.7 Hz, 1H), 4.09 (dt, J=13.3, 6.2 Hz, 1H), 3.90-3.79 (m, 3H), 3.78-3.72 (m, 1H), 3.28-3.20 (m, 2H), 1.65-1.54 (m, 2H), 1.51 (d, J=13.5 Hz, 1H), 1.37 (s, 9H), 1.24-1.13 (m, 2H), 1.11 (d, J=6.7 Hz, 3H).

Synthesis of tert-butyl N-[(3R)-5-benzyl-7-{[(1R)-2,2-difluorocyclopropyl]carbamoyl}-1,1,4-trioxo-2,3,4,5-tetrahydro-1λ⁶,5-benzothiazepin-3-yl]carbamate (Intermediate IX-95)

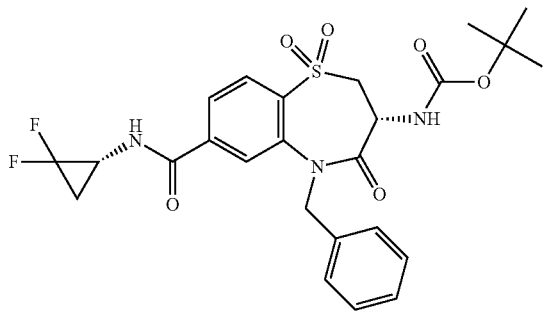 [SMILES: CC(C)(C)OC(=O)N[C@H]1CS(=O)(=O)c2ccc(C(=O)N[C@@H]3CC3(F)F)cc2N(Cc2ccccc2)C1=O]

The title compound was synthesized according to general procedure GP4 to afford the title compound as off white solid in 65% yield.

LCMS: METCR1410 Generic 1.7 min, rt=1.14 min, M/Z (ES+) 558.45 [M+Na+] 100% UV

NMR Data: 1H NMR (500 MHz, Chloroform-d) d 8.10 (d, J=8.1 Hz, 1H), 7.82 (dd, J=8.1, 1.4 Hz, 1H), 7.41-7.30 (m, 6H), 5.99 (s, 1H), 5.73 (d, J=7.4 Hz, 1H), 5.61 (d, J=15.0 Hz, 1H), 4.52 (dt, J=10.9, 7.1 Hz, 1H), 4.45 (d, J=15.0 Hz, 1H), 4.07 (dd, J=13.3, 7.0 Hz, 1H), 3.52 (dd, J=13.3, 11.1 Hz, 1H), 3.49-3.42 (m, 1H), 1.97-1.85 (m, 1H), 1.40 (s, 9H), 1.39-1.35 (m, 1H).

Synthesis of tert-butyl N-[(3R)-5-[(4-chlorophenyl)methyl]-7-{[(6-methylpyridin-3-yl)methyl]carbamoyl}-1,1,4-trioxo-2,3,4,5-tetrahydro-1λ⁶,5-benzothiazepin-3-yl]carbamate (Intermediate IX-96)

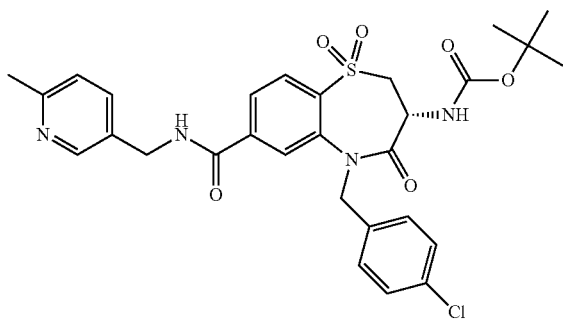 [SMILES: Cc1ccc(CNC(=O)c2ccc3c(c2)N(Cc2ccc(Cl)cc2)C(=O)[C@@H](NC(=O)OC(C)(C)C)CS3(=O)=O)cn1]

The title compound was synthesized according to general procedure GP7 to afford the title compound as white solid in 84% yield.

LCMS: METCR1410 Generic 1.7 min, rt=1.03 min, M/Z (ES+) 599.55/601.20 [M+H+] 99% UV NMR Data: 1H NMR (500 MHz, DMSO-d6) d 9.36 (t, J=5.6 Hz, 1H), 8.41 (d, J=2.0 Hz, 1H), 8.03-7.95 (m, 2H), 7.85 (s, 1H), 7.58 (dd, J=8.0, 2.3 Hz, 1H), 7.52 (d, J=8.1 Hz, 1H), 7.38-7.29 (m, 4H), 7.22 (d, J=7.9 Hz, 1H), 5.20 (d, J=16.0 Hz, 1H), 4.86 (d, J=16.0 Hz, 1H), 4.45 (d, J=5.7 Hz, 2H), 4.38 (dt, J=11.7, 7.6 Hz, 1H), 4.08 (dd, J=13.5, 7.6 Hz, 1H), 3.78-3.70 (m, 1H), 2.45 (s, 3H), 1.36 (s, 9H).

Synthesis of tert-butyl N-[(3R)-5-[(4-chlorophenyl)methyl]-7-{[(1R)-3,3-difluorocyclopentyl]carbamoyl}-1,1,4-trioxo-2,3,4,5-tetrahydro-1λ⁶,5-benzothiazepin-3-yl]carbamate (Intermediate IX-97)

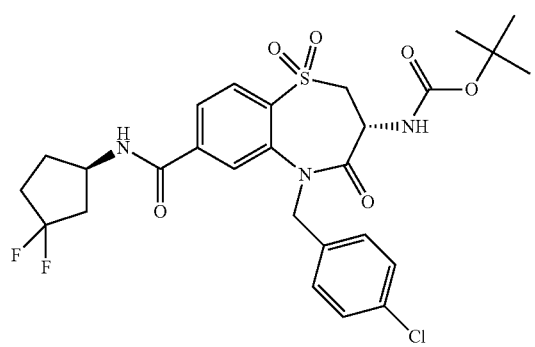 [SMILES: CC(C)(C)OC(=O)N[C@H]1CS(=O)(=O)c2ccc(C(=O)N[C@@H]3CCC(F)(F)C3)cc2N(Cc2ccc(Cl)cc2)C1=O]

The title compound was synthesized according to general procedure GP7 to afford the title compound as white solid in 92% yield.

LCMS: METCR1410 Generic 1.7 min, rt=1.23 min, M/Z (ES+) 620.15/622.20 [M+Na+] 100% UV NMR Data: 1H NMR (500 MHz, DMSO-d6) d 8.88 (d, J=7.0 Hz, 1H), 8.04-7.92 (m, 2H), 7.81 (s, 1H), 7.52 (d, J=8.1 Hz, 1H), 7.33 (s, 4H), 5.21 (d, J=15.9 Hz, 1H), 4.84 (d, J=15.9 Hz, 1H), 4.44-4.31 (m, 2H), 4.07 (dd, J=13.3, 7.3 Hz, 1H), 3.76-3.70 (m, 1H), 2.32-2.04 (m, 4H), 1.86-1.74 (m, 1H), 1.66-1.55 (m, 1H), 1.36 (s, 9H).

Synthesis of tert-butyl N-[(3R)-5-[(4-chlorophenyl)methyl]-7-{[(3,3-difluorocyclobutyl)methyl]carbamoyl}-1,1,4-trioxo-2,3,4,5-tetrahydro-1λ⁶,5-benzothiazepin-3-yl]carbamate (Intermediate IX-98)

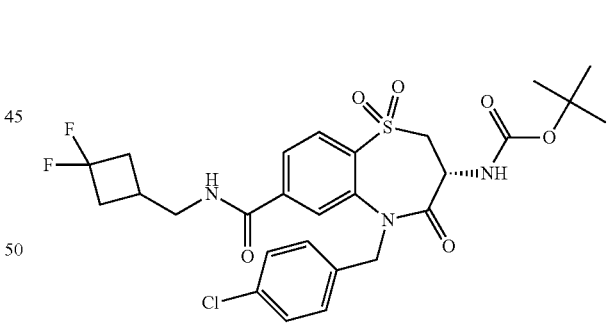

The title compound was synthesized according to general procedure GP4 to afford the title compound as white solid in 87% yield.

LCMS: METCR1410 Generic 1.7 min, rt=1.22 min, M/Z (ES+) 542.05/544.10 [M-tBu+H], 620.10/622.15 [M+Na+] 100% UV; NMR Data: 1H NMR (500 MHz, Chloroform-d) d 8.10 (d, J=8.1 Hz, 1H), 7.74 (dd, J=8.1, 1.3 Hz, 1H), 7.53 (d, J=1.4 Hz, 1H), 7.34-7.26 (m, 4H), 6.03 (t, J=5.5 Hz, 1H), 5.70 (d, J=7.6 Hz, 1H), 5.38 (d, J=15.3 Hz, 1H), 4.63 (d, J=15.2 Hz, 1H), 4.53 (dt, J=10.8, 7.1 Hz, 1H), 4.06 (dd, J=13.3, 6.9 Hz, 1H), 3.73-3.34 (m, 3H), 2.84-2.62 (m, 2H), 2.54-2.39 (m, 1H), 2.38-2.25 (m, 2H), 1.41 (s, 9H).

221

Synthesis of tert-butyl N-[(3R)-5-[(4-chlorophenyl)methyl]-8-fluoro-7-{[2-(2-methoxyethoxy)ethyl]carbamoyl}-1,1,4-trioxo-2,3,4,5-tetrahydro-1λ⁶,5-benzothiazepin-3-yl]carbamate (Intermediate IX-99)

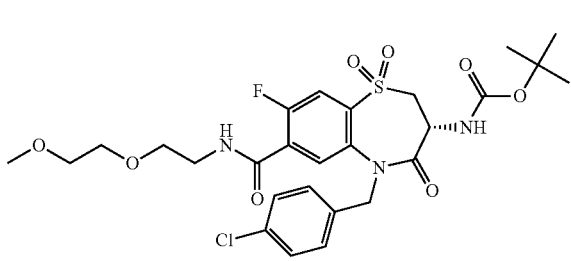 [SMILES: COCCOCCNC(=O)c1cc2c(cc1F)S(=O)(=O)C[C@H](NC(=O)OC(C)(C)C)C(=O)N2Cc1ccc(Cl)cc1]

The title compound was synthesized according to general procedure GP7 to afford the title compound as white solid in 68% yield.

LCMS: METCR1410 Generic 1.7 min, rt=1.16 min, M/Z (ES+) 636.10/638.15 [M+Na+] 100% UV NMR Data: 1H NMR (500 MHz, DMSO-d6) d 8.70 (t, J=5.5 Hz, 1H), 7.74 (d, J=8.5 Hz, 1H), 7.59 (d, J=5.5 Hz, 1H), 7.52 (d, J=8.1 Hz, 1H), 7.34 (s, 4H), 5.19 (d, J=16.0 Hz, 1H), 4.80 (d, J=16.1 Hz, 1H), 4.42 (dt, J=11.6, 7.7 Hz, 1H), 4.09 (dd, J=13.2, 7.3 Hz, 1H), 3.81-3.71 (m, 1H), 3.55-3.48 (m, 4H), 3.45-3.38 (m, 4H), 3.23 (s, 3H), 1.37 (s, 9H).

Synthesis of tert-butyl N-[(3R)-7-[(but-3-yn-1-yl)carbamoyl]-5-[(4-chlorophenyl)methyl]-8-fluoro-1,1,4-trioxo-2,3,4,5-tetrahydro-1λ⁶,5-benzothiazepin-3-yl]carbamate (Intermediate IX-100)

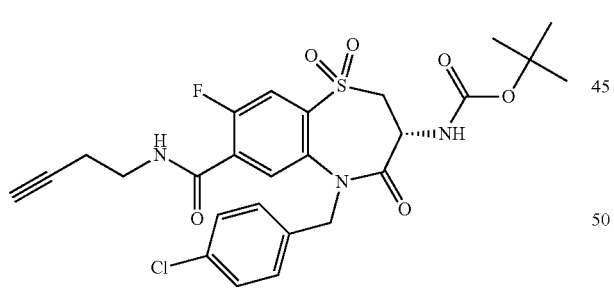

The title compound was synthesized according to general procedure GP7 to afford the title compound as off white solid in 65% yield.

LCMS: METCR1410 Generic 1.7 min, rt=1.19 min, M/Z (ES+) 586.05/588.10 [M+Na+] 98% UV NMR Data: 1H NMR (500 MHz, DMSO-d6) d 8.80 (t, J=5.5 Hz, 1H), 7.75 (d, J=8.5 Hz, 1H), 7.62 (d, J=5.5 Hz, 1H), 7.52 (d, J=8.0 Hz, 1H), 7.34 (s, 4H), 5.19 (d, J=16.1 Hz, 1H), 4.80 (d, J=16.0 Hz, 1H), 4.42 (dt, J=11.5, 7.7 Hz, 1H), 4.09 (dd, J=13.3, 7.3 Hz, 1H), 3.80-3.71 (m, 1H), 3.37 (dd, J=14.4, 7.2 Hz, 2H), 2.78 (t, J=2.6 Hz, 1H), 2.41 (td, J=7.0, 2.6 Hz, 2H), 1.37 (s, 9H).

222

Synthesis of tert-butyl N-[(3R)-5-[(4-chlorophenyl)methyl]-8-fluoro-1,1,4-trioxo-7-[(pent-4-yn-1-yl)carbamoyl]-2,3,4,5-tetrahydro-1λ⁶,5-benzothiazepin-3-yl]carbamate (Intermediate IX-101)

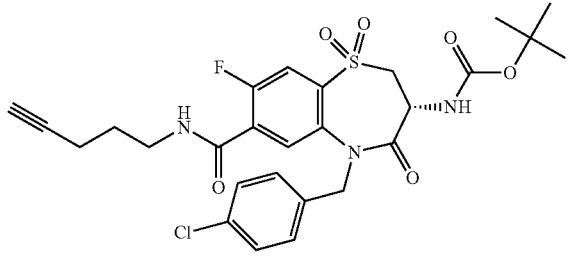 [SMILES: C#CCCCNC(=O)c1cc2c(cc1F)S(=O)(=O)C[C@H](NC(=O)OC(C)(C)C)C(=O)N2Cc1ccc(Cl)cc1]

The title compound was synthesized according to general procedure GP7 to afford the title compound as off white solid in 60% yield.

LCMS: METCR1410 Generic 1.7 min, rt=1.21 min, M/Z (ES+) 600.10/602.10 [M+Na+] 94% UV NMR Data: 1H NMR (500 MHz, DMSO-d6) d 8.70 (t, J=5.3 Hz, 1H), 7.74 (d, J=8.4 Hz, 1H), 7.62 (d, J=5.5 Hz, 1H), 7.52 (d, J=8.1 Hz, 1H), 7.34 (s, 4H), 5.19 (d, J=16.0 Hz, 1H), 4.83 (d, J=16.0 Hz, 1H), 4.41 (dt, J=11.5, 7.7 Hz, 1H), 4.09 (dd, J=13.2, 7.3 Hz, 1H), 3.81-3.72 (m, 1H), 3.30 (s, 2H), 2.80 (t, J=2.6 Hz, 1H), 2.21 (td, J=7.2, 2.6 Hz, 2H), 1.68 (p, J=7.0 Hz, 2H), 1.37 (s, 9H).

Synthesis of tert-butyl N-[(3R)-8-chloro-5-[(4-chlorophenyl)methyl]-7-{[(1R)-2,2-difluorocyclopropyl]carbamoyl}-1,1,4-trioxo-2,3,4,5-tetrahydro-1λ⁶,5-benzothiazepin-3-yl]carbamate (Intermediate IX-102)

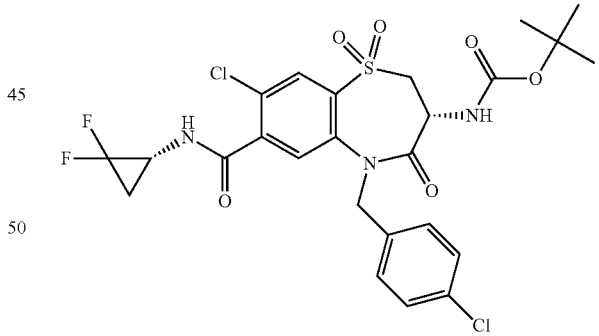

The title compound was synthesized according to general procedure GP4 to afford the title compound as white solid in 77% yield.

LCMS: METCR1410 Generic 1.7 min, rt=1.22 min, M/Z (ES+) 626.05/628.10 [M+Na+] 96% UV NMR Data: 1H NMR (500 MHz, Chloroform-d) d 8.06 (s, 1H), 7.51 (s, 1H), 7.33-7.28 (m, 2H), 7.26 (s, 2H), 6.53 (s, 1H), 5.68 (d, J=7.2 Hz, 1H), 5.25 (d, J=15.3 Hz, 1H), 4.71 (d, J=15.3 Hz, 1H), 4.53 (dt, J=10.9, 7.1 Hz, 1H), 4.06 (dd, J=13.4, 6.9 Hz, 1H), 3.58-3.47 (m, 2H), 1.95 (m, 1H), 1.49 (m, 1H), 1.41 (s, 9H).

Synthesis of tert-butyl N-[(3R)-5-[(4-chlorophenyl)methyl]-7-{[2-(morpholin-4-yl)ethyl]carbamoyl}-1,1,4-trioxo-2,3,4,5-tetrahydro-1λ⁶,5-benzothiazepin-3-yl]carbamate (Intermediate IX-103)

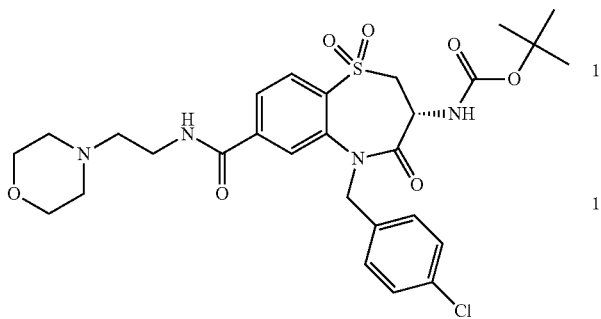

The title compound was synthesized according to general procedure GP7 to afford the title compound as white solid in 61% yield.

LCMS: METCR1410 Generic 1.7 min, rt=1 min, M/Z (ES+) 607.55/609.15 [M+H+] 98% UV NMR Data: 1H NMR (500 MHz, DMSO-d6) d 8.74 (t, J=5.6 Hz, 1H), 8.00 (d, J=8.2 Hz, 1H), 7.94 (d, J=8.2 Hz, 1H), 7.79 (s, 1H), 7.53 (d, J=8.1 Hz, 1H), 7.38-7.31 (m, 4H), 5.21 (d, J=16.0 Hz, 1H), 4.85 (d, J=16.1 Hz, 1H), 4.38 (dt, J=11.6, 7.6 Hz, 1H), 4.08 (dd, J=13.2, 7.2 Hz, 1H), 3.78-3.69 (m, 1H), 3.57-3.52 (m, 4H), 3.41-3.36 (m, 2H), 2.45 (t, J=6.8 Hz, 2H), 2.42-2.37 (m, 4H), 1.37 (s, 9H).

Synthesis of tert-butyl N-[(3R)-5-[(4-chlorophenyl)methyl]-7-{[(6-methoxypyridin-3-yl)methyl]carbamoyl}-1,1,4-trioxo-2,3,4,5-tetrahydro-1λ⁶,5-benzothiazepin-3-yl]carbamate (Intermediate IX-104)

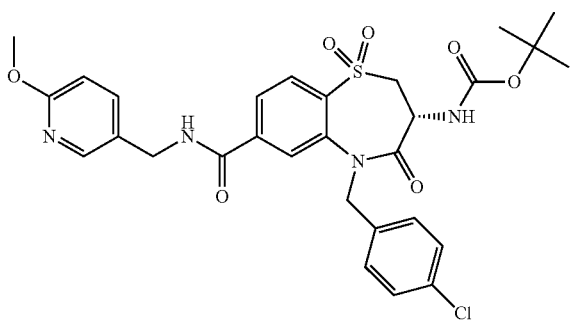 [SMILES: COc1ccc(CNC(=O)c2ccc3c(c2)N(Cc2ccc(Cl)cc2)C(=O)[C@@H](NC(=O)OC(C)(C)C)CS3(=O)=O)cn1]

The title compound was synthesized according to general procedure GP7 to afford the title compound as white solid in 78% yield.

LCMS: METCR1410 Generic 1.7 min, rt=1.18 min, M/Z (ES+) 615.55/617.10 [M+H+] 96% UV NMR Data: 1H NMR (500 MHz, DMSO-d6) d 9.31 (t, J=5.7 Hz, 1H), 8.12 (d, J=2.3 Hz, 1H), 8.01-7.94 (m, 2H), 7.84 (s, 1H), 7.63 (dd, J=8.5, 2.4 Hz, 1H), 7.51 (d, J=8.0 Hz, 1H), 7.37-7.30 (m, 4H), 6.79 (d, J=8.5 Hz, 1H), 5.19 (d, J=16.0 Hz, 1H), 4.85 (d, J=16.0 Hz, 1H), 4.43-4.33 (m, 3H), 4.07 (dd, J=13.1, 7.2 Hz, 1H), 3.83 (s, 3H), 3.76-3.69 (m, 1H), 1.35 (s, 9H).

Synthesis of tert-butyl N-[(3R)-5-[(4-chlorophenyl)methyl]-8-fluoro-1,1,4-trioxo-7-({[4-(prop-2-yn-1-yloxy)phenyl]methyl}carbamoyl)-2,3,4,5-tetrahydro-1λ⁶,5-benzothiazepin-3-yl]carbamate (Intermediate IX-105)

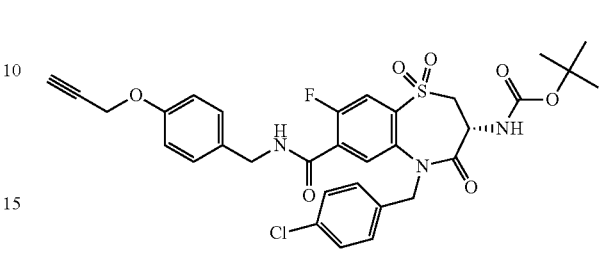

The title compound was synthesized according to general procedure GP7 to afford the title compound as off white solid in 53% yield.

LCMS: METCR1410 Generic 1.7 min, rt=1.26 min, M/Z (ES+) 678.20/680.20 [M+Na+] 93% UV NMR Data: 1H NMR (500 MHz, DMSO-d6) d 9.15 (t, J=5.9 Hz, 1H), 7.75 (d, J=8.5 Hz, 1H), 7.63 (d, J=5.5 Hz, 1H), 7.52 (d, J=8.1 Hz, 1H), 7.35 (s, 4H), 7.23 (d, J=8.6 Hz, 2H), 6.96 (d, J=8.6 Hz, 2H), 5.21 (d, J=15.9 Hz, 1H), 4.83-4.78 (m, 3H), 4.46-4.34 (m, 3H), 4.14-4.05 (m, 1H), 3.82-3.72 (m, 1H), 3.55 (t, J=2.4 Hz, 1H), 1.37 (s, 9H).

Synthesis of tert-butyl N-[(3R)-7-{[(1R)-2,2-difluorocyclopropyl]carbamoyl}-1,1,4-trioxo-5-{[4-(trifluoromethyl)phenyl]methyl}-2,3,4,5-tetrahydro-1λ⁶,5-benzothiazepin-3-yl]carbamate (Intermediate IX-106)

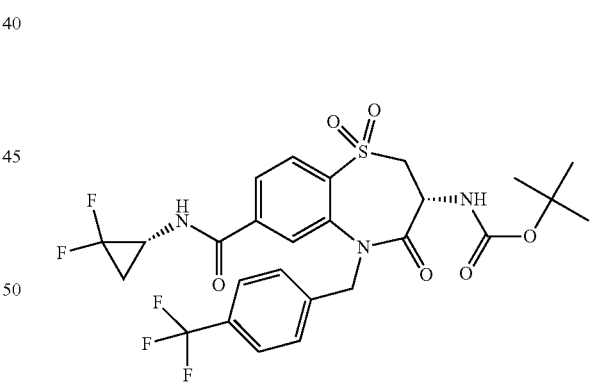

The title compound was synthesized according to general procedure GP4 to afford the title compound as white solid in 80% yield.

LCMS: METCR1410 Generic 1.7 min, rt=1.21 min, M/Z (ES+) 626.1 [M+Na+] 100% UV

NMR Data: 1H NMR (500 MHz, DMSO-d6) d 9.17 (s, 1H), 8.04 (d, J=8.2 Hz, 1H), 7.98 (dd, J=8.2, 1.2 Hz, 1H), 7.80 (s, 1H), 7.66 (d, J=8.2 Hz, 2H), 7.59-7.51 (m, 3H), 5.32 (d, J=16.4 Hz, 1H), 4.91 (d, J=16.4 Hz, 1H), 4.42 (dt, J=11.8, 7.6 Hz, 1H), 4.10 (dd, J=13.2, 7.4 Hz, 1H), 3.79-3.71 (m, 1H), 2.05-1.93 (m, 1H), 1.70-1.56 (m, 2H), 1.36 (s, 9H).

Synthesis of tert-butyl N-[(3R)-5-[(4-bromophenyl)methyl]-7-[(2,2-difluorocyclopropyl)carbamoyl]-1,1,4-trioxo-2,3,4,5-tetrahydro-1λ⁶,5-benzothiazepin-3-yl]carbamate (Intermediate IX-107)

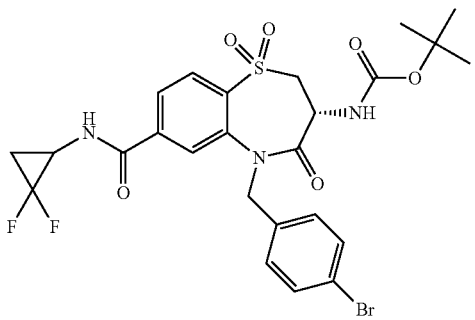 [SMILES: CC(C)(C)OC(=O)N[C@H]1CS(=O)(=O)c2ccc(C(=O)NC3CC3(F)F)cc2N(Cc2ccc(Br)cc2)C1=O]

The title compound was synthesized according to general procedure GP4 to afford the title compound as white solid in 82% yield.

LCMS: METCR1410 Generic 1.7 min, rt=1.2 min, M/Z (ES+) 558.0/560.0 [M-Boc+H+], 636.0/638.0 [M+Na+] 100% UV; NMR Data: 1H NMR (500 MHz, DMSO-d6) d 9.17 (s, 1H), 8.01 (d, J=8.2 Hz, 1H), 7.98-7.92 (m, 1H), 7.82 (d, J=16.4 Hz, 1H), 7.51 (d, J=8.0 Hz, 1H), 7.46 (d, J=8.2 Hz, 2H), 7.27 (d, J=8.3 Hz, 2H), 5.18 (dd, J=16.0, 10.6 Hz, 1H), 4.83 (dd, J=23.0, 16.0 Hz, 1H), 4.37 (dtd, J=11.9, 7.6, 4.6 Hz, 1H), 4.12-4.05 (m, 1H), 2.05-1.93 (m, 1H), 1.75-1.55 (m, 2H), 1.36 (s, 9H).

Synthesis of tert-butyl N-[(3R)-5-[(4-cyanophenyl)methyl]-8-fluoro-7-{[(4-fluorophenyl)methyl]carbamoyl}-1,1,4-trioxo-2,3,4,5-tetrahydro-1λ⁶,5-benzothiazepin-3-yl]carbamate (Intermediate IX-108)

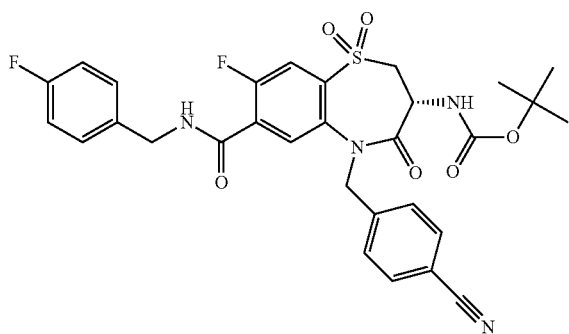 [SMILES: CC(C)(C)OC(=O)N[C@H]1CS(=O)(=O)c2cc(F)c(C(=O)NCc3ccc(F)cc3)cc2N(Cc2ccc(C#N)cc2)C1=O]

The title compound was synthesized according to general procedure GP4 to afford the title compound as White solid in 87% yield.

LCMS: METCR1410 Generic 1.7 min, rt=1.23 min, M/Z (ES+) 555.05 [M-tBu+H] 99% UV

NMR Data: 1H NMR (500 MHz, Chloroform-d) d 8.04 (d, J=6.0 Hz, 1H), 7.83 (d, J=9.8 Hz, 1H), 7.64-7.60 (m, 2H), 7.45 (d, J=8.3 Hz, 2H), 7.34-7.29 (m, 2H), 7.09-7.04 (m, 2H), 7.02 (dd, J=10.9, 5.0 Hz, 1H), 5.65 (d, J=7.2 Hz, 1H), 5.23 (d, J=15.6 Hz, 1H), 4.93 (d, J=15.6 Hz, 1H), 4.70-4.57 (m, 2H), 4.57-4.50 (m, 1H), 4.16-4.09 (m, 1H), 3.52 (dd, J=13.3, 11.1 Hz, 1H), 1.41 (s, 9H).

Synthesis of tert-butyl N-[(3R)-7-(benzylcarbamoyl)-5-[(4-chlorophenyl)methyl]-8-(dimethylamino)-1,1,4-trioxo-2,3,4,5-tetrahydro-1λ⁶,5-benzothiazepin-3-yl]carbamate (Intermediate IX-109)

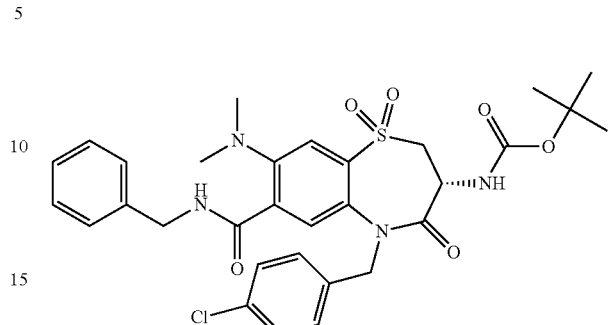

2M N-methylmethanamine in THF (0.15 mL, 0.3 mmol) was added to a stirred solution of Intermediate IX-41 (100%, 36.0 mg, 0.06 mmol) in ethanol (2 mL) in a sealed tube. The reaction was heated to 80° C. for 16 h. The reaction mixture was concentrated under reduced pressure, dissolved in DCM (5 mL), washed with water and brine (5 mL), and dried over Na₂SO₄ filtered and concentrated under reduced pressure to afford the title compound as white solid in 100% Yield.

LCMS: METCR1673 Generic 2 minutes: rt=1.30 min M/Z (ES+) 626.95/629 [M+H+] 100% UV NMR data: ¹H NMR (500 MHz, DMSO-d₆) δ 9.10 (t, J=5.9 Hz, 1H), 7.44 (d, J=8.3 Hz, 1H), 7.37-7.23 (m, 11H), 5.24 (d, J=16.0 Hz, 1H), 4.53 (d, J=16.0 Hz, 1H), 4.39 (dd, J=14.0, 6.6 Hz, 3H), 4.03 (dd, J=13.3, 7.1 Hz, 1H), 3.74-3.66 (m, 1H), 2.81 (s, 6H), 1.37 (s, 9H).

EXAMPLES

The synthesis of (3R)-3-amino-5-[(4-chlorophenyl)methyl]-N-(2,2-difluorocyclopropyl)-8-fluoro-1,1,4-trioxo-2,3,4,5-tetrahydro-1λ⁶,5-benzothiazepine-7-carboxamide hydrochloride (Example 1) has been described as example synthesis towards the beginning of the general procedures section.

According to the above described and exemplified general procedure GP5 the following examples were synthesized from amide intermediate VIII: LCMS data of hydrochloride salts listed below show the mass ions (M/Z) of the corresponding freebase.

Synthesis of (3R)-3-amino-N-butyl-5-[(4-tert-butylphenyl)methyl]-4-oxo-2,3,4,5-tetrahydro-1,5-benzothiazepine-7-carboxamide hydrochloride (Example 2)

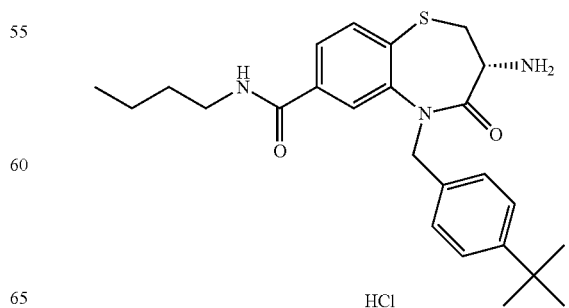

The title compound was synthesized according to general procedure GP5 to afford the title compound as white solid in 51% Yield.

LCMS: MET-UPLCMS-B-007, rt=2.77 min, M/Z (ES+) 440 [M+H+] 92% UV

NMR Data: 1H NMR (400 MHz, DMSO) δ 0.96-0.82 (m, 3H), 1.22 (s, 9H), 1.40-1.26 (m, 2H), 1.57-1.44 (m, 2H), 3.30-3.17 (m, 3H), 3.73-3.60 (m, 1H), 4.07-3.93 (m, 1H), 4.98 (d, J=15.6 Hz, 1H), 5.37 (d, J=15.6 Hz, 1H), 7.25 (q, J=8.5 Hz, 4H), 7.80-7.65 (m, 2H), 8.05 (s, 1H), 8.70 (t, J=5.7 Hz, 1H).

Synthesis of (3R)-3-amino-N-butyl-4-oxo-5-{[4-(trifluoromethoxy)phenyl]methyl}-2,3,4,5-tetrahydro-1,5-benzothiazepine-7-carboxamide hydrochloride (Example 3)

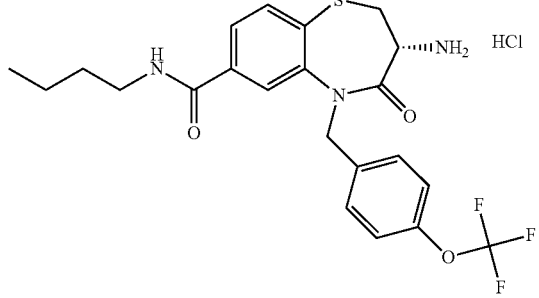

The title compound was synthesized according to general procedure GP5 to afford the title compound as white solid.

LCMS: MET-UPLCMS-B-007, rt=2.83 min, M/Z (ES+) 468 [M+H+] 100% UV

NMR Data: 1H NMR (400 MHz, DMSO) d 0.90 (t, J=7.3 Hz, 3H), 1.38-1.26 (m, 2H), 1.56-1.46 (m, 2H), 3.31-3.19 (m, 3H), 3.68 (dd, J=11.4, 6.9 Hz, 1H), 4.00 (dd, J=11.7, 6.9 Hz, 1H), 5.07 (d, J=15.6 Hz, 1H), 5.42 (d, J=15.6 Hz, 1H), 7.26 (d, J=8.0 Hz, 2H), 7.43 (d, J=8.7 Hz, 2H), 7.72 (d, J=8.0 Hz, 1H), 7.77 (dd, J=8.0, 1.7 Hz, 1H), 8.07 (d, J=1.6 Hz, 1H), 8.52 (s, 3H), 8.76 (t, J=5.7 Hz, 1H).

Synthesis of (3R)-3-amino-5-[(4-tert-butylphenyl) methyl]-4-oxo-N-(propan-2-yl)-2,3,4,5-tetrahydro-1,5-benzothiazepine-7-carboxamide hydrochloride (Example 4)

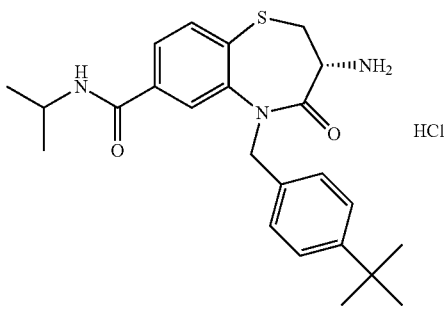 [SMILES: CC(C)NC(=O)c1ccc2c(c1)N(Cc1ccc(C(C)(C)C)cc1)C(=O)[C@@H](N)CS2 ; Cl]

The title compound was synthesized according to general procedure GP5 to afford the title compound as white solid in 63% Yield.

LCMS: MET-UPLCMS-A-006, rt=2.57 min, M/Z (ES+) 426 [M+H+] 99% UV

NMR Data: 1H NMR (300 MHz, DMSO) δ 1.20-1.14 (m, 6H), 1.22 (s, 9H), 3.26 (t, J=11.6 Hz, 1H), 3.69 (dd, J=11.5, 6.8 Hz, 1H), 4.02-3.90 (m, 1H), 4.16-4.02 (m, 1H), 5.01 (d, J=15.5 Hz, 1H), 5.36 (d, J=15.6 Hz, 1H), 7.34-7.15 (m, 4H), 7.72 (d, J=8.0 Hz, 1H), 7.78 (dd, J=8.0, 1.6 Hz, 1H), 8.06 (d, J=1.5 Hz, 1H), 8.49 (d, J=7.7 Hz, 1H), 8.55 (s, 3H).

Synthesis of (3R)-3-amino-N-butyl-8-fluoro-4-oxo-5-{[4-(trifluoromethoxy)phenyl]methyl}-2,3,4,5-tetrahydro-1,5-benzothiazepine-7-carboxamide hydrochloride (Example 5)

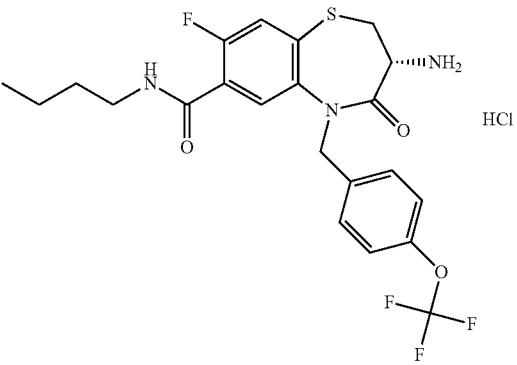 [SMILES: CCCCNC(=O)c1cc2c(cc1F)SC[C@H](N)C(=O)N2Cc1ccc(OC(F)(F)F)cc1 ; Cl]

The title compound was synthesized according to general procedure GP5 to afford the title compound as white solid in 93% Yield.

LCMS: METCR 1416 generic 7 minutes, rt=3.37 min, M/Z (ES+) 486 [M+H+] 99% UV

NMR Data: 1H NMR (300 MHz, DMSO) δ 8.44 (t, J=5.4 Hz, 1H), 8.31 (s, 3H), 7.76 (d, J=6.4 Hz, 1H), 7.64 (d, J=9.3 Hz, 1H), 7.42 (d, J=8.7 Hz, 2H), 7.29 (d, J=8.1 Hz, 2H), 5.32 (d, J=15.5 Hz, 1H), 5.00 (d, J=15.6 Hz, 1H), 4.04 (dd, J=11.6, 6.9 Hz, 1H), 3.65 (dd, J=11.5, 6.9 Hz, 1H), 3.30-3.18 (m, 3H), 1.49 (p, J=7.0 Hz, 2H), 1.32 (h, J=7.4 Hz, 2H), 0.90 (t, J=7.4 Hz, 3H).

Synthesis of (3R)-3-amino-N-benzyl-4-oxo-5-{[4-(trifluoromethoxy)phenyl]methyl}-2,3,4,5-tetrahydro-1,5-benzothiazepine-7-carboxamide hydrochloride (Example 6)

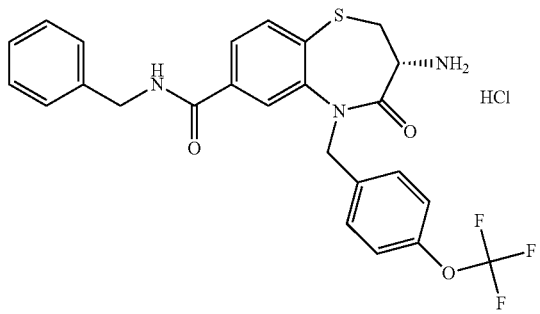 [SMILES: N[C@H]1CSc2ccc(C(=O)NCc3ccccc3)cc2N(Cc2ccc(OC(F)(F)F)cc2)C1=O ; Cl]

The title compound was synthesized according to general procedure GP5 to afford the title compound as white solid in 65% Yield.

LCMS: MET-UPLCMS-A-006., rt=3.78 min, M/Z (ES+) 502 [M+H+] 95% UV

NMR Data: 1H NMR (300 MHz, DMSO) δ 3.25 (t, J=11.6 Hz, 1H), 3.67 (dd, J=11.4, 6.8 Hz, 1H), 4.03 (dd, J=11.7, 6.9 Hz, 1H), 4.59-4.42 (m, 2H), 5.05 (d, J=15.5 Hz, 1H), 5.44 (d, J=15.5 Hz, 1H), 7.29-7.22 (m, 3H), 7.37-7.30 (m, 4H), 7.43 (d, J=8.7 Hz, 2H), 7.75 (d, J=8.0 Hz, 1H), 7.83 (dd, J=8.1, 1.8 Hz, 1H), 8.14 (d, J=1.6 Hz, 1H), 8.49 (s, 2H), 9.37 (s, 1H).

Synthesis of (3R)-3-amino-N-[(4-methoxyphenyl)methyl]-4-oxo-5-{[4-(trifluoromethoxy)-phenyl]methyl}-2,3,4,5-tetrahydro-1,5-benzothiazepine-7-carboxamide hydrochloride (Example 7)

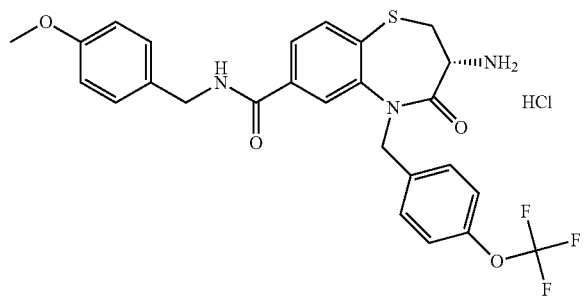 [SMILES: COc1ccc(CNC(=O)c2ccc3c(c2)N(Cc2ccc(OC(F)(F)F)cc2)C(=O)[C@@H](N)CS3)cc1 ; Cl]

The title compound was synthesized according to general procedure GP5 to afford the title compound as white solid in 60% Yield.

LCMS: MET-UPLCMS-A-006, rt=3.73 min, M/Z (ES+) 532 [M+H+] 96% UV

NMR Data: 1H NMR (300 MHz, DMSO) 3.25 (t, J=11.6 Hz, 1H), 3.67 (dd, J=11.4, 6.8 Hz, 1H), 3.72 (s, 3H), 4.02 (dd, J=11.8, 6.9 Hz, 1H), 4.49-4.34 (m, 2H), 5.05 (d, J=15.5 Hz, 1H), 5.44 (d, J=15.5 Hz, 1H), 6.94-6.84 (m, 2H), 7.29-7.21 (m, 4H), 7.42 (d, J=8.7 Hz, 2H), 7.74 (d, J=8.0 Hz, 1H), 7.81 (dd, J=8.1, 1.8 Hz, 1H), 8.12 (d, J=1.6 Hz, 1H), 8.49 (s, 2H), 9.29 (t, J=5.8 Hz, 1H).

Synthesis of (3R)-3-amino-N-(oxan-4-yl)-4-oxo-5-{[4-(trifluoromethoxy)phenyl]methyl}-2,3,4,5-tetrahydro-1,5-benzothiazepine-7-carboxamide hydrochloride (Example 8)

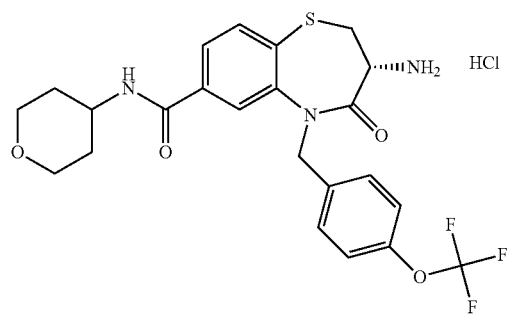 [SMILES: N[C@H]1CSc2ccc(C(=O)NC3CCOCC3)cc2N(Cc2ccc(OC(F)(F)F)cc2)C1=O ; Cl]

The title compound was synthesized according to general procedure GP5 to afford the title compound as yellow solid in 40% Yield.

LCMS: MET-UPLCMS-A-006, rt=2.08 min, M/Z (ES+) 496 [M+H+] 97% UV

NMR Data: 1H NMR (400 MHz, DMSO) δ 1.20 (dd, J=16.6, 9.3 Hz, 1H), 1.60 (dd, J=19.5, 11.8 Hz, 2H), 1.75 (d, J=11.9 Hz, 2H), 3.24 (t, J=11.6 Hz, 1H), 3.38 (dd, J=13.2, 9.0 Hz, 2H), 3.65 (dd, J=11.4, 6.8 Hz, 1H), 3.88 (d, J=9.5 Hz, 2H), 4.00 (dd, J=7.2, 3.8 Hz, 2H), 5.07 (d, J=15.5 Hz, 1H), 5.41 (d, J=15.5 Hz, 1H), 7.27 (d, J=8.1 Hz, 2H), 7.42 (d, J=8.6 Hz, 2H), 7.73 (d, J=8.0 Hz, 1H), 7.80 (dd, J=8.0, 1.6 Hz, 1H), 8.05 (d, J=1.5 Hz, 1H), 8.48 (s, 2H), 8.58 (d, J=7.6 Hz, 1H).

Synthesis of (3R)-3-amino-N-butyl-4-oxo-5-{[3-(trifluoromethoxy)phenyl]methyl}-2,3,4,5-tetrahydro-1,5-benzothiazepine-7-carboxamide hydrochloride (Example 9)

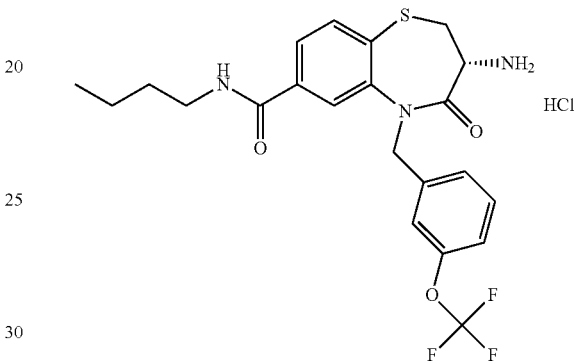

The title compound was synthesized according to general procedure GP5 to afford the title compound as yellow solid in 90% Yield.

LCMS: MET-UPLCMS-A-006, rt=3.19 min, M/Z (ES+) 468 [M+H+] 100% UV

NMR Data: 1H NMR (300 MHz, DMSO) δ 0.89 (t, J=7.2 Hz, 3H), 1.39-1.26 (m, 2H), 1.58-1.43 (m, 2H), 3.31-3.19 (m, 3H), 3.72-3.61 (m, 1H), 4.10-3.95 (m, 1H), 5.07 (d, J=15.7 Hz, 1H), 5.53 (d, J=15.7 Hz, 1H), 7.20 (d, J=7.6 Hz, 1H), 7.45-7.27 (m, 3H), 7.80-7.66 (m, 2H), 8.08 (s, 1H), 8.50 (s, 3H), 8.74 (t, J=5.0 Hz, 1H).

Synthesis of (3R)-3-amino-N-butyl-5-[(4-chlorophenyl)methyl]-4-oxo-2,3,4,5-tetrahydro-1,5-benzothiazepine-7-carboxamide hydrochloride (Example 10)

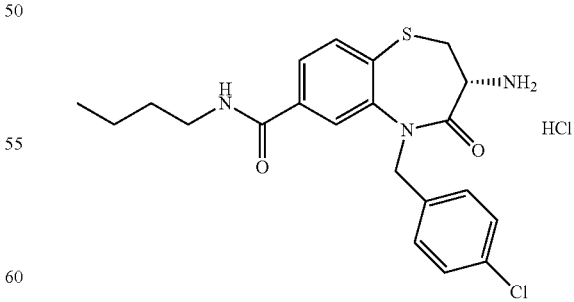

The title compound was synthesized according to general procedure GP5 to afford the title compound as off-white solid in 83% Yield.

LCMS: MET-UPLCMS-A-006, rt=2.4 min, M/Z (ES+) 418/420 [M+H+] 100% UV

NMR Data: 1H NMR (400 MHz, DMSO) δ 0.90 (t, J=7.3 Hz, 3H), 1.39-1.26 (m, 2H), 1.57-1.45 (m, 2H), 3.31-3.15 (m, 3H, hidden under solvent peak), 3.74-3.60 (m, 1H), 4.07-3.93 (m, 1H), 5.01 (d, J=15.4 Hz, 1H), 5.41 (d, J=15.4 Hz, 1H), 7.31 (s, 4H), 7.71 (d, J=8.0 Hz, 1H), 7.76 (d, J=8.3 Hz, 1H), 8.06 (s, 1H), 8.52 (s, 3H), 8.76 (t, J=5.4 Hz, 1H).

Synthesis of (3R)-3-amino-N-{[4-(morpholin-4-yl)phenyl]methyl}-4-oxo-5-{[4-(trifluoromethoxy)phenyl]methyl}-2,3,4,5-tetrahydro-1,5-benzothiazepine-7-carboxamide hydrochloride (Example 11)

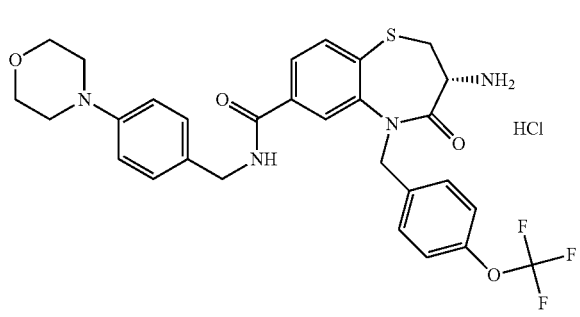 [SMILES: N[C@H]1CSc2ccc(C(=O)NCc3ccc(N4CCOCC4)cc3)cc2N(Cc2ccc(OC(F)(F)F)cc2)C1=O ; Cl]

The title compound was synthesized according to general procedure GP5 to afford the title compound as off-white solid in 91% Yield.

LCMS: MET-UPLCMS-A-006, rt=3.04 min, M/Z (ES+) 587 [M+H+] 100% UV

NMR Data: 1H NMR (400 MHz, DMSO) δ 3.27-3.09 (m, 4H), 3.32 (t, J=11.6 Hz, 1H), 3.75 (dd, J=11.4, 6.8 Hz, 1H), 3.96-3.80 (m, 4H), 4.14-4.00 (m, 1H), 4.55-4.38 (m, 2H), 5.13 (d, J=15.5 Hz, 1H), 5.50 (d, J=15.6 Hz, 1H), 6.61 (s, 1H), 7.16 (bs, 2H), 7.32 (d, J=8.1 Hz, 4H), 7.49 (d, J=8.7 Hz, 2H), 7.80 (d, J=8.0 Hz, 1H), 7.87 (dd, J=8.0, 1.7 Hz, 1H), 8.21 (d, J=1.5 Hz, 1H), 8.62 (s, 3H), 9.42 (t, J=5.4 Hz, 1H).

Synthesis of N-(3-{[(3R)-3-amino-4-oxo-5-{[4-(trifluoromethoxy)phenyl]methyl}-2,3,4,5-tetrahydro-1,5-benzothiazepin-7-yl]formamido}propyl)-2,2-dimethylpropanamide hydrochloride (Example 12)

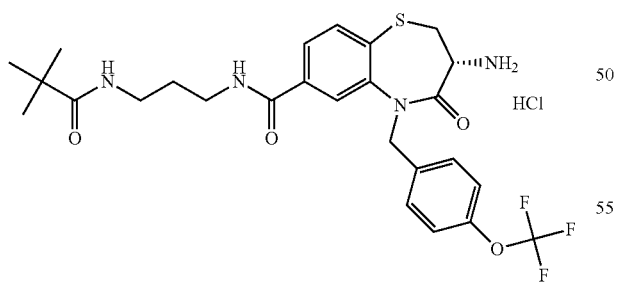

The title compound was synthesized according to general procedure GP5 to afford the title compound as off-white solid in 44% Yield.

LCMS: MET-UPLCMS-A-006, rt=2.32 min, M/Z (ES+) 553 [M+H+] 100% UV

NMR Data: 1H NMR (300 MHz, DMSO) 1.16-1.03 (m, 9H), 1.72-1.55 (m, 2H), 3.15-3.03 (m, 2H), 3.32-3.18 (m, 3H), 3.65 (dd, J=11.4, 6.8 Hz, 1H), 4.07-3.90 (m, 1H, hidden under solvent peak), 5.07 (d, J=15.4 Hz, 1H), 5.46 (d, J=15.4 Hz, 2H), 7.26 (d, J=7.9 Hz, 2H), 7.43 (d, J=8.7 Hz, 2H), 7.60 (t, J=5.7 Hz, 1H), 7.73 (d, J=8.0 Hz, 1H), 7.78 (dd, J=8.1, 1.5 Hz, 1H), 8.11 (d, J=1.2 Hz, 1H), 8.45 (s, 3H), 8.82 (t, J=5.6 Hz, 1H).

Synthesis of (3R)-3-amino-N-butyl-5-{[4-(morpholin-4-yl)phenyl]methyl}-4-oxo-2,3,4,5-tetrahydro-1,5-benzothiazepine-7-carboxamide hydrochloride (Example 13)

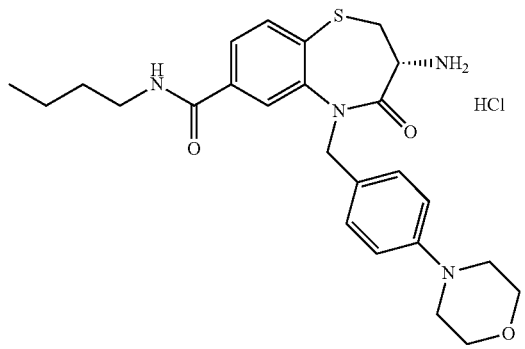 [SMILES: CCCCNC(=O)c1ccc2c(c1)N(Cc1ccc(N3CCOCC3)cc1)C(=O)[C@@H](N)CS2 ; Cl]

The title compound was synthesized according to general procedure GP5 to afford the title compound as off-white solid in 80% Yield.

LCMS: MET-UPLCMS-A-006, rt=1.58 min, M/Z (ES−) 513 [M+Formic acid-H], 467 [M−H] 97% UV NMR Data: 1H NMR (400 MHz, DMSO) δ 8.69 (t, J=5.6 Hz, 1H), 8.44 (s, 3H), 8.06 (d, J=1.6 Hz, 1H), 7.74 (dd, J=8.0, 1.7 Hz, 1H), 7.69 (d, J=8.0 Hz, 1H), 7.13 (d, J=8.7 Hz, 2H), 6.82 (d, J=8.4 Hz, 2H), 5.41 (d, J=15.1 Hz, 1H), 4.83 (d, J=15.1 Hz, 1H), 3.75-3.67 (m, 4H), 3.64 (dd, J=11.4, 6.8 Hz, 1H), 3.34-3.18 (m, 3H), 3.11-2.97 (m, 4H), 1.59-1.45 (m, 2H), 1.33 (dq, J=14.4, 7.3 Hz, 2H), 0.89 (t, 3H).

Synthesis of (3R)-3-amino-8-fluoro-N-(oxan-4-yl)-4-oxo-5-{[4-(trifluoromethoxy)phenyl]methyl}-2,3,4,5-tetrahydro-1,5-benzothiazepine-7-carboxamide hydrochloride (Example 14)

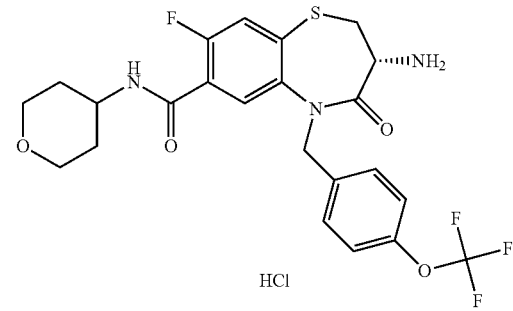 [SMILES: N[C@H]1CSc2cc(F)c(C(=O)NC3CCOCC3)cc2N(Cc2ccc(OC(F)(F)F)cc2)C1=O ; Cl]

The title compound was synthesized according to general procedure GP5 to afford the title compound as off-white solid in 46% Yield.

LCMS: UPLCMS-1 MET-UPLCMS-A-006, rt=2.13 min, M/Z (ES+) 514 [M+H+] 99% UV

NMR Data: 1H NMR (400 MHz, DMSO) δ 1.59-1.46 (m, 2H), 1.81-1.71 (m, 2H), 3.25 (t, J=11.6 Hz, 1H), 3.43-3.37

(m, 2H), 3.69 (dd, J=11.4, 6.9 Hz, 1H), 3.90-3.80 (m, 2H), 4.05-3.92 (m, 2H), 5.02 (d, J=15.6 Hz, 1H), 5.32 (d, J=15.6 Hz, 1H), 7.29 (d, J=7.9 Hz, 2H), 7.42 (d, J=8.7 Hz, 2H), 7.65 (d, J=9.2 Hz, 1H), 7.75 (d, J=6.4 Hz, 1H), 8.49 (d, J=7.6 Hz, 1H), 8.54 (s, 3H).

Synthesis of (3R)-3-amino-8-fluoro-4-oxo-N-(propan-2-yl)-5-{[4-(trifluoromethoxy)phenyl]-methyl}-2,3,4,5-tetrahydro-1,5-benzothiazepine-7-carboxamide hydrochloride (Example 15)

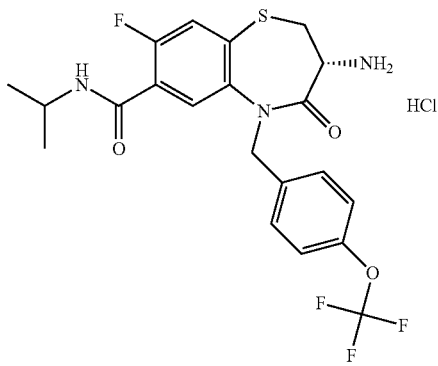 [SMILES: CC(C)NC(=O)c1cc2c(cc1F)SC[C@H](N)C(=O)N2Cc1ccc(OC(F)(F)F)cc1 ; Cl]

The title compound was synthesized according to general procedure GP5 to afford the title compound as off-white solid in 51% Yield.
LCMS: MET-UPLCMS-A-006, rt=2.31 min, M/Z (ES+) 472/474 [M+H+] 97% UV
NMR Data: 1H NMR (400 MHz, DMSO) δ 1.14 (dd, J=6.6, 2.9 Hz, 6H), 3.24 (t, J=11.6 Hz, 1H), 3.66 (dd, J=11.4, 6.9 Hz, 1H), 4.08-3.97 (m, 2H), 5.01 (d, J=15.6 Hz, 1H), 5.33 (d, J=15.5 Hz, 1H), 7.29 (d, J=7.9 Hz, 2H), 7.42 (d, J=8.7 Hz, 2H), 7.64 (d, J=9.2 Hz, 1H), 7.74 (d, J=6.4 Hz, 1H), 8.32 (d, J=7.6 Hz, 1H), 8.48 (s, 3H).

Synthesis of (3R)-3-amino-N-benzyl-8-fluoro-4-oxo-5-{[4-(trifluoromethoxy)phenyl]methyl}-2,3,4,5-tetrahydro-1,5-benzothiazepine-7-carboxamide hydrochloride (Example 16)

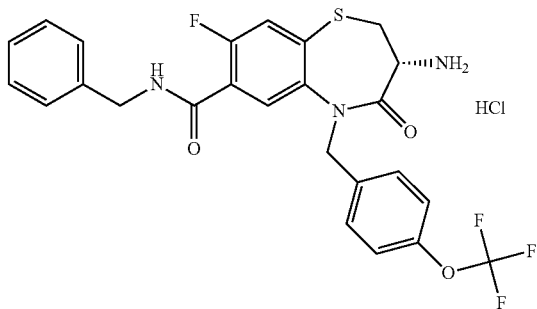 [SMILES: N[C@H]1CSc2cc(F)c(C(=O)NCc3ccccc3)cc2N(Cc2ccc(OC(F)(F)F)cc2)C1=O ; Cl]

The title compound was synthesized according to general procedure GP5 to afford the title compound as off-white solid in 32% Yield.
LCMS: MET-UPLCMS-A-006, rt=2.69 min, M/Z (ES+) 520 [M+H+] 98% UV
NMR Data: 1H NMR (400 MHz, DMSO) δ 3.25 (t, J=11.6 Hz, 1H), 3.66 (dd, J=11.4, 6.9 Hz, 1H), 4.07 (dd, J=11.5, 7.0 Hz, 1H), 4.44 (dd, J=15.1, 5.8 Hz, 1H), 4.52 (dd, J=15.2, 6.2 Hz, 1H), 5.00 (d, J=15.5 Hz, 1H), 5.34 (d, J=15.5 Hz, 1H), 7.38-7.23 (m, 7H), 7.41 (d, J=8.7 Hz, 2H), 7.67 (d, J=9.4 Hz, 1H), 7.84 (d, J=6.5 Hz, 1H), 8.44 (s, 3H), 9.05 (t, J=5.7 Hz, 1H).

Synthesis of (3R)-3-amino-N-methyl-4-oxo-5-{[4-(trifluoromethoxy)phenyl]methyl}-2,3,4,5-tetrahydro-1,5-benzothiazepine-7-carboxamide hydrochloride (Example 17)

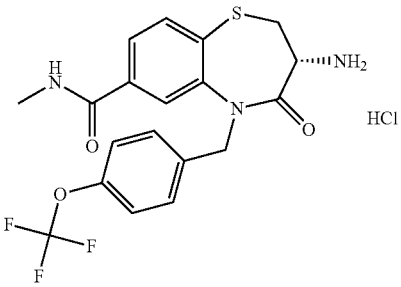 [SMILES: CNC(=O)c1ccc2c(c1)N(Cc1ccc(OC(F)(F)F)cc1)C(=O)[C@@H](N)CS2 ; Cl]

The title compound was synthesized according to general procedure GP5 to afford the title compound as off-white solid in 64% Yield.
LCMS: MET-UPLCMS-A-006, rt=1.92 min, M/Z (ES+) 426 [M+H+] 100% UV
NMR Data: 1H NMR (400 MHz, DMSO) δ 2.80 (d, J=4.5 Hz, 3H), 3.25 (t, J=11.6 Hz, 1H), 3.68 (dd, J=11.4, 6.8 Hz, 1H), 4.09-3.92 (m, 1H), 5.05 (d, J=15.6 Hz, 1H), 5.45 (d, J=15.6 Hz, 1H), 7.26 (d, J=7.9 Hz, 2H), 7.42 (d, J=8.7 Hz, 2H), 7.72 (d, J=8.0 Hz, 1H), 7.75 (dd, J=8.0, 1.6 Hz, 1H), 8.09 (d, J=1.5 Hz, 1H), 8.52 (s, 3H), 8.78 (q, J=4.3 Hz, 1H).

Synthesis of (3R)-3-amino-N-ethyl-4-oxo-5-{[4-(trifluoromethoxy)phenyl]methyl}-2,3,4,5-tetrahydro-1,5-benzothiazepine-7-carboxamide hydrochloride (Example 18)

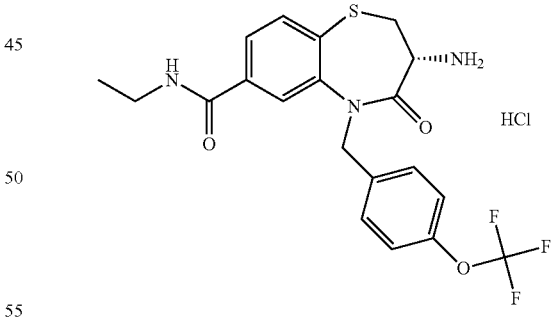

The title compound was synthesized according to general procedure GP5 to afford the title compound as off-white solid in 60% Yield.
LCMS: MET-UPLCMS-A-006, rt=2.31 min, M/Z (ES+) 440 [M+H+] 99% UV
NMR Data: 1H NMR (400 MHz, DMSO) δ 1.13 (t, J=7.2 Hz, 3H), 3.35-3.18 (m, 3H), 3.69 (dd, J=11.4, 6.8 Hz, 1H), 4.06-3.90 (m, 1H), 5.07 (d, J=15.6 Hz, 1H), 5.44 (d, J=15.6 Hz, 1H), 7.26 (d, J=7.9 Hz, 2H), 7.43 (d, J=8.7 Hz, 2H), 7.72 (d, J=8.0 Hz, 1H), 7.77 (dd, J=8.0, 1.7 Hz, 1H), 8.10 (d, J=1.6 Hz, 1H), 8.57 (s, 3H), 8.83 (t, J=5.5 Hz, 1H).

Synthesis of (3R)-3-amino-N-({4-[(5-acetamidopentyl)oxy]phenyl}methyl)-4-oxo-5-{[4-(trifluoromethoxy)phenyl]methyl}-2,3,4,5-tetrahydro-1,5-benzothiazepine-7-carboxamide hydrochloride (Example 19)

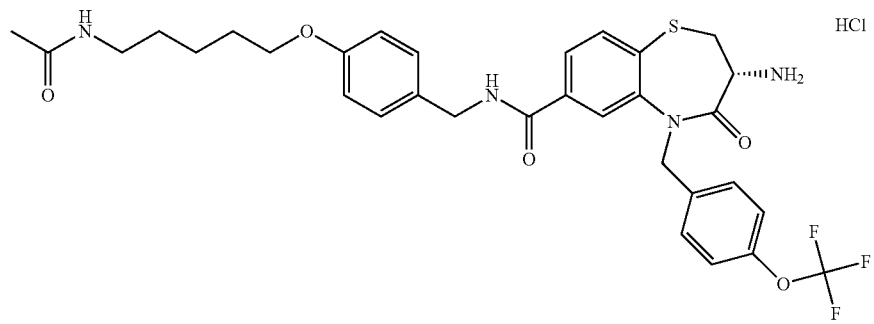 [SMILES: Cl ; CC(=O)NCCCCCOc1ccc(CNC(=O)c2ccc3c(c2)N(Cc2ccc(OC(F)(F)F)cc2)C(=O)[C@@H](N)CS3)cc1]

The title compound was synthesized according to general procedure GP5 to afford the title compound as off-white solid in 69% Yield.

LCMS: MET-UPLCMS-A-006, rt=2.71 min, M/Z (ES+) 645 [M+H+] 97% UV

NMR Data: 1H NMR (400 MHz, DMSO) δ 1.48-1.33 (m, 4H), 1.73-1.64 (m, 2H), 1.77 (s, 3H), 3.02 (dd, J=12.3, 6.4 Hz, 2H), 3.24 (t, J=11.6 Hz, 1H), 3.65 (dd, J=11.3, 6.8 Hz, 1H), 3.92 (t, J=6.5 Hz, 2H), 4.09-4.01 (m, 1H), 4.49-4.34 (m, 2H), 5.03 (d, J=15.5 Hz, 1H), 5.44 (d, J=15.5 Hz, 1H), 6.88 (d, J=8.7 Hz, 2H), 7.24 (dd, J=15.7, 8.3 Hz, 4H), 7.41 (d, J=8.7 Hz, 2H), 7.74 (d, J=8.0 Hz, 1H), 7.81 (dd, J=8.0, 1.7 Hz, 2H), 8.10 (d, J=1.5 Hz, 1H), 8.44 (s, 3H), 9.24 (t, J=5.8 Hz, 1H).

Synthesis of (3R)-3-amino-5-[(4-chlorophenyl)methyl]-N-(2-methoxyethyl)-4-oxo-2,3,4,5-tetrahydro-1,5-benzothiazepine-7-carboxamide hydrochloride (Example 20)

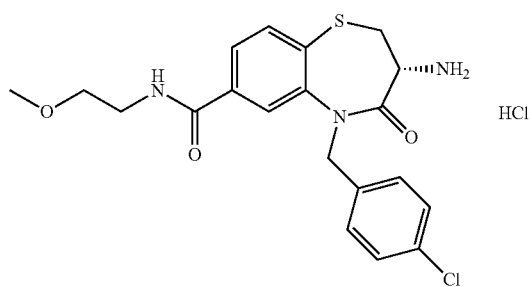 [SMILES: COCCNC(=O)c1ccc2c(c1)N(Cc1ccc(Cl)cc1)C(=O)[C@@H](N)CS2 ; Cl]

The title compound was synthesized according to general procedure GP5 to afford the title compound as off-white solid.

LCMS: MET-UPLCMS-A-006, rt=2.18 min, M/Z (ES+) 420 [M+H+] 89% UV

NMR Data: 1H NMR (400 MHz, DMSO) δ 3.29-3.18 (m, 4H), 3.52-3.39 (m, 4H), 3.68 (dd, J=11.4, 6.8 Hz, 1H), 3.98 (dd, J=11.7, 6.8 Hz, 1H), 5.00 (d, J=15.4 Hz, 1H), 5.43 (d, J=15.5 Hz, 1H), 7.31 (s, 4H), 7.71 (d, J=8.0 Hz, 1H), 7.77 (dd, J=8.0, 1.8 Hz, 1H), 8.09 (d, J=1.7 Hz, 1H), 8.55 (s, 3H), 8.88 (t, J=4.8 Hz, 1H).

Synthesis of (3R)-3-amino-N-butyl-5-[(4-cyanophenyl)methyl]-4-oxo-2,3,4,5-tetrahydro-1,5-benzothiazepine-7-carboxamide hydrochloride (Example 21)

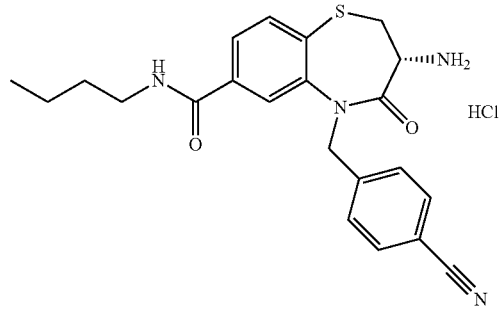 [SMILES: CCCCNC(=O)c1ccc2c(c1)N(Cc1ccc(C#N)cc1)C(=O)[C@@H](N)CS2 ; Cl]

The title compound was synthesized according to general procedure GP5 to afford the title compound as off-white solid.

LCMS: MET-UPLCMS-A-006, rt=1.89 min, M/Z (ES+) 409 [M+H+] 95% UV

NMR Data: 1H NMR (400 MHz, DMSO) δ 0.89 (t, J=7.3 Hz, 3H), 1.38-1.25 (m, 2H), 1.56-1.42 (m, 2H), 3.30-3.16 (m, 3H), 3.69 (dd, J=11.3, 6.8 Hz, 1H), 4.03 (dd, J=11.4, 6.7 Hz, 1H), 5.17 (d, J=16.0 Hz, 1H), 5.43 (d, J=16.0 Hz, 1H), 7.52 (d, J=8.0 Hz, 2H), 7.84-7.67 (m, 4H), 8.03 (s, 1H), 8.52 (s, 3H), 8.75 (t, J=5.3 Hz, 1H).

Synthesis of (3R)-3-amino-5-[(4-chlorophenyl)methyl]-4-oxo-N-(4,4,4-trifluorobutyl)-2,3,4,5-tetrahydro-1,5-benzothiazepine-7-carboxamide hydrochloride (Example 22)

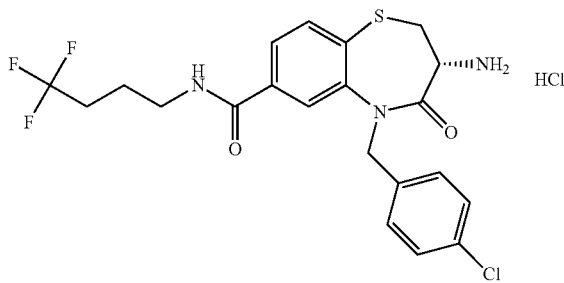 [SMILES: N[C@H]1CSc2ccc(C(=O)NCCCC(F)(F)F)cc2N(Cc2ccc(Cl)cc2)C1=O ; Cl]

The title compound was synthesized according to general procedure GP5 to afford the title compound as off-white solid in 95% Yield.

LCMS: METCR1416 generic 7 minutes, rt=3.25 min, M/Z (ES+) 472/474 [M+H+] 100% UV NMR Data: 1H NMR (500 MHz, DMSO-d6) d 8.82 (d, J=4.1 Hz, 1H), 8.41 (s, 3H), 8.05 (s, 1H), 7.85-7.69 (m, 2H), 7.32 (d, J=2.3 Hz, 4H), 5.44 (d, J=15.5 Hz, 1H), 4.98 (d, J=15.4 Hz, 1H), 4.03 (dd, J=11.7, 6.9 Hz, 1H), 3.65 (dd, J=11.5, 6.7 Hz, 1H), 3.31-3.18 (m, 2H), 2.43-2.25 (m, 3H), 1.76 (dt, J=14.8, 7.1 Hz, 2H).

Synthesis of (3R)-3-amino-5-[(4-chlorophenyl) methyl]-N-(oxan-4-ylmethyl)-4-oxo-2,3,4,5-tetra-hydro-1,5-benzothiazepine-7-carboxamide hydrochloride (Example 23)

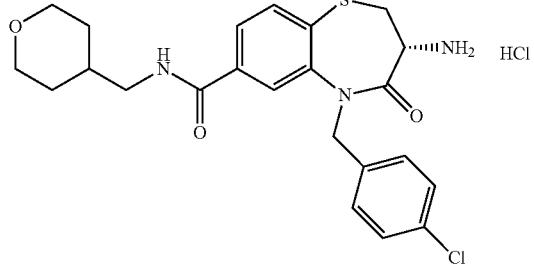

The title compound was synthesized according to general procedure GP5 to afford the title compound as off-white solid in 90% Yield.

LCMS: METCR1416 generic 7 minutes, rt=3 min, M/Z (ES+) 460/462 [M+H+] 100% UV

NMR Data: 1H NMR (500 MHz, DMSO-d6) d 8.74 (t, J=5.7 Hz, 1H), 8.44 (s, 3H), 8.02 (s, 1H), 7.76 (dd, J=8.0, 1.7 Hz, 1H), 7.72 (d, J=8.0 Hz, 1H), 7.39-7.24 (m, 4H), 5.40 (d, J=15.4 Hz, 1H), 5.00 (d, J=15.5 Hz, 1H), 4.02 (dd, J=11.7, 6.9 Hz, 1H), 3.92-3.80 (m, 2H), 3.65 (dd, J=11.5, 6.9 Hz, 1H), 3.30-3.11 (m, 5H), 1.79 (ddd, J=11.3, 7.4, 4.0 Hz, 1H), 1.57 (d, J=13.1 Hz, 2H), 1.19 (qd, J=12.0, 4.4 Hz, 2H).

Synthesis of (3R)-3-amino-N-(5-tert-butyl-1,2-oxazol-3-yl)-5-[(4-chlorophenyl)methyl]-4-oxo-2,3,4,5-tetrahydro-1,5-benzothiazepine-7-carboxamide hydrochloride (Example 24)

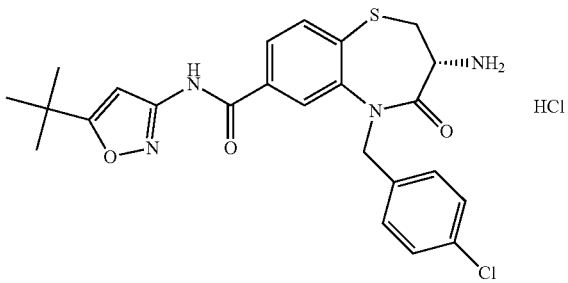 [SMILES: CC(C)(C)c1cc(NC(=O)c2ccc3c(c2)N(Cc2ccc(Cl)cc2)C(=O)[C@@H](N)CS3)no1 ; Cl]

The title compound was synthesized according to general procedure GP5 to afford the title compound as off-white solid in 100% Yield.

LCMS: METCR1416 generic 7 minutes, rt=3.47 min, M/Z (ES+) 485/487 [M+H+] 100% UV NMR Data: 1H NMR (500 MHz, DMSO-d6) d 11.58 (s, 1H), 8.40 (s, 3H), 8.18 (d, J=1.8 Hz, 1H), 7.89 (dd, J=8.1, 1.8 Hz, 1H), 7.78 (d, J=8.1 Hz, 1H), 7.41-7.22 (m, 4H), 5.45 (d, J=15.4 Hz, 1H), 5.00 (d, J=15.4 Hz, 1H), 4.05 (dd, J=11.7, 6.8 Hz, 1H), 3.66 (dd, J=11.4, 6.8 Hz, 1H), 3.29-3.22 (m, 2H), 1.33 (s, 9H).

Synthesis of (3R)-3-amino-4-oxo-N-(pyridin-3-yl)-5-{[4-(trifluoromethoxy)phenyl]methyl}-2,3,4,5-tetrahydro-1,5-benzothiazepine-7-carboxamide dihydrochloride (Example 25)

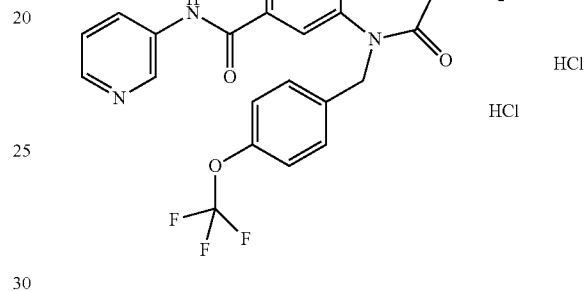

The title compound was synthesized according to general procedure GP5 to afford the title compound as beige solid in 90% Yield.

LCMS: METCR1416 generic 7 minutes, rt=2.96 min, M/Z (ES+) 489 [M+H+] 100% UV

NMR Data: (s, 1H), 9.29 (s, 1H), 8.66 (d, J=8.0 Hz, 1H), 8.55 (s, 4H), 8.45 (s, 1H), 7.98 (d, J=6.7 Hz, 1H), 7.83 (d, J=8.0 Hz, 1H), 7.79 (s, 1H), 7.48 (d, J=8.5 Hz, 2H), 7.27 (d, J=8.2 Hz, 2H), 5.50 (d, J=15.6 Hz, 1H), 5.25 (d, J=15.5 Hz, 1H), 4.05 (s, 1H), 3.71 (dd, J=11.3, 6.8 Hz, 1H), 3.34-3.26 (m, 1H).

Synthesis of (3R)-3-amino-5-[(4-chlorophenyl) methyl]-N-[(4-fluorophenyl)methyl]-4-oxo-2,3,4,5-tetrahydro-1,5-benzothiazepine-7-carboxamide hydrochloride (Example 26)

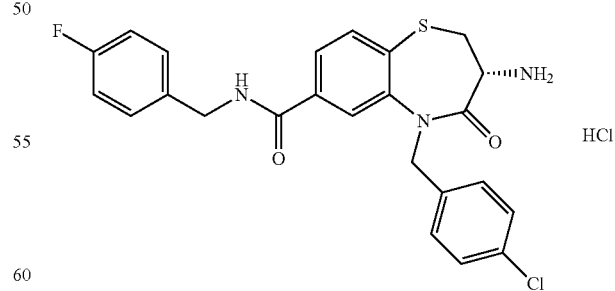

The title compound was synthesized according to general procedure GP5 to afford the title compound as White Solid in 80% Yield.

LCMS: METCR1416 GENERIC 7 MINUTES, rt=3.27 min, M/Z (ES+) 470/472 [M+H+] 100% UV NMR Data: 1H NMR (500 MHz, DMSO-d6) d 9.30 (t, J=5.9 Hz, 1H), 8.30 (s, 2H), 8.06 (d, J=1.6 Hz, 1H), 7.78 (dd, J=8.0, 1.7 Hz, 1H), 7.71 (d, J=8.0 Hz, 1H), 7.34 (dd, J=8.5, 5.7 Hz, 2H), 7.29 (d, J=2.4 Hz, 4H), 7.14 (t, J=8.9 Hz, 2H), 5.40 (d, J=15.4 Hz, 1H), 4.95 (d, J=15.4 Hz, 1H), 4.52-4.39 (m, 2H), 3.98 (s, 1H), 3.65-3.58 (m, 1H), 3.22 (d, J=11.6 Hz, 1H).

Synthesis of (3R)-3-amino-5-[(4-chlorophenyl)methyl]-N-[(1R)-1-(4-methoxyphenyl)ethyl]-4-oxo-2,3,4,5-tetrahydro-1,5-benzothiazepine-7-carboxamide (Example 27)

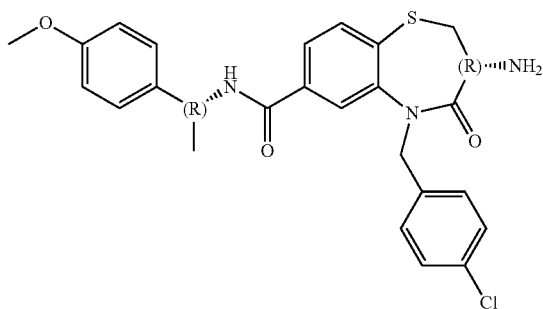

The title compound was synthesized according to general procedure GP5 to afford the title compound as Off-white solid in 51% Yield.

LCMS: METCR1416 GENERIC 7 MINUTES, rt=3.36 min, M/Z (ES+) 496/498 [M+H+] 100% UV NMR Data: 1H NMR (500 MHz, DMSO-d6) d 8.83 (d, J=8.0 Hz, 1H), 7.92 (d, J=1.6 Hz, 1H), 7.74-7.61 (m, 2H), 7.29 (d, J=7.1 Hz, 6H), 6.89 (d, J=8.7 Hz, 2H), 5.35 (d, J=15.5 Hz, 1H), 5.11 (p, J=7.1 Hz, 1H), 4.90 (d, J=15.5 Hz, 1H), 3.73 (s, 3H), 2.97 (s, 1H), 2.87 (t, J=13.2 Hz, 1H), 1.45 (d, J=7.0 Hz, 3H).

Synthesis of (3R)-3-amino-5-[(4-chlorophenyl)methyl]-N-(oxan-3-ylmethyl)-4-oxo-2,3,4,5-tetrahydro-1,5-benzothiazepine-7-carboxamide hydrochloride (Example 28)

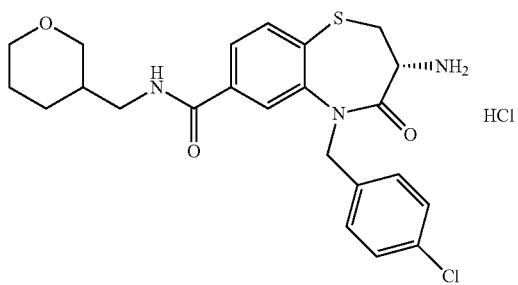 [SMILES: N[C@H]1CSc2ccc(C(=O)NCC3CCCOC3)cc2N(Cc2ccc(Cl)cc2)C1=O ; Cl]

The title compound was synthesized according to general procedure GP5 to afford the title compound as Off-white solid in 98% Yield.

LCMS: METCR1416 GENERIC 7 MINUTES, rt=3.04 min, M/Z (ES+) 460/462 [M+H+] 100% UV NMR Data: 1H NMR (500 MHz, DMSO-d6) d 8.73 (s, 1H), 8.35 (s, 2H), 8.02 (s, 1H), 7.79-7.69 (m, 2H), 7.37-7.28 (m, 4H), 5.42 (d, J=15.4 Hz, 1H), 4.98 (d, J=15.4 Hz, 1H), 4.01 (dd, J=11.7, 6.9 Hz, 1H), 3.80-3.60 (m, 4H), 3.28-3.08 (m, 4H), 1.85-1.73 (m, 2H), 1.59 (dd, J=9.8, 3.7 Hz, 1H), 1.51-1.40 (m, 1H), 1.24 (q, J=9.8 Hz, 1H).

Synthesis of (3R)-3-amino-4-oxo-N-(4,4,4-trifluorobutyl)-5-{[4-(trifluoromethoxy)phenyl]methyl}-2,3,4,5-tetrahydro-1,5-benzothiazepine-7-carboxamide hydrochloride (Example 29)

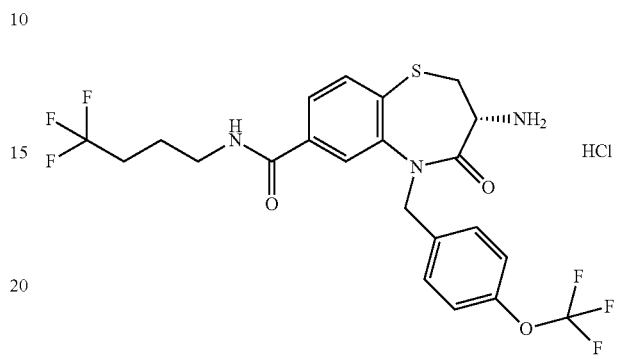

The title compound was synthesized according to general procedure GP5 to afford the title compound as off-white solid in 100% Yield.

LCMS: METCR1416 GENERIC 7 MINUTES, rt=3.33 min, M/Z (ES+) 522 [M+H+] 99% UV

NMR Data: 1H NMR (500 MHz, DMSO) d 1.75 (dt, J=7.06, 14.74 Hz, 2H), 2.24-2.35 (m, 2H), 3.24 (t, J=11.56 Hz, 1H), 3.34-3.43 (m, 2H), 3.63 (dd, J=6.43, 11.14 Hz, 1H), 4.03 (dd, J=6.89, 11.55 Hz, 1H), 5.03 (d, J=15.25 Hz, 1H), 5.43 (d, J=15.56 Hz, 1H), 7.26 (d, J=8.34 Hz, 2H), 7.42 (d, J=8.50 Hz, 2H), 7.71-7.79 (m, 2H), 8.04 (s, 1H), 8.36 (s, 3H), 8.80 (s, 1H)

Synthesis of (3R)-3-amino-N-(oxan-4-ylmethyl)-4-oxo-5-{[4-(trifluoromethoxy)phenyl]methyl}-2,3,4,5-tetrahydro-1,5-benzothiazepine-7-carboxamide hydrochloride (Example 30)

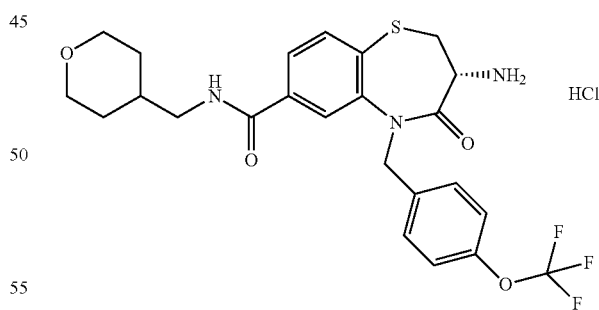

The title compound was synthesized according to general procedure GP5 to afford the title compound as off-white solid in 96% Yield.

LCMS: METCR1416 GENERIC 7 MINUTES, rt=3.09 min, M/Z (ES+) 510 [M+H+] 99% UV

NMR Data: 1H NMR (500 MHz, DMSO) d 1.20 (qd, J=4.28, 12.04 Hz, 2H), 1.54-1.61 (m, 2H), 1.80 (ddt, J=3.88, 7.19, 10.88 Hz, 1H), 3.11-3.30 (m, 5H), 3.59-3.67 (m, 1H), 3.82-3.89 (m, 2H), 4.04 (dd, J=6.98, 11.61 Hz, 1H), 5.03 (d, J=13.61 Hz, 1H), 5.42 (d, J=15.55 Hz, 1H), 7.28 (d, J=8.39

Hz, 2H), 7.42 (d, J=8.49 Hz, 2H), 7.74 (d, J=8.01 Hz, 1H), 7.78 (d, J=8.10 Hz, 1H), 8.01 (s, 1H), 8.35 (s, 3H), 8.70 (s, 1H)

Synthesis of (3R)-3-amino-N-[(4-fluorophenyl)methyl]-4-oxo-5-{[4-(trifluoromethoxy)phenyl]methyl}-2,3,4,5-tetrahydro-1,5-benzothiazepine-7-carboxamide hydrochloride (Example 31)

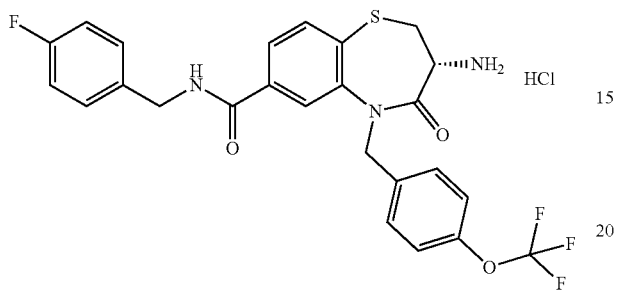

The title compound was synthesized according to general procedure GP5 to afford the title compound as white solid in 94% Yield.

LCMS: METCR1416 GENERIC 7 MINUTES, rt=3.38 min, M/Z (ES+) 520 [M+H+] 100% UV

NMR Data: 1H NMR (500 MHz, d6-DMSO) d 3.25 (t, J=11.59 Hz, 1H), 3.67 (dd, J=6.86, 11.35 Hz, 1H), 4.02 (dd, J=6.88, 11.71 Hz, 1H), 4.47 (qd, J=5.93, 15.05 Hz, 2H), 5.05 (d, J=15.56 Hz, 1H), 5.44 (d, J=15.55 Hz, 1H), 7.12-7.19 (m, 2H), 7.26 (d, J=8.19 Hz, 2H), 7.36 (dd, J=5.63, 8.59 Hz, 2H), 7.42 (d, J=8.66 Hz, 2H), 7.74 (d, J=8.02 Hz, 1H), 7.82 (dd, J=1.74, 8.05 Hz, 1H), 8.13 (d, J=1.51 Hz, 1H), 8.46 (s, 3H), 9.37 (t, J=5.80 Hz, 1H)

Synthesis of (3R)-3-amino-N-[(4-fluorophenyl)methyl]-4-oxo-5-{[4-(1,2,3-thiadiazol-4-yl)phenyl]methyl}-2,3,4,5-tetrahydro-1,5-benzothiazepine-7-carboxamide hydrochloride (Example 32)

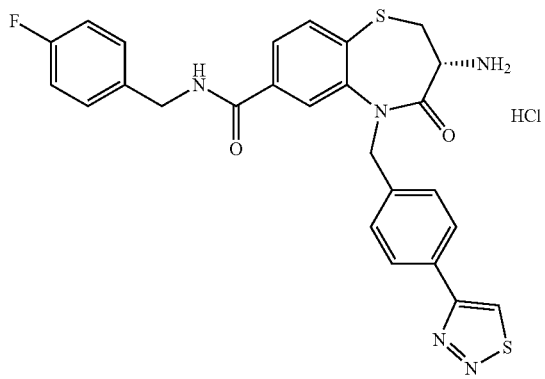 [SMILES: N[C@H]1CSc2ccc(C(=O)NCc3ccc(F)cc3)cc2N(Cc2ccc(-c3csnn3)cc2)C1=O ; Cl]

The title compound was synthesized according to general procedure GP5 to afford the title compound as White Solid in 94% Yield.

LCMS: METCR1416 GENERIC 7 MINUTES, rt=3.14 min, M/Z (ES+) 520 [M+H+] 97% UV

NMR Data: 1H NMR (500 MHz, DMSO-d6) d 9.57 (s, 1H), 9.30 (t, J=5.9 Hz, 1H), 8.24 (s, 2H), 8.14 (d, J=1.6 Hz, 1H), 8.04 (d, J=8.2 Hz, 2H), 7.81 (dd, J=8.0, 1.7 Hz, 1H), 7.75 (d, J=8.0 Hz, 1H), 7.48 (d, J=8.2 Hz, 2H), 7.36 (dd, J=8.5, 5.6 Hz, 2H), 7.16 (t, J=8.9 Hz, 2H), 5.53 (d, J=15.6 Hz, 1H), 5.07 (d, J=15.5 Hz, 1H), 4.57-4.39 (m, 2H), 4.06 (dd, J=11.8, 6.9 Hz, 1H), 3.66 (dd, J=11.4, 6.8 Hz, 1H), 3.31-3.23 (m, 1H).

Synthesis of (3R)-3-amino-5-[(4-chlorophenyl)methyl]-N-(4,4-difluorocyclohexyl)-4-oxo-2,3,4,5-tetrahydro-1,5-benzothiazepine-7-carboxamide hydrochloride (Example 33)

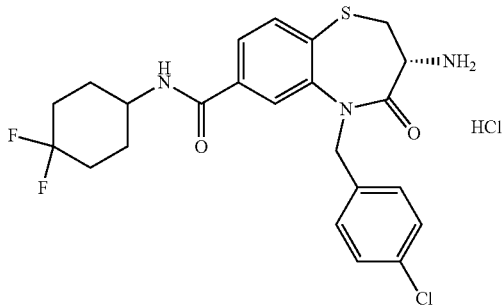 [SMILES: N[C@H]1CSc2ccc(C(=O)NC3CCC(F)(F)CC3)cc2N(Cc2ccc(Cl)cc2)C1=O ; Cl]

The title compound was synthesized according to general procedure GP5 to afford the title compound as White Solid in 97% Yield.

LCMS: METCR1416 GENERIC 7 MINUTES, rt=3.26 min, M/Z (ES+) 480/482 [M+H+] 100% UV NMR Data: 1H NMR (500 MHz, DMSO-d6) d 8.55 (d, J=7.7 Hz, 1H), 8.44 (s, 3H), 8.05 (d, J=1.7 Hz, 1H), 7.79 (dd, J=8.0, 1.7 Hz, 1H), 7.73 (d, J=8.0 Hz, 1H), 7.40-7.26 (m, 4H), 5.40 (d, J=15.4 Hz, 1H), 5.01 (d, J=15.4 Hz, 1H), 3.99 (dd, J=11.7, 6.9 Hz, 2H), 3.66 (dd, J=11.4, 6.8 Hz, 1H), 3.24 (t, J=11.6 Hz, 1H), 1.98 (ddd, J=64.0, 29.8, 11.0 Hz, 6H), 1.67 (q, J=11.7, 10.7 Hz, 2H).

Synthesis of (3R)-3-amino-5-[(4-chlorophenyl)methyl]-N-[1-(4-fluorophenyl)ethyl]-4-oxo-2,3,4,5-tetrahydro-1,5-benzothiazepine-7-carboxamide hydrochloride (Example 34)

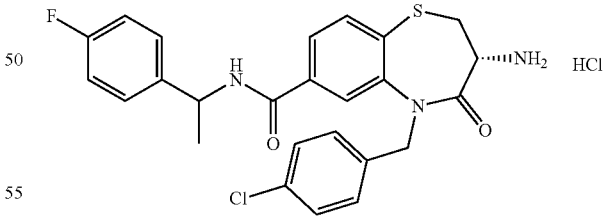

The title compound was synthesized according to general procedure GP5 to afford the title compound as White Solid in 97% Yield.

LCMS: METCR1416 GENERIC 7 MINUTES, rt=3.35 min, M/Z (ES+) 484/486 [M+H+] 100% UV NMR Data: 1H NMR (500 MHz, DMSO-d6) d 9.04 (d, J=7.9 Hz, 1H), 8.23 (s, 3H), 8.05 (dd, J=9.6, 1.6 Hz, 1H), 7.83 (td, J=7.0, 6.1, 1.7 Hz, 1H), 7.74 (d, J=8.0 Hz, 1H), 7.43 (dd, J=8.6, 5.6 Hz, 2H), 7.36-7.27 (m, 4H), 7.16 (t, J=8.9 Hz, 2H), 5.39 (dd, J=15.5, 5.5 Hz, 1H), 5.17 (td, J=7.3, 3.5 Hz, 1H), 5.01 (d, J=15.4 Hz, 1H), 3.99 (dd, J=11.7, 6.8 Hz, 1H), 3.63 (dd, J=11.4, 6.8 Hz, 1H), 3.23 (t, J=11.6 Hz, 1H), 1.49 (dd, J=7.0, 3.2 Hz, 3H).

Synthesis of (3R)-3-amino-5-[(4-chlorophenyl)methyl]-N-[(1S)-1-(4-methoxyphenyl)ethyl]-4-oxo-2,3,4,5-tetrahydro-1,5-benzothiazepine-7-carboxamide (Example 35)

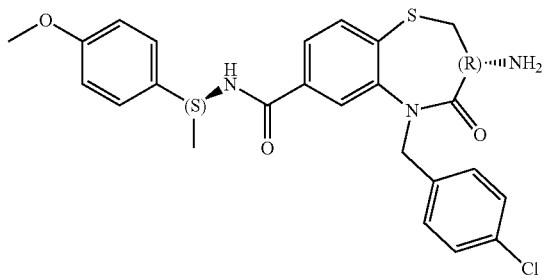

The title compound was synthesized according to general procedure GP5 to afford the title compound as White Solid in 50% Yield.

LCMS: METCR1416 GENERIC 7 MINUTES, rt=3.3 min, M/Z (ES+) 496/498 [M+H+] 96% UV

NMR Data: 1H NMR (500 MHz, DMSO-d6) d 8.82 (d, J=8.0 Hz, 1H), 7.93 (d, J=1.7 Hz, 1H), 7.70 (dd, J=8.0, 1.7 Hz, 1H), 7.64 (d, J=8.0 Hz, 1H), 7.33-7.26 (m, 6H), 6.89 (d, J=8.7 Hz, 2H), 5.37 (d, J=15.5 Hz, 1H), 5.12 (m, 1H), 4.90 (d, J=15.5 Hz, 1H), 3.73 (s, 3H), 3.41 (q, J=6.3 Hz, 2H), 3.03-2.83 (m, 1H), 1.93 (br, 2H), 1.47 (d, J=7.0 Hz, 3H).

Synthesis of (3R)-3-amino-4-oxo-N-(4,4,4-trifluorobutyl)-5-{[6-(trifluoromethyl)pyridin-3-yl]methyl}-2,3,4,5-tetrahydro-1,5-benzothiazepine-7-carboxamide hydrochloride (Example 36)

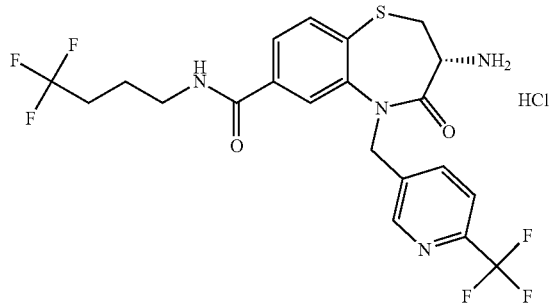 [SMILES: N[C@H]1CSc2ccc(C(=O)NCCCC(F)(F)F)cc2N(Cc2ccc(C(F)(F)F)nc2)C1=O ; Cl]

The title compound was synthesized according to general procedure GP5 to afford the title compound as White Solid in 19% Yield.

LCMS: METCR1416 GENERIC 7 MINUTES, rt=3.11 min, M/Z (ES+) 507 [M+H+] 93% UV

NMR Data: 1H NMR (500 MHz, MEtOH-d4) δ 8.79 (s, 1H), 8.67 (s, 1H), 8.07 (s, 1H), 7.97 (d, J=8.0 Hz, 1H), 7.77 (s, 2H), 7.70 (d, J=8.1 Hz, 1H), 5.70 (d, J=15.4 Hz, 1H), 5.00 (d, J=15.3 Hz, 1H), 4.56 (s, 2H), 4.11 (dd, J=11.6, 6.9 Hz, 1H), 3.75 (dd, J=11.5, 7.4 Hz, 1H), 3.50-3.42 (m, 2H), 3.23 (t, J=11.5 Hz, 1H), 2.33-2.17 (m, 2H), 1.88 (p, J=7.2 Hz, 2H).

Synthesis of (3R)-3-amino-N-[(4-fluorophenyl)methyl]-4-oxo-5-{[6-(trifluoromethyl)pyridin-3-yl]methyl}-2,3,4,5-tetrahydro-1,5-benzothiazepine-7-carboxamide hydrochloride (Example 37)

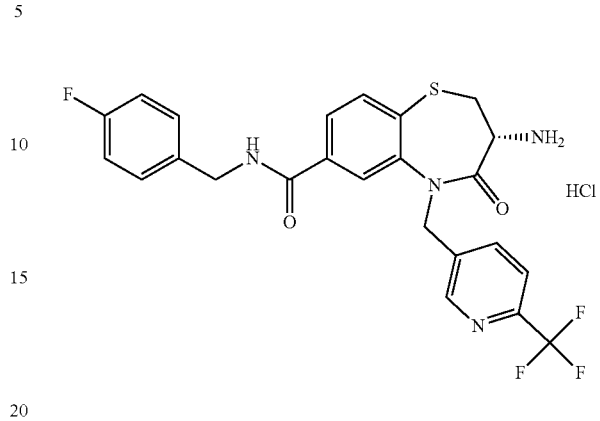

The title compound was synthesized according to general procedure GP5 to afford the title compound as Off-White Solid in 43% Yield.

LCMS: METCR1416 GENERIC 7 MINUTES, rt=3.13 min, M/Z (ES+) 505 [M+H+] 100% UV

NMR Data: 1H NMR (500 MHz, DMSO-d6) δ 9.41 (t, J=5.8 Hz, 1H), 8.72 (d, J=1.4 Hz, 1H), 8.49 (s, 3H), 8.15 (d, J=1.5 Hz, 1H), 7.97 (dd, J=8.1, 1.6 Hz, 1H), 7.86-7.81 (m, 2H), 7.76 (d, J=8.0 Hz, 1H), 7.36 (dd, J=8.6, 5.6 Hz, 2H), 7.19-7.11 (m, 2H), 5.51 (d, J=15.8 Hz, 1H), 5.19 (d, J=15.8 Hz, 1H), 4.47 (qd, J=15.1, 5.9 Hz, 2H), 4.04 (dd, J=11.7, 6.9 Hz, 1H), 3.67 (dd, J=11.4, 6.9 Hz, 1H), 3.24 (t, J=11.6 Hz, 1H).

Synthesis of (3R)-3-amino-5-[(4-chlorophenyl)methyl]-N-[(1R)-1-(4-fluorophenyl)ethyl]-4-oxo-2,3,4,5-tetrahydro-1,5-benzothiazepine-7-carboxamide hydrochloride (Example 38)

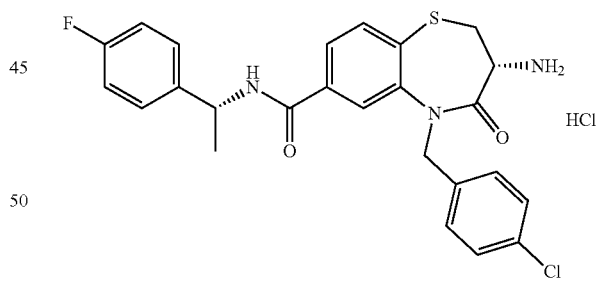

The title compound was synthesized according to general procedure GP5 to afford the title compound as White Solid in 96% Yield.

LCMS: METCR1416 GENERIC 7 MINUTES, rt=3.32 min, M/Z (ES+) 484/486 [M+H+] 97% UV

NMR Data: 1H NMR (500 MHz, DMSO-d6) d 8.98 (d, J=7.9 Hz, 1H), 8.00 (s, 1H), 7.81 (d, J=8.0 Hz, 1H), 7.72 (d, J=8.0 Hz, 1H), 7.41 (dd, J=8.7, 5.6 Hz, 2H), 7.31 (q, J=8.6 Hz, 4H), 7.15 (t, J=8.9 Hz, 2H), 5.37 (d, J=15.4 Hz, 1H), 5.15 (t, J=7.3 Hz, 1H), 4.97 (d, J=15.4 Hz, 1H), 3.99-3.89 (m, 1H), 3.62-3.56 (m, 1H), 3.18 (t, J=11.7 Hz, 1H), 1.48 (d, J=7.0 Hz, 3H).

Synthesis of (3R)-3-amino-5-[(4-chlorophenyl)methyl]-8-fluoro-N-[(4-fluorophenyl)methyl]-4-oxo-2,3,4,5-tetrahydro-1,5-benzothiazepine-7-carboxamide hydrochloride (Example 39)

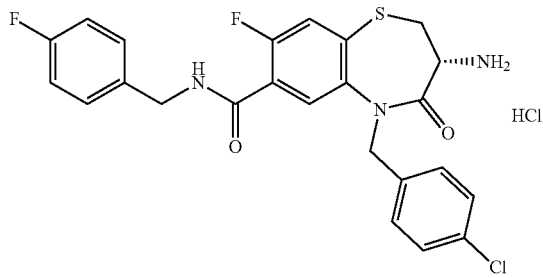 [SMILES: N[C@H]1CSc2cc(F)c(C(=O)NCc3ccc(F)cc3)cc2N(Cc2ccc(Cl)cc2)C1=O ; Cl]

The title compound was synthesized according to general procedure GP5 to afford the title compound as White Solid in 95% Yield.

LCMS: METCR1416 GENERIC 7 MINUTES, rt=3.29 min, M/Z (ES+) 488/490 [M+H+] 99% UV

NMR Data: 1H NMR (500 MHz, DMSO-d6) d 9.12 (t, J=5.8 Hz, 1H), 8.56 (s, 3H), 7.83 (d, J=6.4 Hz, 1H), 7.67 (d, J=9.4 Hz, 1H), 7.38-7.29 (m, 6H), 7.18 (t, J=8.8 Hz, 2H), 5.33 (d, J=15.5 Hz, 1H), 4.96 (d, J=15.5 Hz, 1H), 4.45 (qd, J=15.1, 6.0 Hz, 2H), 4.04 (dd, J=11.6, 6.9 Hz, 1H), 3.69 (dd, J=11.4, 6.9 Hz, 1H), 3.26 (t, J=11.6 Hz, 1H).

Synthesis of (3R)-3-amino-5-[(4-chlorophenyl)methyl]-8-fluoro-4-oxo-N-(4,4,4-trifluorobutyl)-2,3,4,5-tetrahydro-1,5-benzothiazepine-7-carboxamide hydrochloride (Example 40)

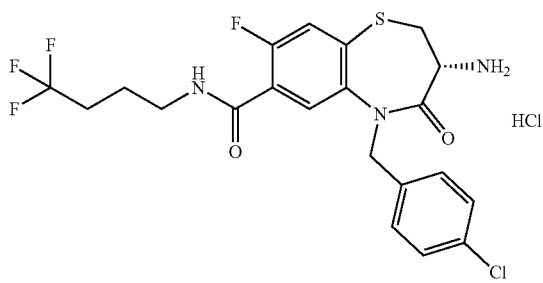 [SMILES: N[C@H]1CSc2cc(F)c(C(=O)NCCCC(F)(F)F)cc2N(Cc2ccc(Cl)cc2)C1=O ; Cl]

The title compound was synthesized according to general procedure GP5 to afford the title compound as White Solid in 100% Yield.

LCMS: METCR1416 GENERIC 7 MINUTES, rt=3.21 min, M/Z (ES+) 490/492 [M+H+] 100% UV NMR Data: 1H NMR (500 MHz, DMSO-d6) d 8.64 (t, J=5.5 Hz, 1H), 8.52 (s, 3H), 7.81 (d, J=6.4 Hz, 1H), 7.65 (d, J=9.3 Hz, 1H), 7.32 (q, J=8.6 Hz, 4H), 5.34 (d, J=15.5 Hz, 1H), 4.94 (d, J=15.5 Hz, 1H), 4.02 (dd, J=11.7, 6.9 Hz, 1H), 3.68 (dd, J=11.4, 6.9 Hz, 1H), 3.33-3.21 (m, 3H), 2.35-2.24 (m, 2H), 1.73 (dt, J=14.7, 7.0 Hz, 2H).

Synthesis of (3R)-3-amino-N-butyl-5-[(4-chlorophenyl)methyl]-8-fluoro-4-oxo-2,3,4,5-tetrahydro-1,5-benzothiazepine-7-carboxamide hydrochloride (Example 41)

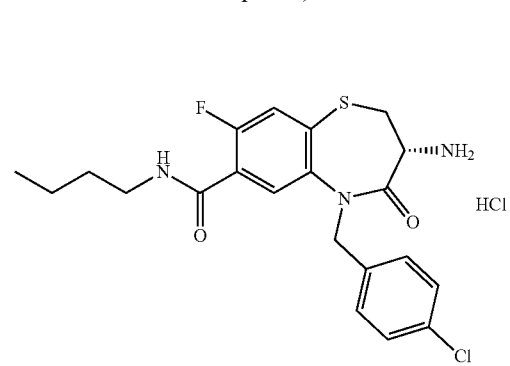

The title compound was synthesized according to general procedure GP5 to afford the title compound as White Solid in 100% Yield.

LCMS: METCR1416 GENERIC 7 MINUTES, rt=3.19 min, M/Z (ES+) 436/438 [M+H+] 100% UV NMR Data: 1H NMR (500 MHz, DMSO-d6) d 8.60-8.47 (m, 4H), 7.75 (d, J=6.3 Hz, 1H), 7.63 (d, J=9.3 Hz, 1H), 7.32 (q, J=8.4 Hz, 4H), 5.31 (d, J=15.5 Hz, 1H), 4.95 (d, J=15.5 Hz, 1H), 4.01 (dd, J=11.6, 6.9 Hz, 1H), 3.68 (dd, J=11.3, 6.8 Hz, 1H), 3.28-3.16 (m, 3H), 1.48 (p, J=7.2 Hz, 2H), 1.31 (h, J=7.3 Hz, 2H), 0.89 (t, J=7.3 Hz, 3H).

Synthesis of (3R)-3-amino-5-[(4-chlorophenyl)methyl]-8-fluoro-N-(oxan-4-ylmethyl)-4-oxo-2,3,4,5-tetrahydro-1,5-benzothiazepine-7-carboxamide hydrochloride (Example 42)

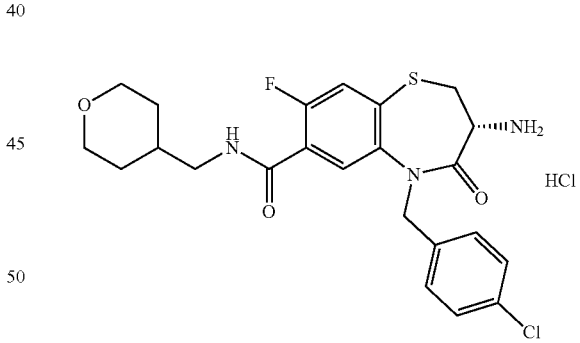

The title compound was synthesized according to general procedure GP5 to afford the title compound as Pale orange solid in 98% Yield.

LCMS: METCR1416 GENERIC 7 MINUTES, rt=2.98 min, M/Z (ES+) 478/490 [M+H+] 100% UV NMR Data: 1H NMR (500 MHz, DMSO-d6) d 8.62-8.54 (m, 4H), 7.73 (d, J=6.4 Hz, 1H), 7.64 (d, J=9.2 Hz, 1H), 7.32 (q, J=8.6 Hz, 4H), 5.29 (d, J=15.5 Hz, 1H), 4.97 (d, J=15.5 Hz, 1H), 4.01 (dd, J=11.5, 7.0 Hz, 1H), 3.85 (dd, J=11.2, 2.9 Hz, 2H), 3.69 (dd, J=11.6, 7.0 Hz, 1H), 3.27-3.22 (m, 3H), 3.14 (dq, J=31.8, 6.8 Hz, 2H), 1.80-1.69 (m, 1H), 1.56 (d, J=12.7 Hz, 2H), 1.18 (qd, J=12.2, 4.4 Hz, 2H).

Synthesis (3R)-3-amino-5-[(4-chlorophenyl)methyl]-8-fluoro-N-[(4-methoxyphenyl)methyl]-4-oxo-2,3,4,5-tetrahydro-1,5-benzothiazepine-7-carboxamide hydrochloride (Example 43)

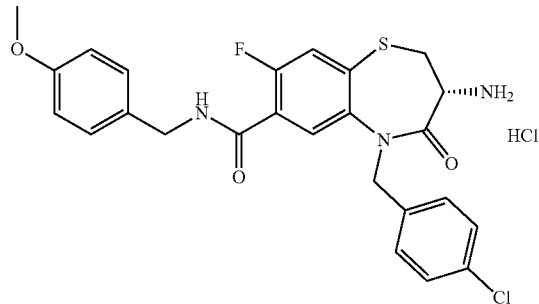 [SMILES: COc1ccc(CNC(=O)c2cc3c(cc2F)SC[C@H](N)C(=O)N3Cc2ccc(Cl)cc2)cc1 ; Cl]

The title compound was synthesized according to general procedure GP5 to afford the title compound as Pale orange solid in 100% Yield.

LCMS: METCR1416 GENERIC 7 MINUTES, rt=3.23 min, M/Z (ES+) 500/502 [M+H+] 99% UV

NMR Data: 1H NMR (500 MHz, DMSO-d6) d 9.03 (t, J=5.8 Hz, 1H), 8.59 (s, 3H), 7.80 (d, J=6.4 Hz, 1H), 7.64 (d, J=9.3 Hz, 1H), 7.32 (q, J=8.4 Hz, 4H), 7.23 (d, J=8.4 Hz, 2H), 6.89 (d, J=8.5 Hz, 2H), 5.30 (d, J=15.4 Hz, 1H), 4.96 (d, J=15.5 Hz, 1H), 4.39 (qd, J=14.9, 5.9 Hz, 2H), 4.01 (dd, J=11.5, 6.9 Hz, 1H), 3.74-3.67 (m, 4H), 3.25 (t, J=11.6 Hz, 1H).

Synthesis of (3R)-3-amino-5-{[4-(5-methyl-1,2,4-oxadiazol-3-yl)phenyl]methyl}-N-(oxan-4-ylmethyl)-4-oxo-2,3,4,5-tetrahydro-1,5-benzothiazepine-7-carboxamide hydrochloride (Example 44)

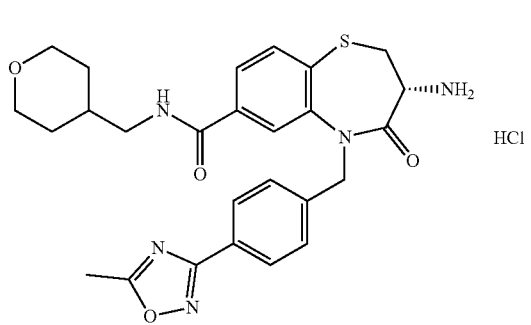 [SMILES: Cc1nc(-c2ccc(CN3C(=O)[C@@H](N)CSc4ccc(C(=O)NCC5CCOCC5)cc43)cc2)no1 ; Cl]

The title compound was synthesized according to general procedure GP5 to afford the title compound as Off-White Solid in 96% Yield.

LCMS: METCR1416 GENERIC 7 MINUTES, rt=2.83 min, M/Z (ES+) 508 [M+H+] 97% UV

NMR Data: 1H NMR (500 MHz, DMSO-d6) d 8.73 (t, J=5.8 Hz, 1H), 8.14 (br, 2H), 8.02 (d, J=1.6 Hz, 1H), 7.89 (d, J=8.3 Hz, 2H), 7.80-7.70 (m, 2H), 7.49 (d, J=8.3 Hz, 2H), 5.45 (d, J=15.7 Hz, 1H), 5.10 (d, J=15.8 Hz, 1H), 4.03 (dd, J=11.7, 6.9 Hz, 1H), 3.84 (d, J=7.3 Hz, 2H), 3.63 (dd, J=11.4, 6.8 Hz, 1H), 3.28-3.12 (m, 5H), 2.65 (s, 3H), 1.85-1.71 (m, 1H), 1.56 (d, J=12.7 Hz, 2H), 1.19 (qd, J=12.2, 4.7 Hz, 2H).

Synthesis of (3R)-3-amino-5-[(4-fluorophenyl)methyl]-N-(oxan-4-ylmethyl)-4-oxo-2,3,4,5-tetrahydro-1,5-benzothiazepine-7-carboxamide (Example 45)

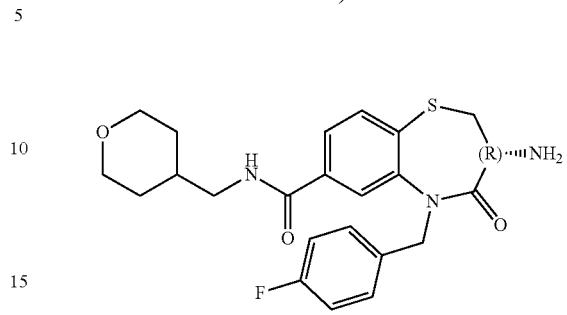

The title compound was synthesized according to general procedure GP5 to afford the title compound as White Solid in 28% Yield.

LCMS: METCR1416 GENERIC 7 MINUTES, rt=2.86 min, M/Z (ES+) 444 [M+H+] 94% UV

NMR Data: 1H NMR (500 MHz, DMSO-d6) d 8.64 (t, J=5.8 Hz, 1H), 7.92 (d, J=1.4 Hz, 1H), 7.78-7.56 (m, 2H), 7.31 (dd, J=8.6, 5.6 Hz, 2H), 7.06 (t, J=8.9 Hz, 2H), 5.39 (d, J=15.3 Hz, 1H), 4.88 (d, J=15.3 Hz, 1H), 3.92-3.77 (m, 2H), 3.31-3.23 (m, 3H), 3.23-3.07 (m, 3H), 2.97-2.82 (m, 1H), 1.77 (d, J=3.6 Hz, 1H), 1.58 (d, J=11.5 Hz, 2H), 1.39-1.31 (m, 1H), 1.19 (qd, J=12.0, 4.5 Hz, 3H).

Synthesis of (3R)-3-amino-N-butyl-4-oxo-5-{[4-(1H-1,2,4-triazol-1-yl)phenyl]methyl}-2,3,4,5-tetrahydro-1,5-benzothiazepine-7-carboxamide hydrochloride (Example 46)

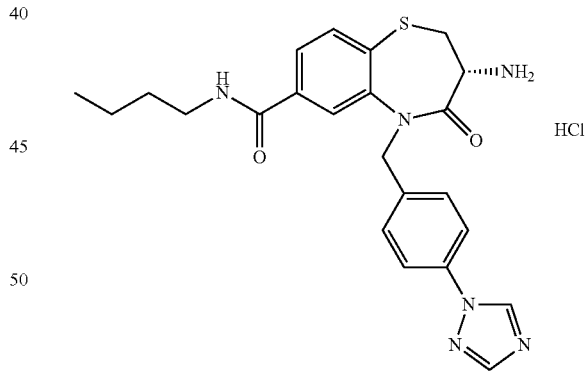

The title compound was synthesized according to general procedure GP5 to afford the title compound as Light brown solid in 98% Yield.

LCMS: METCR1416 GENERIC 7 MINUTES, rt=2.82 min, M/Z (ES+) 451 [M+H+] 99% UV

NMR Data: 1H NMR (500 MHz, DMSO-d6) d 9.23 (s, 1H), 8.67 (t, J=5.6 Hz, 1H), 8.43 (s, 3H), 8.20 (s, 1H), 8.05 (s, 1H), 7.84-7.64 (m, 4H), 7.46 (d, J=8.5 Hz, 2H), 5.49 (d, J=15.6 Hz, 1H), 5.05 (d, J=15.6 Hz, 1H), 4.05 (s, 1H), 3.65 (dd, J=11.4, 6.9 Hz, 1H), 3.28-3.23 (m, 3H), 1.50 (p, J=7.0 Hz, 2H), 1.32 (h, J=7.3 Hz, 2H), 0.89 (t, J=7.4 Hz, 3H).

Synthesis of (3R)-3-amino-N-butyl-5-[(4-carbamoylphenyl)methyl]-4-oxo-2,3,4,5-tetrahydro-1,5-benzothiazepine-7-carboxamide hydrochloride (Example 47)

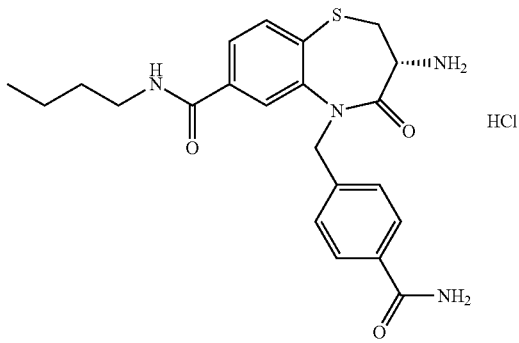 [SMILES: CCCCNC(=O)c1ccc2c(c1)N(Cc1ccc(C(N)=O)cc1)C(=O)[C@@H](N)CS2 ; Cl]

The title compound was synthesized according to general procedure GP5 to afford the title compound as Brown Solid in 95% Yield.

LCMS: MET-UHPLC-AB-101, rt=1.44 min, M/Z (ES+) 427 [M+H+] 100% UV

NMR Data: 1H NMR (500 MHz, DMSO-d6) d 8.67 (t, J=5.6 Hz, 1H), 8.35 (s, 3H), 8.03 (d, J=1.5 Hz, 1H), 7.90 (s, 1H), 7.81-7.64 (m, 4H), 7.37 (d, J=8.3 Hz, 2H), 7.31 (s, 1H), 5.45 (d, J=15.7 Hz, 1H), 5.07 (d, J=15.7 Hz, 1H), 4.04 (dd, J=11.7, 6.8 Hz, 1H), 3.72-3.63 (m, 1H), 3.29-3.22 (m, 3H), 1.51 (quin, J=7.1 Hz, 2H), 1.32 (h, J=7.3 Hz, 2H), 0.90 (t, J=7.4 Hz, 3H).

Synthesis of (3R)-3-amino-5-[(4-chlorophenyl)methyl]-N-(2-hydroxy-2-methylpropyl)-4-oxo-2,3,4,5-tetrahydro-1,5-benzothiazepine-7-carboxamide (Example 48)

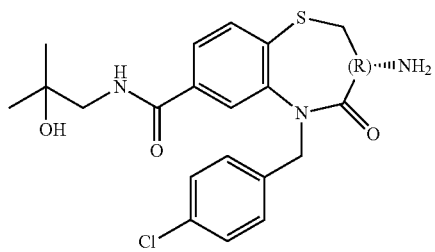

The title compound was synthesized according to general procedure GP5 to afford the title compound as yellow pale solid in 52% Yield.

LCMS: METCR1416 GENERIC 7 MINUTES, rt=2.91 min, M/Z (ES+) 434/436 [M+H+] 99% UV

NMR Data: 1H NMR (500 MHz, DMSO-d6) d 8.39 (t, J=6.2 Hz, 1H), 7.94 (d, J=1.6 Hz, 1H), 7.70-7.61 (m, 2H), 7.29 (s, 4H), 5.38 (d, J=15.5 Hz, 1H), 4.90 (d, J=15.5 Hz, 1H), 4.53 (s, 1H), 3.41 (q, J=6.5 Hz, 2H), 3.28-3.17 (m, 2H), 2.91-2.83 (m, 1H), 2.03 (d, J=40.0 Hz, 2H), 1.09 (d, J=3.2 Hz, 6H)

Synthesis of (3R)-3-amino-5-[(4-chlorophenyl)methyl]-N-[(1S)-1-(4-fluorophenyl)ethyl]-4-oxo-2,3,4,5-tetrahydro-1,5-benzothiazepine-7-carboxamide hydrochloride (Example 49)

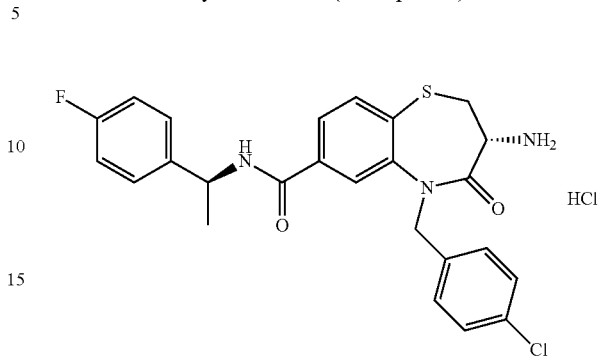

The title compound was synthesized according to general procedure GP5 to afford the title compound as off white solid in 90% Yield.

LCMS: METCR1416 GENERIC 7 MINUTES, rt=3.45 min, M/Z (ES+) 484/486 [M+H+] 100% UV NMR Data: 1H NMR (500 MHz, DMSO-d6) 9.02 (d, J=7.9 Hz, 1H), 8.31 (s, 3H), 8.05 (d, J=1.6 Hz, 1H), 7.81 (dd, J=8.0, 1.7 Hz, 1H), 7.72 (d, J=8.0 Hz, 1H), 7.41 (dd, J=8.6, 5.6 Hz, 2H), 7.35-7.26 (m, 4H), 7.15 (t, J=8.9 Hz, 2H), 5.39 (d, J=15.4 Hz, 1H), 5.16 (p, J=7.1 Hz, 1H), 5.00 (d, J=15.4 Hz, 1H), 3.99 (dd, J=11.7, 6.8 Hz, 1H), 3.62 (dd, J=11.4, 6.9 Hz, 1H), 3.22 (t, J=11.5 Hz, 1H), 1.48 (d, J=7.1 Hz, 3H).

Synthesis of (3R)-3-amino-5-[(4-chlorophenyl)methyl]-8-fluoro-N-(2-hydroxy-2-methylpropyl)-4-oxo-2,3,4,5-tetrahydro-1,5-benzothiazepine-7-carboxamide (Example 50)

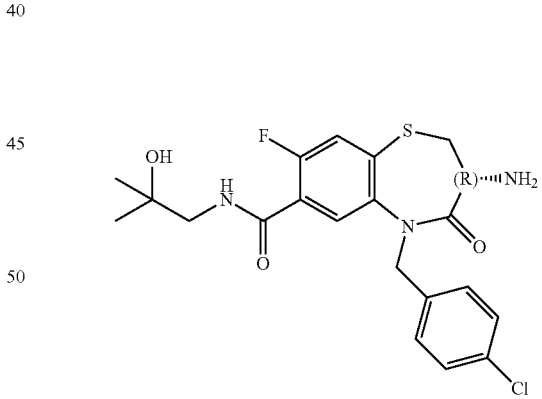

The title compound was synthesized according to general procedure GP5 to afford the title compound as yellow solid in 64% Yield.

LCMS: METCR1416 GENERIC 7 MINUTES, rt=3 min, M/Z (ES+) 452/454 [M+H+] 100% UV

NMR Data: 1H NMR (500 MHz, Chloroform-d) d 8.06 (d, J=7.0 Hz, 1H), 7.37 (d, J=10.7 Hz, 1H), 7.24-7.16 (m, 4H), 7.16-7.09 (m, 1H), 5.52 (d, J=15.1 Hz, 1H), 4.63 (d, J=15.0 Hz, 1H), 3.70-3.56 (m, 2H), 3.57-3.40 (m, 2H), 3.05-2.94 (m, 1H), 1.30 (s, 6H)

Synthesis of (2R,3R)-3-amino-5-[(4-chlorophenyl)methyl]-2-methyl-4-oxo-N-(4,4,4-trifluorobutyl)-2,3,4,5-tetrahydro-1,5-benzothiazepine-7-carboxamide hydrochloride (Example 51)

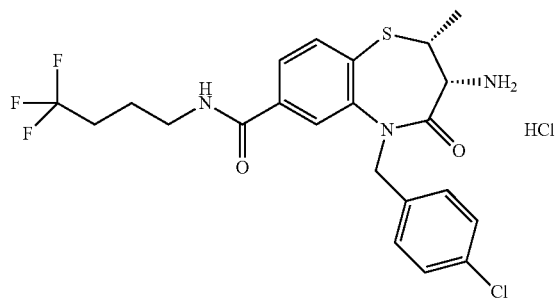 [SMILES: C[C@H]1Sc2ccc(C(=O)NCCCC(F)(F)F)cc2N(Cc2ccc(Cl)cc2)C(=O)[C@H]1N ; Cl]

The title compound was synthesized according to general procedure GP5 to afford the title compound as cream solid in 74% Yield.

LCMS: METCR1416 GENERIC 7 MINUTES, rt=3.25 min, M/Z (ES+) 486/488 [M+H+] 99% UV

NMR Data: 1H NMR (500 MHz, DMSO-d6) d 8.82 (t, J=5.7 Hz, 1H), 8.25 (s, 3H), 8.06 (d, J=1.6 Hz, 1H), 7.76 (dd, J=8.0, 1.7 Hz, 1H), 7.71 (d, J=8.0 Hz, 1H), 7.32 (s, 4H), 5.49 (d, J=15.5 Hz, 1H), 4.99 (d, J=15.5 Hz, 1H), 4.14 (d, J=6.1 Hz, 1H), 4.04 (p, J=6.5 Hz, 1H), 3.41-3.35 (m, 2H), 2.36-2.26 (m, 2H), 1.76 (dt, J=14.8, 7.1 Hz, 2H), 1.32 (d, J=6.6 Hz, 3H).

Synthesis of (3R)-3-amino-5-[(4-chlorophenyl)methyl]-8-fluoro-N'-(4-fluorophenyl)-4-oxo-2,3,4,5-tetrahydro-1,5-benzothiazepine-7-carbohydrazide hydrochloride (Example 52)

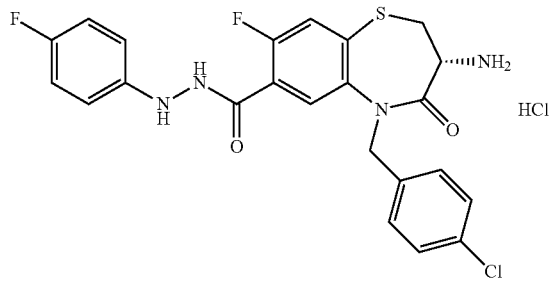 [SMILES: N[C@H]1CSc2cc(F)c(C(=O)NNc3ccc(F)cc3)cc2N(Cc2ccc(Cl)cc2)C1=O ; Cl]

The title compound was synthesized according to general procedure GP5 to afford the title compound as light orange solid in 91% Yield.

LCMS: METCR1416 GENERIC 7 MINUTES, rt=3.14 min, M/Z (ES+) 489/491 [M+H+] 93% UV

NMR Data: 1H NMR (500 MHz, DMSO-d6) d 3.26 (t, J=11.58 Hz, 1H), 3.68 (dd, J=6.86, 11.42 Hz, 1H), 4.08 (dd, J=6.87, 11.67 Hz, 1H), 5.00 (d, J=15.42 Hz, 1H), 5.30 (d, J=15.44 Hz, 1H), 6.76-6.82 (m, 2H), 6.99-7.06 (m, 2H), 7.29-7.39 (m, 4H), 7.69 (d, J=9.20 Hz, 1H), 7.80 (d, J=6.32 Hz, 1H), 8.02 (d, J=2.78 Hz, 1H), 8.44 (s, 3H), 10.36 (d, J=2.57 Hz, 1H).

Synthesis of (3R)-3-amino-N'-butanoyl-5-[(4-chlorophenyl)methyl]-4-oxo-2,3,4,5-tetrahydro-1,5-benzothiazepine-7-carbohydrazide hydrochloride (Example 53)

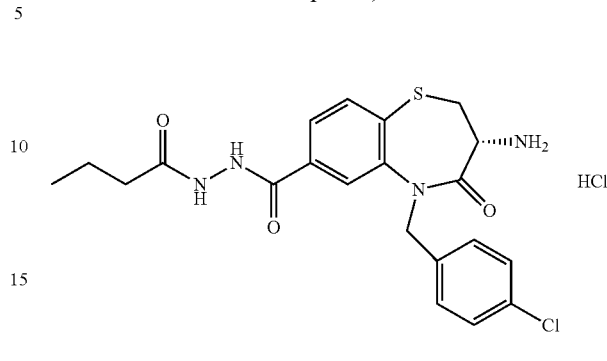

The title compound was synthesized according to general procedure GP5 to afford the title compound as yellow solid in 81% Yield.

LCMS: METCR1416 GENERIC 7 MINUTES, rt=2.87 min, M/Z (ES+) 447/449 [M+H+] 82% UV

NMR Data: 1H NMR (500 MHz, DMSO-d6) d 10.49 (s, 1H), 9.93 (s, 1H), 8.31 (s, 3H), 8.06-8.00 (m, 1H), 7.80-7.73 (m, 2H), 7.35-7.27 (m, 4H), 5.49-5.39 (m, 1H), 4.99-4.89 (m, 1H), 4.05 (dd, J=11.7, 6.9 Hz, 1H), 3.68-3.60 (m, 1H), 3.24 (t, J=11.6 Hz, 1H), 2.17 (t, J=7.3 Hz, 2H), 1.58 (h, J=7.4 Hz, 2H), 0.92 (t, J=7.4 Hz, 3H)

Synthesis of (3R)-3-amino-N-butyl-5-[(4-chloro-2-fluorophenyl)methyl]-8-fluoro-4-oxo-2,3,4,5-tetrahydro-1,5-benzothiazepine-7-carboxamide hydrochloride (Example 54)

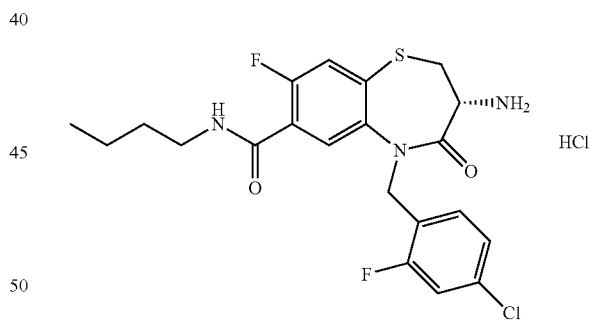

The title compound was synthesized according to general procedure GP5 to afford the title compound as pale yellow solid in 99% Yield.

LCMS: MET-uPLC-AB-101, rt=2.39 min, M/Z (ES+) 454/456 [M+H+] 99% UV

NMR Data: 1H NMR (500 MHz, DMSO-d6) d 8.46 (t, J=5.4 Hz, 1H), 8.42-8.19 (m, 3H), 7.85 (d, J=6.4 Hz, 1H), 7.63 (d, J=9.3 Hz, 1H), 7.43 (t, J=8.2 Hz, 1H), 7.36 (dd, J=9.8, 2.0 Hz, 1H), 7.22 (dd, J=8.3, 2.0 Hz, 1H), 5.35 (d, J=15.3 Hz, 1H), 4.90 (d, J=15.3 Hz, 1H), 3.98 (dd, J=11.6, 6.9 Hz, 1H), 3.64 (dd, J=11.4, 6.9 Hz, 1H), 3.30-3.22 (m, 2H), 3.18 (t, J=11.6 Hz, 1H), 1.50 (p, J=7.1 Hz, 2H), 1.39-1.28 (m, 2H), 0.91 (t, J=7.4 Hz, 3H).

Synthesis of (3R)-3-amino-5-[(4-chloro-2-fluorophenyl)methyl]-8-fluoro-N-(oxan-4-ylmethyl)-4-oxo-2,3,4,5-tetrahydro-1,5-benzothiazepine-7-carboxamide hydrochloride (Example 55)

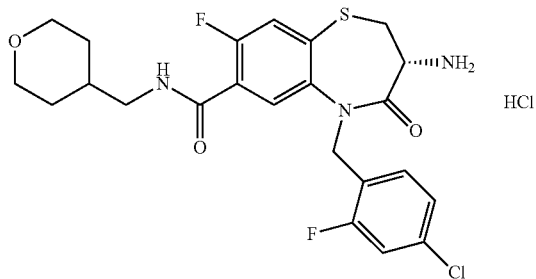 [SMILES: N[C@H]1CSc2cc(F)c(C(=O)NCC3CCOCC3)cc2N(Cc2ccc(Cl)cc2F)C1=O ; Cl]

The title compound was synthesized according to general procedure GP5 to afford the title compound as pale yellow solid in 100% Yield.

LCMS: MET-uPLC-AB-101, rt=2.05 min, M/Z (ES+) 496/498 [M+H+] 100% UV

NMR Data: 1H NMR (500 MHz, DMSO-d6) d 8.52 (t, J=5.7 Hz, 1H), 8.48-8.27 (m, 3H), 7.83 (d, J=6.4 Hz, 1H), 7.63 (d, J=9.3 Hz, 1H), 7.42 (t, J=8.2 Hz, 1H), 7.36 (dd, J=9.8, 2.0 Hz, 1H), 7.21 (dd, J=8.3, 1.9 Hz, 1H), 5.34 (d, J=15.3 Hz, 1H), 4.90 (d, J=15.3 Hz, 1H), 3.99 (dd, J=11.7, 6.9 Hz, 1H), 3.85 (dd, J=11.3, 2.6 Hz, 2H), 3.67-3.60 (m, 1H), 3.26 (td, J=11.7, 1.8 Hz, 2H), 3.22-3.10 (m, 3H), 1.83-1.71 (m, 1H), 1.62-1.53 (m, 2H), 1.26-1.15 (m, 2H).

Synthesis of (3R)-3-amino-5-[(4-chloro-3-fluorophenyl)methyl]-8-fluoro-N-(oxan-4-ylmethyl)-4-oxo-2,3,4,5-tetrahydro-1,5-benzothiazepine-7-carboxamide hydrochloride (Example 56)

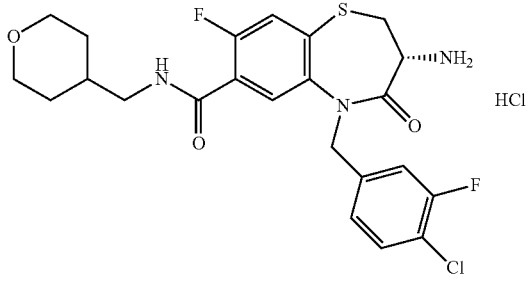 [SMILES: N[C@H]1CSc2cc(F)c(C(=O)NCC3CCOCC3)cc2N(Cc2ccc(Cl)c(F)c2)C1=O ; Cl]

The title compound was synthesized according to general procedure GP5 to afford the title compound as off-white solid in 76% Yield.

LCMS: METCR1600, rt=4.01 min, M/Z (ES+) 496/498 [M+H+] 100% UV

NMR Data: 1H NMR (500 MHz, DMSO-d6) d 8.63-8.46 (m, 4H), 7.70 (d, J=6.4 Hz, 1H), 7.65 (d, J=9.2 Hz, 1H), 7.51 (t, J=8.0 Hz, 1H), 7.36 (d, J=10.4 Hz, 1H), 7.16 (d, J=8.2 Hz, 1H), 5.25 (d, J=15.7 Hz, 1H), 5.04 (d, J=15.7 Hz, 1H), 4.03 (dd, J=11.7, 6.8 Hz, 1H), 3.89-3.81 (m, 2H), 3.75-3.64 (m, 1H), 3.30-3.21 (m, 3H), 3.21-3.07 (m, 2H), 1.81-1.66 (m, 1H), 1.56 (d, J=11.1 Hz, 2H), 1.25-1.13 (m, 2H).

Synthesis of (3R)-3-amino-N-butyl-5-[(4-chloro-3-fluorophenyl)methyl]-8-fluoro-4-oxo-2,3,4,5-tetrahydro-1,5-benzothiazepine-7-carboxamide (Example 57)

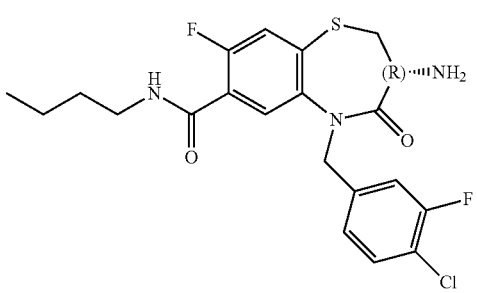

The title compound was synthesized according to general procedure GP5 to afford the title compound as yellow solid in 27% Yield.

LCMS: METCR1278 Generic 3.5 minutes, rt=2.4 min, M/Z (ES+) 454/456 [M+H+] 96% UV NMR Data: 1H NMR (500 MHz, MEtOH-d4) d 7.74 (d, J=6.6 Hz, 1H), 7.47 (d, J=9.8 Hz, 1H), 7.32 (t, J=7.9 Hz, 1H), 7.25 (dd, J=10.1, 1.9 Hz, 1H), 7.10 (d, J=8.2 Hz, 1H), 5.41 (d, J=15.4 Hz, 1H), 4.81 (d, J=10.2 Hz, 1H), 3.62-3.49 (m, 2H), 3.45-3.34 (m, 2H), 3.01-2.89 (m, 1H), 1.59 (p, J=7.2 Hz, 2H), 1.50-1.35 (m, 2H), 0.97 (t, J=7.4 Hz, 3H).

Synthesis of (3R)-3-amino-5-[(4-chlorophenyl)methyl]-8-fluoro-4-oxo-N-propoxy-2,3,4,5-tetrahydro-1,5-benzothiazepine-7-carboxamide hydrochloride (Example 58)

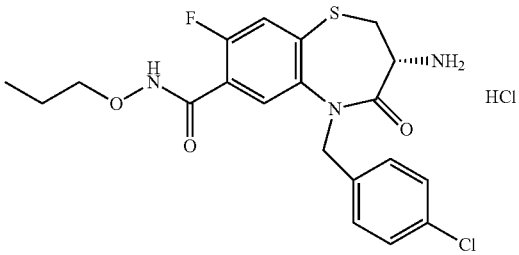 [SMILES: CCCONC(=O)c1cc2c(cc1F)SC[C@H](N)C(=O)N2Cc1ccc(Cl)cc1 ; Cl]

The title compound was synthesized according to general procedure GP5 to afford the title compound as beige solid in 68% Yield.

LCMS: METCR1416 GENERIC 7 MINUTES, rt=3.06 min, M/Z (ES+) 438/440 [M+H+] 98% UV

NMR Data: 1H NMR (500 MHz, DMSO-d6) d 11.62 (s, 1H), 8.42 (s, 3H), 7.79 (d, J=6.2 Hz, 1H), 7.64 (d, J=9.1 Hz, 1H), 7.31 (dd, 4H), 5.34 (d, J=15.4 Hz, 1H), 4.91 (d, J=15.4 Hz, 1H), 4.08-3.99 (m, 1H), 3.84 (t, J=6.5 Hz, 2H), 3.68-3.61 (m, 1H), 3.24 (t, J=11.5 Hz, 1H), 1.61 (h, J=7.2 Hz, 2H), 0.93 (t, J=7.4 Hz, 3H).

Synthesis of (3R)-3-amino-5-[(4-chlorophenyl)methyl]-8-fluoro-N-(2-methylpropoxy)-4-oxo-2,3,4,5-tetrahydro-1,5-benzothiazepine-7-carboxamide hydrochloride (Example 59)

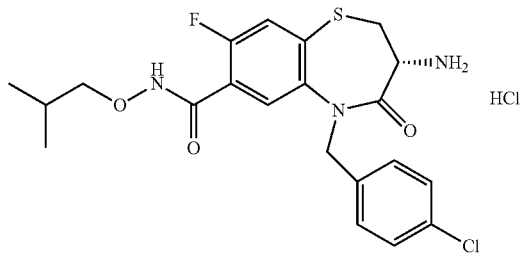 [SMILES: CC(C)CONC(=O)c1cc2c(cc1F)SC[C@H](N)C(=O)N2Cc1ccc(Cl)cc1 ; Cl]

The title compound was synthesized according to general procedure GP5 to afford the title compound as white solid in 90% Yield.

LCMS: METCR1416 GENERIC 7 MINUTES, rt=3.21 min, M/Z (ES+) 452/453 [M+H+] 97% UV

NMR Data: 1H NMR (500 MHz, DMSO-d6) d 11.65 (s, 1H), 8.35 (s, 3H), 7.80 (d, J=6.2 Hz, 1H), 7.65 (d, J=9.0 Hz, 1H), 7.34 (d, J=8.4 Hz, 2H), 7.30 (d, J=8.4 Hz, 2H), 5.35 (d, J=15.5 Hz, 1H), 4.92 (d, J=15.3 Hz, 1H), 4.04 (dd, J=11.2, 7.0 Hz, 1H), 3.67 (dd, J=17.1, 5.6 Hz, 3H), 3.24 (t, J=11.5 Hz, 1H), 1.93 (dt, J=13.4, 6.7 Hz, 1H), 0.94 (d, J=6.7 Hz, 6H)

Synthesis of (3R)-3-amino-5-[(4-chlorophenyl)methyl]-8-fluoro-N'-(2-methylpropyl)-4-oxo-2,3,4,5-tetrahydro-1,5-benzothiazepine-7-carbohydrazide hydrochloride (Example 60)

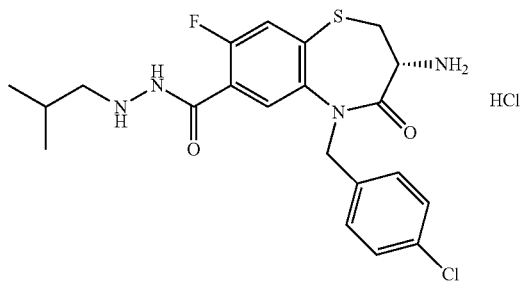 [SMILES: CC(C)CNNC(=O)c1cc2c(cc1F)SC[C@H](N)C(=O)N2Cc1ccc(Cl)cc1 ; Cl]

The title compound was synthesized according to general procedure GP5 to afford the title compound as Off-White Solid in 99% Yield.

LCMS: MET-UHPLC-AB-101, rt=2.28 min, M/Z (ES+) 451/452 [M+H+] 94% UV

NMR Data: 1H NMR (500 MHz, DMSO-d6) d 10.15 (s, 1H), 8.44 (s, 3H), 7.74 (d, J=6.3 Hz, 1H), 7.64 (d, J=9.2 Hz, 1H), 7.37-7.28 (m, 4H), 5.29 (d, J=15.4 Hz, 1H), 4.96 (d, J=15.4 Hz, 1H), 4.05 (s, 1H), 3.65 (dd, J=11.4, 6.8 Hz, 1H), 3.24 (s, 1H), 2.66 (d, J=6.7 Hz, 2H), 1.75 (m, 1H), 0.92 (d, J=6.7 Hz, 6H).

Synthesis of (3R)-3-amino-5-[(4-chlorophenyl)methyl]-4-oxo-N-(propan-2-yl)-2,3,4,5-tetrahydro-1,5-benzothiazepine-7-carboxamide hydrochloride (Example 61)

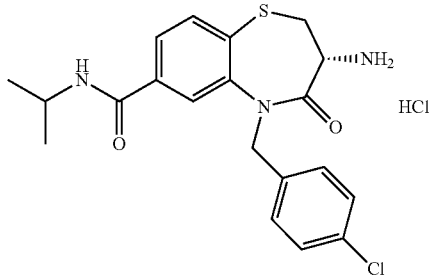 [SMILES: CC(C)NC(=O)c1ccc2c(c1)N(Cc1ccc(Cl)cc1)C(=O)[C@@H](N)CS2 ; Cl]

The title compound was synthesized according to general procedure GP5 to afford the title compound as cream solid in 92% Yield.

LCMS: METCR1416 GENERIC 7 MINUTES, rt=3.08 min, M/Z (ES+) 404/406 [M+H+] 100% UV NMR Data: 1H NMR (250 MHz, DMSO-d6) d 1.19 (d, J=6.60 Hz, 6H), 3.16-3.29 (m, 1H), 3.58-3.74 (m, 1H), 4.00 (dd, J=6.76, 11.58 Hz, 1H), 4.12 (dq, J=6.60, 13.83 Hz, 1H), 4.99 (d, J=15.41 Hz, 1H), 5.41 (d, J=15.39 Hz, 1H), 7.24-7.40 (m, 4H), 7.71 (d, J=8.03 Hz, 1H), 7.79 (dd, J=1.65, 8.05 Hz, 1H), 8.03 (d, J=1.53 Hz, 1H), 8.20-8.66 (m, 4H).

Synthesis of (3R)-3-amino-5-[(4-chlorophenyl)methyl]-N-(2-methylpropoxy)-4-oxo-2,3,4,5-tetrahydro-1,5-benzothiazepine-7-carboxamide hydrochloride (Example 62)

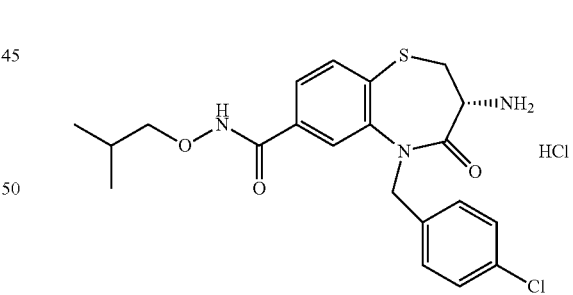

The title compound was synthesized according to general procedure GP5 to afford the title compound as yellow solid in 82% Yield.

LCMS: METCR1416 GENERIC 7 MINUTES, rt=3.19 min, M/Z (ES+) 434/436 [M+H+] 93% UV

NMR Data: 1H NMR (500 MHz, DMSO-d6) d 11.93 (s, 1H), 8.43 (s, 3H), 7.99-7.92 (m, 1H), 7.85-7.70 (m, 1H), 7.69-7.62 (m, 1H), 7.40-7.25 (m, 4H), 5.44-5.26 (m, 1H), 5.05-4.92 (m, 1H), 4.09-3.96 (m, 1H), 3.72-3.62 (m, 3H), 3.24 (t, J=11.6 Hz, 1H), 2.00-1.86 (m, 1H), 1.01-0.80 (m, 6H)

Synthesis of (3R)-3-amino-5-[(4-chlorophenyl) methyl]-N-(3-methylbutan-2-yl)-4-oxo-2,3,4,5-tetrahydro-1,5-benzothiazepine-7-carboxamide hydrochloride (Example 63)

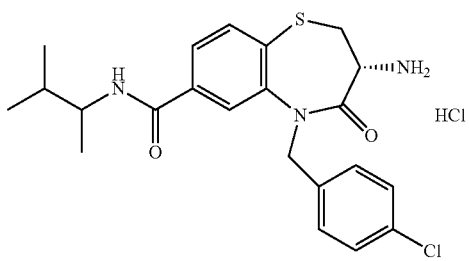 [SMILES: CC(C)C(C)NC(=O)c1ccc2c(c1)N(Cc1ccc(Cl)cc1)C(=O)[C@@H](N)CS2 ; Cl]

The title compound was synthesized according to general procedure GP5 to afford the title compound as yellow solid in 98% Yield.

LCMS: METCR1416 GENERIC 7 MINUTES, rt=3.27 min, M/Z (ES+) 432/434 [M+H+] 99% UV

NMR Data: 1H NMR (500 MHz, DMSO-d6) d 8.40-8.12 (m, 4H), 7.97 (dd, J=4.5, 1.7 Hz, 1H), 7.80-7.75 (m, 1H), 7.71 (d, J=8.0 Hz, 1H), 7.35-7.27 (m, 4H), 5.36 (d, J=15.3 Hz, 1H), 5.00 (dd, J=15.5, 7.8 Hz, 1H), 4.01 (dd, J=11.1, 7.5 Hz, 1H), 3.88-3.76 (m, 1H), 3.65-3.58 (m, 1H), 3.22 (td, J=11.6, 3.9 Hz, 1H), 1.76 (h, J=6.9 Hz, 1H), 1.11 (dd, J=6.8, 3.3 Hz, 3H), 0.88 (t, J=7.1 Hz, 6H)

Synthesis of (3R)-3-amino-N-(but-3-en-1-yl)-5-[(4-chlorophenyl)methyl]-4-oxo-2,3,4,5-tetrahydro-1,5-benzothiazepine-7-carboxamide hydrochloride (Example 64)

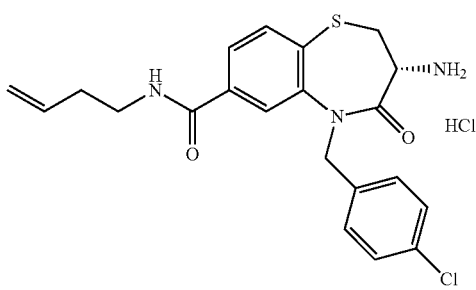 [SMILES: C=CCCNC(=O)c1ccc2c(c1)N(Cc1ccc(Cl)cc1)C(=O)[C@@H](N)CS2 ; Cl]

The title compound was synthesized according to general procedure GP5 to afford the title compound as Off-White Solid in 98% Yield.

LCMS: MET-UHPLC-AB-101, rt=2.1 min, M/Z (ES+) 416/418 [M+H+] 99% UV

NMR Data: 1H NMR (500 MHz, DMSO-d6) d 8.74 (t, J=5.6 Hz, 1H), 8.53-8.16 (m, 3H), 8.02 (d, J=1.4 Hz, 1H), 7.77-7.66 (m, 2H), 7.34-7.28 (m, 4H), 5.82 (ddt, J=17.0, 10.3, 6.7 Hz, 1H), 5.42 (d, J=15.5 Hz, 1H), 5.11-5.00 (m, 2H), 4.98 (d, J=15.5 Hz, 1H), 4.01 (dd, J=11.7, 6.7 Hz, 1H), 3.64 (dd, J=11.4, 6.8 Hz, 1H), 3.39-3.35 (m, 2H), 3.23 (dd, J=13.1, 10.0 Hz, 1H), 2.29 (q, J=7.0 Hz, 2H).

Synthesis of (3R)-3-amino-5-[(4-chlorophenyl) methyl]-N'-(2-methylpropyl)-4-oxo-2,3,4,5-tetrahydro-1,5-benzothiazepine-7-carbohydrazide hydrochloride (Example 65)

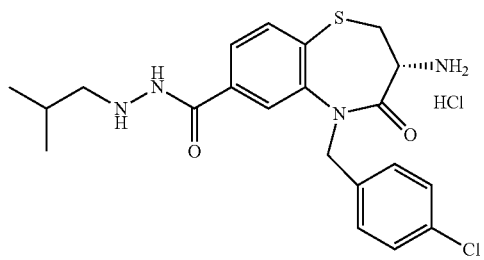 [SMILES: CC(C)CNNC(=O)c1ccc2c(c1)N(Cc1ccc(Cl)cc1)C(=O)[C@@H](N)CS2 ; Cl]

The title compound was synthesized according to general procedure GP5 to afford the title compound as cream solid in 61% Yield.

LCMS: METCR1416 GENERIC 7 MINUTES, rt=3.11 min, M/Z (ES+) 433/435 [M+H+] 92% UV

NMR Data: 1H NMR (500 MHz, DMSO-d6) d 10.96 (s, 2H), 8.44 (s, 3H), 8.08 (s, 1H), 7.81-7.71 (m, 2H), 7.35-7.26 (m, 4H), 5.43 (d, J=15.4 Hz, 1H), 5.01 (d, J=15.5 Hz, 1H), 4.09-3.97 (m, 1H), 3.68-3.61 (m, 1H), 3.30-3.21 (m, 1H), 2.77 (d, J=6.5 Hz, 2H), 1.89-1.78 (m, 1H), 0.98-0.91 (m, 6H).

According to the above described and exemplified general procedure GP5 the following examples were synthesized from intermediate IX:

Synthesis of (3R)-3-amino-N-butyl-5-[(4-chlorophenyl)methyl]-1,4-dioxo-2,3,4,5-tetrahydro-1$\lambda^4$,5-benzothiazepine-7-carboxamide hydrochloride (Example 66)

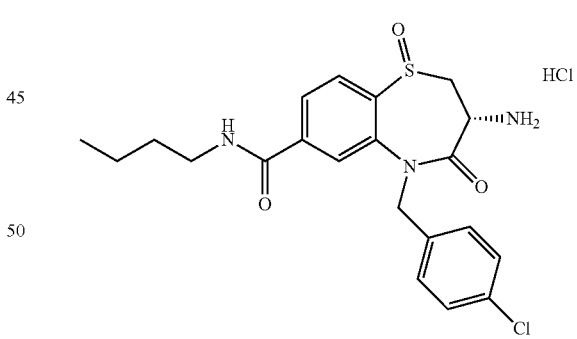

The title compound was synthesized according to general procedure GP5 to afford the title compound as off white solid in 75% Yield.

LCMS: METCR1600, rt=3.77 min, M/Z (ES+) 434/436 [M+H+] 96% UV

NMR Data: 1H NMR (500 MHz, DMSO-d6) 8.76 (t, J=5.6 Hz, 1H), 8.25 (s, 3H), 8.16-8.02 (m, 2H), 7.75 (d, J=8.1 Hz, 1H), 7.37 (d, J=8.4 Hz, 2H), 7.26 (d, J=8.4 Hz, 2H), 5.38 (d, J=15.0 Hz, 1H), 4.90 (d, J=15.0 Hz, 1H), 4.22-4.10 (m, 2H), 3.32-3.22 (m, 3H), 1.54 (p, J=7.1 Hz, 2H), 1.45-1.24 (m, 2H), 0.92 (t, J=7.4 Hz, 3H).

Synthesis of (3R)-3-amino-N-butyl-1,1,4-trioxo-5-{[4-(trifluoromethoxy)phenyl]methyl}-2,3,4,5-tetrahydro-1λ⁶,5-benzothiazepine-7-carboxamide hydrochloride (Example 67)

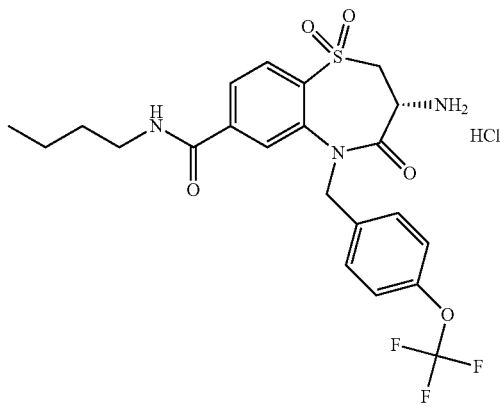 [SMILES: CCCCNC(=O)c1ccc2c(c1)N(Cc1ccc(OC(F)(F)F)cc1)C(=O)[C@@H](N)CS2(=O)=O ; Cl]

The title compound was synthesized according to general procedure GP5 to afford the title compound as off-white solid in 72% Yield.

LCMS: METCR1416 GENERIC 7 MINUTES, rt=3.27 min, M/Z (ES+) 500 [M+H+] 100% UV

NMR Data: 1H NMR (500 MHz, DMSO-d6) 8.87 (t, J=5.6 Hz, 1H), 8.46 (s, 3H), 8.04 (s, 2H), 7.93 (s, 1H), 7.52 (d, J=8.7 Hz, 2H), 7.32 (d, J=8.1 Hz, 2H), 5.27 (d, J=15.8 Hz, 1H), 4.99 (d, J=15.8 Hz, 1H), 4.46 (dd, J=10.9, 7.6 Hz, 1H), 4.13 (dd, J=13.3, 7.5 Hz, 1H), 3.96 (dd, J=13.1, 11.2 Hz, 1H), 3.27 (q, J=6.6 Hz, 2H), 1.50 (p, J=7.1 Hz, 2H), 1.31 (h, J=7.3 Hz, 2H), 0.89 (t, J=7.4 Hz, 3H).

Synthesis of (3R)-3-amino-5-[(4-chlorophenyl)methyl]-8-fluoro-N-[(4-fluorophenyl)methyl]-1,1,4-trioxo-2,3,4,5-tetrahydro-1λ⁶,5-benzothiazepine-7-carboxamide hydrochloride (Example 68)

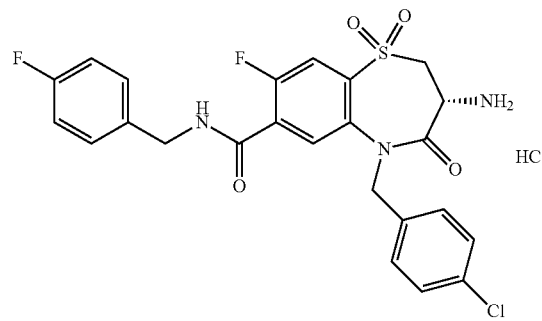

The title compound was synthesized according to general procedure GP5 to afford the title compound as off white solid in 87% Yield.

LCMS: MET-uPLC-AB-101: rt=2.43 min, M/Z (ES+) 520/522 [M+H+] 90% UV

NMR Data: 1H NMR (500 MHz, DMSO-d6) d 9.20 (t, J=6.0 Hz, 1H), 8.45 (s, 2H), 7.84 (d, J=8.5 Hz, 1H), 7.71 (d, J=5.5 Hz, 1H), 7.38 (s, 4H), 7.33 (dd, J=8.6, 5.6 Hz, 2H), 7.17 (t, J=8.9 Hz, 2H), 5.20 (d, J=15.7 Hz, 1H), 4.88 (d, J=15.7 Hz, 1H), 4.52-4.37 (m, 3H), 4.11 (dd, J=13.3, 7.4 Hz, 1H), 4.03-3.93 (m, 1H).

Synthesis of (3R)-3-amino-N-butyl-5-[(4-chlorophenyl)methyl]-8-fluoro-1,1,4-trioxo-2,3,4,5-tetrahydro-1λ⁶,5-benzothiazepine-7-carboxamide hydrochloride (Example 69)

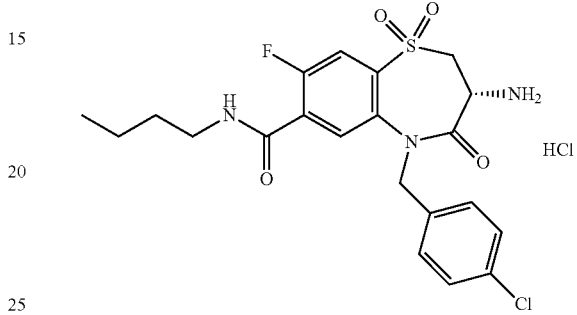

The title compound was synthesized according to general procedure GP5 to afford the title compound as off white solid in 72% Yield.

LCMS: METCR1416 GENERIC 7 MINUTES, rt=2.33 min, M/Z (ES+) 468/470 [M+H+] 94% UV

NMR Data: 1H NMR (500 MHz, DMSO-d6) d 8.68-8.50 (m, 4H), 7.81 (d, J=8.4 Hz, 1H), 7.63 (d, J=5.5 Hz, 1H), 7.38 (s, 4H), 5.21 (d, J=15.7 Hz, 1H), 4.86 (d, J=15.7 Hz, 1H), 4.48 (dd, J=10.9, 7.5 Hz, 1H), 4.14 (dd, J=13.3, 7.5 Hz, 1H), 4.04-3.90 (m, 1H), 3.29-3.11 (m, 2H), 1.47 (p, J=7.0 Hz, 2H), 1.35-1.24 (m, 2H), 0.88 (t, J=7.4 Hz, 3H).

Synthesis of (3R)-3-amino-5-[(4-chlorophenyl)methyl]-8-fluoro-1,1,4-trioxo-N-(4,4,4-trifluorobutyl)-2,3,4,5-tetrahydro-1λ⁶,5-benzothiazepine-7-carboxamide hydrochloride (Example 70)

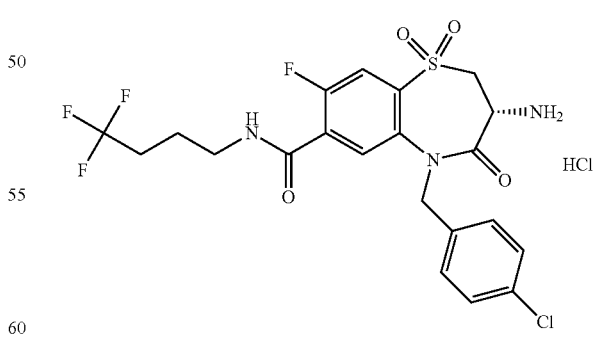

The title compound was synthesized according to general procedure GP5 to afford the title compound as pink solid in 99% Yield.

LCMS: METCR1416 GENERIC 7 MINUTES, rt=3.29 min, M/Z (ES+) 522/524 [M+H+]99% UV

NMR Data: 1H NMR (500 MHz, DMSO-d6) 8.76 (t, J=5.6 Hz, 1H), 8.52 (s, 3H), 7.83 (d, J=8.4 Hz, 1H), 7.71 (d, J=5.5 Hz, 1H), 7.42-7.32 (m, 4H), 5.18 (d, J=15.7 Hz, 1H), 4.91 (d, J=15.7 Hz, 1H), 4.47 (dd, J=10.9, 7.6 Hz, 1H), 4.13 (dd, J=13.3, 7.5 Hz, 1H), 3.98 (dd, J=13.2, 11.0 Hz, 1H), 3.37 (d, J=6.6 Hz, 2H), 2.35-2.22 (m, 2H), 1.72 (dt, J=14.7, 6.9 Hz, 2H).

Synthesis of (3R)-3-amino-5-[(4-chlorophenyl)methyl]-8-fluoro-N-(oxan-4-ylmethyl)-1,1,4-trioxo-2,3,4,5-tetrahydro-1λ⁶,5-benzothiazepine-7-carboxamide hydrochloride (Example 71)

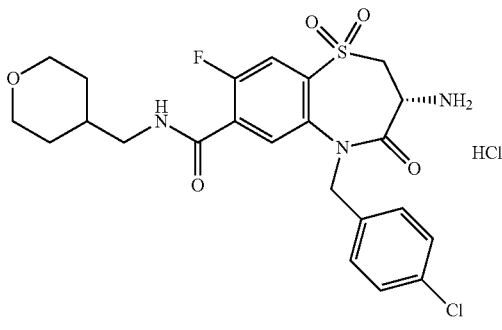 [SMILES: N[C@H]1CS(=O)(=O)c2cc(F)c(C(=O)NCC3CCOCC3)cc2N(Cc2ccc(Cl)cc2)C1=O ; Cl]

The title compound was synthesized according to general procedure GP5 to afford the title compound as off white solid in 87% Yield.

LCMS: METCR1673 Generic 2 minutes, rt=1.02 min, M/Z (ES+) 510/512 [M+H+] 92% UV

NMR Data: 1H NMR (500 MHz, DMSO-d6) 8.65 (s, 1H), 7.96 (bs, 3H), 7.81 (d, J=8.7 Hz, 1H), 7.60 (s, 1H), 7.39 (s, 4H), 5.22 (d, J=14.8 Hz, 1H), 4.84 (d, J=16.0 Hz, 1H), 4.39 (s, 1H), 4.10 (s, 1H), 3.97 (s, 1H), 3.85 (s, 2H), 3.14 (s, 2H), 1.74 (s, 1H), 1.53 (d, J=11.7 Hz, 3H), 1.18 (d, J=9.0 Hz, 3H).

Synthesis of (3R)-3-amino-8-fluoro-N-(oxan-4-ylmethyl)-1,1,4-trioxo-5-{[4-(trifluoromethoxy)-phenyl]methyl}-2,3,4,5-tetrahydro-1λ⁶,5-benzothiazepine-7-carboxamide hydrochloride (Example 72)

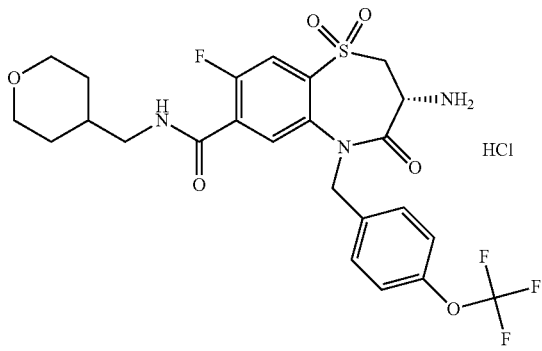 [SMILES: N[C@H]1CS(=O)(=O)c2cc(F)c(C(=O)NCC3CCOCC3)cc2N(Cc2ccc(OC(F)(F)F)cc2)C1=O ; Cl]

The title compound was synthesized according to general procedure GP5 to afford the title compound as cream solid in 95% Yield.

LCMS: METCR1416 GENERIC 7 MINUTES, rt=3.12 min, M/Z (ES+) 560 [M+H+], 94% UV

NMR Data: 1H NMR (500 MHz, DMSO-d6) d 1.18 (qd, J=4.32, 12.21 Hz, 2H), 1.53 (d, J=12.72 Hz, 2H), 1.66-1.80 (m, 1H), 3.14 (dh, J=6.24, 25.75 Hz, 2H), 3.25 (t, J=11.57 Hz, 2H), 3.78-3.89 (m, 2H), 3.93-4.05 (m, 1H), 4.13 (dd, J=7.47, 13.32 Hz, 1H), 4.48 (dd, J=7.59, 10.81 Hz, 1H), 4.87 (d, J=15.84 Hz, 1H), 5.25 (d, J=15.77 Hz, 1H), 7.32 (d, J=8.27 Hz, 2H), 7.50 (d, J=8.61 Hz, 2H), 7.63 (d, J=5.42 Hz, 1H), 7.83 (d, J=8.33 Hz, 1H), 8.47 (s, 3H), 8.67 (t, J=5.83 Hz, 1H).

Synthesis of (3R)-3-amino-8-fluoro-1,1,4-trioxo-N-(4,4,4-trifluorobutyl)-5-{[4-(trifluoromethoxy)-phenyl]methyl}-2,3,4,5-tetrahydro-1λ⁶,5-benzothiazepine-7-carboxamide hydrochloride (Example 73)

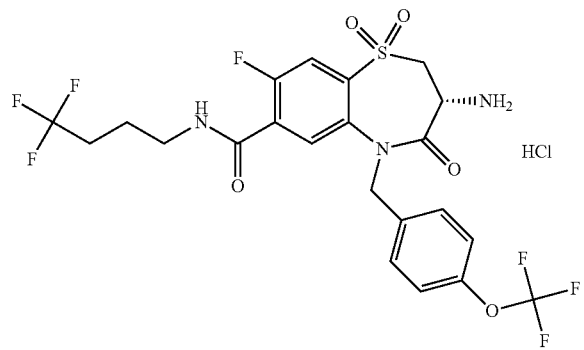 [SMILES: N[C@H]1CS(=O)(=O)c2cc(F)c(C(=O)NCCCC(F)(F)F)cc2N(Cc2ccc(OC(F)(F)F)cc2)C1=O ; Cl]

The title compound was synthesized according to general procedure GP5 to afford the title compound as cream solid in 100% Yield.

LCMS: METCR1416 GENERIC 7 MINUTES, rt=3.35 min, M/Z (ES+) 572 [M+H+]97% UV

NMR Data: 1H NMR (500 MHz, DMSO-d6) d 1.72 (dt, J=7.00, 14.60 Hz, 2H), 2.21-2.34 (m, 2H), 3.32-3.40 (m, 2H), 3.99 (dd, J=11.15, 13.06 Hz, 1H), 4.14 (dd, J=7.51, 13.32 Hz, 1H), 4.47 (dd, J=7.60, 10.84 Hz, 1H), 4.91 (d, J=15.77 Hz, 1H), 5.24 (d, J=15.77 Hz, 1H), 7.31 (d, J=8.33 Hz, 2H), 7.50 (d, J=8.60 Hz, 2H), 7.69 (d, J=5.47 Hz, 1H), 7.84 (d, J=8.42 Hz, 1H), 8.49 (s, 3H), 8.76 (t, J=5.66 Hz, 1H).

Synthesis of (3R)-3-amino-8-fluoro-1,1,4-trioxo-N-phenoxy-5-{[4-(trifluoromethoxy)phenyl]methyl}-2,3,4,5-tetrahydro-1λ⁶,5-benzothiazepine-7-carboxamide hydrochloride (Example 74)

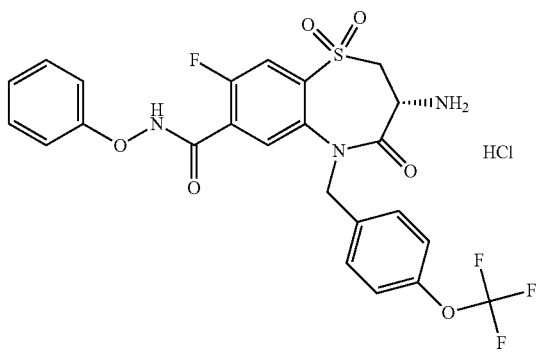 [SMILES: N[C@H]1CS(=O)(=O)c2cc(F)c(C(=O)NOc3ccccc3)cc2N(Cc2ccc(OC(F)(F)F)cc2)C1=O ; Cl]

The title compound was synthesized according to general procedure GP5 to afford the title compound as cream solid in 46% Yield.
LCMS: METCR1416 GENERIC 7 MINUTES, rt=3.31 min, M/Z (ES+) 554 [M+H+]96% UV
NMR Data: 1H NMR (500 MHz, DMSO-d6) d 3.97-4.07 (m, 1H), 4.16 (dd, J=7.42, 13.19 Hz, 1H), 4.53 (dd, J=7.86, 10.51 Hz, 1H), 4.98 (d, J=15.63 Hz, 1H), 5.25 (d, J=15.87 Hz, 1H), 7.08 (d, J=7.91 Hz, 3H), 7.26-7.42 (m, 4H), 7.52 (d, J=8.50 Hz, 2H), 7.88 (d, J=4.07 Hz, 1H), 7.93 (d, J=8.27 Hz, 1H), 8.59 (s, 3H), 12.80 (s, 1H).

Synthesis of (3R)-3-amino-5-[(4-chlorophenyl)methyl]-8-fluoro-N-(2-methylpropoxy)-1,1,4-trioxo-2,3,4,5-tetrahydro-1λ⁶,5-benzothiazepine-7-carboxamide hydrochloride (Example 75)

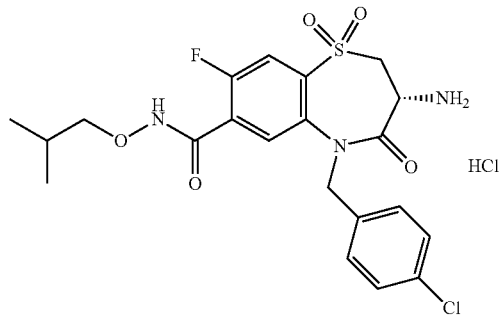 [SMILES: CC(C)CONC(=O)c1cc2c(cc1F)S(=O)(=O)C[C@H](N)C(=O)N2Cc1ccc(Cl)cc1 ; Cl]

The title compound was synthesized according to general procedure GP5 to afford the title compound as white solid in 100% Yield.
LCMS: METCR1416 GENERIC 7 MINUTES, rt=3.16 min, M/Z (ES+) 484/486 [M+H+]98% UV
NMR Data: 1H NMR (500 MHz, DMSO-d6) d 0.93 (d, J=6.69 Hz, 6H), 1.90 (dp, J=6.97, 13.67 Hz, 1H), 3.67 (dd, J=2.94, 6.55 Hz, 2H), 3.99 (t, J=11.95 Hz, 1H), 4.06-4.20 (m, 1H), 4.48 (dd, J=7.77, 10.75 Hz, 1H), 4.92 (d, J=15.64 Hz, 1H), 5.17 (d, J=15.57 Hz, 1H), 7.38 (s, 4H), 7.72 (d, J=4.81 Hz, 1H), 7.84 (d, J=8.21 Hz, 1H), 8.62 (s, 3H), 11.83 (s, 1H).

Synthesis of (3R)-3-amino-5-[(4-chlorophenyl)methyl]-8-fluoro-1,1,4-trioxo-N-phenoxy-2,3,4,5-tetrahydro-1λ⁶,5-benzothiazepine-7-carboxamide hydrochloride (Example 76)

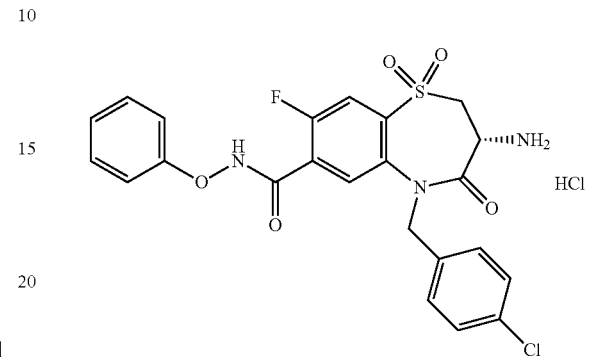

The title compound was synthesized according to general procedure GP5 to afford the title compound as white solid in 57% Yield.
LCMS: METCR1416 GENERIC 7 MINUTES, rt=3.21 min, M/Z (ES+) 504/506 [M+H+] 99% UV
NMR Data: 1H NMR (500 MHz, DMSO-d6) 7.89 (d, J=8.4 Hz, 1H), 7.83 (d, J=5.2 Hz, 1H), 7.40 (d, J=6.6 Hz, 6H), 7.09 (dd, J=13.1, 7.7 Hz, 3H), 5.21 (d, J=15.8 Hz, 1H), 4.94 (d, J=15.8 Hz, 1H), 4.28 (s, 1H), 4.07 (dd, J=13.2, 7.4 Hz, 1H), 3.96-3.84 (m, 1H).

Synthesis of (3R)-3-amino-5-[(4-chlorophenyl)methyl]-8-fluoro-1,1,4-trioxo-N-(propan-2-yl)-2,3,4,5-tetrahydro-1λ⁶,5-benzothiazepine-7-carboxamide hydrochloride (Example 77)

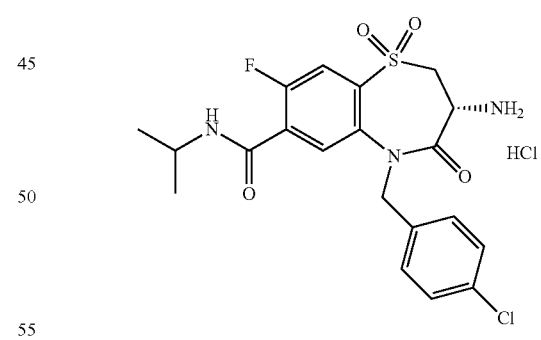

The title compound was synthesized according to general procedure GP5 to afford the title compound as White Solid in 95% Yield.
LCMS: MET-uHPLC-AB-101, rt=2.09 min, M/Z (ES+) 454/456 [M+H+] 100% UV
NMR Data: 1H NMR (500 MHz, DMSO-d6) d 8.71-8.18 (m, 4H), 7.80 (d, J=8.2 Hz, 1H), 7.62 (d, J=5.4 Hz, 1H), 7.38 (s, 4H), 5.20 (d, J=15.6 Hz, 1H), 4.88 (d, J=15.6 Hz, 1H), 4.46-4.39 (m, 1H), 4.12 (dd, J=13.2, 7.4 Hz, 1H), 4.07-3.93 (m, 2H), 1.14 (dd, J=8.4, 6.7 Hz, 6H).

Synthesis of (3R)-3-amino-5-[(4-chlorophenyl) methyl]-N-({4-[(5-acetamidopentyl)oxy]phenyl}-methyl)-1,1,4-trioxo-2,3,4,5-tetrahydro-1λ⁶,5-benzo-thiazepine-7-carboxamide hydrochloride (Example 78.)

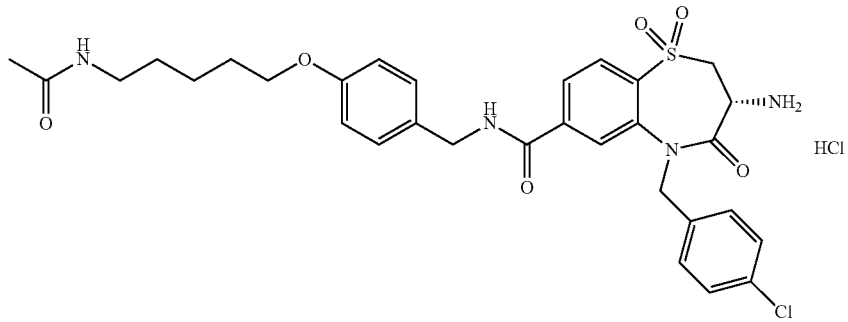 [SMILES: CC(=O)NCCCCCOc1ccc(CNC(=O)c2ccc3c(c2)N(Cc2ccc(Cl)cc2)C(=O)[C@@H](N)CS3(=O)=O)cc1 ; Cl]

The title compound was synthesized according to general procedure GP5 to afford the title compound as cream solid in 95% Yield.

LCMS: METCR1416 GENERIC 7 MINUTES, rt=3.2 min, M/Z (ES+) 627/629 [M+H+] 95% UV

NMR Data: 1H NMR (500 MHz, DMSO-d6) 9.39 (t, J=5.9 Hz, 1H), 8.60 (s, 3H), 8.10-8.01 (m, 2H), 7.99 (s, 1H), 7.81 (s, 1H), 7.44-7.33 (m, 4H), 7.21 (d, J=8.6 Hz, 2H), 6.89 (d, J=8.7 Hz, 2H), 5.22 (d, J=15.7 Hz, 1H), 5.00 (d, J=15.7 Hz, 1H), 4.49 (dd, J=10.9, 7.6 Hz, 1H), 4.42 (d, J=5.9 Hz, 2H), 4.11 (dd, J=13.3, 7.5 Hz, 1H), 4.03-3.89 (m, 3H), 3.03 (q, J=6.5 Hz, 2H), 1.78 (s, 3H), 1.69 (p, J=6.7 Hz, 2H), 1.50-1.31 (m, 4H).

Synthesis of (3R)-3-amino-5-[(4-chlorophenyl) methyl]-1,1,4-trioxo-N-(propan-2-yl)-2,3,4,5-tetra-hydro-1λ⁶,5-benzothiazepine-7-carboxamide hydrochloride (Example 79)

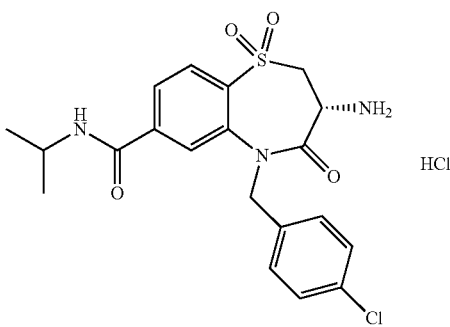 [SMILES: CC(C)NC(=O)c1ccc2c(c1)N(Cc1ccc(Cl)cc1)C(=O)[C@@H](N)CS2(=O)=O ; Cl]

The title compound was synthesized according to general procedure GP5 to afford the title compound as cream solid in 92% Yield.

LCMS: METCR1416 GENERIC 7 MINUTES, rt=3.02 min, M/Z (ES+) 436/438 [M+H+], 100% UV NMR Data: 1H NMR (500 MHz, DMSO-d6) d 1.17 (dd, J=1.56, 6.58 Hz, 6H), 3.95 (dd, J=11.30, 13.11 Hz, 1H), 4.01-4.17 (m, 2H), 4.42 (dd, J=7.48, 11.05 Hz, 1H), 4.95 (d, J=15.70 Hz, 1H), 5.24 (d, J=15.70 Hz, 1H), 7.32-7.45 (m, 4H), 7.92 (s, 1H), 7.97-8.08 (m, 2H), 8.50 (s, 3H), 8.65 (d, J=7.61 Hz, 1H)

Synthesis of (3R)-3-amino-5-[(4-chlorophenyl) methyl]-1,1,4-trioxo-N-(4,4,4-trifluorobutyl)-2,3,4, 5-tetrahydro-1λ⁶,5-benzothiazepine-7-carboxamide hydrochloride (Example 80)

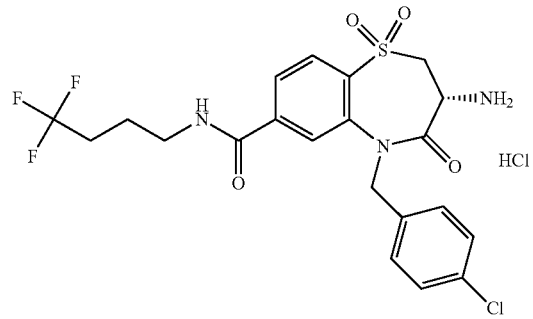 [SMILES: N[C@H]1CS(=O)(=O)c2ccc(C(=O)NCCCC(F)(F)F)cc2N(Cc2ccc(Cl)cc2)C1=O ; Cl]

The title compound was synthesized according to general procedure GP5 to afford the title compound as Off-White Solid in 98% Yield.

LCMS: MET-uHPLC-AB-101, rt=2.29 min, M/Z (ES+) 504/506 [M+H+] 99% UV

NMR Data: 1H NMR (500 MHz, DMSO-d6) d 9.02 (t, J=5.6 Hz, 1H), 8.49 (s, 3H), 8.04 (s, 2H), 7.97 (s, 1H), 7.42-7.33 (m, 4H), 5.23 (d, J=15.7 Hz, 1H), 4.99 (d, J=15.7 Hz, 1H), 4.45 (dd, J=10.9, 7.6 Hz, 1H), 4.11 (dd, J=13.3, 7.5 Hz, 1H), 3.96 (dd, J=13.1, 11.3 Hz, 1H), 3.37-3.35 (m, 2H), 2.34-2.24 (m, 2H), 1.75 (dt, J=14.7, 7.1 Hz, 2H).

Synthesis of (3R)-3-amino-5-[(4-chlorophenyl) methyl]-N-(2-methylpropoxy)-1,1,4-trioxo-2,3,4,5-tetrahydro-1λ⁶,5-benzothiazepine-7-carboxamide hydrochloride (Example 81)

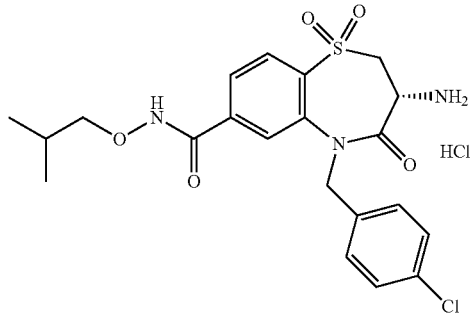 [SMILES: CC(C)CONC(=O)c1ccc2c(c1)N(Cc1ccc(Cl)cc1)C(=O)[C@@H](N)CS2(=O)=O ; Cl]

The title compound was synthesized according to general procedure GP5 to afford the title compound as yellow solid in 79% Yield.

LCMS: METCR1416 GENERIC 7 MINUTES, rt=3.14 min, M/Z (ES+) 466/468 [M+H+] 96% UV

NMR Data: 1H NMR (500 MHz, DMSO-d6) d 12.11 (s, 1H), 8.54 (s, 3H), 8.15-7.98 (m, 1H), 8.01-7.89 (m, 1H), 7.89-7.84 (m, 1H), 7.46-7.28 (m, 4H), 5.33-5.16 (m, 1H), 5.02-4.79 (m, 1H), 4.54-4.41 (m, 1H), 4.17-4.06 (m, 1H), 4.03-3.90 (m, 1H), 3.77-3.62 (m, 2H), 1.91 (dt, J=13.4, 6.8 Hz, 1H), 1.00-0.78 (m, 6H)

Synthesis of (3R)-3-amino-5-[(4-chlorophenyl)methyl]-1,1,4-trioxo-N-propoxy-2,3,4,5-tetrahydro-1λ⁶,5-benzothiazepine-7-carboxamide hydrochloride (Example 82)

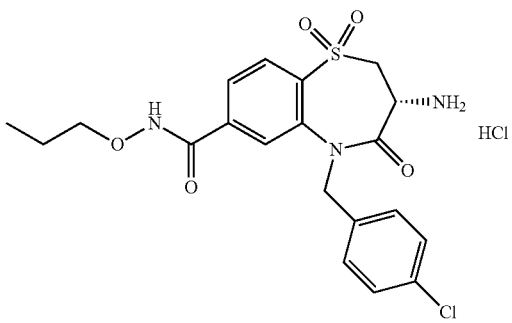 [SMILES: CCCONC(=O)c1ccc2c(c1)N(Cc1ccc(Cl)cc1)C(=O)[C@@H](N)CS2(=O)=O ; Cl]

The title compound was synthesized according to general procedure GP5 to afford the title compound as yellow solid in 68% Yield.

LCMS: METCR1416 GENERIC 7 MINUTES, rt=3 min, M/Z (ES+) 452/454 [M+H+] 95% UV

NMR Data: 1H NMR (500 MHz, DMSO-d6) d 12.10 (s, 1H), 8.57 (s, 3H), 8.14-7.82 (m, 3H), 7.46-7.32 (m, 4H), 5.32-5.14 (m, 1H), 5.02-4.77 (m, 1H), 4.55-4.40 (m, 1H), 4.18-4.05 (m, 1H), 4.03-3.89 (m, 1H), 3.84 (t, J=6.5 Hz, 2H), 1.60 (h, J=7.1 Hz, 2H), 0.99-0.82 (m, 3H)

Synthesis of (3R)-3-amino-5-[(4-chlorophenyl)methyl]-N-(3-methylbutan-2-yl)-1,1,4-trioxo-2,3,4,5-tetrahydro-1λ⁶,5-benzothiazepine-7-carboxamide hydrochloride (Example 83)

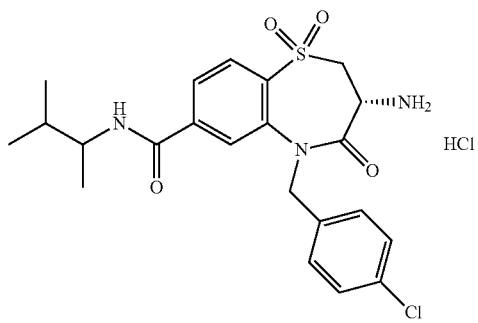 [SMILES: CC(C)C(C)NC(=O)c1ccc2c(c1)N(Cc1ccc(Cl)cc1)C(=O)[C@@H](N)CS2(=O)=O ; Cl]

The title compound was synthesized according to general procedure GP5 to afford the title compound as white solid in 86% Yield.

LCMS: METCR1416 GENERIC 7 MINUTES, rt=3.23 min, M/Z (ES+) 464/466 [M+H+] 100% UV NMR Data: 1H NMR (500 MHz, DMSO-d6) d 8.86-8.17 (m, 4H), 8.09-7.98 (m, 2H), 7.86 (d, J=20.5 Hz, 1H), 7.45-7.35 (m, 4H), 5.28 (dd, J=15.7, 11.0 Hz, 1H), 4.92 (dd, J=15.7, 4.5 Hz, 1H), 4.47 (dt, J=11.0, 7.3 Hz, 1H), 4.16-4.07 (m, 1H), 3.97 (dd, J=13.2, 11.2 Hz, 1H), 3.81 (dt, J=13.9, 6.8 Hz, 1H), 1.75 (dp, J=13.6, 6.7 Hz, 1H), 1.11 (d, J=6.8 Hz, 3H), 0.93-0.80 (m, 6H)

Synthesis of (3R)-3-amino-N-(but-3-en-1-yl)-5-[(4-chlorophenyl)methyl]-1,1,4-trioxo-2,3,4,5-tetrahydro-1λ⁶,5-benzothiazepine-7-carboxamide hydrochloride (Example 84)

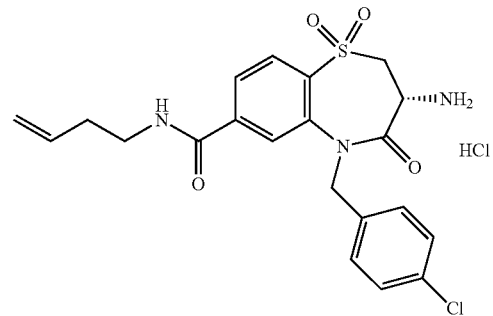 [SMILES: C=CCCNC(=O)c1ccc2c(c1)N(Cc1ccc(Cl)cc1)C(=O)[C@@H](N)CS2(=O)=O ; Cl]

The title compound was synthesized according to general procedure GP5 to afford the title compound as Off-White Solid in 96% Yield.

LCMS: MET-uHPLC-AB-101, rt=2.11 min, M/Z (ES+) 448/450 [M+H+] 94% UV

NMR Data: 1H NMR (500 MHz, DMSO-d6) d 8.91 (t, J=5.5 Hz, 1H), 8.55 (s, 3H), 8.02 (q, J=8.2 Hz, 2H), 7.92 (s, 1H), 7.41-7.35 (m, 4H), 5.80 (ddt, J=17.0, 10.2, 6.7 Hz, 1H), 5.22 (d, J=15.8 Hz, 1H), 5.09-4.99 (m, 2H), 4.97 (d, J=15.8 Hz, 1H), 4.47 (dd, J=10.9, 7.6 Hz, 1H), 4.11 (dd, J=13.3, 7.5 Hz, 1H), 4.00-3.93 (m, 1H), 3.37-3.34 (m, 2H), 2.28 (q, J=6.9 Hz, 2H).

Synthesis of (3R)-3-amino-5-[(4-chlorophenyl)methyl]-N-cyclopropyl-8-fluoro-1,1,4-trioxo-2,3,4,5-tetrahydro-1λ⁶,5-benzothiazepine-7-carboxamide hydrochloride (Example 85)

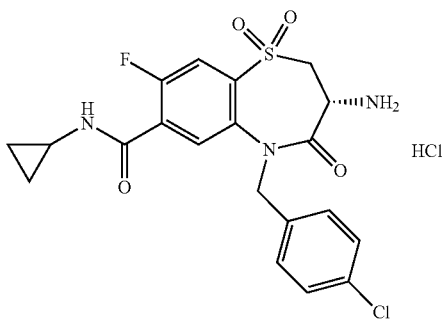 [SMILES: N[C@H]1CS(=O)(=O)c2cc(F)c(C(=O)NC3CC3)cc2N(Cc2ccc(Cl)cc2)C1=O ; Cl]

The title compound was synthesized according to general procedure GP5 to afford the title compound as white solid in 99% Yield.

LCMS: METCR1416 GENERIC 7 MINUTES, rt=3.02 min, M/Z (ES+) 452/454 [M+H+] 100% UV NMR Data: 1H NMR (500 MHz, DMSO-d6) 8.70 (d, J=4.3 Hz, 1H), 8.39 (s, 3H), 7.79 (d, J=8.3 Hz, 1H), 7.68 (d, J=5.5 Hz, 1H), 7.37 (s, 4H), 5.16 (d, J=15.6 Hz, 1H), 4.91 (d, J=15.6 Hz, 1H), 4.42 (dd, J=10.9, 7.6 Hz, 1H), 4.11 (dd, J=13.3, 7.5 Hz, 1H), 3.96 (dd, J=13.2, 11.1 Hz, 1H), 2.83 (tq, J=7.9, 4.0 Hz, 1H), 0.76-0.65 (m, 2H), 0.53 (dd, J=3.8, 1.9 Hz, 2H).

Synthesis of (3R)-3-amino-5-[(4-chlorophenyl)methyl]-N-cyclobutyl-8-fluoro-1,1,4-trioxo-2,3,4,5-tetrahydro-1λ⁶,5-benzothiazepine-7-carboxamide hydrochloride (Example 86)

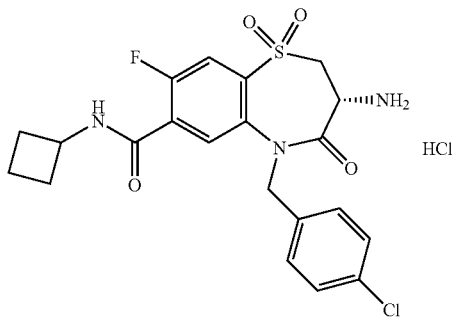 [SMILES: N[C@H]1CS(=O)(=O)c2cc(F)c(C(=O)NC3CCC3)cc2N(Cc2ccc(Cl)cc2)C1=O ; Cl]

The title compound was synthesized according to general procedure GP5 to afford the title compound as cream solid in 95% Yield.

LCMS: METCR1416 GENERIC 7 MINUTES, rt=3.13 min, M/Z (ES+) 466/468 [M+H+] 99% UV

NMR Data: 1H NMR (500 MHz, DMSO-d6) d 8.90 (d, J=7.6 Hz, 1H), 8.64 (s, 3H), 7.80 (d, J=8.3 Hz, 1H), 7.66 (d, J=5.5 Hz, 1H), 7.42-7.32 (m, 4H), 5.18 (d, J=15.7 Hz, 1H), 4.91 (d, J=15.7 Hz, 1H), 4.44 (dd, J=11.0, 7.5 Hz, 1H), 4.35 (h, J=8.0 Hz, 1H), 4.17 (dd, J=13.3, 7.5 Hz, 1H), 3.99 (dd, J=13.2, 11.1 Hz, 1H), 2.22 (dtp, J=15.2, 7.8, 4.0, 3.5 Hz, 2H), 2.00 (p, J=9.6 Hz, 2H), 1.68 (ddt, J=14.7, 10.4, 5.8 Hz, 2H)

Synthesis of (3R)-3-amino-5-[(4-chloro-2-fluorophenyl)methyl]-8-fluoro-1,1,4-trioxo-N-(propan-2-yl)-2,3,4,5-tetrahydro-1λ⁶,5-benzothiazepine-7-carboxamide hydrochloride (Example 87)

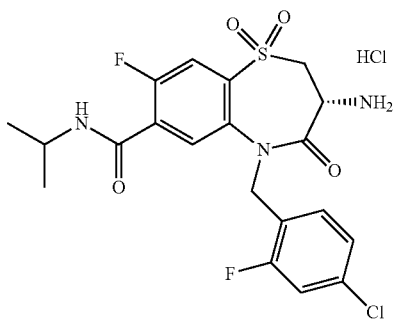 [SMILES: CC(C)NC(=O)c1cc2c(cc1F)S(=O)(=O)C[C@H](N)C(=O)N2Cc1ccc(Cl)cc1F ; Cl]

The title compound was synthesized according to general procedure GP5 to afford the title compound as beige solid in 66% Yield.

LCMS: METCR1416 GENERIC 7 MINUTES, rt=3.09 min, M/Z (ES+) 472/474 [M+H+] 99% UV

NMR Data: 1H NMR (500 MHz, DMSO-d6) d 8.64 (s, 3H), 8.57 (d, J=7.6 Hz, 1H), 7.87 (d, J=5.4 Hz, 1H), 7.79 (d, J=8.3 Hz, 1H), 7.46 (t, J=8.2 Hz, 1H), 7.35 (dd, J=9.8, 2.0 Hz, 1H), 7.22 (dd, J=8.3, 1.9 Hz, 1H), 5.14-4.99 (m, 2H), 4.39 (dd, J=10.9, 7.5 Hz, 1H), 4.12 (dd, J=13.4, 7.5 Hz, 1H), 4.05 (dt, J=13.4, 6.7 Hz, 1H), 3.91 (dd, J=13.2, 11.1 Hz, 1H), 1.17 (t, J=6.2 Hz, 6H)

Synthesis of (3R)-3-amino-5-[(3,4-dichlorophenyl)methyl]-1,1,4-trioxo-N-(propan-2-yl)-2,3,4,5-tetrahydro-1λ⁶,5-benzothiazepine-7-carboxamide hydrochloride (Example 88)

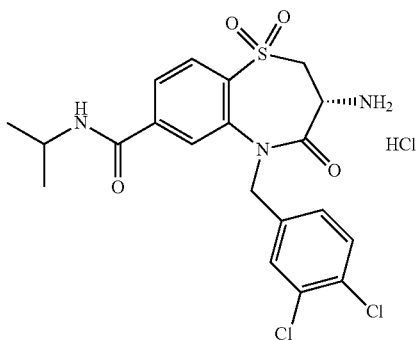 [SMILES: CC(C)NC(=O)c1ccc2c(c1)N(Cc1ccc(Cl)c(Cl)c1)C(=O)[C@@H](N)CS2(=O)=O ; Cl]

The title compound was synthesized according to general procedure GP5 to afford the title compound as cream solid in 94% Yield.

LCMS: METCR1416 GENERIC 7 MINUTES, rt=3.13 min, M/Z (ES+) 470/472/474 [M+H+] 100% UV NMR Data: 1H NMR (500 MHz, DMSO-d6) d 8.66 (d, J=7.7 Hz, 1H), 8.58 (s, 3H), 8.08-8.00 (m, 2H), 7.94 (d, 1H), 7.68 (d, J=1.9 Hz, 1H), 7.58 (d, J=8.3 Hz, 1H), 7.33 (dd, J=8.3, 2.0 Hz, 1H), 5.22 (d, J=15.8 Hz, 1H), 5.00 (d, J=15.8 Hz, 1H), 4.45 (dd, J=11.0, 7.5 Hz, 1H), 4.16-4.02 (m, 2H), 3.96 (dd, J=13.2, 11.2 Hz, 1H), 1.18 (dd, J=6.6, 2.6 Hz, 6H)

Synthesis of (3R)-3-amino-5-[(4-chloro-3-fluorophenyl)methyl]-1,1,4-trioxo-N-(propan-2-yl)-2,3,4,5-tetrahydro-1λ⁶,5-benzothiazepine-7-carboxamide hydrochloride (Example 89)

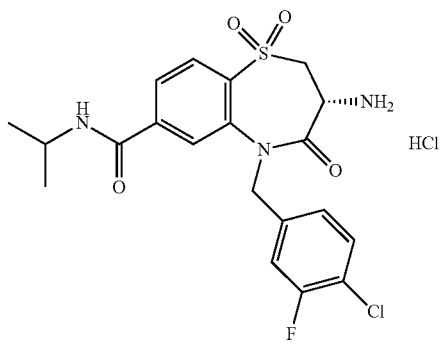 [SMILES: CC(C)NC(=O)c1ccc2c(c1)N(Cc1ccc(Cl)c(F)c1)C(=O)[C@@H](N)CS2(=O)=O ; Cl]

The title compound was synthesized according to general procedure GP5 to afford the title compound as cream solid in 92% Yield.

LCMS: METCR1416 GENERIC 7 MINUTES, rt=3.05 min, M/Z (ES+) 454/456 [M+H+] 99% UV

NMR Data: 1H NMR (500 MHz, DMSO-d6) d 8.65 (d, J=7.7 Hz, 1H), 8.58 (s, 3H), 8.09-8.00 (m, 2H), 7.90 (d, J=1.1 Hz, 1H), 7.54 (t, J=8.0 Hz, 1H), 7.45 (dd, J=10.4, 1.8 Hz, 1H), 7.23 (dd, J=8.3, 1.6 Hz, 1H), 5.26 (d, J=16.0 Hz, 1H), 4.95 (d, J=16.0 Hz, 1H), 4.46 (dd, J=11.0, 7.5 Hz, 1H), 4.17-4.02 (m, 2H), 3.97 (dd, J=13.2, 11.2 Hz, 1H), 1.17 (dd, J=6.6, 2.4 Hz, 6H)

Synthesis of (3R)-3-amino-5-[(4-chlorophenyl) methyl]-N-(cyclohexyloxy)-1,1,4-trioxo-2,3,4,5-tetrahydro-1λ⁶,5-benzothiazepine-7-carboxamide hydrochloride (Example 90)

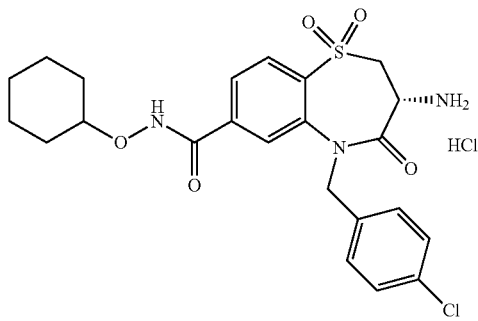 [SMILES: N[C@H]1CS(=O)(=O)c2ccc(C(=O)NOC3CCCCC3)cc2N(Cc2ccc(Cl)cc2)C1=O ; Cl]

The title compound was synthesized according to general procedure GP5 to afford the title compound as cream solid in 44% Yield.

LCMS: METCR1416 GENERIC 7 MINUTES, rt=3.28 min, M/Z (ES+) 492/494 [M+H+] 100% UV NMR Data: 1H NMR (500 MHz, DMSO-d6) d 1.14-1.56 (m, 6H), 1.71 (s, 2H), 1.86 (s, 2H), 3.85 (s, 1H), 3.96 (t, J=11.84 Hz, 1H), 4.06-4.23 (m, 1H), 4.45 (s, 1H), 4.93 (d, J=15.42 Hz, 1H), 5.23 (d, J=15.64 Hz, 1H), 7.21-7.51 (m, 4H), 7.84 (s, 1H), 7.98 (m, 2H), 8.47 (s, 3H), 11.89 (s, 1H).

Synthesis of (3R)-3-amino-5-[(4-chlorophenyl) methyl]-N-(cyclohexylmethoxy)-1,1,4-trioxo-2,3,4,5-tetrahydro-1λ⁶,5-benzothiazepine-7-carboxamide hydrochloride (Example 91)

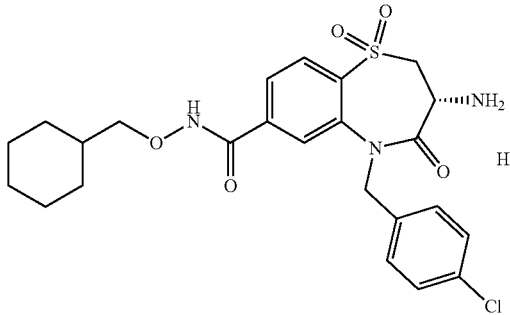

The title compound was synthesized according to general procedure GP5 to afford the title compound as cream solid in 82% Yield.

LCMS: METCR1416 GENERIC 7 MINUTES, rt=3.47 min, M/Z (ES+) 506/508 [M+H+] 100% UV NMR Data: 1H NMR (250 MHz, DMSO-d6) d 0.75-1.39 (m, 5H), 1.47-1.92 (m, 6H), 3.70 (d, J=5.77 Hz, 2H), 3.83-4.04 (m, 1H), 4.13 (dd, J=7.51, 13.25 Hz, 1H), 4.33-4.53 (m, 1H), 4.96 (d, J=15.65 Hz, 1H), 5.22 (d, J=15.95 Hz, 1H), 7.39 (s, 4H), 7.78-8.12 (m, 3H), 8.44 (s, 3H), 12.12 (s, 1H).

Synthesis of (3R)-3-amino-5-[(4-chlorophenyl) methyl]-8-fluoro-1,1,4-trioxo-N-(2,2,2-trifluoro-ethyl)-2,3,4,5-tetrahydro-1λ⁶,5-benzothiazepine-7-carboxamide hydrochloride (Example 92)

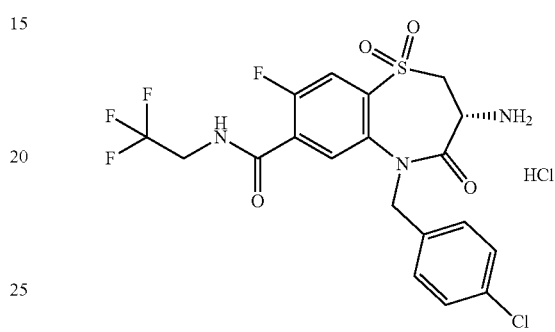

The title compound was synthesized according to general procedure GP5 to afford the title compound as Off white solid in 86% Yield.

LCMS: METCR1416 GENERIC 7 MINUTES, rt=3.14 min, M/Z (ES+) 494/496 [M+H+] 100% UV NMR Data: 1H NMR (500 MHz, DMSO-d6) δ 9.36 (t, J=6.3 Hz, 1H), 8.68 (s, 3H), 7.86 (d, J=8.4 Hz, 1H), 7.70 (d, J=5.5 Hz, 1H), 7.55-7.22 (m, 4H), 5.21 (d, J=15.7 Hz, 1H), 4.89 (d, J=15.7 Hz, 1H), 4.49 (dd, J=10.9, 7.5 Hz, 1H), 4.26-3.92 (m, 4H).

Synthesis of (3R)-3-amino-5-[(4-chlorophenyl) methyl]-8-fluoro-1,1,4-trioxo-N-(3,3,3-trifluoro-propyl)-2,3,4,5-tetrahydro-1λ⁶,5-benzothiazepine-7-carboxamide hydrochloride (Example 93)

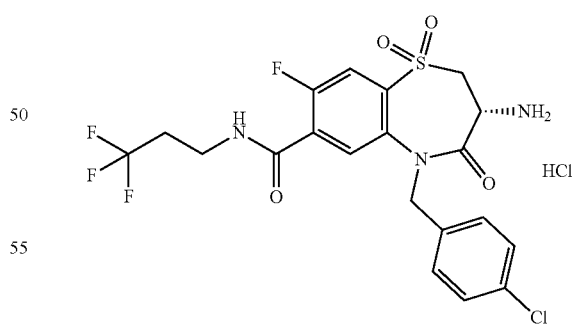

The title compound was synthesized according to general procedure GP5 to afford the title compound as Off white solid in 97% Yield.

LCMS: METCR1416 GENERIC 7 MINUTES, rt=3.11 min, M/Z (ES+) 508/510 [M+H+] 100% UV NMR Data: 1H NMR (500 MHz, DMSO-d6) δ 8.89 (t, J=5.5 Hz, 1H), 8.73 (s, 3H), 7.84 (d, J=8.5 Hz, 1H), 7.69 (d, J=5.5 Hz, 1H), 7.51-7.13 (m, 4H), 5.21 (d, J=15.7 Hz, 1H), 4.86 (d, J=15.7 Hz, 1H), 4.49 (dd, J=10.9, 7.5 Hz, 1H), 4.18 (dd, J=13.3, 7.5 Hz, 1H), 4.01 (dd, J=13.2, 11.1 Hz, 1H), 3.54-3.46 (m, 2H), 2.58-2.51 (m, 2H).

Synthesis of (3R)-3-amino-5-[(4-chlorophenyl)methyl]-8-fluoro-1,1,4-trioxo-N-[(2S)-1,1,1-trifluoropropan-2-yl]-2,3,4,5-tetrahydro-1λ⁶,5-benzothiazepine-7-carboxamide hydrochloride (Example 94)

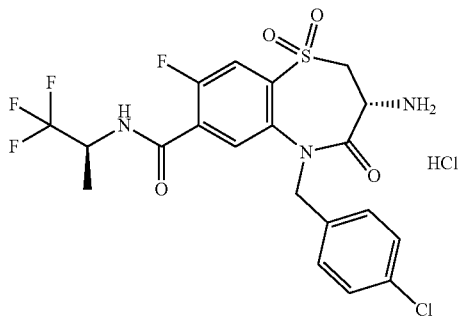 [SMILES: C[C@H](NC(=O)c1cc2c(cc1F)S(=O)(=O)C[C@H](N)C(=O)N2Cc1ccc(Cl)cc1)C(F)(F)F ; Cl]

The title compound was synthesized according to general procedure GP5 to afford the title compound as Off white solid in 45% Yield.

LCMS: METCR1416 GENERIC 7 MINUTES, rt=3.27 min, M/Z (ES+) 508/510 [M+H+] 98% UV

NMR Data: 1H NMR (500 MHz, DMSO-d6) δ 9.27 (d, J=8.8 Hz, 1H), 8.68 (s, 3H), 7.86 (d, J=8.2 Hz, 1H), 7.59 (d, J=5.4 Hz, 1H), 7.39 (q, J=8.6 Hz, 4H), 5.24 (d, J=15.6 Hz, 1H), 4.93-4.68 (m, 2H), 4.45 (dd, J=10.9, 7.5 Hz, 1H), 4.18 (dd, J=13.3, 7.5 Hz, 1H), 4.01 (dd, J=13.2, 11.2 Hz, 1H), 1.33 (d, J=7.0 Hz, 3H).

Synthesis of (3R)-3-amino-N-(butan-2-yl)-5-[(4-chlorophenyl)methyl]-8-fluoro-1,1,4-trioxo-2,3,4,5-tetrahydro-1λ⁶,5-benzothiazepine-7-carboxamide hydrochloride (Example 95)

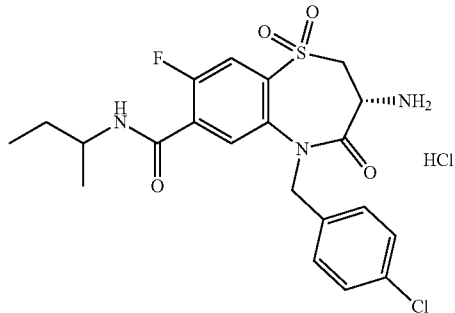 [SMILES: CCC(C)NC(=O)c1cc2c(cc1F)S(=O)(=O)C[C@H](N)C(=O)N2Cc1ccc(Cl)cc1 ; Cl]

The title compound was synthesized according to general procedure GP5 to afford the title compound as White Solid in 95% Yield.

LCMS: MET-uHPLC-AB-101, rt=2.27 min, M/Z (ES+) 468/470 [M+H+] 97% UV

NMR Data: 1H NMR (500 MHz, DMSO-d6) d 8.49 (s, 3H), 8.39 (d, J=8.2 Hz, 1H), 7.81 (d, J=8.2 Hz, 1H), 7.55 (d, J=5.4 Hz, 1H), 7.40-7.37 (m, 4H), 5.25 (d, J=15.6 Hz, 1H), 4.83 (d, J=15.7 Hz, 1H), 4.45 (dd, J=10.9, 7.6 Hz, 1H), 4.14 (dd, J=13.3, 7.4 Hz, 1H), 4.04-3.95 (m, 1H), 3.85 (dt, J=14.1, 7.6 Hz, 1H), 1.51-1.40 (m, 2H), 1.11 (d, J=6.6 Hz, 3H), 0.81 (t, J=7.4 Hz, 3H).

Synthesis of (3R)-3-amino-N-tert-butyl-5-[(4-chlorophenyl)methyl]-8-fluoro-1,1,4-trioxo-2,3,4,5-tetrahydro-1λ⁶,5-benzothiazepine-7-carboxamide hydrochloride (Example 96)

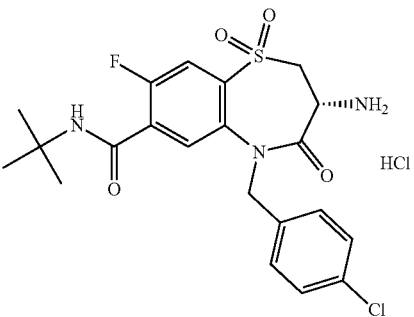 [SMILES: CC(C)(C)NC(=O)c1cc2c(cc1F)S(=O)(=O)C[C@H](N)C(=O)N2Cc1ccc(Cl)cc1 ; Cl]

The title compound was synthesized according to general procedure GP5 to afford the title compound as Off-White Solid in 97% Yield.

LCMS: MET-uHPLC-AB-101, rt=2.38 min, M/Z (ES+) 468/470 [M+H+] 94% UV

NMR Data: 1H NMR (500 MHz, DMSO-d6) d 8.53 (s, 3H), 8.15 (s, 1H), 7.78 (d, J=8.1 Hz, 1H), 7.54 (d, J=5.4 Hz, 1H), 7.39 (s, 4H), 5.22 (d, J=15.6 Hz, 1H), 4.85 (d, J=15.6 Hz, 1H), 4.42 (dd, J=10.8, 7.6 Hz, 1H), 4.13 (dd, J=13.3, 7.4 Hz, 1H), 4.02-3.95 (m, 1H), 1.34 (s, 9H).

Synthesis of (3R)-3-amino-N-(tert-butoxy)-5-[(4-chlorophenyl)methyl]-1,1,4-trioxo-2,3,4,5-tetrahydro-1λ⁶,5-benzothiazepine-7-carboxamide hydrochloride (Example 97)

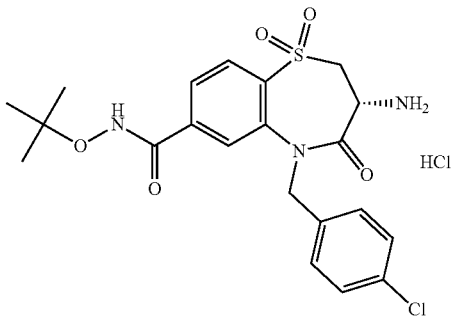 [SMILES: CC(C)(C)ONC(=O)c1ccc2c(c1)N(Cc1ccc(Cl)cc1)C(=O)[C@@H](N)CS2(=O)=O ; Cl]

The title compound was synthesized according to general procedure GP5 to afford the title compound as Off-White Solid in 99% Yield.

LCMS: MET-uHPLC-AB-101, rt=2.07 min, M/Z (ES+) 467/469 [M+H+] 97% UV

NMR Data: 1H NMR (500 MHz, DMSO-d6) d 11.32 (s, 1H), 8.51 (s, 3H), 8.04 (d, J=8.1 Hz, 1H), 7.96 (d, J=8.3 Hz, 1H), 7.79 (s, 1H), 7.40 (q, J=8.6 Hz, 4H), 5.28 (d, J=15.7 Hz, 1H), 4.88 (d, J=15.7 Hz, 1H), 4.54-4.41 (m, 1H), 4.12 (dd, J=13.3, 7.4 Hz, 1H), 4.02-3.92 (m, 1H), 1.21 (s, 9H).

Synthesis of (3R)-3-amino-5-[(4-chlorophenyl)methyl]-8-fluoro-1,1,4-trioxo-N-[(1S,2R)-2-phenyl-cyclopropyl]-2,3,4,5-tetrahydro-1λ⁶,5-benzothiazepine-7-carboxamide hydrochloride (Example 98)

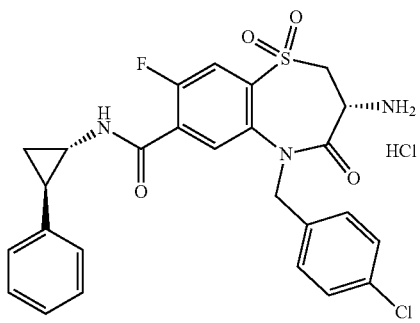 [SMILES: N[C@H]1CS(=O)(=O)c2cc(F)c(C(=O)N[C@H]3C[C@@H]3c3ccccc3)cc2N(Cc2ccc(Cl)cc2)C1=O ; Cl]

The title compound was synthesized according to general procedure GP5 to afford the title compound as Off-White Solid in 94% Yield.

LCMS: MET-uHPLC-AB-101, rt=2.66 min, M/Z (ES+) 528/530 [M+H+] 98% UV

NMR Data: 1H NMR (500 MHz, DMSO-d6) d 9.00 (s, 1H), 8.65 (s, 3H), 7.83 (d, J=8.3 Hz, 1H), 7.73 (d, J=3.9 Hz, 1H), 7.38 (s, 4H), 7.28 (t, J=7.5 Hz, 2H), 7.21-7.12 (m, 3H), 5.18 (d, J=15.7 Hz, 1H), 4.94 (dd, J=15.6, 4.7 Hz, 1H), 4.51-4.44 (m, 1H), 4.15 (dd, J=12.0, 7.6 Hz, 1H), 4.03-3.95 (m, 1H), 3.04 (dt, J=7.8, 3.9 Hz, 1H), 2.07 (td, J=6.3, 3.1 Hz, 1H), 1.28 (ddq, J=28.7, 12.0, 5.3 Hz, 2H).

Synthesis of (3R)-3-amino-5-[(4-chlorophenyl)methyl]-8-fluoro-N-(1-methylcyclopropyl)-1,1,4-trioxo-2,3,4,5-tetrahydro-1λ⁶,5-benzothiazepine-7-carboxamide hydrochloride (Example 99)

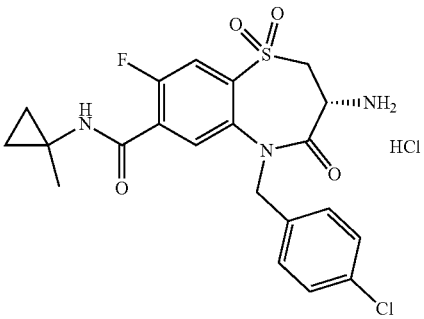 [SMILES: CC1(NC(=O)c2cc3c(cc2F)S(=O)(=O)C[C@H](N)C(=O)N3Cc2ccc(Cl)cc2)CC1 ; Cl]

The title compound was synthesized according to general procedure GP5 to afford the title compound as Off-White Solid in 99% Yield.

LCMS: MET-uHPLC-AB-101, rt=2.13 min, M/Z (ES+) 466/468 [M+H+] 98% UV

NMR Data: 1H NMR (500 MHz, DMSO-d6) d 8.85 (s, 1H), 8.57 (s, 3H), 7.78 (d, J=8.3 Hz, 1H), 7.62 (d, J=5.5 Hz, 1H), 7.38 (s, 4H), 5.17 (d, J=15.6 Hz, 1H), 4.90 (d, J=15.6 Hz, 1H), 4.42 (dd, J=10.9, 7.5 Hz, 1H), 4.14 (dd, J=13.3, 7.5 Hz, 1H), 3.97 (dd, J=13.2, 11.1 Hz, 1H), 1.35 (s, 3H), 0.74-0.67 (m, 2H), 0.67-0.61 (m, 2H).

Synthesis of (3R)-3-amino-5-[(4-chlorophenyl)methyl]-8-fluoro-N-(1-methylcyclobutyl)-1,1,4-trioxo-2,3,4,5-tetrahydro-1λ⁶,5-benzothiazepine-7-carboxamide hydrochloride (Example 100)

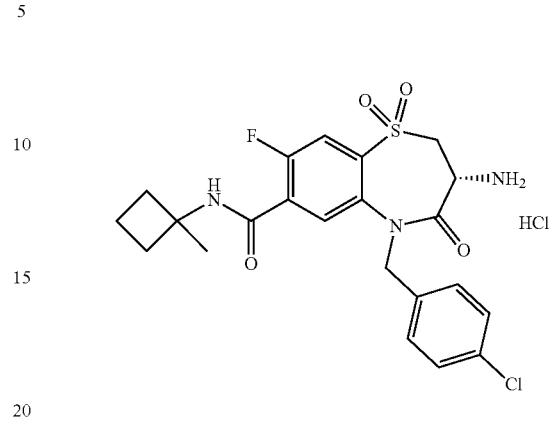

The title compound was synthesized according to general procedure GP5 to afford the title compound as Brown Solid in 97% Yield.

LCMS: MET-uHPLC-AB-101, rt=2.36 min, M/Z (ES+) 480/482 [M+H+] 100% UV

NMR Data: 1H NMR (500 MHz, DMSO-d6) d 8.63 (s, 1H), 8.59-7.82 (m, 2H), 7.78 (d, J=8.2 Hz, 1H), 7.61 (d, J=5.4 Hz, 1H), 7.38 (s, 4H), 5.20 (d, J=15.7 Hz, 1H), 4.89 (d, J=15.6 Hz, 1H), 4.42-4.35 (m, 1H), 4.10 (dd, J=13.4, 7.4 Hz, 1H), 3.99-3.91 (m, 1H), 2.35-2.24 (m, 2H), 2.02-1.94 (m, 2H), 1.87-1.76 (m, 2H), 1.45 (s, 3H).

Synthesis of (3R)-3-amino-5-[(4-chlorophenyl)methyl]-N-(2,2-dimethylcyclopropyl)-8-fluoro-1,1,4-trioxo-2,3,4,5-tetrahydro-1λ⁶,5-benzothiazepine-7-carboxamide hydrochloride (Example 101)

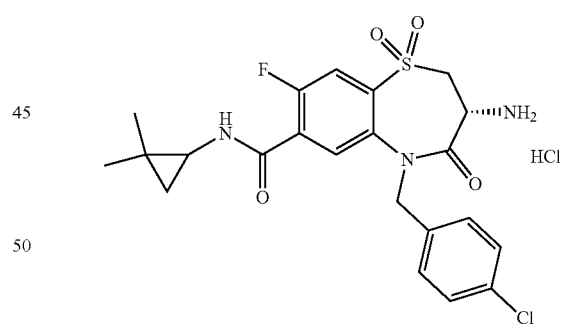

The title compound was synthesized according to general procedure GP5 to afford the title compound as Off-White Solid in 100% Yield.

LCMS: MET-uHPLC-AB-101, rt=2.35 min, M/Z (ES+) 480/482 [M+H+] 99% UV

NMR Data: 1H NMR (500 MHz, DMSO-d6) d 8.58 (d, J=3.9 Hz, 1H), 8.41 (s, 3H), 7.81 (d, J=8.2 Hz, 1H), 7.53 (d, J=5.4 Hz, 1H), 7.40-7.35 (m, 4H), 5.25 (d, J=15.6 Hz, 1H), 4.82 (d, J=15.6 Hz, 1H), 4.46 (dd, J=10.8, 7.6 Hz, 1H), 4.13 (dd, J=13.3, 7.4 Hz, 1H), 3.99 (dd, J=13.1, 11.2 Hz, 1H), 2.55 (dt, J=8.2, 4.2 Hz, 1H), 1.06 (s, 3H), 0.92 (s, 3H), 0.69 (dd, J=7.9, 5.2 Hz, 1H), 0.45 (t, J=4.8 Hz, 1H).

Synthesis of (3R)-3-amino-5-[(4-chlorophenyl)methyl]-N-(3,3-difluorocyclobutyl)-8-fluoro-1,1,4-trioxo-2,3,4,5-tetrahydro-1$\lambda^6$,5-benzothiazepine-7-carboxamide hydrochloride (Example 102)

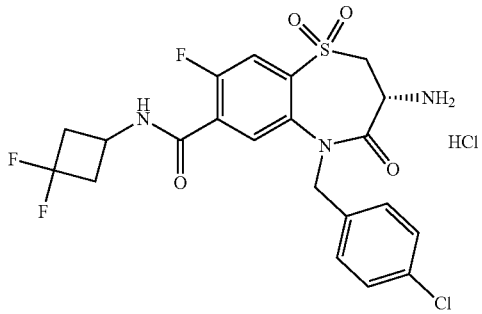 [SMILES: N[C@H]1CS(=O)(=O)c2cc(F)c(C(=O)NC3CC(F)(F)C3)cc2N(Cc2ccc(Cl)cc2)C1=O ; Cl]

The title compound was synthesized according to general procedure GP5 to afford the title compound as Off-white solid in 59% Yield.

LCMS: METCR1416 GENERIC 7 MINUTES, rt=3.11 min, M/Z (ES+) 502/504 [M+H+] 96% UV

NMR Data: 1H NMR (500 MHz, DMSO-d6) d 9.17 (d, J=6.5 Hz, 1H), 8.49 (s, 3H), 7.85 (d, J=8.4 Hz, 1H), 7.75 (d, J=5.5 Hz, 1H), 7.38 (s, 4H), 5.18 (d, J=15.6 Hz, 1H), 4.94 (d, J=15.7 Hz, 1H), 4.46 (dd, J=10.9, 7.6 Hz, 1H), 4.31-4.19 (m, 1H), 4.14 (dd, J=13.3, 7.5 Hz, 1H), 3.98 (dd, J=13.2, 11.1 Hz, 1H), 3.06-2.92 (m, 2H), 2.77-2.65 (m, 2H).

Synthesis of (3R)-3-amino-N-benzyl-5-[(4-chlorophenyl)methyl]-8-fluoro-1,1,4-trioxo-2,3,4,5-tetrahydro-1$\lambda^6$,5-benzothiazepine-7-carboxamide hydrochloride (Example 103)

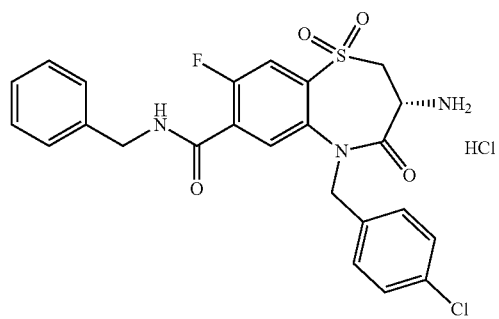 [SMILES: N[C@H]1CS(=O)(=O)c2cc(F)c(C(=O)NCc3ccccc3)cc2N(Cc2ccc(Cl)cc2)C1=O ; Cl]

The title compound was synthesized according to general procedure GP5 to afford the title compound as white solid in 97% Yield.

LCMS: METCR1416 GENERIC 7 MINUTES, rt=3.28 min, M/Z (ES+) 502/504 [M+H+] 95% UV

NMR Data: 1H NMR (500 MHz, DMSO-d6) 9.20 (t, J=6.0 Hz, 1H), 7.91 (s, 3H), 7.83 (d, J=8.5 Hz, 1H), 7.71 (d, J=5.5 Hz, 1H), 7.43-7.32 (m, 6H), 7.32-7.22 (m, 3H), 5.21 (d, J=15.7 Hz, 1H), 4.88 (d, J=15.7 Hz, 1H), 4.48 (qd, J=15.2, 6.0 Hz, 2H), 4.42-4.36 (m, 1H), 4.11 (dd, J=13.3, 7.4 Hz, 1H), 4.00-3.85 (m, 1H).

Synthesis of (3R)-3-amino-5-[(4-chlorophenyl)methyl]-8-fluoro-N-heptyl-1,1,4-trioxo-2,3,4,5-tetrahydro-1$\lambda^6$,5-benzothiazepine-7-carboxamide hydrochloride (Example 104)

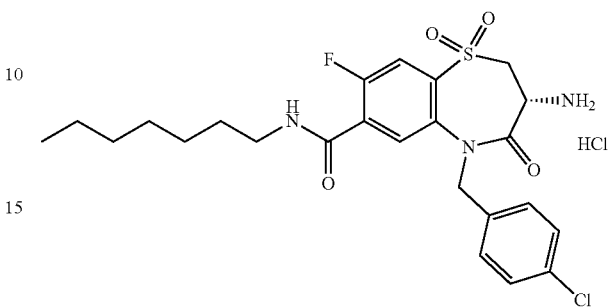

The title compound was synthesized according to general procedure GP5 to afford the title compound as light brown solid in 67% Yield.

LCMS: METCR1416 GENERIC 7 MINUTES, rt=3.62 min, M/Z (ES+) 510/512 [M+H+] 95% UV

NMR Data: 1H NMR (500 MHz, DMSO-d6) 8.62 (t, J=5.6 Hz, 4H), 7.82 (d, J=8.4 Hz, 1H), 7.65 (d, J=5.5 Hz, 1H), 7.39 (t, J=2.6 Hz, 4H), 5.21 (d, J=15.8 Hz, 1H), 4.87 (d, J=15.7 Hz, 1H), 4.48 (dd, J=10.9, 7.6 Hz, 1H), 4.16 (dd, J=13.3, 7.5 Hz, 1H), 3.99 (dd, J=13.2, 11.1 Hz, 1H), 3.24 (dq, J=18.8, 7.1, 6.6 Hz, 2H), 1.53-1.44 (m, 2H), 1.27 (t, J=11.3 Hz, 8H), 0.87 (t, J=7.0 Hz, 3H).

Synthesis of (3R)-3-amino-5-[(4-chlorophenyl)methyl]-N-(3,3-difluorocyclopentyl)-8-fluoro-1,1,4-trioxo-2,3,4,5-tetrahydro-1$\lambda^6$,5-benzothiazepine-7-carboxamide hydrochloride (Example 105)

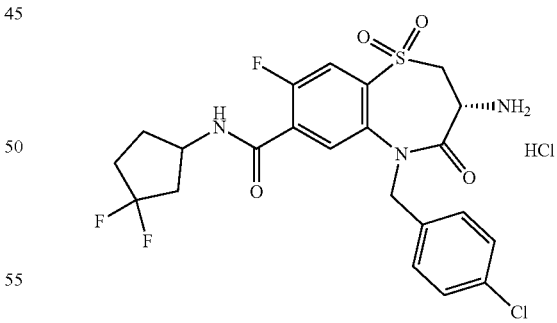

The title compound was synthesized according to general procedure GP5 to afford the title compound as off white solid in 81% Yield.

LCMS: METCR1416 GENERIC 7 MINUTES, rt=3.18 min, M/Z (ES+) 516/518 [M+H+] 99% UV

NMR Data: 1H NMR (500 MHz, DMSO-d6) 8.89 (d, J=7.0 Hz, 1H), 8.33 (s, 3H), 7.83 (d, J=8.3 Hz, 1H), 7.68 (d, J=5.4 Hz, 1H), 7.42-7.32 (m, 4H), 5.19 (d, J=15.7 Hz, 1H), 4.91 (d, J=15.6 Hz, 1H), 4.48-4.32 (m, 2H), 4.12 (dd, J=13.0, 7.2 Hz, 1H), 4.01-3.93 (m, 1H), 2.31-2.20 (m, 1H), 2.20-2.03 (m, 4H), 1.84-1.71 (m, 1H).

Synthesis of (3R)-3-amino-5-[(4-chlorophenyl) methyl]-N-[(1R)-2,2-difluorocyclopropyl]-8-fluoro-1,1,4-trioxo-2,3,4,5-tetrahydro-1λ⁶,5-benzothiaz-epine-7-carboxamide hydrochloride (Example 106)

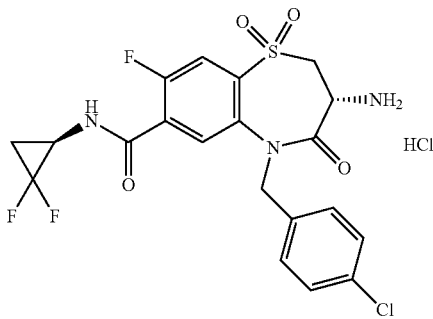 [SMILES: N[C@H]1CS(=O)(=O)c2cc(F)c(C(=O)N[C@@H]3CC3(F)F)cc2N(Cc2ccc(Cl)cc2)C1=O ; Cl]

The title compound was synthesized according to general procedure GP5 from intermediate IX-46 (stereochemistry arbitrarily assigned) to afford the title compound as off-white solid in 71% Yield.

LCMS: METCR1416 GENERIC 7 MINUTES, rt=3.05 min, M/Z (ES+) 488/490 [M+H+] 100% UV NMR Data: 1H NMR (500 MHz, DMSO-d6) d 9.15 (s, 1H), 8.44 (s, 3H), 7.85 (d, J=8.4 Hz, 1H), 7.71 (d, J=5.4 Hz, 1H), 7.38 (s, 4H), 5.20 (d, J=15.6 Hz, 1H), 4.92 (d, J=15.6 Hz, 1H), 4.53-4.40 (m, 1H), 4.07-4.20 (m, 1H), 3.99 (t, J=12.0 Hz, 1H), 3.50 (dd, J=9.8, 6.2 Hz, 1H), 2.07-1.94 (m, 1H), 1.64 (d, J=5.3 Hz, 1H).

Alternatively example 106 was synthesised from intermediate VII-01 using (1R)-2,2-difluorocyclopropan-1-amine hydrochloride following GP7 and GP5.

Synthesis of (3R)-3-amino-5-[(4-chlorophenyl) methyl]-N-[(1S)-2,2-difluorocyclopropyl]-8-fluoro-1,1,4-trioxo-2,3,4,5-tetrahydro-1λ⁶,5-benzothiaz-epine-7-carboxamide hydrochloride (Example 107)

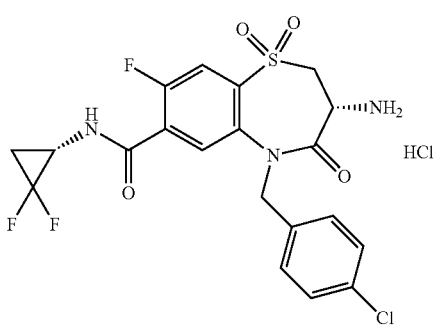 [SMILES: N[C@H]1CS(=O)(=O)c2cc(F)c(C(=O)N[C@H]3CC3(F)F)cc2N(Cc2ccc(Cl)cc2)C1=O ; Cl]

The title compound was synthesized according to general procedure GP5 from intermediate IX-47 (stereochemistry arbitrarily assigned) to afford the title compound as off-white solid in 86% Yield.

LCMS: METCR1416 GENERIC 7 MINUTES, rt=3.05 min, M/Z (ES+) 488/490 [M+H+] 100% UV NMR Data: 1H NMR (500 MHz, DMSO-d6) d 9.15 (s, 1H), 8.44 (s, 3H), 7.85 (d, J=8.4 Hz, 1H), 7.71 (d, J=5.4 Hz, 1H), 7.38 (s, 4H), 5.20 (d, J=15.6 Hz, 1H), 4.92 (d, J=15.6 Hz, 1H), 4.53-4.40 (m, 1H), 4.07-4.20 (m, 1H), 3.99 (t, J=12.0 Hz, 1H), 3.50 (dd, J=9.8, 6.2 Hz, 1H), 2.07-1.94 (m, 1H), 1.64 (d, J=5.3 Hz, 1H).

Synthesis of (2R,3R)-3-amino-5-[(4-chlorophenyl) methyl]-N-(2,2-difluorocyclopropyl)-2-methyl-1,1,4-trioxo-2,3,4,5-tetrahydro-1λ⁶,5-benzothiazepine-7-carboxamide hydrochloride (Example 108)

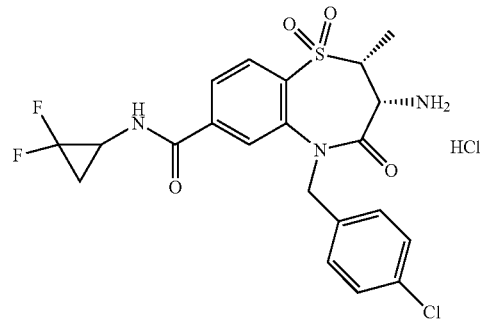 [SMILES: C[C@@H]1[C@H](N)C(=O)N(Cc2ccc(Cl)cc2)c2cc(C(=O)NC3CC3(F)F)ccc2S1(=O)=O ; Cl]

The title compound was synthesized according to general procedure GP5 to afford the title compound as Off white solid in 91% Yield.

LCMS: METCR1416 GENERIC 7 MINUTES, rt=3.09 min, M/Z (ES+) 484/486 [M+H+] 96% UV

NMR Data: 1H NMR (500 MHz, DMSO-d6) 9.32 (d, J=16.5 Hz, 1H), 8.58 (s, 3H), 8.12 (dd, J=8.2, 1.5 Hz, 1H), 8.07 (ddd, J=8.2, 4.1, 1.4 Hz, 1H), 8.04-7.94 (m, 1H), 7.39 (d, J=4.6 Hz, 4H), 5.28-5.18 (m, 1H), 5.09-4.94 (m, 1H), 4.64 (dd, J=9.9, 6.9 Hz, 1H), 4.16-4.06 (m, 1H), 3.49 (dd, J=15.2, 4.8 Hz, 1H), 2.09-1.96 (m, 1H), 1.80-1.69 (m, 1H), 1.47-1.37 (m, 3H).

Synthesis of (3R)-3-amino-5-[(4-chlorophenyl) methyl]-8-fluoro-N-hexadecyl-1,1,4-trioxo-2,3,4,5-tetrahydro-1λ$^6$,5-benzothiazepine-7-carboxamide hydrochloride (Example 109)

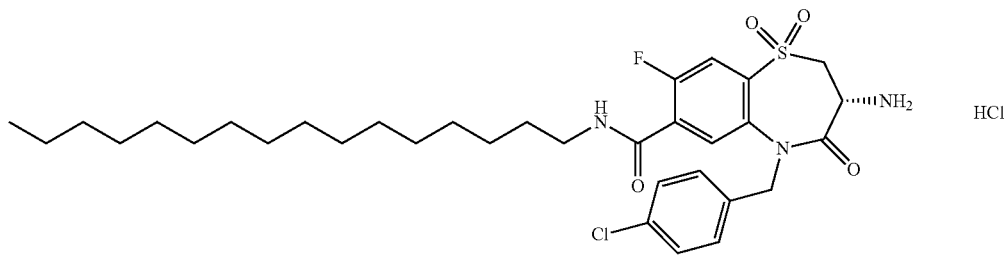 [SMILES: CCCCCCCCCCCCCCCCNC(=O)c1cc2c(cc1F)S(=O)(=O)C[C@H](N)C(=O)N2Cc1ccc(Cl)cc1 ; Cl]

The title compound was synthesized according to general procedure GP5 to afford the title compound as white solid in 100% Yield.

LCMS: METCR1416 GENERIC 7 MINUTES, rt=5.52 min, M/Z (ES+) 636/638 [M+H+] 94% UV

NMR Data: 1H NMR (500 MHz, DMSO-d6) 8.60 (t, J=5.6 Hz, 1H), 8.23 (s, 3H), 7.81 (d, J=8.4 Hz, 1H), 7.65 (d, J=5.5 Hz, 1H), 7.39 (s, 4H), 5.21 (d, J=15.7 Hz, 1H), 4.87 (d, J=15.7 Hz, 1H), 4.49-4.35 (m, 1H), 4.11 (dd, J=13.3, 7.5 Hz, 1H), 3.95 (d, J=13.0 Hz, 1H), 3.23 (dt, J=16.4, 7.0 Hz, 2H), 1.54-1.41 (m, 2H), 1.25 (s, 26H), 0.92-0.79 (m, 3H).

Synthesis of (3R)-3-amino-5-[(4-chlorophenyl) methyl]-N-(cyclopropylmethyl)-8-fluoro-1,1,4-trioxo-2,3,4,5-tetrahydro-1λ$^6$,5-benzothiazepine-7-carboxamide hydrochloride (Example 110)

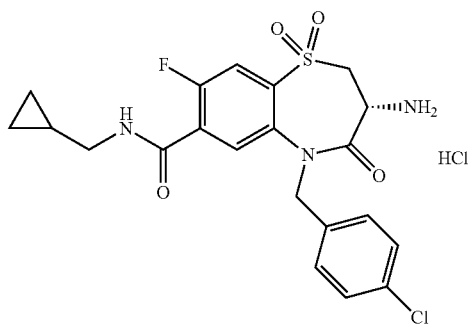 [SMILES: N[C@H]1CS(=O)(=O)c2cc(F)c(C(=O)NCC3CC3)cc2N(Cc2ccc(Cl)cc2)C1=O ; Cl]

The title compound was synthesized according to general procedure GP5 to afford the title compound as white solid in 46% Yield.

LCMS: METCR1416 GENERIC 7 MINUTES, rt=3.23 min, M/Z (ES+) 466/468 [M+H+] 99% UV

NMR Data: 1H NMR (500 MHz, DMSO-d6) δ 8.75-8.43 (m, 3H), 7.81 (d, J=8.4 Hz, 1H), 7.65 (d, J=5.5 Hz, 1H), 7.41-7.34 (m, 4H), 5.20 (d, J=15.7 Hz, 1H), 4.86 (d, J=15.7 Hz, 1H), 4.49-4.43 (m, 1H), 4.18-4.11 (m, 1H), 4.02-3.95 (m, 1H), 3.21-3.08 (m, 2H), 1.02-0.95 (m, 1H), 0.45-0.40 (m, 2H), 0.21-0.17 (m, 2H).

(2R,3R)-3-amino-5-[(4-chlorophenyl)methyl]-2-methyl-1,1,4-trioxo-N-(4,4,4-trifluorobutyl)-2,3,4,5-tetrahydro-1λ$^6$,5-benzothiazepine-7-carboxamide hydrochloride (Example 111)

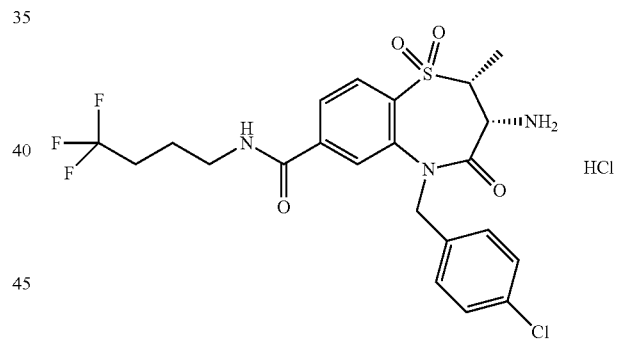

The title compound was synthesized according to general procedure GP5 to afford the title compound as white solid in 79% Yield.

LCMS: METCR1416 GENERIC 7 MINUTES, rt=3.27 min, M/Z (ES+) 518/520 [M+H+] 100% UV NMR Data: 1H NMR (500 MHz, DMSO-d6) δ 9.00 (t, J=5.6 Hz, 1H), 8.47 (s, 3H), 8.10 (d, J=8.2 Hz, 1H), 8.05 (dd, J=8.2, 1.4 Hz, 1H), 7.95 (d, J=1.2 Hz, 1H), 7.42-7.34 (m, 4H), 5.21 (d, J=15.8 Hz, 1H), 5.00 (d, J=15.7 Hz, 1H), 4.60 (d, J=6.7 Hz, 1H), 4.11 (p, J=6.9 Hz, 1H), 3.37 2H m, under water peak), 2.36-2.24 (m, 2H), 1.75 (dt, J=14.7, 7.1 Hz, 2H), 1.42 (d, J=7.0 Hz, 3H).

According to the above described and exemplified general procedure GP5 the following additional examples were synthesized from intermediate VIII:

Synthesis of (3R)-3-amino-N-butyl-8-fluoro-4-oxo-5-(quinolin-2-ylmethyl)-2,3,4,5-tetrahydro-1,5-benzothiazepine-7-carboxamide dihydrochloride (Example 112)

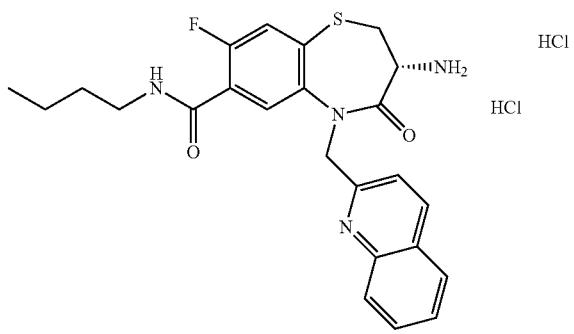 [SMILES: CCCCNC(=O)c1cc2c(cc1F)SC[C@H](N)C(=O)N2Cc1ccc2ccccc2n1 ; Cl ; Cl]

The title compound was synthesized according to general procedure GP5 to afford the title compound as beige solid in 76% Yield.

LCMS: METCR1416 GENERIC 7 MINUTES, rt=3.2 min, M/Z (ES+) 453 [M+H+] 100% UV

NMR Data: 1H NMR (500 MHz, DMSO-d6) δ 0.84 (t, J=7.32 Hz, 3H), 1.28 (dt, J=7.29, 14.80 Hz, 2H), 1.44 (p, J=7.03 Hz, 2H), 3.21 (dp, J=6.46, 13.47 Hz, 2H), 3.29 (t, J=11.56 Hz, 1H), 3.73 (dd, J=6.91, 11.38 Hz, 1H), 4.05-4.18 (m, 1H), 5.30 (d, J=12.79 Hz, 1H), 5.41 (d, J=16.21 Hz, 1H), 7.62 (t, J=7.45 Hz, 1H), 7.65-7.74 (m, 2H), 7.78 (t, J=7.59 Hz, 1H), 7.98 (dd, J=8.25, 14.13 Hz, 2H), 8.02-8.08 (m, 1H), 8.37-8.47 (m, 2H), 8.54 (s, 3H)

Synthesis of (3R)-3-amino-5-[(5-cyclopropyl-1,3,4-thiadiazol-2-yl)methyl]-8-fluoro-N-[(4-fluorophenyl)methyl]-4-oxo-2,3,4,5-tetrahydro-1,5-benzothiazepine-7-carboxamide hydrochloride (Example 113)

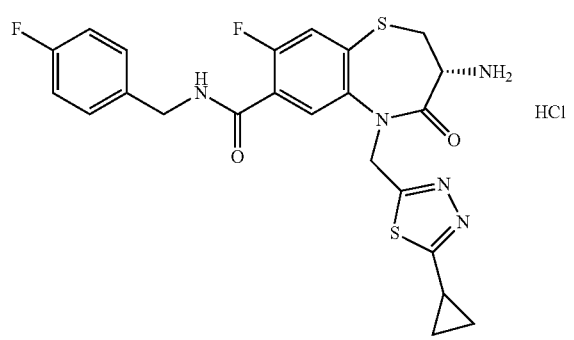 [SMILES: N[C@H]1CSc2cc(F)c(C(=O)NCc3ccc(F)cc3)cc2N(Cc2nnc(C3CC3)s2)C1=O ; Cl]

The title compound was synthesized according to general procedure GP5 to afford the title compound as Pale yellow solid in 86% Yield.

LCMS: METCR1416 GENERIC 7 MINUTES, rt=2.92 min, M/Z (ES+) 502 [M+H+] 99% UV

NMR Data: 1H NMR (500 MHz, DMSO-d6) δ 9.13 (t, J=5.8 Hz, 1H), 8.58 (s, 3H), 8.05 (d, J=6.5 Hz, 1H), 7.69 (d, J=9.4 Hz, 1H), 7.39 (dd, J=8.6, 5.6 Hz, 2H), 7.22-7.15 (m, 2H), 5.49 (d, J=15.7 Hz, 1H), 5.31 (d, J=15.7 Hz, 1H), 4.55-4.40 (m, 2H), 4.02 (dd, J=11.5, 7.0 Hz, 1H), 3.68 (dd, J=11.5, 6.9 Hz, 1H), 3.21 (t, J=11.6 Hz, 1H), 2.49-2.44 (m, 1H), 1.24-1.15 (m, 2H), 1.03-0.91 (m, 2H).

Synthesis of (3R)-3-amino-N-butyl-5-[(4-chlorophenyl)methyl]-8-(dimethylamino)-1,1,4-trioxo-2,3,4,5-tetrahydro-1$\lambda^6$,5-benzothiazepine-7-carboxamide hydrochloride (Example 114)

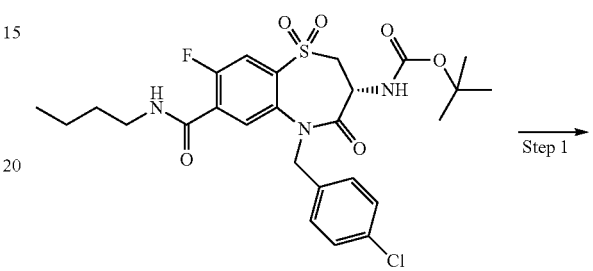

Intermediate IX-04

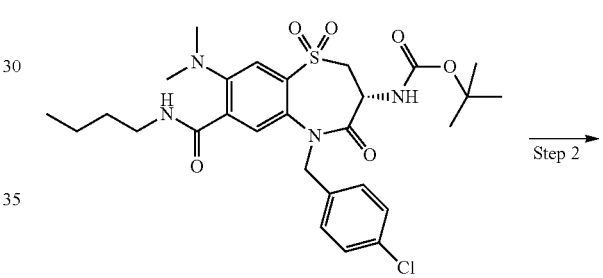

Intermediate IX-48

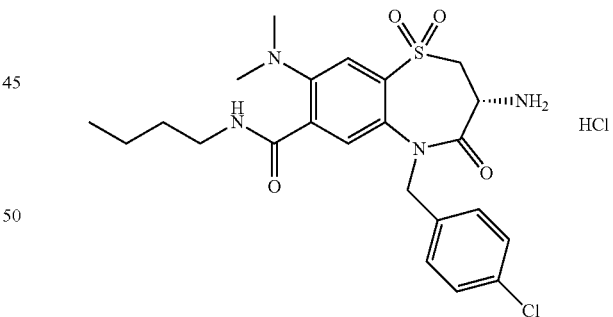

Example 114

Step 1: Synthesis of tert-butyl N-[(3R)-7-(butylcarbamoyl)-5-[(4-chlorophenyl)methyl]-8-(dimethylamino)-1,1,4-trioxo-2,3,4,5-tetrahydro-1$\lambda^6$,5-benzothiazepin-3-yl] carbamate (Intermediate IX-48)

2M N-methylmethanamine in THF (170.76 μL, 0.342 mmol) was added to a stirred solution of Intermediate IX-04 (97%, 40.0 mg, 0.068 mmol) in ethanol (2 mL) in a sealed tube. The reaction was heated to 80° C. for 16 h. The reaction mixture was concentrated under reduced pressure, dissolved in DCM (5 mL), washed with water (5 mL), dried over Na₂SO₄ filtered and concentrated under reduced pressure. The residue was purified by reverse-phase column chromatography (Biotage, acetonitrile: water) to afford the title compound as white solid in 53% Yield.

LCMS: METCR1673 Generic 2 minutes: rt=1.48 min M/Z (ES+) 593.15 [M+H+] 98% UV

NMR data: 1H NMR (500 MHz, DMSO-d6) δ 8.52 (t, J=5.7 Hz, 1H), 7.43 (d, J=8.3 Hz, 1H), 7.34 (s, 4H), 7.27 (s, 1H), 7.15 (s, 1H), 5.24 (d, J=16.0 Hz, 1H), 4.48 (d, J=15.9 Hz, 1H), 4.37 (dt, J=11.6, 7.6 Hz, 1H), 4.02 (dd, J=13.3, 7.3 Hz, 1H), 3.74-3.65 (m, 1H), 3.17 (q, J=6.7 Hz, 2H), 2.84 (s, 6H), 1.42 (dt, J=14.5, 6.9 Hz, 2H), 1.36 (s, 9H), 1.25-1.22 (m, 2H), 0.86 (t, J=7.4 Hz, 3H).

Step 2: Synthesis of (3R)-3-amino-N-butyl-5-[(4-chlorophenyl)methyl]-8-(dimethylamino)-1,1,4-trioxo-2,3,4,5-tetrahydro-1 $\lambda^6$,5-benzothiazepine-7-carboxamide hydrochloride (Example 114)

The title compound was synthesized according to general procedure GP5 to afford the title compound as yellow solid in 89% Yield.

LCMS: METCR-uPLC-AB101 rt=2.32 min M/Z (ES+) 493 [M+H+] 99% UV

NMR data: 1H NMR (500 MHz, DMSO-d6) d 8.64 (s, 3H), 8.46 (t, J=5.7 Hz, 1H), 7.40 (s, 4H), 7.26 (s, 1H), 7.18 (s, 1H), 5.24 (d, J=15.7 Hz, 1H), 4.55 (d, J=15.7 Hz, 1H), 4.36 (s, 1H), 4.12 (dd, J=13.3, 7.4 Hz, 1H), 3.91 (dd, J=13.2, 11.1 Hz, 1H), 3.18 (qt, J=13.1, 6.7 Hz, 2H), 2.87 (s, 6H), 1.48-1.37 (m, 2H), 1.25 (m, 2H), 0.87 (t, J=7.3 Hz, 3H).

Synthesis of tert-butyl N-(5-{[(3R)-5-[(4-chlorophenyl)methyl]-8-fluoro-7-{[(4-methoxyphenyl)methyl]carbamoyl}-4-oxo-2,3,4,5-tetrahydro-1,5-benzothiazepin-3-yl]amino}pentyl)carbamate (Example 115)

Example 43 (200 mg, 0.37 mmol) was dissolved in anhydrous MeCN (10 mL) and K₂CO₃ (129 mg, 2.5 eq) was added followed by potassium iodide (62 mg, 1 eq). Tert-butyl N-{5-[(4-methylbenzenesulfonyl)oxy]pentyl}carbamate (159.93 mg, 0.45 mmol) (Reference: Otsuki, S. et al. Bioorg. Med. Chem. Lett., 23(6), 1608-1611) was added as solution in MeCN (3 mL) and the reaction mixture was stirred at 80° C. for 12 h. Additional K₂CO₃ (115 mg, 2.2 eq), potassium iodide (65 mg, 1 eq) and tert-butyl N-{5-[(4-methylbenzenesulfonyl)oxy]pentyl}carbamate (160 mg, 0.45 mmol) were added to the reaction mixture and heating was continued for 3 h. Additional tert-butyl N-{5-[(4-methylbenzenesulfonyl)-oxy]pentyl}carbamate (160 mg, 0.45 mmol) was added and the reaction mixture was stirred at 80° C. for 16 h. The reaction mixture was cooled to RT and concentrated under reduced pressure. The residue was dissolved in DCM (15 mL) and washed with water (2×10 mL) and brine (10 mL). The organic layer was dried over Na₂SO₄ and concentrated under reduced pressure. The residues was purified by flash column chromatography (silica, eluent: heptanes, 0-100% ethyl acetate) to afford 155 mg of the title compound as white solid in 61% yield.

LCMS: METCR-uPLC-AB101 rt=2.92 min M/Z (ES+) 685/687 [M+H+] 99% UV

NMR data: 1H NMR (500 MHz, DMSO-d6) δ 8.88 (t, J=6.1 Hz, 1H), 7.72 (d, J=6.5 Hz, 1H), 7.52 (d, J=9.5 Hz, 1H), 7.38-7.18 (m, 6H), 6.90 (d, J=8.6 Hz, 2H), 6.72 (s, 1H), 5.25 (d, J=15.4 Hz, 1H), 4.89 (d, J=15.5 Hz, 1H), 4.47-4.29 (m, 2H), 3.74 (s, 3H), 3.48 (dd, J=11.2, 6.6 Hz, 1H), 3.28-3.22 (m, 1H), 2.94-2.82 (m, 3H), 2.41 (d, J=9.8 Hz, 1H), 2.21 (s, 1H), 2.11 (s, 1H), 1.36 (s, 9H), 1.34-1.25 (m, 4H), 1.24-1.14 (m, 2H).

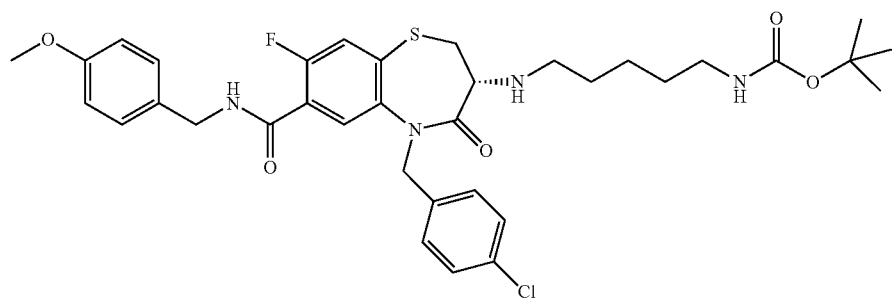 [SMILES: COc1ccc(CNC(=O)c2cc3c(cc2F)SC[C@H](NCCCCCNC(=O)OC(C)(C)C)C(=O)N3Cc2ccc(Cl)cc2)cc1]

Synthesis of (3R)-3-amino-N-benzyl-5-[(4-chlorophenyl)methyl]-8-(dimethylamino)-1,1,4-trioxo-2,3,4,5-tetrahydro-1λ⁶,5-benzothiazepine-7-carboxamide hydrochloride (Example 116)

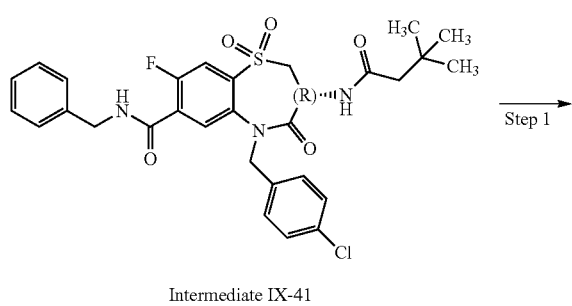

Intermediate IX-41

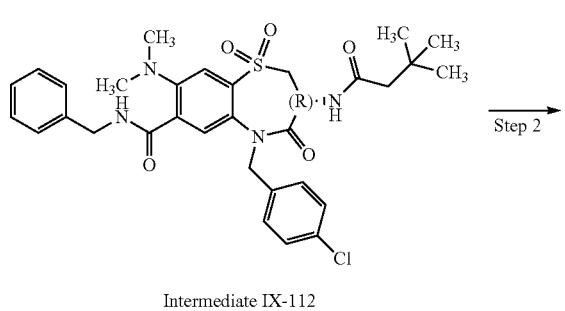

Intermediate IX-112

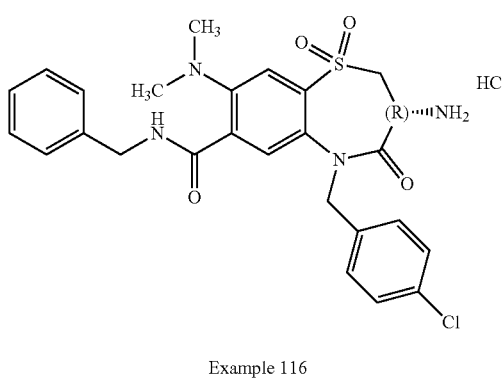

Example 116

Step 1: Synthesis of tert-butyl N-[(3R)-7-(benzylcarbamoyl)-5-[(4-chlorophenyl)methyl]-8-(dimethylamino)-1,1,4-trioxo-2,3,4,5-tetrahydro-1λ⁶,5-benzothiazepin-3-yl]carbamate (Intermediate IX-112)

2M N-methylmethanamine in THF (0.15 mL, 0.3 mmol) was added to a stirred solution of Intermediate IX-41 (100%, 36.0 mg, 0.06 mmol) in ethanol (2 mL) in a sealed tube. The reaction was heated to 80° C. for 16 h. The reaction mixture was concentrated under reduced pressure, dissolved in DCM (5 mL), washed with water and brine (5 mL), and dried over Na₂SO₄ filtered and concentrated under reduced pressure to afford the title compound as white solid in 100% Yield.

LCMS: METCR1673 Generic 2 minutes: rt=1.30 min M/Z (ES+) 627/629 [M+H+] 100% UV

NMR data: ¹H NMR (500 MHz, DMSO-d₆) δ 9.10 (t, J=5.9 Hz, 1H), 7.44 (d, J=8.3 Hz, 1H), 7.37-7.23 (m, 11H), 5.24 (d, J=16.0 Hz, 1H), 4.53 (d, J=16.0 Hz, 1H), 4.39 (dd, J=14.0, 6.6 Hz, 3H), 4.03 (dd, J=13.3, 7.1 Hz, 1H), 3.74-3.66 (m, 1H), 2.81 (s, 6H), 1.37 (s, 9H).

Step 2: Synthesis of (3R)-3-amino-N-benzyl-5-[(4-chlorophenyl)methyl]-8-(dimethylamino)-1,1,4-trioxo-2,3,4,5-tetrahydro-1λ⁶,5-benzothiazepine-7-carboxamide hydrochloride (Example 116)

The title compound was synthesized according to general procedure GP5 to afford the title compound as off white solid in 98% yield.

LCMS: METCR1416 Generic 7 minutes, rt=3.31 min, M/Z (ES+) 526.95/529.05 [M+H+] 99% UV NMR Data: 1H NMR (500 MHz, DMSO-d6) d 9.03 (t, J=6.0 Hz, 1H), 8.35 (s, 3H), 7.43-7.36 (m, 4H), 7.34-7.29 (m, 2H), 7.28-7.22 (m, 5H), 5.21 (d, J=15.7 Hz, 1H), 4.58 (d, J=15.7 Hz, 1H), 4.47-4.28 (m, 3H), 4.08 (dd, J=13.4, 7.4 Hz, 1H), 3.92-3.83 (m, 1H), 2.82 (s, 6H).

Synthesis of (3R)-3-amino-N-(2,2-difluorocyclopropyl)-8-fluoro-5-{[4-methoxy-3-(trifluoromethyl)phenyl]methyl}-1,1,4-trioxo-2,3,4,5-tetrahydro-1λ⁶,5-benzothiazepine-7-carboxamide hydrochloride (Example 117)

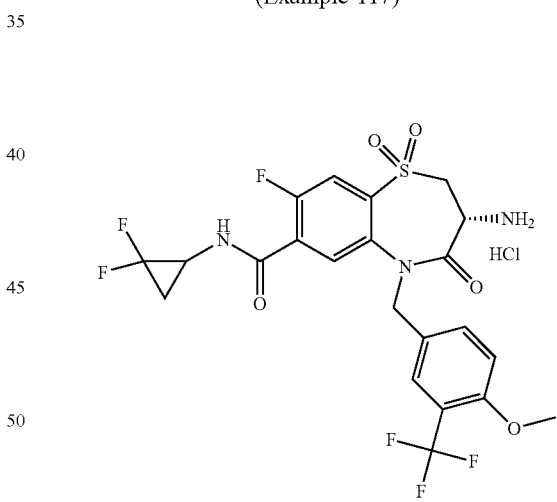

The title compound was synthesized according to general procedure GP5 to afford the title compound as off white solid in 99% yield.

LCMS: METCR1416 Generic 7 minutes, rt=3.28 min, M/Z (ES+) 551.95 [M+H+] 99% UV

NMR Data: 1H NMR (500 MHz, DMSO-d6) d 9.17 (d, J=14.6 Hz, 1H), 8.43 (s, 3H), 7.96-7.76 (m, 2H), 7.64 (s, 1H), 7.55 (d, J=8.6 Hz, 1H), 7.15 (d, J=8.7 Hz, 1H), 5.18-5.06 (m, 2H), 4.47-4.39 (m, 1H), 4.11 (dd, J=13.2, 7.4 Hz, 1H), 4.02-3.94 (m, 1H), 3.85 (d, J=1.2 Hz, 3H), 3.51 (s, 1H), 2.08-1.96 (m, 1H), 1.70-1.60 (m, 1H).

Synthesis of (2R,3R)-3-amino-5-[(4-chlorophenyl)methyl]-8-fluoro-2-methyl-1,1,4-trioxo-N-(4,4,4-trifluorobutyl)-2,3,4,5-tetrahydro-1λ⁶,5-benzothiazepine-7-carboxamide hydrochloride (Example 118)

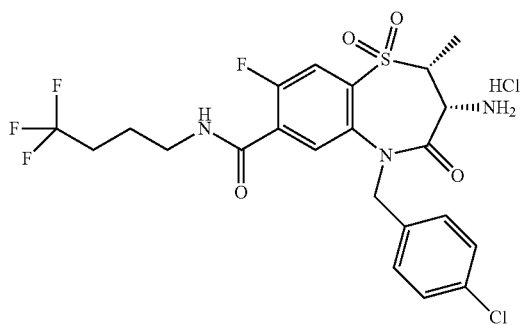 [SMILES: C[C@@H]1[C@H](N)C(=O)N(Cc2ccc(Cl)cc2)c2cc(C(=O)NCCCC(F)(F)F)c(F)cc2S1(=O)=O ; Cl]

The title compound was synthesized according to general procedure GP5 to afford the title compound as colourless solid in 95% yield.

LCMS: METCR1416 Generic 7 minutes, rt=2.51 min, M/Z (ES+) 536/538 [M+H+] 96% UV

NMR Data: 1H NMR (500 MHz, DMSO-d6) d 8.72 (s, 4H), 7.88 (d, J=8.5 Hz, 1H), 7.70 (d, J=5.5 Hz, 1H), 7.43-7.33 (m, 4H), 5.19 (d, J=15.7 Hz, 1H), 4.92 (d, J=15.7 Hz, 1H), 4.63 (d, J=6.8 Hz, 1H), 4.21 (m, 1H), 3.36 (d, J=7.4 Hz, 2H), 2.35-2.23 (m, 2H), 1.73 (dt, J=14.7, 7.0 Hz, 2H), 1.43 (d, J=7.0 Hz, 3H).

Synthesis of (3R)-3-amino-5-{[4-(5-methyl-1,2,4-oxadiazol-3-yl)phenyl]methyl}-1,1,4-trioxo-N-(4,4,4-trifluorobutyl)-2,3,4,5-tetrahydro-1λ⁶,5-benzothiazepine-7-carboxamide hydrochloride (Example 119)

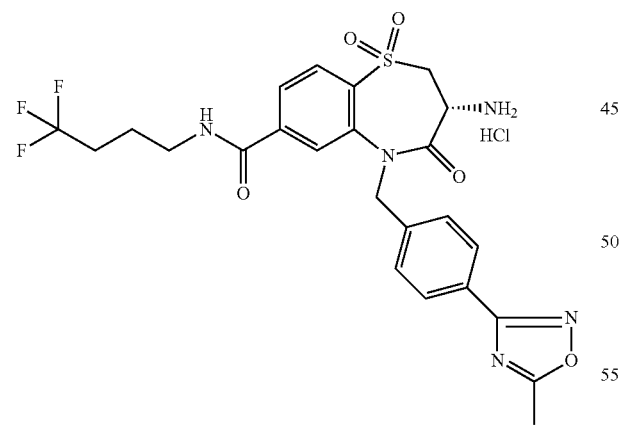

The title compound was synthesized according to general procedure GP5 to afford the title compound as colourless solid in 91% yield.

LCMS: METCR1416 Generic 7 minutes, rt=2.13 min, M/Z (ES+) 552 [M+H] 100% UV

NMR Data: 1H NMR (500 MHz, DMSO-d6) d 9.02 (d, J=5.3 Hz, 1H), 8.62 (s, 3H), 8.06 (s, 2H), 7.97 (s, 1H), 7.94 (d, J=8.3 Hz, 2H), 7.58 (d, J=8.2 Hz, 2H), 5.35 (d, J=16.0 Hz, 1H), 5.01 (d, J=16.0 Hz, 1H), 4.51 (dd, J=11.0, 7.6 Hz, 1H), 4.15 (dd, J=13.2, 7.4 Hz, 1H), 4.04-3.95 (m, 1H), 3.35 (d, J=6.9 Hz, 2H), 2.66 (s, 3H), 2.29 (m, 2H), 1.74 (dt, J=14.7, 7.1 Hz, 2H).

Synthesis of (3R)-3-amino-5-[(4-chlorophenyl)methyl]-8-fluoro-N-(2-methoxyethyl)-1,1,4-trioxo-2,3,4,5-tetrahydro-1λ⁶,5-benzothiazepine-7-carboxamide hydrochloride (Example 120)

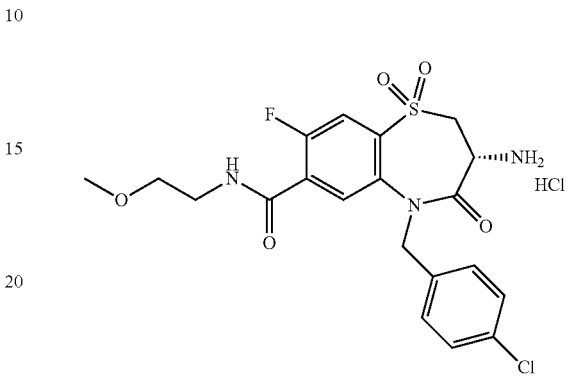

The title compound was synthesized according to general procedure GP5 to afford the title compound as white solid in 87% yield.

LCMS: MET-UHPLC-AB-101, rt=1.9 min, M/Z (ES+) 470/472 [M+H+] 100% UV

NMR Data: 1H NMR (500 MHz, DMSO-d6) d 8.67 (d, J=5.1 Hz, 1H), 8.43 (s, 3H), 7.82 (d, J=8.5 Hz, 1H), 7.68 (d, J=5.5 Hz, 1H), 7.39 (s, 4H), 5.20 (d, J=15.7 Hz, 1H), 4.88 (d, J=15.7 Hz, 1H), 4.46 (dd, J=10.9, 7.5 Hz, 1H), 4.13 (dd, J=13.3, 7.5 Hz, 1H), 3.98 (dd, J=13.2, 11.0 Hz, 1H), 3.48-3.37 (m, 4H), 3.26 (s, 3H).

Synthesis of (3R)-3-amino-N-(2,2-difluorocyclopropyl)-5-{[4-(5-methyl-1,2,4-oxadiazol-3-yl)phenyl]methyl}-1,1,4-trioxo-2,3,4,5-tetrahydro-1λ⁶,5-benzothiazepine-7-carboxamide hydrochloride (Example 121)

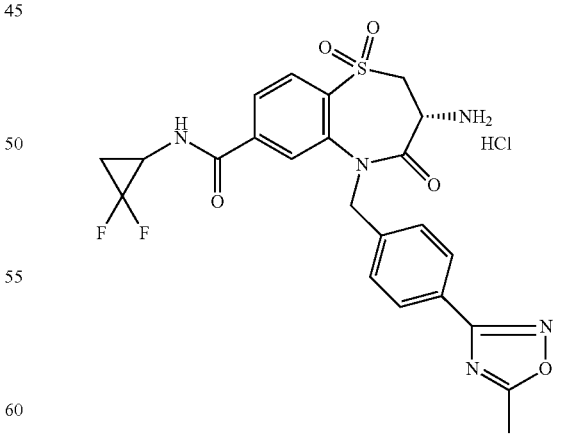

The title compound was synthesized according to general procedure GP5 to afford the title compound as colourless solid in 79% yield.

LCMS: METCR1416 Generic 7 minutes, rt=2.96 min, M/Z (ES+) 518 [M+H+] 98% UV

NMR Data: 1H NMR (500 MHz, DMSO-d6) d 9.38 (br. s, 1H), 8.61 (s, 3H), 8.10-7.96 (m, 3H), 7.93 (t, J=6.4 Hz, 2H), 7.57 (d, J=7.3 Hz, 2H), 5.36 (d, J=15.6 Hz, 1H), 5.06-5.00 (m, 1H), 4.51 (q, J=10.9 Hz, 1H), 4.21-4.05 (m, 1H), 4.00 (d, J=11.0 Hz, 1H), 3.46 (s, 1H), 2.66 (s, 3H), 1.99 (s, 1H), 1.75 (s, 1H).

Synthesis of (1S,3R)-3-amino-5-[(4-chlorophenyl) methyl]-8-fluoro-4-oxo-7-[(4,4,4-trifluorobutyl)carbamoyl]-2,3,4,5-tetrahydro-1H-1,5-benzothiazepin-1-ium-1-olate hydrochloride (Example 122)

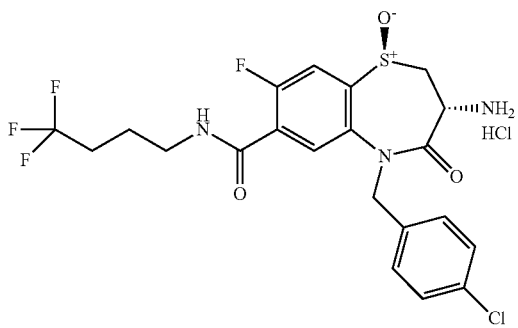 [SMILES: N[C@H]1C[S@+]([O-])c2cc(F)c(C(=O)NCCCC(F)(F)F)cc2N(Cc2ccc(Cl)cc2)C1=O ; Cl]

The title compound was synthesized from intermediate IX-53 (later eluting enantiomer, stereochemistry of sulfoxide arbitrarily assigned) according to general procedure GP5 to afford the title compound as white solid in 74% yield.

LCMS: METCR1416 Generic 7 minutes, rt=3.09 min, M/Z (ES+) 506.05 [M+H+] 99% UV

NMR Data: 1H NMR (500 MHz, DMSO-d6) d 8.72 (t, J=5.6 Hz, 1H), 8.28 (s, 3H), 7.90 (d, J=5.4 Hz, 1H), 7.47 (d, J=8.5 Hz, 1H), 7.38 (d, J=8.4 Hz, 2H), 7.26 (d, J=8.4 Hz, 2H), 5.33 (d, J=15.0 Hz, 1H), 4.87 (d, J=15.1 Hz, 1H), 4.20 (s, 2H), 3.40 (dd, J=13.2, 6.4 Hz, 3H), 2.40-2.26 (m, 2H), 1.76 (dt, J=14.5, 7.0 Hz, 2H).

Synthesis of (1R,3R)-3-amino-5-[(4-chlorophenyl) methyl]-8-fluoro-4-oxo-7-[(4,4,4-trifluorobutyl)carbamoyl]-2,3,4,5-tetrahydro-1H-1,5-benzothiazepin-1-ium-1-olate hydrochloride (Example 123)

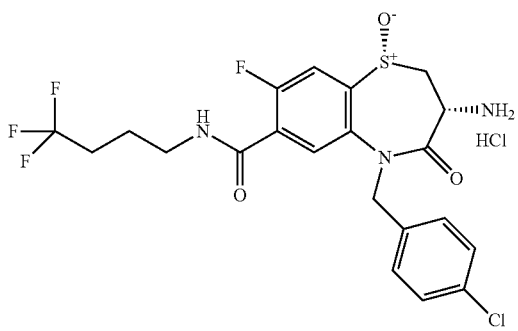 [SMILES: N[C@H]1C[S@@+]([O-])c2cc(F)c(C(=O)NCCCC(F)(F)F)cc2N(Cc2ccc(Cl)cc2)C1=O ; Cl]

The title compound was synthesized from intermediate IX-54 (earlier eluting enantiomer, stereochemistry of sulfoxide arbitrarily assigned) according to general procedure GP5 to afford the title compound as white solid in 43% yield.

LCMS: METCR1416 Generic 7 minutes, rt=3.03 min, M/Z (ES+) 506 [M+H+] 96% UV

NMR Data: 1H NMR (500 MHz, DMSO-d6) d 8.72 (t, J=5.6 Hz, 1H), 8.28 (s, 3H), 7.90 (d, J=5.4 Hz, 1H), 7.47 (d, J=8.5 Hz, 1H), 7.38 (d, J=8.4 Hz, 2H), 7.26 (d, J=8.4 Hz, 2H), 5.33 (d, J=15.0 Hz, 1H), 4.87 (d, J=15.1 Hz, 1H), 4.20 (s, 2H), 3.40 (dd, J=13.2, 6.4 Hz, 3H), 2.40-2.26 (m, 2H), 1.76 (dt, J=14.5, 7.0 Hz, 2H).

Synthesis of (3R)-3-amino-5-[(4-cyanophenyl) methyl]-N-(2,2-difluorocyclopropyl)-8-fluoro-1,1,4-trioxo-2,3,4,5-tetrahydro-1$\lambda^6$,5-benzothiazepine-7-carboxamide hydrochloride (Example 124)

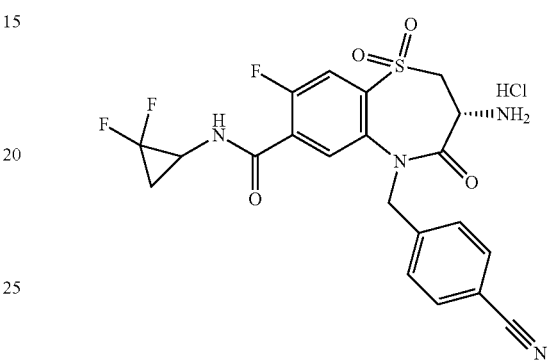

The title compound was synthesized according to general procedure GP5 to afford the title compound as yellow solid in 43% yield.

LCMS: METCR1416 Generic 7 minutes, rt=2.83 min, M/Z (ES+) 479 [M+H+] 99% UV

NMR Data: 1H NMR (500 MHz, DMSO-d6) d 9.12 (d, J=14.5 Hz, 1H), 8.56 (s, 3H), 7.89-7.86 (m, 1H), 7.83 (dd, J=8.4, 3.2 Hz, 2H), 7.70 (dd, J=23.2, 5.4 Hz, 1H), 7.58 (dd, J=8.4, 2.3 Hz, 2H), 5.33-5.22 (m, 1H), 5.05-4.94 (m, 1H), 4.54 (q, J=9.9, 9.5 Hz, 1H), 4.19-4.10 (m, 1H), 4.00 (dd, J=13.3, 11.0 Hz, 1H), 3.55-3.45 (m, 1H), 2.08-1.94 (m, 1H), 1.71-1.55 (m, 1H).

Synthesis of (3R)-3-amino-5-[(4-cyanophenyl) methyl]-8-fluoro-1,1,4-trioxo-N-(4,4,4-trifluorobutyl)-2,3,4,5-tetrahydro-1$\lambda^6$,5-benzothiazepine-7-carboxamide hydrochloride (Example 125)

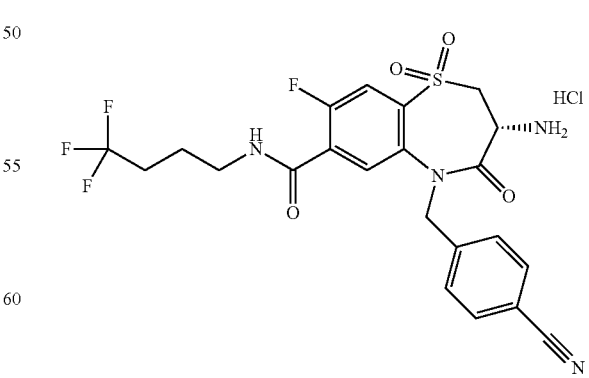

The title compound was synthesized according to general procedure GP5 to afford the title compound as yellow solid in 96% yield.

LCMS: METCR1416 Generic 7 minutes, rt=3.02 min, M/Z (ES+) 513.45 [M+H+]100% UV

NMR Data: 1H NMR (500 MHz, DMSO-d6) ä 8.75 (t, J=5.6 Hz, 1H), 8.45 (s, 3H), 7.86 (d, J=8.4 Hz, 1H), 7.82 (d, J=8.3 Hz, 2H), 7.68 (d, J=5.5 Hz, 1H), 7.58 (d, J=8.3 Hz, 2H), 5.28 (d, J=16.2 Hz, 1H), 4.98 (d, J=16.3 Hz, 1H), 4.57-4.45 (m, 1H), 4.14 (dd, J=13.3, 7.6 Hz, 1H), 4.03-3.93 (m, 1H), 3.32-3.29 (m, 2H), 2.36-2.19 (m, 2H), 1.72 (dt, J=14.6, 7.0 Hz, 2H).

Synthesis of (3R)-3-amino-5-[(4-chlorophenyl)methyl]-N-(4,4-difluorocyclohexyl)-8-fluoro-1,1,4-trioxo-2,3,4,5-tetrahydro-1λ⁶,5-benzothiazepine-7-carboxamide hydrochloride (Example 126)

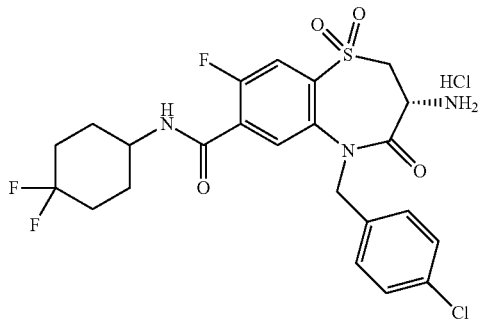 [SMILES: N[C@H]1CS(=O)(=O)c2cc(F)c(C(=O)NC3CCC(F)(F)CC3)cc2N(Cc2ccc(Cl)cc2)C1=O ; Cl]

The title compound was synthesized according to general procedure GP5 to afford the title compound as white solid in 83% yield.

LCMS: MET-UHPLC-AB-101, rt=2.46 min, M/Z (ES+) 530.1/532.1 [M+H+]100% UV

NMR Data: 1H NMR (500 MHz, DMSO-d6) d 8.63 (d, J=7.5 Hz, 1H), 8.40 (s, 3H), 7.83 (d, J=8.2 Hz, 1H), 7.63 (d, J=5.4 Hz, 1H), 7.39 (s, 4H), 5.21 (d, J=15.6 Hz, 1H), 4.88 (d, J=15.6 Hz, 1H), 4.47-4.40 (m, 1H), 4.17-4.09 (m, 1H), 4.02-3.93 (m, 2H), 2.10-1.82 (m, 6H), 1.67-1.53 (m, 2H).

Synthesis of (3R)-3-amino-5-[(4-chlorophenyl)methyl]-8-fluoro-1,1,4-trioxo-N-[2-(trifluoromethyl)cyclopropyl]-2,3,4,5-tetrahydro-1λ⁶,5-benzothiazepine-7-carboxamide hydrochloride (Example 127)

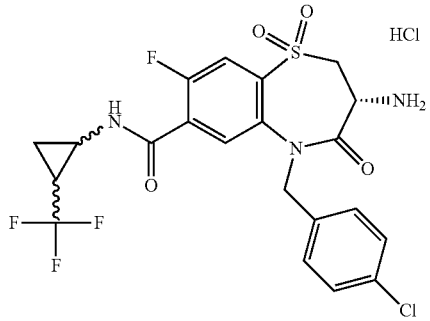 [SMILES: N[C@H]1CS(=O)(=O)c2cc(F)c(C(=O)NC3CC3C(F)(F)F)cc2N(Cc2ccc(Cl)cc2)C1=O ; Cl]

The title compound was synthesized according to general procedure GP5 to afford the title compound as off white solid in 70% yield.

LCMS: METCR1416 Generic 7 minutes, rt=3.26 min, M/Z (ES+) 520/522 [M+H+]100% UV

NMR Data: 1H NMR (500 MHz, DMSO-d6) d 9.03 (s, 1H), 8.49-8.07 (m, 3H), 7.84 (d, J=8.4 Hz, 1H), 7.78 (t, J=5.6 Hz, 1H), 7.38 (s, 4H), 5.20-5.13 (m, 1H), 5.05-4.90 (m, 1H), 4.47-4.40 (m, 1H), 4.12 (ddd, J=13.1, 7.5, 2.8 Hz, 1H), 4.03-3.90 (m, 1H), 3.26-3.20 (m, 1H), 2.16-2.03 (m, 1H), 1.34-1.18 (m, 2H).

Synthesis of (3R)-3-amino-5-[(4-chlorophenyl)methyl]-N-(3,3-difluorocyclobutyl)-8-fluoro-4-oxo-2,3,4,5-tetrahydro-1,5-benzothiazepine-7-carboxamide hydrochloride (Example 128)

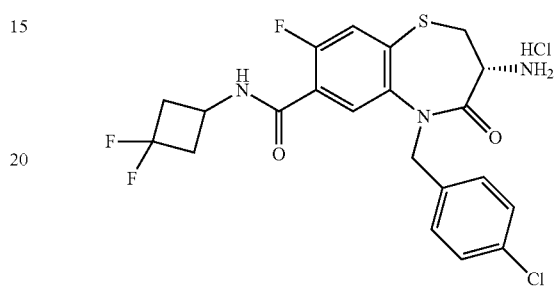

The title compound was synthesized according to general procedure GP5 to afford the title compound as pink solid in 30% yield.

LCMS: METCR1416 Generic 7 minutes, rt=3.18 min, M/Z (ES+) 469/471 [M+H+] 98% UV

NMR Data: 1H NMR (500 MHz, DMSO-d6) d 8.99 (d, J=6.5 Hz, 1H), 8.37 (s, 3H), 7.84 (d, J=6.4 Hz, 1H), 7.66 (d, J=9.3 Hz, 1H), 7.37-7.28 (m, 4H), 5.37 (d, J=15.4 Hz, 1H), 4.94 (d, J=15.4 Hz, 1H), 4.31-4.19 (m, 1H), 4.02 (dd, J=11.6, 6.9 Hz, 1H), 3.67 (dd, J=11.5, 6.9 Hz, 1H), 3.25 (t, J=11.6 Hz, 1H), 3.04-2.92 (m, 2H), 2.80-2.66 (m, 2H).

Synthesis of (3R)-3-amino-8-fluoro-5-[(4-fluorophenyl)methyl]-1,1,4-trioxo-N-(4,4,4-trifluorobutyl)-2,3,4,5-tetrahydro-1λ⁶,5-benzothiazepine-7-carboxamide hydrochloride (Example 129)

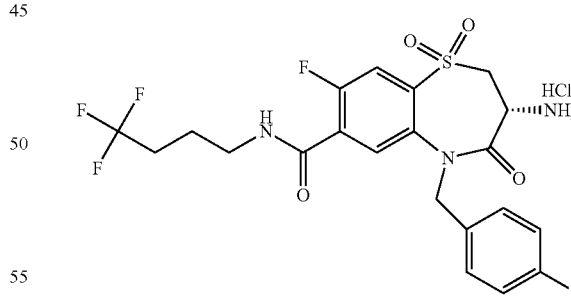

The title compound was synthesized according to general procedure GP5 to afford the title compound as off white solid in 91% yield.

LCMS: MET-UHPLC-AB-101, rt=2.29 min, M/Z (ES+) 506.1 [M+H+] 97% UV

NMR Data: 1H NMR (500 MHz, DMSO-d6) d 8.75 (t, J=5.4 Hz, 1H), 8.57 (s, 3H), 7.83 (d, J=8.4 Hz, 1H), 7.70 (d, J=5.5 Hz, 1H), 7.39 (dd, J=8.6, 5.6 Hz, 2H), 7.13 (t, J=8.9 Hz, 2H), 5.19 (d, J=15.5 Hz, 1H), 4.90 (d, J=15.5 Hz, 1H), 4.47 (dd, J=10.9, 7.6 Hz, 1H), 4.13 (dd, J=13.3, 7.5 Hz, 1H), 3.99 (dd, J=13.2, 11.1 Hz, 1H), 3.40-3.23 (m, 2H), 2.34-2.21 (m, 2H), 1.72 (dt, J=14.6, 6.9 Hz, 2H).

Synthesis of (3R)-3-amino-N-(2,2-difluorocyclopropyl)-8-fluoro-5-[(4-fluorophenyl)methyl]-1,1,4-trioxo-2,3,4,5-tetrahydro-1λ⁶,5-benzothiazepine-7-carboxamide hydrochloride (Example 130)

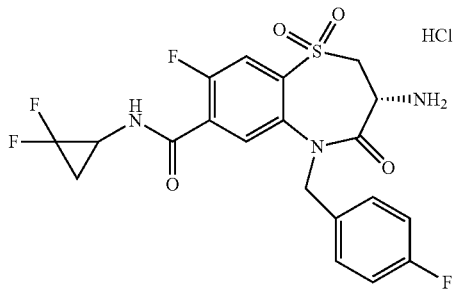 [SMILES: N[C@H]1CS(=O)(=O)c2cc(F)c(C(=O)NC3CC3(F)F)cc2N(Cc2ccc(F)cc2)C1=O ; Cl]

The title compound was synthesized according to general procedure GP5 to afford the title compound as pale yellow solid in 95% yield.

LCMS: MET-UHPLC-AB-101, rt=1.98 & 2.01 min, M/Z (ES+) 472.1 [M+H+] 98% UV

NMR Data: 1H NMR (500 MHz, DMSO-d6) d 9.14 (d, J=14.9 Hz, 1H), 8.60 (s, 3H), 7.84 (d, J=8.3 Hz, 1H), 7.71 (dd, J=22.9, 5.5 Hz, 1H), 7.39 (dd, J=8.3, 5.7 Hz, 2H), 7.18-7.10 (m, 2H), 5.19 (dd, J=15.4, 10.4 Hz, 1H), 4.91 (dd, J=15.5, 9.3 Hz, 1H), 4.47 (dt, J=10.8, 7.7 Hz, 1H), 4.18-4.09 (m, 1H), 3.99 (dd, J=13.2, 11.1 Hz, 1H), 3.48 (dd, J=14.8, 5.0 Hz, 1H), 2.06-1.94 (m, 1H), 1.69-1.58 (m, 1H).

Synthesis of (3R)-3-amino-N-butyl-8-fluoro-5-[(4-fluorophenyl)methyl]-4-oxo-2,3,4,5-tetrahydro-1,5-benzothiazepine-7-carboxamide hydrochloride (Example 131)

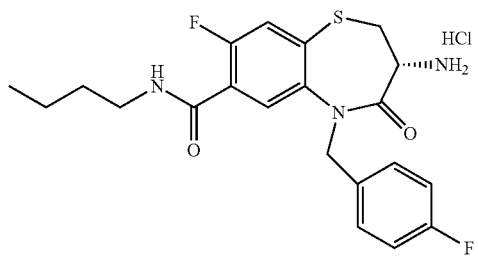 [SMILES: CCCCNC(=O)c1cc2c(cc1F)SC[C@H](N)C(=O)N2Cc1ccc(F)cc1 ; Cl]

The title compound was synthesized according to general procedure GP5 to afford the title compound as cream solid in 74% yield.

LCMS: MET-UHPLC-AB-101, rt=2.24 min, M/Z (ES+) 420.1 [M+H+] 99% UV

NMR Data: 1H NMR (500 MHz, DMSO-d6) d 8.51 (s, 3H), 8.47 (t, J=5.6 Hz, 1H), 7.76 (d, J=6.4 Hz, 1H), 7.62 (d, J=9.3 Hz, 1H), 7.31 (dd, J=8.6, 5.6 Hz, 2H), 7.10 (t, J=8.9 Hz, 2H), 5.31 (d, J=15.3 Hz, 1H), 4.93 (d, J=15.3 Hz, 1H), 4.01 (dd, J=11.7, 6.9 Hz, 1H), 3.67 (dd, J=11.4, 6.9 Hz, 1H), 3.29-3.19 (m, 3H), 1.48 (m, 2H), 1.31 (h, J=7.3 Hz, 2H), 0.89 (t, J=7.4 Hz, 3H).

Synthesis of (3R)-3-amino-N-benzyl-8-fluoro-5-[(4-fluorophenyl)methyl]-4-oxo-2,3,4,5-tetrahydro-1,5-benzothiazepine-7-carboxamide hydrochloride (Example 132)

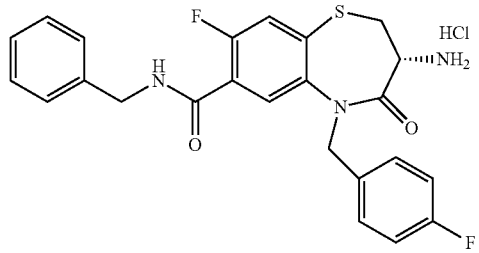 [SMILES: N[C@H]1CSc2cc(F)c(C(=O)NCc3ccccc3)cc2N(Cc2ccc(F)cc2)C1=O ; Cl]

The title compound was synthesized according to general procedure GP5 to afford the title compound as cream solid in 100% yield.

LCMS: MET-UHPLC-AB-101, rt=2.31 min, M/Z (ES+) 454.1 [M+H+] 99% UV

NMR Data: 1H NMR (500 MHz, DMSO-d6) d 9.04 (t, J=5.8 Hz, 1H), 8.34 (s, 3H), 7.83 (d, J=6.5 Hz, 1H), 7.65 (d, J=9.4 Hz, 1H), 7.31 (m, 7H), 7.10 (t, J=8.9 Hz, 2H), 5.33 (d, J=15.3 Hz, 1H), 4.93 (d, J=15.3 Hz, 1H), 4.56-4.41 (m, 2H), 4.04 (dd, J=11.7, 6.9 Hz, 1H), 3.63 (dd, J=11.4, 6.8 Hz, 1H), 3.23 (t, J=11.6 Hz, 1H).

Synthesis of (3R)-3-amino-N-butyl-8-fluoro-5-[(4-fluorophenyl)methyl]-1,1,4-trioxo-2,3,4,5-tetrahydro-1λ⁶,5-benzothiazepine-7-carboxamide hydrochloride (Example 133)

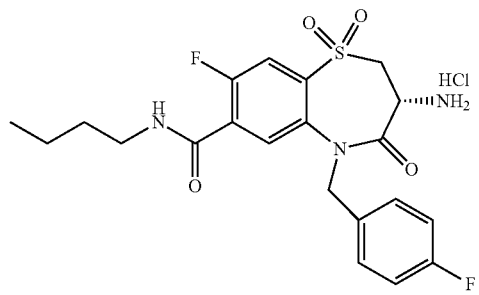 [SMILES: CCCCNC(=O)c1cc2c(cc1F)S(=O)(=O)C[C@H](N)C(=O)N2Cc1ccc(F)cc1 ; Cl]

The title compound was synthesized according to general procedure GP5 to afford the title compound as off white solid in 100% yield.

LCMS: MET-UHPLC-AB-101, rt=2.17 min, M/Z (ES+) 452.1 [M+H+] 98% UV

NMR Data: 1H NMR (500 MHz, DMSO-d6) d 8.61 (t, J=5.4 Hz, 1H), 8.50 (s, 3H), 7.81 (d, J=8.4 Hz, 1H), 7.64 (d, J=5.5 Hz, 1H), 7.39 (dd, J=8.5, 5.6 Hz, 2H), 7.15 (t, J=8.9 Hz, 2H), 5.20 (d, J=15.6 Hz, 1H), 4.86 (d, J=15.5 Hz, 1H), 4.47 (dd, J=10.8, 7.7 Hz, 1H), 4.14-4.07 (m, 1H), 4.02-3.93 (m, 1H), 3.27-3.19 (m, 2H), 1.46 (p, J=7.0 Hz, 2H), 1.29 (h, J=7.3 Hz, 2H), 0.88 (t, J=7.4 Hz, 3H).

Synthesis of (3R)-3-amino-N-benzyl-8-fluoro-5-[(4-fluorophenyl)methyl]-1,1,4-trioxo-2,3,4,5-tetrahydro-1λ⁶,5-benzothiazepine-7-carboxamide hydrochloride (Example 134)

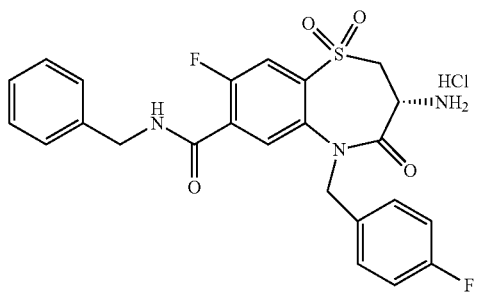 [SMILES: N[C@H]1CS(=O)(=O)c2cc(F)c(C(=O)NCc3ccccc3)cc2N(Cc2ccc(F)cc2)C1=O ; Cl]

The title compound was synthesized according to general procedure GP5 to afford the title compound as off white solid in 100% yield.

LCMS: MET-UHPLC-AB-101, rt=2.23 min, M/Z (ES+) 486.1 [M+H+] 99% UV

NMR Data: 1H NMR (500 MHz, DMSO-d6) d 9.22 (t, J=5.9 Hz, 1H), 8.61 (s, 3H), 7.84 (d, J=8.4 Hz, 1H), 7.71 (d, J=5.5 Hz, 1H), 7.40 (dd, J=8.5, 5.6 Hz, 2H), 7.37-7.32 (m, 2H), 7.30-7.25 (m, 3H), 7.14 (t, J=8.8 Hz, 2H), 5.20 (d, J=15.5 Hz, 1H), 4.88 (d, J=15.5 Hz, 1H), 4.53-4.41 (m, 3H), 4.14 (dd, J=13.2, 7.5 Hz, 1H), 4.04-3.95 (m, 1H).

Synthesis of (3R)-3-amino-5-[(4-chlorophenyl)methyl]-8-fluoro-N-[2-(oxan-4-yl)ethyl]-1,1,4-trioxo-2,3,4,5-tetrahydro-1λ⁶,5-benzothiazepine-7-carboxamide hydrochloride (Example 135)

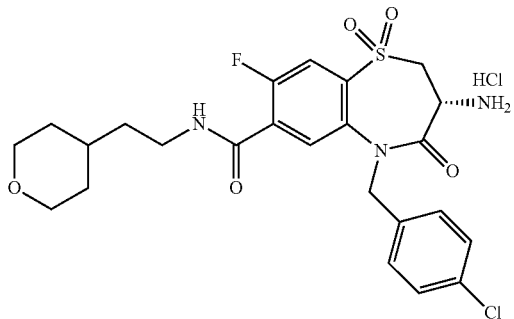 [SMILES: N[C@H]1CS(=O)(=O)c2cc(F)c(C(=O)NCCC3CCOCC3)cc2N(Cc2ccc(Cl)cc2)C1=O ; Cl]

The title compound was synthesized according to general procedure GP5 to afford the title compound as off white solid in 92% yield.

LCMS: MET-UHPLC-AB-101, rt=2.14 min, M/Z (ES+) 524/526 [M+H+] 100% UV

NMR Data: 1H NMR (500 MHz, DMSO-d6) d 8.64 (t, J=5.6 Hz, 1H), 8.55 (s, 3H), 7.83 (d, J=8.4 Hz, 1H), 7.65 (d, J=5.5 Hz, 1H), 7.39 (s, 4H), 5.21 (d, J=15.8 Hz, 1H), 4.88 (d, J=15.8 Hz, 1H), 4.48 (dd, J=10.9, 7.6 Hz, 1H), 4.18-4.11 (m, 1H), 3.99 (dd, J=13.2, 11.1 Hz, 1H), 3.83 (dd, J=11.3, 3.0 Hz, 2H), 3.30-3.20 (m, 4H), 1.58 (d, J=14.4 Hz, 2H), 1.55-1.47 (m, 1H), 1.44 (q, J=6.6 Hz, 2H), 1.21-1.10 (m, 2H).

Synthesis of (3R)-3-amino-5-benzyl-8-fluoro-1,1,4-trioxo-N-(4,4,4-trifluorobutyl)-2,3,4,5-tetrahydro-1λ⁶,5-benzothiazepine-7-carboxamide hydrochloride (Example 136)

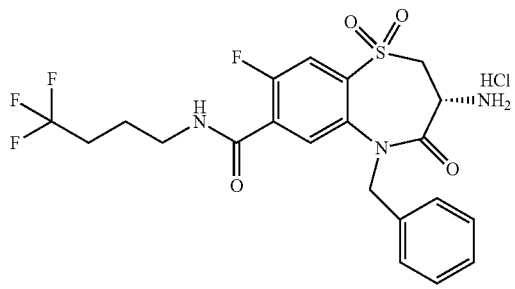 [SMILES: N[C@H]1CS(=O)(=O)c2cc(F)c(C(=O)NCCCC(F)(F)F)cc2N(Cc2ccccc2)C1=O ; Cl]

The title compound was synthesized according to general procedure GP5 to afford the title compound as white solid in 39% yield.

LCMS: METCR1416 Generic 7 minutes, rt=2.18 min, M/Z (ES+) 488.12 [M+H+] 98% UV

NMR Data: 1H NMR (500 MHz, DMSO-d6) d 8.71 (t, J=5.8 Hz, 1H), 8.37 (s, 3H), 7.83 (d, J=8.5 Hz, 1H), 7.62 (d, J=5.5 Hz, 1H), 7.46-7.25 (m, 5H), 5.27 (d, J=15.7 Hz, 1H), 4.79 (d, J=15.7 Hz, 1H), 4.53-4.38 (m, 1H), 4.11 (dd, J=13.3, 7.5 Hz, 1H), 4.05-3.89 (m, 1H), 3.28 (d, part obsc, J=7.3 Hz, 2H), 2.33-2.16 (m, 2H), 1.71 (dt, J=14.6, 6.9 Hz, 2H).

Synthesis of (3R)-3-amino-5-[(4-chlorophenyl)methyl]-8-fluoro-N-[(4-methoxyphenyl)methyl]-1,1,4-trioxo-2,3,4,5-tetrahydro-1λ⁶,5-benzothiazepine-7-carboxamide hydrochloride (Example 137)

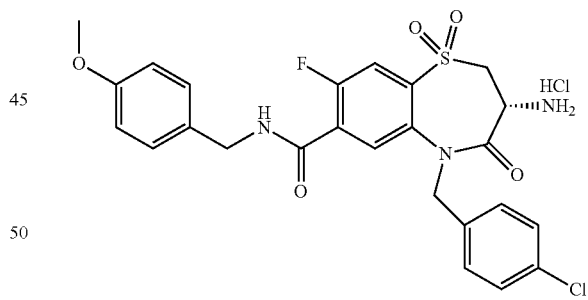

The title compound was synthesized according to general procedure GP5 to afford the title compound as white solid in 100% yield.

LCMS: MET-UHPLC-AB-101, rt=2.4 min, M/Z (ES+) 532.15/534.10 [M+H+] 99% UV

NMR Data: 1H NMR (250 MHz, DMSO-d6) d 9.13 (t, J=5.9 Hz, 1H), 8.56 (s, 3H), 7.83 (d, J=8.5 Hz, 1H), 7.69 (d, J=5.6 Hz, 1H), 7.38 (s, 4H), 7.21 (d, J=8.7 Hz, 2H), 6.98-6.80 (m, 2H), 5.20 (d, J=15.7 Hz, 1H), 4.87 (d, J=15.7 Hz, 1H), 4.48 (dd, J=10.9, 7.4 Hz, 1H), 4.44-4.30 (m, 2H), 4.14 (dd, J=13.2, 7.4 Hz, 1H), 4.05-3.91 (m, 1H), 3.74 (s, 3H).

Synthesis of (3R)-3-amino-5-[(5-cyclopropyl-1,3,4-thiadiazol-2-yl)methyl]-8-fluoro-N-[(4-fluorophenyl)methyl]-1,1,4-trioxo-2,3,4,5-tetrahydro-1λ⁶,5-benzothiazepine-7-carboxamide hydrochloride (Example 138)

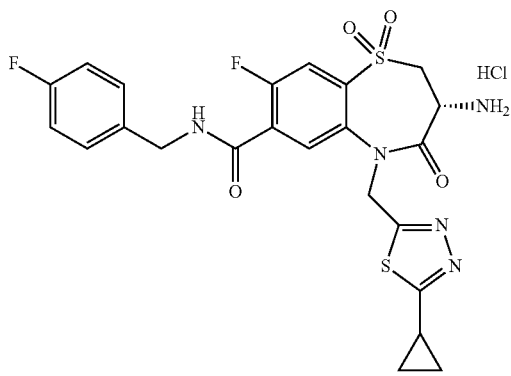 [SMILES: N[C@H]1CS(=O)(=O)c2cc(F)c(C(=O)NCc3ccc(F)cc3)cc2N(Cc2nnc(C3CC3)s2)C1=O ; Cl]

The title compound was synthesized according to general procedure GP5 to afford the title compound as yellow solid in 51% yield.
LCMS: MET-UHPLC-AB-101, rt=2.01 min, M/Z (ES+) 534.1 [M+H+] 96% UV
NMR Data: 1H NMR (500 MHz, Methanol-d4) d 8.20 (d, J=5.5 Hz, 1H), 7.90 (d, J=8.6 Hz, 1H), 7.45-7.38 (m, 2H), 7.12-7.06 (m, 2H), 5.47 (d, J=15.9 Hz, 1H), 5.26 (d, J=15.9 Hz, 1H), 4.64-4.53 (m, 2H), 4.49 (dd, J=10.9, 7.6 Hz, 1H), 4.13 (dd, J=13.3, 7.6 Hz, 1H), 3.88 (dd, J=13.3, 11.0 Hz, 1H), 2.46 (tt, J=8.3, 4.9 Hz, 1H), 1.31-1.26 (m, 2H), 1.10-1.04 (m, 2H). NH amide and NH2.HCl not visible by NMR Synthesis of (3R)-3-amino-8-fluoro-5-[(4-fluorophenyl)methyl]-N-[(oxan-4-yl)methyl]-1,1,4-trioxo-2,3,4,5-tetrahydro-1λ⁶,5-benzothiazepine-7-carboxamide hydrochloride (Example 139)

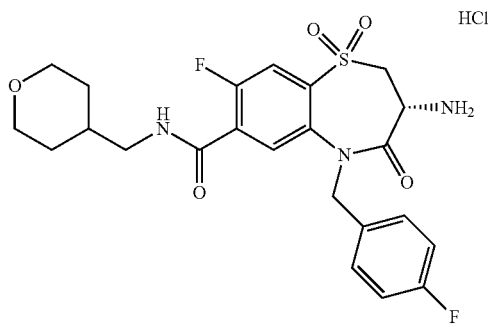 [SMILES: Cl ; N[C@H]1CS(=O)(=O)c2cc(F)c(C(=O)NCC3CCOCC3)cc2N(Cc2ccc(F)cc2)C1=O]

The title compound was synthesized according to general procedure GP5 to afford the title compound as white solid in 83% yield.
LCMS: MET-UHPLC-AB-101, rt=1.84 min, M/Z (ES+) 494.1 [M+H+] 99% UV
NMR Data: 1H NMR (500 MHz, DMSO-d6) δ 8.65 (t, J=5.8 Hz, 1H), 8.46 (s, 3H), 7.81 (d, J=8.3 Hz, 1H), 7.60 (d, J=5.5 Hz, 1H), 7.39 (dd, J=8.6, 5.5 Hz, 2H), 7.15 (t, J=8.9 Hz, 2H), 5.22 (d, J=15.5 Hz, 1H), 4.84 (d, J=15.6 Hz, 1H), 4.46 (dd, J=10.7, 7.7 Hz, 1H), 4.11 (dd, J=13.3, 7.4 Hz, 1H), 3.98 (dd, J=13.2, 11.1 Hz, 1H), 3.85 (dd, J=11.0, 2.9 Hz, 2H), 3.25 (t, J=11.0 Hz, 2H), 3.20-3.08 (m, 2H), 1.80-1.66 (m, 1H), 1.52 (d, J=12.3 Hz, 2H), 1.17 (qd, J=12.1, 4.5 Hz, 2H).

Synthesis of (3R)-3-amino-N-(3,3-difluorocyclobutyl)-8-fluoro-5-[(4-fluorophenyl)methyl]-1,1,4-trioxo-2,3,4,5-tetrahydro-1λ⁶,5-benzothiazepine-7-carboxamide hydrochloride (Example 140)

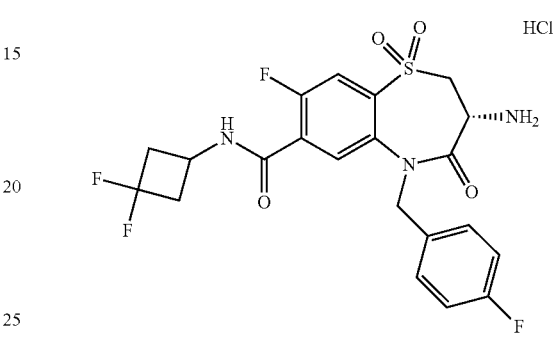

The title compound was synthesized according to general procedure GP5 to afford the title compound as cream solid in 71% yield.
LCMS: MET-UHPLC-AB-101, rt=2.11 min, M/Z (ES+) 486.0 [M+H+] 98% UV
NMR Data: 1H NMR (500 MHz, DMSO-d6) d 9.20 (d, J=6.5 Hz, 1H), 8.68 (s, 3H), 7.84 (d, J=8.4 Hz, 1H), 7.74 (d, J=5.5 Hz, 1H), 7.39 (dd, J=8.7, 5.5 Hz, 2H), 7.17-7.09 (m, 2H), 5.17 (d, J=15.4 Hz, 1H), 4.94 (d, J=15.5 Hz, 1H), 4.46 (dd, J=10.9, 7.5 Hz, 1H), 4.24 (dt, J=14.8, 6.8 Hz, 1H), 4.16 (dd, J=13.3, 7.5 Hz, 1H), 3.99 (dd, J=13.2, 11.0 Hz, 1H), 3.05-2.92 (m, 2H), 2.75-2.65 (m, 2H).

Synthesis of (3R)-3-amino-8-fluoro-5-[(4-methoxyphenyl)methyl]-1,1,4-trioxo-N-(4,4,4-trifluorobutyl)-2,3,4,5-tetrahydro-1λ⁶,5-benzothiazepine-7-carboxamide (Example 141)

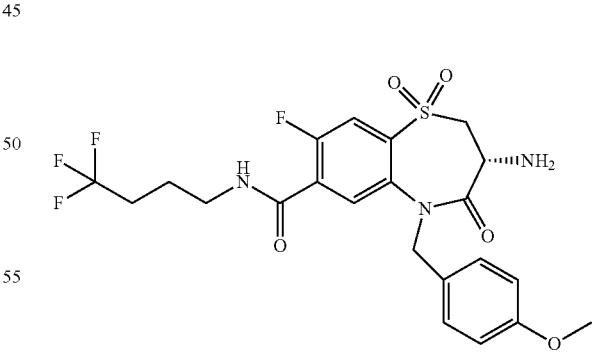

The title compound was synthesized according to general procedure GP5 to afford the title compound as white solid in 79% yield.
LCMS: METCR1416 Generic 7 minutes, rt=3.18 min, M/Z (ES+) 518.25 [M+H+] 99% UV
NMR Data: 1H NMR (500 MHz, DMSO-d6) d 8.65 (t, J=5.6 Hz, 1H), 7.71 (d, J=8.6 Hz, 1H), 7.57 (d, J=5.6 Hz, 1H), 7.26 (d, J=8.7 Hz, 2H), 6.86-6.82 (m, 2H), 5.17-5.07

(m, 1H), 4.76-4.68 (m, 1H), 3.89 (dd, J=12.1, 5.8 Hz, 1H), 3.71 (s, 3H), 3.71-3.57 (m, 2H), 2.33-2.19 (m, 2H), 2.00 (s, 2H), 1.71 (dt, J=14.6, 6.9 Hz, 2H). [2H hidden under the water peak]

Synthesis of (3R)-3-amino-8-fluoro-5-[(4-methoxyphenyl)methyl]-N-[(oxan-4-yl)methyl]-1,1,4-trioxo-2,3,4,5-tetrahydro-1λ⁶,5-benzothiazepine-7-carboxamide (Example 142)

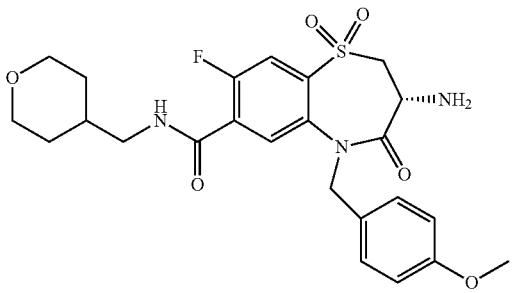 [SMILES: COc1ccc(CN2C(=O)[C@@H](N)CS(=O)(=O)c3cc(F)c(C(=O)NCC4CCOCC4)cc32)cc1]

The title compound was synthesized according to general procedure GP5 to afford the title compound as white solid in 95% yield.

LCMS: METCR1416 Generic 7 minutes, rt=2.85 min, M/Z (ES+) 506.3 [M+H+] 99% UV

NMR Data: 1H NMR (500 MHz, DMSO-d6) d 8.57 (t, J=5.8 Hz, 1H), 7.70 (d, J=8.5 Hz, 1H), 7.48 (d, J=5.6 Hz, 1H), 7.26 (d, J=8.7 Hz, 2H), 6.87-6.82 (m, 2H), 5.22-5.11 (m, 1H), 4.67-4.58 (m, 1H), 3.89 (dd, J=12.2, 5.8 Hz, 1H), 3.86-3.81 (m, 2H), 3.72 (s, 3H), 3.71-3.58 (m, 2H), 3.25 (td, J=11.7, 1.8 Hz, 2H), 3.17-3.07 (m, 2H), 2.03 (s, 2H), 1.78-1.66 (m, 1H), 1.52 (d, J=12.9 Hz, 2H), 1.18 (td, J=12.9, 12.4, 4.3 Hz, 2H).

Synthesis of (3R)-3-amino-N-(2,2-difluorocyclopropyl)-8-fluoro-5-[(4-methoxyphenyl)methyl]-1,1,4-trioxo-2,3,4,5-tetrahydro-1λ⁶,5-benzothiazepine-7-carboxamide (Example 143)

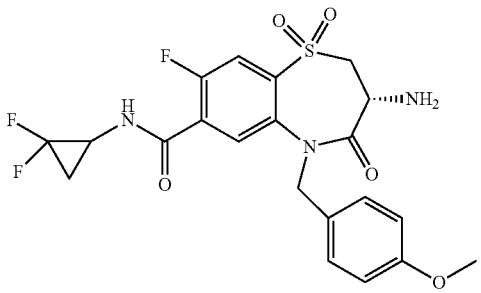 [SMILES: COc1ccc(CN2C(=O)[C@@H](N)CS(=O)(=O)c3cc(F)c(C(=O)NC4CC4(F)F)cc32)cc1]

The title compound was synthesized according to general procedure GP5 to afford the title compound as white solid in 57% yield.

LCMS: METCR1416 Generic 7 minutes, rt=3.03 min, M/Z (ES+) 484.2 [M+H+] 97% UV

NMR Data: 1H NMR (250 MHz, DMSO-d6) d 9.06-8.95 (m, 1H), 7.72 (d, J=8.6 Hz, 1H), 7.56 (dd, J=5.5, 4.3 Hz, 1H), 7.25 (dd, J=8.6, 1.3 Hz, 2H), 6.84 (dd, J=8.7, 1.7 Hz, 2H), 5.18-5.07 (m, 1H), 4.76-4.65 (m, 1H), 3.98-3.80 (m, 1H), 3.72 (s, 3H), 3.72-3.58 (m, 2H), 3.57-3.40 (m, 1H), 2.10-1.88 (m, 3H), 1.69-1.50 (m, 1H).

Synthesis of (3R)-3-amino-5-[(4-chlorophenyl)methyl]-8-fluoro-N-(oxan-4-yl)-1,1,4-trioxo-2,3,4,5-tetrahydro-1λ⁶,5-benzothiazepine-7-carboxamide (Example 144)

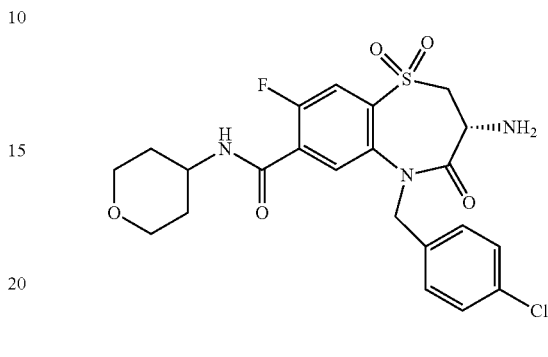

The title compound was synthesized according to general procedure GP5 to afford the title compound as white crystalline solid in 52% yield.

LCMS: METCR1416 Generic 7 minutes, rt=2.94 min, M/Z (ES+) 496.1/498.2 [M+H+] 100% UV NMR Data: 1H NMR (250 MHz, DMSO-d6) d 8.55 (d, J=7.7 Hz, 1H), 7.72 (d, J=8.5 Hz, 1H), 7.53 (d, J=5.6 Hz, 1H), 7.37 (s, 4H), 5.19 (d, J=15.6 Hz, 1H), 4.78 (d, J=15.6 Hz, 1H), 4.11-3.82 (m, 4H), 3.80-3.59 (m, 2H), 3.41 (d, J=11.4 Hz, 2H), 2.02 (s, 2H), 1.74 (s, 2H), 1.59-1.40 (m, 2H).

Synthesis of (3R)-3-amino-5-[(4-chlorophenyl)methyl]-N-(3,3-difluorocyclobutyl)-1,1,4-trioxo-2,3,4,5-tetrahydro-1λ⁶,5-benzothiazepine-7-carboxamide (Example 145)

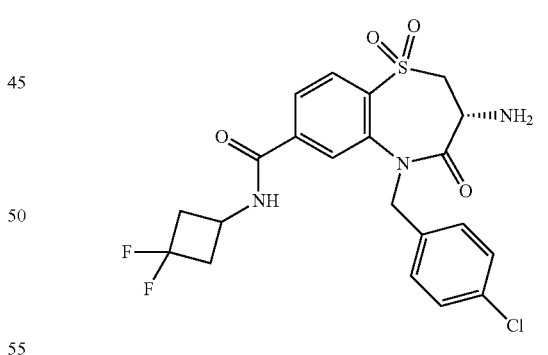

The title compound was synthesized according to general procedure GP5 to afford the title compound as light yellow solid in 65% yield.

LCMS: METCR1416 Generic 7 minutes, rt=2.21 min, M/Z (ES+) 484.1/486.1 [M+H+] 98% UV NMR Data: 1H NMR (500 MHz, DMSO-d6) d 9.11 (d, J=6.4 Hz, 1H), 8.00 (d, J=8.1 Hz, 1H), 7.95 (d, J=7.9 Hz, 1H), 7.82 (s, 1H), 7.37 (s, 4H), 5.22-4.81 (m, 2H), 4.31-4.19 (m, 1H), 3.89 (dd, J=12.6, 6.2 Hz, 1H), 3.69 (s, 1H), 3.66-3.57 (m, 1H), 2.97 (td, J=13.3, 6.7 Hz, 2H), 2.74 (s, 2H), 2.00 (s, 2H).

303

Synthesis of (3R)-3-amino-5-[(4-chlorophenyl)methyl]-N-[(1S)-3,3-difluorocyclopentyl]-8-fluoro-1,1,4-trioxo-2,3,4,5-tetrahydro-1λ⁶,5-benzothiazepine-7-carboxamide (Example 146)

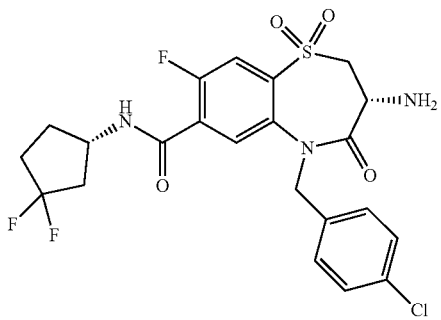 [SMILES: N[C@H]1CS(=O)(=O)c2cc(F)c(C(=O)N[C@H]3CCC(F)(F)C3)cc2N(Cc2ccc(Cl)cc2)C1=O]

The title compound was synthesized according to general procedure GP5 to afford the title compound as colourless crystalline solid in 72% yield.

LCMS: METCR1416 Generic 7 minutes, rt=3.22 min, M/Z (ES+) 516.20/518.2 [M+H+] 100% UV NMR Data: 1H NMR (500 MHz, DMSO-d6) d 8.79 (d, J=7.0 Hz, 1H), 7.72 (d, J=8.4 Hz, 1H), 7.57 (d, J=5.5 Hz, 1H), 7.36 (s, 4H), 5.15 (d, J=15.6 Hz, 1H), 4.81 (d, J=15.7 Hz, 1H), 4.36 (q, J=7.5 Hz, 1H), 3.90 (dd, J=12.2, 5.9 Hz, 1H), 3.75-3.60 (m, 2H), 2.30-2.18 (m, 1H), 2.19-1.90 (m, 6H), 1.75 (dt, J=12.1, 7.7 Hz, 1H).

Synthesis of (3R)-3-amino-5-[(4-chlorophenyl)methyl]-N-[(1R,2S)-2-fluorocyclopropyl]-1,1,4-trioxo-2,3,4,5-tetrahydro-1λ⁶,5-benzothiazepine-7-carboxamide (Example 147)

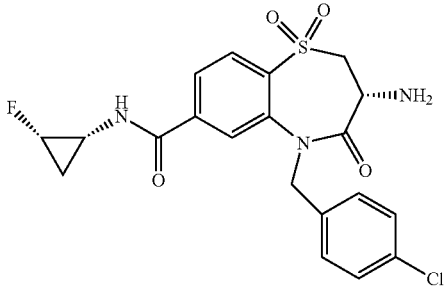 [SMILES: N[C@H]1CS(=O)(=O)c2ccc(C(=O)N[C@@H]3C[C@@H]3F)cc2N(Cc2ccc(Cl)cc2)C1=O]

The title compound was synthesized according to general procedure GP5 to afford the title compound as off white solid in 67% yield.

LCMS: METCR1416 Generic 7 minutes, rt=2.93 min, M/Z (ES+) 452.05/454.05 [M+H+]; 474/476 [M+Na+] 96% UV NMR Data: 1H NMR (250 MHz, DMSO-d6) d 8.87 (d, J=3.5 Hz, 1H), 8.06-7.87 (m, 2H), 7.83 (s, 1H), 7.37 (s, 4H), 5.19 (d, J=15.8 Hz, 1H), 4.98-4.79 (m, 1H), 4.76-4.56 (m, 1H), 3.98-3.83 (m, 1H), 3.79-3.53 (m, 2H), 2.80 (d, J=8.4 Hz, 1H), 1.99 (s, 2H), 1.26-1.03 (m, 2H).

304

Synthesis of (3R)-3-amino-N-(3,3-difluorocyclobutyl)-5-[(2-fluorophenyl)methyl]-1,1,4-trioxo-2,3,4,5-tetrahydro-1λ⁶,5-benzothiazepine-7-carboxamide (Example 148)

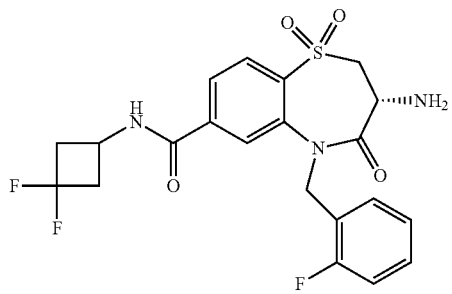 [SMILES: N[C@H]1CS(=O)(=O)c2ccc(C(=O)NC3CC(F)(F)C3)cc2N(Cc2ccccc2F)C1=O]

The title compound was synthesized according to general procedure GP5 to afford the title compound as off white solid in 79% yield.

LCMS: METCR1416 Generic 7 minutes, rt=2.93 min, M/Z (ES+) 468.4 [M+H+], 490.05 [M+Na+] 99% UV; NMR Data: 1H NMR (250 MHz, DMSO-d6) d 9.12 (d, J=6.3 Hz, 1H), 8.08-7.93 (m, 2H), 7.90 (s, 1H), 7.45 (t, J=7.7 Hz, 1H), 7.30 (t, J=5.9 Hz, 1H), 7.21-7.01 (m, 2H), 5.17 (d, J=16.0 Hz, 1H), 4.90 (d, J=15.2 Hz, 1H), 4.25 (s, 1H), 3.96-3.79 (m, 1H), 3.75-3.54 (m, 2H), 2.96 (s, 2H), 2.78 (s, 2H), 1.97 (s, 2H)

Synthesis of (3R)-3-amino-N-(3,3-difluorocyclobutyl)-5-[(3-methoxyphenyl)methyl]-1,1,4-trioxo-2,3,4,5-tetrahydro-1λ⁶,5-benzothiazepine-7-carboxamide (Example 149)

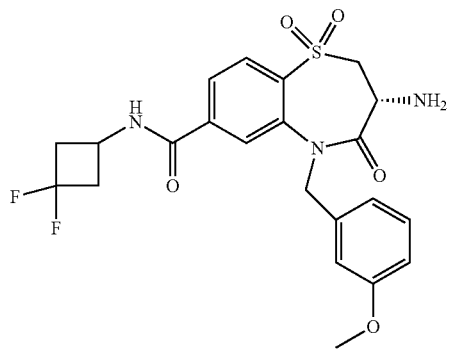 [SMILES: COc1cccc(CN2C(=O)[C@@H](N)CS(=O)(=O)c3ccc(C(=O)NC4CC(F)(F)C4)cc32)c1]

The title compound was synthesized according to general procedure GP5 to afford the title compound as off white solid in 62% yield.

LCMS: METCR1416 Generic 7 minutes 215 and 254 nm, rt=2.98 min, M/Z (ES+) 480.5 [M+H+]; 502.1 [M+Na+] 98% UV NMR Data: 1H NMR (250 MHz, DMSO-d6) d 9.09 (d, J=6.6 Hz, 1H), 8.08-7.91 (m, 2H), 7.82 (s, 1H), 7.22 (t, J=7.9 Hz, 1H), 6.93 (d, J=7.6 Hz, 2H), 6.88-6.74 (m, 1H), 5.20 (d, J=15.7 Hz, 1H), 4.80 (d, J=15.6 Hz, 1H), 4.24 (s, 1H), 4.02-3.85 (m, 1H), 3.71 (s, 4H), 3.58 (s, 1H), 3.12-2.89 (m, 2H), 2.85-2.66 (m, 2H), 2.07 (s, 2H).

Synthesis of (3R)-3-amino-5-[(4-methoxyphenyl)methyl]-1,1,4-trioxo-N-(4,4,4-trifluorobutyl)-2,3,4,5-tetrahydro-1λ⁶,5-benzothiazepine-7-carboxamide (Example 150)

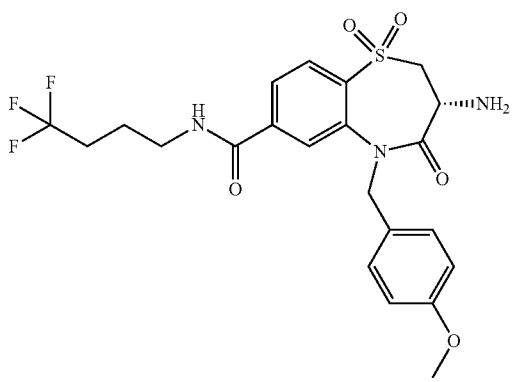 [SMILES: COc1ccc(CN2C(=O)[C@@H](N)CS(=O)(=O)c3ccc(C(=O)NCCCC(F)(F)F)cc32)cc1]

The title compound was synthesized according to general procedure GP5 to afford the title compound as white solid in 89% yield.

LCMS: MET-UHPLC-AB-101, rt=2.1 min, M/Z (ES+) 500.2 [M+H+] 100% UV

NMR Data: 1H NMR (500 MHz, DMSO-d6) d 8.80 (t, J=5.6 Hz, 1H), 7.95 (d, J=8.1 Hz, 1H), 7.90 (d, J=8.9 Hz, 1H), 7.83 (s, 1H), 7.26 (d, J=8.6 Hz, 2H), 6.83 (d, J=8.7 Hz, 2H), 5.11 (d, J=15.4 Hz, 1H), 4.82 (d, J=15.3 Hz, 1H), 3.87 (dd, J=12.4, 6.1 Hz, 1H), 3.71 (s, 3H), 3.70-3.58 (m, 2H), 3.38-3.33 (m, 2H), 2.35-2.24 (m, 2H), 2.07 (s, 2H), 1.74 (dt, J=14.8, 7.0 Hz, 2H).

Synthesis of (3R)-3-amino-N,5-bis[(4-methoxyphenyl)methyl]-1,1,4-trioxo-2,3,4,5-tetrahydro-1λ⁶,5-benzothiazepine-7-carboxamide (Example 151)

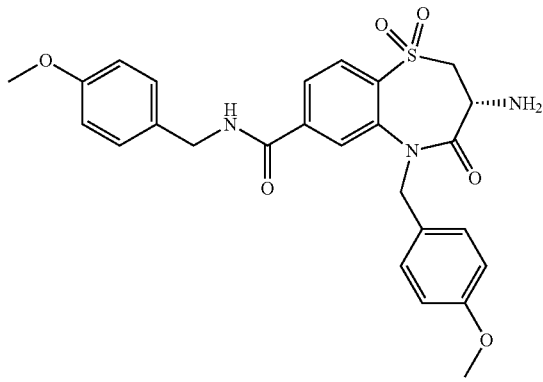 [SMILES: COc1ccc(CNC(=O)c2ccc3c(c2)N(Cc2ccc(OC)cc2)C(=O)[C@@H](N)CS3(=O)=O)cc1]

The title compound was synthesized according to general procedure GP5 to afford the title compound as white solid in 82% yield.

LCMS: MET-UHPLC-AB-101, rt=2.11 min, M/Z (ES+) 510.2 [M+H+] 99% UV

NMR Data: 1H NMR (500 MHz, DMSO-d6) d 9.22 (t, J=6.0 Hz, 1H), 7.98-7.89 (m, 2H), 7.86 (s, 1H), 7.26 (d, J=8.6 Hz, 2H), 7.22 (d, J=8.6 Hz, 2H), 6.89 (d, J=8.7 Hz, 2H), 6.83 (d, J=8.7 Hz, 2H), 5.11 (d, J=15.4 Hz, 1H), 4.83 (d, J=15.3 Hz, 1H), 4.40 (d, J=5.8 Hz, 2H), 3.86 (dd, J=12.6, 6.1 Hz, 1H), 3.73 (s, 3H), 3.71 (s, 3H), 3.69-3.64 (m, 1H), 3.64-3.57 (m, 1H), 2.00 (s, 2H).

Synthesis of (3R)-3-amino-5-benzyl-N-[(4-methoxyphenyl)methyl]-1,1,4-trioxo-2,3,4,5-tetrahydro-1λ⁶,5-benzothiazepine-7-carboxamide (Example 152)

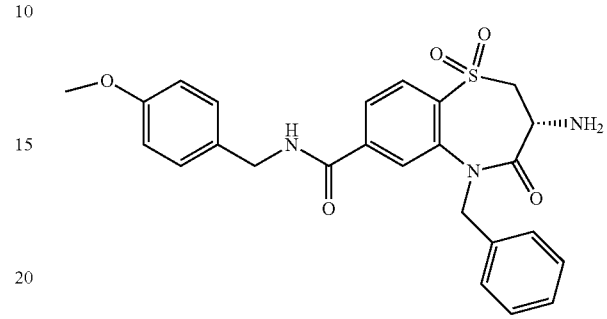

The title compound was synthesized according to general procedure GP5 to afford the title compound as white solid in 82% yield.

LCMS: METCR1416 Generic 7 minutes, rt=3.04 min, M/Z (ES+) 480.5 [M+H+] 99% UV

NMR Data: 1H NMR (500 MHz, Chloroform-d) d 8.06 (d, J=8.1 Hz, 1H), 7.78 (dd, J=8.1, 1.5 Hz, 1H), 7.36-7.11 (m, 8H), 6.94-6.86 (m, 2H), 6.01-5.90 (m, 1H), 5.57 (d, J=15.0 Hz, 1H), 4.54-4.41 (m, 3H), 3.83 (s, 3H), 3.77 (dd, J=12.9, 6.7 Hz, 1H), 3.70 (dd, J=9.9, 7.3 Hz, 1H), 3.48 (dd, J=12.9, 11.0 Hz, 1H). (NH2 not visible)

Synthesis of (3R)-3-amino-5-[(4-chlorophenyl)methyl]-N-[(4-methoxyphenyl)methyl]-1,1,4-trioxo-2,3,4,5-tetrahydro-1λ⁶,5-benzothiazepine-7-carboxamide (Example 153)

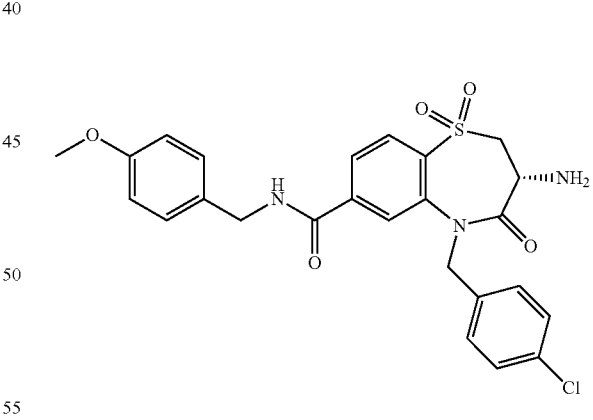

The title compound was synthesized according to general procedure GP5 to afford the title compound as off white solid in 67% yield.

LCMS: METCR1416 Generic 7 minutes, rt=3.27 min, M/Z (ES+) 514.10/516.10 [M+H+] 97% UV NMR Data: 1H NMR (500 MHz, DMSO-d6) d 9.23 (t, J=5.8 Hz, 1H), 7.97 (s, 2H), 7.85 (s, 1H), 7.42-7.32 (m, 4H), 7.22 (d, J=8.6 Hz, 2H), 6.95-6.84 (m, 2H), 5.16 (d, J=15.7 Hz, 1H), 4.89 (d, J=15.7 Hz, 1H), 4.40 (d, J=5.9 Hz, 2H), 3.88 (dd, J=12.8, 6.6 Hz, 1H), 3.83-3.61 (m, 4H), 3.65-3.55 (m, 1H), 1.98 (s, 2H).

Synthesis of (3R)-3-amino-N-(4,4-difluorocyclohexyl)-5-[(4-methoxyphenyl)methyl]-1,1,4-trioxo-2,3,4,5-tetrahydro-1λ⁶,5-benzothiazepine-7-carboxamide (Example 154)

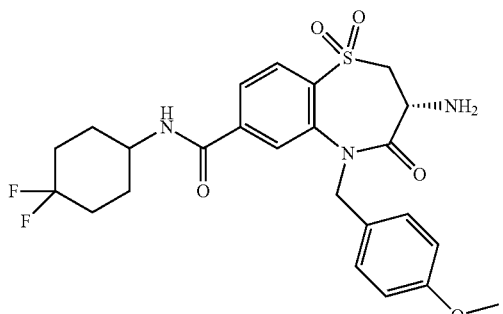

The title compound was synthesized according to general procedure GP5 to afford the title compound as white solid in 90% yield.

LCMS: METCR1416 Generic 7 minutes, rt=3.08 min, M/Z (ES+) 508.50 [M+H+] 99% UV

NMR Data: 1H NMR (500 MHz, DMSO-d6) d 8.54 (d, J=7.6 Hz, 1H), 7.98-7.88 (m, 2H), 7.78 (d, J=1.2 Hz, 1H), 7.27 (d, J=8.7 Hz, 2H), 6.85 (d, J=8.7 Hz, 2H), 5.17 (d, J=15.3 Hz, 1H), 4.75 (d, J=15.2 Hz, 1H), 4.01-3.92 (m, 1H), 3.89-3.83 (m, 1H), 3.72 (s, 3H), 3.71-3.58 (m, 2H), 2.12-1.83 (m, 8H), 1.68-1.57 (m, 2H).

Synthesis of (3R)-3-amino-5-[(4-chlorophenyl)methyl]-1,1,4-trioxo-N-(3,3,3-trifluoropropyl)-2,3,4,5-tetrahydro-1λ⁶,5-benzothiazepine-7-carboxamide (Example 155)

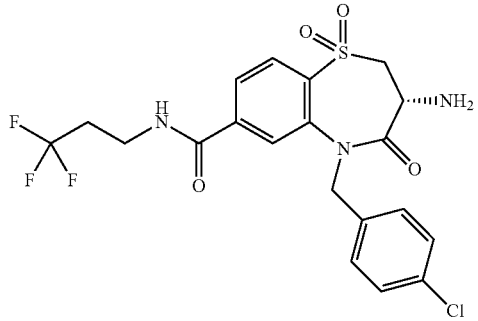 [SMILES: N[C@H]1CS(=O)(=O)c2ccc(C(=O)NCCC(F)(F)F)cc2N(Cc2ccc(Cl)cc2)C1=O]

The title compound was synthesized according to general procedure GP5 to afford the title compound as white solid in 82% yield.

LCMS: METCR1416 Generic 7 minutes, rt=3.21 min, M/Z (ES+) 490.10/492.10 [M+H+] 100% UV NMR Data: 1H NMR (500 MHz, DMSO-d6) d 8.98 (t, J=5.6 Hz, 1H), 7.99 (d, J=8.1 Hz, 1H), 7.91 (d, J=8.1 Hz, 1H), 7.81 (s, 1H), 7.36 (s, 4H), 5.17 (d, J=15.8 Hz, 1H), 4.88 (d, J=15.8 Hz, 1H), 3.89 (dd, J=12.9, 6.5 Hz, 1H), 3.74-3.68 (m, 1H), 3.66-3.59 (m, 1H), 3.50 (q, J=6.4 Hz, 2H), 2.60-2.53 (m, 2H), 2.15-1.88 (m, 2H).

Synthesis of (3R)-3-amino-5-[(4-chlorophenyl)methyl]-1,1,4-trioxo-N-[(3R)-oxolan-3-yl]-2,3,4,5-tetrahydro-1λ⁶,5-benzothiazepine-7-carboxamide (Example 156)

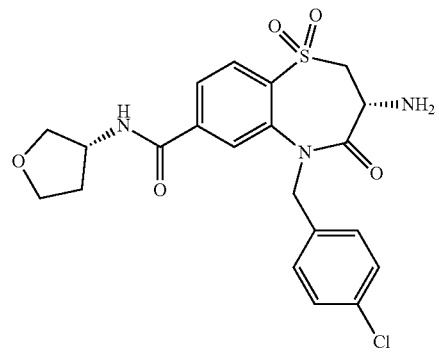 [SMILES: N[C@H]1CS(=O)(=O)c2ccc(C(=O)N[C@@H]3CCOC3)cc2N(Cc2ccc(Cl)cc2)C1=O]

The title compound was synthesized according to general procedure GP5 to afford the title compound as white solid in 37% yield.

LCMS: MET-UHPLC-AB-101, rt=1.86 min, M/Z (ES+) 464.1/466.1 [M+H+] 97% UV

NMR Data: 1H NMR (500 MHz, DMSO-d6) d 8.82 (d, J=6.6 Hz, 1H), 7.95 (s, 2H), 7.81 (s, 1H), 7.36 (s, 4H), 5.18 (d, J=15.7 Hz, 1H), 4.86 (d, J=15.7 Hz, 1H), 4.49-4.39 (m, 1H), 3.91-3.80 (m, 3H), 3.75-3.65 (m, 2H), 3.65-3.55 (m, 2H), 2.21-2.10 (m, 1H), 1.99 (s, 2H), 1.92-1.82 (m, 1H).

Synthesis of (3R)-3-amino-5-[(4-chlorophenyl)methyl]-1,1,4-trioxo-N-[(oxolan-3-yl)methyl]-2,3,4,5-tetrahydro-1λ⁶,5-benzothiazepine-7-carboxamide (Example 157)

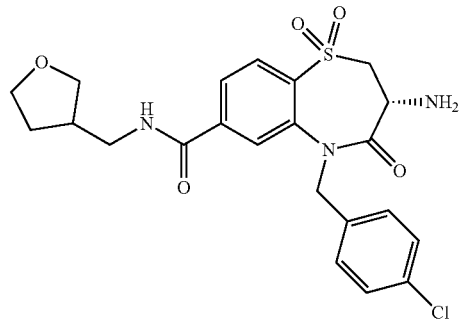 [SMILES: N[C@H]1CS(=O)(=O)c2ccc(C(=O)NCC3CCOC3)cc2N(Cc2ccc(Cl)cc2)C1=O]

The title compound was synthesized according to general procedure GP5 to afford the title compound as white crystalline solid in 40% yield.

LCMS: MET-UHPLC-AB-101, rt=1.9 min, M/Z (ES+) 478.1/480.1 [M+H+] 94% UV

NMR Data: 1H NMR (500 MHz, Chloroform-d) d 8.12 (dd, J=8.1, 1.1 Hz, 1H), 7.75 (ddd, J=8.1, 4.1, 1.6 Hz, 1H), 7.58 (dd, J=3.6, 1.5 Hz, 1H), 7.32 (s, 4H), 6.25 (s, 1H), 5.44-4.66 (m, 2H), 3.93 (dtd, J=13.7, 8.5, 5.2 Hz, 1H), 3.85-3.71 (m, 4H), 3.65 (dt, J=9.3, 5.0 Hz, 1H), 3.50 (m, 3H), 2.60 (dt, J=11.6, 6.5 Hz, 1H), 2.17-2.08 (m, 1H), 1.71-1.63 (m, 1H).

309

Synthesis of (3R)-3-amino-5-[(4-chlorophenyl)methyl]-N-[(1R)-2,2-difluorocyclopropyl]-1,1,4-trioxo-2,3,4,5-tetrahydro-1λ⁶,5-benzothiazepine-7-carboxamide (Example 158)

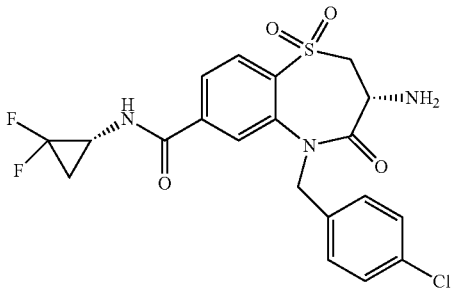 [SMILES: N[C@H]1CS(=O)(=O)c2ccc(C(=O)N[C@@H]3CC3(F)F)cc2N(Cc2ccc(Cl)cc2)C1=O]

The title compound was synthesized according to general procedure GP5 to afford the title compound as off-white solid in 78% yield.

LCMS: METCR1416 Generic 7 minutes, rt=3.03 min, M/Z (ES+) 470.1/472.10 [M+H+] 98% UV NMR Data: 1H NMR (500 MHz, DMSO-d6) d 9.12 (s, 1H), 7.99 (d, J=8.1 Hz, 1H), 7.93 (d, J=8.2 Hz, 1H), 7.81 (s, 1H), 7.36 (s, 4H), 5.17 (d, J=15.7 Hz, 1H), 4.86 (d, J=15.8 Hz, 1H), 3.88 (dd, J=12.9, 6.5 Hz, 1H), 3.71 (dd, J=11.0, 6.6 Hz, 1H), 3.67-3.56 (m, 1H), 3.50-3.42 (m, 1H), 2.17-1.91 (m, 3H), 1.70-1.60 (m, 1H).

Synthesis of (3R)-3-amino-5-[(4-cyclopropylphenyl)methyl]-N-[(1R)-2,2-difluorocyclopropyl]-1,1,4-trioxo-2,3,4,5-tetrahydro-1λ⁶,5-benzothiazepine-7-carboxamide (Example 159)

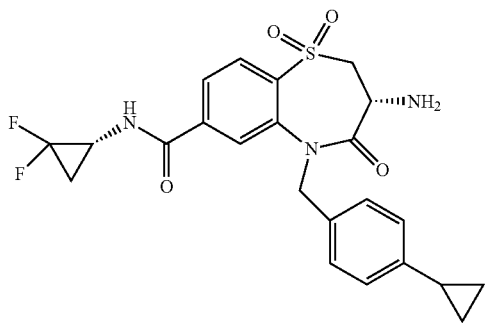 [SMILES: N[C@H]1CS(=O)(=O)c2ccc(C(=O)N[C@@H]3CC3(F)F)cc2N(Cc2ccc(C3CC3)cc2)C1=O]

The title compound was synthesized according to general procedure GP5 to afford the title compound as white solid in 69% yield.

LCMS: METCR1416 Generic 7 minutes, rt=2.22 min, M/Z (ES+) 476.1 [M+H+] 97% UV

NMR Data: 1H NMR (500 MHz, DMSO-d6) d 9.09 (s, 1H), 7.98 (d, J=8.1 Hz, 1H), 7.91 (d, J=8.1 Hz, 1H), 7.80 (s, 1H), 7.21 (d, J=8.1 Hz, 2H), 6.99 (d, J=8.2 Hz, 2H), 5.17 (d, J=15.6 Hz, 1H), 4.73 (d, J=15.6 Hz, 1H), 3.87 (dd, J=12.8, 6.4 Hz, 1H), 3.70 (dd, J=11.0, 6.5 Hz, 1H), 3.66-3.56 (m, 1H), 3.51-3.40 (m, 1H), 2.22-1.91 (m, 3H), 1.92-1.82 (m, 1H), 1.70-1.61 (m, 1H), 0.95-0.88 (m, 2H), 0.65-0.60 (m, 2H).

310

Synthesis of (3R)-3-amino-N-[(1R)-2,2-difluorocyclopropyl]-5-{[4-(difluoromethoxy)phenyl]methyl}-1,1,4-trioxo-2,3,4,5-tetrahydro-1λ⁶,5-benzothiazepine-7-carboxamide (Example 160)

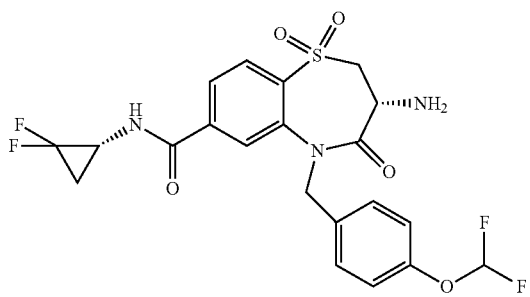 [SMILES: N[C@H]1CS(=O)(=O)c2ccc(C(=O)N[C@@H]3CC3(F)F)cc2N(Cc2ccc(OC(F)F)cc2)C1=O]

The title compound was synthesized according to general procedure GP5 to afford the title compound as white solid in 70% yield.

LCMS: METCR1416 Generic 7 minutes, rt=3.01 min, M/Z (ES+) 502.5 [M+H+] 99% UV

NMR Data: 1H NMR (500 MHz, DMSO-d6) d 9.12 (s, 1H), 8.00 (d, J=8.1 Hz, 1H), 7.93 (d, J=8.2 Hz, 1H), 7.84 (s, 1H), 7.40 (d, J=8.6 Hz, 2H), 7.21 (t, J=74.2 Hz, 1H), 7.11 (d, J=8.6 Hz, 2H), 5.19 (d, J=15.7 Hz, 1H), 4.85 (d, J=15.7 Hz, 1H), 3.89 (dd, J=12.8, 6.5 Hz, 1H), 3.72 (dd, J=11.2, 6.3 Hz, 1H), 3.67-3.58 (m, 1H), 3.51-3.43 (m, 1H), 2.11-1.89 (m, 3H), 1.71-1.59 (m, 1H).

Synthesis of (3R)-3-amino-N-[(1R)-2,2-difluorocyclopropyl]-5-[(4-methoxyphenyl)methyl]-1,1,4-trioxo-2,3,4,5-tetrahydro-1λ⁶,5-benzothiazepine-7-carboxamide (Example 161)

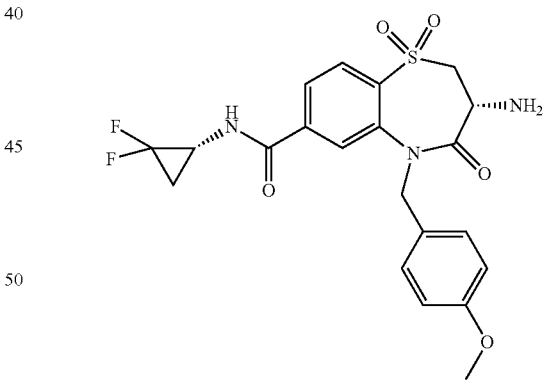

The title compound was synthesized according to general procedure GP5 to afford the title compound as off-white Solid in 59% yield.

LCMS: MET-UHPLC-AB-101, rt=1.84 min, M/Z (ES+) 466.1 [M+H+] 95% UV

NMR Data: 1H NMR (500 MHz, DMSO-d6) d 9.09 (s, 1H), 7.97 (d, J=8.1 Hz, 1H), 7.90 (d, J=8.3 Hz, 1H), 7.82 (d, J=1.1 Hz, 1H), 7.26 (d, J=8.6 Hz, 2H), 6.84 (d, J=8.7 Hz, 2H), 5.13 (d, J=15.3 Hz, 1H), 4.78 (d, J=15.3 Hz, 1H), 3.86 (dd, J=12.6, 6.2 Hz, 1H), 3.72 (s, 3H), 3.71-3.65 (m, 1H), 3.65-3.58 (m, 1H), 3.50-3.43 (m, 1H), 2.20-1.94 (m, 3H), 1.70-1.61 (m, 1H).

Synthesis of (3R)-3-amino-5-benzyl-1,1,4-trioxo-N-(4,4,4-trifluorobutyl)-2,3,4,5-tetrahydro-1λ⁶,5-benzothiazepine-7-carboxamide (Example 162)

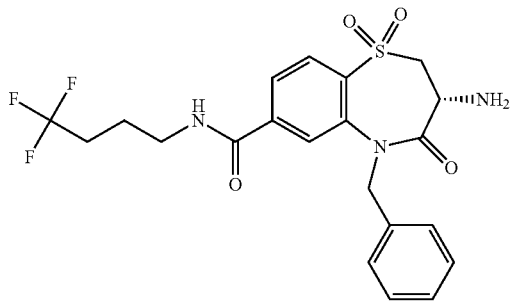 [SMILES: N[C@H]1CS(=O)(=O)c2ccc(C(=O)NCCCC(F)(F)F)cc2N(Cc2ccccc2)C1=O]

The title compound was synthesized according to general procedure GP5 to afford the title compound as cream foam/solid in 46% yield.

LCMS: METCR1416 Generic 7 minutes, rt=3 min, M/Z (ES+) 470.50 [M+H+] 100% UV

NMR Data: 1H NMR (500 MHz, DMSO-d6) d 8.79 (t, J=5.6 Hz, 1H), 7.97 (d, J=8.1 Hz, 1H), 7.91 (d, J=9.0 Hz, 1H), 7.78 (s, 1H), 7.35 (d, J=7.2 Hz, 2H), 7.30 (t, J=7.4 Hz, 2H), 7.24 (t, J=7.2 Hz, 1H), 5.23 (d, J=15.7 Hz, 1H), 4.79 (d, J=15.7 Hz, 1H), 3.88 (dd, J=12.9, 6.5 Hz, 1H), 3.71 (dd, J=11.1, 6.3 Hz, 1H), 3.67-3.59 (m, 1H), 3.37-3.32 (m, 2H), 2.34-2.22 (m, 2H), 2.05 (s, 2H), 1.72 (dt, J=14.7, 7.1 Hz, 2H).

Synthesis of (3R)-3-amino-8-chloro-5-[(4-chlorophenyl)methyl]-1,1,4-trioxo-N-(4,4,4-trifluorobutyl)-2,3,4,5-tetrahydro-1λ⁶,5-benzothiazepine-7-carboxamide (Example 163)

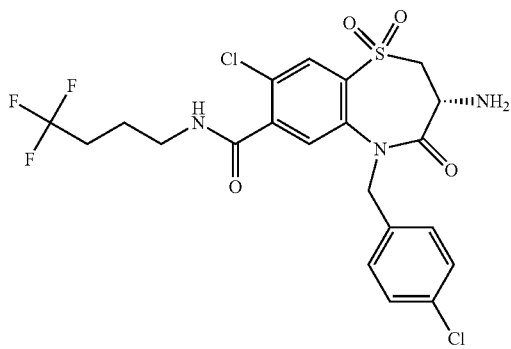 [SMILES: N[C@H]1CS(=O)(=O)c2cc(Cl)c(C(=O)NCCCC(F)(F)F)cc2N(Cc2ccc(Cl)cc2)C1=O]

The title compound was synthesized according to general procedure GP5 to afford the title compound as off white solid in 53% yield.

LCMS: MET-UHPLC-AB-101, rt=1.05 min, M/Z (ES+) 538.05/540.05 [M+H+] 96% UV

NMR Data: 1H NMR (500 MHz, DMSO-d6) d 8.68 (t, J=5.7 Hz, 1H), 7.85 (s, 1H), 7.55 (s, 1H), 7.39-7.31 (m, 4H), 5.12 (d, J=15.6 Hz, 1H), 4.93 (d, J=15.6 Hz, 1H), 3.94 (dd, J=12.6, 6.3 Hz, 1H), 3.76-3.69 (m, 1H), 3.69-3.63 (m, 1H), 3.30-3.24 (m, 2H), 2.35-2.06 (m, 4H), 1.71 (dt, J=14.6, 6.9 Hz, 2H).

Synthesis of (3R)-3-amino-5-{[4-(difluoromethoxy)phenyl]methyl}-N-[(oxan-4-yl)methyl]-1,1,4-trioxo-2,3,4,5-tetrahydro-1λ⁶,5-benzothiazepine-7-carboxamide (Example 164)

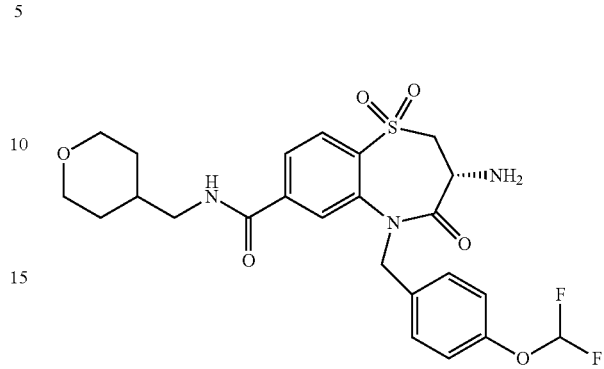

The title compound was synthesized according to general procedure GP5 to afford the title compound as white solid in 86% yield.

LCMS: METCR1416 Generic 7 minutes, rt=2.87 min, M/Z (ES+) 524.2 [M+H+] 100% UV

NMR Data: 1H NMR (500 MHz, DMSO-d6) d 8.75 (t, J=5.7 Hz, 1H), 7.97 (d, J=8.1 Hz, 1H), 7.92 (d, J=8.2 Hz, 1H), 7.80 (s, 1H), 7.41 (d, J=8.6 Hz, 2H), 7.21 (t, J=74.2 Hz, 1H), 7.10 (d, J=8.5 Hz, 2H), 5.19 (d, J=15.7 Hz, 1H), 4.85 (d, J=15.7 Hz, 1H), 3.92-3.80 (m, 3H), 3.74-3.67 (m, 1H), 3.66-3.59 (m, 1H), 3.29-3.21 (m, 2H), 3.15 (ap. t, J=6.3 Hz, 2H), 2.15-1.88 (m, 2H), 1.81-1.70 (br. m, 1H), 1.59-1.49 (m, 2H), 1.18 (ap. qd, J=12.3, 4.4 Hz, 2H).

Synthesis of (3R)-3-amino-5-[(4-chlorophenyl)methyl]-N-[(4-fluorooxan-4-yl)methyl]-1,1,4-trioxo-2,3,4,5-tetrahydro-1λ⁶,5-benzothiazepine-7-carboxamide (Example 165)

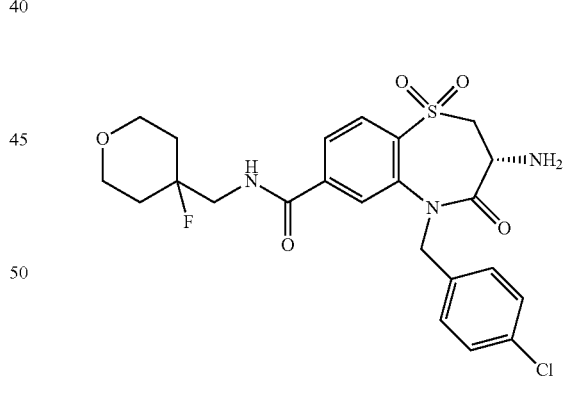

The title compound was synthesized according to general procedure GP5 to afford the title compound as white solid in 99% yield.

LCMS: METCR1416 Generic 7 minutes, rt=2.86 min, M/Z (ES+) 510.50/512 [M+H+] 99% UV NMR Data: 1H NMR (500 MHz, DMSO-d6) d 8.92 (t, J=6.1 Hz, 1H), 8.00-7.93 (m, 2H), 7.81 (s, 1H), 7.40-7.33 (m, 4H), 5.20 (d, J=15.7 Hz, 1H), 4.87 (d, J=15.6 Hz, 1H), 3.89 (dd, J=12.8, 6.5 Hz, 1H), 3.77-3.68 (m, 3H), 3.66-3.60 (m, 1H), 3.54 (dd, J=21.1, 6.4 Hz, 4H), 2.23-1.87 (m, 2H), 1.79-1.70 (m, 1H), 1.70-1.64 (m, 3H).

Synthesis of (3R)-3-amino-5-[(4-chlorophenyl)methyl]-N-[(1R)-1-(oxan-4-yl)ethyl]-1,1,4-trioxo-2,3,4,5-tetrahydro-1λ⁶,5-benzothiazepine-7-carboxamide (Example 166)

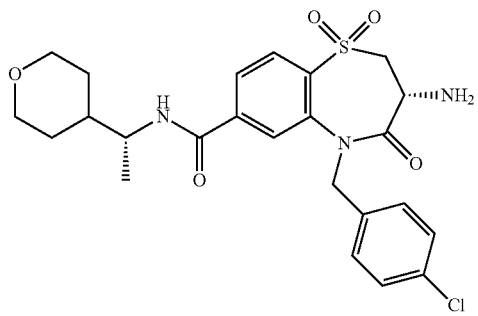 [SMILES: C[C@@H](NC(=O)c1ccc2c(c1)N(Cc1ccc(Cl)cc1)C(=O)[C@@H](N)CS2(=O)=O)C1CCOCC1]

The title compound was synthesized according to general procedure GP5 to afford the title compound as white solid in 93% yield.

LCMS: METCR1416 Generic 7 minutes, rt=2.9 min, M/Z (ES+) 507.05/509.20 [M+H+] 99% UV NMR Data: 1H NMR (500 MHz, DMSO-d6) d 8.41 (d, J=8.6 Hz, 1H), 7.96 (d, J=8.1 Hz, 1H), 7.91 (d, J=8.1 Hz, 1H), 7.72 (d, J=1.3 Hz, 1H), 7.42-7.33 (m, 4H), 5.23 (d, J=15.7 Hz, 1H), 4.83 (d, J=15.8 Hz, 1H), 3.92-3.77 (m, 4H), 3.75-3.69 (m, 1H), 3.66-3.58 (m, 1H), 3.29-3.18 (m, 2H), 2.00 (s, 2H), 1.66-1.48 (m, 3H), 1.26-1.14 (m, 2H), 1.12 (d, J=6.7 Hz, 3H).

Synthesis of (3R)-3-amino-5-benzyl-N-[(1R)-2,2-difluorocyclopropyl]-1,1,4-trioxo-2,3,4,5-tetrahydro-1λ⁶,5-benzothiazepine-7-carboxamide (Example 167)

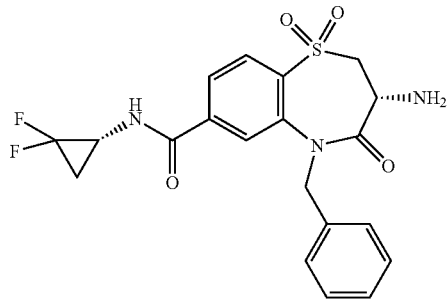 [SMILES: N[C@H]1CS(=O)(=O)c2ccc(C(=O)N[C@@H]3CC3(F)F)cc2N(Cc2ccccc2)C1=O]

The title compound was synthesized according to general procedure GP5 to afford the title compound as white solid in 88% yield.

LCMS: METCR1416 Generic 7 minutes, rt=2.75 min, M/Z (ES+) 436.45 [M+H+] 95.6% UV NMR Data: 1H NMR (500 MHz, DMSO-d6) d 9.09 (s, 1H), 7.99 (d, J=8.1 Hz, 1H), 7.91 (d, J=8.2 Hz, 1H), 7.79 (s, 1H), 7.39-7.22 (m, 5H), 5.24 (d, J=15.7 Hz, 1H), 4.77 (d, J=15.7 Hz, 1H), 3.88 (dd, J=12.9, 6.5 Hz, 1H), 3.73 (dd, J=11.0, 6.6 Hz, 1H), 3.63 (dd, J=12.8, 11.2 Hz, 1H), 3.45 (d, J=9.2 Hz, 1H), 2.19-1.92 (m, 3H), 1.64 (m, 1H).

Synthesis of (3R)-3-amino-5-[(4-chlorophenyl)methyl]-N-[(6-methylpyridin-3-yl)methyl]-1,1,4-trioxo-2,3,4,5-tetrahydro-1λ⁶,5-benzothiazepine-7-carboxamide (Example 168)

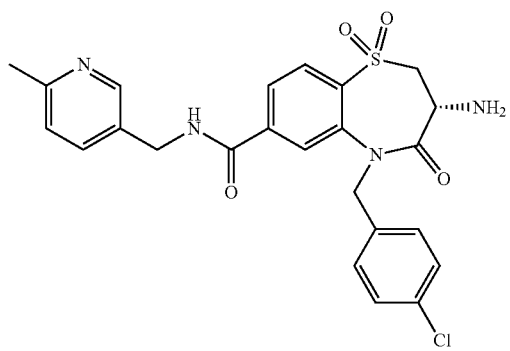 [SMILES: Cc1ccc(CNC(=O)c2ccc3c(c2)N(Cc2ccc(Cl)cc2)C(=O)[C@@H](N)CS3(=O)=O)cn1]

The title compound was synthesized according to general procedure GP5 to afford the title compound as white solid in 96% yield.

LCMS: METCR1416 Generic 7 minutes, rt=2.38 min, M/Z (ES+) 499.10/501.20 [M+H+] 100% UV NMR Data: 1H NMR (500 MHz, DMSO-d6) d 9.31 (t, J=5.8 Hz, 1H), 8.40 (d, J=1.8 Hz, 1H), 7.99-7.89 (m, 2H), 7.85 (s, 1H), 7.57 (dd, J=7.9, 2.3 Hz, 1H), 7.39-7.29 (m, 4H), 7.21 (d, J=8.0 Hz, 1H), 5.15 (d, J=15.8 Hz, 1H), 4.89 (d, J=15.8 Hz, 1H), 4.45 (d, J=5.8 Hz, 2H), 3.87 (dd, J=12.7, 6.3 Hz, 1H), 3.77-3.65 (m, 1H), 3.65-3.55 (m, 1H), 2.44 (s, 3H), 1.99 (br. s, 2H).

Synthesis of (3R)-3-amino-5-[(4-chlorophenyl)methyl]-N-[(1R)-3,3-difluorocyclopentyl]-1,1,4-trioxo-2,3,4,5-tetrahydro-1λ⁶,5-benzothiazepine-7-carboxamide (Example 169)

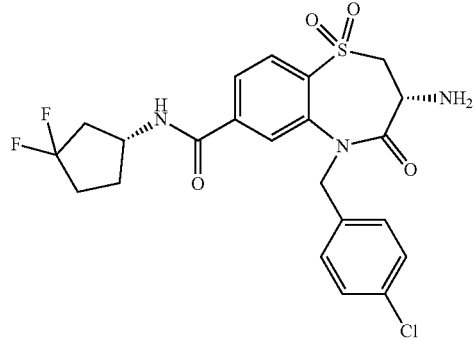 [SMILES: N[C@H]1CS(=O)(=O)c2ccc(C(=O)N[C@@H]3CCC(F)(F)C3)cc2N(Cc2ccc(Cl)cc2)C1=O]

The title compound was synthesized according to general procedure GP5 to afford the title compound as white solid in 80% yield.

LCMS: METCR1416 Generic 7 minutes, rt=3.11 min, M/Z (ES+) 498.50/500.10 [M+H+] 100% UV NMR Data: 1H NMR (500 MHz, DMSO-d6) d 8.82 (d, J=7.0 Hz, 1H), 8.01-7.90 (m, 2H), 7.79 (s, 1H), 7.36 (s, 4H), 5.18 (d, J=15.7 Hz, 1H), 4.84 (d, J=15.7 Hz, 1H), 4.39 (h, J=7.6 Hz, 1H), 3.87 (dd, J=12.6, 6.2 Hz, 1H), 3.73-3.66 (m, 1H), 3.66-3.53 (m, 1H), 2.58-2.43 (m, 1H), 2.33-2.20 (m, 1H), 2.20-2.04 (m, 3H), 1.99 (s, 2H), 1.85-1.74 (m, 1H).

Synthesis of (3R)-3-amino-5-[(4-cyanophenyl)methyl]-8-fluoro-N-[(4-fluorophenyl)methyl]-1,1,4-trioxo-2,3,4,5-tetrahydro-1λ$^6$,5-benzothiazepine-7-carboxamide (Example 170)

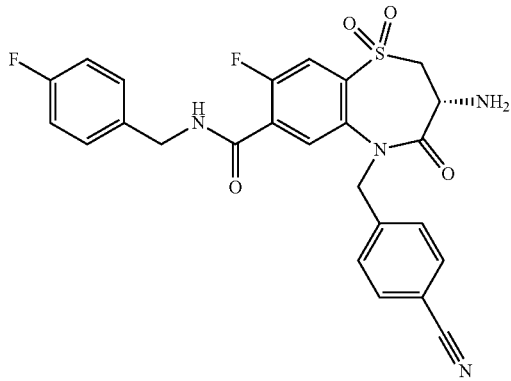 [SMILES: N#Cc1ccc(CN2C(=O)[C@@H](N)CS(=O)(=O)c3cc(F)c(C(=O)NCc4ccc(F)cc4)cc32)cc1]

The title compound was synthesized according to general procedure GP5 to afford the title compound as white solid in 42% yield.

LCMS: MET-UHPLC-AB-101, rt=2.16 min, M/Z (ES+) 511.1 [M+H+] 99% UV

NMR Data: 1H NMR (500 MHz, DMSO-d6) d 9.12 (t, J=5.9 Hz, 1H), 7.81-7.77 (m, 2H), 7.74 (d, J=8.6 Hz, 1H), 7.60 (d, J=5.5 Hz, 1H), 7.54 (d, J=8.3 Hz, 2H), 7.35-7.27 (m, 2H), 7.22-7.13 (m, 2H), 5.23 (d, J=16.3 Hz, 1H), 4.88 (d, J=16.2 Hz, 1H), 4.49-4.36 (m, 2H), 3.91 (dd, J=13.0, 6.7 Hz, 1H), 3.81-3.72 (m, 1H), 3.65 (dd, J=12.9, 11.1 Hz, 1H), 2.00 (s, 2H).

Synthesis of (3R)-3-amino-5-[(4-chlorophenyl)methyl]-N-[(3,3-difluorocyclobutyl)methyl]-1,1,4-trioxo-2,3,4,5-tetrahydro-1λ$^6$,5-benzothiazepine-7-carboxamide (Example 171)

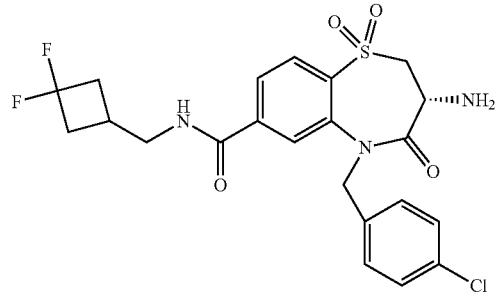 [SMILES: N[C@H]1CS(=O)(=O)c2ccc(C(=O)NCC3CC(F)(F)C3)cc2N(Cc2ccc(Cl)cc2)C1=O]

The title compound was synthesized according to general procedure GP5 to afford the title compound as off white solid in 62% yield.

LCMS: MET-UHPLC-AB-101, rt=2.31 min, M/Z (ES+) 498.1/500.1 [M+H+] 100% UV

NMR Data: 1H NMR (250 MHz, Chloroform-d) d 8.09 (d, J=8.1 Hz, 1H), 7.71 (dd, J=8.2, 1.4 Hz, 1H), 7.53 (s, 1H), 7.29 (s, 4H), 6.13-6.00 (m, 1H), 5.37 (d, J=15.2 Hz, 1H), 4.69 (d, J=15.1 Hz, 1H), 3.93-3.64 (m, 2H), 3.64-3.42 (m, 3H), 2.87-2.60 (m, 2H), 2.55-2.17 (m, 3H) [NH2 not visible]

Synthesis of (3R)-3-amino-5-[(4-chlorophenyl)methyl]-8-fluoro-N-[2-(2-methoxyethoxy)ethyl]-1,1,4-trioxo-2,3,4,5-tetrahydro-1λ$^6$,5-benzothiazepine-7-carboxamide (Example 172)

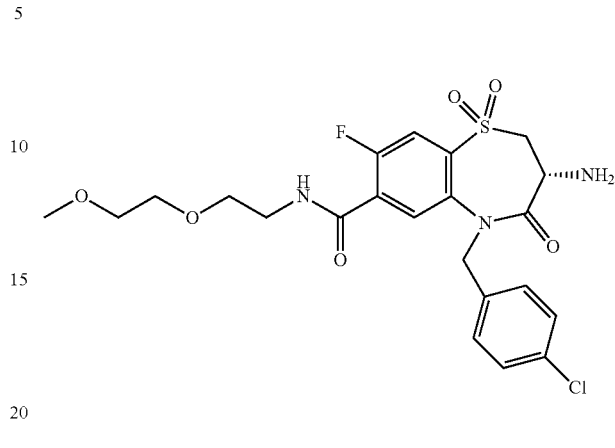

The title compound was synthesized according to general procedure GP5 to afford the title compound as off white solid in 66% yield.

LCMS: METCR1416 Generic 7 minutes, rt=2.87 min, M/Z (ES+) 515/517.25 [M+H+]; 536.10/538.05 [M+Na+] 99% UV; NMR Data: 1H NMR (500 MHz, DMSO-d6) d 8.61 (t, J=5.4 Hz, 1H), 7.72 (d, J=8.6 Hz, 1H), 7.59 (d, J=5.5 Hz, 1H), 7.37 (s, 4H), 5.15 (d, J=15.8 Hz, 1H), 4.80 (d, J=15.8 Hz, 1H), 3.90 (dd, J=12.9, 6.5 Hz, 1H), 3.77-3.70 (m, 1H), 3.69-3.61 (m, 1H), 3.55-3.48 (m, 4H), 3.45-3.38 (m, 4H), 3.24 (s, 3H), 2.02 (s, 2H).

Synthesis of (3R)-3-amino-N-(but-3-yn-1-yl)-5-[(4-chlorophenyl)methyl]-8-fluoro-1,1,4-trioxo-2,3,4,5-tetrahydro-1λ$^6$,5-benzothiazepine-7-carboxamide (Example 173)

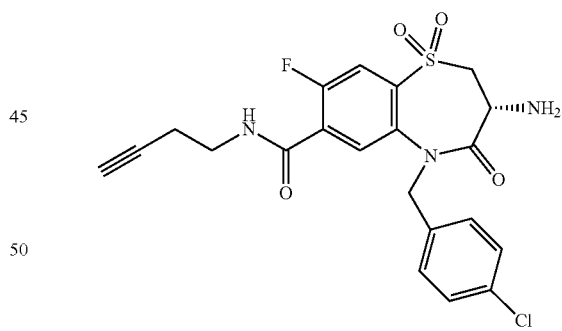

The title compound was synthesized according to general procedure GP5 to afford the title compound as off white solid in 79% yield.

LCMS: METCR1416 Generic 7 minutes, rt=2.97 min, M/Z (ES+) 464.05/466.05 [M+H+] 96% UV NMR Data: 1H NMR (500 MHz, DMSO-d6) d 8.71 (t, J=5.5 Hz, 1H), 7.73 (d, J=8.6 Hz, 1H), 7.62 (d, J=5.6 Hz, 1H), 7.37 (s, 4H), 5.15 (d, J=15.8 Hz, 1H), 4.80 (d, J=15.8 Hz, 1H), 3.90 (dd, J=12.9, 6.5 Hz, 1H), 3.73 (dd, J=10.9, 6.6 Hz, 1H), 3.68-3.61 (m, 1H), 3.37 (dt, J=13.7, 7.1 Hz, 2H), 2.80 (t, J=2.6 Hz, 1H), 2.41 (td, J=7.0, 2.6 Hz, 2H), 2.12-1.97 (m, 2H).

Synthesis of (3R)-3-amino-5-[(4-chlorophenyl)methyl]-8-fluoro-1,1,4-trioxo-N-(pent-4-yn-1-yl)-2,3,4,5-tetrahydro-1λ⁶,5-benzothiazepine-7-carboxamide (Example 174)

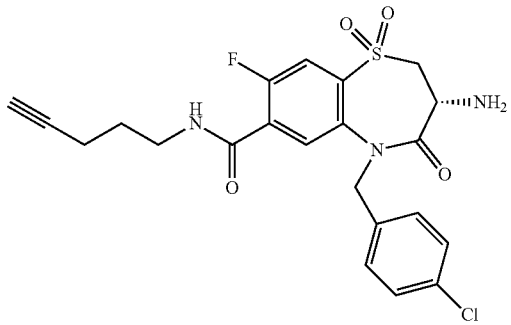 [SMILES: C#CCCCNC(=O)c1cc2c(cc1F)S(=O)(=O)C[C@H](N)C(=O)N2Cc1ccc(Cl)cc1]

The title compound was synthesized according to general procedure GP5 to afford the title compound as off white solid in 81% yield.

LCMS: METCR1416 Generic 7 minutes, rt=3.04 min, M/Z (ES+) 477/479 [M+H+] 95% UV

NMR Data: 1H NMR (500 MHz, DMSO-d6) d 8.61 (t, J=5.5 Hz, 1H), 7.72 (d, J=8.5 Hz, 1H), 7.60 (d, J=5.5 Hz, 1H), 7.37 (s, 4H), 5.15 (d, J=15.7 Hz, 1H), 4.82 (d, J=15.7 Hz, 1H), 3.90 (dd, J=12.7, 6.3 Hz, 1H), 3.76-3.70 (m, 1H), 3.68-3.60 (m, 1H), 3.32 (s, 2H), 2.80 (t, J=2.6 Hz, 1H), 2.21 (td, J=7.1, 2.6 Hz, 2H), 2.01 (s, 2H), 1.68 (t, J=7.0 Hz, 2H)

Synthesis of (3R)-3-amino-8-chloro-5-[(4-chlorophenyl)methyl]-N-[(1R)-2,2-difluorocyclopropyl]-1,1,4-trioxo-2,3,4,5-tetrahydro-1λ⁶,5-benzothiazepine-7-carboxamide (Example 175)

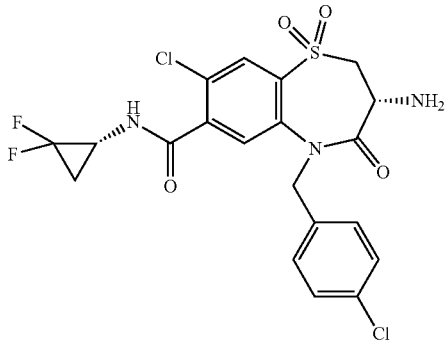 [SMILES: N[C@H]1CS(=O)(=O)c2cc(Cl)c(C(=O)N[C@@H]3CC3(F)F)cc2N(Cc2ccc(Cl)cc2)C1=O]

The title compound was synthesized according to general procedure GP5 to afford the title compound as white solid in 64% yield.

LCMS: METCR1416 Generic 7 minutes, rt=3.03 min, M/Z (ES+) 504.95/507.05 [M+H+] 97% UV NMR Data: 1H NMR (500 MHz, DMSO-d6) d 9.07 (s, 1H), 7.86 (s, 1H), 7.56 (s, 1H), 7.35 (s, 4H), 5.12 (d, J=15.7 Hz, 1H), 4.91 (d, J=15.6 Hz, 1H), 3.93 (dd, J=12.4, 6.0 Hz, 1H), 3.79-3.58 (m, 2H), 3.55-3.43 (m, 1H), 2.20-1.93 (m, 3H), 1.54 (ddt, J=14.6, 9.0, 5.6 Hz, 1H).

Synthesis of (3R)-3-amino-5-[(4-chlorophenyl)methyl]-N-[2-(morpholin-4-yl)ethyl]-1,1,4-trioxo-2,3,4,5-tetrahydro-1λ⁶,5-benzothiazepine-7-carboxamide (Example 176)

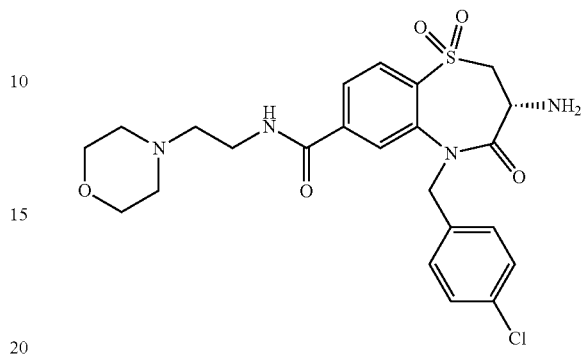

The title compound was synthesized according to general procedure GP5 to afford the title compound as white solid in 93% yield.

LCMS: MET-UHPLC-AB-101, rt=1.28 min, M/Z (ES+) 507.1/509.1 [M+H+] 95% UV

NMR Data: 1H NMR (500 MHz, DMSO-d6) d 8.70 (t, J=5.7 Hz, 1H), 7.97 (d, J=8.1 Hz, 1H), 7.91 (d, J=8.2 Hz, 1H), 7.80 (s, 1H), 7.39-7.32 (m, 4H), 5.17 (d, J=15.8 Hz, 1H), 4.88 (d, J=15.9 Hz, 1H), 3.88 (dd, J=13.0, 6.6 Hz, 1H), 3.76-3.67 (m, 1H), 3.67-3.58 (m, 1H), 3.58-3.50 (m, 4H), 3.41-3.36 (m, 2H), 2.45 (t, J=6.8 Hz, 2H), 2.42-2.38 (m, 4H), 2.00 (br. s, 2H).

Synthesis of (3R)-3-amino-5-[(4-chlorophenyl)methyl]-N-[(6-methoxypyridin-3-yl)methyl]-1,1,4-trioxo-2,3,4,5-tetrahydro-1λ⁶,5-benzothiazepine-7-carboxamide (Example 177)

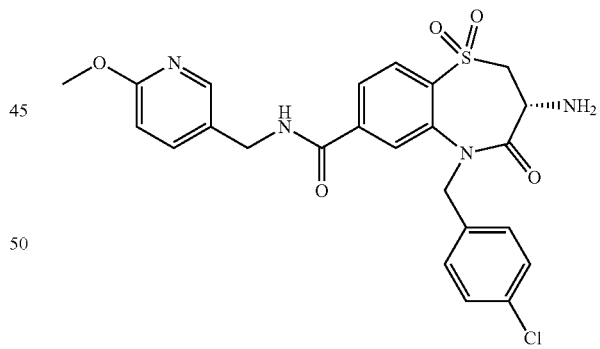

The title compound was synthesized according to general procedure GP5 to afford the title compound as off-white solid in 76% yield.

LCMS: MET-UHPLC-AB-101, rt=2.16 min, M/Z (ES+) 515.1/517.1 [M+H+] 98% UV

NMR Data: 1H NMR (500 MHz, DMSO-d6) d 9.28 (t, J=5.8 Hz, 1H), 8.13 (d, J=2.3 Hz, 1H), 8.01-7.91 (m, 2H), 7.86 (s, 1H), 7.64 (dd, J=8.5, 2.5 Hz, 1H), 7.40-7.30 (m, 4H), 6.80 (d, J=8.5 Hz, 1H), 5.16 (d, J=15.7 Hz, 1H), 4.90 (d, J=15.7 Hz, 1H), 4.42 (d, J=5.7 Hz, 2H), 3.88 (dd, J=13.3, 7.0 Hz, 1H), 3.84 (s, 3H), 3.73-3.66 (m, 1H), 3.66-3.56 (m, 1H), 1.96 (s, 2H).

Synthesis of (3R)-3-amino-5-[(4-chlorophenyl)methyl]-8-fluoro-1,1,4-trioxo-N-{[4-(prop-2-yn-1-yloxy)phenyl]methyl}-2,3,4,5-tetrahydro-1λ⁶,5-benzothiazepine-7-carboxamide (Example 178)

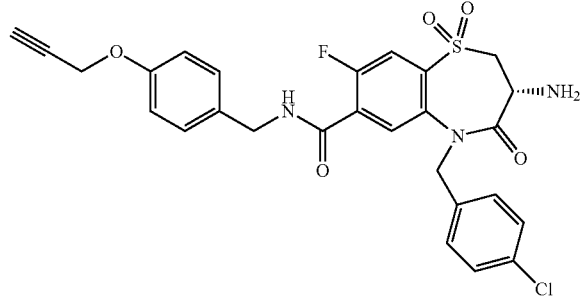 [SMILES: C#CCOc1ccc(CNC(=O)c2cc3c(cc2F)S(=O)(=O)C[C@H](N)C(=O)N3Cc2ccc(Cl)cc2)cc1]

The title compound was synthesized according to general procedure GP5 to afford the title compound as off white solid in 65% yield.
LCMS: METCR1416 Generic 7 minutes, rt=3.27 min, M/Z (ES+) 556.50/558.10 [M+H+] 100% UV
NMR Data: 1H NMR (500 MHz, DMSO-d6) d 9.06 (t, J=5.7 Hz, 1H), 7.73 (d, J=8.6 Hz, 1H), 7.62 (d, J=5.5 Hz, 1H), 7.37 (s, 4H), 7.23 (d, J=8.6 Hz, 2H), 6.96 (d, J=8.7 Hz, 2H), 5.17 (d, J=15.7 Hz, 1H), 4.84-4.74 (m, 3H), 4.49-4.31 (m, 2H), 3.91 (dd, J=12.8, 6.4 Hz, 1H), 3.77-3.69 (m, 1H), 3.68-3.62 (m, 1H), 3.55 (t, J=2.4 Hz, 1H), 2.00 (s, 2H).

Synthesis of (3R)-3-amino-N-[(1R)-2,2-difluorocyclopropyl]-1,1,4-trioxo-5-{[4-(trifluoromethyl)phenyl]methyl}-2,3,4,5-tetrahydro-1λ⁶,5-benzothiazepine-7-carboxamide (Example 179)

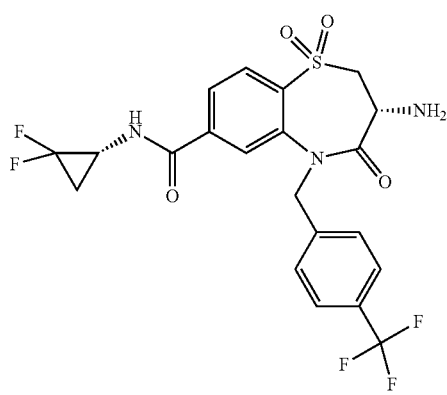 [SMILES: N[C@H]1CS(=O)(=O)c2ccc(C(=O)N[C@@H]3CC3(F)F)cc2N(Cc2ccc(C(F)(F)F)cc2)C1=O]

The title compound was synthesized according to general procedure GP5 to afford the title compound as white solid in 87% yield.
LCMS: METCR1416 Generic 7 minutes, rt=3.07 min, M/Z (ES+) 504.5 [M+H+] 99% UV
NMR Data: 1H NMR (500 MHz, DMSO-d6) d 9.11 (s, 1H), 8.01 (d, J=8.1 Hz, 1H), 7.95 (d, J=8.2 Hz, 1H), 7.82 (s, 1H), 7.68 (d, J=8.2 Hz, 2H), 7.58 (d, J=8.1 Hz, 2H), 5.28 (d, J=16.1 Hz, 1H), 4.93 (d, J=16.1 Hz, 1H), 3.90 (dd, J=13.0, 6.6 Hz, 1H), 3.74 (dd, J=11.0, 6.7 Hz, 1H), 3.64 (dd, J=12.9, 11.1 Hz, 1H), 3.52-3.40 (m, 1H), 2.08-1.91 (m, 3H), 1.69-1.58 (m, 1H).

Synthesis of (3R)-3-amino-5-[(4-bromophenyl)methyl]-N-(2,2-difluorocyclopropyl)-1,1,4-trioxo-2,3,4,5-tetrahydro-1λ⁶,5-benzothiazepine-7-carboxamide (Example 180)

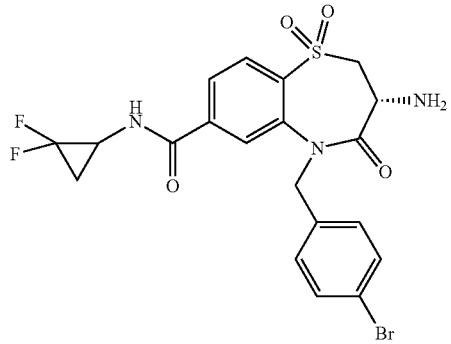 [SMILES: N[C@H]1CS(=O)(=O)c2ccc(C(=O)NC3CC3(F)F)cc2N(Cc2ccc(Br)cc2)C1=O]

The title compound was synthesized according to general procedure GP5 to afford the title compound as white solid in 88% yield.
LCMS: METCR1416 Generic 7 minutes, rt=3.01 min, M/Z (ES+) 515.75/517.10 [M+H+] 99% UV
NMR Data: 1H NMR (500 MHz, DMSO-d6) d 9.12 (s, 1H), 8.00 (d, J=8.1 Hz, 1H), 7.97-7.91 (m, 1H), 7.84 (d, J=11.6 Hz, 1H), 7.50 (dd, J=8.5, 2.2 Hz, 2H), 7.31 (d, J=8.0 Hz, 2H), 5.21-5.07 (m, 1H), 4.92-4.77 (m, 1H), 3.89 (dd, J=12.6, 5.9 Hz, 1H), 3.78-3.67 (m, 1H), 3.67-3.58 (m, 1H), 3.52-3.41 (m, 1H), 2.25 (br. s, 2H), 2.07-1.95 (m, 1H), 1.74-1.57 (m, 1H).

Synthesis of (3R)-3-amino-5-[(4-chlorophenyl)methyl]-N-{2-oxaspiro[3.3]heptan-6-yl}-1,1,4-trioxo-2,3,4,5-tetrahydro-1λ⁶,5-benzothiazepine-7-carboxamide (Example 181)

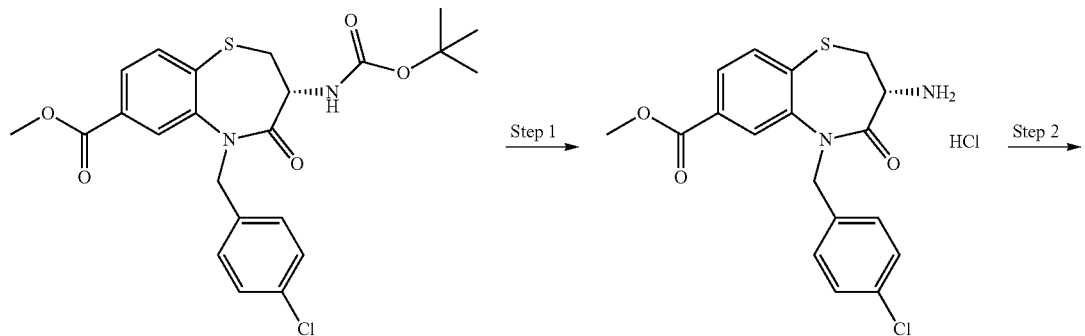

Intermediate VI-06

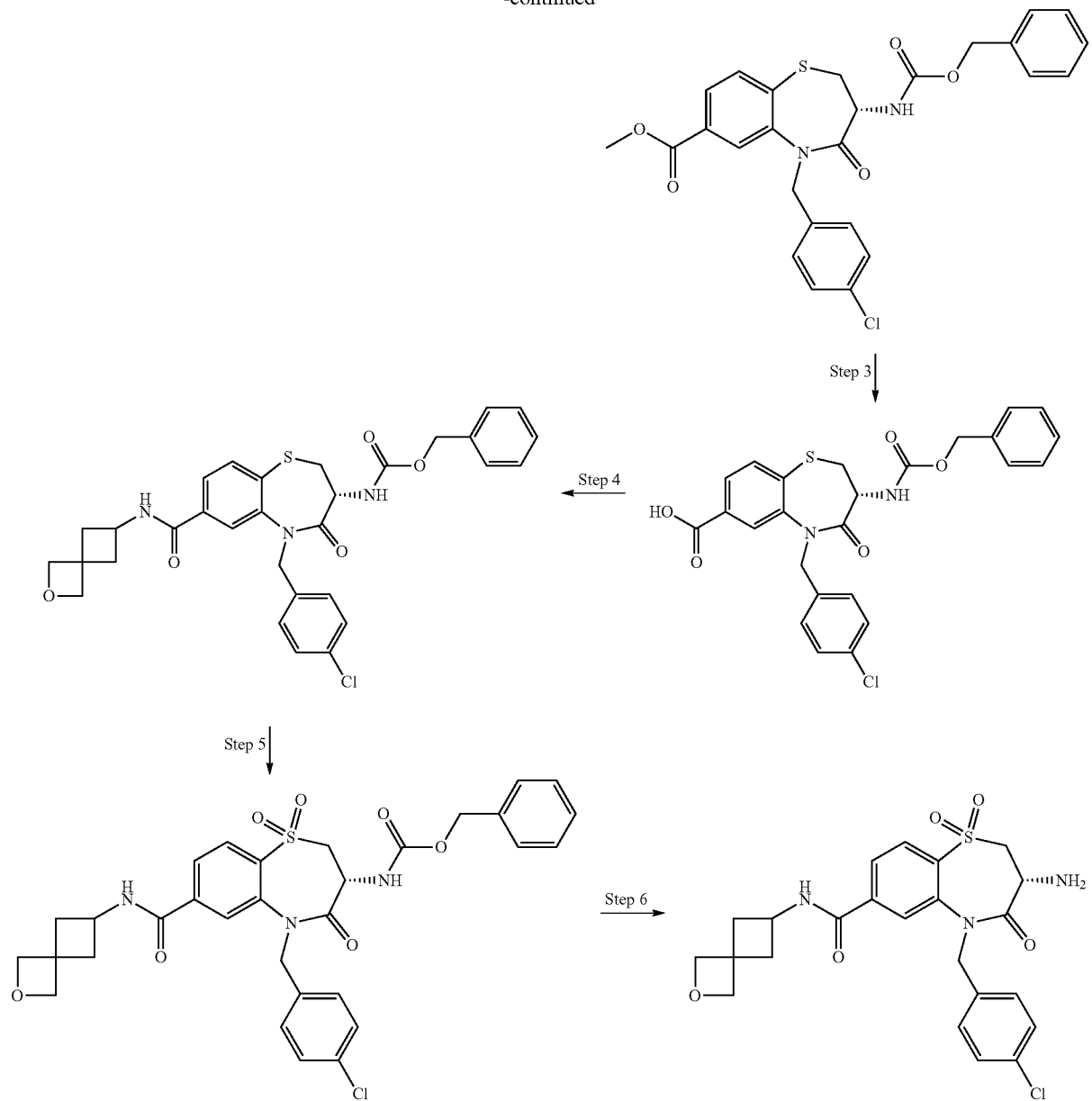

Step 1: Synthesis of methyl (3R)-3-amino-5-[(4-chlorophenyl)methyl]-4-oxo-2,3,4,5-tetrahydro-1,5-benzothiazepine-7-carboxylate hydrochloride The title compound was synthesized from intermediate IV-06 according to general procedure GP5 to afford the title compound in quantitative yield.

LCMS: METCR1410 Generic 1.7 minutes, rt=0.94 min, M/Z (ES+) 377/379 [M+H+] 98% UV 1H NMR (500 MHz, DMSO-d6) δ 8.59 (s, 3H), 8.00 (d, J=1.6 Hz, 1H), 7.84 (dd, J=8.0, 1.7 Hz, 1H), 7.79 (d, J=8.0 Hz, 1H), 7.36-7.28 (m, 4H), 5.31 (d, J=15.6 Hz, 1H), 5.02 (d, J=15.6 Hz, 1H), 4.02 (dd, J=11.8, 6.8 Hz, 1H), 3.87 (s, 3H), 3.74-3.67 (m, 1H), 3.28 (t, J=11.7 Hz, 1H).

Step 2: Synthesis of methyl (3R)-3-{[(benzyloxy)carbonyl]amino}-5-[(4-chlorophenyl)methyl]-4-oxo-2,3,4,5-tetrahydro-1,5-benzothiazepine-7-carboxylate To a solution of methyl (3R)-3-amino-5-[(4-chlorophenyl)methyl]-4-oxo-2,3,4,5-tetrahydro-1,5-benzothiazepine-7-carboxylate hydrochloride (230 mg, 0.56 mmol) in DCM (6 ml) was added DIPEA (290 μl, 1.67 mmol) then benzyl chloroformate (945 μl, 0.67 mmol). The resultant mixture was stirred at RT for 1.5 h. To the reaction mixture was added water (20 ml) and DCM (20 ml). The mixture was partitioned through a phase separator (TELOS). The organic layer was concentrated to give a pale yellow oil. The residue was purified by column chromatography (silica, eluent: heptanes, 0-50% EtOAc) to obtain the desired title compound as a white solid (0.28 g, quantitative yield) in 99% purity.

LCMS: METCR1410 Generic 1.7 min, rt=1.31 min, M/Z (ES+) 533/535 [M+Na+] 99% UV

1H NMR (500 MHz, Chloroform-d) δ 7.92 (s, 1H), 7.84 (dd, J=8.0, 1.7 Hz, 1H), 7.66 (d, J=8.0 Hz, 1H), 7.37-7.27 (m, 5H), 7.19 (s, 4H), 5.82 (d, J=7.7 Hz, 1H), 5.44 (d, J=15.1 Hz, 1H), 5.04 (s, 2H), 4.72 (d, J=15.1 Hz, 1H), 4.51-4.37 (m, 1H), 3.93 (s, 3H), 3.74 (dd, J=10.9, 6.6 Hz, 1H), 2.94 (t, J=11.2 Hz, 1H).

Step 3: Synthesis of (3R)-3-{[(benzyloxy)carbonyl]amino}-5-[(4-chlorophenyl)methyl]-4-oxo-2,3,4,5-tetrahydro-1,5-benzothiazepine-7-carboxylic acid The title compound was synthesized from methyl (3R)-3-{[(benzyloxy)carbonyl]amino}-5-[(4-chlorophenyl)methyl]-4-oxo-2,3,4,5-tetrahydro-1,5-benzothiazepine-7-carboxylate according to general procedure GP2 to afford the title compound in 94% yield (94% purity).

LCMS: METCR1410 Generic 1.7 min, rt=1.19 min, M/Z (ES+) 519/521 [M+Na+] 99% UV

1H NMR (500 MHz, Chloroform-d) δ 7.94 (d, J=1.5 Hz, 1H), 7.84 (d, J=8.0 Hz, 1H), 7.69 (d, J=8.0 Hz, 1H), 7.38-7.28 (m, 5H), 7.20 (s, 4H), 5.90 (d, J=7.9 Hz, 1H), 5.45 (d, J=15.1 Hz, 1H), 5.06 (s, 2H), 4.74 (d, J=15.1 Hz, 1H), 4.55-4.46 (m, 1H), 3.81-3.72 (m, 1H), 2.98 (t, J=11.3 Hz, 1H).

Step 4: Synthesis of benzyl N-[(3R)-5-[(4-chlorophenyl)methyl]-7-({2-oxaspiro[3.3]heptan-6-yl}carbamoyl)-4-oxo-2,3,4,5-tetrahydro-1,5-benzothiazepin-3-yl]carbamate The title compound was synthesized from (3R)-3-{[(benzyloxy)carbonyl]amino}-5-[(4-chlorophenyl)methyl]-4-oxo-2,3,4,5-tetrahydro-1,5-benzothiazepine-7-carboxylic acid according to general procedure GP3 to afford the title compound in 83% yield (94% purity).

LCMS: METCR1410 Generic 1.7 min, rt=1.18 min, M/Z (ES+) 592/594 [M+H+] and 614/616 [M+Na+]100% UV; 1H NMR (500 MHz, DMSO-d6) δ 8.70 (d, J=7.0 Hz, 1H), 7.93 (d, J=9.0 Hz, 2H), 7.68 (s, 2H), 7.37-7.21 (m, 9H), 5.33 (d, J=15.5 Hz, 1H), 4.99 (s, 2H), 4.88 (d, J=15.5 Hz, 1H), 4.63 (s, 2H), 4.51 (s, 2H), 4.24-4.14 (m, 2H), 3.50 (dd, J=11.1, 6.9 Hz, 1H), 3.11 (t, J=11.8 Hz, 1H), 2.62-2.55 (m, 2H), 2.29-2.19 (m, 2H).

Step 5: Synthesis of benzyl N-[(3R)-5-[(4-chlorophenyl)methyl]-7-({2-oxaspiro[3.3]heptan-6-yl}carbamoyl)-1,1,4-trioxo-2,3,4,5-tetrahydro-1λ$^6$,5-benzothiazepin-3-yl]carbamate The title compound was synthesized from benzyl N-[(3R)-5-[(4-chlorophenyl)methyl]-7-({2-oxaspiro[3.3]heptan-6-yl}carbamoyl)-4-oxo-2,3,4,5-tetrahydro-1,5-benzothiazepin-3-yl]carbamate according to general procedure GP4 to afford the title compound in 84% yield (92% purity).

LCMS: METCR1410 Generic 1.7 min, rt=1.12 min, M/Z (ES+) 624/626 [M+H+] and 646/648 [M+Na+]100% UV; 1H NMR (500 MHz, DMSO-d6) δ 8.90 (d, J=7.0 Hz, 1H), 8.03-7.92 (m, 3H), 7.81 (s, 1H), 7.33 (t, J=8.3 Hz, 9H), 5.19 (d, J=15.9 Hz, 1H), 5.03 (s, 2H), 4.86 (d, J=15.9 Hz, 1H), 4.63 (s, 2H), 4.51 (s, 2H), 4.47-4.39 (m, 1H), 4.23-4.09 (m, 2H), 3.77-3.67 (m, 1H), 2.59 (dd, J=11.8, 7.5 Hz, 2H), 2.28-2.18 (m, 2H).

Step 6: Synthesis of (3R)-3-amino-5-[(4-chlorophenyl)methyl]-N-{2-oxaspiro[3.3]heptan-6-yl}-1,1,4-trioxo-2,3,4,5-tetrahydro-1λ$^6$,5-benzothiazepine-7-carboxamide (Example 181)

A suspension of benzyl N-[(3R)-5-[(4-chlorophenyl)methyl]-7-({2-oxaspiro[3.3]heptan-6-yl}carbamoyl)-1,1,4-trioxo-2,3,4,5-tetrahydro-1λ$^6$,5-benzothiazepin-3-yl]carbamate (55 mg, 0.08 mmol) and Pd/C (10%, 8.63 mg, 0.01 mmol) in a mixture of EtOH (2 ml) and DCM (2 ml) was stirred under hydrogen atmosphere at RT for 3 h. The reaction mixture was filtered through a pad of Celite® and washed with EtOH. The filtrate was concentrated under reduced pressure. The residue was purified by column chromatography (silica, 0-10% (7N NH3 in MeOH) in DCM) to yield a mixture of the title compound (86%) and dehalogenated by-product (14%)

LCMS: METCR1416 Generic 7 minutes: rt=2.81 min, M/Z (ES+) 490/492 [M+H+] UV=86%

NMR Data: 1H NMR (500 MHz, DMSO-d6) δ 8.84 (d, J=7.1 Hz, 1H), 7.96 (d, J=8.1 Hz, 1H), 7.91 (d, J=7.9 Hz, 1H), 7.78 (s, 1H), 7.35 (s, 4H), 5.17 (d, J=15.7 Hz, 1H), 4.85 (d, J=15.7 Hz, 1H), 4.62 (s, 2H), 4.50 (s, 2H), 4.18 (ap. h, J=8.1 Hz, 1H), 3.87 (dd, J=12.6, 6.2 Hz, 1H), 3.67 (s, 1H), 3.64-3.57 (m, 1H), 2.58 (td, J=7.5, 4.0 Hz, 2H), 2.22 (ddd, J=12.9, 8.2, 4.9 Hz, 2H), 1.98 (br. s, 2H).

Synthesis of (3R)-5-[(4-chlorophenyl)methyl]-3-(ethylamino)-8-fluoro-1,1,4-trioxo-N-(4,4,4-trifluorobutyl)-2,3,4,5-tetrahydro-1λ$^6$,5-benzothiazepine-7-carboxamide (Example 182)

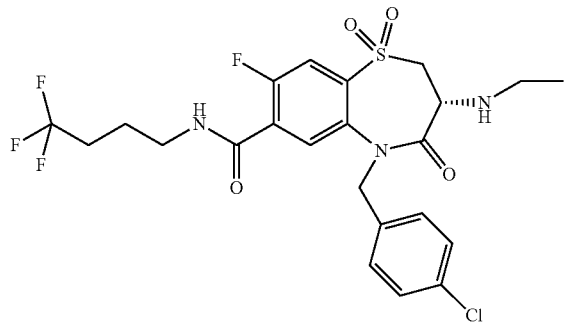 [SMILES: CCN[C@H]1CS(=O)(=O)c2cc(F)c(C(=O)NCCCC(F)(F)F)cc2N(Cc2ccc(Cl)cc2)C1=O]

To a solution of (3R)-3-amino-5-[(4-chlorophenyl)methyl]-8-fluoro-1,1,4-trioxo-N-(4,4,4-trifluorobutyl)-2,3,4,5-tetrahydro-1λ$^6$,5-benzothiazepine-7-carboxamide (100 mg, 0.19 mmol) in 1.2 DCE (2 mL) was added acetaldehyde (8.2 μL, 0.15 mmol). Sodium acetate (19 mg, 0.23 mmol) was added followed by sodium triacetoxyborohydride (61 mg, 0.287 mmol). The mixture was stirred at RT for 2 h. The reaction mixture was diluted with DCM (10 mL) and washed with water (5 mL), dried (Na2SO4), filtered and concentrated under reduced pressure, to give the crude residue, 125 mg containing the title compound (70%), closely eluting starting amine (~10%) and diethyl by-product (10%). The crude product was treated with Boc2O (47 mg, 0.22 mmol) and DIPEA (28 μL, 0.22 mmol) in THF (2 mL) for 3 h at RT. The reaction mixture was concentrated to dryness under reduced pressure, redissolved in DCM (10 mL) and washed with water (5 mL). The organic extracts were dried over Na2SO4, filtered and concentrated under reduced pressure. The crude product was purified by preparative HPLC (Acidic method) to afford the title compound as a formic acid salt, followed by SCX (2 g, washed with MeOH, eluted with 7M NH₃ solution in MeOH) to give 27 mg (23%) of the title compound as a white solid.

LCMS: MET-UHPLC-AB-101, rt=2.56 min, M/Z (ES+) 550.1/552.1 [M+H+] 100% UV

NMR Data: 1H NMR (500 MHz, DMSO-d6) δ 8.67 (t, J=5.4 Hz, 1H), 7.72 (d, J=8.6 Hz, 1H), 7.62 (d, J=5.6 Hz, 1H), 7.40-7.27 (m, 4H), 5.19 (d, J=15.8 Hz, 1H), 4.80 (d, J=15.8 Hz, 1H), 3.96 (dd, J=12.5, 6.2 Hz, 1H), 3.74-3.57 (m, 2H), 3.35-3.31 (m, 2H), 2.48-2.42 (m, 1H), 2.34-2.15 (m, 4H), 1.72 (dt, J=14.7, 7.0 Hz, 2H), 0.92 (t, J=7.0 Hz, 3H).

Procedures for 1H,2H,3H,4H-5λ⁶-pyrido[3,4-b][1,4] thiazepine derivatives

Synthesis of (3R)-3-amino-N-butyl-1-[(4-chlorophenyl)methyl]-2,5,5-trioxo-1H,2H,3H,4H-5λ⁶-pyrido [3,4-b][1,4]thiazepine-8-carboxamide hydrochloride (Example 183)

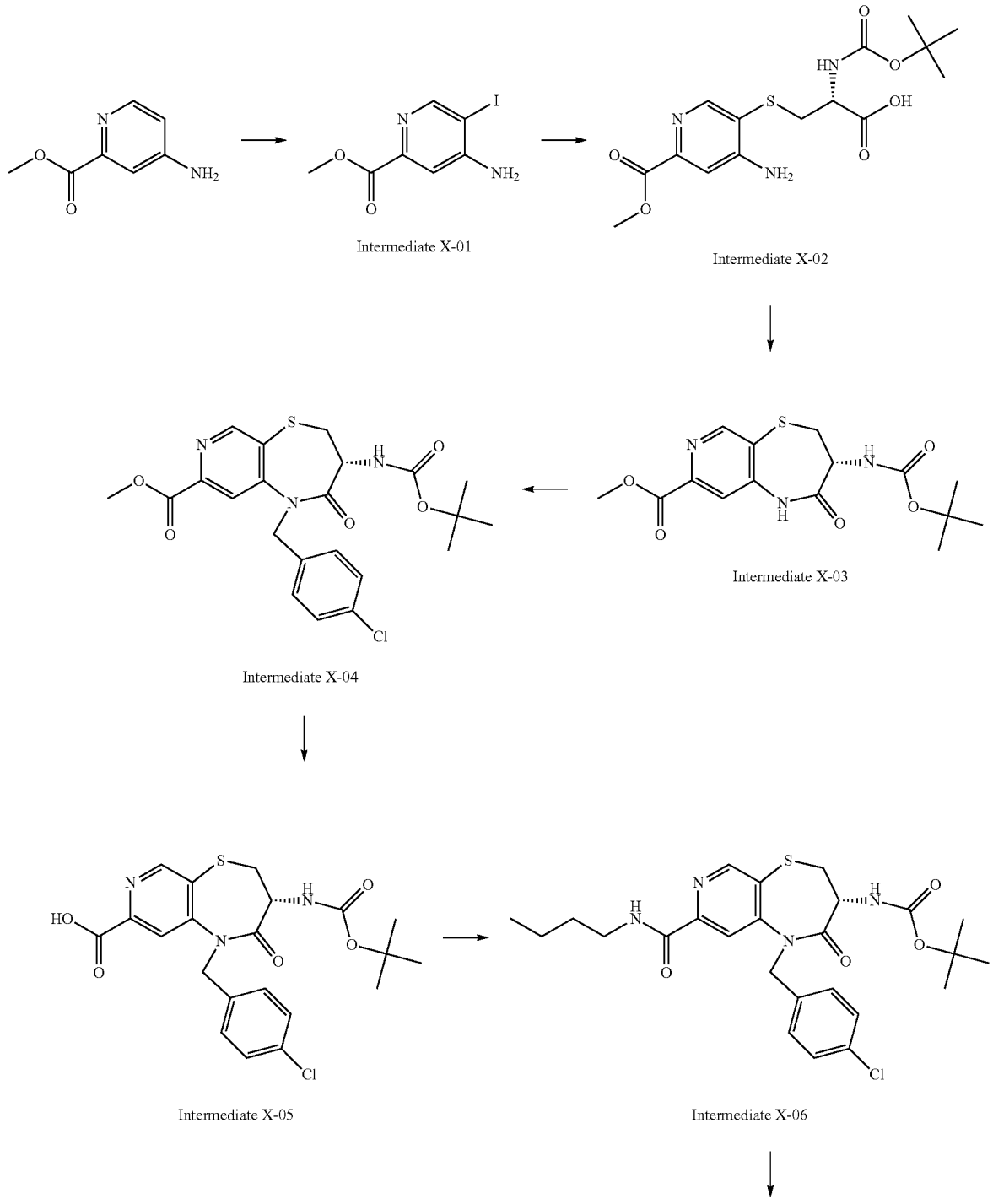

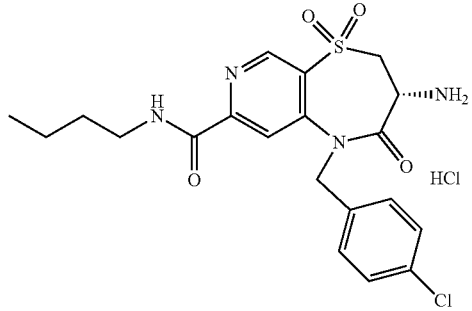

Example 183

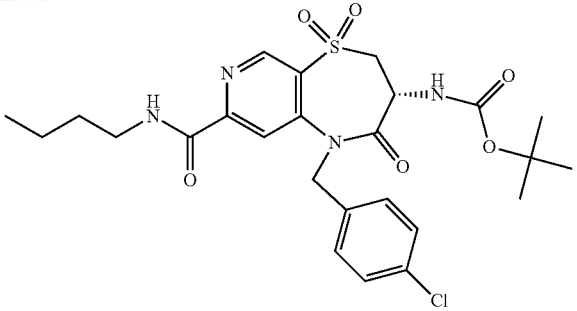

Intermediate X-07

Synthesis of methyl 4-amino-5-iodopyridine-2-carboxylate (intermediate X-01)

N-Iodosuccinimide (4.44 g, 19.72 mmol) was added to a solution of methyl 4-aminopyridine-2-carboxylate (3 g, 19.72 mmol) in 1.2-DCE (115 mL) cooled in an ice bath. The resulting mixture was allowed to warm up to RT and then stirred at 80° C. for 16 h. Further N-iodosuccinimide (1 g, 0.23 eq) was added to the reaction mixture and heating was continued for 5 h. The reaction mixture was then partitioned between DCM (50 mL) and water (50 mL). The organic phase was washed with water and brine (100 mL), dried over $Na_2SO_4$ and filtrated. The filtrate was concentrated under reduced pressure to afford the title compound as red solid in 95% Yield.

LCMS: METCR0990: rt=1.12 min M/Z (ES+) 279 [M+H+] 97% UV

NMR data: $^1$H NMR (500 MHz, DMSO-$d_6$) δ 8.48 (s, 1H), 7.35 (s, 1H), 6.50 (s, 2H), 3.82 (s, 3H).

Synthesis of (2R)-3-{[4-amino-6-(methoxycarbonyl)pyridin-3-yl]sulfanyl}-2-{[(tert-butoxy)carbonyl]amino}propanoic acid (intermediate X-02)

A mixture of intermediate X-01 (97%, 1500 mg, 5.23 mmol), Boc-L-cysteine (1.16 g, 5.23 mmol) and DIPEA (1.87 mL, 10.47 mmol) in anhydrous toluene (30 mL) was degassed with and placed under nitrogen atmosphere. Then, (1E,4E)-1,5-diphenylpenta-1,4-dien-3-one-palladium (3:2) (120 mg, 0.131 mmol) and (9,9-dimethyl-9H-xanthene-4,5-diyl)bis(diphenylphosphane) (151 mg, 0.262 mmol) were added. The reaction mixture was degassed, placed under nitrogen atmosphere and heated at 100° C. for 1.5 h. The reaction mixture was cooled to RT, diluted with DCM and filtrated through Celite®. The filtrate was concentrated under reduced pressure and purified by reverse-phase column chromatography to afford 2.88 g of the title compound as brown solid in 66% purity by NMR (DIPEA as main impurity), 98% Yield.

LCMS: MS19 METCR1410 rt=0.75 min M/Z (ES+) 372[M+H+] 96% UV

NMR data: 1H NMR (500 MHz, Methanol-d4) δ 8.35 (s, 1H), 7.43 (s, 1H), 4.19 (s, 1H), 3.93 (s, 3H), 3.30-3.26 (m, 1H), 3.20-3.12 (m, 1H), 1.40 (s, 9H).

Synthesis of methyl (3R)-3-{[(tert-butoxy)carbonyl]amino}-2-oxo-1H,2H,3H,4H-pyrido[3,4-b][1,4]thiazepine-8-carboxylate (intermediate X-03)

To a suspension intermediate X-02 (66%, 2.38 g, 4.23 mmol) in THF (25 mL) were added DIPEA (1.47 mL, 1.78 mmol) and T3P® (50% solution in EtOAc, 5 mL, 8.46 mmol) and the reaction was stirred at RT for 1 h. The mixture was quenched with water (15 mL) and extracted with EtOAc (15 mL×2). The combined organic extracts were washed with brine, dried over $Na_2SO_4$ and filtered. The filtrate was concentrated under reduced pressure and the residue was purified by flash column chromatography (silica, eluent: heptanes, 20-100% EtOAc) to afford 0.69 g of the title compound as off-white solid in 90% purity by NMR, yield 41%.

LCMS: METCR1410 rt=0.94 min M/Z (ES+) 354 [M+H+] 99% UV

NMR data: 1H NMR (500 MHz, DMSO-d6) δ 10.62 (s, 1H), 8.72 (s, 1H), 7.72 (s, 1H), 7.45 (d, J=8.0 Hz, 1H), 4.20-4.11 (m, 1H), 3.90 (s, 3H), 3.63 (dd, J=11.3, 6.4 Hz, 1H), 3.28 (t, J=11.7 Hz, 1H), 1.34 (s, 9H).

Synthesis of methyl (3R)-3-{[(tert-butoxy)carbonyl]amino}-1-[(4-chlorophenyl)methyl]-2-oxo-1H,2H,3H,4H-pyrido[3,4-b][1,4]thiazepine-8-carboxylate (intermediate X-04)

A mixture of intermediate X-03 (135 mg, 0.38 mmol), 1-(bromomethyl)-4-chlorobenzene (117.74 mg, 0.57 mmol), $K_2CO_3$ (158.39 mg, 1.15 mmol) and KI (31.71 mg, 0.19 mmol) in DMSO (2 mL) was stirred at RT for 1.5 h. The reaction mixture was cooled in an ice bath and water (5 mL) was added. The resulting precipitate was isolated by filtration and washed with water (10 mL) to afford 182 mg of the title compound as cream solid in 90% purity.

LCMS: METCR1673 Generic 2 minutes rt=1.21 min M/Z (ES+) 478/480 [M+H+] 90% UV

NMR data: 1H NMR (500 MHz, DMSO-d6) δ 8.78 (s, 1H), 8.04 (s, 1H), 7.67-7.59 (m, 1H), 7.35-7.28 (m, 4H), 5.19 (q, J=16.3 Hz, 2H), 4.20 (s, 1H), 3.89 (s, 3H), 3.59 (dd, J=11.1, 6.7 Hz, 1H), 3.30-3.22 (m, 1H), 1.36 (s, 9H).

Synthesis of (3R)-3-{[(tert-butoxy)carbonyl]amino}-1-[(4-chlorophenyl)methyl]-2-oxo-1H,2H,3H,4H-pyrido[3,4-b][1,4]thiazepine-8-carboxylic acid (intermediate X-05)

A mixture of intermediate X-04 (95%, 371 mg, 0.74 mmol) and lithium hydroxide hydrate (1:1:1) (61.89 mg, 1.47 mmol) in THF/MeOH/water (10/3/1, 20 mL)) was stirred at RT for 1.5 h. The reaction mixture was concentrated under reduced pressure. The residue was dissolved in DCM and washed with 1M aq. HCl solution (20 mL). The organic phase was dried over $Na_2SO_4$ and filtered. The filtrate was concentrated under reduced pressure to afford the title compound as a pale yellow solid, in 89% purity and 84% yield.

LCMS: METCR1673 Generic 2 minutes rt=1.24 min M/Z (ES+) 464/466 [M+H+] 89% UV

NMR data: 1H NMR (500 MHz, Chloroform-d) δ 8.72 (s, 1H), 8.07 (s, 1H), 7.24-7.17 (m, 4H), 5.56 (d, J=15.7 Hz, 1H), 5.51 (s, 1H), 4.81 (d, J=15.6 Hz, 1H), 4.50-4.39 (m, 1H), 3.78 (dd, J=10.9, 6.3 Hz, 1H), 3.11 (t, J=11.4 Hz, 1H), 1.40 (s, 9H)

Synthesis of tert-butyl N-[(3R)-8-(butylcarbamoyl)-1-[(4-chlorophenyl)methyl]-2-oxo-1H,2H,3H,4H-pyrido[3,4-b][1,4]thiazepin-3-yl]carbamate (intermediate X-06)

DIPEA (0.12 mL, 0.67 mmol) was added to a solution of intermediate X-05 (89%, 100 mg, 0.19 mmol) in DMF (2.6 mL). The resulting mixture was cooled in an ice bath and HATU (109.41 mg, 0.29 mmol) was added. The reaction was stirred at 0° C. for 15 min then butan-1-amine (28.44 µL, 0.29 mmol) was added. After 15 min at 0° C., the reaction was allowed to warm up to RT and stirred for 1.5 h. The reaction mixture was concentrated under reduced pressure. The residue was purified by column chromatography (silica, eluent: heptanes, 12-100% EtOAc) to afford the title compound as a yellow pale oil (84 mg) in 86% purity by NMR and 72% yield.

LCMS: METCR1673 Generic 2 minutes rt=1.57 min M/Z (ES+) 519/521 [M+H+] 99% UV

NMR data: 1H NMR (500 MHz, Chloroform-d) δ 8.62 (s, 1H), 8.09 (s, 1H), 7.91 (t, J=5.9 Hz, 1H), 7.21 (s, 4H), 5.57-5.48 (m, 2H), 4.81 (d, J=15.5 Hz, 1H), 4.45-4.37 (m, 1H), 3.74 (dd, J=10.9, 6.4 Hz, 1H), 3.47 (dh, J=13.7, 6.8 Hz, 2H), 3.04 (t, J=11.3 Hz, 1H), 1.62 (p, J=7.2 Hz, 2H), 1.44 (dd, J=15.1, 7.5 Hz, 2H), 1.39 (s, 9H), 0.96 (t, J=7.4 Hz, 3H)

Synthesis of tert-butyl N-[(3R)-8-(butylcarbamoyl)-1-[(4-chlorophenyl)methyl]-2,5,5-trioxo-1H,2H,3H,4H-5λ$^6$-pyrido[3,4-b][1,4]thiazepin-3-yl]carbamate (intermediate X-07)

m-CPBA (77%, 32.75 mg, 0.15 mmol) was added to a solution of intermediate X-06 (86%, 42 mg, 0.07 mmol) in DCM (1.5 mL) cooled in an ice bath. The resulting mixture was allowed to warm up to RT and stirred for 16 h. The reaction mixture was partitioned between DCM (5 mL) and 1M aq. NaOH solution (2 mL). The organic phase was washed with 1M aq. NaOH (2 mL) and then concentrated under reduced pressure to afford the title compound as a white solid (34 mg) in 100% purity and in 87% yield.

LCMS: METCR1673 Generic 2 minutes rt=1.47 min M/Z (ES+) 551/553 [M+H+] 100% UV

NMR data: 1H NMR (500 MHz, Chloroform-d) δ 9.04 (s, 1H), 8.13 (s, 1H), 7.95 (t, J=6.0 Hz, 1H), 7.27 (s, 4H), 5.64 (d, J=7.3 Hz, 1H), 5.19 (d, J=15.5 Hz, 1H), 5.12 (d, J=15.6 Hz, 1H), 4.58 (dt, J=11.2, 7.1 Hz, 1H), 4.18 (dd, J=13.3, 7.0 Hz, 1H), 3.59 (dd, J=13.1, 11.4 Hz, 1H), 3.54-3.42 (m, J=6.6 Hz, 2H), 1.63 (p, J=7.2 Hz, 2H), 1.47-1.41 (m, 2H), 1.41 (s, 9H), 0.97 (t, J=7.4 Hz, 3H)

Synthesis of (3R)-3-amino-N-butyl-1-[(4-chlorophenyl)methyl]-2,5,5-trioxo-1H,2H,3H,4H-5λ$^6$-pyrido[3,4-b][1,4]thiazepine-8-carboxamide hydrochloride 4M HCl in dioxane (1 mL) and MeOH (1 mL) were added to intermediate X-07 (98%, 31 mg, 0.06 mmol). The reaction mixture was stirred at RT for 3 h. The reaction mixture was concentrated under reduced pressure to afford the title compound as a brown solid (34 mg) in 96% purity in quantitative yield.

LCMS: METCR1416 GENERIC 7 MINUTES, rt=1.47 min M/Z (ES+) 451/453 [M+H+], 98% UV

NMR data: 1H NMR (500 MHz, DMSO-d6) δ 8.91 (t, J=6.0 Hz, 1H), 8.72 (t, J=5.7 Hz, 1H), 8.52 (s, 1H), 8.50 (s, 1H), 7.57 (s, 1H), 7.35 (dd, J=8.3 Hz, 4H), 4.69-4.63 (m, 1H), 4.36-4.30 (m, 2H), 3.89-3.64 (m, 2H), 3.28-3.20 (m, 2H), 1.52-1.44 (m, 2H), 1.33-1.21 (m, 2H), 0.88 (t, J=7.3 Hz, 3H).

Biological Activity

In order to determine their biological activity, compounds were assessed in a variety of assays.
Summary of Experimental Methods
Isolation of PBMCs from Buffy-Coat
  Buffy coat content was transferred to sterile plastic bottle and filled up to 480 ml with PBS, and distributed equally to 16×50 ml tubes (30 ml/tube)
  Underlayed with ~11 ml Lymphoprep and centrifuged 20 min (2200 rpm)
  The interphase containing lymphocytes was taken off with transfer pipette, cells were washed twice with PBS and pooled to one tube to determine cell count (Coulter Diff ACT)
Isolation of Immune Cell Subfractions from PBMCs by MACS
  PBMCs were resuspended in MACS buffer (80 µl MACS-buffer/10^7 cells) and cells were isolated with Auto-MACS device using respective kits following manufacturer's recommendations
TCR Stimulation and Measurement of T Cell Activation
  Isolated T cells were plated in Xvivo medium at 1.5*10^5 cells per in 96 well culture plates and TCR-stimulated with anti-CD3/28 mAbs in the presence of compound as indicated. Cytokine production was determined at 24 h or 48 h following TCR stimulation in cell culture supernatants using commercially available ELISA kits (BD and eBioscience) as recommended by the manufacturer. T cell proliferation and CD25 expression (CD25-PC5 reagent purchased from Beckman Coulter) was determined by flow cytometry (Beckman-Coulter FC500) and analysed with Kaluza Software. For measurement of CD69 expression, isolated CD4 and CD8 T cells were plated in Xvivo medium at 0.8*10^=cells per in 96 well culture plates and TCR-stimulated with anti-CD3/28 mAbs in the presence of compound. CD69 expression was determined at 24 h following TCR stimulation by flow cytometry (CD4eF450, CD8APCeF780 and CD69-PC7 reagent purchased from eBioscience) and analysed with Kaluza Software.
Immune Cell Stimulation by Tumor Contact
  Isolated PBMCs, NK cells or CD8 positive cells were plated in Xvivo medium at 1.5*10^5 cells per in 96 well culture plates in the presence of 0.3*10^4 tumor cells where indicated. Cytokine secretion was determined by ELISA, immune cell activation (using Beckman-Coulter Abs CD25-PC5, CD69-PC7), cell viability and numbers by flow cytometry (Beckman-Coulter FC500 or Gallios) using 7-AAD exclusion as criterion for living cells.
  For experiments investigating effects of PD-1 blockade, PBMCs were preincubated with 1 h UV-irradiated M21 tumor cells (50000 tumor cells per 1 Mill. PBMCs) for 14 days. Afterwards, CD8 T cells were isolated and stimulated with M21 tumor cells as described above. Compounds and anti-PD-1 antibody (Nivolumab) or control antibody without direct effects on CD8 T cells (Ipilimumab) were added where indicated.

NK Cell Stimulation by IL-2

Isolated NK cells were plated in Xvivo medium at $1.5*10^5$ cells per in 96 well culture plates and stimulated with 50 ng/ml IL-2 (Aldesleukin) where indicated. Cytokine secretion was determined by ELISA, immune cell activation by flow cytometry (Beckman-Coulter Abs CD25-PC5, CD69-PC7 and acquisition on Beckman-Coulter Gallios) using 7-AAD exclusion as criterion for living cells.

FC Receptor Stimulation on Myeolid Cells

Isolated Monocytes were plated in Xvivo medium at $1.5*10^5$ cells per in 96 well culture plates and stimulated by precoated anti-GD2-Abs (10 μg/ml, Apeiron) where indicated. Cytokine secretion was determined by enzyme-linked immunosorbent assay (ELISA).

Isolation of Murine Splenocytes
- Single cell suspension of splenocytes was prepared from the spleen by rinsing cells through a sterile 70 μm filter with PBS
- Cells were collected by centrifugation in an 15 ml tube, the cell pellet was resuspended in 1 ml of Erylyse buffer and incubated at room temperature for 5 minutes, tubes were filled up with PBS and cells were washed twice
- Cells were counted and resuspended in the desired buffer volume for MACS-enrichment or flow cytometric analysis Isolation of CD4 T Cells from OT-II Transgenic Mice
- Splenocytes were resuspended in MACS buffer (8011 MACS-buffer/$10^7$ cells)
- CD4 T cells were isolated using the CD4 T cell isolation kit (Miltenyi) with LS-columns following manufacturer's recommendations CFSE-Labeling of T Cells
- Cells were resuspended in PBS with 0.1% BSA at $1\times10^7$ cells/ml and CFSE-solution was added to final concentration of 2.5 μM CFSE
- Incubated for 10 min at 37° C., swung each 2 min
- Same volume of FCS added and incubated for 5 min at room temperature
- Cells were washed twice with RMPI-10% FCS medium
- Cells were counted and resuspended in PBS or medium at desired concentration OT-II Transfer
- Day 0: OT-II cells were transferred in PBS ($3*10^6$. Cells in 100 μl PBS) by retro-orbital injection
- Day 1: WT mice got OVA vaccinated (subcut. flank, 10 μg LPS, 2 μg OVA per animal)
  - 2 & 4 h later compounds were administered; for oral dosing compound was used as suspension (0.5% methylcellulose in water), for i.v. dosing compound was solubilized in DMSO and diluted with PBS
- Day 2: compounds were administrated twice in the morning (with 2 h time interval)
- Day 3: Mice were sacrificed & splenocytes were isolated
- T cell proliferation & phenotype was determined by flow cytometry
  - Flow cytometry-Staining (all Abs purchased from eBioscience and used as recommended by the manufacturer): B220-eF450, CD4-PE, CD25PerCPCy5.5, CD69-PC7, TCRVa2-APC, CD8-AF700, CD3-eF780; CFSE; 7-AAD
  - Acquisition on Beckman-Coulter Gallios, Analysis using Kaluza Software OT-I Transfer to Mice with B16-F10-OVA Tumors
- Day 0: 100000 B16-F10-OVA tumor cells were inoculated subcutaneously at the flank of WT-mice
- Day 7: OT-I cells were transferred in PBS ($3*10^6$. Cells in 100 μl PBS) by retro-orbital injection
  - 2 & 4 h later compounds were administered by oral dosing compound as suspension (0.5% methylcellulose in water)
- Day 10: Mice were sacrificed & immune cells from tumor-draining lymph nodes and splenocytes were isolated
- T cell proliferation & phenotype was determined by flow cytometry
  - Flow cytometry-Staining (all Abs purchased from eBioscience or Biolegend and used as recommended by the manufacturer): CD4-eF450, B220-BV510, CD107a-PE, CD69-PC5, PD1-PC7, TCRVa2-APC, CD8-AF700, CD3-eF780; CFSE; 7-AAD
  - Acquisition on Beckman-Coulter Gallios, Analysis using Kaluza Software Immune Modulation of B16-F10-OVA Tumors Bearing Mice
- Day 0: 100000 B16-F10-OVA tumor cells were inoculated subcutaneously at the flank of WT-mice
- Day 7 & 8: compounds were administered by oral dosing compound as suspension (0.5% methylcellulose in water) twice daily (separated by 4 h interval)
- Day 9-14: compounds were administered by oral dosing compound as suspension (0.5% methylcellulose in water) once per day
- Day 15: Mice were sacrificed & immune cells from tumor-draining lymph nodes and splenocytes were isolated; tumor specimens were explanted and snap frozen in liquid nitrogen and mRNA was isolated kit using GenElute mammalian total RNA miniprep kit (RTN350-1KT)
- T cell phenotype was determined by flow cytometry
  - Flow cytometry-Staining (all Abs purchased from eBioscience or Biolegend and used as recommended by the manufacturer): CD4-eF450, B220-BV510, PD1-FITC, CD107a-PE, CD25-PerCPCy5.5, CD69-PC7, NK1.1-APC, CD8-AF700, CD3-eF780; CFSE; 7-AAD
  - Acquisition on Beckman-Coulter Gallios, Analysis using Kaluza Software
- Tumor infiltration by immune cells was determined by quantitative RT-PCR on an Agilent Mx3005P QPCR System (Stratagene) using TaqMan® Gene Expression Assays for the housekeeping calibrator gene EF1a and for the analytes CD4, CD8, IL-2, IL-12, IL-23, EOMES, Foxp3, IFN-g, Rorgc, T-bet, TNF-α according to the manufacturers recommendations.

TABLE 2

List of Reagents used

| Reagent | Supplier | Catalog Number |
| --- | --- | --- |
| Lymphorep | Axis Shield | 1114547 |
| CD4 MicroBeads | Miltenyi | 130-045-101 |
| CD8 MicroBeads | Miltenyi | 130-045-201 |
| NK cell isolation kit | Miltenyi | 130-092-657 |
| Monocyte isolation kit II | Miltenyi | 130-091-153 |
| X-Vivo Medium | Lonza | LONBE04-418F |
| Cell Trace CFSE Cell Proliferation Kit | Invitrogen | C34554 |
| ahuCD25-PC5 | Beckman-Coulter | IM2646 |
| ahuCD69-PC7 | Biolegend | 310912 |
| amuB220-eF450 | eBioscience | 48-0452-82 |

TABLE 2-continued

List of Reagents used

| Reagent | Supplier | Catalog Number |
|---|---|---|
| amuCD4-PE | eBioscience | 12-0042-83 |
| amuCD25-PerCP-Cy5.5 | eBioscience | 45-0251-82 |
| amuCD69-PC7 | eBioscience | 25-0691-81 |
| amuTCRVa2-APC | eBioscience | 17-5812-82 |
| amuCD8-aF700 | eBioscience | 56-0081-82 |
| amuCD3-eF780 | eBioscience | 47-0031-82 |
| 7-AAD | TONBO | 13-6993-T500 |
| DMSO | Sigma | D2650 |
| αhuCD3 LEAF-purified | Biolegend | 317315 |
| αhuCD28 LEAF-purified | Biolegend | 302923 |
| Dynabeads | Gibco | 11131D |
| αmuCD3 LEAF-purified | Biolegend | 100331 |
| αmuCD28 LEAF-purified | Biolegend | 102112 |
| Granzyme-ELISA | Mabtech | 3485-1H-20 |
| ELISA kits for IL-1b and IL-6 | BD Biosciences | |
| ELISA kits for IL-2, IFN-gamma and TNF-alpha | eBioscience | |
| GenElute mammalian total RNA miniprep kit | Sigma Aldrich | RTN350-1KT |
| CD4-eF450 | eBioscience | 48-0041-82 |
| PD1-FITC | eBioscience | 53-0251-82 |
| CD107a-PE | eBioscience | 12-1071-83 |
| NK1.1-APC | eBioscience | 17-5941-82 |
| B220-BV510 | Biolegend | 103247 |

Compound Activity in aCD3/aCD28 Stimulated Human PBMCs

In order to determine the immune modulatory effect of compounds of compounds of the present invention in human PBMCs, compounds were assessed in the following assay set-up:

Buffy coats were obtained from a local hospital, diluted 3 fold with PBS and layered onto an isotonic Ficoll separating solution d=1.077 g/mL in 50 mL centrifuge tubes. The tubes were centrifuged at 914 g for 25 min at room temperature with the brakes off. The PBMC layer was removed and washed twice with ice-cold PBS. Erythrocytes were lysed by addition of ddH$_2$O and cells were resuspended in X-Vivo15 (Lonza).

1e6 cells/mL were stimulated with soluble anti CD3/CD28 antibodies (1 μg/mL both, clones OKT3 and 28.2) in the presence of described compounds. Cells were incubated for 18 h at 37° C., 5% CO$_2$. Assay plates were centrifuged at 400 g for 5 min and supernatants harvested. Cytokine concentration in tissue culture supernatants were determined with MSD or HTRF kits (MSD and Cisbio), according to manufacturer's instructions.

Compound examples of the present invention were classified according to the following activity criteria and are listed in Table 3:

Activity Class A: IL-2 or IFN-γ pEC$_{50}$ >5.8 M
Activity Class B IL-2 or IFN-γ pEC$_{50}$ between 5.3-5.8M
Activity Class C: IL-2 or IFN-γ pEC$_{50}$<5.3 M and more than 2-fold increase of cytokine secretion as compared to stimulated cells in the absence of compounds

TABLE 3

Enhancement of cytokine production in aCD3/aCD28-stimulated human PBMCs

| Example No | Activity Class IL-2 | Activity Class IFN-γ |
|---|---|---|
| 1 | A | A |
| 2 | B | A |
| 3 | B | B |
| 4 | B | C |
| 5 | C | B |
| 6 | B | A |
| 7 | B | A |
| 9 | C | B |
| 10 | C | B |
| 11 | C | C |
| 12 | C | C |
| 17 | C | — |
| 18 | B | A |
| 20 | C | B |
| 21 | C | A |
| 22 | B | B |
| 23 | C | B |
| 25 | B | C |
| 26 | B | A |
| 27 | B | A |
| 28 | C | B |
| 29 | A | A |
| 30 | B | C |
| 31 | A | A |
| 33 | B | A |
| 34 | B | B |
| 35 | C | C |
| 36 | C | A |
| 37 | B | C |
| 38 | B | B |
| 39 | B | A |
| 41 | B | A |
| 42 | C | B |
| 43 | B | A |
| 44 | C | B |
| 46 | C | B |
| 48 | C | B |
| 50 | C | B |
| 51 | B | A |
| 53 | C | C |
| 54 | B | B |
| 55 | B | B |
| 56 | B | A |
| 57 | B | A |
| 58 | C | C |
| 59 | B | B |
| 60 | B | A |
| 61 | C | B |
| 63 | B | B |
| 64 | C | B |
| 65 | B | B |
| 66 | B | A |
| 67 | A | A |
| 68 | A | A |
| 69 | A | A |
| 70 | A | A |
| 71 | A | A |
| 72 | A | A |
| 73 | A | A |
| 74 | C | B |
| 75 | C | B |
| 77 | B | B |
| 78 | A | A |
| 79 | C | B |
| 80 | A | A |
| 83 | C | A |
| 84 | B | A |
| 85 | B | B |
| 86 | B | A |
| 87 | C | C |
| 88 | C | B |
| 89 | C | B |
| 92 | B | B |
| 93 | A | B |
| 94 | C | B |

TABLE 3-continued

Enhancement of cytokine production in aCD3/aCD28-stimulated human PBMCs

| Example No | Activity Class IL-2 | Activity Class IFN-γ |
|---|---|---|
| 95 | B | A |
| 96 | A | A |
| 98 | A | A |
| 99 | B | B |
| 100 | A | A |
| 101 | B | A |
| 102 | A | A |
| 103 | A | A |
| 104 | A | A |
| 105 | A | A |
| 106 | B | B |
| 107 | A | A |
| 108 | C | C |
| 109 | A | A |
| 110 | A | A |
| 111 | B | B |
| 113 | C | B |
| 114 | C | B |
| 116 | C | B |
| 117 | C | A |
| 118 | B | A |
| 119 | C | B |
| 120 | C | C |
| 121 | C | C |
| 122 | B | A |
| 123 | B | A |
| 124 | C | B |
| 125 | B | A |
| 126 | A | A |
| 127 | B | A |
| 128 | B | B |
| 129 | B | A |
| 130 | C | B |
| 131 | C | B |
| 132 | C | B |
| 133 | B | A |
| 134 | A | A |
| 135 | B | A |
| 136 | A | A |
| 137 | A | A |
| 138 | C | B |
| 139 | B | B |
| 140 | B | B |
| 141 | A | A |
| 142 | B | B |
| 143 | B | B |
| 144 | C | B |
| 145 | B | B |
| 146 | A | A |
| 147 | C | C |
| 148 | C | B |
| 149 | C | C |
| 150 | B | B |
| 151 | B | B |
| 152 | C | B |
| 153 | A | A |
| 154 | C | B |
| 155 | B | B |
| 156 | C | C |
| 157 | C | C |
| 158 | B | A |
| 159 | B | B |
| 160 | C | C |
| 161 | C | C |
| 162 | C | C |
| 163 | B | A |
| 164 | C | C |
| 165 | B | A |
| 166 | C | C |
| 167 | C | C |
| 168 | C | B |
| 169 | A | A |
| 170 | A | A |
| 171 | A | B |
| 172 | C | B |
| 173 | C | B |
| 174 | B | B |
| 175 | C | B |
| 176 | C | C |
| 177 | B | A |
| 178 | A | A |
| 179 | A | B |
| 180 | A | A |
| 181 | C | C |
| 182 | C | B |
| 183 | C | C |

The following compound examples were tested with non-stimulated PBMCs and did not enhance cytokine secretion or other signs of T-cell activation: compound examples 1, 40, 67, 77, 78 and 107. This is an important finding for compounds that shall selectively act on T cells which have been activated by presence of antigen from pathogens or tumors, but shall not lead to an unwanted general activation of all T cells of a patient.

Compound Activity in aCD3/aCD28 Stimulated Isolated Human CD4+-T-Cells

Buffy coats were obtained from Austrian Red Cross, diluted 3 fold with PBS and layered onto an isotonic Ficoll separating solution d=1.077 g/m in 50 ml centrifuge tubes. The tubes were centrifuged at 914 g for 25 min at room temperature with the brakes off. The PBMC layer was removed and washed twice with ice-cold PBS. CD4 T cells were isolated using CD4 microbeads (Milteny) and the AutoMACS device following manufacturer's instructions.

Compound examples of the present invention were classified according to the following activity criteria and are listed in Table 4a:

Activity Class A: IL-2 production at 3 μM compound concentration >10 ng/mL

Activity Class B: IL-2 production at 3 μM compound concentration between 2-10 ng/mL Activity Class C: IL-2 production at 3 μM compound concentration between 2-fold increase as compared to mean IL-2 production of stimulated cells in the absence of compounds and <2 ng/mL

TABLE 4a

Enhancement of cytokine production in aCD3/aCD28-stimulated human CD4+-T-cells

| Example No | Activity Class CD4+ | Example No | Activity Class CD4+ | Example No | Activity Class CD4+ |
|---|---|---|---|---|---|
| 1 | A | 38 | C | 79 | B |
| 2 | B | 39 | B | 80 | A |
| 3 | B | 40 | B | 81 | C |
| 4 | C | 41 | C | 82 | C |
| 5 | B | 42 | C | 83 | B |
| 6 | B | 43 | C | 84 | B |
| 7 | B | 44 | C | 85 | C |
| 8 | C | 45 | C | 86 | B |
| 9 | C | 46 | C | 87 | C |
| 10 | C | 47 | C | 88 | C |
| 11 | C | 48 | C | 89 | C |

TABLE 4a-continued

Enhancement of cytokine production in aCD3/aCD28-stimulated human CD4+-T-cells

| Example No | Activity Class CD4+ | Example No | Activity Class CD4+ | Example No | Activity Class CD4+ |
|---|---|---|---|---|---|
| 12 | C | 49 | C | 90 | A |
| 13 | C | 50 | C | 91 | B |
| 14 | C | 51 | C | 92 | B |
| 15 | B | 52 | C | 93 | A |
| 16 | B | 53 | C | 94 | C |
| 17 | C | 54 | B | 95 | B |
| 18 | C | 55 | B | 96 | A |
| 19 | C | 56 | C | 97 | C |
| 21 | C | 57 | C | 98 | A |
| 22 | B | 58 | C | 99 | B |
| 23 | B | 59 | C | 100 | A |
| 24 | C | 60 | C | 101 | B |
| 25 | C | 62 | C | 102 | A |
| 26 | B | 63 | B | 103 | A |
| 27 | B | 64 | C | 104 | A |
| 28 | C | 65 | C | 105 | A |
| 29 | B | 66 | C | 106 | B |
| 30 | B | 67 | A | 107 | A |
| 31 | B | 68 | A | 108 | C |
| 32 | C | 69 | A | 109 | A |
| 33 | B | 70 | A | 110 | A |
| 34 | C | 71 | B | 111 | B |
| 35 | C | 72 | A | 112 | C |
| 36 | C | 73 | A | 113 | C |
| 37 | C | 75 | B | 114 | C |
| 74 | C | 76 | C | 115 | C |
|  |  | 77 | C | 183 | C |

In addition to the data listed in Table 4a, compounds of activity class A and B showed a significant induction of at least one of the activation markers CD25, CD69, CD71 or CD154 (CD40L) as measured by flow cytometry.

Compound Activity in aCD3/aCD28 Stimulated Isolated Human CD4+ and CD8+ T-Cells

For measurement of CD69 expression, isolated CD4 and CD8 T cells were plated in Xvivo medium at 80000 cells per in 96 well culture plates and TCR-stimulated with anti-CD3/28 mAbs in the presence of compound. CD69 expression was determined at 24 h following TCR stimulation by flow cytometry (CD4eF450, CD8APCeF780 and CD69-PC7 reagent purchased from eBioscience) and analysed with Kaluza Software.

Compound examples of the present invention were classified according to the following activity criteria and are listed in Table 4b:

Activity Class A: CD69+ on CD4 or CD8 T– cells $pEC_{50}$ >5.8 M
Activity Class B CD69+ on CD4 or CD8 T– cells $pEC_{50}$ between 5.3-5.8M
Activity Class C: CD69+ on CD4 or CD8 T– cells $pEC_{50}$<5.3 M

TABLE 4b

Enhancement of cytokine production in aCD3/aCD28-stimulated human T-lymphocytes as measured by flow cytometry

| Example No | Activity Class CD69 (CD4) | Activity Class CD69 (CD8) |
|---|---|---|
| 68 | A | A |
| 69 | A | A |
| 70 | A | A |
| 71 | A | A |
| 72 | A | B |
| 73 | A | A |
| 105 | A | A |
| 106 | B | B |
| 107 | A | A |
| 122 | B | B |
| 123 | C | C |
| 124 | C | C |
| 125 | B | B |
| 126 | A | A |
| 127 | A | A |
| 128 | C | B |
| 129 | A | A |
| 130 | C | B |
| 131 | C | C |
| 132 | C | C |
| 133 | A | A |
| 134 | A | A |
| 135 | B | B |
| 136 | A | A |
| 137 | A | A |
| 139 | B | C |
| 140 | B | C |
| 141 | A | A |
| 142 | C | C |
| 143 | B | C |
| 145 | A | A |
| 146 | B | B |
| 150 | C | C |
| 151 | B | A |
| 152 | B | B |
| 153 | A | A |
| 154 | B | A |
| 155 | A | A |
| 158 | B | B |
| 159 | A | A |
| 160 | A | B |
| 163 | A | A |
| 165 | A | A |
| 169 | A | A |
| 171 | A | A |
| 175 | A | B |
| 176 | C | C |
| 178 | A | A |
| 179 | A | A |
| 180 | A | A |

Enhancement of Relevant Aspects of TCR-Mediated CD4 T Cell Activation

Isolated CD4 T cells were CFSE-labeled and stimulated with anti-CD3 and anti-CD28 antibodies. Compound example 67 strongly enhanced production of key cytokines for anti-tumor and anti-pathogen immune responses (IL-2, IFN-gamma, TNF-alpha). Moreover, compound example 67 enhanced also T cell proliferation and expression of the surface activation marker CD25 (a component of the IL-2 receptor), further substantiating the potential effects on immune responses in vivo, since rapid expansion of T cells upon TCR stimulation is a hallmark for protective T cell immunity.

TABLE 5

| μM cmpd ex. 67 | IFN-gamma production [ng/ml] | | IL-2 production [ng/ml] | | TNF-alpha production [ng/ml] | |
|---|---|---|---|---|---|---|
| | Average | Standard deviation | Average | Standard deviation | Average | Standard deviation |
| 0 | 0.02 | 0.01 | 0.04 | 0.03 | 0.18 | 0.01 |
| 0.05 | 0.06 | 0.01 | 0.13 | 0.01 | 0.26 | 0.03 |
| 0.1 | 0.10 | 0.01 | 0.21 | 0.05 | 0.42 | 0.04 |
| 0.25 | 0.23 | 0.02 | 0.56 | 0.05 | 0.71 | 0.04 |
| 0.5 | 0.40 | 0.09 | 1.00 | 0.19 | 1.12 | 0.03 |
| 1 | 0.64 | 0.08 | 2.50 | 0.23 | 1.65 | 0.13 |
| 2.5 | 1.46 | 0.18 | 7.48 | 1.22 | 4.11 | 0.22 |
| 5 | 2.22 | 0.33 | 11.11 | 1.17 | 5.47 | 0.39 |
| 10 | 2.81 | 0.41 | 13.62 | 1.60 | 7.19 | 0.60 |
| 20 | 3.29 | 0.58 | 15.11 | 1.94 | 9.31 | 1.15 |

TABLE 6

| μM cmpd ex. 67 | Cell Proliferation [Cell divisions/cell] | | CD25 expression [% positive cells] | |
|---|---|---|---|---|
| | Average | Standard deviation | Average | Standard deviation |
| 0 | 0.28 | 0.03 | 34.10 | 1.18 |
| 0.05 | 0.49 | 0.02 | 47.88 | 1.75 |
| 0.1 | 0.58 | 0.01 | 50.80 | 1.60 |
| 0.25 | 0.84 | 0.00 | 59.10 | 0.49 |
| 0.5 | 1.03 | 0.00 | 69.50 | 0.26 |
| 1 | 1.20 | 0.01 | 79.50 | 1.70 |
| 2.5 | 1.35 | 0.05 | 77.71 | 12.83 |
| 5 | 1.40 | 0.05 | 79.53 | 12.35 |
| 10 | 1.38 | 0.10 | 79.64 | 16.01 |
| 20 | 1.33 | 0.05 | 75.14 | 16.45 |

Enhancement of Reactivity of CD8 T Cells to TCR Stimulation

Isolated CD8 T cells were CFSE-labeled and stimulated with anti-CD3 and anti-CD28 antibodies. Apart from its enhancement of relevant aspects of TCR-mediated CD4 T cell activation shown above, with respect to CD8 T cells compound example 67 strongly enhanced production of the cytokines IL-2, IFN-gamma and TNF-alpha, as well as CD25 expression and T cell proliferation. These results demonstrate that compound example 67 enhanced both CD4 and CD8 T cell responses to TCR activation.

TABLE 7

| μM cmpd ex. 67 | IFN-gamma production [ng/ml] | | IL-2 production [ng/ml] | | TNF-alpha production [ng/ml] | |
|---|---|---|---|---|---|---|
| | Average | Standard deviation | Average | Standard deviation | Average | Standard deviation |
| 0 | 0.02 | 0.02 | 0.14 | 0.02 | 0.38 | 0.01 |
| 0.05 | 0.14 | 0.01 | 1.17 | 0.04 | 1.09 | 0.05 |
| 0.1 | 0.22 | 0.05 | 2.32 | 0.21 | 1.55 | 0.06 |
| 0.25 | 0.31 | 0.12 | 4.01 | 0.30 | 2.16 | 0.05 |
| 0.5 | 0.43 | 0.07 | 7.64 | 1.19 | 3.13 | 0.36 |
| 1 | 0.61 | 0.03 | 11.30 | 0.14 | 4.04 | 0.63 |
| 2.5 | 0.79 | 0.04 | 16.77 | 1.62 | 5.37 | 0.44 |
| 5 | 0.91 | 0.06 | 17.30 | 0.73 | 6.68 | 0.17 |
| 10 | 1.15 | 0.09 | 19.63 | 2.91 | 7.50 | 0.23 |
| 20 | 1.32 | 0.11 | 19.92 | 3.70 | 7.13 | 0.34 |

TABLE 8

| μM cmpd ex. 67 | Cell Proliferation [Cell divisions/cell] | | CD25 expression [% positive cells] | |
|---|---|---|---|---|
| | Average | Standard deviation | Average | Standard deviation |
| 0 | 0.83 | 0.04 | 38.56 | 1.79 |
| 0.05 | 1.57 | 0.00 | 61.07 | 1.19 |
| 0.1 | 1.72 | 0.01 | 64.24 | 1.65 |
| 0.25 | 1.84 | 0.02 | 68.81 | 1.56 |
| 0.5 | 1.88 | 0.01 | 67.89 | 1.99 |
| 1 | 1.94 | 0.01 | 71.00 | 1.91 |
| 2.5 | 1.93 | 0.01 | 71.35 | 3.74 |
| 5 | 1.91 | 0.02 | 71.76 | 1.93 |
| 10 | 1.83 | 0.04 | 71.90 | 1.22 |
| 20 | 1.68 | 0.01 | 69.70 | 1.57 |

Enhancement of Anti-Tumor Reactivity of CD8 Positive Lymphocytes

CD8-positive immune cells were isolated from PBMCs and were incubated with and without compound example 67, either alone or in co-culture with M21 melanoma cells. Tumor cell contact resulted in activation of immune cells to produce IL-2 and IFN-gamma. Compound example 67 enhanced production of both cytokines specifically upon tumor cell contact; such effect was not detected in the absence of tumor cells. Moreover, compound example 67 also enhanced the tumor-cell contact mediated release of the cytotoxic effector granzyme, which is directly related to tumor cell killing. In agreement, the presence of compound example 67 in immune cell cocultures with tumor cells resulted in a strong reduction in viable tumor cells, while neither the number of CD8 T cells nor the number of tumor cells in the absence of CD8 T cells was substantially modulated.

TABLE 9

| IFN-gamma [ng/ml] | avg | compound ex. 67 [μM] | 0 | 0.03 | 0.10 | 0.30 | 1 | 3 | 10 |
|---|---|---|---|---|---|---|---|---|---|
| | | CD8 cells & M21 | Below detection limit | 0.06 | 0.15 | 0.20 | 0.40 | 0.54 | 0.68 |
| | | CD8 only + ex. 67 | Below detection limit | Below detection limit | Below detection limit | Below detection limit | Below detection limit | Below detection limit | Below detection limit |
| | std dev | compound ex. 67 [μM] | 0 | 0.03 | 0.10 | 0.30 | 1 | 3 | 10 |
| | | CD8 cells & M21 | 0.00 | 0.04 | 0.02 | 0.01 | 0.02 | 0.04 | 0.05 |

TABLE 9-continued

| | | | | | | | | | |
|---|---|---|---|---|---|---|---|---|---|
| IL-2 [ng/ml] | avg | compound ex. 67 [μM] | 0 | 0.03 | 0.10 | 0.30 | 1 | 3 | 10 |
| | | CD8 cells & M21 | 0.57 | 1.32 | 2.13 | 2.75 | 3.38 | 3.44 | 3.26 |
| | | CD8 only + ex. 67 | Below detection limit | Below detection limit | Below detection limit | Below detection limit | Below detection limit | Below detection limit | Below detection limit |
| | std dev | compound ex. 67 [μM] | 0 | 0.03 | 0.10 | 0.30 | 1 | 3 | 10 |
| | | CD8 cells & M21 | 0.06 | 0.14 | 0.26 | 0.34 | 0.18 | 0.35 | 0.17 |
| Granzyme [ng/ml] | avg | compound ex. 67 [μM] | 0 | 0.03 | 0.10 | 0.30 | 1 | 3 | 10 |
| | | CD8 cells & M21 | 0.10 | 0.10 | 0.12 | 0.18 | 0.34 | 0.43 | 0.37 |
| | | CD8 only + ex. 67 | 0.01 | 0.01 | 0.01 | 0.01 | 0.02 | 0.01 | 0.02 |
| | std dev | compound ex. 67 [μM] | 0 | 0.03 | 0.10 | 0.30 | 1 | 3 | 10 |
| | | CD8 cells & M21 | 0.02 | 0.01 | 0.01 | 0.01 | 0.04 | 0.01 | 0.06 |

TABLE 10

M21 Viability
[Number of Living Cells]

| | compound ex. 67 [μM] | CD8 cells & M21 | M21 only |
|---|---|---|---|
| average | 0 | 18418.50 | 19442 |
| | 0.03 | 13077.00 | |
| | 0.1 | 11586.67 | |
| | 0.3 | 9525.67 | |
| | 1 | 3916.67 | |
| | 3 | 3604.00 | |
| | 10 | 3448.67 | 18139 |

| | compound ex. 67 [μM] | CD8 cells & M21 | M21 only |
|---|---|---|---|
| standard deviation | 0 | 1891.95 | 697.08 |
| | 0.03 | 1654.67 | |
| | 0.1 | 1312.97 | |
| | 0.3 | 869.52 | |
| | 1 | 451.12 | |
| | 3 | 312.77 | |
| | 10 | 1097.26 | 676.93 |

CD8 T cell viability
[Number of Living Cells]

| | compound ex. 67 [μM] | CD8 cells & M21 | CD8 only |
|---|---|---|---|
| average | 0 | 27006.67 | 25131.33 |
| | 0.03 | 22933.00 | 23523.00 |
| | 0.1 | 23942.33 | 24094.33 |
| | 0.3 | 23944.67 | 23739.00 |
| | 1 | 24569.67 | 23066.67 |
| | 3 | 24633.67 | 23975.33 |
| | 10 | 24006.33 | 25522.67 |

| | compound ex. 67 [μM] | CD8 cells & M21 | CD8 only |
|---|---|---|---|
| standard deviation | 0 | 1134.55 | 260.58 |
| | 0.03 | 617.36 | 797.60 |
| | 0.1 | 688.59 | 644.29 |
| | 0.3 | 172.98 | 493.01 |
| | 1 | 116.90 | 335.87 |
| | 3 | 558.63 | 284.42 |
| | 10 | 798.83 | 298.16 |

Enhancement of Anti-Tumor Reactivity of NK Cells

One of the physiological functions of NK cells in anti-tumor immunity is the recognition and destruction of tumor cells that have a low expression of MHC-molecules, thus avoiding recognition by CD8 T cells. Downregulation of MHC molecules is often actively mediated by an infecting virus or occurs during development of malignant neoplasms. The K52 leukemia cell line expresses only very low amounts of MHC-molecules and thus is often used as a model system to investigate anti-tumor NK cell reactivity.

NK cells were isolated from PBMCs and were incubated with and without compounds, either alone or in co-culture with K562 leukemia cells. Tumor cell contact resulted in activation of NK cells to produce IFN-gamma and TNF-alpha. Both compound example 67 and 77 enhanced production of both cytokines specifically upon tumor cell contact; such effect was not detected in the absence of tumor cells. The increased activation of NK cells by tumor contact was also demonstrated on a single-cell basis by determination of surface activation marker expression, where the fraction of CD25 and CD69 double positive NK cells represent strongly activated NK cells. Compounds also enhanced the tumor-cell contact mediated release of the cytotoxic effector granzyme, which resulted in a significant reduction of viable tumor cells in the presence of NK cells.

TABLE 11

| | | IFN-gamma [ng/ml] | | | |
|---|---|---|---|---|---|
| | | NK cells & K562 | | NK cells only | |
| | μM Comp ex. | 67 | 77 | 67 | 77 |
| Avg | no cmpd | 1.14 | 1.14 | below detection limit | below detection limit |
| | 0.03 | 7.47 | 2.20 | below detection limit | below detection limit |
| | 0.1 | 10.14 | 2.38 | below detection limit | below detection limit |
| | 0.3 | 11.24 | 6.06 | below detection limit | below detection limit |
| | 1 | 16.40 | 11.75 | below detection limit | below detection limit |
| | 3 | 17.80 | 12.11 | below detection limit | below detection limit |
| | 10 | 22.65 | 17.15 | below detection limit | below detection limit |
| | 30 | 19.98 | 19.12 | below detection limit | below detection limit |

TABLE 11-continued

IFN-gamma [ng/ml]

| | | NK cells & K562 | | NK cells only | |
|---|---|---|---|---|---|
| | μM Comp ex. | 67 | 77 | 67 | 77 |
| Stdev | no cmpd | 0.29 | 0.29 | | |
| | 0.03 | 1.64 | 0.66 | | |
| | 0.1 | 3.60 | 1.36 | | |
| | 0.3 | 1.36 | 0.28 | | |
| | 1 | 2.74 | 2.39 | | |
| | 3 | 3.64 | 0.53 | | |
| | 10 | 1.09 | 2.36 | | |
| | 30 | 1.22 | 1.55 | | |

TABLE 12

TNF-alpha [ng/ml]

| | | NK cells & K562 | | NK cells only | |
|---|---|---|---|---|---|
| | μM Comp ex. | 67 | 77 | 67 | 77 |
| avg | no cmpd | 0.05 | 0.05 | below detection limit | below detection limit |
| | 0.03 | 0.21 | 0.08 | below detection limit | below detection limit |
| | 0.1 | 0.26 | 0.11 | below detection limit | below detection limit |
| | 0.3 | 0.33 | 0.19 | below detection limit | below detection limit |
| | 1 | 0.57 | 0.34 | below detection limit | below detection limit |
| | 3 | 0.58 | 0.47 | below detection limit | below detection limit |
| | 10 | 0.80 | 0.57 | below detection limit | below detection limit |
| | 30 | 0.79 | 0.70 | below detection limit | below detection limit |

| | | NK cells & K562 | | NK cells only | |
|---|---|---|---|---|---|
| | μM Comp ex. | 67 | 77 | 67 | 77 |
| stdev | no cmpd | 0.01 | 0.00 | | |
| | 0.03 | 0.01 | 0.02 | | |
| | 0.1 | 0.01 | 0.03 | | |
| | 0.3 | 0.01 | 0.02 | | |
| | 1 | 0.02 | 0.05 | | |
| | 3 | 0.02 | 0.05 | | |
| | 10 | 0.04 | 0.03 | | |
| | 30 | 0.04 | 0.04 | | |

TABLE 13

Granzyme [ng/ml]

| | | NK cells & K562 | | NK cells only | |
|---|---|---|---|---|---|
| | μM Comp ex. | 67 | 77 | 67 | 77 |
| avg | no cmpd | 0.34 | 0.36 | 0.13 | 0.15 |
| | 0.03 | 0.65 | 0.48 | 0.08 | 0.08 |
| | 0.1 | 0.93 | 0.52 | 0.09 | 0.06 |
| | 0.3 | 1.01 | 0.68 | 0.08 | 0.08 |
| | 1 | 1.47 | 0.90 | 0.06 | 0.05 |
| | 3 | 1.62 | 1.15 | 0.12 | 0.05 |
| | 10 | 2.52 | 1.41 | 0.15 | 0.10 |
| | 30 | 2.43 | 2.12 | 0.25 | 0.16 |

| | | NK cells & K562 | | NK cells only | |
|---|---|---|---|---|---|
| | μM Comp ex. | 67 | 77 | 671 | 77 |
| stdev | no cmpd | 0.05 | 0.05 | 0.03 | 0.05 |
| | 0.03 | 0.19 | 0.05 | 0.04 | 0.05 |
| | 0.1 | 0.24 | 0.12 | 0.04 | 0.02 |
| | 0.3 | 0.23 | 0.10 | 0.02 | 0.03 |
| | 1 | 0.40 | 0.13 | 0.05 | 0.03 |
| | 3 | 0.54 | 0.31 | 0.03 | 0.03 |
| | 10 | 0.51 | 0.18 | 0.03 | 0.04 |
| | 30 | 0.48 | 0.61 | 0.05 | 0.07 |

TABLE 14

CD25+CD69+ [% gated]

| | | NK cells & K562 | | NK cells only | |
|---|---|---|---|---|---|
| | μM Comp ex. | 67 | 77 | 67 | 77 |
| avg | 0 | 1.64 | 1.66 | 0.01 | 0.02 |
| | 0.03 | 6.90 | 1.77 | 0.05 | 0.01 |
| | 0.1 | 8.44 | 2.29 | 0.06 | 0.02 |
| | 0.3 | 9.68 | 4.44 | 0.15 | 0.05 |
| | 1 | 18.80 | 10.74 | 0.39 | 0.15 |
| | 3 | 21.66 | 13.55 | 0.47 | 0.24 |
| | 10 | 31.98 | 17.81 | 0.95 | 0.46 |
| | 30 | 35.89 | 25.06 | 1.24 | 0.95 |

| | | NK cells & K562 | | NK cells only | |
|---|---|---|---|---|---|
| | μM Comp ex. | 67 | 77 | 67 | 77 |
| stdev | 0 | 0.30 | 0.32 | 0.00 | 0.01 |
| | 0.03 | 0.13 | 0.34 | 0.04 | 0.00 |
| | 0.1 | 0.69 | 0.00 | 0.01 | 0.00 |
| | 0.3 | 0.13 | 1.57 | 0.04 | 0.00 |
| | 1 | 1.62 | 0.35 | 0.02 | 0.04 |
| | 3 | 0.31 | 1.34 | 0.01 | 0.01 |
| | 10 | 2.76 | 0.10 | 0.16 | 0.03 |
| | 30 | 1.64 | 2.46 | 0.02 | 0.07 |

TABLE 15

Living tumor cells

| | | NK cells & K562 | | K562 only | K562 only |
|---|---|---|---|---|---|
| | μM Comp ex. | 67 | 77 | 67 | 77 |
| avg | 0 | 826.33 | 714.67 | 27775.00 | 23066.33 |
| | 0.01 | 709.00 | 696.00 | | |
| | 0.03 | 779.67 | 636.00 | | |
| | 0.1 | 712.67 | 567.00 | | |
| | 0.3 | 676.00 | 589.00 | 22199.00 | 31786.33 |
| | 1 | 623.33 | 520.33 | | |
| | 3 | 620.33 | 406.33 | 20750.33 | 21495.00 |
| | 10 | 611.67 | 398.33 | | |
| | 30 | 632.00 | 408.33 | 22719.33 | 22503.00 |

| | | NK cells & K562 | | K562 only | K562 only |
|---|---|---|---|---|---|
| | μM Comp ex. | 67 | 77 | 67 | 77 |
| stdev | 0 | 21.73 | 34.44 | 5756.71 | 3782.50 |
| | 0.01 | 69.20 | 29.72 | | |
| | 0.03 | 155.32 | 53.36 | | |
| | 0.1 | 29.57 | 22.34 | | |
| | 0.3 | 39.15 | 94.64 | 1414.94 | 7731.91 |

TABLE 15-continued

| | Living tumor cells | | | |
|---|---|---|---|---|
| 1  | 21.50 | 42.03 | | |
| 3  | 77.20 | 66.83 | 890.83  | 3905.46 |
| 10 | 36.50 | 13.65 | | |
| 30 | 20.00 | 43.52 | 1506.47 | 779.36 |

Enhancement of Reactivity of Immune Cells to Tumor Cells of Diverse Origin

The tumor cell lines M21 and K562 represent two widely used tumor lines of melanoma and leukemia origin, respectively. However, tumor cells are known to employ different mechanisms to suppress immune functions, therefore it was investigated if the effects of compounds on immune cell activities against tumor cells can be generalized to a wide array of tumor cells of very diverse origins from different types of tumors.

PBMCs were isolated and incubated with and without compounds, either alone or in co-culture with different tumor cells. Tumor cell contact resulted in activation of immune cells to produce cytokines IL-2 and IFN-gamma and release granzyme, although to a different extent, based also on the MHC and KIR expression pattern of different tumor cell lines. Compound example 40 enhanced secretion of cytokines and granzyme strongly specifically upon tumor cell contact in diverse tumor cell lines; such effect was not detected in the absence of tumor cells. Similar results were obtained in follow-up experiments with compound example 70 with isolated CD8 cells, including also additional tumor cell lines.

TABLE 16

| | IFN-gamma [ng/ml] | | IL-2 [ng/ml] | | Granzyme [ng/ml] | |
|---|---|---|---|---|---|---|
| sample | no compound | compound ex. 40 [3 μM] | no compound | compound ex. 40 [3 μM] | no compound | compound ex. 40 [3 μM] |
| PBMC only | 0.000 | 0.000 | 0.000 | 0.000 | 0.001 | 0.001 |
| PBMC & K562 | 0.000 | 0.000 | 0.000 | 0.000 | 0.003 | 0.011 |

TABLE 16-continued

| | IFN-gamma [ng/ml] | | IL-2 [ng/ml] | | Granzyme [ng/ml] | |
|---|---|---|---|---|---|---|
| sample | no compound | compound ex. 40 [3 μM] | no compound | compound ex. 40 [3 μM] | no compound | compound ex. 40 [3 μM] |
| PBMC & SKBR3 | 0.000 | 0.000 | 0.000 | 0.005 | 0.001 | 0.001 |
| PBMC & BxPc3 | 0.000 | 0.088 | 0.000 | 0.092 | 0.008 | 0.008 |
| PBMC & Panc1 | 0.000 | 0.000 | 0.000 | 0.013 | 0.000 | 0.005 |
| PBMC & HT-29 | 0.000 | 0.022 | 0.000 | 0.033 | 0.000 | 0.003 |
| PBMC & A549 | 0.000 | 0.214 | 0.000 | 0.018 | 0.000 | 0.020 |
| PBMC & HTB46 | 0.213 | 0.665 | 0.021 | 0.168 | 0.069 | 0.404 |
| PBMC & HTB47 | 0.018 | 0.277 | 0.009 | 0.075 | 0.014 | 0.072 |
| PBMC & A375 | 0.042 | 0.142 | 0.116 | 0.278 | 0.008 | 0.053 |
| PBMC & M21 | 0.000 | 0.000 | 0.001 | 0.037 | 0.000 | 0.001 |
| PBMC & CRL2505 | 0.510 | 0.663 | 0.000 | 0.012 | 0.626 | 0.780 |

TABLE 17

| Origin of Tumor Cell Lines: | |
|---|---|
| Leukemia | K562 |
| Pancreatic Cancer | Panc1, BxPc3 |
| Colon Cancer: | HT-29 |
| Non-small cell lung carcinoma | A549 |
| Renal Cancer | HTB46, HTB47 |
| Melanoma | A375, M21 |
| Breast Cancer | SKBR3 |
| Prostate Cancer | CRL2505 |

TABLE 18

| | | IFN-gamma [ng/ml] | | | | | | | | |
|---|---|---|---|---|---|---|---|---|---|---|
| | conc. Compound ex. 70 | CD8 cells only | CD8 cells & A549 | CD8 cells & TC71 | CD8 cells & U138MG | CD8 cells & MG63 | CD8 cells & RD | CD8 cells & M21 | CD8 cells & K562 | CD8 cells & MDA-MB-231 |
| avg | no cmpd | 0.00 | 0.00 | 0.00 | 0.00 | 0.11 | 0.01 | 0.00 | 1.12 | 3.96 |
|     | 0.1 μM  | 0.00 | 0.01 | 0.04 | 0.00 | 0.92 | 0.12 | 0.00 | 6.97 | 10.72 |
|     | 0.3 μM  | 0.00 | 0.03 | 0.11 | 0.01 | 1.43 | 0.45 | 0.02 | 7.57 | 20.55 |
|     | 1 μM    | 0.00 | 0.08 | 0.14 | 0.02 | 1.79 | 0.54 | 0.06 | 11.23 | 22.31 |
|     | 3 μM    | 0.00 | 0.07 | 0.27 | 0.02 | 1.92 | 0.65 | 0.03 | 8.44 | 25.24 |
|     | 10 μM   | 0.00 | 0.16 | 0.38 | 0.06 | 2.36 | 1.59 | 0.10 | 8.26 | 24.22 |
| std dev | no cmpd | 0.00 | 0.00 | 0.00 | 0.00 | 0.08 | 0.01 | 0.00 | 0.58 | 1.42 |
|     | 0.1 μM  | 0.00 | 0.01 | 0.02 | 0.00 | 0.23 | 0.04 | 0.00 | 1.53 | 2.85 |
|     | 0.3 μM  | 0.00 | 0.01 | 0.03 | 0.00 | 0.21 | 0.17 | 0.03 | 1.42 | 3.62 |
|     | 1 μM    | 0.00 | 0.02 | 0.07 | 0.02 | 1.01 | 0.14 | 0.07 | 3.30 | 3.20 |
|     | 3 μM    | 0.00 | 0.03 | 0.19 | 0.00 | 0.47 | 0.14 | 0.04 | 2.48 | 0.82 |
|     | 10 μM   | 0.00 | 0.02 | 0.11 | 0.03 | 0.45 | 0.55 | 0.06 | 3.63 | 4.59 |

TABLE 19

IL-2 [ng/ml]

|  | concentration compound ex. 70 | CD8 cells only | CD8 cells & A549 | CD8 cells & TC71 | CD8 cells & U138MG | CD8 cells & MG63 | CD8 cells & RD | CD8 cells & M21 | CD8 cells & K562 | CD8 cells & MDA-MB-231 |
|---|---|---|---|---|---|---|---|---|---|---|
| avg | no cmpd | 0.00 | 0.00 | 0.01 | 0.00 | 0.00 | 0.00 | 0.02 | 0.59 | 0.48 |
|  | 0.1 µM | 0.00 | 0.00 | 0.58 | 0.00 | 0.00 | 0.00 | 0.39 | 3.86 | 1.51 |
|  | 0.3 µM | 0.00 | 0.15 | 0.97 | 0.00 | 0.00 | 0.00 | 0.31 | 3.20 | 2.14 |
|  | 1 µM | 0.00 | 0.36 | 1.25 | 0.04 | 0.00 | 0.00 | 0.67 | 4.08 | 2.40 |
|  | 3 µM | 0.00 | 0.28 | 1.14 | 0.02 | 0.00 | 0.00 | 0.64 | 3.72 | 3.21 |
|  | 10 µM | 0.00 | 0.59 | 1.57 | 0.08 | 0.00 | 0.00 | 0.47 | 2.82 | 3.63 |
| std dev | no cmpd | 0.00 | 0.00 | 0.03 | 0.00 | 0.00 | 0.00 | 0.03 | 0.25 | 0.12 |
|  | 0.1 µM | 0.00 | 0.00 | 0.08 | 0.00 | 0.00 | 0.00 | 0.05 | 1.18 | 0.53 |
|  | 0.3 µM | 0.00 | 0.08 | 0.11 | 0.00 | 0.00 | 0.00 | 0.23 | 0.15 | 0.77 |
|  | 1 µM | 0.00 | 0.06 | 0.22 | 0.07 | 0.00 | 0.00 | 0.20 | 0.65 | 0.63 |
|  | 3 µM | 0.00 | 0.05 | 0.19 | 0.03 | 0.00 | 0.00 | 0.12 | 0.79 | 0.73 |
|  | 10 µM | 0.00 | 0.04 | 0.26 | 0.07 | 0.00 | 0.00 | 0.10 | 0.87 | 0.85 |

TABLE 20

Granzyme [ng/ml]

|  | concentration compound ex. 70 | CD8 cells only | CD8 cells & A549 | CD8 cells & TC71 | CD8 cells & U138MG | CD8 cells & MG63 | CD8 cells & RD | CD8 cells & M21 | CD8 cells & K562 | CD8 cells & MDA-MB-231 |
|---|---|---|---|---|---|---|---|---|---|---|
| avg | no cmpd | 0.03 | 0.03 | 0.03 | 0.00 | 0.07 | 0.01 | 0.33 | 1.33 | 1.59 |
|  | 0.1 µM | 0.05 | 0.04 | 0.06 | 0.03 | 0.23 | 0.09 | 0.24 | 1.58 | 1.86 |
|  | 0.3 µM | 0.04 | 0.09 | 0.08 | 0.04 | 0.29 | 0.16 | 0.53 | 2.38 | 3.40 |
|  | 1 µM | 0.05 | 0.10 | 0.10 | 0.01 | 0.28 | 0.20 | 0.41 | 1.81 | 4.23 |
|  | 3 µM | 0.04 | 0.07 | 0.10 | 0.03 | 0.38 | 0.17 | 0.40 | 3.91 | 5.20 |
|  | 10 µM | 0.05 | 0.16 | 0.15 | 0.05 | 0.44 | 0.30 | 0.50 | 4.83 | 5.93 |
| std dev | no cmpd | 0.02 | 0.03 | 0.01 | 0.00 | 0.01 | 0.01 | 0.23 | 0.58 | 0.34 |
|  | 0.1 µM | 0.01 | 0.03 | 0.01 | 0.01 | 0.09 | 0.01 | 0.10 | 0.62 | 0.37 |
|  | 0.3 µM | 0.01 | 0.05 | 0.02 | 0.01 | 0.07 | 0.01 | 0.30 | 0.46 | 2.40 |
|  | 1 µM | 0.02 | 0.02 | 0.01 | 0.01 | 0.01 | 0.05 | 0.31 | 0.42 | 2.17 |
|  | 3 µM | 0.01 | 0.03 | 0.03 | 0.01 | 0.12 | 0.04 | 0.37 | 0.65 | 0.99 |
|  | 10 µM | 0.01 | 0.04 | 0.02 | 0.01 | 0.09 | 0.11 | 0.22 | 2.46 | 1.68 |

TABLE 21

Origin of Tumor Cell Lines:

| Leukemia | K562 |
| Melanoma | M21 |
| Prostate Cancer | CRL2505 |
| Breast Cancer | MDA-MB-231 |
| Lung Cancer | A549 |
| Ewings sarcoma | TC71 |
| Osteosarcoma | MG63, RD |
| Glioblastoma | U138MG |

Enhancement of Reactivity of NK Cells to Cytokine Stimulation

IL-2 is a key factor for survival, proliferation and activation of NK cells, thus linking adaptive immunity mediated by T cells with the innate immunity mediated by NK cells. Especially CD8 T cells release IL-2 locally at the site of antigen-encounter in the tumor, and thus support and activate NK cell anti-tumor functions. Compound example 67 has been chosen as an example. As already shown above, compounds enhanced T cell mediated release of IL-2 and enhanced tumor-cell contact mediated activation of NK cells. In addition, the below data show that compound example 67 also can directly enhance the responsiveness of NK cells upon IL-2 activation, as determined by release of cytokines IFN-gamma and TNF-alpha. Thus, compounds have a unique potential to support the interlinked anti-tumor immunity of T and NK cells in the physiological context in vivo.

TABLE 22

|  |  | IFN-gamma [ng/ml] | | TNF-alpha [ng/ml] | |
|---|---|---|---|---|---|
|  | Compound ex. 67[µM] | IL-2 stimulation | control | IL-2 stimulation | control |
| average | 0 | 0.48 | below detection limit | 0.02 | below detection limit |
|  | 0.01 | below detection limit | below detection limit |  |  |
|  | 0.03 | 0.71 | below detection limit | 0.04 | below detection limit |
|  | 0.1 | 0.72 | below detection limit | 0.03 | below detection limit |
|  | 0.3 | 1.00 | below detection limit | 0.06 | below detection limit |
|  | 1 | 1.23 | below detection limit | 0.09 | below detection limit |

TABLE 22-continued

| Compound ex. 67[µM] | IFN-gamma [ng/ml] | | TNF-alpha [ng/ml] | |
|---|---|---|---|---|
| | IL-2 stimulation | control | IL-2 stimulation | control |
| 3 | 1.50 | below detection limit | 0.10 | below detection limit |
| 10 | 1.40 | below detection limit | 0.12 | below detection limit |
| 30 | 1.22 | below detection limit | 0.14 | below detection limit |

| | Compound ex. 67[µM] | IL-2 stimulation | control | IL-2 stimulation | control |
|---|---|---|---|---|---|
| standard deviation | 0 | 0.15 | | 0.00 | |
| | 0.01 | | | | |
| | 0.03 | 0.26 | | 0.00 | |
| | 0.1 | 0.12 | | 0.01 | |
| | 0.3 | 0.26 | | 0.01 | |
| | 1 | 0.06 | | 0.00 | |
| | 3 | 0.09 | | 0.01 | |
| | 10 | 0.13 | | 0.01 | |
| | 30 | 0.11 | | 0.01 | |

Enhancement of Reactivity of Immune Cells to Stimulation by Tumor-Cell Bound Therapeutic Antibody Efficient immune responses against pathogens generally do not only rely on cellular immune functions (as mediated by T and NK cells), but also on humoral immunity that is mediated by antibodies. Antibodies that are bound to pathogens or pathogen-infected cells trigger activation of immune cells via Fc-receptors, that are expressed particularly on NK cells and myeloid cells. This mechanism is also utilized for cancer therapies when therapeutic antibodies against antigens which are preferentially expressed on cancer cells are administrated to patients which in turn recruit and activate immune cells to directly attack cancer cells. The GD2-antigen is strongly expressed on cancer cells of particular origins (among neuroblastoma and melanoma) and is therefore developed clinically as anti-cancer therapy. For M21 melanoma cells, GD2 is the only antigen that has been characterized to be accessible as tumor antigen. Therefore, an anti-GD2-antibody that was available in clinically grade quality was employed to test whether compounds can enhance the Fc-receptor mediated activation of immune cells to tumor-cell bound therapeutic antibodies. The below data show, that compound ex. 40 enhanced reactivity of immune cells to anti-GD2-antibodies bound on M21 melanoma cells, resulting in increased secretion of cytokine and activation of NK cells. Thus, compounds do not only increase the reactivity of immune cells to tumor cell contact but also to antibodies targeting tumor antigens on cancer cells.

TABLE 23

| | | TNF-alpha [pg/ml] | | | | |
|---|---|---|---|---|---|---|
| | | Compound ex. 40 | | | | |
| | sample | no cmpd | 0.3 µM | 1 µM | 3 µM | 10 µM |
| avg | PBMC & M21 tumor cells only | 8.76 | 17.47 | 17.59 | 28.95 | 38.00 |
| | PBMC & M21 tumor cells & anti-GD2 Ab low concentration | 15.69 | 36.53 | 55.72 | 93.25 | 114.88 |
| | PBMC & M21 tumor cells & anti-GD2 Ab high concentration | 61.37 | 106.30 | 142.98 | 192.34 | 257.96 |
| std dev | PBMC & M21 tumor cells | 2.69 | 4.75 | 3.71 | 3.51 | 7.76 |
| | PBMC & M21 tumor cells & anti-GD2 Ab low concentration | 0.32 | 2.92 | 6.13 | 2.86 | 5.81 |
| | PBMC & M21 tumor cells & anti-GD2 Ab | 9.53 | 7.81 | 13.73 | 2.41 | 9.53 |

TABLE 24

| | | strongly activated NK cells [% CD25+CD69+] | | | | |
|---|---|---|---|---|---|---|
| | | Compound ex. 40 | | | | |
| | sample | no cmpd | 0.3 µM | 1 µM | 3 µM | 10 µM |
| avg | PBMC & M21 tumor cells only | 0.80 | 0.75 | 1.10 | 2.40 | 2.19 |
| | PBMC & M21 tumor cells & anti-GD2 Ab low concentration | 2.73 | 6.92 | 11.88 | 17.22 | 20.25 |
| | PBMC & M21 tumor cells & anti-GD2 Ab high concentration | 12.66 | 23.55 | 32.63 | 42.50 | 42.22 |
| std dev | PBMC & M21 tumor cells | 0.26 | 0.04 | 0.26 | 0.15 | 0.37 |
| | PBMC & M21 tumor cells & anti-GD2 Ab low concentration | 0.21 | 0.54 | 0.21 | 0.25 | 0.47 |
| | PBMC & M21 tumor cells & anti-GD2 Ab | 1.36 | 2.94 | 0.42 | 1.61 | 0.08 |

Enhancement of Reactivity of Myeloid Cells to FcR Stimulation

The results of the above experiment titled "Enhancement of reactivity of immune cells to stimulation by tumor-cell bound therapeutic antibody" indicate that compounds can enhance FcR stimulation of immune cells. However, in a set-up as used therein, it is difficult to subtract the effects of tumor-cell contact from the effects of Fc-receptor stimulation. Therefore, the effect of FcR-stimulation by the same anti-GD2-Ab was tested in a tumor-cell free assay set-up, where the anti-GD2 antibodies were coated to cell culture plates, thereby mimicking cell-bound antibodies. The below data show compound ex. 77 as an example and depict that the compound directly enhanced the activation of myeloid cells by FcR stimulation, which resulted in increased secretion of TNF-alpha, IL-1 and IL-6. Together, the data of these two experiments demonstrate that compounds can support the anti-tumor effects of therapeutic antibodies against antigens on tumor cells by enhanced responsiveness of immune cells to FcR stimulation by cell bound antibodies.

TABLE 25

TNF-alpha [ng/ml]

|  | Compound concentration Ex. 77 [μM] | unstimulated | FcR stimulated |
|---|---|---|---|
| avg | no cmpd | below detection limit | 1.99 |
|  | 0.01 |  | 1.62 |
|  | 0.03 |  | 2.49 |
|  | 0.1 | below detection limit | 2.57 |
|  | 0.3 | below detection limit | 6.57 |
|  | 1 | below detection limit | 11.02 |
|  | 3 | below detection limit | 14.11 |
|  | 10 | below detection limit | 16.44 |
|  | 30 | 0.02 | 14.85 |
| stdev | no cmpd |  | 0.35 |
|  | 0.01 | — | 0.15 |
|  | 0.03 | — | 0.18 |
|  | 0.1 |  | 0.40 |
|  | 0.3 |  | 0.67 |
|  | 1 |  | 1.53 |
|  | 3 |  | 0.48 |
|  | 10 |  | 1.93 |
|  | 30 | 0.03 | 0.53 |

TABLE 26

IL-1 [ng/ml]

|  | Compound concentration Ex. 77 [μM] | unstimulated | FcR stimulated |
|---|---|---|---|
| avg | no cmpd | below detection limit | 1.32 |
|  | 0.01 |  | 1.14 |
|  | 0.03 |  | 1.52 |
|  | 0.1 | below detection limit | 1.09 |
|  | 0.3 | below detection limit | 4.16 |
|  | 1 | below detection limit | 5.88 |
|  | 3 | below detection limit | 5.50 |
|  | 10 | below detection limit | 7.44 |
|  | 30 | below detection limit | 7.77 |
| stdev | no cmpd |  | 0.15 |
|  | 0.01 |  | 0.25 |
|  | 0.03 |  | 0.12 |
|  | 0.1 |  | 0.14 |
|  | 0.3 |  | 0.96 |

TABLE 26-continued

IL-1 [ng/ml]

| Compound concentration Ex. 77 [μM] | unstimulated | FcR stimulated |
|---|---|---|
| 1 |  | 0.27 |
| 3 |  | 0.70 |
| 10 |  | 0.27 |
| 30 |  | 0.67 |

TABLE 27

IL-6 [ng/ml]

|  | Compound concentration Ex. 77 [μM] | unstimulated | FcR stimulated |
|---|---|---|---|
| avg | no cmpd | 0.15 | 2.30 |
|  | 0.01 | — | 1.61 |
|  | 0.03 | — | 2.33 |
|  | 0.1 | 0.14 | 2.10 |
|  | 0.3 | 0.13 | 5.65 |
|  | 1 | 0.14 | 7.46 |
|  | 3 | 0.13 | 5.93 |
|  | 10 | 0.13 | 5.86 |
|  | 30 | 0.13 | 6.20 |
| stdev | no cmpd | 0.02 | 0.12 |
|  | 0.01 | — | 0.23 |
|  | 0.03 | — | 0.27 |
|  | 0.1 | 0.00 | 0.27 |
|  | 0.3 | 0.01 | 1.14 |
|  | 1 | 0.00 | 1.38 |
|  | 3 | 0.00 | 0.99 |
|  | 10 | 0.00 | 0.94 |
|  | 30 | 0.01 | 0.64 |

Compound Activity in Isolated Purified Human CD19+ B-Cells

Buffy coats were obtained from a local hospital, diluted 3 fold with PBS and layered onto an isotonic Ficoll separating solution d=1.077 g/mL in 50 mL centrifuge tubes. The tubes were centrifuged at 914 g for 25 min at room temperature with the brakes off. The PBMC layer was removed and washed twice with ice-cold PBS. Erythrocytes were lysed by addition of $ddH_2O$ and cells were resuspended in X-Vivo15 (Lonza).

CD19+ B cells were isolated from PBMCs by negative selection with the aid MACs kits (Miltenyi), according to manufacturer's instructions. Purified fractions were >95% CD19-positive as judged by antibody staining and assessment by cytometry. B-cells were stimulated by adding varying concentrations of human IgM (1.25-20 μg/mL goat F (ab') 2 anti human IgM-LE/AF, Biozol) in the presence of example 1. Cells were incubated for 18 h at 37° C., 5% $CO_2$.

Assay plates were centrifuged at 400 g for 5 min and supernatants harvested. Cytokine concentration in tissue culture supernatants were determined with MSD or HTRF kits (MSD and Cisbio), according to manufacturer's instructions.

TABLE 28

Enhancement of cytokine production in
IgM-stimulated human CD19+ B-cells

| Antibody | | Example 1 pEC$_{50}$ | | Example 1 Fold Diff | |
|---|---|---|---|---|---|
| IgM [µg/mL] | Cytokine | Mean | sd | Mean | sd |
| 20 | IL-6 | 5.49 | 0.30 | 1.92 | 0.07 |
| 20 | TNF-α | 5.53 | 0.29 | 1.87 | 0.04 |
| 5 | IL-6 | 5.33 | 0.06 | 1.92 | 0.50 |
| 5 | TNF-α | 5.35 | 0.14 | 2.08 | 0.12 |
| 1.25 | IL-6 | 5.61 | 0.11 | 1.61 | 0.23 |
| 1.25 | TNF-α | 5.48 | 0.06 | 1.64 | 0.27 |

Enhancement of Reactivity of Murine T Cells to TCR Stimulation

The immune system of mammals is evolutionary conserved and therefore most signalling pathways are similar for murine and human immune cells. For pharmaceutical development of compounds, it is vital to generate data in vivo, mostly by the use of murine mechanistic and disease models. It was therefore investigated, whether compounds have similar effects on murine T cells as demonstrated for human T cells. Splenocytes serve an easily accessible immune cell fraction in mice, since PBMCs cannot be obtained in sufficient numbers for in vitro experiments as it is routinely done with human PBMCs. Splenocytes were isolated from spleens of BL6 mice and stimulated with anti-CD3 and anti-CD28 antibodies or remained unstimulated as control. Both compound examples 1 and 70 strongly enhanced production of cytokine comparable to the data for human PBMCs, again specifically for TCR-stimulated immune cells; such effect was not detected on unstimulated cells. Likewise, expression of CD25 was enhanced both on CD4 and CD8 T cells specifically in the presence of TCR-stimulation.

TABLE 29

| | | IL-2 production [ng/ml] | | | |
|---|---|---|---|---|---|
| | compound concentration [µM] | aCD3/28 stim & compound ex. 70 | aCD3/28 stim & compound ex. 1 | unstim & compound ex. 70 | unstim & compound ex. 1 |
| avg | 0 | 0.16 | 0.16 | 0.00 | 0.00 |
| | 0.3 | 0.77 | 0.29 | 0.00 | 0.00 |
| | 1 | 0.91 | 0.45 | 0.00 | 0.00 |
| | 3 | 1.54 | 0.61 | 0.00 | 0.00 |
| | 10 | 1.90 | 1.46 | 0.00 | 0.00 |
| | 30 | 1.71 | 1.71 | 0.00 | 0.00 |
| std dev | 0 | 0.00 | 0.00 | 0.00 | 0.00 |
| | 0.3 | 0.04 | 0.01 | 0.00 | 0.00 |
| | 1 | 0.13 | 0.04 | 0.00 | 0.00 |
| | 3 | 0.10 | 0.05 | 0.00 | 0.00 |
| | 10 | 0.08 | 0.05 | 0.00 | 0.00 |
| | 30 | 0.17 | 0.21 | 0.00 | 0.00 |

TABLE 30

| | | CD25+ CD4 T cells [% gated] | | | |
|---|---|---|---|---|---|
| | Compound concentration [µM] | aCD3/28 stim & compound ex. 70 | aCD3/28 stim & compound ex. 1 | unstim & compound ex. 70 | unstim & compound ex. 1 |
| avg | 0 | 4.80 | 4.80 | 0.55 | 0.55 |
| | 0.3 | 8.10 | 7.48 | 0.55 | 0.50 |
| | 1 | 9.28 | 7.42 | 0.45 | 0.50 |
| | 3 | 11.88 | 9.19 | 0.48 | 0.42 |
| | 10 | 13.41 | 12.15 | 0.45 | 0.41 |
| | 30 | 11.94 | 12.01 | 0.47 | 0.38 |
| std dev | 0 | 1.05 | 1.05 | 0.08 | 0.08 |
| | 0.3 | 1.03 | 0.27 | 0.01 | 0.02 |
| | 1 | 0.35 | 0.69 | 0.06 | 0.00 |
| | 3 | 0.50 | 0.79 | 0.06 | 0.00 |
| | 10 | 0.70 | 1.51 | 0.03 | 0.04 |
| | 30 | 1.04 | 0.28 | 0.08 | 0.03 |

TABLE 31

| | | CD25+ CD8 T cells [% gated] | | | |
|---|---|---|---|---|---|
| | Compound concentration [µM] | aCD3/28 stim & compound ex. 70 | aCD3/28 stim & compound ex. 1 | unstim & compound ex. 70 | unstim & compound ex. 1 |
| avg | 0 | 3.17 | 3.17 | 1.47 | 1.47 |
| | 0.3 | 10.10 | 5.86 | 0.61 | 0.61 |
| | 1 | 10.41 | 7.17 | 0.65 | 0.65 |
| | 3 | 14.58 | 10.90 | 0.60 | 0.61 |
| | 10 | 16.68 | 15.76 | 0.60 | 0.62 |
| | 30 | 17.50 | 16.51 | 0.64 | 0.56 |
| std dev | 0 | 0.68 | 0.68 | 1.52 | 1.52 |
| | 0.3 | 1.21 | 1.20 | 0.11 | 0.04 |
| | 1 | 0.55 | 0.01 | 0.07 | 0.04 |
| | 3 | 0.68 | 0.71 | 0.12 | 0.05 |
| | 10 | 1.33 | 1.03 | 0.11 | 0.01 |
| | 30 | 1.57 | 0.89 | 0.10 | 0.04 |

In Vivo Assessment of Compound Effect in an Anti-CD3 PD Model

Detection of antigen-specific T cell activation and proliferation in vivo is technically challenging since it requires the development and validation of research reagents to detect low-frequency T cells specific for a cognate antigen and also the establishment of specific measurement procedure for following cellular activation and/or proliferation in blood or secondary lymphoid organs. As a surrogate model for the determination of polyclonal T-cell activation in mice, a pharmacological system was designed and employed where adult B57/BL6 mice were injected with anti-CD3 antibody to elicit TCR triggering and responses of a broad population of peripheral T-cells. To quantitatively determine T-cell responses, systemic IL-2, TNF-alpha and IFN-gamma levels were measured in blood serum as well as the expression of the early activation marker CD69 on splenic CD4 or CD8 T-cells 5 hours after treatment.

It was investigated whether the oral application of compound affected the low-level of activation of a major subset of splenic T-cells by injection of anti-CD3 antibody as exemplified by increased serum levels of IL-2, IFN-gamma and TNF-alpha vis-à-vis untreated mice as well as an increase of CD69-expressing splenic T-cells from 2-10% to 15-20%. Surprisingly, a significant, substantial and dose-dependent increase of all these T-cell activation read-out parameters was detected upon oral application of 25, 50 or 100 mg/kg compound in addition to anti-CD3 application.

These data indicate that compound example 1 is able to substantially enhance TCR-mediated activation of CD4 and CD8 cells in vivo already after a short period of time (five hours).

In order to determine the immune modulatory effect of compounds of claim (1), a mouse model as described by Hirsch et al, *J Immunol.* 1989, 142(3), 737-43 was adapted as follows:

1. 8-14 week old male C57BL/6N mice were intraperitoneally injected with 0.1 µg/mouse anti-CD3 monoclonal antibody (BD Bioscience, cat no: 553058; Hamster Anti-Mouse CD3e Clone 145-2C11) at t=0 h to achieve a lower level of T-cell pre-activation as compared to Hirsch et al., 1989
2. Compound example 1 was dosed twice orally as suspension (0.5% methylcellulose in water) at t=−1.0 h and t=1.0 h.
3. Mice were terminated at t=4.0 h and their spleens and plasma harvested for flow cytometry and cytokine analysis respectively.
4. Cytokine concentrations in terminal plasma samples were determined with MSD kits according to manufacturer's instructions.

only the transferred OT-Ill T cells are stimulated, T cells of the recipient mice can serve as control for unspecific activation by compounds, since flow cytometric analysis of CFSE-levels in the OT-Ill cells can be combined with measurement of the activation marker CD69.

For this experiment, mice received CFSE-labeled OT-II T cells as outlined in the method section, and were then divided into groups which either received no antigen for vaccination and no compound (LPS only), or received antigen but no compound (LPS & OVA) or received antigen and compound example 1 at 10 mg/kg dosed orally. The below data show, that while in the absence of antigen, only minimal T cell proliferation and no upregulation of CD69 was observed on the transferred OT-II cells. In contrast, proliferation and CD69 upregulation was clearly detectable when the antigen for the OT-II cells was present. Proliferation of OT-II cells was highly significantly (p<0.00001) enhanced by the presence of compound example 1, while CD69 was not further upregulated; this is in agreement with

TABLE 32

Flowcytometry

| Anti-CD3 Ab [µg/ml] | Exp. 1 Dose [mg/kg] | CD69+ [%] | CD69+ [%]_SD | CD8+ [%] | CD8+ [%]_SD | CD69+ in CD8+ [%] | CD69+ in CD8+ [%]_SD | CD4+ [%] | CD4+ [%]_SD | CD69+ in CD4+ [%] | CD69+ in CD4+ [%]_SD |
|---|---|---|---|---|---|---|---|---|---|---|---|
| 0.1 | 0 | 8.27 | 1.58 | 16.46 | 0.79 | 17.82 | 4.59 | 23.90 | 1.31 | 19.18 | 3.28 |
| 0.1 | 25 | 12.65 | 1.15 | 16.33 | 0.26 | 32.40 | 3.77 | 22.95 | 2.39 | 26.75 | 3.23 |
| 0.1 | 50 | 17.06 | 4.20 | 16.42 | 1.36 | 46.44 | 10.59 | 22.86 | 1.51 | 32.14 | 5.85 |
| 0.1 | 100 | 28.58 | 5.93 | 16.70 | 1.54 | 63.96 | 5.91 | 23.18 | 2.46 | 47.50 | 6.51 |

TABLE 33

Cytokine analysis

| Anti-CD3 Ab [µg/ml] | Compound Dose [mg/kg] | IL-2 [pg/mL] | IL-2 [pg/mL]_SD | IFN-γ [pg/mL] | IFN-γ [pg/mL]_SD | IL-6 [pg/mL] | IL-6 [pg/mL]_SD | TNF-α [pg/mL] | TNF-α [pg/mL]_SD | IL-10 [pg/mL] | IL-10 [pg/mL]_SD |
|---|---|---|---|---|---|---|---|---|---|---|---|
| 0.1 | 0 | 133.12 | 32.49 | 3.87 | 1.70 | 624.65 | 521.25 | 33.08 | 5.13 | 26.48 | 33.25 |
| 0.1 | 25 | 391.33 | 137.48 | 5.26 | 2.87 | 461.65 | 406.87 | 46.78 | 19.50 | 39.88 | 12.70 |
| 0.1 | 50 | 849.50 | 811.47 | 12.99 | 6.54 | 1186.80 | 528.11 | 97.78 | 51.96 | 50.88 | 33.14 |
| 0.1 | 100 | 1413.82 | 409.47 | 50.77 | 29.60 | 2185.05 | 362.17 | 170.92 | 60.74 | 68.38 | 64.37 |

Oral Administration of Compounds Enhances Antigen-Specific T Cell Activation In Vivo Direct detection of antigen-specific T cell proliferation in vivo is technically challenging, since it requires the presence of T cells specific for a cognate antigen and also a specific measurement procedure for cell proliferation. Both these requirements are fulfilled in the OT-Ill transfer model, which utilizes the direct transfer of CD4 T cells transgenic for a T cell receptor recognizing an Ovalbumin-derived peptide as antigen. Before transfer, these cells are labeled with the fluorescent dye CFSE, which is diluted by every cell division and therefore allows detection of cell proliferation. After transfer of the CFSE-labeled T cells, mice are vaccinated with the Ovalbumin antigen and a TLR-agonist (LPS) as adjuvant to activate and mature the antigen-presenting cells (APCs). These APCs then migrate to lymphoid organs (especially lymph nodes and spleen) and present the OVA-antigen to the T cells in the lymphoid organs. However, only transferred OT-Ill cells are able to recognize the OVA-antigen and only these transferred T cells then get activated.

Thus, the OT-Ill model is optimal for detecting the influence of compounds on the physiological stimulation of antigen-specific T cells via APC-presented antigen, where the natural environment for T cell activation and costimulation provided by APCs is the lymphoid organs. Moreover, the kinetic of T cell activation, as strongly proliferating T cells tend to downregulate CD69 over the next days. Importantly, CD69 expression of CD4 and CD8 T cells as well as on B cells of the recipient mice itself was not enhanced by presence of the compound, showing that there is no activation of T cells by compound alone if the cognate antigen is not supplied. Thus, the effects of compound in vivo on T cell activation match those observed in vitro. Moreover, no signs of compound toxicities were noted during the time of the experiment, further confirming the conclusions of the in vitro data, that immune cell functions are enhanced in the context of cell-specific stimuli but not in an undesired general manner.

TABLE 34

| Proliferated OT-II cells | LPS only | LPS & OVA | LPS & OVA 10 mg/kg compound ex. 1 |
|---|---|---|---|
| [% gated] average | 6.59 | 12.20 | 29.03 |
| std. dev. | 2.05 | 10.01 | 5.65 |

TABLE 35

|  | LPS only | LPS & OVA | LPS & OVA 10 mg/kg compound ex. 1 |
|---|---|---|---|
| CD69+ cells [% gated] | | | |
| transferred OT-II cells | 8.70 | 48.73 | 46.92 |
| WT CD4 T cells of recipient animal | 7.28 | 6.20 | 7.00 |
| CD8 T cells of recipient animal | 4.40 | 2.87 | 3.48 |
| B cells of recipient animal | 2.41 | 1.34 | 2.10 |
| std dev | | | |
| transferred OT-II cells | 5.08 | 22.31 | 11.49 |
| WT CD4 T cells of recipient animal | 1.81 | 1.60 | 0.99 |
| CD8 T cells of recipient animal | 0.98 | 0.91 | 0.76 |
| B cells of recipient animal | 0.91 | 0.36 | 0.46 |

Intravenous Administration of Compounds Enhances Antigen-Specific T Cell Activation In Vivo Oral administration of drugs is generally the desired route for uptake in the outpatient context. However, in advanced cancer stages, tumor therapies are often administrated to in-patients. Intravenous administration is chosen for therapies where high levels of drug have to be kept steadily over extended periods of time. Moreover, side effects of past treatments can have damaged the gastrointestinal tract and it is therefore advantageous when intravenous administration would be an effective route as well. Therefore, it was investigated whether intravenous administration of compounds has the potential to be effective in an identical setting as above.

The below data show that intravenous administration of compounds is as effective as oral administration in specifically enhancing proliferation of antigen-stimulated T cells (p=0.0012) while not substantially affecting resting T cells of the recipient mice. Importantly, also in this experiment no signs of acute toxicities were noted, demonstrating that also intravenous administration of compounds is a safe and effective route.

TABLE 36

| Proliferated OT-II cells | LPS only | LPS & OVA | LPS & OVA 1 mg/kg compound ex. 70 |
|---|---|---|---|
| [% gated] average | 1.98 | 9.32 | 18.70 |
| std dev. | 0.61 | 2.62 | 9.96 |

TABLE 37

|  | LPS only | LPS & OVA | LPS & OVA 10 mg/kg compound ex. 70 |
|---|---|---|---|
| CD69+ cells [% gated] | | | |
| transferred OT-II cells | 5.96 | 51.85 | 59.47 |
| WT CD4 T cells of recipient animal | 10.51 | 11.54 | 12.26 |
| CD8 T cells of recipient animal | 5.38 | 6.39 | 7.08 |
| B cells of recipient animal | 5.94 | 7.66 | 8.62 |
| std dev | | | |
| transferred OT-II cells | 2.97 | 11.21 | 11.58 |
| WT CD4 T cells of recipient animal | 0.84 | 2.87 | 1.55 |
| CD8 T cells of recipient animal | 1.65 | 2.74 | 1.71 |
| B cells of recipient animal | 3.48 | 5.04 | 5.22 |

Enhancement of Anti-Tumor Reactivity of CD8 Positive Lymphocytes is Synergistic with PD-1 Blockade CD8 T cells were isolated from M21-prestimulated PBMCs and restimulated with M21 tumor cells as described in the materials & methods section. Example 107, no antibody (no Ig), anti-PD-1 antibody (Nivolumab) or control antibody without direct effects on CD8 T cells (Ipilimumab) were included where indicated.

Tumor cell contact resulted in activation of immune cells to secrete the cytokines IL-2, IFN-gamma and the cytotoxic mediator granzyme. Example 107 enhanced production of both cytokines specifically upon tumor cell contact, such effect was not detected in the absence of tumor cells. Likewise, PD-1 blockade also enhanced cytokine secretion since the M21 tumor cell line expresses PD-L1, the PD-1 ligand. When both example 107 and anti-PD-1 antibody (Nivolumab) was present, the enhancement of cytokine production was synergistic, i.e. more than additive (Table 38 & 39). No such effects were observed when no antibody (no Ig) or an antibody not targeting CD8 T cells (Ipilimumab) were used as control.

TABLE 38

|  | Compound concentration Ex. 107 [µM] | no Ig | Ipilimumab | Nivolumab |
|---|---|---|---|---|
| Average IL-2 [ng/ml] | no cpd | 0.025 | 0.024 | 0.046 |
| | 0.03 | 0.048 | 0.041 | 0.105 |
| | 0.1 | 0.106 | 0.100 | 0.258 |
| | 0.3 | 0.259 | 0.222 | 0.590 |
| | 1 | 0.389 | 0.478 | 0.954 |
| | 3 | 0.523 | 0.555 | 1.285 |
| | 10 | 0.643 | 0.669 | 1.596 |
| Std. dev. | no cpd | 0.003 | 0.001 | 0.011 |
| | 0.03 | 0.006 | 0.003 | 0.012 |
| | 0.1 | 0.011 | 0.009 | 0.057 |
| | 0.3 | 0.027 | 0.053 | 0.028 |
| | 1 | 0.028 | 0.018 | 0.099 |
| | 3 | 0.008 | 0.018 | 0.125 |
| | 10 | 0.029 | 0.103 | 0.110 |

TABLE 39

|  | Compound concentration Ex. 107 [µM] | no Ig | Ipilimumab | Nivolumab |
|---|---|---|---|---|
| Average IFN-g [ng/ml] | no cpd | 0.000 | 0.000 | 0.014 |
| | 0.03 | 0.059 | 0.057 | 0.772 |
| | 0.1 | 0.313 | 0.363 | 2.282 |
| | 0.3 | 1.114 | 1.098 | 4.565 |
| | 1 | 1.963 | 2.350 | 5.846 |
| | 3 | 2.469 | 2.745 | 6.041 |
| | 10 | 3.113 | 3.171 | 6.729 |
| Std. dev. | no cpd | 0.000 | 0.000 | 0.025 |
| | 0.03 | 0.042 | 0.066 | 0.091 |
| | 0.1 | 0.029 | 0.056 | 0.163 |
| | 0.3 | 0.244 | 0.036 | 0.063 |
| | 1 | 0.096 | 0.083 | 0.464 |
| | 3 | 0.051 | 0.294 | 0.365 |
| | 10 | 0.103 | 0.088 | 0.553 |

Moreover, example 107 also mediated an synergistic enhancement of the cytotoxic effector granzyme release upon tumor-cell contact (table 40), which is directly related to tumor cell killing. In agreement, the presence of example 107 in immune cell cocultures with tumor cells resulted in a strong reduction of viable tumor cells, which was even more pronounced and reached with lower compound concentrations in the presence of Nivolumab (table 41). Nivolumab alone was not able to cause a significant reduction in viable tumor cells.

TABLE 40

| | Compound concentration Ex. 107 [µM] | no Ig | Ipilimumab | Nivolumab |
|---|---|---|---|---|
| Average Granzyme B [ng/ml] | no cpd | 0.690 | 0.612 | 1.758 |
| | 0.03 | 1.971 | 1.639 | 5.522 |
| | 0.1 | 3.645 | 3.905 | 9.246 |
| | 0.3 | 5.469 | 6.001 | 12.040 |
| | 1 | 7.246 | 7.906 | 12.985 |
| | 3 | 8.208 | 9.283 | 14.403 |
| | 10 | 8.378 | 8.227 | 13.079 |
| Std. dev. | no cpd | 0.131 | 0.089 | 0.291 |
| | 0.03 | 0.216 | 0.138 | 0.506 |
| | 0.1 | 0.110 | 0.205 | 0.364 |
| | 0.3 | 0.605 | 0.065 | 1.080 |
| | 1 | 0.567 | 0.247 | 0.425 |
| | 3 | 0.290 | 0.550 | 0.229 |
| | 10 | 0.255 | 0.312 | 0.386 |

TABLE 41

| | Compound concentration Ex. 107 [µM] | no Ig | Ipilimumab | Nivolumab |
|---|---|---|---|---|
| Average Number of living M21 tumor cells | no cpd | 22786 | 22648 | 20344 |
| | no cpd | 21566 | 25130 | 22655 |
| | 0.03 | 16433 | 21424 | 5574 |
| | 0.1 | 9029 | 10688 | 3361 |
| | 0.3 | 3822 | 4339 | 1648 |
| | 1 | 2642 | 2104 | 1574 |
| | 3 | 2075 | 2083 | 1429 |
| | 10 | 2000 | 2033 | 1799 |
| Std. dev. | no cpd | 1444 | 1130 | 2708 |
| | no cpd | 4758 | 2627 | 1328 |
| | 0.03 | 1644 | 2360 | 1062 |
| | 0.1 | 896 | 1570 | 223 |
| | 0.3 | 1267 | 1061 | 239 |
| | 1 | 172 | 463 | 328 |
| | 3 | 394 | 152 | 284 |
| | 10 | 52 | 180 | 77 |

Compounds Enhance Tumor Antigen-Specific T Cell Activation In Vivo

Direct detection of tumor antigen-specific T cell proliferation in vivo requires the presence of T cells specific for a cognate tumor antigen. The widely used B16-F10-OVA melanoma model however is characterized by aggressive tumor growth within days, not allowing de novo generation of an anti-tumor immune response giving rise to a robust population of tumor-antigen specific T cells against its ovalbumin antigen which could be used for specific measurement of T cell proliferation. As an alternative, in the OT-I transfer model, the direct transfer of CD8 T cells transgenic for a T cell receptor recognizing an Ovalbumin-derived peptide as antigen can be utilized. Before transfer, these cells are labeled with the fluorescent dye CFSE, allowing detection of cell proliferation as in the OT-II transfer model described above. After transfer of the CFSE-labeled T cells to B16-F10-OVA tumor bearing mice, a fraction of these cells gets in contact with the tumor-antigen ovalbumin, either directly at the site of the tumor or in the context of antigen-presenting cells (APCs). These APCs are present in lymphoid organs (especially lymph nodes and spleen) and present the OVA-antigen to the OT-I T cells in the lymphoid organs.

Thus, the OT-I transfer model is optimal for detecting the influence of compounds on the stimulation of antigen-specific T cells by tumor-expressed antigens.

For this experiment, B16-F10-OVA tumor bearing mice received CFSE-labeled OT-I T cells as outlined in the method section, and were then divided into groups which either received no compound or example 1 at 10 mg/kg dosed orally. Table 42 shows, that OT-I T cell proliferation was highly significantly (p=0.0002) enhanced by the presence of example 1 in tumor-draining lymphnodes. In addition, OT-I T cell proliferation was also found to be significantly (p=0.006) increased among OT-I T cells isolated from spleen when example 1 had been administrated to the animals.

Thus, the effects of the compound on enhancement of T cell proliferation are relevant in vivo also in the absence of vaccination when the only antigen-source is the tumor itself and clearly show that the compound enhances tumor antigen-specific T cell activation in vivo.

TABLE 42

| | Lymph node | | Spleen | |
|---|---|---|---|---|
| Proliferation | vehicle | 10 mg/kg example 1 | vehicle | 10 mg/kg example 1 |
| [% proliferated OT-I T cells] | 5.85 | 12.28 | 5.18 | 8.62 |
| std dev. | 0.72 | 2.83 | 2.04 | 3.15 |

Compounds have Immunomodulatory Activities and Enhance Anti-Tumor Immunity In Vivo Wildtype mice were inoculated with B16-F10-OVA tumor cells and randomized at day 7, when all mice in the experimental set had clearly visible tumors, into groups which either received vehicle only or example 1 at 10 mg/kg or 30 mg/kg dosed orally as outlined in the method section. In addition, a set of 3 mice without tumors was included that was treated only with vehicle control. At day 15, mice were sacrificed and the activation status of immune cells in tumor draining lymph nodes was analysed by flow cytometry.

Analysis of CD4 T cell activation markers in the lymph nodes showed significant upregulation of CD25 (p=0.006 for 10 mg/kg and 0.015 for 30 mg/kg), CD69 (p=0.011 for 10 mg/kg and 0.021 for 30 mg/kg), CD107a (p=0.023 for 10 mg/kg and 0.018 for 30 mg/kg) and PD-1 (p=0.0005 for 10 mg/kg and 0.005 for 30 mg/kg) in compound treated groups compared to vehicle control treated animals (table 43). Likewise, CD8 T cell activation markers in the lymph nodes showed similar upregulation of CD25 (p=0.002 for 30 mg/kg), CD69 (p=0.026 for 30 mg/kg), CD107a (p=0.046 for 30 mg/kg) and PD-1 (p=0.0004 for 30 mg/kg) in compound treated groups compared to vehicle control treated animals (table 43). Comparison of tumor bearing mice with untreated control mice without tumor showed that the presence of tumor resulted in profound suppression of T cell activation. Notably, when comparing T cell activation markers, compound treatment was able to restore the immunosuppression in tumor bearing mice to levels of healthy control animals indicating the immunomodulatory activities of these compounds in vivo.

TABLE 43

| | no tumor | vehicle | 10 mg/kg Compound Ex. 1 | 30 mg/kg Compound Ex. 1 |
|---|---|---|---|---|
| | | CD4 T cells | | |
| Average CD25+ cells [% gated] | 17.12 | 13.12 | 15.63 | 15.91 |
| Std. Dev. | 0.69 | 1.10 | 1.67 | 2.49 |

TABLE 43-continued

|  | no tumor | vehicle | 10 mg/kg Compound Ex. 1 | 30 mg/kg Compound Ex. 1 |
|---|---|---|---|---|
| Average CD69+ cells [% gated] | 14.92 | 11.68 | 13.34 | 14.25 |
| Std. Dev. | 1.96 | 1.07 | 1.06 | 2.45 |
| Average CD107a+ cells [% gated] | 6.59 | 2.80 | 5.03 | 5.43 |
| Std. Dev. | 0.74 | 1.23 | 1.90 | 2.38 |
| Average PD1+ cells [% gated] | 10.62 | 5.86 | 10.73 | 10.36 |
| Std. Dev. | 0.45 | 1.23 | 2.29 | 3.33 |
| CD8 T cells | | | | |
| Average CD25+ cells [% gated] | 3.34 | 1.54 | 1.95 | 2.88 |
| Std. Dev. | 0.54 | 0.43 | 0.60 | 0.84 |
| Average CD69+ cells [% gated] | 7.35 | 4.91 | 5.25 | 5.91 |
| Std. Dev. | 0.98 | 0.44 | 0.48 | 1.01 |
| Average CD107a+ cells [% gated] | 4.56 | 2.74 | 2.00 | 4.24 |
| Std. Dev. | 0.97 | 1.27 | 0.80 | 1.40 |
| Average PD1+ cells [% gated] | 6.21 | 3.31 | 3.12 | 6.71 |
| Std. Dev. | 1.01 | 0.96 | 1.01 | 1.72 |

Also for NK cells, upregulation of activation markers CD69 (NK cells: p=0.044 for 10 mg/kg), CD107a (NK cells: p=0.013 for 10 mg/kg) and PD-1 (NK cells: p=0.0002 for 10 mg/kg and 0.018 for 30 mg/kg) in compound treated groups compared to vehicle group was observed (table 44), again resulting in at least partial restoration to levels of untreated tumor-free healthy control animals.

TABLE 44

NK cells

|  | no tumor | vehicle | 10 mg/kg Compound Ex. 1 | 30 mg/kg Compound Ex. 1 |
|---|---|---|---|---|
| Average CD69+ cells [% gated] | 37.48 | 29.91 | 34.43 | 32.55 |
| Std. Dev. | 1.26 | 2.95 | 4.42 | 5.18 |
| Average CD107a+ cells [% gated] | 15.27 | 8.65 | 12.85 | 10.98 |
| Std. Dev. | 2.77 | 1.83 | 3.28 | 4.00 |
| Average PD1+ cells [% gated] | 19.59 | 9.53 | 19.91 | 13.61 |
| Std. Dev. | 1.83 | 1.44 | 4.24 | 3.84 |

A key feature for anti-tumor immunity is the infiltration of tumor by activated immune cells. As a viable detection method for levels and activities of tumor infiltrating leukocytes (TILs) analysis of mRNA transcripts present in the tumor by RT-PCR is commonly employed. For all explantable tumors of the mice in the set, tumor specimens were obtained and mRNA isolated. Tumor infiltration by immune cells was then determined by quantitative RT-PCR for CD4, CD8, IL-2, IL-12, IL-23, EOMES, Foxp3, IFN-g, Rorgc, T-bet, TNF-a. Notably, compared to vehicle control, tumor infiltration by CD4 (p=0.04 for 30 mg/kg) and CD8 T cells was enhanced in compound treated animal groups as well as expression levels of cytokines IL-2 (p=0.02 for 30 mg/kg), IFN-g and TNF-a (table 45).

TABLE 45

|  | vehicle | 10 mg/kg Compound Ex. 1 | 30 mg/kg Compound Ex. 1 |
|---|---|---|---|
| Average CD4 expression [EF1a * 10^4] | 6.17 | 7.07 | 9.65 |
| Std. Dev. | 1.39 | 4.30 | 4.00 |
| Average CD8 expression [EF1a * 10^4] | 7.24 | 6.28 | 10.72 |
| Std. Dev. | 5.32 | 5.35 | 6.10 |
| Average IL-2 expression [EF1a * 10^4] | 0.041 | 0.043 | 0.085 |
| Std. Dev. | 0.028 | 0.043 | 0.039 |
| Average IFN-g expression [EF1a * 10^4] | 0.64 | 0.75 | 1.23 |
| Std. Dev. | 0.45 | 0.66 | 0.65 |
| Average TNF-a expression [EF1a * 10^4] | 10.49 | 9.96 | 14.97 |
| Std. Dev. | 4.592 | 4.009 | 3.813 |

Tumor infiltration by effector T cells is commonly associated with improved anti-tumor immunity and better overall survival, while tumor infiltration by T regulatory cells is not and can be viewed as suppressor of anti-tumor immune responses. Therefore, the relative ratio of transcription factors which either characterise T regulatory cells (Foxp3) or effector cells of the Th1 and Th17 lineage (T-bet, Rorgc, EOMES) was determined by RT-PCR. The results clearly show that this ratio was skewed towards anti-tumor Th1 and Th17 immune responses in compound treated animals when compared with the vehicle control group (table 46). In agreement, production of the key driving cytokines for Th1 and Th17 responses, IL-12 and IL-23, were present in enhanced levels in the compound treated animal groups (table 47).

TABLE 46

|  | vehicle | 10 mg/kg Compound Ex. 1 | 30 mg/kg Compound Ex. 1 |
|---|---|---|---|
| Average Ratio T-bet/Foxp3 | 6.56 | 8.35 | 9.59 |
| Std. Dev. | 3.53 | 6.05 | 4.09 |
| Average Ratio Eomes/Foxp3 | 0.43 | 0.66 | 0.64 |
| Std. Dev. | 0.25 | 0.40 | 0.45 |
| Average Ratio Rorgc/Foxp3 | 4.49 | 5.38 | 6.17 |
| Std. Dev. | 1.55 | 1.71 | 5.17 |

TABLE 47

|  | vehicle | 10 mg/kg Compound Ex. 1 | 30 mg/kg Compound Ex. 1 |
|---|---|---|---|
| Average IL-12 expression [EF1a * 10^4] | 0.074 | 0.074 | 0.120 |
| Std. Dev. | 0.042 | 0.037 | 0.041 |
| Average IL-23 expression [EF1a * 10^4] | 0.325 | 0.480 | 0.611 |
| Std. Dev. | 0.079 | 0.276 | 0.170 |

Together, these data show that compound example has immunomodulatory activities and thus can enhance directly anti-tumor immunity in vivo.

The invention claimed is:
1. A pharmaceutical composition comprising at least one pharmaceutically acceptable carrier and at least one compound of formula (I)

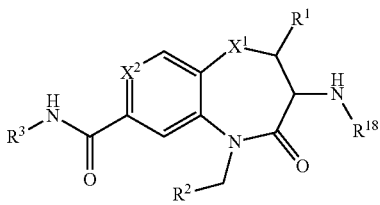

(I)

or a pharmaceutically acceptable salt thereof, wherein
$X^1$ is S; S(O); or S(O)$_2$;
$X^2$ is N; or C(R$^4$);
$R^1$ is H; or methyl;
$R^2$ is phenyl; 3 to 7 membered heterocyclyl; or 7 to 11 membered heterobicyclyl, wherein $R^2$ is optionally substituted with one or more $R^5$, which are the same or different;
$R^5$ is halogen; CN; C(O)OR$^6$; OR$^6$; C(O)R$^6$; C(O)N(R$^6$R$^{6a}$); S(O)$_2$N(R$^6$R$^{6a}$); S(O)N(R$^6$R$^{6a}$); S(O)$_2$R$^6$; S(O)R$^6$; N(R$^6$)S(O)$_2$N(R$^{6a}$R$^{6b}$); SR$^6$; N(R$^6$R$^{6a}$); OC(O)R$^6$; N(R$^6$)C(O)R$^{6a}$; N(R$^6$)S(O)$_2$R$^{6a}$; N(R$^6$)S(O)R$^{6a}$; N(R$^6$)C(O)OR$^{6a}$; N(R$^6$)C(O)N(R$^{6a}$R$^{6b}$); OC(O)N(R$^6$R$^{6a}$); oxo (=O), where the ring is at least partially saturated; T$^1$; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more halogen, which are the same or different;
$R^6$, $R^{6a}$, and $R^{6b}$ are independently selected from the group consisting of H; C$_{1-6}$ alkyl, C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;
T$^1$ is phenyl; C$_{3-7}$ cycloalkyl; or 3 to 7 membered heterocyclyl, wherein T$^1$ is optionally substituted with one or more R$^7$, which are the same or different;
$R^7$ is halogen; CN; C(O)OR$^8$; OR$^8$; C(O)R$^8$; C(O)N(R$^8$R$^{8a}$); S(O)$_2$N(R$^8$R$^{8a}$); S(O)N(R$^8$R$^{8a}$); S(O)$_2$R$^8$; S(O)R$^8$; N(R$^8$)S(O)$_2$N(R$^{8a}$R$^{8b}$); SR$^8$; N(R$^8$R$^{8a}$); OC(O)R$^8$; N(R$^8$)C(O)R$^{8a}$; N(R$^8$)S(O)$_2$R$^{8a}$; N(R$^8$)S(O)R$^{8a}$; N(R$^8$)C(O)OR$^{8a}$; N(R$^8$)C(O)N(R$^{8a}$R$^{8b}$); OC(O)N(R$^8$R$^{8a}$); oxo (=O), where the ring is at least partially saturated; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more halogen, which are the same or different;
$R^8$, $R^{8a}$, and $R^{8b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;
$R^3$ is R$^{3a}$; OR$^{3a}$; NHR$^{3a}$; or NHC(O)R$^{3a}$;
$R^{3a}$ is T$^2$; C$_{1-12}$ alkyl; C$_{2-12}$ alkenyl; or C$_{2-12}$ alkynyl, wherein C$_{1-12}$ alkyl; C$_{2-12}$ alkenyl; and C$_{2-12}$ alkynyl are optionally substituted with one or more R$^9$, which are the same or different;
$R^9$ is halogen; CN; C(O)OR$^{10}$; OR$^{10}$; C(O)R$^{10}$; C(O)N(R$^{10}$R$^{10a}$); S(O)$_2$N(R$^{10}$R$^{10a}$); S(O)N(R$^{10}$R$^{10a}$); S(O)$_2$R$^{10}$; S(O)R$^{10}$; N(R$^{10}$)S(O)$_2$N(R$^{10a}$R$^{10b}$); SR$^{10}$; N(R$^{10}$R$^{10a}$); OC(O)R$^{10}$; N(R$^{10}$)C(O)R$^{10a}$; N(R$^{10}$)S(O)$_2$R$^{10a}$; N(R$^{10}$)S(O)R$^{10a}$; N(R$^{10}$)C(O)N(R$^{10a}$R$^{10b}$); N(R$^{10}$)C(O)OR$^{10a}$; OC(O)N(R$^{10}$R$^{10a}$); T$^2$; C$_{1-12}$ alkyl; C$_{2-12}$ alkenyl; or C$_{2-12}$ alkynyl, wherein C$_{1-12}$ alkyl; C$_{2-12}$ alkenyl; and C$_{2-12}$ alkynyl are optionally substituted with one or more R$^{11}$, which are the same or different;

$R^{10}$, $R^{10a}$, and $R^{10b}$ are independently selected from the group consisting of H; T$^2$; C$_{1-12}$ alkyl; C$_{2-12}$ alkenyl; and C$_{2-12}$ alkynyl, wherein C$_{1-12}$ alkyl; C$_{2-12}$ alkenyl; and C$_{2-12}$ alkynyl are optionally substituted with one or more R$^{11}$, which are the same or different;
T$^2$ is phenyl; C$_{3-7}$ cycloalkyl; 3 to 7 membered heterocyclyl; or 7 to 11 membered heterobicyclyl, wherein T$^2$ is optionally substituted with one or more R$^{12}$, which are the same or different;
$R^{12}$ is halogen; CN; C(O)OR$^{13}$; OR$^{13}$; C(O)R$^{13}$; C(O)N(R$^{13}$R$^{13a}$); S(O)$_2$N(R$^{13}$R$^{13a}$); S(O)N(R$^{13}$R$^{13a}$); S(O)$_2$R$^{13}$; S(O)R$^{13}$; N(R$^{13}$)S(O)$_2$N(R$^{13a}$R$^{13b}$); SR$^{13}$; N(R$^{13}$R$^{13a}$); OC(O)R$^{13}$; N(R$^{13}$)C(O)R$^{13a}$; N(R$^{13}$)S(O)$_2$R$^{13a}$; N(R$^{13}$)S(O)R$^{13a}$; N(R$^{13}$)C(O)OR$^{13a}$; N(R$^{13}$)C(O)N(R$^{13a}$R$^{13b}$); OC(O)N(R$^{13}$R$^{13a}$); oxo (=O), where the ring is at least partially saturated; T$^3$; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more R$^{14}$, which are the same or different;
$R^{13}$, $R^{13a}$, and $R^{13b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^{14}$, which are the same or different;
$R^{11}$ and $R^{14}$ are independently selected from the group consisting of halogen; CN; C(O)OR$^{15}$; OR$^{15}$; C(O)R$^{15}$; C(O)N(R$^{15}$R$^{15a}$); S(O)$_2$N(R$^{15}$R$^{15a}$); S(O)N(R$^{15}$R$^{15a}$); S(O)$_2$R$^{15}$; S(O)R$^{15}$; N(R$^{15}$)S(O)$_2$N(R$^{15a}$R$^{15b}$); SR$^{15}$; N(R$^{15}$R$^{15a}$); OC(O)R$^{15}$; N(R$^{15}$)C(O)R$^{15a}$; N(R$^{15}$)S(O)$_2$R$^{15a}$; N(R$^{15}$)S(O)R$^{15a}$; N(R$^{15}$)C(O)OR$^{15a}$; N(R$^{15}$)C(O)N(R$^{15a}$R$^{15b}$); OC(O)N(R$^{15}$R$^{15a}$); and T$^3$;
$R^{15}$, $R^{15a}$, and $R^{15b}$ are independently selected from the group consisting of H; T$^3$; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;
T$^3$ is phenyl; C$_{3-7}$ cycloalkyl; or 3 to 7 membered heterocyclyl, wherein T$^3$ is optionally substituted with one or more R$^{16}$, which are the same or different;
$R^{16}$ is halogen; CN; C(O)OR$^{17}$; OR$^{17}$; C(O)R$^{17}$; C(O)N(R$^{17}$R$^{17a}$); S(O)$_2$N(R$^{17}$R$^{17a}$); S(O)N(R$^{17}$R$^{17a}$); S(O)$_2$R$^{17}$; S(O)R$^{17}$; N(R$^{17}$)S(O)$_2$N(R$^{17a}$R$^{17b}$); SR$^{17}$; N(R$^{17}$R$^{17a}$); OC(O)R$^{17}$; N(R$^{17}$)C(O)R$^{17a}$; N(R$^{17}$)S(O)$_2$R$^{17a}$; N(R$^{17}$)S(O)R$^{17a}$; N(R$^{17}$)C(O)OR$^{17a}$; N(R$^{17}$)C(O)N(R$^{17a}$R$^{17b}$); OC(O)N(R$^{17}$R$^{17a}$); oxo (=O), where the ring is at least partially saturated; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more halogen, which are the same or different;
$R^{17}$, $R^{17a}$, and $R^{17b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;
$R^4$ is H; F; Cl; or N(CH$_3$)$_2$;
$R^{18}$ is H; C$_{1-6}$ alkyl; C$_{2-6}$ alkenyl; or C$_{2-6}$ alkynyl; wherein C$_{1-6}$ alkyl, C$_{2-6}$ alkenyl; and C$_{2-6}$ alkynyl are optionally substituted with one or more R$^{19}$, which are the same or different;
$R^{19}$ is halogen; CN; C(O)OR$^{20}$; OR$^{20}$; C(O)R$^{20}$; C(O)N(R$^{20}$R$^{20a}$); S(O)$_2$N(R$^{20}$R$^{20a}$); S(O)N(R$^{20}$R$^{20a}$); S(O)$_2$R$^{20}$; S(O)R$^{20}$; N(R$^{20}$)S(O)$_2$N(R$^{20a}$R$^{20b}$); SR$^{20}$; N(R$^{20}$R$^{20a}$); NO$_2$; OC(O)R$^{20}$; N(R$^{20}$)C(O)R$^{20a}$; N(R$^{20}$)SO$_2$R$^{20a}$; N(R$^{20}$)S(O)R$^{20a}$; N(R$^{20}$)C(O)N(R$^{20a}$R$^{20b}$); N(R$^{20}$)C(O)OR$^{20a}$; or OC(O)N(R$^{20}$R$^{20a}$); and 2. The pharmaceutical composition of claim 1 having formula (IIa)

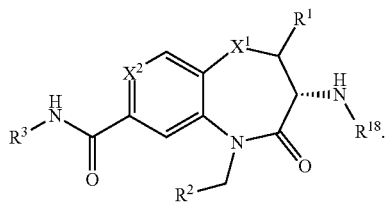

(IIa)

3. The pharmaceutical composition of claim 1, wherein $R^{18}$ is H.

4. The pharmaceutical composition of claim 1, wherein $X^1$ is $S(O)_2$.

5. The pharmaceutical composition of claim 1, wherein $R^1$ is H.

6. The pharmaceutical composition of claim 1, wherein $X^2$ is $C(R^4)$.

7. The pharmaceutical composition of claim 1, wherein $R^4$ is H; F; or $N(CH_3)_2$.

8. The pharmaceutical composition of claim 1, wherein $R^2$ is phenyl, 5 to 6 membered aromatic heterocyclyl, or 9 to 11 membered aromatic heterobicyclyl; and wherein $R^2$ is optionally substituted with one or two $R^5$, which are the same or different.

9. The pharmaceutical composition of claim 1, wherein $R^2$ is substituted with one or two $R^5$, which are the same or different.

10. The pharmaceutical composition of claim 1, wherein $R^5$ is halogen; CN; $OR^6$; $C(O)N(R^6R^{6a})$; $T^1$; or $C_{1-6}$ alkyl, wherein $C_{1-6}$ alkyl is optionally substituted with one or more halogen, which are the same or different.

11. The pharmaceutical composition of claim 1, wherein $T^1$ is cyclopropyl; or 3 to 7 membered heterocyclyl, wherein $T^1$ is unsubstituted or substituted with unsubstituted $C_{1-6}$ alkyl.

12. The pharmaceutical composition of claim 1, wherein $R^2$ in formula (I) is selected to give formula (IIaa) or (IIab)

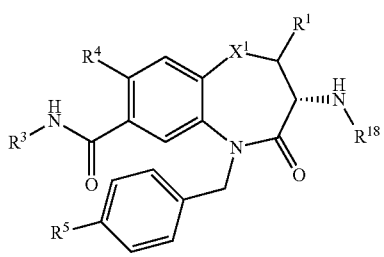

(IIaa)

or

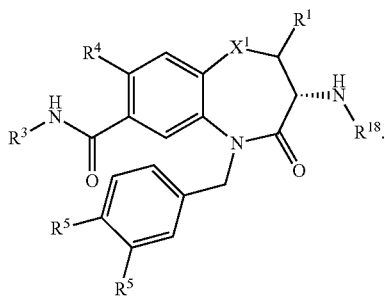

(IIab)

13. The pharmaceutical composition of claim 1, wherein $R^{3a}$ is $T^2$; $C_{1-12}$ alkyl; unsubstituted $C_{2-12}$ alkenyl; or unsubstituted $C_{2-12}$ alkynyl, wherein $C_{1-12}$ alkyl is optionally substituted with one, two or three $R^9$, which are the same or different.

14. The pharmaceutical composition of claim 1, wherein $T^2$ is phenyl; $C_{3-7}$ cycloalkyl; or 3 to 7 membered heterocyclyl, wherein $T^2$ is optionally substituted with one or more $R^{12}$, which are the same or different.

15. The pharmaceutical composition of claim 1, wherein $T^2$ is unsubstituted or substituted with one or two $R^{12}$, which are the same or different.

16. The pharmaceutical composition of claim 1, wherein $R^{12}$ is halogen; $OR^{13}$; unsubstituted $T^3$; $T^3$ which is substituted with unsubstituted $C_{1-6}$ alkyl; or unsubstituted $C_{1-6}$ alkyl.

17. The pharmaceutical composition of claim 1, wherein in formula (I) $X^1$, $X^2$, $R^1$, $R^2$, $R^3$, and $R^{18}$ are selected to give:
(3R)-3-amino-5-[(4-chlorophenyl)methyl]-N-(2,2-difluorocyclopropyl)-8-fluoro-1,1,4-trioxo-2,3,4,5-tetrahydro-1λ⁶,5-benzothiazepine-7-carboxamide;
(3R)-3-amino-N-butyl-5-[(4-tert-butylphenyl)methyl]-4-oxo-2,3,4,5-tetrahydro-1,5-benzothiazepine-7-carboxamide;
(3R)-3-amino-N-butyl-4-oxo-5-{[4-(trifluoromethoxy)phenyl]methyl}-2,3,4,5-tetrahydro-1,5-benzothiazepine-7-carboxamide;
(3R)-3-amino-5-[(4-tert-butylphenyl)methyl]-4-oxo-N-(propan-2-yl)-2,3,4,5-tetrahydro-1,5-benzothiazepine-7-carboxamide;
(3R)-3-amino-N-butyl-8-fluoro-4-oxo-5-{[4-(trifluoromethoxy)phenyl]methyl}-2,3,4,5-tetrahydro-1,5-benzothiazepine-7-carboxamide;
(3R)-3-amino-N-benzyl-4-oxo-5-{[4-(trifluoromethoxy)phenyl]methyl}-2,3,4,5-tetrahydro-1,5-benzothiazepine-7-carboxamide;
(3R)-3-amino-N-[(4-methoxyphenyl)methyl]-4-oxo-5-{[4-(trifluoromethoxy)-phenyl]methyl}-2,3,4,5-tetrahydro-1,5-benzothiazepine-7-carboxamide;
(3R)-3-amino-N-(oxan-4-yl)-4-oxo-5-{[4-(trifluoromethoxy)phenyl]methyl}-2,3,4,5-tetrahydro-1,5-benzothiazepine-7-carboxamide;
(3R)-3-amino-N-butyl-4-oxo-5-{[3-(trifluoromethoxy)phenyl]methyl}-2,3,4,5-tetrahydro-1,5-benzothiazepine-7-carboxamide;
(3R)-3-amino-N-butyl-5-[(4-chlorophenyl)methyl]-4-oxo-2,3,4,5-tetrahydro-1,5-benzothiazepine-7-carboxamide;
(3R)-3-amino-N-{[4-(morpholin-4-yl)phenyl]methyl}-4-oxo-5-{[4-(trifluoromethoxy)-phenyl]methyl}-2,3,4,5-tetrahydro-1,5-benzothiazepine-7-carboxamide;

N-(3-{[(3R)-3-amino-4-oxo-5-{[4-(trifluoromethoxy)phenyl]methyl}-2,3,4,5-tetrahydro-1,5-benzothiazepin-7-yl]formamido}propyl)-2,2-dimethylpropanamide;

(3R)-3-amino-N-butyl-5-{[4-(morpholin-4-yl)phenyl]methyl}-4-oxo-2,3,4,5-tetrahydro-1,5-benzothiazepine-7-carboxamide;

(3R)-3-amino-8-fluoro-N-(oxan-4-yl)-4-oxo-5-{[4-(trifluoromethoxy)phenyl]methyl}-2,3,4,5-tetrahydro-1,5-benzothiazepine-7-carboxamide;

(3R)-3-amino-8-fluoro-4-oxo-N-(propan-2-yl)-5-{[4-(trifluoromethoxy)phenyl]-methyl}-2,3,4,5-tetrahydro-1,5-benzothiazepine-7-carboxamide;

(3R)-3-amino-N-benzyl-8-fluoro-4-oxo-5-{[4-(trifluoromethoxy)phenyl]methyl}-2,3,4,5-tetrahydro-1,5-benzothiazepine-7-carboxamide;

(3R)-3-amino-N-methyl-4-oxo-5-{[4-(trifluoromethoxy)phenyl]methyl}-2,3,4,5-tetrahydro-1,5-benzothiazepine-7-carboxamide;

(3R)-3-amino-N-ethyl-4-oxo-5-{[4-(trifluoromethoxy)phenyl]methyl}-2,3,4,5-tetrahydro-1,5-benzothiazepine-7-carboxamide;

(3R)-3-amino-N-({4-[(5-acetamidopentyl)oxy]phenyl}methyl)-4-oxo-5-{[4-(trifluoromethoxy)phenyl]methyl}-2,3,4,5-tetrahydro-1,5-benzothiazepine-7-carboxamide;

(3R)-3-amino-5-[(4-chlorophenyl)methyl]-N-(2-methoxyethyl)-4-oxo-2,3,4,5-tetrahydro-1,5-benzothiazepine-7-carboxamide;

(3R)-3-amino-N-butyl-5-[(4-cyanophenyl)methyl]-4-oxo-2,3,4,5-tetrahydro-1,5-benzothiazepine-7-carboxamide;

(3R)-3-amino-5-[(4-chlorophenyl)methyl]-4-oxo-N-(4,4,4-trifluorobutyl)-2,3,4,5-tetrahydro-1,5-benzothiazepine-7-carboxamide;

(3R)-3-amino-5-[(4-chlorophenyl)methyl]-N-(oxan-4-ylmethyl)-4-oxo-2,3,4,5-tetrahydro-1,5-benzothiazepine-7-carboxamide;

(3R)-3-amino-N-(5-tert-butyl-1,2-oxazol-3-yl)-5-[(4-chlorophenyl)methyl]-4-oxo-2,3,4,5-tetrahydro-1,5-benzothiazepine-7-carboxamide;

(3R)-3-amino-4-oxo-N-(pyridin-3-yl)-5-{[4-(trifluoromethoxy)phenyl]methyl}-2,3,4,5-tetrahydro-1,5-benzothiazepine-7-carboxamide;

(3R)-3-amino-5-[(4-chlorophenyl)methyl]-N-[(4-fluorophenyl)methyl]-4-oxo-2,3,4,5-tetrahydro-1,5-benzothiazepine-7-carboxamide;

(3R)-3-amino-5-[(4-chlorophenyl)methyl]-N-[(1R)-1-(4-methoxyphenyl)ethyl]-4-oxo-2,3,4,5-tetrahydro-1,5-benzothiazepine-7-carboxamide;

(3R)-3-amino-5-[(4-chlorophenyl)methyl]-N-(oxan-3-ylmethyl)-4-oxo-2,3,4,5-tetrahydro-1,5-benzothiazepine-7-carboxamide;

(3R)-3-amino-4-oxo-N-(4,4,4-trifluorobutyl)-5-{[4-(trifluoromethoxy)phenyl]methyl}2,3,4,5-tetrahydro-1,5-benzothiazepine-7-carboxamide;

(3R)-3-amino-N-(oxan-4-ylmethyl)-4-oxo-5-{[4-(trifluoromethoxy)phenyl]-methyl}-2,3,4,5-tetrahydro-1,5-benzothiazepine-7-carboxamide;

(3R)-3-amino-N-[(4-fluorophenyl)methyl]-4-oxo-5-{[4-(trifluoromethoxy)phenyl]-methyl}-2,3,4,5-tetrahydro-1,5-benzothiazepine-7-carboxamide;

(3R)-3-amino-N-[(4-fluorophenyl)methyl]-4-oxo-5-{[4-(1,2,3-thiadiazol-4-yl)phenyl]-methyl}-2,3,4,5-tetrahydro-1,5-benzothiazepine-7-carboxamide;

(3R)-3-amino-5-[(4-chlorophenyl)methyl]-N-(4,4-difluorocyclohexyl)-4-oxo-2,3,4,5-tetrahydro-1,5-benzothiazepine-7-carboxamide;

(3R)-3-amino-5-[(4-chlorophenyl)methyl]-N-[1-(4-fluorophenyl)ethyl]-4-oxo-2,3,4,5-tetrahydro-1,5-benzothiazepine-7-carboxamide;

(3R)-3-amino-5-[(4-chlorophenyl)methyl]-N-[(1S)-1-(4-methoxyphenyl)ethyl]-4-oxo-2,3,4,5-tetrahydro-1,5-benzothiazepine-7-carboxamide;

(3R)-3-amino-4-oxo-N-(4,4,4-trifluorobutyl)-5-{[6-(trifluoromethyl)pyridin-3-yl]methyl}-2,3,4,5-tetrahydro-1,5-benzothiazepine-7-carboxamide;

(3R)-3-amino-N-[(4-fluorophenyl)methyl]-4-oxo-5-{[6-(trifluoromethyl)pyridin-3-yl]methyl}-2,3,4,5-tetrahydro-1,5-benzothiazepine-7-carboxamide;

(3R)-3-amino-5-[(4-chlorophenyl)methyl]-N-[(1R)-1-(4-fluorophenyl)ethyl]-4-oxo-2,3,4,5-tetrahydro-1,5-benzothiazepine-7-carboxamide;

(3R)-3-amino-5-[(4-chlorophenyl)methyl]-8-fluoro-N-[(4-fluorophenyl)methyl]-4-oxo-2,3,4,5-tetrahydro-1,5-benzothiazepine-7-carboxamide;

(3R)-3-amino-5-[(4-chlorophenyl)methyl]-8-fluoro-4-oxo-N-(4,4,4-trifluorobutyl)-2,3,4,5-tetrahydro-1,5-benzothiazepine-7-carboxamide;

(3R)-3-amino-N-butyl-5-[(4-chlorophenyl)methyl]-8-fluoro-4-oxo-2,3,4,5-tetrahydro-1,5-benzothiazepine-7-carboxamide;

(3R)-3-amino-5-[(4-chlorophenyl)methyl]-8-fluoro-N-(oxan-4-yl methyl)-4-oxo-2,3,4,5-tetrahydro-1,5-benzothiazepine-7-carboxamide;

(3R)-3-amino-5-[(4-chlorophenyl)methyl]-8-fluoro-N-[(4-methoxyphenyl)methyl]-4-oxo-2,3,4,5-tetrahydro-1,5-benzothiazepine-7-carboxamide;

(3R)-3-amino-5-{[4-(5-methyl-1,2,4-oxadiazol-3-yl)phenyl]methyl}-N-(oxan-4-ylmethyl)-4-oxo-2,3,4,5-tetrahydro-1,5-benzothiazepine-7-carboxamide;

(3R)-3-amino-5-[(4-fluorophenyl)methyl]-N-(oxan-4-ylmethyl)-4-oxo-2,3,4,5-tetrahydro-1,5-benzothiazepine-7-carboxamide;

(3R)-3-amino-N-butyl-4-oxo-5-{[4-(1H-1,2,4-triazol-1-yl)phenyl]methyl}-2,3,4,5-tetrahydro-1,5-benzothiazepine-7-carboxamide;

(3R)-3-amino-N-butyl-5-[(4-carbamoyl phenyl)methyl]-4-oxo-2,3,4,5-tetrahydro-1,5-benzothiazepine-7-carboxamide;

(3R)-3-amino-5-[(4-chlorophenyl)methyl]-N-(2-hydroxy-2-methylpropyl)-4-oxo-2,3,4,5-tetrahydro-1,5-benzothiazepine-7-carboxamide;

(3R)-3-amino-5-[(4-chlorophenyl)methyl]-N-[(1S)-1-(4-fluorophenyl)ethyl]-4-oxo-2,3,4,5-tetrahydro-1,5-benzothiazepine-7-carboxamide;

(3R)-3-amino-5-[(4-chlorophenyl)methyl]-8-fluoro-N-(2-hydroxy-2-methylpropyl)-4-oxo-2,3,4,5-tetrahydro-1,5-benzothiazepine-7-carboxamide;

(3R)-3-amino-5-[(4-chlorophenyl)methyl]-4-oxo-N-(4,4,4-trifluorobutyl)-2,3,4,5-tetrahydro-1,5-benzothiazepine-7-carboxamide;

(3R)-3-amino-5-[(4-chlorophenyl)methyl]-8-fluoro-N'-(4-fluorophenyl)-4-oxo-2,3,4,5-tetrahydro-1,5-benzothiazepine-7-carbohydrazide;

(3R)-3-amino-N-butanoyl-5-[(4-chlorophenyl)methyl]-4-oxo-2,3,4,5-tetrahydro-1,5-benzothiazepine-7-carbohydrazide;

(3R)-3-amino-N-butyl-5-[(4-chloro-2-fluorophenyl)methyl]-8-fluoro-4-oxo-2,3,4,5-tetrahydro-1,5-benzothiazepine-7-carboxamide;

(3R)-3-amino-5-[(4-chloro-2-fluorophenyl)methyl]-8-fluoro-N-(oxan-4-ylmethyl)-4-oxo-2,3,4,5-tetrahydro-1,5-benzothiazepine-7-carboxamide;
(3R)-3-amino-5-[(4-chloro-3-fluorophenyl)methyl]-8-fluoro-N-(oxan-4-ylmethyl)-4-oxo-2,3,4,5-tetrahydro-1,5-benzothiazepine-7-carboxamide;
(3R)-3-amino-N-butyl-5-[(4-chloro-3-fluorophenyl)methyl]-8-fluoro-4-oxo-2,3,4,5-tetrahydro-1,5-benzothiazepine-7-carboxamide;
(3R)-3-amino-5-[(4-chlorophenyl)methyl]-8-fluoro-4-oxo-N-propoxy-2,3,4,5-tetrahydro-1,5-benzothiazepine-7-carboxamide;
(3R)-3-amino-5-[(4-chlorophenyl)methyl]-8-fluoro-N-(2-methyl propoxy)-4-oxo-2,3,4,5-tetrahydro-1,5-benzothiazepine-7-carboxamide;
(3R)-3-amino-5-[(4-chlorophenyl)methyl]-8-fluoro-N'-(2-methyl propyl)-4-oxo-2,3,4,5-tetrahydro-1,5-benzothiazepine-7-carbohydrazide;
(3R)-3-amino-5-[(4-chlorophenyl)methyl]-4-oxo-N-(propan-2-yl)-2,3,4,5-tetrahydro-1,5-benzothiazepine-7-carboxamide;
(3R)-3-amino-5-[(4-chlorophenyl)methyl]-N-(2-methylpropoxy)-4-oxo-2,3,4,5-tetrahydro-1,5-benzothiazepine-7-carboxamide;
(3R)-3-amino-5-[(4-chlorophenyl)methyl]-N-(3-methylbutan-2-yl)-4-oxo-2,3,4,5-tetrahydro-1,5-benzothiazepine-7-carboxamide;
(3R)-3-amino-N-(but-3-en-1-yl)-5-[(4-chlorophenyl)methyl]-4-oxo-2,3,4,5-tetrahydro-1,5-benzothiazepine-7-carboxamide;
(3R)-3-amino-5-[(4-chlorophenyl)methyl]-N'-(2-methylpropyl)-4-oxo-2,3,4,5-tetrahydro-1,5-benzothiazepine-7-carbohydrazide;
(3R)-3-amino-N-butyl-5-[(4-chlorophenyl)methyl]-1,4-dioxo-2,3,4,5-tetrahydro-1$\lambda^4$,5-benzothiazepine-7-carboxamide;
(3R)-3-amino-N-butyl-1,1,4-trioxo-5-{[4-(trifluoromethoxy)phenyl]methyl}-2,3,4,5-tetrahydro-1$\lambda^6$,5-benzothiazepine-7-carboxamide;
(3R)-3-amino-5-[(4-chlorophenyl)methyl]-8-fluoro-N-[(4-fluorophenyl)methyl]-1,1,4-trioxo-2,3,4,5-tetrahydro-1$\lambda^6$,5-benzothiazepine-7-carboxamide;
(3R)-3-amino-N-butyl-5-[(4-chlorophenyl)methyl]-8-fluoro-1,1,4-trioxo-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-(4,4,4-trifluoro-butyl)-2,3,4,5-tetrahydro-1$\lambda^6$,5-benzothiazepine-7-carboxamide;
(3R)-3-amino-5-[(4-chlorophenyl)methyl]-8-fluoro-N-(oxan-4-ylmethyl)-1,1,4-trioxo-2,3,4,5-tetrahydro-1$\lambda^6$,5-benzothiazepine-7-carboxamide;
(3R)-3-amino-8-fluoro-N-(oxan-4-yl methyl)-1,1,4-trioxo-5-{[4-(trifluoromethoxy)-phenyl]methyl}-2,3,4,5-tetrahydro-1$\lambda^6$,5-benzothiazepine-7-carboxamide;
(3R)-3-amino-8-fluoro-1,1,4-trioxo-N-(4,4,4-trifluorobutyl)-5-{[4-(trifluoromethoxy)-phenyl]methyl}-2,3,4,5-tetrahydro-1$\lambda^6$,5-benzothiazepine-7-carboxamide;
(3R)-3-amino-8-fluoro-1,1,4-trioxo-N-phenoxy-5-{[4-(trifluoromethoxy)phenyl]methyl}-2,3,4,5-tetrahydro-1$\lambda^6$,5-benzothiazepine-7-carboxamide;
(3R)-3-amino-5-[(4-chlorophenyl)methyl]-8-fluoro-N-(2-methylpropoxy)-1,1,4-trioxo-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-phenoxy-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-(propan-2-yl)-2,3,4,5-tetrahydro-1$\lambda^6$,5-benzothiazepine-7-carboxamide;
(3R)-3-amino-5-[(4-chlorophenyl)methyl]-N-({4-[(5-acetamidopentyl)oxy]phenyl}-methyl)-1,1,4-trioxo-2,3,4,5-tetrahydro-1$\lambda^6$,5-benzothiazepine-7-carboxamide;
(3R)-3-amino-5-[(4-chlorophenyl)methyl]-1,1,4-trioxo-N-(propan-2-yl)-2,3,4,5-tetrahydro-1$\lambda^6$,5-benzothiazepine-7-carboxamide;
(3R)-3-amino-5-[(4-chlorophenyl)methyl]-1,1,4-trioxo-N-(4,4,4-trifluorobutyl)-2,3,4,5-tetrahydro-1$\lambda^6$,5-benzothiazepine-7-carboxamide;
(3R)-3-amino-5-[(4-chlorophenyl)methyl]-N-(2-methylpropoxy)-1,1,4-trioxo-2,3,4,5-tetrahydro-1$\lambda^6$,5-benzothiazepine-7-carboxamide;
(3R)-3-amino-5-[(4-chlorophenyl)methyl]-1,1,4-trioxo-N-propoxy-2,3,4,5-tetrahydro-1$\lambda^6$,5-benzothiazepine-7-carboxamide;
(3R)-3-amino-5-[(4-chlorophenyl)methyl]-N-(3-methylbutan-2-yl)-1,1,4-trioxo-2,3,4,5-tetrahydro-1$\lambda^6$,5-benzothiazepine-7-carboxamide;
(3R)-3-amino-N-(but-3-en-1-yl)-5-[(4-chlorophenyl)methyl]-1,1,4-trioxo-2,3,4,5-tetrahydro-1$\lambda^6$,5-benzothiazepine-7-carboxamide;
(3R)-3-amino-5-[(4-chlorophenyl)methyl]-N-cyclopropyl-8-fluoro-1,1,4-trioxo-2,3,4,5-tetrahydro-1$\lambda^6$,5benzothiazepine-7-carboxamide;
(3R)-3-amino-5-[(4-chlorophenyl)methyl]-N-cyclobutyl-8-fluoro-1,1,4-trioxo-2,3,4,5-tetrahydro-1$\lambda^6$,5-benzothiazepine-7-carboxamide;
(3R)-3-amino-5-[(4-chloro-2-fluorophenyl)methyl]-8-fluoro-1,1,4-trioxo-N-(propan-2-yl)-2,3,4,5-tetrahydro-1$\lambda^6$,5-benzothiazepine-7-carboxamide;
(3R)-3-amino-5-[(3,4-dichlorophenyl)methyl]-1,1,4-trioxo-N-(propan-2-yl)-2,3,4,5-tetrahydro-1$\lambda^6$,5-benzothiazepine-7-carboxamide;
(3R)-3-amino-5-[(4-chloro-3-fluorophenyl)methyl]-1,1,4-trioxo-N-(propan-2-yl)-2,3,4,5-tetrahydro-1$\lambda^6$,5-benzothiazepine-7-carboxamide;
(3R)-3-amino-5-[(4-chlorophenyl)methyl]-N-(cyclohexyloxy)-1,1,4-trioxo-2,3,4,5-tetrahydro-1$\lambda^6$,5-benzothiazepine-7-carboxamide;
(3R)-3-amino-5-[(4-chlorophenyl)methyl]-N-(cyclohexylmethoxy)-1,1,4-trioxo-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-(2,2,2-trifluoro-ethyl)-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-(3,3,3-trifluoro-propyl)-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-[(2S)-1,1,1-trifluoropropan-2-yl]-2,3,4,5-tetrahydro-1$\lambda^6$,5-benzothiazepine-7-carboxamide;
(3R)-3-amino-N-(butan-2-yl)-5-[(4-chlorophenyl)methyl]-8-fluoro-1,1,4-trioxo-2,3,4,5-tetrahydro-1$\lambda^6$,5-benzothiazepine-7-carboxamide;
(3R)-3-amino-N-tert-butyl-5-[(4-chlorophenyl)methyl]-8-fluoro-1,1,4-trioxo-2,3,4,5-tetrahydro-1$\lambda^6$,5-benzothiazepine-7-carboxamide;
(3R)-3-amino-N-(tert-butoxy)-5-[(4-chlorophenyl)methyl]-1,1,4-trioxo-2,3,4,5-tetrahydro-1$\lambda^6$,5-benzothiazepine-7-carboxamide;
(3R)-3-amino-5-[(4-chlorophenyl)methyl]-8-fluoro-1,1,4-trioxo-N-[(1S,2R)-2-phenylcyclopropyl]-2,3,4,5-tetrahydro-1$\lambda^6$,5-benzothiazepine-7-carboxamide;

(3R)-3-amino-5-[(4-chlorophenyl)methyl]-8-fluoro-N-(1-methylcyclopropyl)-1,1,4-trioxo-2,3,4,5-tetrahydro-1λ⁶,5-benzothiazepine-7-carboxamide;

(3R)-3-amino-5-[(4-chlorophenyl)methyl]-8-fluoro-N-(1-methylcyclobutyl)-1,1,4-trioxo-2,3,4,5-tetrahydro-1λ⁶,5-benzothiazepine-7-carboxamide;

(3R)-3-amino-5-[(4-chlorophenyl)methyl]-N-(2,2-dimethylcyclopropyl)-8-fluoro-1,1,4-trioxo-2,3,4,5-tetrahydro-1λ⁶,5-benzothiazepine-7-carboxamide;

(3R)-3-amino-5-[(4-chlorophenyl)methyl]-N-(3,3-difluorocyclobutyl)-8-fluoro-1,1,4-trioxo-2,3,4,5-tetrahydro-1λ⁶,5-benzothiazepine-7-carboxamide;

(3R)-3-amino-N-benzyl-5-[(4-chlorophenyl)methyl]-8-fluoro-1,1,4-trioxo-2,3,4,5-tetrahydro-1λ⁶,5-benzothiazepine-7-carboxamide;

(3R)-3-amino-5-[(4-chlorophenyl)methyl]-8-fluoro-N-heptyl-1,1,4-trioxo-2,3,4,5-tetrahydro-1λ⁶,5-benzothiazepine-7-carboxamide;

(3R)-3-amino-5-[(4-chlorophenyl)methyl]-N-(3,3-difluorocyclopentyl)-8-fluoro-1,1,4-trioxo-2,3,4,5-tetrahydro-1λ⁶,5-benzothiazepine-7-carboxamide;

(3R)-3-amino-5-[(4-chlorophenyl)methyl]-N-[(1R)-2,2-difluorocyclopropyl]-8-fluoro-1,1,4-trioxo-2,3,4,5-tetrahydro-1λ⁶,5-benzothiazepine-7-carboxamide;

(3R)-3-amino-5-[(4-chlorophenyl)methyl]-N-[(1S)-2,2-difluorocyclopropyl]-8-fluoro-1,1,4-trioxo-2,3,4,5-tetrahydro-1λ⁶,5-benzothiazepine-7-carboxamide;

(2R,3R)-3-amino-5-[(4-chlorophenyl)methyl]-N-(2,2-difluorocyclopropyl)-2-methyl-1,1,4-trioxo-2,3,4,5-tetrahydro-1λ⁶,5-benzothiazepine-7-carboxamide;

(3R)-3-amino-5-[(4-chlorophenyl)methyl]-8-fluoro-N-hexadecyl-1,1,4-trioxo-2,3,4,5-tetrahydro-1λ⁶,5-benzothiazepine-7-carboxamide;

(3R)-3-amino-5-[(4-chlorophenyl)methyl]-N-(cyclopropylmethyl)-8-fluoro-1,1,4-trioxo-2,3,4,5-tetrahydro-1λ⁶,5-benzothiazepine-7-carboxamide;

(2R,3R)-3-amino-5-[(4-chlorophenyl)methyl]-2-methyl-1,1,4-trioxo-N-(4,4,4-trifluorobutyl)-2,3,4,5-tetrahydro-1λ⁶,5-benzothiazepine-7-carboxamide;

(3R)-3-amino-N-butyl-8-fluoro-4-oxo-5-(quinolin-2-ylmethyl)-2,3,4,5-tetrahydro-1,5-benzothiazepine-7-carboxamide;

(3R)-3-amino-5-[(5-cyclopropyl-1,3,4-thiadiazol-2-yl)methyl]-8-fluoro-N-[(4-fluorophenyl)methyl]-4-oxo-2,3,4,5-tetrahydro-1,5-benzothiazepine-7-carboxamide;

(3R)-3-amino-N-butyl-5-[(4-chlorophenyl)methyl]-8-(dimethylamino)-1,1,4-trioxo-2,3,4,5-tetrahydro-1λ⁶,5-benzothiazepine-7-carboxamide;

tert-butyl N-(5-{[(3R)-5-[(4-chlorophenyl)methyl]-8-fluoro-7-{[(4-methoxyphenyl)methyl]carbamoyl}-4-oxo-2,3,4,5-tetrahydro-1,5-benzothiazepin-3-yl]amino}pentyl)carbamate;

(3R)-3-amino-N-butyl-1-[(4-chlorophenyl)methyl]-2,5,5-trioxo-1H,2H,3H,4H-5λ⁶-pyrido[3,4-b][1,4]thiazepine-8-carboxamide;

(3R)-3-amino-N-benzyl-5-[(4-chlorophenyl)methyl]-8-(dimethylamino)-1,1,4-trioxo-2,3,4,5-tetrahydro-1λ⁶,5-benzothiazepine-7-carboxamide;

(3R)-3-amino-N-(2,2-difluorocyclopropyl)-8-fluoro-5-{[4-methoxy-3-(trifluoromethyl)phenyl]methyl}-1,1,4-trioxo-2,3,4,5-tetrahydro-1λ⁶,5-benzothiazepine-7-carboxamide;

(2R,3R)-3-amino-5-[(4-chlorophenyl)methyl]-8-fluoro-2-methyl-1,1,4-trioxo-N-(4,4,4-trifluorobutyl)-2,3,4,5-tetrahydro-1λ⁶,5-benzothiazepine-7-carboxamide;

(3R)-3-amino-5-{[4-(5-methyl-1,2,4-oxadiazol-3-yl)phenyl]methyl}-1,1,4-trioxo-N-(4,4,4-trifluorobutyl)-2,3,4,5-tetrahydro-1λ⁶,5-benzothiazepine-7-carboxamide;

(3R)-3-amino-5-[(4-chlorophenyl)methyl]-8-fluoro-N-(2-methoxyethyl)-1,1,4-trioxo-2,3,4,5-tetrahydro-1λ⁶,5-benzothiazepine-7-carboxamide;

(3R)-3-amino-N-(2,2-difluorocyclopropyl)-5-{[4-(5-methyl-1,2,4-oxadiazol-3-yl)phenyl]methyl}-1,1,4-trioxo-2,3,4,5-tetrahydro-1λ⁶,5-benzothiazepine-7-carboxamide;

(1S,3R)-3-amino-5-[(4-chlorophenyl)methyl]-8-fluoro-4-oxo-7-[(4,4,4-trifluorobutyl)carbamoyl]-2,3,4,5-tetrahydro-1H-1,5-benzothiazepin-1-ium-1-olate;

(1R,3R)-3-amino-5-[(4-chlorophenyl)methyl]-8-fluoro-4-oxo-7-[(4,4,4-trifluorobutyl)carbamoyl]-2,3,4,5-tetrahydro-1H-1,5-benzothiazepin-1-ium-1-olate;

(3R)-3-amino-5-[(4-cyanophenyl)methyl]-N-(2,2-difluorocyclopropyl)-8-fluoro-1,1,4-trioxo-2,3,4,5-tetrahydro-1λ⁶,5-benzothiazepine-7-carboxamide;

(3R)-3-amino-5-[(4-cyanophenyl)methyl]-8-fluoro-1,1,4-trioxo-N-(4,4,4-trifluorobutyl)-2,3,4,5-tetrahydro-1λ⁶,5-benzothiazepine-7-carboxamide;

(3R)-3-amino-5-[(4-chlorophenyl)methyl]-N-(4,4-difluorocyclohexyl-8-fluoro-1,1,4-trioxo-2,3,4,5-tetrahydro-1λ⁶,5-benzothiazepine-7-carboxamide;

(3R)-3-amino-5-[(4-chlorophenyl)methyl]-8-fluoro-1,1,4-trioxo-N-[2-(trifluoromethyl)cyclopropyl]-2,3,4,5-tetrahydro-1λ⁶,5-benzothiazepine-7-carboxamide;

(3R)-3-amino-5-[(4-chlorophenyl)methyl]-N-(3,3-difluorocyclobutyl)-8-fluoro-4-oxo-2,3,4,5-tetrahydro-1,5-benzothiazepine-7-carboxamide;

(3R)-3-amino-8-fluoro-5-[(4-fluorophenyl)methyl]-1,1,4-trioxo-N-(4,4,4-trifluorobutyl)-2,3,4,5-tetrahydro-1λ⁶,5-benzothiazepine-7-carboxamide;

(3R)-3-amino-N-(2,2-difluorocyclopropyl)-8-fluoro-5-[(4-fluorophenyl)methyl]-1,1,4-trioxo-2,3,4,5-tetrahydro-1λ⁶,5-benzothiazepine-7-carboxamide;

(3R)-3-amino-N-butyl-8-fluoro-5-[(4-fluorophenyl)methyl]-4-oxo-2,3,4,5-tetrahydro-1,5-benzothiazepine-7-carboxamide;

(3R)-3-amino-N-benzyl-8-fluoro-5-[(4-fluorophenyl)methyl]-4-oxo-2,3,4,5-tetrahydro-1,5-benzothiazepine-7-carboxamide;

(3R)-3-amino-N-butyl-8-fluoro-5-[(4-fluorophenyl)methyl]-1,1,4-trioxo-2,3,4,5-tetrahydro-1λ⁶,5-benzothiazepine-7-carboxamide;

(3R)-3-amino-N-benzyl-8-fluoro-5-[(4-fluorophenyl)methyl]-1,1,4-trioxo-2,3,4,5-tetrahydro-1λ⁶,5-benzothiazepine-7-carboxamide;

(3R)-3-amino-5-[(4-chlorophenyl)methyl]-8-fluoro-N-[2-(oxan-4-yl)ethyl]-1,1,4-trioxo-2,3,4,5-tetrahydro-1λ⁶,5-benzothiazepine-7-carboxamide;

(3R)-3-amino-5-benzyl-8-fluoro-1,1,4-trioxo-N-(4,4,4-trifluorobutyl)-2,3,4,5-tetrahydro-1λ⁶,5-benzothiazepine-7-carboxamide;

(3R)-3-amino-5-[(4-chlorophenyl)methyl]-8-fluoro-N-[(4-methoxyphenyl)methyl]-1,1,4-trioxo-2,3,4,5-tetrahydro-1λ⁶,5-benzothiazepine-7-carboxamide;

(3R)-3-amino-5-[(5-cyclopropyl-1,3,4-thiadiazol-2-yl)methyl]-8-fluoro-N-[(4-fluorophenyl)methyl]-1,1,4-trioxo-2,3,4,5-tetrahydro-1λ⁶,5-benzothiazepine-7-carboxamide;

(3R)-3-amino-8-fluoro-5-[(4-fluorophenyl)methyl]-N-[(oxan-4-yl)methyl]-1,1,4-trioxo-2,3,4,5-tetrahydro-1λ⁶,5-benzothiazepine-7-carboxamide;

(3R)-3-amino-N-(3,3-difluorocyclobutyl-8-fluoro-5-[(4-fluorophenyl)methyl]-1,1,4-trioxo-2,3,4,5-tetrahydro-1$\lambda^6$,5-benzothiazepine-7-carboxamide;

(3R)-3-amino-8-fluoro-5-[(4-methoxyphenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-8-fluoro-5-[(4-methoxyphenyl)methyl]-N-[(oxan-4-yl)methyl]-1,1,4-trioxo-2,3,4,5-tetrahydro-1$\lambda^6$,5-benzothiazepine-7-carboxamide;

(3R)-3-amino-N-(2,2-difluorocyclopropyl)-8-fluoro-5-[(4-methoxyphenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-N-(oxan-4-yl)-1,1,4-trioxo-2,3,4,5-tetrahydro-1$\lambda^6$,5-benzothiazepine-7-carboxamide;

(3R)-3-amino-5-[(4-chlorophenyl)methyl]-N-(3,3-difluorocyclobutyl)-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1S)-3,3-difluorocyclopentyl]-8-fluoro-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1R,2S)-2-fluorocyclopropyl]-1,1,4-trioxo-2,3,4,5-tetrahydro-1$\lambda^6$,5-benzothiazepine-7-carboxamide;

(3R)-3-amino-N-(3,3-difluorocyclobutyl)-5-[(2-fluorophenyl)methyl]-1,1,4-trioxo-2,3,4,5-tetrahydro-1$\lambda^6$,5-benzothiazepine-7-carboxamide;

(3R)-3-amino-N-(3,3-difluorocyclobutyl)-5-[(3-methoxyphenyl)methyl]-1,1,4-trioxo-2,3,4,5-tetrahydro-1$\lambda^6$,5-benzothiazepine-7-carboxamide;

(3R)-3-amino-5-[(4-methoxyphenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-N,5-bis[(4-methoxyphenyl)methyl]-1,1,4-trioxo-2,3,4,5-tetrahydro-1$\lambda^6$,5-benzothiazepine-7-carboxamide;

(3R)-3-amino-5-benzyl-N-[(4-methoxyphenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(4-methoxyphenyl)methyl]-1,1,4-trioxo-2,3,4,5-tetrahydro-1$\lambda^6$,5-benzothiazepine-7-carboxamide;

(3R)-3-amino-N-(4,4-difluorocyclohexyl)-5-[(4-methoxyphenyl)methyl]-1,1,4-trioxo-2,3,4,5-tetrahydro-1$\lambda^6$, 5-benzothiazepine-7-carboxamide;

(3R)-3-amino-5-[(4-chlorophenyl)methyl]-1,1,4-trioxo-N-(3,3,3-trifluoropropyl)-2,3,4,5-tetrahydro-1$\lambda^6$,5-benzothiazepine-7-carboxamide;

(3R)-3-amino-5-[(4-chlorophenyl)methyl]-1,1,4-trioxo-N-[(3R)-oxolan-3-yl]-2,3,4,5-tetrahydro-1$\lambda^6$,5-benzothiazepine-7-carboxamide;

(3R)-3-amino-5-[(4-chlorophenyl)methyl]-1,1,4-trioxo-N-[(oxolan-3-yl)methyl]-2,3,4,5-tetrahydro-1$\lambda^6$,5-benzothiazepine-7-carboxamide;

(3R)-3-amino-5-[(4-chlorophenyl)methyl]-N-[(1R)-2,2-difluorocyclopropyl]-1,1,4-trioxo-2,3,4,5-tetrahydro-1$\lambda^6$,5-benzothiazepine-7-carboxamide;

(3R)-3-amino-5-[(4-cyclopropylphenyl)methyl]-N-[(1R)-2,2-difluorocyclopropyl]-1,1,4-trioxo-2,3,4,5-tetrahydro-1$\lambda^6$,5-benzothiazepine-7-carboxamide;

(3R)-3-amino-N-[(1R)-2,2-difluorocyclopropyl]-5-{[4-(difluoromethoxy)phenyl]methyl}-1,1,4-trioxo-2,3,4,5-tetrahydro-1$\lambda^6$,5-benzothiazepine-7-carboxamide;

(3R)-3-amino-N-[(1R)-2,2-difluorocyclopropyl]-5-[(4-methoxyphenyl)methyl]-1,1,4-trioxo-2,3,4,5-tetrahydro-1$\lambda^6$,5-benzothiazepine-7-carboxamide;

(3R)-3-amino-5-benzyl-1,1,4-trioxo-N-(4,4,4-trifluorobutyl)-2,3,4,5-tetrahydro-1$\lambda^6$,5-benzothiazepine-7-carboxamide;

(3R)-3-amino-8-chloro-5-[(4-chlorophenyl)methyl]-1,1,4-trioxo-N-(4,4,4-trifluorobutyl)-2,3,4,5-tetrahydro-1$\lambda^6$,5-benzothiazepine-7-carboxamide;

(3R)-3-amino-5-{[4-(difluoromethoxy)phenyl]methyl}-N-[(oxan-4-yl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(4-fluorooxan-4-yl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1R)-1-(oxan-4-yl)ethyl]-1,1,4-trioxo-2,3,4,5-tetrahydro-1$\lambda^6$,5-benzothiazepine-7-carboxamide;

(3R)-3-amino-5-benzyl-N-[(1R)-2,2-difluorocyclopropyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(6-methylpyridin-3-yl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(1R)-3,3-difluorocyclopentyl]-1,1,4-trioxo-2,3,4,5-tetrahydro-1$\lambda^6$,5-benzothiazepine-7-carboxamide;

(3R)-3-amino-5-[(4-cyanophenyl)methyl]-8-fluoro-N-[(4-fluorophenyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[(3,3-difluorocyclobutyl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-N-[2-(2-methoxyethoxy)ethyl]-1,1,4-trioxo-2,3,4,5-tetrahydro-1$\lambda^6$,5-benzothiazepine-7-carboxamide;

(3R)-3-amino-N-(but-3-yn-1-yl)-5-[(4-chlorophenyl)methyl]-8-fluoro-1,1,4-trioxo-2,3,4,5-tetrahydro-1$\lambda^6$, 5-benzothiazepine-7-carboxamide;

(3R)-3-amino-5-[(4-chlorophenyl)methyl]-8-fluoro-1,1,4-trioxo-N-(pent-4-yn-1-yl)-2,3,4,5-tetrahydro-1$\lambda^6$, 5-benzothiazepine-7-carboxamide;

(3R)-3-amino-8-chloro-5-[(4-chlorophenyl)methyl]-N-[(1R)-2,2-difluorocyclopropyl]-1,1,4-trioxo-2,3,4,5-tetrahydro-1$\lambda^6$,5-benzothiazepine-7-carboxamide;

(3R)-3-amino-5-[(4-chlorophenyl)methyl]-N-[2-(morpholin-4-yl)ethyl]-1,1,4-trioxo-2,3,4,5-tetrahydro-1$\lambda^6$, 5-benzothiazepine-7-carboxamide;

(3R)-3-amino-5-[(4-chlorophenyl)methyl]-N-[(6-methoxypyridin-3-yl)methyl]-1,1,4-trioxo-2,3,4,5-tetrahydro-1$\lambda^6$,5-benzothiazepine-7-carboxamide;

(3R)-3-amino-5-[(4-chlorophenyl)methyl]-8-fluoro-1,1,4-trioxo-N-{[4-(prop-2-yn-1-yloxy)phenyl]methyl}-2,3,4,5-tetrahydro-1$\lambda^6$,5-benzothiazepine-7-carboxamide;

(3R)-3-amino-N-[(1R)-2,2-difluorocyclopropyl]-1,1,4-trioxo-5-{[4-(trifluoromethyl)phenyl]methyl}-2,3,4,5-tetrahydro-1$\lambda^6$,5-benzothiazepine-7-carboxamide;

(3R)-3-amino-5-[(4-bromophenyl)methyl]-N-(2,2-difluorocyclopropyl)-1,1,4-trioxo-2,3,4,5-tetrahydro-1$\lambda^6$,5-benzothiazepine-7-carboxamide;

(3R)-3-amino-5-[(4-chlorophenyl)methyl]-N-{2-oxaspiro[3.3]heptan-6-yl}-, 1,4-trioxo-2,3,4,5-tetrahydro-1$\lambda^6$,5-benzothiazepine-7-carboxamide; or (3R)-5-[(4-chlorophenyl)methyl]-3-(ethylamino)-8-fluoro-1,1,4-trioxo-N-(4,4,4-trifluorobutyl)-2,3,4,5-tetrahydro-1$\lambda^6$,5-benzothiazepine-7-carboxamide.

18. A compound or a pharmaceutically acceptable salt thereof as defined claim 1.

19. The compound or pharmaceutically acceptable salt thereof of claim 18, wherein the following compound or a pharmaceutically acceptable salt thereof is excluded:

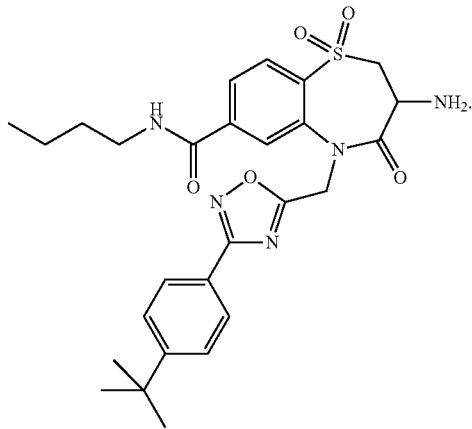 [SMILES: CCCCNC(=O)c1ccc2c(c1)N(Cc1nc(-c3ccc(C(C)(C)C)cc3)no1)C(=O)C(N)CS2(=O)=O]

20. The compound or pharmaceutically acceptable salt thereof claim 18, wherein the following compounds or pharmaceutically acceptable salts thereof are excluded:

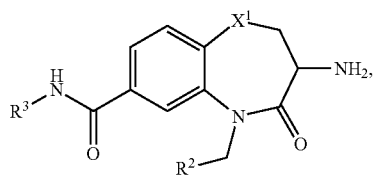

wherein $X^1$ is S; S(O); or S(O)$_2$;
  $R^2$ is phenyl; 3-chlorophenyl; 4-fluorophenyl; 4-methoxyphenyl; 3,5-dimethyl-1,2-oxazol-4-yl; 2-chlorothiophen-5-yl; pyridin-4-yl; 1,3-benzodioxol-5-yl; 5-phenyl-1,2,4-oxadiazol-3-yl; 3-(4-tert butylphenyl)-1,2,4-oxadiazol-5-yl; biphen-4-yl; or 3,4,5-trimethoxyphenyl; and
  $R^3$ is n-butyl; 2-hydroxy-1-hydroxycarbonyl-ethyl; 2-hydroxycarbonylethyl; phenyl; or benzyl.

21. The compound or pharmaceutically acceptable salt thereof of claim 18, wherein the following compounds or pharmaceutically acceptable salts thereof are excluded:

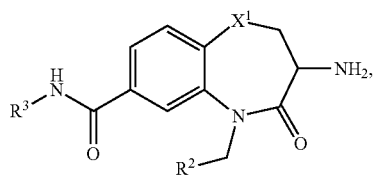

wherein $X^1$ is S; S(O); or S(O)$_2$;
  $R^2$ is phenyl; 3 to 7 membered heterocyclyl; or 7 to 11 membered heterobicyclyl, wherein $R^2$ is optionally substituted with one or more $R^5$, which are the same or different; and
  $R^3$ is n-butyl; 2-hydroxy-1-hydroxycarbonyl-ethyl; 2-hydroxycarbonylethyl; phenyl; or benzyl.

22. The pharmaceutical composition of claim 7, wherein $R^4$ is H or F.

23. The pharmaceutical composition of claim 8, wherein $R^2$ is phenyl, pyridyl, thiadiazolyl, or quinolinyl; and wherein $R^2$ is optionally substituted with one or two $R^5$, which are the same or different.

24. The pharmaceutical composition of claim 8, wherein $R^2$ is phenyl or pyridyl; and wherein $R^2$ is optionally substituted with one or two $R^5$, which are the same or different.

25. The pharmaceutical composition of claim 8, wherein $R^2$ is phenyl; and wherein $R^2$ is optionally substituted with one or two $R^5$, which are the same or different.

26. The pharmaceutical composition of claim 10, wherein $R^5$ is F; Cl; Br; CN; OCH$_3$; OCHF$_2$; OCF$_3$; C(O)NH$_2$; 1H-1,2,4-triazol-1yl; cyclopropyl; 5-methyl-1,2,4-oxadiazol-3-yl; 1,2,3thiadiazol-4yl; morpholin-4-yl; tert-butyl; or CF$_3$.

27. The pharmaceutical composition of claim 10, wherein $R^5$ is F; Cl; CN; OCF$_3$; C(O)NH$_2$; 1H-1,2,4-triazol-1-yl; cyclopropyl; 5-methyl-1,2,4-oxadiazol-3-yl; 1,2,3-thiadiazol-4-yl; morpholin-4-yl; tert-butyl; or CF$_3$.

28. The pharmaceutical composition of claim 13, wherein $R^{3a}$ is $T^2$; $C_{1-12}$ alkyl; or $C_{2-12}$ alkenyl, wherein $C_{1-12}$ alkyl is optionally substituted with one, two or three $R^9$, which are the same or different.

29. The pharmaceutical composition of claim 13, wherein $R^{3a}$ is $T^2$; CH$_2$T$^2$; CH$_2$CH$_2$T$^2$; C(CH$_3$)T$^2$; unsubstituted $C_{1-12}$ alkyl; unsubstituted $C_{2-12}$ alkenyl; $C_{1-12}$ alkyl which is substituted with OR$^{10}$; N(R$^{10}$)C(O)R$^{10a}$; $C_{1-12}$ alkyl; or CF$_3$.

30. An in vitro or ex vivo method for the production of activated immune cells comprising the steps of:
  (i) providing immune cells;
  (ii) contacting the cells of step (i) with:
    (a) at least one compound or pharmaceutically acceptable salt thereof as defined in claim 1, and optionally
    (b) one or more further stimulating agents activating said immune cells; and
  (iii) cultivating the cells of step (ii) under conditions suitable for maintaining the viability of said cells.

* * * * *